US007947839B2

(12) United States Patent
Gazzard et al.

(10) Patent No.: US 7,947,839 B2
(45) Date of Patent: *May 24, 2011

(54) HETEROCYCLIC-SUBSTITUTED BIS-1,8 NAPHTHALIMIDE COMPOUNDS, ANTIBODY DRUG CONJUGATES, AND METHODS OF USE

(75) Inventors: Lewis J. Gazzard, Belmont, CA (US); Edward HyungSuk Ha, San Francisco, CA (US); David Y. Jackson, Belmont, CA (US); Joann M. Um, Berkeley, CA (US)

(73) Assignee: Genentech, Inc., South San Francisco, CA (US)

( * ) Notice: Subject to any disclaimer, the term of this patent is extended or adjusted under 35 U.S.C. 154(b) by 1397 days.
This patent is subject to a terminal disclaimer.

(21) Appl. No.: 11/342,937

(22) Filed: Jan. 30, 2006

(65) Prior Publication Data
US 2006/0182751 A1    Aug. 17, 2006

Related U.S. Application Data

(63) Continuation-in-part of application No. 11/311,591, filed on Nov. 29, 2005.
(60) Provisional application No. 60/632,613, filed on Dec. 1, 2004.

(51) Int. Cl.
*A61K 31/4375* (2006.01)
*C07D 221/14* (2006.01)
*C07D 403/14* (2006.01)
*C07D 413/14* (2006.01)

(52) U.S. Cl. .......... 546/98; 544/126; 544/361; 544/392; 514/296

(58) Field of Classification Search .................. None
See application file for complete search history.

(56) References Cited

U.S. PATENT DOCUMENTS

| 4,146,720 | A | 3/1979 | Roldan et al. |
| 4,874,863 | A | 10/1989 | Brana et al. |
| 5,206,249 | A | 4/1993 | Sun |
| 5,329,048 | A | 7/1994 | Sun |
| 5,376,664 | A | 12/1994 | Kaltenbach, III et al. |
| 5,416,089 | A | 5/1995 | Patten et al. |
| 5,488,110 | A | 1/1996 | Sun |
| 5,552,544 | A | 9/1996 | Brana et al. |
| 5,585,382 | A | 12/1996 | Patten et al. |
| 5,616,589 | A | 4/1997 | Keilhauer et al. |
| 5,641,782 | A | 6/1997 | Sun et al. |
| 5,789,418 | A | 8/1998 | Keilhauer et al. |
| 5,981,753 | A | 11/1999 | Keilhauer et al. |
| 6,177,570 | B1 | 1/2001 | Viergutz et al. |
| 6,262,054 | B1 * | 7/2001 | Fennelly et al. .............. 514/249 |
| 2003/0216309 | A1 | 11/2003 | Krag et al. |

FOREIGN PATENT DOCUMENTS

| WO | WO 94/02466 | | 2/1994 |
| WO | WO 95/05365 | | 2/1995 |
| WO | WO 96/03384 A1 | | 2/1996 |
| WO | WO 96/25400 | * | 8/1996 |
| WO | WO 2005/117986 A2 | | 12/2005 |
| WO | WO 2006/060533 | | 6/2006 |

OTHER PUBLICATIONS

Chari Ravi VJ, "Targeted delivery of chemotherapeutics: tumor-activated prodrug therapy," Advanced Drug Delivery Reviews, 1998, 31: 89-104.*
Awada et al., "An EORTC-ECSG phase I study of LU 79553 administered ever 21 or 42 days in patients with solid tumours" *Eur J Cancer* 39(6):742-747 (Apr. 2003).
Bailly et al., "Chromophore-modified bisnaphthalimides: DNA recognition, topoisomerase inhibitions, and cytotoxic properties of two mono- and bisfuronaphthalimides" *Biochemistry* 42(14):4136-4150 (Apr. 15, 2003).
Bousquet et al., "Preclinical evaluation of Lu 79553: a novel bis-naphthalimide with potent antitumor activity" *Cancer Research* 55(5):1176-1180 (Mar. 1, 1995).
Brana et al., "Bis-naphthalimides 3: synthesis and antitumor activity of N,N'-bis[2-(1,8-naphthalimido)-ethyl] alkanediamines" *Anticancer Drug Des* 11(4):297-330 (Jun. 1996).
Brana at al., "Bis-naphthalimides: a new class of antitumor agents" *Anticancer Drug Des.* 8(4):257-268 (Aug. 1993).
Brana at al., "Naphthalimides as anti-cancer agents: synthesis and biological activity" *Curr Med Chem Anticancer Agents* 1(3):237-255 (Nov. 2001).
Brana et al., "New analogues of amonafide and elinafide, containing aromatic heterocycles: synthesis, antitumor activity, molecular modeling, and DNA binding properties" *J Med Chem.* 47(6):1391-1399 (Mar. 11, 2004).
Brana et al., "Synthesis, biological activity, and quantitative structure-activity relationship study of azanaphthalimide and arylnaphthalimide dericatives" *J Med Chem.* 47(9):2236-2242 (Apr. 22, 2004).
Brana et al., "Synthesis, biological evaluation and DNA binding properties of novel mono and bisnaphthalimides" *Org Biomol Chem.* 1(4):648-654 (Feb. 21, 2003).
Carrasco et al., "DNA sequence recognition by bispyrazinonaphthalimides antitumor agents" *Biochemistry* 42(40):11751-11761 (Oct. 14, 2003).
Hamann et al., "Monoclonal antibody-drug conjugates" *Expert Opin. Ther. Patents* 15(9):1087-1103 (2005).
Hargreaves et al., "Cyclic Carboxylic Monoimides" *Chemical Reviews* 70(4):439-469 (Aug. 1970).
Kupriyan et al., "Synthesis of 4-Substituted Bisnaphthalimides" *Russian Journal of Organic Chemistry* 40(5):699-704 (2004).
Lukas et al, "Femtosecond Optical Switching of Electron Transport Direction in Branches Donor-Acceptor Arrays" *J. Phys. Chem.* 104:931-940 (2000).

(Continued)

*Primary Examiner* — Julie Ha
(74) *Attorney, Agent, or Firm* — Alex Andrus

(57) ABSTRACT

Bis 1,8 naphthalimide compounds including antibody drug conjugate (ADC) are described. Pharmaceutical compositions comprising an effective amount of a 1,8 bis-naphthalimide compound for treatment of hyperproliferative disorders and other disorders are described. Methods are described for killing or inhibiting the proliferation of tumor cells or cancer cells including administering to a patient an effective amount of a 1,8 bis-naphthalimide compound.

16 Claims, 8 Drawing Sheets

OTHER PUBLICATIONS

Lukas et al., "Ultrafast Molecular Logic Gate Based on optical Switching between Two Long-Lived Radical Ion Pair States" *J. Am. Chem. Soc.* 123:2440-2441 (2001).

Mekapati et al., "QSAR of anticancer compounds. Bis(11-oxo-11H-indeno [1,2-b] quinoline-6-carboxamides), bis(phenazine-1-carboxamides), and bis(naphthalimides)" *Bioorg Med Chem.* 9(11):2757-2762 (Nov. 2001).

Villalona-Calero et al., "Phase I and pharmacokinetic study of LU79553, a DNA intercalating bisnaphthalimide, in patients with solid malignancies" *J Clin Oncol.* 19(3):857-869 (Feb. 1, 2001).

Chari et al., "Immunoconjugates Containing Novel Maytansinoids: Promising Anticancer Drugs" *Cancer Research* 52:127-131 (Jan. 1992).

Chen et al., "Antibody-cytotoxic agent conjugates for cancer therapy" *Lancet Oncology* 2:873-890 (2005).

Harris, M., "Monoclonal antibodies as therapeutic agents for cancer" *The Lancet Oncology* 5:292-302 (2004).

Ren et al., "Synthesis and fluorescence properties of novel co-facial folded naphthalimide dimers" *Dyes and Pigments* 64:179-186 (2005).

Zhu et al., "A novel family of twisted molecular luminescent materials containing carbazole unit for single-layer organic electroluminescent devices" *J. of Photochemistry and Photobiology A: Chemistry* 154:169-177 (2003).

Zhu et al., "Molecular twist elecroluminescent materials with charge carrier transporting functional groups and their use" *Database CA [Online] Chemical Abstracts Service*, Columbus, Ohio, US (Accession No. 2001:436688) (Nov. 8, 2000).

* cited by examiner

HETEROCYCLIC-SUBSTITUTED BIS-1,8 NAPHTHALIMIDE COMPOUNDS, ANTIBODY DRUG CONJUGATES, AND METHODS OF USE

This non-provisional application filed under 37 CFR §1.53 (b), is a continuation-in-part, claiming the benefit under 35 USC §120 of U.S. non-provisional application Ser. No. 11/311,591, filed 29 Nov. 2005, and which claims the benefit under 35 USC §119(e) of U.S. Provisional Application Ser. No. 60/632,613 filed on 1 Dec. 2004, both of which are incorporated by reference in their entirety.

FIELD OF THE INVENTION

The invention relates generally to compounds with anti-cancer activity and more specifically to heterocyclic-substituted bis-1,8 naphthalimide chemotherapeutic drugs and bis-1,8 naphthalimide chemotherapeutic drugs conjugated to antibodies. The invention also relates to methods of using the compounds for in vitro, in situ, and in vivo treatment of mammalian cells, or associated pathological conditions.

BACKGROUND OF THE INVENTION

Improving the delivery of drugs and other agents to target cells, tissues and tumors to achieve maximal efficacy and minimal toxicity has been the focus of considerable research for many years. Though many attempts have been made to develop effective methods for importing biologically active molecules into cells, both in vivo and in vitro, none has proved to be entirely satisfactory. Optimizing the association of the drug with its intracellular target, while minimizing intercellular redistribution of the drug, e.g. to neighboring cells, is often difficult or inefficient.

Monoclonal antibody therapy has been established for the targeted treatment of patients with cancer, immunological and angiogenic disorders. One example, HERCEPTIN® (trastuzumab; Genentech, Inc.; South San Francisco, Calif.) is a recombinant DNA-derived humanized monoclonal antibody that selectively binds with high affinity in a cell-based assay (Kd=5 nM) to the extracellular domain of the human epidermal growth factor receptor2 protein, HER2 (ErbB2) (U.S. Pat. No. 5,821,337; U.S. Pat. No. 6,054,297; U.S. Pat. No. 6,407,213; U.S. Pat. No. 6,639,055; Coussens L, et al (1985) Science 230:1132-9; Slamon D J, et al (1989) Science 244:707-12). Trastuzumab is an IgG1 kappa antibody that contains human framework regions with the complementarity-determining regions (cdr) of a murine antibody (4D5) that binds to HER2. Trastuzumab binds to the HER2 antigen and thus inhibits the growth of cancerous cells. Because Trastuzumab is a humanized antibody, it minimizes any HAMA (Human Anti-Mouse Antibody) response in patients. Trastuzumab has been shown, in both in vitro assays and in animals, to inhibit the proliferation of human tumor cells that overexpress HER2 (Hudziak R M, et al (1989) Mol Cell Biol 9:1165-72; Lewis G D, et al (1993) Cancer Immunol Immunother; 37:255-63; Baselga J, et al (1998) Cancer Res. 58:2825-2831). Trastuzumab is a mediator of antibody-dependent cellular cytotoxicity, ADCC (Hotaling T E, et al (1996) [abstract]. Proc. Annual Meeting Am Assoc Cancer Res; 37:471; Pegram M D, et al (1997) [abstract]. Proc Am Assoc Cancer Res; 38:602). In vitro, Trastuzumab-mediated ADCC has been shown to be preferentially exerted on HER2 overexpressing cancer cells compared with cancer cells that do not overexpress HER2. HERCEPTIN® as a single agent is indicated for the treatment of patients with metastatic breast cancer whose tumors overexpress the HER2 protein and who have received one or more chemotherapy regimens for their metastatic disease. HERCEPTIN® in combination with paclitaxel is indicated for treatment of patients with metastatic breast cancer whose tumors overexpress the HER2 protein and who have not received chemotherapy for their metastatic disease. HERCEPTIN® is clinically active in patients with ErbB2-overexpressing metastatic breast cancers that have received extensive prior anti-cancer therapy (Baselga et al, (1996) J. Clin. Oncol. 14:737-744).

The use of antibody-drug conjugates (ADC), i.e. immunoconjugates, for the local delivery of cytotoxic or cytostatic agents to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) theoretically allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Efforts to design and refine ADC have focused on the selectivity of monoclonal antibodies (mAbs) as well as drug-linking and drug-releasing properties. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92 (19):1573-1581; Mandler et al (2000) Bioorganic & Med. Chem. Letters 10:1025-1028; Mandler et al (2002) Bioconjugate Chem. 13:786-791), maytansinoids (US 20050169933 A1; EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al (2000) Eur. Jour. Nucl. Med. 27 (7):766-77; Wiseman et al (2002) Blood 99 (12):4336-42; Witzig et al (2002) J. Clin. Oncol. 20 (10):2453-63; Witzig et al (2002) J. Clin. Oncol. 20 (15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a huCD33 antibody linked to calicheamicin, was approved in 2000 for the treatment of acute myeloid leukemia by injection (Drugs of the Future (2000) 25 (7):686; U.S. Pat. No. 4,970,198; U.S. Pat. No. 5,079,233; U.S. Pat. No. 5,585,089; U.S. Pat. No. 5,606,040; U.S. Pat. No. 5,693,762; U.S. Pat. No. 5,739,116; U.S. Pat. No. 5,767,285; U.S.

Pat. No. 5,773,001). Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE) synthetic analogs of dolastatin, were conjugated to chimeric monoclonal antibodies including: cBR96 (specific to Lewis Y on carcinomas); cAC10 (specific to CD30 on hematological malignancies); and other antibodies (US 20050238649 A1) and are under therapeutic development (Doronina et al (2003) Nature Biotechnology 21 (7):778-784).

DNA intercalation is a proposed mechanism for inhibiting the progression of tumorigenesis. Bis-1,8 naphthalimide compounds strongly bind DNA and may disrupt the DNA-topoisomerase II complex (Bailly et al (2003) Biochemistry 42:4136-4150) by stacking with purine nucleobases on opposite strands (Gallego et al (1999) Biochemistry 38 (46): 15104-15115). Bis-1,8 naphthalimide compounds have been investigated for their anti-cancer properties (Brana et al (2004) Jour. Med. Chem. 47 (6):1391-1399; Brana et al (2004) J. Med. Chem. 47:2236-2242; Bailly et al (2003) Biochemistry 42:4136-4150; Carrasco et al (2003) 42:11751-11761; Brana, M. F. and Ramos, A. (2001) Current Med. Chem.-Anti-Cancer Agents 1:237-255; Mekapati et al (2001) Bioorganic & Med. Chem. 9:2757-2762; U.S. Pat. No. 5,641, 782; U.S. Pat. No. 5,376,664). The investigational antitumor drug bis-1,8 naphthalimide mesylate (LU79553, also known as elinafide dimesylate, N,N-bis[1,8-naphthalimido)ethyl]-1, 3-diaminopropane bismethane sulfonate; or N,N'-Bis[2-(1,3-dioxo-2,3-dihydro-1H-benz[de]isoquinolin-2-yl)ethyl]-1,3-diaminopropane dimethanesulfonate; 2,2'-Propane-1,3-diylbis(iminoethylene)bis(2,3-dihydro-1H-benz[de] isoquinoline-1,3-dione) dimethanesulfonate, (Abbott Laboratories, Knoll A G, Ludwigshafen, D E)), is composed of two tricyclic 1,8-naphthalimide chromophores separated by an aminoalkyl linker chain and designed to permit bisintercalation of the drug into DNA (Villalona-Calero et al (2001) Jour. Clinical Oncology 19 (3):857-869; Bousquet et al (1995) Cancer Res. 55:1176-1180; U.S. Pat. No. 4,874, 863; U.S. Pat. No. 5,416,089; U.S. Pat. No. 5,616,589; U.S. Pat. No. 5,789,418; WO 95/05365). Clinical trials with Elinafide were conducted in Germany (Awada et al (2003) Euro. J. of Cancer 39 (6):742-747). Unlike most other known topoisomerase II inhibitors, elinafide does not cause significant DNA cleavage suggesting Elinafide inhibits topoisomerase II via a different mechanism. This could mean that cancer cells resistant to coventional topoisomerase II inhibitors may not be cross-resistant to elinafide. Elinafide also inhibits topoisomerase I isolated from calf thymus with and IC50 value of 5 µMolar assessed by a supercoiled DNA relaxation assay. In mouse xenograft models, repeated dosing regimens with elinafide demonstrated antitumor activity and did not demonstrate a strong schedule dependency (Bousquet et al (1995) Cancer Res. 55:1176-1180). In human xenograft models, complete regression of MX-1 (mammary carcinoma) xenografts was observed when LU-79553 was administered iv for five daily doses at 20 mg/kg (2 cycles, beginning on days 6 and 20), or every 3 days for two doses at 55 mg/kg (2 cycles, beginning on days 6 and 13) or weekly for four doses (Bousquet et al (1995) Cancer Res. 55:1176-1180). Elinafide has been shown to be curative also in human melanoma (LOX) models and give partial and complete tumor regression, as well as some cures, in human lung (LX-1) and human colon (CX-1) carcinoma xenograft models.

It is desirable to test further analogs of bis-1,8 naphthalimide compounds for their anticancer properties. It is desirable to discover such analogs with optimized biological in vivo properties such as pharmacokinetics, pharmacodynamics, metabolism, potency, safety, and bioavailability. It is also desirable to discover such analogs with optimized physical properties such as increased aqueous solubility and stability.

It is further desirable to the known anticancer properties of bis-1,8 naphthalimide compounds by conjugation to antibodies in order to improve their delivery to target cells, and achieve maximal efficacy and minimal toxicity.

SUMMARY OF THE INVENTION

The present invention provides novel compounds with biological activity against cancer cells. The compounds of the invention may inhibit tumor growth in mammals. The compounds of the invention may be useful for treating human cancer patients.

One aspect of the invention includes antibody drug conjugate (ADC) compounds represented by Formula I:

$$\text{Ab-(L-D)}_p \qquad \text{I}$$

where one or more 1,8 bis-naphthalimide drug moieties (D) are covalently linked by a linker (L) to an antibody (Ab).

In certain embodiments, Ab binds to a tumor-associated antigen or cell-surface receptor.

In another aspect, the antibody of the Formula I ADC of the invention specifically binds to a receptor encoded by an ErbB gene such as, but not limited to, EGFR, HER2, HER3 and HER4. The antibody may bind specifically to an HER2 receptor.

In another aspect, the antibody of the antibody-drug conjugate is a humanized antibody selected from huMAb4D5-1, huMAb4D5-2, huMAb4D5-3, huMAb4D5-4, huMAb4D5-5, huMAb4D5-6, huMAb4D5-7 and huMAb4D5-8 (Trastuzumab).

In still another aspect, the invention provides pharmaceutical compositions comprising an effective amount of a Formula I ADC and a pharmaceutically acceptable carrier or vehicle.

In another aspect, the invention includes a method of treating cancer comprising administering to a mammal, such as a patient with a hyperproliferative disorder, a formulation of a Formula I ADC and a pharmaceutically acceptable diluent, carrier or excipient.

In another aspect, the invention provides methods for preventing the proliferation of a tumor cell or cancer cell including administering to a mammal, such as a patient with a hyperproliferative disorder, an effective amount of a Formula I ADC.

In yet another aspect, the invention provides methods for preventing cancer including administering to a patient with a hyperproliferative disorder, an effective amount of a Formula I ADC.

In another aspect, the invention includes a pharmaceutical composition comprising an effective amount of a Formula I ADC, or a pharmaceutically acceptable salt thereof, and a pharmaceutically acceptable diluent, carrier or excipient. The composition may further comprise a therapeutically effective amount of chemotherapeutic agent such as a tubulin-forming inhibitor, a topoisomerase inhibitor, or a DNA binder.

In another aspect, the invention includes a method for killing or inhibiting the proliferation of tumor cells or cancer cells comprising treating tumor cells or cancer cells with an amount of a Formula I ADC, or a pharmaceutically acceptable salt or solvate thereof, being effective to kill or inhibit the proliferation of the tumor cells or cancer cells.

In another aspect, the invention includes a method of inhibiting cellular proliferation comprising exposing mammalian cells in a cell culture medium to an ADC of the invention.

In another aspect, the invention includes a method for treating an autoimmune disease, comprising administering to a patient, for example a human with a hyperproliferative disorder, an amount of the ADC of Formula I or a pharmaceutically acceptable salt or solvate thereof, said amount being effective to treat an autoimmune disease.

In another aspect, the invention includes a method for killing or inhibiting the proliferation of tumor cells or cancer cells comprising administering to a patient, for example a human, with a hyperproliferative disorder, an amount of the ADC of Formula I or a pharmaceutically acceptable salt or solvate thereof, said amount being effective to kill or inhibit the proliferation of a tumor cell or cancer cell.

In another aspect, the invention includes a method for treating cancer comprising administering to a patient, for example a human, with a hyperproliferative disorder, an amount of the ADC of Formula I or a pharmaceutically acceptable salt or solvate thereof, said amount being effective to treat cancer, alone or together with an effective amount of an additional anticancer agent.

In another aspect, the invention includes a method of inhibiting the growth of tumor cells that overexpress a growth factor receptor selected from the group consisting of HER2 receptor and EGF receptor comprising administering to a patient an antibody drug conjugate compound of the invention which binds specifically to said growth factor receptor and a chemotherapeutic agent wherein said antibody drug conjugate and said chemotherapeutic agent are each administered in amounts effective to inhibit growth of tumor cells in the patient.

In another aspect, the invention includes a method for the treatment of a human patient susceptible to or diagnosed with a disorder characterized by overexpression of ErbB2 receptor, comprising administering an effective amount of a combination of an ADC and a chemotherapeutic agent.

In another aspect, the invention includes an assay for detecting cancer cells comprising exposing cells to a Formula I ADC; and determining the extent of binding of the antibody-drug conjugate compound to the cells.

In another aspect, the present invention provides assays for identifying ADC which specifically target and bind the overexpressed HER2 protein, the presence of which is correlated with abnormal cellular function, and in the pathogenesis of cellular proliferation and/or differentiation of mammary gland that is causally related to the development of breast tumors.

In another aspect, the invention includes an article of manufacture comprising an antibody-drug conjugate compound of the invention; a container; and a package insert or label indicating that the compound can be used to treat cancer characterized by the overexpression of an ErbB receptor.

In another aspect, the invention includes a method for the treatment of cancer in a mammal, wherein the cancer is characterized by the overexpression of an ErbB receptor and does not respond, or responds poorly, to treatment with an anti-ErbB antibody, comprising administering to the mammal a therapeutically effective amount of a Formula I ADC.

In another aspect, the invention includes a method of making an antibody drug conjugate compound comprising conjugating a 1,8 bis-naphthalimide drug moiety and an antibody.

In another aspect, the invention includes heterocyclic-substituted 1,8 bis-naphthalimide compounds which have structures according to Formula XV:

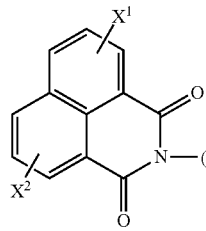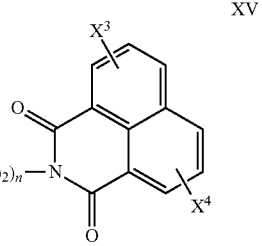

XV or a pharmaceutically acceptable salt or solvate thereof; wherein Y is $N(R^b)$, $C(R^a)_2$, O or S; and at least one of $X^1$, $X^2$, $X^3$, and $X^4$ is nitrogen-linked $C_1$-$C_{20}$ heterocyclyl having the structure:

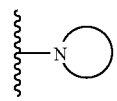

where the wavy line indicates the site of attachment to a 1,8 naphthalimide carbon;

with the proviso that when at least one of $X^1$, $X^2$, $X^3$, and $X^4$ is nitrogen-linked $C_1$-$C_{20}$ heterocyclyl at the 3 position of the 1,8 naphthalimide, and each of $R^a$ is H or $C_1$-$C_8$ alkyl, then Y is not $N(R^b)$.

In another aspect, the invention includes a pharmaceutical composition comprising an effective amount of the compound of Formula XV, or a pharmaceutically acceptable salt thereof, and a pharmaceutically acceptable diluent, carrier or excipient. The pharmaceutical composition may further comprise a therapeutically effective amount of chemotherapeutic agent selected from a tubulin-forming modulator, a topoisomerase inhibitor, and a DNA binder.

In another aspect, the invention includes a method for killing or inhibiting the proliferation of tumor cells or cancer cells comprising treating tumor cells or cancer cells in a cell culture medium with an amount of the compound of Formula XV, or a pharmaceutically acceptable salt or solvate thereof, being effective to kill or inhibit the proliferation of the tumor cells or cancer cells.

In another aspect, the invention includes a method of treating cancer comprising administering to a patient with a hyperproliferative disorder, a therapeutically effective amount of the compound of Formula XV. The method may further comprise administering an effective amount of an additional compound selected from a chemotherapeutic agent, cytotoxic agent, cytokine, growth inhibitory agent, anti-hormonal agent, immunosuppressant, and cardioprotectant. The compound of Formula XV, or a pharmaceutically acceptable salt or solvate thereof, may be formulated with a pharmaceutically acceptable diluent, carrier or excipient. In the method, the compound may specifically bind to a receptor encoded by an ErbB gene.

In another aspect, the invention includes an article of manufacture comprising a compound of Formula XV; a container; and a package insert or label indicating that the compound can be used to treat cancer characterized by the overexpression of an ErbB receptor.

DETAILED DESCRIPTION OF THE EXEMPLARY EMBODIMENTS

Figure 1:
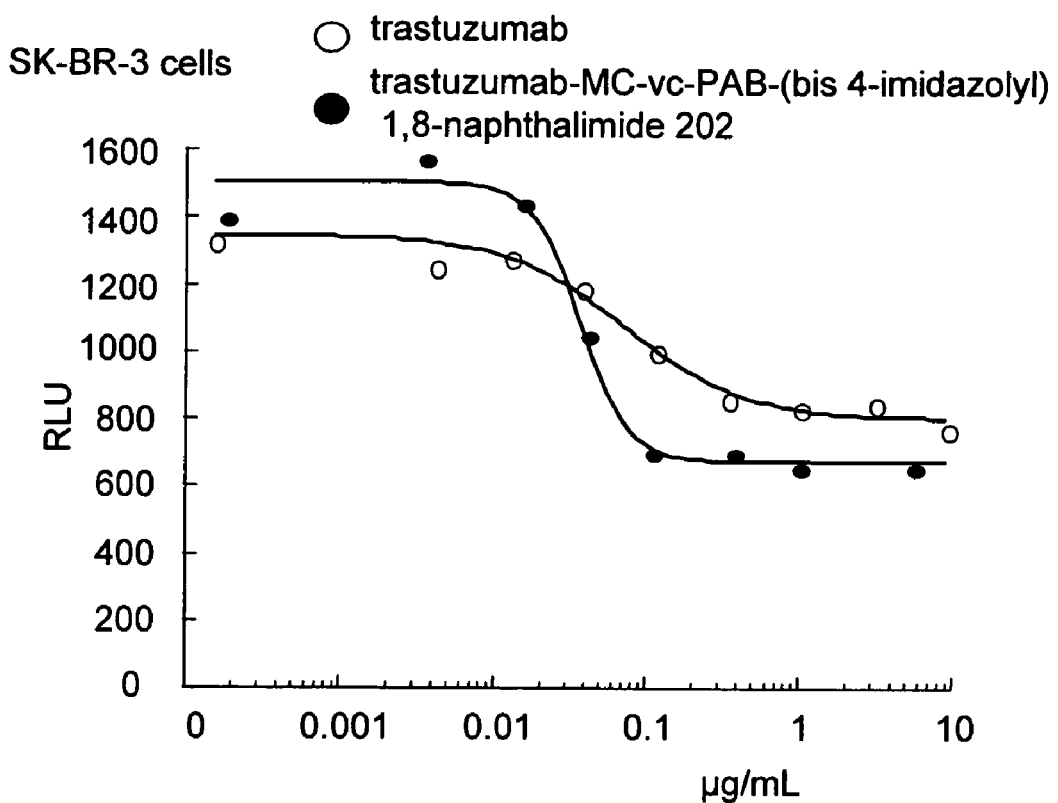
FIG. 1 shows an in vitro, cell proliferation assay with SK-BR-3 cells treated with: -o-trastuzumab and -●-trastuzumab-MC-vc-PAB-(N,N'-(bis-aminoethyl-1,3-propanediamine)-bis-(4-N-imidazolyl)-1,8 naphthalimide) 202, measured in Relative Fluorescence Units (RLU, ×1000) versus μg/ml concentration of antibody or ADC. trastuzumab is linked via a cysteine [cys].

Reference will now be made in detail to certain exemplary embodiments of the invention, examples of which are illustrated in the accompanying structures, drawings, figures, formulas and Examples. While the invention will be described in conjunction with the enumerated embodiments, it will be understood that they are not intended to limit the invention to those embodiments. The discussion below is descriptive, illustrative and exemplary and is not to be taken as limiting the scope defined by any appended claims. On the contrary, the invention is intended to cover all alternatives, modifications, and equivalents, which may be included within the scope of the present invention as defined by the claims. One skilled in the art will recognize many methods and materials similar or equivalent to those described herein, which could be used in the practice of the present invention. The present invention is in no way limited to the methods and materials described.

Unless defined otherwise, technical and scientific terms used herein have the same meaning as commonly understood by one of ordinary skill in the art to which this invention belongs, and are consistent with: Singleton et al., (1994) *Dictionary of Microbiology and Molecular Biology, 2nd Ed.*, J. Wiley & Sons, New York, N.Y.; and Janeway, C., Travers, P., Walport, M., Shlomchik (2001) *Immunobiology*, 5th Ed., Garland Publishing, New York.

When trade names are used herein, applicants intend to independently include the trade name product formulation, the generic drug, and the active pharmaceutical ingredient(s) of the trade name product.

DEFINITIONS

Unless stated otherwise, the following terms and phrases as used herein are intended to have the following meanings:

The term "antibody" herein is used in the broadest sense and specifically covers monoclonal antibodies, polyclonal antibodies, multispecific antibodies (e.g., bispecific antibodies), and antibody fragments, so long as they exhibit the desired biological activity. Antibodies may be murine, human, humanized, chimeric, or derived from other species.

"Antibody fragments" comprise a portion of a full length antibody, generally the antigen binding or variable region thereof. Examples of antibody fragments include Fab, Fab', F(ab')$_2$, and Fv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

An "intact antibody" herein is one comprising a VL and VH domains, as well as complete light and heavy chain constant domains.

An antibody is a protein generated by the immune system that is capable of recognizing and binding to a specific antigen. (Janeway, C., Travers, P., Walport, M., Shlomchik (2001) *Immuno Biology,* 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody.

The term "antibody," as used herein, also refers to a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin disclosed herein can be of any type (e.g., IgG, IgE, IgM, IgD, and IgA), class (e.g., IgG1, IgG2, IgG3, IgG4, IgA1 and IgA2) or subclass of immunoglobulin molecule. The immunoglobulins can be derived from any species. In one aspect, however, the immunoglobulin is of human, murine, or rabbit origin.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) *Nature* 256:495, or may be made by recombinant DNA methods (see, U.S. Pat. No. 4,816,567). The "monoclonal antibodies" may also be isolated from phage antibody libraries using the techniques described in Clackson et al (1991) Nature, 352:624-628; Marks et al (1991) J. Mol. Biol., 222:581-597; for example.

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al (1984) *Proc. Natl. Acad. Sci. USA,* 81:6851-6855). Chimeric antibodies of interest herein include "primatized" antibodies comprising variable domain antigen-binding sequences derived from a non-human primate (e.g., Old World Monkey, Ape etc) and human constant region sequences.

Various methods have been employed to produce monoclonal antibodies (MAbs). Hybridoma technology, which refers to a cloned cell line that produces a single type of antibody, uses the cells of various species, including mice (murine), hamsters, rats, and humans. Another method to prepare MAbs uses genetic engineering including recombinant DNA techniques. Monoclonal antibodies made from these techniques include, among others, chimeric antibodies and humanized antibodies. A chimeric antibody combines DNA encoding regions from more than one type of species. For example, a chimeric antibody may derive the variable region from a mouse and the constant region from a human. A humanized antibody comes predominantly from a human, even though it contains nonhuman portions. Like a chimeric antibody, a humanized antibody may contain a completely human constant region. But unlike a chimeric antibody, the variable region may be partially derived from a human. The nonhuman, synthetic portions of a humanized antibody often come from CDRs in murine antibodies. In any event, these regions are crucial to allow the antibody to recognize and bind to a specific antigen. While useful for diagnostics and short-term therapies, murine antibodies cannot be administered to people long-term without increasing the risk of a deleterious immunogenic response. This response, called Human Anti-Mouse Antibody (HAMA), occurs when a human immune system recognizes the murine antibody as foreign and attacks it. A HAMA response can cause toxic shock or even death.

Chimeric and humanized antibodies reduce the likelihood of a HAMA response by minimizing the nonhuman portions of administered antibodies. Furthermore, chimeric and humanized antibodies can have the additional benefit of activating secondary human immune responses, such as antibody dependent cellular cytotoxicity.

"Antibody fragments" comprise a portion of an intact antibody, e.g. comprising the antigen-binding or variable region thereof. Examples of antibody fragments include Fab, Fab', F(ab')2, and Fv fragments; diabodies; linear antibodies; single-chain antibody molecules; and multispecific antibodies formed from antibody fragment(s).

An "intact" antibody is one which comprises an antigen-binding variable region as well as a light chain constant domain (CL) and heavy chain constant domains, CH1, CH2 and CH3. The constant domains may be native sequence constant domains (e.g., human native sequence constant domains) or amino acid sequence variant thereof.

The intact antibody may have one or more "effector functions" which refer to those biological activities attributable to the Fc region (a native sequence Fc region or amino acid sequence variant Fc region) of an antibody. Examples of antibody effector functions include C1q binding; complement dependent cytotoxicity; Fc receptor binding; antibody-dependent cell-mediated cytotoxicity (ADCC); phagocytosis; down regulation of cell surface receptors (e.g., B cell receptor; BCR), etc.

Depending on the amino acid sequence of the constant domain of their heavy chains, intact antibodies can be assigned to different "classes." There are five major classes of intact antibodies: IgA, IgD, IgE, IgG, and IgM, and several of these may be further divided into "subclasses" (isotypes), e.g., IgG1, IgG2, IgG3, IgG4, IgA, and IgA2. The heavy-chain constant domains that correspond to the different classes of antibodies are called $\alpha$, $\delta$, $\epsilon$, $\gamma$, and $\mu$, respectively. The subunit structures and three-dimensional configurations of different classes of immunoglobulins are well known.

Useful non-immunoreactive protein, polypeptide, or peptide antibodies include, but are not limited to, transferrin, epidermal growth factors ("EGF"), bombesin, gastrin, gastrin-releasing peptide, platelet-derived growth factor, IL-2, IL-6, transforming growth factors ("TGF"), such as TGF-α and TGF-β, vaccinia growth factor ("VGF"), insulin and insulin-like growth factors I and II, lectins and apoprotein from low density lipoprotein.

Useful polyclonal antibodies are heterogeneous populations of antibody molecules derived from the sera of immunized animals. Various procedures well known in the art may be used for the production of polyclonal antibodies to an antigen-of-interest. For example, for the production of polyclonal antibodies, various host animals can be immunized by injection with an antigen of interest or derivative thereof, including but not limited to rabbits, mice, rats, and guinea pigs. Various adjuvants may be used to increase the immunological response, depending on the host species, and including but not limited to Freund's (complete and incomplete) adjuvant, mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and corynebacterium parvum. Such adjuvants are also well known in the art.

Useful monoclonal antibodies are homogeneous populations of antibodies to a particular antigenic determinant (e.g., a cancer cell antigen, a viral antigen, a microbial antigen, a protein, a peptide, a carbohydrate, a chemical, nucleic acid, or fragments thereof). A monoclonal antibody (mAb) to an antigen-of-interest can be prepared by using any technique known in the art which provides for the production of antibody molecules by continuous cell lines in culture. These include, but are not limited to, the hybridoma technique originally described by Köhler and Milstein (1975, *Nature* 256, 495-497), the human B cell hybridoma technique (Kozbor et al., 1983, *Immunology Today* 4:72), and the EBV-hybridoma technique (Cole et al., 1985, *Monoclonal Antibodies and Cancer Therapy*, Alan R. Liss, Inc., pp. 77-96). Such antibodies may be of any immunoglobulin class including IgG, IgM, IgE, IgA, and IgD and any subclass thereof. The hybridoma producing the mAbs of use in this invention may be cultivated in vitro or in vivo.

Useful monoclonal antibodies include, but are not limited to, human monoclonal antibodies, humanized monoclonal antibodies, antibody fragments, or chimeric human-mouse (or other species) monoclonal antibodies. Human monoclonal antibodies may be made by any of numerous techniques known in the art (e.g., Teng et al., 1983, *Proc. Natl. Acad. Sci. U.S.A.* 80, 7308-7312; Kozbor et al., 1983, *Immunology Today* 4, 72-79; and Olsson et al., 1982, *Meth. Enzymol.* 92, 3-16).

The antibody can also be a bispecific antibody. Methods for making bispecific antibodies are known in the art. Traditional production of full-length bispecific antibodies is based on the coexpression of two immunoglobulin heavy chain-light chain pairs, where the two chains have different specificities (Milstein et al., 1983, *Nature* 305:537-539). Because of the random assortment of immunoglobulin heavy and light chains, these hybridomas (quadromas) produce a potential mixture of 10 different antibody molecules, of which only one has the correct bispecific structure. Purification of the correct molecule, which is usually performed using affinity chromatography steps, is rather cumbersome, and the product yields are low. Similar procedures are disclosed in WO 93/08829, and in Traunecker et al., *EMBO J.* 10:3655-3659 (1991).

According to a different approach, antibody variable domains with the desired binding specificities (antibody-antigen combining sites) are fused to immunoglobulin constant domain sequences. The fusion may be with an immunoglobulin heavy chain constant domain, comprising at least part of the hinge, $C_H2$, and $C_H3$ regions. The first heavy-chain constant region ($C_H1$) may contain the site necessary for light chain binding, present in at least one of the fusions. Nucleic acids with sequences encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

Bispecific antibodies may have a hybrid immunoglobulin heavy chain with a first binding specificity in one arm, and a hybrid immunoglobulin heavy chain-light chain pair (providing a second binding specificity) in the other arm. This asymmetric structure facilitates the separation of the desired bispecific compound from unwanted immunoglobulin chain combinations, as the presence of an immunoglobulin light chain in only one half of the bispecific molecule provides for a facile way of separation (WO 94/04690; Suresh et al., *Methods in Enzymology*, 1986, 121:210; Rodrigues et al., 1993, *J. of Immunology* 151:6954-6961; Carter et al., 1992, *Bio/Technology* 10:163-167; Carter et al., 1995, *J. of Hematotherapy* 4:463-470; Merchant et al., 1998, *Nature Biotechnology* 16:677-681. Using such techniques, bispecific antibodies can be prepared for conjugation as ADC in the treatment or prevention of disease as defined herein.

Hybrid or bifunctional antibodies can be derived either biologically, i.e., by cell fusion techniques, or chemically, especially with cross-linking agents or disulfide-bridge forming reagents, and may comprise whole antibodies or fragments thereof (EP 105360; WO 83/03679; EP 217577).

The antibody can be a functionally active fragment, derivative or analog of an antibody that immunospecifically binds to cancer cell antigens, viral antigens, or microbial antigens or other antibodies bound to tumor cells or matrix. In this regard, "functionally active" means that the fragment, derivative or analog is able to elicit anti-anti-idiotype antibodies that recognize the same antigen that the antibody from which the fragment, derivative or analog is derived recognized. Specifically, in an exemplary embodiment the antigenicity of the idiotype of the immunoglobulin molecule can be enhanced by deletion of framework and CDR sequences that are C-terminal to the CDR sequence that specifically recognizes the antigen. To determine which CDR sequences bind the antigen, synthetic peptides containing the CDR sequences can be used in binding assays with the antigen by any binding assay method known in the art (e.g., the BIA core assay) (See, for e.g., Kabat et al., 1991, *Sequences of Proteins of Immunological Interest*, Fifth Edition, National Institute of Health, Bethesda, Md.; Kabat E et al., 1980, *J. of Immunology* 125 (3):961-969).

Other useful antibodies include fragments of antibodies such as, but not limited to, F(ab')2 fragments, which contain the variable region, the light chain constant region and the CH1 domain of the heavy chain can be produced by pepsin digestion of the antibody molecule, and Fab fragments, which can be generated by reducing the disulfide bridges of the F(ab')2 fragments. Other useful antibodies are heavy chain and light chain dimers of antibodies, or any minimal fragment thereof such as Fvs or single chain antibodies (SCAs) (e.g., as described in U.S. Pat. No. 4,946,778; Bird, 1988, Science 242:423-42; Huston et al., 1988, Proc. Natl. Acad. Sci. USA 85:5879-5883; and Ward et al., (1989) Nature 334:544-54), or any other molecule with the same specificity as the antibody.

Additionally, recombinant antibodies, such as chimeric and humanized monoclonal antibodies, comprising both human and non-human portions, which can be made using standard recombinant DNA techniques, are useful antibodies. A chimeric antibody is a molecule in which different portions are derived from different animal species, such as those having a variable region derived from a murine monoclonal and human immunoglobulin constant regions. (See, e.g., Cabilly et al., U.S. Pat. No. 4,816,567; and Boss et al., U.S. Pat. No. 4,816,397, which are incorporated herein by reference in their entirety.) Humanized antibodies are antibody molecules from non-human species having one or more complementarity determining regions (CDRs) from the non-human species and a framework region from a human immunoglobulin molecule. (See, e.g., Queen, U.S. Pat. No. 5,585,089, which is incorporated herein by reference in its entirety.) Such chimeric and humanized monoclonal antibodies can be produced by recombinant DNA techniques known in the art, for example using methods described in WO 87/02671; EP 184, 187; EP 171496; EP 173494; WO 86/01533; U.S. Pat. No. 4,816,567; EP 12023; Berter et al., 1988, Science 240:1041-1043; Liu et al., 1987, Proc. Natl. Acad. Sci. USA 84:3439-3443; Liu et al., 1987, J. Immunol. 139:3521-3526; Sun et al., 1987, Proc. Natl. Acad. Sci. USA 84:214-218; Nishimura et al., 1987, Cancer. Res. 47:999-1005; Wood et al., 1985, Nature 314:446-449; and Shaw et al., 1988, J. Natl. Cancer Inst. 80:1553-1559; Morrison, 1985, Science 229:1202-1207; Oi et al., 1986, BioTechniques 4: 214; U.S. Pat. No. 5,225,539; Jones et al., 1986, Nature 321 :552-525; Verhoeyan et al. (1988) Science 239:1534; and Beidler et al., 1988, J. Immunol. 141:4053-4060; each of which is incorporated herein by reference in its entirety.

Completely human antibodies can be produced using transgenic mice that are incapable of expressing endogenous immunoglobulin heavy and light chains genes, but which can express human heavy and light chain genes. The transgenic mice are immunized in the normal fashion with a selected antigen, e.g., all or a portion of a polypeptide of the invention. Monoclonal antibodies directed against the antigen can be obtained using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies. See, e.g., U.S. Pat. Nos. 5,625,126; 5,633,425; 5,569,825; 5,661,016; 5,545,806; each of which is incorporated herein by reference in its entirety. Other human antibodies can be obtained commercially from, for example, Abgenix, Inc. (Freemont, Calif.) and Genpharm (San Jose, Calif.).

Completely human antibodies that recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al. (1994) Biotechnology 12:899-903). Human antibodies can also be produced using various techniques known in the art, including phage display libraries (Hoogenboom and Winter, J. Mol. Biol., 227:381 (1991); Marks et al., J. Mol. Biol., 222:581 (1991)).

The antibody may be a fusion protein of an antibody, or a functionally active fragment thereof, for example in which the antibody is fused via a covalent bond (e.g., a peptide bond), at either the N-terminus or the C-terminus to an amino acid sequence of another protein (or portion thereof, such as at least 10, 20 or 50 amino acid portion of the protein) that is not the antibody. The antibody or fragment thereof may be covalently linked to the other protein at the N-terminus of the constant domain.

Antibodies include analogs and derivatives that are either modified, i.e., by the covalent attachment of any type of molecule as long as such covalent attachment permits the antibody to retain its antigen binding immunospecificity. For example, but not by way of limitation, the derivatives and analogs of the antibodies include those that have been further modified, e.g., by glycosylation, acetylation, pegylation, phosphorylation, amidation, derivatization by known protecting/blocking groups, proteolytic cleavage, linkage to a cellular antibody unit or other protein, etc. Any of numerous chemical modifications can be carried out by known techniques, including, but not limited to specific chemical cleavage, acetylation, formylation, metabolic synthesis in the presence of tunicamycin, etc. Additionally, the analog or derivative can contain one or more unnatural amino acids.

The antibodies in ADC include antibodies having modifications (e.g., substitutions, deletions or additions) in amino acid residues that interact with Fc receptors. In particular, antibodies include antibodies having modifications in amino acid residues identified as involved in the interaction between the anti-Fc domain and the FcRn receptor (see, e.g., WO 97/34631, which is incorporated herein by reference in its entirety). Antibodies immunospecific for a cancer cell antigen can be obtained commercially, for example, from Genentech (San Francisco, Calif.) or produced by any method known to one of skill in the art such as, e.g., chemical synthesis or recombinant expression techniques. The nucleotide sequence encoding antibodies immunospecific for a cancer cell antigen can be obtained, e.g., from the GenBank database or a database like it, the literature publications, or by routine cloning and sequencing.

The antibody of the antibody-drug conjugates (ADC) of the invention may specifically bind to a receptor encoded by an ErbB gene. The antibody may bind specifically to an ErbB receptor selected from EGFR, HER2, HER3 and HER4. The ADC may specifically bind to the extracellular domain of the HER2 receptor and inhibit the growth of tumor cells which overexpress HER2 receptor. The antibody of the ADC may be a monoclonal antibody, e.g. a murine monoclonal antibody, a chimeric antibody, or a humanized antibody. A humanized antibody may be huMAb4D5-1, huMAb4D5-2, huMAb4D5-3, huMAb4D5-4, huMAb4D5-5, huMAb4D5-6, huMAb4D5-7 or huMAb4D5-8 (Trastuzumab). The antibody may be an antibody fragment, e.g. a Fab fragment.

Known antibodies for the treatment or prevention of cancer can be conjugated as ADC. Antibodies immunospecific for a cancer cell antigen can be obtained commercially or produced by any method known to one of skill in the art such as, e.g., recombinant expression techniques. The nucleotide sequence encoding antibodies immunospecific for a cancer cell antigen can be obtained, e.g., from the GenBank database or a database like it, the literature publications, or by routine cloning and sequencing. Examples of antibodies available for the treatment of cancer include, but are not limited to, humanized anti-HER2 monoclonal antibody for the treatment of patients with metastatic breast cancer; RITUXAN® (rituximab;

Genentech) which is a chimeric anti-CD20 monoclonal antibody for the treatment of patients with non-Hodgkin's lymphoma; OvaRex (AltaRex Corporation, MA) which is a murine antibody for the treatment of ovarian cancer; Panorex (Glaxo Wellcome, NC) which is a murine $IgG_{2a}$ antibody for the treatment of colorectal cancer; Cetuximab Erbitux (Imclone Systems Inc., NY) which is an anti-EGFR IgG chimeric antibody for the treatment of epidermal growth factor positive cancers, such as head and neck cancer; Vitaxin (MedImmune, Inc., MD) which is a humanized antibody for the treatment of sarcoma; Campath I/H (Leukosite, MA) which is a humanized $IgG_1$ antibody for the treatment of chronic lymphocytic leukemia (CLL); Smart MI95 (Protein Design Labs, Inc., CA) which is a humanized anti-CD33 IgG antibody for the treatment of acute myeloid leukemia (AML); LymphoCide (Immunomedics, Inc., NJ) which is a humanized anti-CD22 IgG antibody for the treatment of non-Hodgkin's lymphoma; Smart ID10 (Protein Design Labs, Inc., CA) which is a humanized anti-HLA-DR antibody for the treatment of non-Hodgkin's lymphoma; Oncolym (Techniclone, Inc., CA) which is a radiolabeled murine anti-HLA-Dr10 antibody for the treatment of non-Hodgkin's lymphoma; Allomune (BioTransplant, CA) which is a humanized anti-CD2 mAb for the treatment of Hodgkin's Disease or non-Hodgkin's lymphoma; Avastin (Genentech, Inc., CA) which is an anti-VEGF humanized antibody for the treatment of lung and colorectal cancers; Epratuzamab (Immunomedics, Inc., NJ and Amgen, CA) which is an anti-CD22 antibody for the treatment of non-Hodgkin's lymphoma; and CEAcide (Immunomedics, NJ) which is a humanized anti-CEA antibody for the treatment of colorectal cancer.

Other antibodies useful in the treatment of cancer include, but are not limited to, antibodies against the following antigens: CA125 (ovarian), CA15-3 (carcinomas), CA19-9 (carcinomas), L6 (carcinomas), Lewis Y (carcinomas), Lewis X (carcinomas), alpha fetoprotein (carcinomas), CA 242 (colorectal), placental alkaline phosphatase (carcinomas), prostate specific antigen (prostate), prostatic acid phosphatase (prostate), epidermal growth factor (carcinomas), MAGE-1 (carcinomas), MAGE-2 (carcinomas), MAGE-3 (carcinomas), MAGE-4 (carcinomas), anti-transferrin receptor (carcinomas), p97 (melanoma), MUC1-KLH (breast cancer), CEA (colorectal), gp100 (melanoma), MART1 (melanoma), PSA (prostate), IL-2 receptor (T-cell leukemia and lymphomas), CD20 (non-Hodgkin's lymphoma), CD52 (leukemia), CD33 (leukemia), CD22 (lymphoma), human chorionic gonadotropin (carcinoma), CD38 (multiple myeloma), CD40 (lymphoma), mucin (carcinomas), P21 (carcinomas), MPG (melanoma), and Neu oncogene product (carcinomas). Some specific, useful antibodies include, but are not limited to, BR96 mAb (Trail, P. A., et al Science (1993) 261, 212-215), BR64 (Trail, P A, et al Cancer Research (1997) 57, 100-105, mAbs against the CD40 antigen, such as S2C6 mAb (Francisco, J. A., et al Cancer Res. (2000) 60:3225-3231), mAbs against the CD70 antigen, such as 1F6 mAb, and mAbs against the CD30 antigen, such as AC10 (Bowen, M. A., et al (1993) J. Immunol., 151:5896-5906; Wahl et al., 2002 *Cancer Res.* 62 (13):3736-42). Many other internalizing antibodies that bind to tumor associated antigens can be used and have been reviewed (Franke, A. E., et al Cancer Biother Radiopharm. (2000) 15:459-76; Murray, J. L., (2000) Semin Oncol., 27:64-70; Breitling, F., and Dubel, S., *Recombinant Antibodies*, John Wiley, and Sons, New York, 1998).

Known antibodies for the treatment or prevention of an autoimmune disorders may be conjugated as ADC. Autoimmune disorders include systemic lupus erythematosus (SLE), rheumatoid arthritis, Sjogren's syndrome, immune thromobocytopenia, and multiple sclerosis. Antibodies immunospecific for an antigen of a cell that is responsible for producing autoimmune antibodies can be obtained by any method known to one of skill in the art such as, e.g., chemical synthesis or recombinant expression techniques. SLE is marked by the overexpression of interferon-alpha (IFN-$\alpha$) cytokine genes (Bennett et al (2003) Jour. Exp. Med. 197:711-723). Type-1 interferons (IFN-$\alpha/\beta$) play a significant role in the pathogenesis of lupus (Santiago-Raber (2003) Jour. Exp. Med. 197:777-788). Knockout mice (-IFN-$\alpha/\beta$) showed significantly reduced anti-erythrocyte autoantibodies, erythroblastosis, hemolytic anemia, anti-DNA autobodies, kidney disease, and mortality. These results suggest that Type-1 IFNs mediate murine lupus, and that reducing their activity in the human counterpart may be beneficial. Anti-IFN Ab conjugated to bis 1,8 naphthalimide drug moieties may be effective therapeutic agents against SLE and other autoimmune disorders.

In another embodiment, useful antibodies in ADC are immunospecific for the treatment of autoimmune diseases include, but are not limited to, Anti-Nuclear Antibody; Anti ds DNA; Anti ss DNA, Anti Cardiolipin Antibody IgM, IgG; Anti Phospholipid Antibody IgM, IgG; Anti SM Antibody; Anti Mitochondrial Antibody; Thyroid Antibody; Microsomal Antibody; Thyroglobulin Antibody; Anti SCL-70; Anti-Jo; Anti-$U_1$RNP; Anti-La/SSB; Anti SSA; Anti SSB; Anti Perital Cells Antibody; Anti Histones; Anti-RNP; C-ANCA; P-ANCA; Anti centromere; Anti-Fibrillarin, and Anti-GBM Antibody.

Antibodies of an ADC can bind to both a receptor or a receptor complex expressed on an activated lymphocyte, such as one associated with an autoimmune disease. The receptor or receptor complex can comprise an immunoglobulin gene superfamily member, a TNF receptor superfamily member, an integrin, a cytokine receptor, a chemokine receptor, a major histocompatibility protein, a lectin, or a complement control protein. Non-limiting examples of suitable immunoglobulin superfamily members are CD2, CD3, CD4, CD8, CD 19, CD22, CD28, CD79, CD90, CD 152/CTLA-4, PD-1, and ICOS. Non-limiting examples of suitable TNF receptor superfamily members are CD27, CD40, CD95/Fas, CD134/OX40, CD137/4-1BB, TNF-R1, TNFR-2, RANK, TACI, BCMA, osteoprotegerin, Apo2/TRAIL-R1, TRAIL-R2, TRAIL-R3, TRAIL-R4, and APO-3. Non-limiting examples of suitable integrins are CD11a, CD11b, CD11c, CD18, CD29, CD41, CD49a, CD49b, CD49c, CD49d, CD49e, CD49f, CD 103, and CD 104. Non-limiting examples of suitable lectins are C-type, S-type, and I-type lectin.

As used herein, the term "viral antigen" includes, but is not limited to, any viral peptide, polypeptide protein (e.g., HIV gp120, HIV nef, RSV F glycoprotein, influenza virus neuraminidase, influenza virus hemagglutinin, HTLV tax, herpes simplex virus glycoprotein (e.g., Gb, Gc, Gd, and Ge) and hepatitis B surface antigen) that is capable of eliciting an immune response. As used herein, the term "microbial antigen" includes, but is not limited to, any microbial peptide, polypeptide, protein, saccharide, polysaccharide, or lipid molecule (e.g., a bacterial, fungi, pathogenic protozoa, or yeast polypeptide including, e.g., LPS and capsular polysaccharide 5/8) that is capable of eliciting an immune response.

Antibodies immunospecific for a viral or microbial antigen can be obtained commercially, for example, from BD Biosciences (San Francisco, Calif.), Chemicon International, Inc. (Temecula, Calif.), or Vector Laboratories, Inc. (Burlingame, Calif.) or produced by any method known to one of skill in the art such as, e.g., chemical synthesis or recombinant expression techniques. The nucleotide sequence encoding antibodies that are immunospecific for a viral or microbial antigen can be obtained, e.g., from the GenBank database or a database like it, the literature publications, or by routine cloning and sequencing.

In a specific embodiment, useful antibodies in ADC are those that treat or prevent viral or microbial infection in accordance with the methods disclosed herein. Examples of antibodies available useful for the treatment of viral infection or microbial infection include, but are not limited to, SYNAGIS (MedImmune, Inc., MD) which is a humanized anti-respiratory syncytial virus (RSV) monoclonal antibody useful for the treatment of patients with RSV infection; PRO542 (Progenics) which is a CD4 fusion antibody useful for the treatment of HIV infection; OSTAVIR (Protein Design Labs, Inc., CA) which is a human antibody useful for the treatment of hepatitis B virus; PROTOVIR (Protein Design Labs, Inc., CA) which is a humanized IgG, antibody useful for the treatment of cytomegalovirus (CMV); and anti-LPS antibodies.

Other antibodies useful in ADC for the treatment of infectious diseases include, but are not limited to, antibodies against the antigens from pathogenic strains of bacteria (*Streptococcus pyogenes, Streptococcus pneumoniae, Neisseria gonorrheae, Neisseria meningitidis, Corynebacterium diphtheriae, Clostridium botulinum, Clostridium perfringens, Clostridium tetani, Hemophilus influenzae, Klebsiella pneumoniae, Klebsiella ozaenas, Klebsiella rhinoscleromotis, Staphylococcus aureus, Vibrio colerae, Escherichia coli, Pseudomonas aeruginosa, Campylobacter (Vibrio) fetus, Aeromonas hydrophila, Bacillus cereus, Edwardsiella tarda, Yersinia enterocolitica, Yersinia pestis, Yersinia pseudotuberculosis, Shigella dysenteriae, Shigella flexneri, Shigella sonnei, Salmonella typhimurium, Treponema pallidum, Treponema pertenue, Treponema carateneum, Borrelia vincentii, Borrelia burgdorferi, Leptospira icterohemorrhagiae, Mycobacterium tuberculosis, Pneumocystis carinii, Francisella tularensis, Brucella abortus, Brucella suis, Brucella melitensis, Mycoplasma spp., Rickettsia prowazeki, Rickettsia tsutsugumushi, Chlamydia spp.*); pathogenic fungi (*Coccidioides immitis, Aspergillus fumigatus, Candida albicans, Blastomyces dermatitidis, Cryptococcus neoformans, Histoplasma capsulatum*); protozoa (*Entomoeba histolytica, Toxoplasma gondii, Trichomonas tenas, Trichomonas hominis, Trichomonas vaginalis, Tryoanosoma gambiense, Trypanosoma rhodesiense, Trypanosoma cruzi, Leishmania donovani, Leishmania tropica, Leishmania braziliensis, Pneumocystis pneumonia, Plasmodium vivax, Plasmodium falciparum, Plasmodium malaria*); or Helminiths (*Enterobius vermicularis, Trichuris trichiura, Ascaris lumbricoides, Trichinella spiralis, Strongyloides stercoralis, Schistosoma japonicum, Schistosoma mansoni, Schistosoma haematobium*, and hookworms).

Other antibodies useful in ADC for treatment of viral disease include, but are not limited to, antibodies against antigens of pathogenic viruses, including as examples and not by limitation: Poxviridae, Herpesviridae, Herpes Simplex virus 1, Herpes Simplex virus 2, Adenoviridae, Papovaviridae, Enteroviridae, Picornaviridae, Parvoviridae, Reoviridae, Retroviridae, influenza viruses, parainfluenza viruses, mumps, measles, respiratory syncytial virus, rubella, Arboviridae, Rhabdoviridae, Arenaviridae, Hepatitis A virus, Hepatitis B virus, Hepatitis C virus, Hepatitis E virus, Non-A/Non-B Hepatitis virus, Rhinoviridae, Coronaviridae, Rotoviridae, and Human Immunodeficiency Virus.

An "ErbB receptor" is a receptor protein tyrosine kinase which belongs to the ErbB receptor family whose members are mediators of cell growth, differentiation and survival. The ErbB receptor family includes four distinct members including epidermal growth factor receptor (EGFR, ErbB 1, HER1), HER2 (ErbB2 or p185$^{neu}$), HER3 (ErbB3) and HER4 (ErbB4 or tyro2). A panel of anti-ErbB2 antibodies has been characterized using the human breast tumor cell line SKBR3 (Hudziak et al., (1989) *Mol. Cell. Biol.* 9 (3): 1165-1172. Maximum inhibition was obtained with the antibody called 4D5 which inhibited cellular proliferation by 56%. Other antibodies in the panel reduced cellular proliferation to a lesser extent in this assay. The antibody 4D5 was further found to sensitize ErbB2-overexpressing breast tumor cell lines to the cytotoxic effects of TNF-α (U.S. Pat. No. 5,677,171). The anti-ErbB2 antibodies discussed in Hudziak et al. are further characterized in Fendly et al (1990) Cancer Research 50:1550-1558; Kotts et al. (1990) In Vitro 26 (3):59A; Sarup et al. (1991) Growth Regulation 1:72-82; Shepard et al. J. (1991) Clin. Immunol. 11 (3):117-127; Kumar et al. (1991) Mol. Cell. Biol. 11 (2):979-986; Lewis et al. (1993) Cancer Immunol. Immunother. 37:255-263; Pietras et al. (1994) Oncogene 9:1829-1838; Vitetta et al. (1994) Cancer Research 54:5301-5309; Sliwkowski et al. (1994) J. Biol. Chem. 269 (20): 14661-14665; Scott et al. (1991) J. Biol. Chem. 266:14300-5; D'souza et al. Proc. Natl. Acad. Sci. (1994) 91:7202-7206; Lewis et al. (1996) Cancer Research 56:1457-1465; and Schaefer et al. (1997) Oncogene 15:1385-1394.

The ErbB receptor will generally comprise an extracellular domain, which may bind an ErbB ligand; a lipophilic transmembrane domain; a conserved intracellular tyrosine kinase domain; and a carboxyl-terminal signaling domain harboring several tyrosine residues which can be phosphorylated. The ErbB receptor may be a "native sequence" ErbB receptor or an "amino acid sequence variant" thereof. The ErbB receptor may be a native sequence human ErbB receptor. Accordingly, a "member of the ErbB receptor family" is EGFR (ErbB1), ErbB2, ErbB3, ErbB4 or any other ErbB receptor currently known or to be identified in the future.

The terms "ErbB1", "epidermal growth factor receptor", "EGFR" and "HER1" are used interchangeably herein and refer to EGFR as disclosed, for example, in Carpenter et al (1987) *Ann. Rev. Biochem.*, 56:881-914, including naturally occurring mutant forms thereof (e.g., a deletion mutant EGFR as in Humphrey et al., *PNAS (USA)*, 87:4207-4211 (1990)). The term erbB1 refers to the gene encoding the EGFR protein product. Antibodies against HER1 are described, for example, in Murthy et al (1987) *Arch. Biochem. Biophys.*, 252:549-560 and in WO 95/25167.

The term "ERRP", "EGF-Receptor Related Protein", "EGFR Related Protein" and "epidermal growth factor receptor related protein" are used interchangeably herein and refer to ERRP as disclosed, for example in U.S. Pat. No. 6,399,743 and US Publication No. 2003/0096373.

The expressions "ErbB2" and "HER2" are used interchangeably herein and refer to human HER2 protein described, for example, in Semba et al., *PNAS (USA)*, 82:6497-6501 (1985) and Yamamoto et al., (1986) *Nature*, 319:230-234 (Genebank accession number X03363). The term "erbB2" refers to the gene encoding human ErbB2 and "neu" refers to the gene encoding rat p185neu. ErbB2 may be a native sequence human ErbB2.

"ErbB3" and "HER3" refer to the receptor polypeptide as disclosed, for example, in U.S. Pat. No. 5,183,884 and U.S. Pat. No. 5,480,968 as well as Kraus et al., PNAS (USA), 86:9193-9197 (1989). Antibodies against ErbB3 are known in the art and are described, for example, in U.S. Pat. Nos. 5,183,884, 5,480,968 and in WO 97/35885.

The terms "ErbB4" and "HER4" herein refer to the receptor polypeptide as disclosed, for example, in EP Pat. Application No 599,274; Plowman et al., *Proc. Natl. Acad. Sci.*

USA, 90:1746-1750 (1993); and Plowman et al., Nature, 366: 473-475 (1993), including isoforms thereof, e.g., as disclosed in WO 99/19488. Antibodies against HER4 are described, for example, in WO 02/18444.

Antibodies to ErbB receptors are available commercially from a number of sources, including, for example, Santa Cruz Biotechnology, Inc., California, USA.

The term "amino acid sequence variant" refers to polypeptides having amino acid sequences that differ to some extent from a native sequence polypeptide. Ordinarily, amino acid sequence variants will possess at least about 70% sequence identity with at least one receptor binding domain of a native antibody or with at least one ligand binding domain of a native receptor, and preferably, they will be at least about 80%, more preferably, at least about 90% homologous by sequence with such receptor or ligand binding domains. The amino acid sequence variants possess substitutions, deletions, and/or insertions at certain positions within the amino acid sequence of the native amino acid sequence. Amino acids are designated by the conventional names, one-letter and three-letter codes.

"Sequence identity" is defined as the percentage of residues in the amino acid sequence variant that are identical after aligning the sequences and introducing gaps, if necessary, to achieve the maximum percent sequence identity. Methods and computer programs for the alignment are well known in the art. One such computer program is "Align 2," authored by Genentech, Inc., which was filed with user documentation in the United States Copyright Office, Washington, D.C. 20559, on Dec. 10, 1991.

The terms "Fc receptor" or "FcR" are used to describe a receptor that binds to the Fc region of an antibody. An exemplary FcR is a native sequence human FcR. Moreover, a FcR may be one which binds an IgG antibody (a gamma receptor) and includes receptors of the FcγRI, FcγRII, and Fcγ RIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (See review M. in *Daëron, Annu. Rev. Immunol.*, 15:203-234 (1997)). FcRs are reviewed in Ravetch and Kinet, *Annu. Rev. Immunol.*, 9:457-92 (1991); Capel et al., *Immunomethods*, 4:25-34 (1994); and de Haas et al., *J. Lab. Clin. Med.*, 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.*, 117:587 (1976) and Kim et al., *J. Immunol.*, 24:249 (1994)).

"Complement dependent cytotoxicity" or "CDC" refers to the ability of a molecule to lyse a target in the presence of complement. The complement activation pathway is initiated by the binding of the first component of the complement system (C1q) to a molecule (e.g., an antibody) complexed with a cognate antigen. To assess complement activation, a CDC assay, e.g., as described in Gazzano-Santoro et al., *J. Immunol. Methods*, 202:163 (1996), may be performed.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light-chain variable domain is aligned with the variable domain of the heavy chain. Particular amino acid residues are believed to form an interface between the light chain and heavy chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al (1991) Sequences of Proteins of Immunological Interest, 5th Ed. Public Health Service, National Institutes of Health, Bethesda, Md.). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody which are responsible for antigen-binding. The hypervariable region generally comprises amino acid residues from a "complementarity determining region" or "CDR" (e.g., residues 24-34 (L1), 50-56 (L2) and 89-97 (L3) in the light chain variable domain and 31-35 (H1), 50-65 (H2) and 95-102 (H3) in the heavy chain variable domain; Kabat et al supra) and/or those residues from a "hypervariable loop" (e.g., residues 26-32 (L1), 50-52 (L2) and 91-96 (L3) in the light chain variable domain and 26-32 (H1), 53-55 (H2) and 96-101 (H3) in the heavy chain variable domain; Chothia and Lesk (1987) J. Mol. Biol., 196:901-917). "Framework Region" or "FR" residues are those variable domain residues other than the hypervariable region residues as herein defined.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-binding sites and is still capable of cross-linking antigen.

"Fv" is the minimum antibody fragment which contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the VH-VL dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')2 antibody fragments originally were produced as pairs of Fab' fragments which have hinge cysteines between them. Other chemical couplings of antibody fragments are also known.

The "light chains" of antibodies from any vertebrate species can be assigned to one of two clearly distinct types, called kappa (κ) and lambda (λ), based on the amino acid sequences of their constant domains.

"Single-chain Fv" or "scFv" antibody fragments comprise the VH and VL domains of antibody, wherein these domains are present in a single polypeptide chain. The Fv polypeptide may further comprise a polypeptide linker between the VH and VL domains which enables the scFv to form the desired structure for antigen binding. For a review of scFv, see Plückthun in The Pharmacology of Monoclonal Antibodies, vol. 113, Rosenburg and Moore eds., Springer-Verlag, New York, pp. 269-315 (1994). Anti-ErbB2 antibody scFv fragments are described in WO 93/16185; U.S. Pat. Nos. 5,571,894; and 5,587,458.

The term "diabodies" refers to small antibody fragments with two antigen-binding sites, which fragments comprise a variable heavy domain (VH) connected to a variable light domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al (1993) Proc. Natl. Acad. Sci. USA 90:6444-6448.

"Humanized" forms of non-human (e.g., rodent) antibodies are chimeric antibodies that contain minimal sequence derived from non-human immunoglobulin. Humanization is a method to transfer the murine antigen binding information to a non-immunogenic human antibody acceptor, and has resulted in many therapeutically useful drugs. The method of humanization generally begins by transferring all six murine complementarity determining regions (CDRs) onto a human antibody framework (Jones et al, (1986) Nature 321:522-525). These CDR-grafted antibodies generally do not retain their original affinity for antigen binding, and in fact, affinity is often severely impaired. Besides the CDRs, select non-human antibody framework residues must also be incorporated to maintain proper CDR conformation (Chothia et al (1989) Nature 342:877). The transfer of key mouse framework residues to the human acceptor in order to support the structural conformation of the grafted CDRs has been shown to restore antigen binding and affinity (Riechmann et al., (1992) J. Mol. Biol. 224, 487-499; Foote and Winter, (1992) J. Mol. Biol. 224:487-499; Presta et al., (1993) J. Immunol. 151, 2623-2632; Werther et al., (1996) J. Immunol. Methods 157:4986-4995; and Presta et al (2001) Thromb. Haemost. 85:379-389). For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence. The humanized antibody optionally also will comprise at least a portion of an immunoglobulin constant region (Fc), typically that of a human immunoglobulin. For further details, see U.S. Pat. No. 6,407,213; Jones et al (1986) Nature, 321:522-525; Riechmann et al (1988) Nature 332:323-329; and Presta, (1992) Curr. Op. Struct. Biol., 2:593-596.

Humanized anti-ErbB2 antibodies include huMAb4D5-1, huMAb4D5-2, huMAb4D5-3, huMAb4D5-4, huMAb4D5-5, huMAb4D5-6, huMAb4D5-7 and huMAb4D5-8 (HERCEPTIN®) as described in Table 3 of U.S. Pat. No. 5,821,337, expressly incorporated herein by reference; humanized 520C9 (WO 93/21319) and humanized 2C4 antibodies as described herein below.

A "parent antibody" is an antibody comprising an amino acid sequence from which one or more amino acid residues are replaced by one or more cysteine residues. The parent antibody may comprise a native or wild type sequence. The parent antibody may have pre-existing amino acid sequence modifications (such as additions, deletions and/or substitutions) relative to other native, wild type, or modified forms of an antibody. A parent antibody is directed against a target antigen of interest. Antibodies directed against nonpolypeptide antigens (such as tumor-associated glycolipid antigens; see U.S. Pat. No. 5,091,178) are also contemplated.

Other exemplary parent antibodies include those selected from, and without limitation, anti-estrogen receptor antibody, anti-progesterone receptor antibody, anti-p53 antibody, anti-HER-2/neu antibody, anti-EGFR antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD10 antibody, anti-CD11c antibody, anti-CD13 antibody, anti-CD14 antibody, anti-CD15 antibody, anti-CD19 antibody, anti-CD20 antibody, anti-CD22 antibody, anti-CD23 antibody, anti-CD30 antibody, anti-CD31 antibody, anti-CD33 antibody, anti-CD34 antibody, anti-CD35 antibody, anti-CD38 antibody, anti-CD41 antibody, anti-LCA/CD45 antibody, anti-CD45RO antibody, anti-CD45RA antibody, anti-CD39 antibody, anti-CD100 antibody, anti-CD95/Fas antibody, anti-CD99 antibody, anti-CD106 antibody, anti-ubiquitin antibody, anti-CD71 antibody, anti-c-myc antibody, anti-cytokeratins antibody, anti-vimentins antibody, anti-HPV proteins antibody, anti-kappa light chains antibody, anti-lambda light chains antibody, anti-melanosomes antibody, anti-prostate specific antigen antibody, anti-S-100 antibody, anti-tau antigen antibody, anti-fibrin antibody, anti-keratins antibody and anti-Tn-antigen antibody.

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In certain embodiments, the antibody will be purified (1) to greater than 95% by weight of antibody as determined by the Lowry method, or more than 99% by weight, (2) to a degree sufficient to obtain at least 15 residues of N-terminal or internal amino acid sequence by use of a gas phase protein sequencer, or (3) to homogeneity by SDS-PAGE under reducing or nonreducing conditions using Coomassie blue or silver stain. Isolated antibody includes the antibody in situ within recombinant cells since at least one component of the antibody's natural environment will not be present. Ordinarily, however, isolated antibody will be prepared by at least one purification step.

An antibody "which binds" a molecular target or an antigen of interest, e.g., ErbB2 antigen, is one capable of binding that antigen with sufficient affinity such that the antibody is useful in targeting a cell expressing the antigen. Where the antibody is one which binds ErbB2, it will usually preferentially bind ErbB2 as opposed to other ErbB receptors, and may be one which does not significantly cross-react with other proteins such as EGFR, ErbB3 or ErbB4. In such embodiments, the extent of binding of the antibody to these non-ErbB2 proteins (e.g., cell surface binding to endogenous receptor) will be less than 10% as determined by fluorescence activated cell sorting (FACS) analysis or radioimmunoprecipitation (RIA). Sometimes, the anti-ErbB2 antibody will not significantly cross-react with the rat neu protein, e.g., as described in Schecter et al., Nature 312:513 (1984) and Drebin et al., Nature 312:545-548 (1984).

Molecular targets for the antibody drug conjugates (ADC) encompassed by the present invention include: (i) tumor-associated antigens; (ii) cell surface receptors, (iii) CD proteins and their ligands, such as CD3, CD4, CD8, CD19, CD20, CD22, CD34, CD40, CD79α (CD79a), and CD79β (CD79b); (iv) members of the ErbB receptor family such as the EGF receptor, HER2, HER3 or HER4 receptor; (v) cell adhesion molecules such as LFA-1, Mac1, p150,95, VLA-4, ICAM-1, VCAM and αv/β3 integrin including either alpha or beta subunits thereof (e.g. anti-CD11a, anti-CD18 or anti-CD11b antibodies); and (vi) growth factors such as VEGF; IgE; blood group antigens; flk2/flt3 receptor; obesity (OB) receptor; mpl receptor; CTLA-4; protein C, BR3, c-met, tissue factor, β7 etc.

Unless indicated otherwise, the term "monoclonal antibody 4D5" refers to an antibody that has antigen binding residues of, or derived from, the murine 4D5 antibody (ATCC CRL 10463). For example, the monoclonal antibody 4D5 may be murine monoclonal antibody 4D5 or a variant thereof, such as a humanized 4D5. Exemplary humanized 4D5 antibodies include huMAb4D5-1, huMAb4D5-2, huMAb4D5-3, huMAb4D5-4, huMAb4D5-5, huMAb4D5-6, huMAb4D5-7 and huMAb4D5-8 (Trastuzumab, HERCEPTIN®) as in U.S. Pat. No. 5,821,337.

The terms "treat" or "treatment" refer to both therapeutic treatment and prophylactic or preventative measures, wherein the object is to prevent or slow down (lessen) an undesired physiological change or disorder, such as the development or spread of cancer. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. Those in need of treatment include those already with the condition or disorder as well as those prone to have the condition or disorder or those in which the condition or disorder is to be prevented.

The term "therapeutically effective amount" refers to an amount of a drug effective to treat a disease or disorder in a mammal. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can, for example, be measured by assessing the time to disease progression (TTP) and/or determining the response rate (RR).

The term "bioavailability" refers to the systemic availability (i.e., blood/plasma levels) of a given amount of drug administered to a patient. Bioavailability is an absolute term that indicates measurement of both the time (rate) and total amount (extent) of drug that reaches the general circulation from an administered dosage form.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

An "ErbB-expressing cancer" is one comprising cells which have ErbB protein present at their cell surface. An "ErbB2-expressing cancer" is one which produces sufficient levels of ErbB2 at the surface of cells thereof, such that an anti-ErbB2 antibody can bind thereto and have a therapeutic effect with respect to the cancer.

A cancer "characterized by excessive activation" of an ErbB receptor is one in which the extent of ErbB receptor activation in cancer cells significantly exceeds the level of activation of that receptor in non-cancerous cells of the same tissue type. Such excessive activation may result from overexpression of the ErbB receptor and/or greater than normal levels of an ErbB ligand available for activating the ErbB receptor in the cancer cells. Such excessive activation may cause and/or be caused by the malignant state of a cancer cell. In some embodiments, the cancer will be subjected to a diagnostic or prognostic assay to determine whether amplification and/or overexpression of an ErbB receptor is occurring which results in such excessive activation of the ErbB receptor. Alternatively, or additionally, the cancer may be subjected to a diagnostic or prognostic assay to determine whether amplification and/or overexpression an ErbB ligand is occurring in the cancer which attributes to excessive activation of the receptor. In a subset of such cancers, excessive activation of the receptor may result from an autocrine stimulatory pathway.

A cancer which "overexpresses" an ErbB receptor is one which has significantly higher levels of an ErbB receptor, such as ErbB2, at the cell surface thereof, compared to a noncancerous cell of the same tissue type. Such overexpression may be caused by gene amplification or by increased transcription or translation. ErbB receptor overexpression may be determined in a diagnostic or prognostic assay by evaluating increased levels of the ErbB protein present on the surface of a cell (e.g., via an immunohistochemistry assay; IHC). Alternatively, or additionally, one may measure levels of ErbB-encoding nucleic acid in the cell, e.g., via fluorescent in situ hybridization (FISH; see WO 98/45479), southern blotting, or polymerase chain reaction (PCR) techniques, such as real time quantitative PCR (RT-PCR). Overexpression of the ErbB ligand, may be determined diagnostically by evaluating levels of the ligand (or nucleic acid encoding it) in the patient, e.g., in a tumor biopsy or by various diagnostic assays such as the IHC, FISH, southern blotting, PCR or in vivo assays described above. One may also study ErbB receptor overexpression by measuring shed antigen (e.g., ErbB extracellular domain) in a biological fluid such as serum (see, e.g., U.S. Pat. No. 4,933,294; WO 91/05264; U.S. Pat. No. 5,401,638; and Sias et al., (1990) *J. Immunol. Methods,* 132: 73-80). Aside from the above assays, various other in vivo assays are available to the skilled practitioner. For example, one may expose cells within the body of the patient to an antibody which is optionally labeled with a detectable label, e.g., a radioactive isotope, and binding of the antibody to cells in the patient can be evaluated, e.g., by external scanning for radioactivity or by analyzing a biopsy taken from a patient previously exposed to the antibody.

The tumors overexpressing ErbB2 (HER2) are rated by immunohistochemical scores corresponding to the number of copies of HER2 molecules expressed per cell, and can be determined biochemically: 0=0-10,000 copies/cell, 1+=at least about 200,000 copies/cell, 2+=at least about 500,000 copies/cell, 3+=about 1-2×10$^6$ copies/cell. Overexpression of HER2 at the 3+ level, which leads to ligand-independent activation of the tyrosine kinase (Hudziak et al., (1987) *Proc. Natl. Acad. Sci. USA,* 84:7159-7163), occurs in approximately 30% of breast cancers, and in these patients, relapse-free survival and overall survival are diminished (Slamon et al., (1989) *Science,* 244:707-712; Slamon et al., (1987) *Science,* 235:177-182).

Conversely, a cancer which is "not characterized by overexpression of the ErbB2 receptor" is one which, in a diagnostic assay, does not express higher than normal levels of ErbB2 receptor compared to a noncancerous cell of the same tissue type.

The term "cytotoxic agent" as used herein refers to a substance that inhibits or prevents the function of cells and/or causes destruction of cells. The term is intended to include radioactive isotopes (e.g., $^{211}$At, $^{131}$I, $^{125}$I, $^{90}$Y, $^{186}$Re, $^{188}$Re, $^{153}$Sm, $^{212}$Bi, $^{32}$P, $^{60}$C, and radioactive isotopes of Lu), chemotherapeutic agents, and toxins such as small molecule toxins or enzymatically active toxins of bacterial, fungal, plant or animal origin, including synthetic analogs and derivatives thereof.

A "chemotherapeutic agent" and "anticancer agent" are terms that denote a chemical compound useful in the treatment of cancer, and which may be administered in combination therapy with the antibody drug conjugate compounds of the invention. Examples of chemotherapeutic agents include Erlotinib (TARCEVA®, Genentech/OSI Pharm.), Bortezomib (VELCADE®, Millenium Pharm.), Fulvestrant (FASLODEX®, Astrazeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNE®, Wyeth), Lapatinib (GSK572016, GlaxoSmithKline), Lonafarnib (SCH 66336), Sorafenib (BAY43-9006, Bayer Labs.), and Gefitinib (IRESSA®, Astrazeneca), AG1478, AG1571 (SU 5271; Sugen), alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylolomelamine; TLK 286 (TELCYTA™); acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; bisphosphonates, such as clodronate; antibiotics such as the enediyne antibiotics (e.g., calicheamicin, especially calicheamicin gamma1I and calicheamicin omega1I (see, e.g., Agnew, *Chem Intl. Ed. Engl.,* 33: 183-186 (1994)) and anthracyclines such as annamycin, AD 32, alcarubicin, daunorubicin, dexrazoxane, DX-52-1, epirubicin, GPX-100, idarubicin, KRN5500, menogaril, dynemicin, including dynemicin A, an esperamicin, neocarzinostatin chromophore and related chromoprotein enediyne antibiotic chromophores, aclacinomysins, actinomycin, authramycin, azaserine, bleomycins, cactinomycin, carabicin, carminomycin, carzinophilin, chromomycinis, dactinomycin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin, liposomal doxorubicin, and deoxydoxorubicin), esorubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, and zorubicin; folic acid analogues such as denopterin, pteropterin, and trimetrexate; purine analogs such as fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replenisher such as folinic acid (leucovorin); aceglatone; anti-folate anti-neoplastic agents such as ALIMTA®, LY231514 pemetrexed, dihydrofolate reductase inhibitors such as methotrexate, anti-metabolites such as 5-fluorouracil (5-FU) and its prodrugs such as UFT, S-1 and capecitabine, and thymidylate synthase inhibitors and glycinamide ribonucleotide formyltransferase inhibitors such as raltitrexed (TOMUDEX®, TDX); inhibitors of dihydropyrimidine dehydrogenase such as eniluracil; aldophosphamide glycoside; aminolevulinic acid; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); cyclophosphamide; thiotepa; taxoids and taxanes, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; gemcitabine (GEMZAR®); 6-thioguanine; mercaptopurine; platinum; platinum analogs or platinum-based analogs such as cisplatin, oxaliplatin and carboplatin; vinblastine (VELBAN®); etoposide (VP-16); ifosfamide; mitoxantrone; vincristine (ONCOVIN®); vinca alkaloid; vinorelbine (NAVELBINE®); novantrone; edatrexate; daunomycin; aminopterin; xeloda; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin-(ELOXATIN™) combined with 5-FU and leucovorin.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON® toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

As used herein, the term "EGFR-targeted drug" refers to a therapeutic agent that binds to EGFR and, optionally, inhibits EGFR activation. Examples of such agents include antibodies and small molecules that bind to EGFR. Examples of antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533, Mendelsohn et al.) and variants thereof, such as chimerized 225 (C225 or Cetuximab; ERBITUX®) and reshaped human 225 (H225) (see, WO 96/40210, Imclone Systems Inc.); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF (see WO 98/50433). The anti-EGFR antibody may be conjugated with a cytotoxic agent, thus generating an immunoconjugate (see, e.g., EP 659,439A2, Merck Patent GmbH). Examples of small molecules that bind to EGFR include ZD1839 or Gefitinib (IRESSA™; Astra Zeneca), Erlotinib HCl (CP-358774, TARCEVA™; Genentech/OSI) and AG1478, AG1571 (SU 5271; Sugen).

A "tyrosine kinase inhibitor" is a molecule which inhibits to some extent tyrosine kinase activity of a tyrosine kinase such as an ErbB receptor. Examples of such inhibitors include the EGFR-targeted drugs noted in the preceding paragraph as well as quinazolines such as PD 153035,4-(3-chloroanilino) quinazoline, pyridopyrimidines, pyrimidopyrimidines, pyrrolopyrimidines, such as CGP 59326, CGP 60261 and CGP 62706, and pyrazolopyrimidines, 4-(phenylamino)-7H-pyrrolo[2,3-d]pyrimidines, curcumin (diferuloyl methane, 4,5-bis (4-fluoroanilino)phthalimide), tyrphostines containing nitrothiophene moieties; PD-0183805 (Warner-Lambert); antisense molecules (e.g., those that bind to ErbB-encoding nucleic acid); quinoxalines (U.S. Pat. No. 5,804,396); tryphostins (U.S. Pat. No. 5,804,396); ZD6474 (Astra Zeneca); PTK-787 (Novartis/Schering AG); pan-ErbB inhibitors such as CI-1033 (Pfizer); Affinitac (ISIS 3521; Isis/Lilly); Imatinib mesylate (Gleevec; Novartis); PKI 166 (Novartis); GW2016 (Glaxo SmithKline); CI-1033 (Pfizer); EKB-569 (Wyeth); Semaxanib (Sugen); ZD6474 (AstraZeneca); PTK-787 (Novartis/Schering AG); INC-1C11 (Imclone); or as described in any of the following patent publications: WO 99/09016 (American Cyanamid); WO 98/43960 (American Cyanamid); WO 97/38983 (Warner Lambert); WO 99/06378 (Warner Lambert); WO 99/06396 (Warner Lambert); WO 96/30347 (Pfizer, Inc); WO 96/33978 (Zeneca); WO 96/3397 (Zeneca); and WO 96/33980 (Zeneca).

An "anti-angiogenic agent" refers to a compound which blocks, or interferes with to some degree, the development of blood vessels. The anti-angiogenic factor may, for instance, be a small molecule or antibody that binds to a growth factor or growth factor receptor involved in promoting angiogenesis. An exemplary anti-angiogenic factor herein is an antibody that binds to Vascular Endothelial Growth Factor (VEGF).

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-Bβ; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1α, IL-2, IL-3, IL-4, IL-5, IL-6, IL-7, IL-8, IL-9, IL-10, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

A "liposome" is a small vesicle composed of various types of lipids, phospholipids and/or surfactant which is useful for delivery of a drug (such as the anti-ErbB2 antibodies disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

"Phage display" is a technique by which variant polypeptides are displayed as fusion proteins to a coat protein on the surface of phage, e.g., filamentous phage, particles. One utility of phage display lies in the fact that large libraries of randomized protein variants can be rapidly and efficiently sorted for those sequences that bind to a target molecule with high affinity. Display of peptide and protein libraries on phage has been used for screening millions of polypeptides for ones with specific binding properties. Polyvalent phage display methods have been used for displaying small random peptides and small proteins, typically through fusions to either PIII or PVIII of filamentous phage. Wells and Lowman, *Curr. Opin. Struct. Biol.*, 3:355-362 (1992), and references cited therein. In monovalent phage display, a protein or peptide library is fused to a phage coat protein or a portion thereof, and expressed at low levels in the presence of wild type protein. Avidity effects are reduced relative to polyvalent phage so that sorting is on the basis of intrinsic ligand affinity, and phagemid vectors are used, which simplify DNA manipulations. Lowman and Wells, *Methods: A companion to Methods in Enzymology*, 3:205-0216 (1991). Phage display includes techniques for producing antibody-like molecules (Janeway, C., Travers, P., Walport, M., Shlomchik (2001) *Immunobiology*, 5th Ed., Garland Publishing, New York, p 627-628).

A "phagemid" is a plasmid vector having a bacterial origin of replication, e.g., Co1E1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle.

"Alkyl" is a $C_1$-$C_{18}$ hydrocarbon moiety containing normal, secondary, tertiary or cyclic carbon atoms. Examples of alkyl radicals include $C_1$-$C_8$ hydrocarbon moieties such as: methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), 1-heptyl, 1-octyl, cyclopropyl, cyclobutyl, cyclopentyl, cyclohexyl, cycloheptyl, and cyclooctyl.

"Alkenyl" is a $C_2$-$C_{18}$ hydrocarbon moiety containing normal, secondary, tertiary or cyclic carbon atoms with at least one site of unsaturation, i.e. a carbon-carbon, $sp^2$ double bond. Examples include, but are not limited to: ethylene or vinyl (—$CH=CH_2$), allyl (—$CH_2CH=CH_2$), 1-cyclopent-1-enyl, 1-cyclopent-2-enyl, 1-cyclopent-3-enyl, 5-hexenyl (—$CH_2CH_2CH_2CH_2CH=CH_2$), 1-cyclohex-1-enyl, 1-cyclohex-2-enyl, and 1-cyclohex-3-enyl.

"Alkynyl" is a $C_2$-$C_{18}$ hydrocarbon moiety containing normal, secondary, tertiary or cyclic carbon atoms with at least one site of unsaturation, i.e. a carbon-carbon, sp triple bond. Examples include, but are not limited to: acetylenic (—C≡CH) and propargyl (—$CH_2$C≡CH), "Alkylene" refers to a saturated, branched or straight chain or cyclic hydrocarbon radical of 1-18 carbon atoms, and having two monovalent radical centers derived by the removal of two hydrogen atoms from the same or two different carbon atoms of a parent alkane. Typical alkylene radicals include, but are not limited to: methylene (—$CH_2$—) 1,2-ethyl (—$CH_2CH_2$—), 1,3-propyl (—$CH_2CH_2CH_2$—), 1,4-butyl (—$CH_2CH_2CH_2CH_2$—), and the like.

"Alkenylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkene. Typical alkenylene radicals include, but are not limited to: 1,2-ethylene (—CH=CH—).

"Alkynylene" refers to an unsaturated, branched or straight chain or cyclic hydrocarbon radical of 2-18 carbon atoms, and having two monovalent radical centers derived by the removal of two hydrogen atoms from the same or two different carbon atoms of a parent alkyne. Typical alkynylene radicals include, but are not limited to: acetylene (—C≡C—), propargyl (—$CH_2$C≡C—), and 4-pentynyl (—$CH_2CH_2CH_2$C≡C—).

"Aryl" means a monovalent aromatic hydrocarbon radical of 6-20 carbon atoms derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, naphthalene, anthracene, biphenyl, and the like.

"Arylalkyl" refers to an acyclic alkyl radical in which one of the hydrogen atoms bonded to a carbon atom, typically a terminal or $sp^3$ carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. The arylalkyl group comprises 6 to 20 carbon atoms, e.g. the alkyl moiety, including alkanyl, alkenyl or alkynyl groups, of the arylalkyl group is 1 to 6 carbon atoms and the aryl moiety is 5 to 14 carbon atoms.

"Heteroarylalkyl" refers to an acyclic alkyl radical in which one of the hydrogen atoms bonded to a carbon atom, typically a terminal or $sp^3$ carbon atom, is replaced with a heteroaryl radical. Typical heteroarylalkyl groups include, but are not limited to, 2-benzimidazolylmethyl, 2-furylethyl, and the like. The heteroarylalkyl group comprises 6 to 20 carbon atoms, e.g. the alkyl moiety, including alkanyl, alkenyl or alkynyl groups, of the heteroarylalkyl group is 1 to 6 carbon atoms and the heteroaryl moiety is 5 to 14 carbon atoms and 1 to 3 heteroatoms selected from N, O, P, and S. The heteroaryl moiety of the heteroarylalkyl group may be a monocycle having 3 to 7 ring members (2 to 6 carbon atoms or a bicycle having 7 to 10 ring members (4 to 9 carbon atoms and 1 to 3 heteroatoms selected from N, O, P, and S), for example: a bicyclo [4,5], [5,5], [5,6], or [6,6] system.

"Substituted alkyl", "substituted aryl", and "substituted arylalkyl" mean alkyl, aryl, and arylalkyl respectively, in which one or more hydrogen atoms are each independently replaced with a substituent. Typical substituents include, but are not limited to, —X, —R, —O⁻, —OR, —SR, —S⁻, —NR₂, —NR₃, =NR, —CX₃, —CN, —OCN, —SCN, —N=C=O, —NCS, —NO, —NO₂, =N₂, —N₃, NC(=O)R, —C(=O)R, —C(=O)NR₂, —SO₃⁻, —SO₃H, —S(=O)₂R, —OS(=O)₂OR, —S(=O)₂NR, —S(=O)R, —OP(=O)(OR)₂, —P(=O)(OR)₂, —PO⁻₃, —PO₃H₂, —C(=O)R, —C(=O)X, —C(=S)R, —CO₂R, —CO₂⁻, —C(=S)OR, —C(=O)SR, —C(=S)SR, —C(=O)NR₂, —C(=S)NR₂, —C(=NR)NR₂, where each X is independently a halogen: F, Cl, Br, or I; and each R is independently H, $C_1$-$C_{18}$ alkyl, $C_6$-$C_{20}$ aryl, $C_3$-$C_{14}$ heterocycle, or protecting group. Alkylene, alkenylene, and alkynylene groups as described above may also be similarly substituted.

"Heteroaryl", "heterocyclyl", and "heterocycle" refer to a saturated, a partially unsaturated (i.e., having one or more double and/or triple bonds within the ring), or aromatic radical in which at least one ring atom is a heteroatom independently selected from nitrogen, oxygen and sulfur, the remaining ring atoms being carbon, where one or more ring atoms is optionally substituted independently with one or more substituents described below. The heterocycle radical comprises 1 to 20 carbon atoms and 1 to 5 heteroatoms selected from N, O, P, and S. A heterocycle may be a monocycle having 3 to 7 ring members (2 to 6 carbon atoms and 1 to 3 heteroatoms selected from N, O, P, and S) or a bicycle having 7 to 10 ring members (4 to 9 carbon atoms and 1 to 3 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566.

Examples of heterocycles include by way of example and not limitation pyridyl, dihydroypyridyl, tetrahydropyridyl (piperidyl), thiazolyl, tetrahydrothiophenyl, sulfur oxidized tetrahydrothiophenyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4Ah-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl.

By way of example and not limitation, carbon bonded heterocycles are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, "nitrogen-linked $C_1$-$C_{20}$ heterocyclyl" are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

"Carbocycle" and "carbocyclyl" mean a saturated or unsaturated ring having 3 to 7 carbon atoms as a monocycle or 7 to 12 carbon atoms as a bicycle. Monocyclic carbocycles have 3 to 6 ring atoms, still more typically 5 or 6 ring atoms. Bicyclic carbocycles have 7 to 12 ring atoms, e.g. arranged as a bicyclo [4,5], [5,5], [5,6] or [6,6] system, or 9 or 10 ring atoms arranged as a bicyclo [5,6] or [6,6] system. Examples of monocyclic carbocycles include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cycloheptyl, and cyclooctyl.

"Linker", "Linker Unit", "Linker reagent" or "link" means a chemical moiety comprising a covalent bond or a chain of atoms that covalently attaches an antibody to a drug moiety. In various embodiments, a linker is specified as L. Linkers include, but are not limited to, a divalent radical such as an alkyldiyl, an aryldiyl, a heteroaryldiyl, moieties such as: —(CR₂)ₙO(CR₂)ₙ—, repeating units of alkyloxy (e.g. polyethylenoxy, PEG, polymethyleneoxy) and alkylamino (e.g. polyethyleneamino, Jeffamine™); and diacid ester and amides including maleimide, succinate, succinamide, diglycolate, malonate, and caproamide.

The term "label" means any moiety which can be covalently attached to an antibody and that functions to: (i) provide a detectable signal; (ii) interact with a second label to modify the detectable signal provided by the first or second label, e.g. FRET (fluorescence resonance energy transfer); (iii) stabilize interactions or increase affinity of binding, with antigen or ligand; (iv) affect mobility, e.g. electrophoretic mobility, or cell-permeability, by charge, hydrophobicity, shape, or other physical parameters, or (v) provide a capture moiety, to modulate ligand affinity, antibody/antigen binding, or ionic complexation.

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds* (1994) John Wiley & Sons, Inc., New York. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and I or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The phrase "pharmaceutically acceptable salt," as used herein, refers to pharmaceutically acceptable organic or inorganic salts of an ADC. Exemplary salts include, but are not limited, to sulfate, citrate, acetate, trifluoroacetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. A pharmaceutically acceptable salt may involve the inclusion of another molecule such as an acetate ion, a succinate ion or other counterion. The counterion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counterion.

"Pharmaceutically acceptable solvate" refers to an association of one or more solvent molecules and an ADC. Examples of solvents that form pharmaceutically acceptable solvates include, but are not limited to, water, isopropanol, ethanol, methanol, DMSO, ethyl acetate, acetic acid, and ethanolamine.

The following acronyms, terms, and abbreviations are used herein and have the indicated definitions:

Boc is N-(t-butoxycarbonyl), cit is citrulline (2-amino-5-ureido pentanoic acid), dap is dolaproine, DCC is 1,3-dicyclohexylcarbodiimide, DCM is dichloromethane, DEA is diethylamine, DEAD is diethylazodicarboxylate, DEPC is diethylphosphorylcyanidate, DIAD is diisopropylazodicarboxylate, DIEA is N,N-diisopropylethylamine, dil is dolaisoleuine, DMAP is 4-dimethylaminopyridine, DME is ethyleneglycol dimethyl ether (or 1,2-dimethoxyethane), DMF is N,N-dimethylformamide, DMSO is dimethylsulfoxide, doe is dolaphenine, dov is N,N-dimethylvaline, DTNB is 5,5'-dithiobis(2-nitrobenzoic acid), DTPA is diethylenetriaminepentaacetic acid, DTT is dithiothreitol, EDCI is 1-(3-dimethylaminopropyl)-3-ethylcarbodiimide hydrochloride, EEDQ is 2-ethoxy-1-ethoxycarbonyl-1,2-dihydroquinoline, ES-MS is electrospray mass spectrometry, EtOAc is ethyl acetate, Fmoc is N-(9-fluorenylmethoxycarbonyl), gly is glycine, HATU is O-(7-azabenzotriazol-1-yl)-N,N,N',N'-tetramethyluronium hexafluorophosphate, HOBt is 1-hydroxybenzotriazole, HPLC is high pressure liquid chromatography, ile is isoleucine, lys is lysine, MeCN ($CH_3CN$) is acetonitrile, LC/MS is liquid chromatography and mass spectrometry, MeOH is methanol, Mtr is 4-anisyldiphenylmethyl (or 4-methoxytrityl), nor is (1S,2R)-(+)-norephedrine, PBS is phosphate-buffered saline (Ph 7.4), PEG is polyethylene glycol, Ph is phenyl, Pnp is p-nitrophenyl, PyBrop is bromo tris-pyrrolidino phosphonium hexafluorophosphate, SEC is size-exclusion chromatography, Su is succinimide, TFA is trifluoroacetic acid, TLC is thin layer chromatography, UV is ultraviolet, and val is valine.

Antibodies: HERCEPTIN® (trastuzumab)=full length, humanized antiHER2 (MW 145167), trastuzumab F(ab') 2=derived from antiHER2 enzymatically (MW 100000), 4D5=full-length, murine antiHER2, from hybridoma, rhu4D5=transiently expressed, full-length humanized antibody, rhuFab4D5=recombinant humanized Fab (MW 47738), 4D5Fc8=full-length, murine antiHER2, with mutated FcRn binding domain Linkers: MC=6-maleimidocaproyl, MP=maleimidopropanoyl, val-cit=valine-citrulline, dipeptide site in protease-cleavable linker, ala-phe=alanine-phenylalanine, dipeptide site in protease-cleavable linker, PAB=p-aminobenzyloxycarbonyl ("self immolative" portion of linker), SPP=N-Succinimidyl 4-(2-pyridylthio) pentanoate, SMCC=N-Succinimidyl 4-(N-maleimidomethyl) cyclohexane-1 carboxylate, SIAB=N-Succinimidyl (4-iodo-acetyl) aminobenzoate Antibody Drug Conjugates The compounds of the invention include those with potential utility for anticancer activity, treatment of hyperproliferative disorders, autoimmune disorders, and infectious disease. In particular, the compounds include an antibody conjugated, i.e. covalently attached by a linker, to a 1,8 bis-naphthalimide drug moiety where the corresponding drug when not conjugated to an antibody has a cytotoxic or cytostatic effect. The biological activity of the drug is thus modulated by conjugation to an antibody. The antibody drug conjugates (ADC) of the invention may selectively deliver an effective dose of a cytotoxic agent to tumor tissue whereby greater selectivity, i.e. a lower efficacious dose may be achieved, than upon delivery of the same dose of the 1,8 bis-naphthalimide compound not conjugated to an antibody.

In one embodiment, the bioavailability of the ADC of the invention, or an intracellular metabolite of the ADC, is improved in a mammal when compared to a 1,8 bis-naphthalimide compound comprising the 1,8 bis-naphthalimide moiety of the ADC. Also, the bioavailability of the ADC, or an intracellular metabolite of the ADC is improved in a mammal when compared to the analog of the ADC not having the 1,8 bis-naphthalimide drug moiety.

In one embodiment, the drug moiety of the ADC is not cleaved from the antibody until the antibody-drug conjugate enters a cell with a cell-surface receptor specific for the antibody of the antibody-drug conjugate, and the drug moiety is cleaved from the antibody when the antibody-drug conjugate does enter the cell. The 1,8 bis-naphthalimide drug moiety may be intracellularly cleaved in a mammal from the antibody of the compound, or an intracellular metabolite of the compound, by enzymatic action, hydrolysis, oxidation, or other mechanism.

An antibody-drug conjugate compound comprises an antibody covalently attached by a linker to one or more 1,8 bis-naphthalimide drug moieties, the compound having Formula I $$Ab\text{-}(L\text{-}D)_p \qquad I$$

or a pharmaceutically acceptable salt or solvate thereof, wherein

Ab is an antibody;

L is a linker covalently attached to an Ab, and L is covalently attached to D;

D is a 1,8 bis-naphthalimide drug moiety selected from Formulas IIa and IIb:

the wavy line indicates the covalent attachment to L,

Y is $N(R^b)$, $C(R^a)_2$, O, or S;

$R^a$ is independently selected from H, F, Cl, Br, I, OH, $-N(R^b)_2$, $-N(R^b)_3^+$, $C_1$-$C_8$ alkylhalide, carboxylate, sulfate, sulfamate, sulfonate, $-SO_2R^b$, $-S(=O)R^b$, $-SR^b$, $-SO_2N(R^b)_2$, $-C(=O)R^b$, $-CO_2R^b$, $-C(=O)N(R^b)_2$, $-CN$, $-N_3$, $-NO_2$, $C_1$-$C_8$ alkoxy, $C_1$-$C_8$ trifluoroalkyl, polyethyleneoxy, phosphonate, phosphate, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_1$-$C_{20}$ heterocycle, and $C_1$-$C_{20}$ substituted heterocycle; or when taken together, two $R^a$ groups on the same carbon atom form a carbonyl (=O), or on different carbon atoms form a carbocyclic, heterocyclic, or aryl ring of 3 to 7 carbon atoms;

$R^b$ is independently selected from H, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_1$-$C_{20}$ heterocycle, and $C_1$-$C_{20}$ substituted heterocycle;

where $C_1$-$C_8$ substituted alkyl, $C_2$-$C_8$ substituted alkenyl, $C_2$-$C_8$ substituted alkynyl, $C_6$-$C_{20}$ substituted aryl, and $C_2$-$C_{20}$ substituted heterocycle are independently substituted with one or more substituents selected from F, Cl, Br, I, OH, $-N(R^b)_2$, $-N(R^b)_3^+$, $C_1$-$C_8$ alkylhalide, carboxylate, sulfate, sulfamate, sulfonate, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, $-SO_2R^b$, $-S(=O)R^b$, $-SR^b$, $-SO_2N(R^b)_2$, $-C(=O)R^b$, $-CO_2R^b$, $-C(=O)N(R^b)_2$, $-CN$, $-N_3$, $-NO_2$, $C_1$-$C_8$ trifluoroalkyl, $C_1$-$C_8$ alkyl, $C_3$-$C_{12}$ carbocycle, $C_6$-$C_{20}$ aryl, $C_2$-$C_{20}$ heterocycle, polyethyleneoxy, phosphonate, and phosphate;

m is 1, 2, 3, 4, 5, or 6;

n is independently selected from 1, 2, and 3;

$X^1$, $X^2$, $X^3$, and $X^4$ are independently selected from F, Cl, Br, I, OH, $-N(R^b)_2$, $-N(R^b)_3^+$, $-N(R^b)C(=O)R^b$, $-N(R^b)C(=O)N(R^b)_2$, $-N(R^b)SO_2N(R^b)_2$, $-N(R^b)SO_2R^b$, OR, $OC(=O)R^b$, $OC(=O)N(R^b)_2$, $C_1$-$C_8$ alkylhalide, carboxylate, sulfate, sulfamate, sulfonate, $-SO_2R^b$, $-SO_2Ar$, $-SOAr$, $-SAr$, $-SO_2N(R^b)_2$, $-SOR^b$, $-CO_2R^b$, $-C(=O)N(R^b)_2$, $-CN$, $-N_3$, $-NO_2$, $C_1$-$C_8$

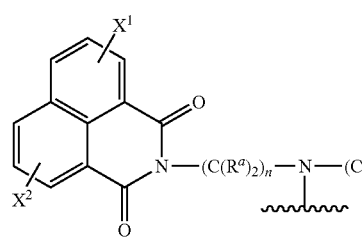
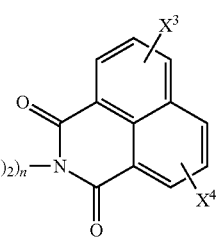

IIa

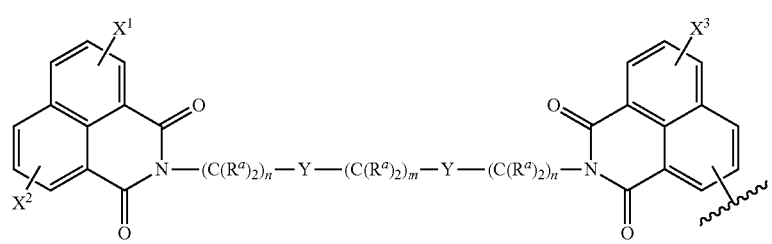

IIb alkoxy, $C_1$-$C_8$ trifluoroalkyl, polyethyleneoxy, phosphonate, phosphate, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_1$-$C_{20}$ heterocycle, and $C_1$-$C_{20}$ substituted heterocycle; or $X^1$ and $X^2$ together, and $X^3$ and $X^4$ together, independently form —$CH_2CH_2$— or —$CH_2$ $CH_2CH_2$—;

D may independently have more than one $X^1$, $X^2$, $X^3$, or $X^4$; and where D has more than one $X^1$, $X^2$, $X^3$, or $X^4$, then two $X_1$, $X^2$, $X^3$, or $X^4$ may form a fused $C_6$-$C_{20}$ aryl, $C_6$-$C_{20}$ substituted aryl, $C_1$-$C_{20}$ heterocycle, or $C_1$-$C_{20}$ substituted heterocycle; and p is an integer from 1 to 20.

The drug loading is represented by p, the average number of drugs per antibody in a molecule of Formula I. Drug loading may range from 1 to 20 drugs (D) per antibody (Ab or mAb). Compositions of ADC of Formula I include collections of antibodies conjugated with a range of drugs, from 1 to 20. The average number of drugs per antibody in preparations of ADC from conjugation reactions may be characterized by conventional means such as mass spectroscopy, ELISA assay, and HPLC. The quantitative distribution of ADC in terms of p may also be determined. In some instances, separation, purification, and characterization of homogeneous ADC where p is a certain value from ADC with other drug loadings may be achieved by means such as reverse phase HPLC or electrophoresis.

For some antibody drug conjugates, p may be limited by the number of attachment sites on the antibody. For example, where the attachment is a cysteine thiol, as in the exemplary embodiments above, an antibody may have only one or several cysteine thiol groups, or may have only one or several sufficiently reactive thiol groups through which a linker may be attached. Higher drug loading, e.g. p>5, may cause aggregation, insolubility, toxicity, or loss of cellular permeability of certain antibody drug conjugates.

Typically, fewer than the theoretical maximum of drug moieties are conjugated to an antibody during a conjugation reaction. An antibody may contain, for example, many lysine residues that do not react with the drug-linker intermediate or linker reagent. Only the most reactive lysine groups may react with an amine-reactive linker reagent. Also, only the most reactive cysteine thiol groups may react with a thiol-reactive linker reagent. Generally, antibodies do not contain many, if any, free and reactive cysteine thiol groups which may be linked to a drug moiety. Most cysteine thiol residues in the antibodies of the compounds of the invention exist as disulfide bridges and must be reduced with a reducing agent such as dithiothreitol (DTT), under partial or total reducing conditions. Additionally, the antibody must be subjected to denaturing conditions to reveal reactive nucleophilic groups such as lysine or cysteine. The loading (drug/antibody ratio) of an ADC may be controlled in several different manners, including: (i) limiting the molar excess of drug-linker intermediate or linker reagent relative to antibody, (ii) limiting the conjugation reaction time or temperature, and (iii) partial or limiting reductive conditions for cysteine thiol modification.

It is to be understood that where more than one nucleophilic group reacts with a drug-linker intermediate, or linker reagent followed by drug moiety reagent, then the resulting product is a mixture of ADC compounds with a distribution of one or more drug moieties attached to an antibody. The average number of drugs per antibody may be calculated from the mixture by dual ELISA antibody assay, specific for antibody and specific for the drug. Individual ADC molecules may be identified in the mixture by mass spectroscopy, and separated by HPLC, e.g. hydrophobic interaction chromatography ("Effect of drug loading on the pharmacology, pharmacokinetics, and toxicity of an anti-CD30 antibody-drug conjugate", Hamblett, K. J., et al, Abstract No. 624, American Association for Cancer Research; 2004 Annual Meeting, Mar. 27-31, 2004, Proceedings of the AACR, Volume 45, March 2004; "Controlling the Location of Drug Attachment in Antibody-Drug Conjugates", Alley, S. C., et al, Abstract No. 627, American Association for Cancer Research; 2004 Annual Meeting, Mar. 27-31, 2004, Proceedings of the AACR, Volume 45, March 2004). Thus, a homogeneous ADC with a single loading value, may be isolated from the conjugation mixture by electrophoresis or chromatography.

1,8 Bis-Naphthalimide Drug Moieties

Drug moieties (D) are the 1,8 bis-naphthalimide type and have Formulas IIa and IIb. For descriptive purposes herein, each of the 1,8 naphthalimide aromatic carbon atoms are numbered according to the structure:

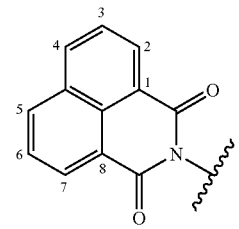

The 1,8 naphthalimide aromatic carbon atoms may be independently substituted with a range of substituents ($X^1$—$X^4$) besides H at the 2, 3, 4, 5, 6, 7, and 8 positions, at each of the 1,8 naphthalimide groups. One embodiment of a bis 1,8 naphthalimide drug moiety is the unsubstituted bis 1,8 naphthalimide, "elinafide", drug moiety (E) having the structure:

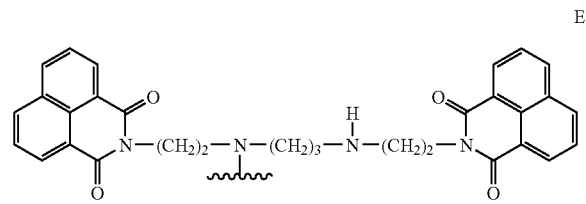

where Y is $N(R^b)$, $R^b$ is H, m is 3, and n is 2, and the wavy line indicates the covalent attachment to L.

The 1,8 naphthalimide aromatic carbon atoms D moieties IIa and IIb may be independently substituted with a range of substituents ($X^1$—$X^4$) besides H. Exemplary embodiments of IIa where the two 1,8 naphthalimide groups are the same, and where Y is $N(R^b)$, n is 2, m is 3, $R^a$ and $R^b$ are H, include the exemplary structures, where the wavy line indicates the covalent attachment to L:

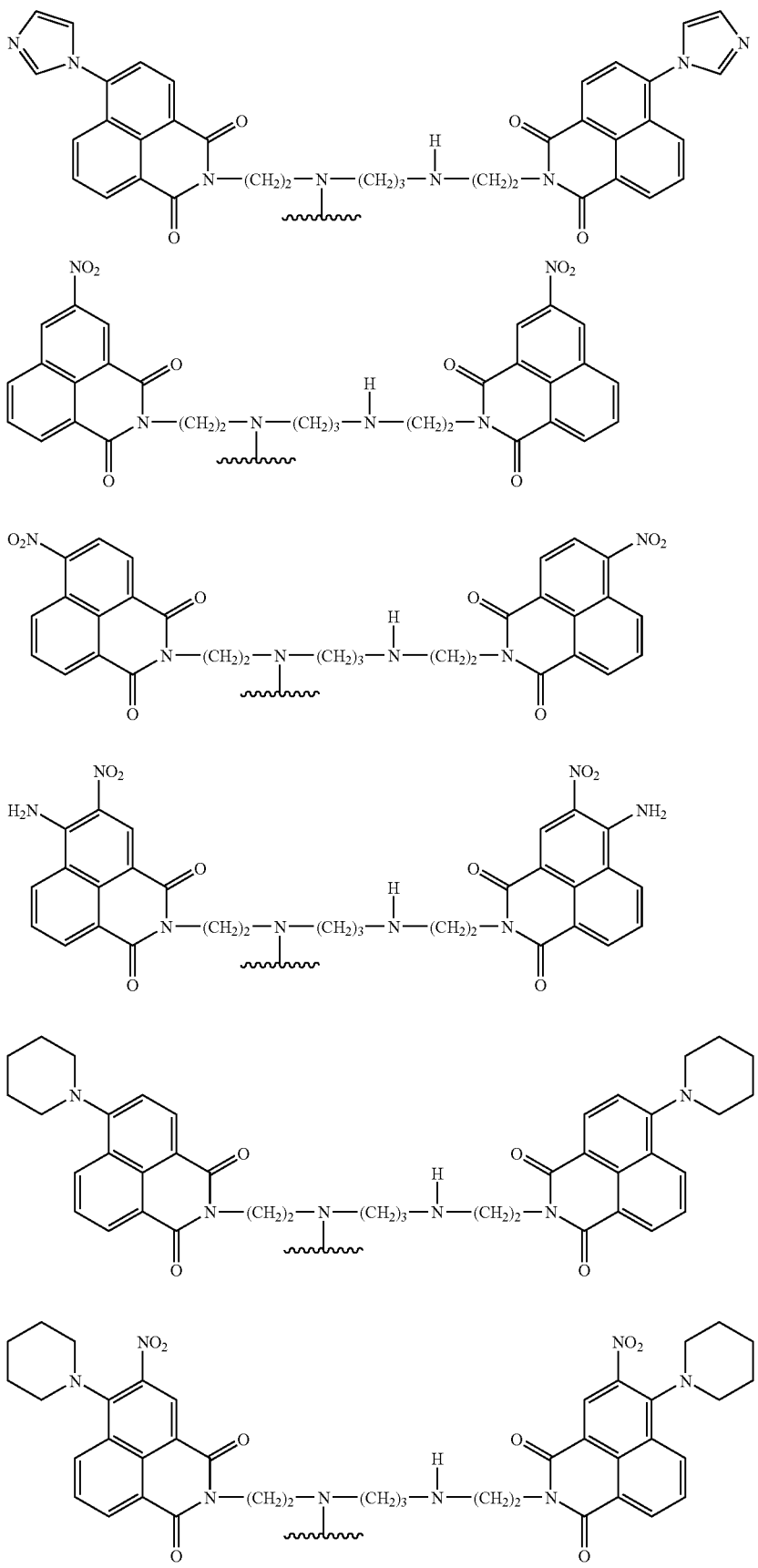

-continued
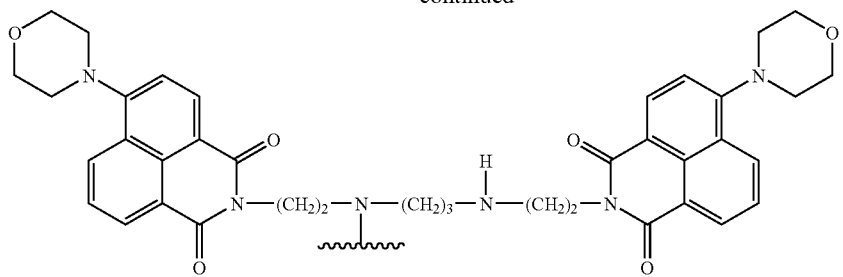
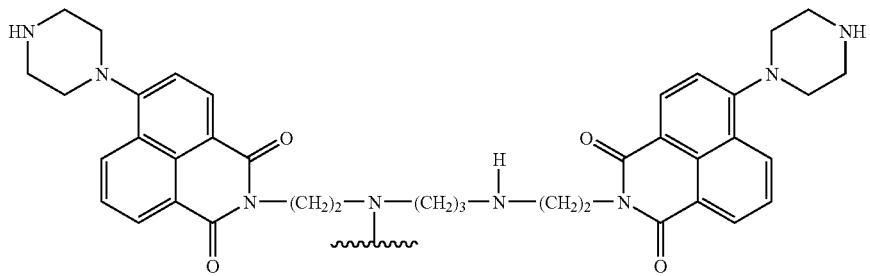
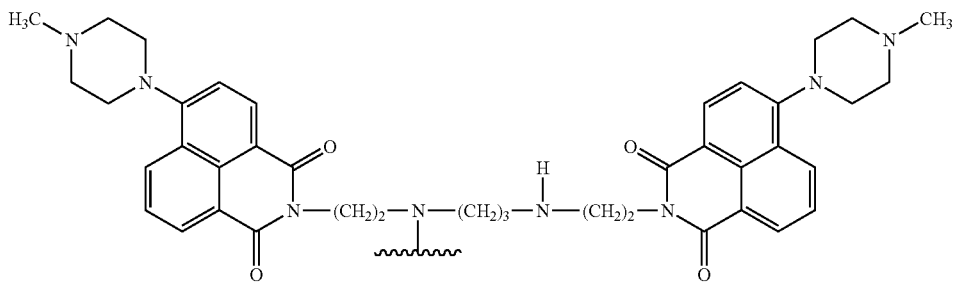
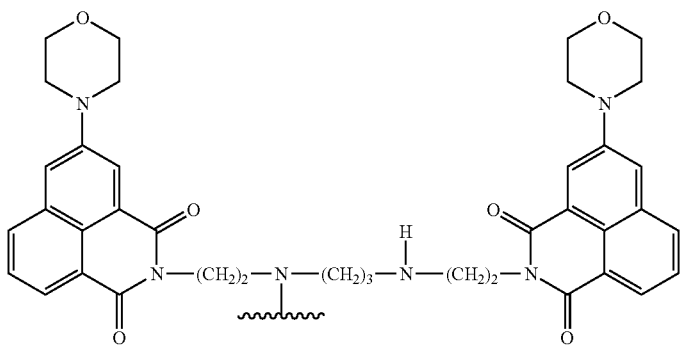
Exemplary embodiments of D moiety IIa where the two 1,8 naphthalimide groups are not the same, and where Y is N(R$^b$), n is 2, m is 3, R$^a$ and R$^b$ b are H, include the structures:
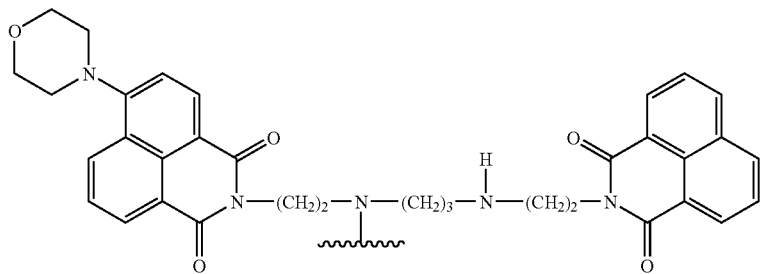

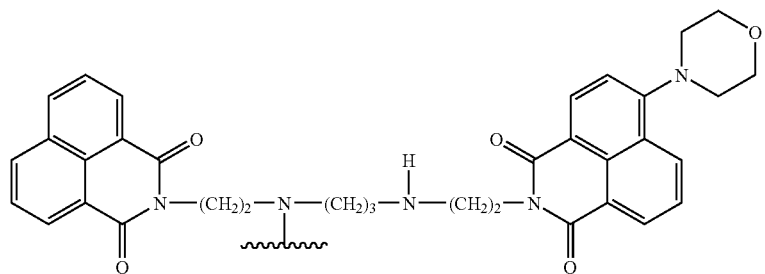
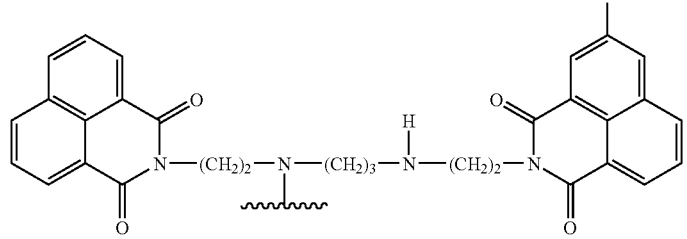
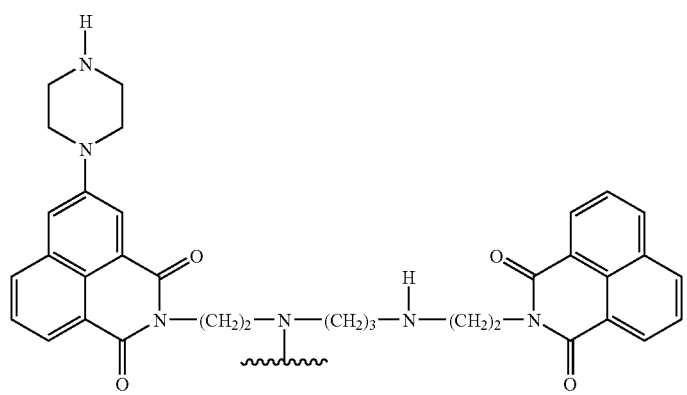
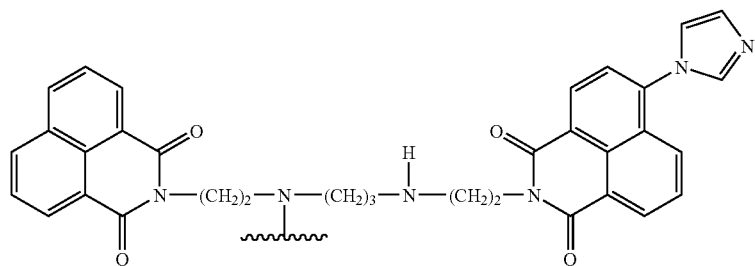
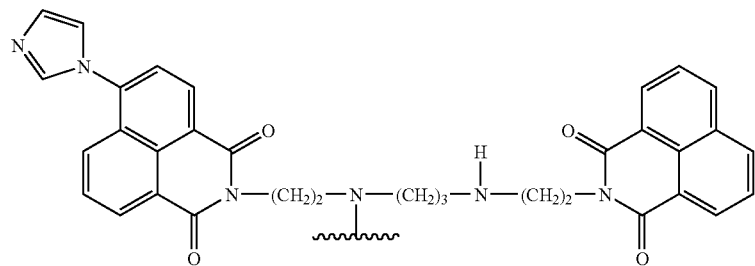

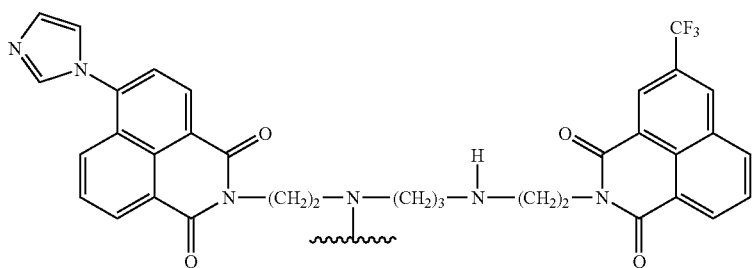
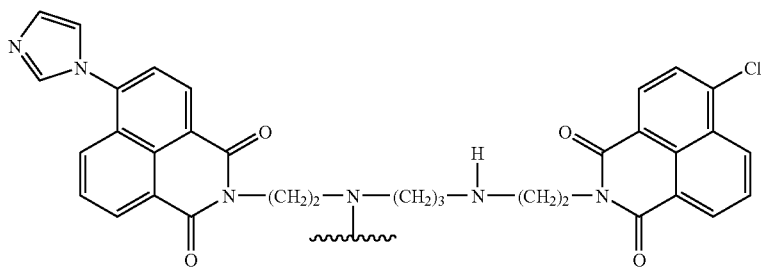
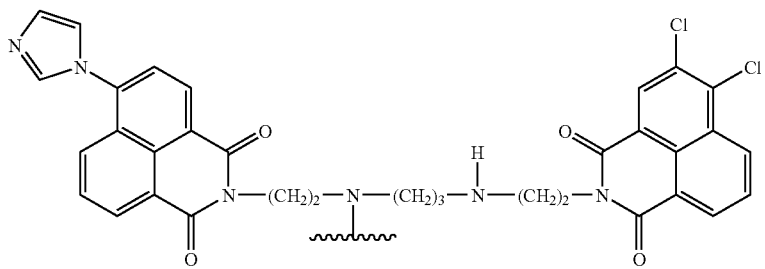
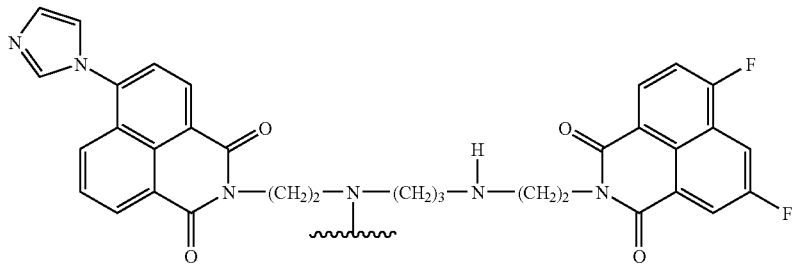
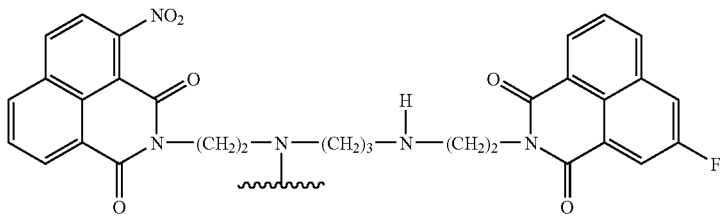
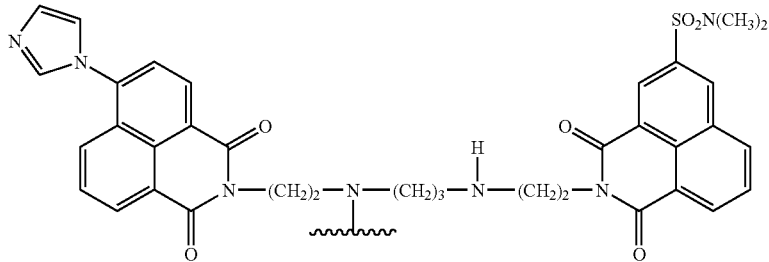

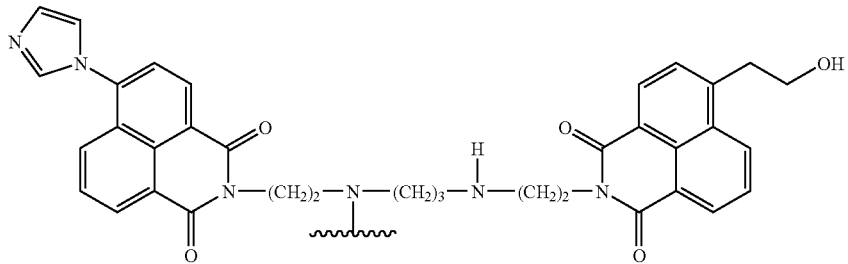

X¹ and X² together, or X³ and X⁴ together, independently may form —CH$_2$CH$_2$— or —CH$_2$CH$_2$CH$_2$—. Exemplary embodiments of such, and where Y is N(R$^b$), n is 2, m is 3, R$^a$ and R$^b$ are H, include the D moiety IIa structures:

Two X¹, X², X³, or X⁴ on adjacent carbon atoms may form a fused C$_6$-C$_{20}$ aryl, C$_6$-C$_{20}$ substituted aryl, C$_1$-C$_{20}$ heterocycle, or C$_1$-C$_{20}$ substituted heterocycle. Exemplary embodiments of such, and where Y is N(R$^b$), n is 2, m is 3, R$^a$ and R$^b$ are H, include the D moiety IIa structures:

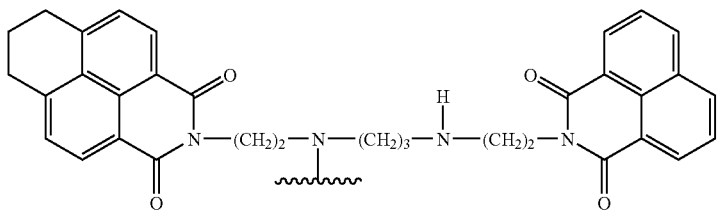

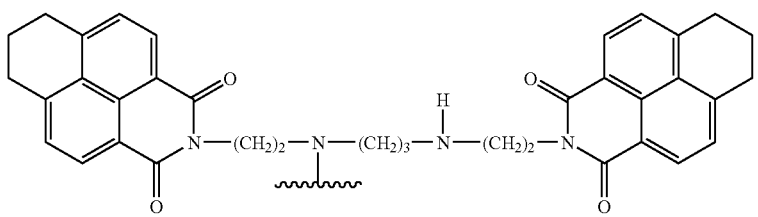

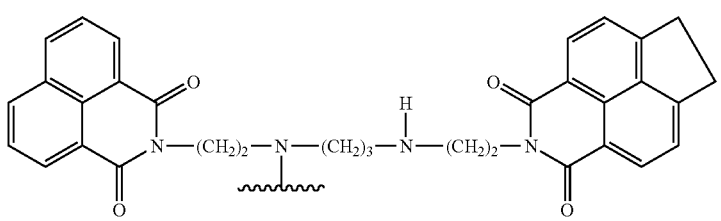

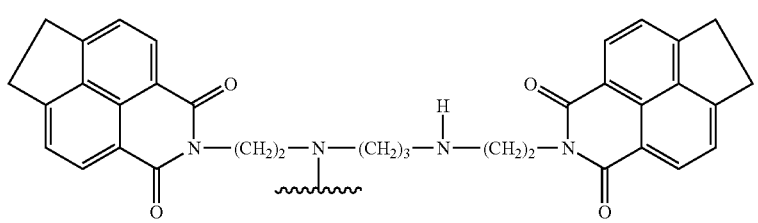

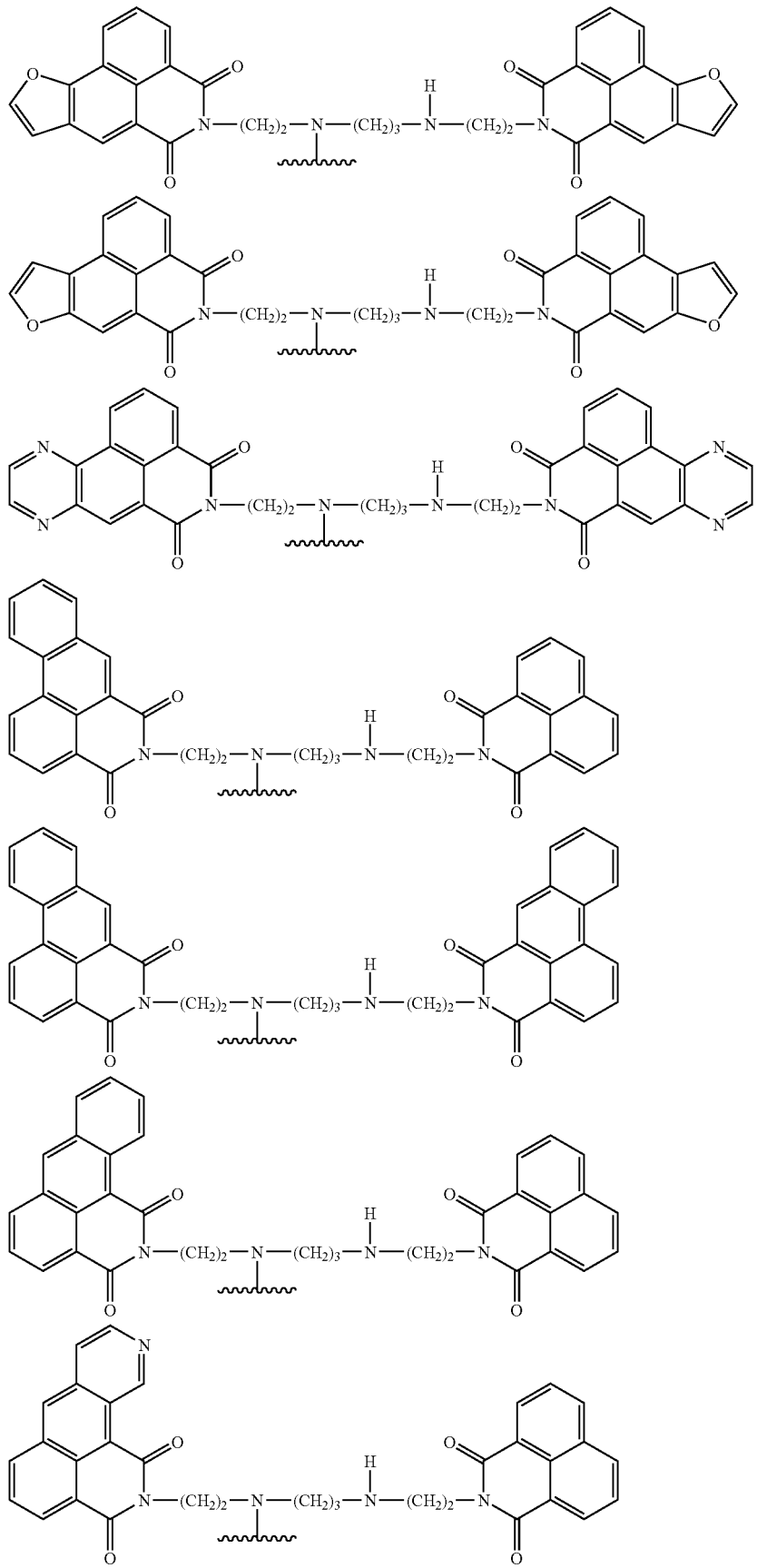

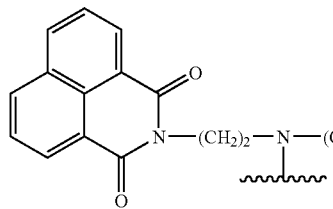
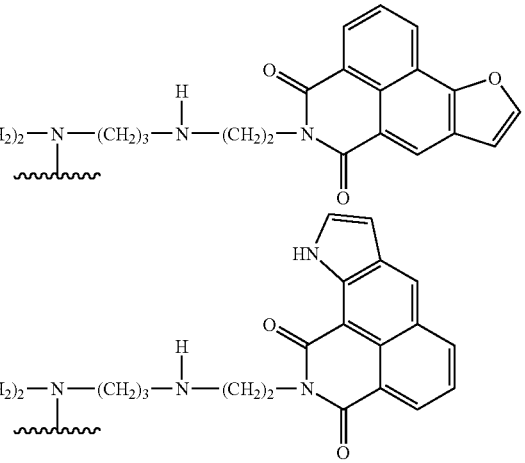
The bis-amino alkyl group that attaches the two 1,8 naphthalimide groups may bear a range of substituents besides H on the carbon atoms ($R^a$) and the nitrogen atom not linked to L ($R^b$). Exemplary embodiments of D where Y is N($R^b$), m is 3 and n is 2 in the bis-amino alkyl group include the D moiety IIa structures:
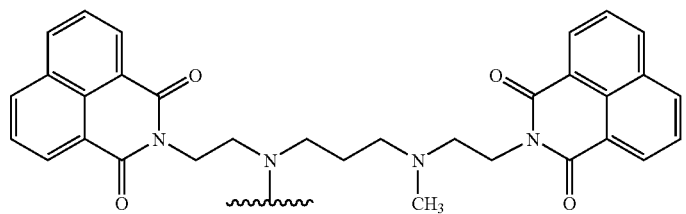
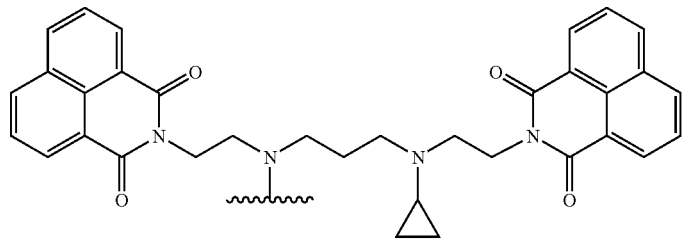
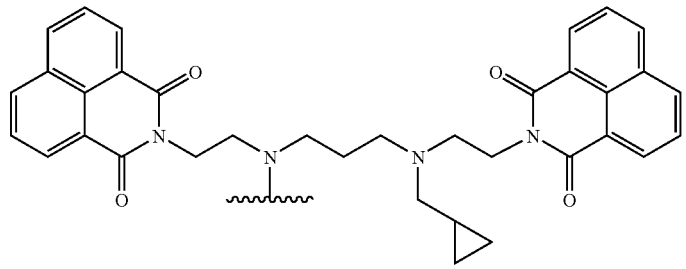
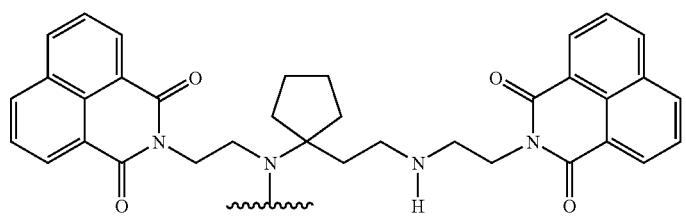

-continued
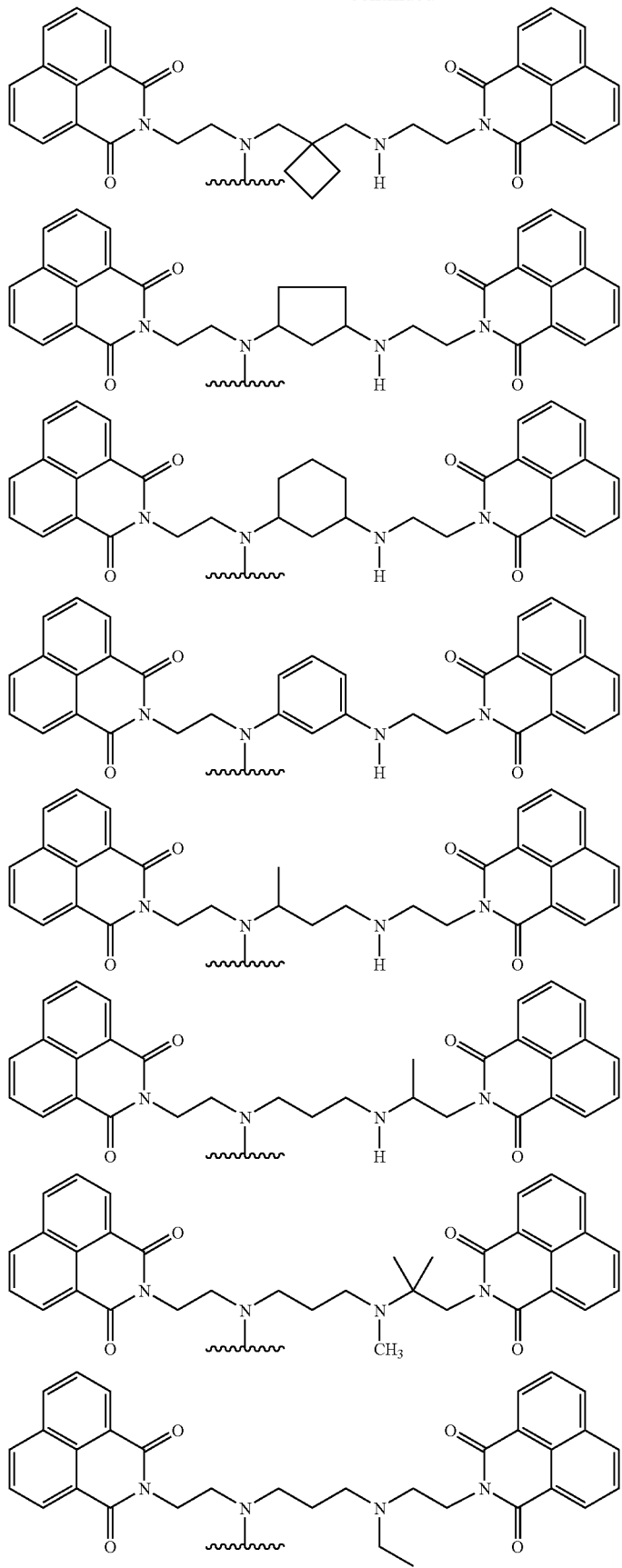

-continued
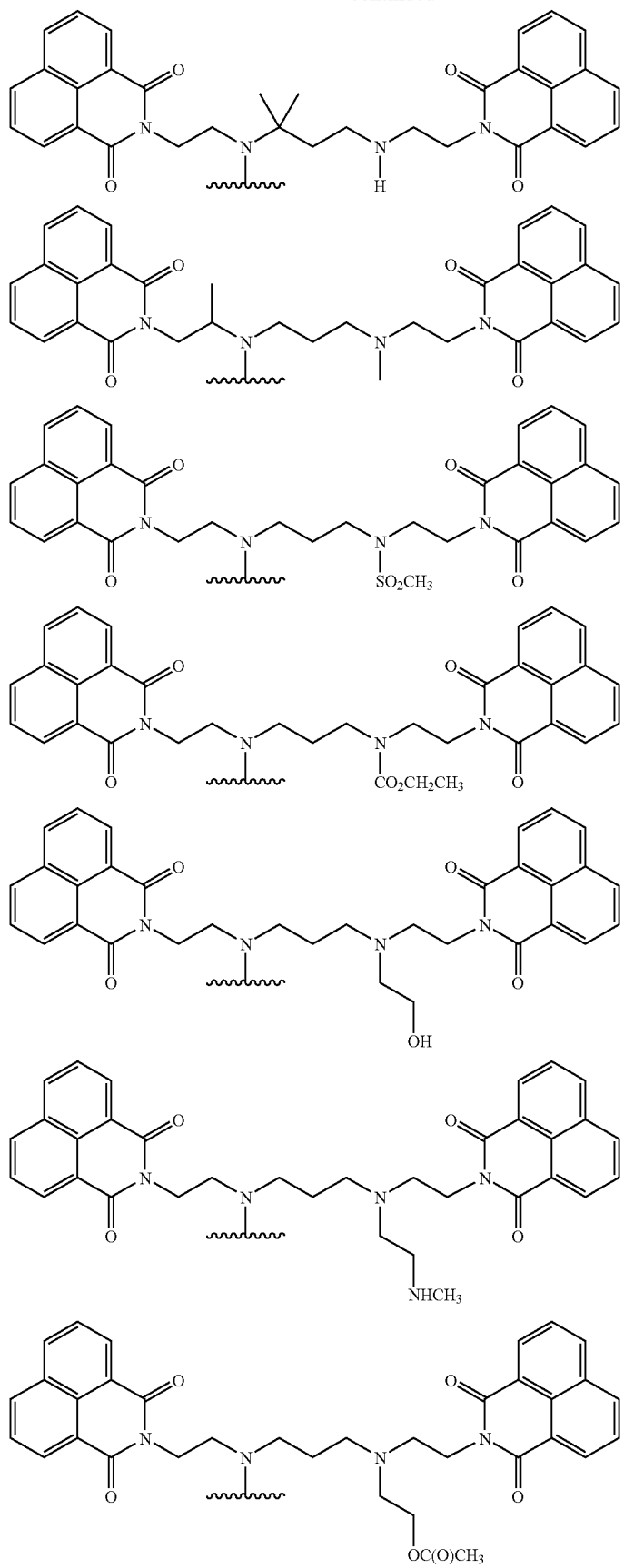

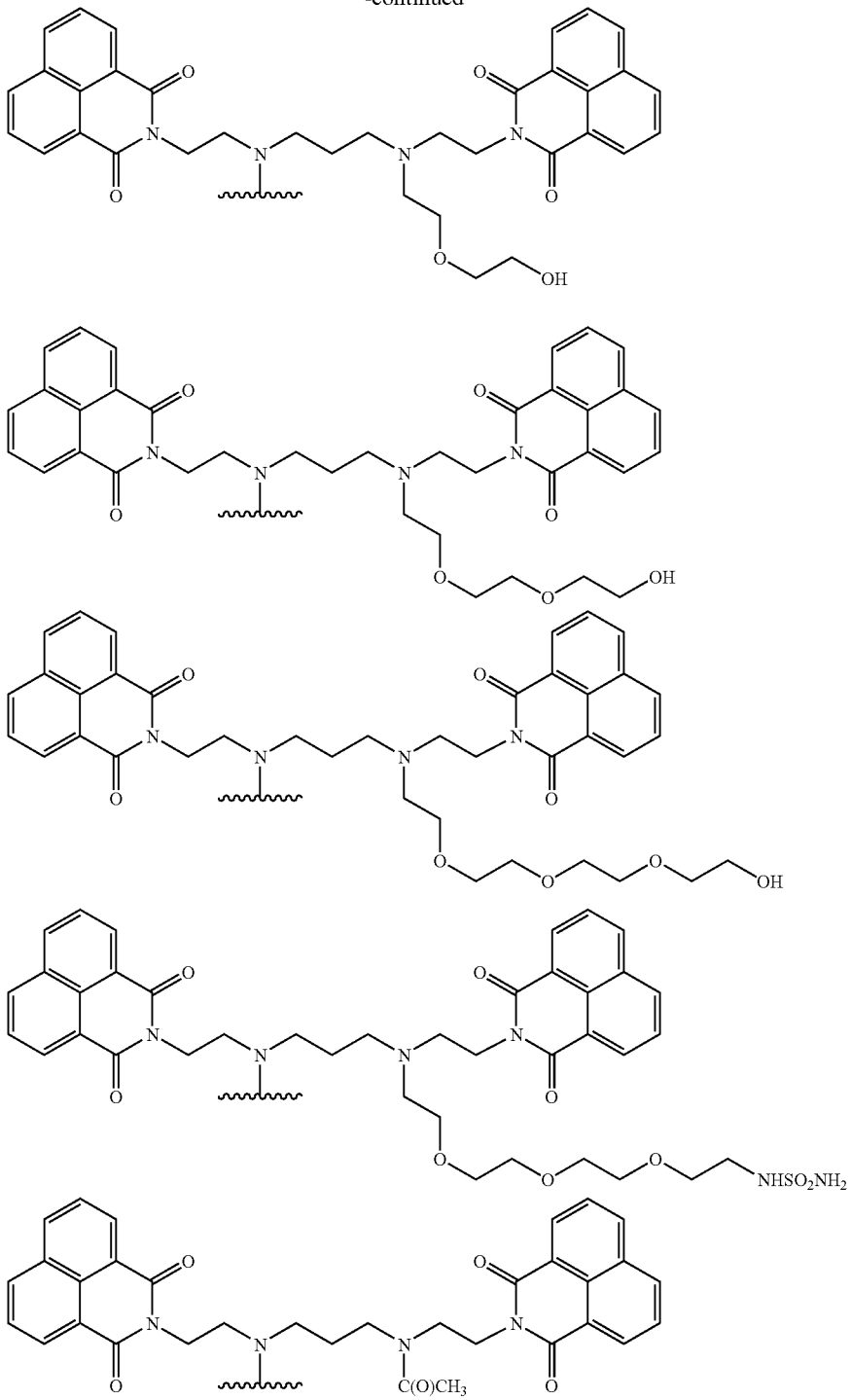

The three alkylene groups of the bis-amino alkyl group that attaches the two 1,8 naphthalimide groups may independently be of different lengths and bear a range of substituents besides H on the carbon atoms ($R^a$) and the nitrogen atom ($Y=NR^b$) not linked to L ($R^b$). The two non-equivalent alkylene groups between each 1,8 naphthalimide group and a nitrogen atom (n) are independently 1, 2, or 3 carbons in length. The alkylene group between the nitrogen atoms (m) is 1, 2, 3, 4, 5, or 6 carbons in length. The compounds of the invention thus include all 54 possible combinations of lengths of the three alkylene groups in a drug moiety (D) IIa and IIb ($Y=NR^b$). A numerical matrix designating the n and m values of the alkylene groups of the bis-amino alkyl group wherein: the length (n) of the alkylene group including the nitrogen atom bonded to the linker (N to L) is first; the length (m) of the alkylene group between the nitrogen atoms is second; and the length (n) of the alkylene group bonded to the nitrogen atom not linked to L (N not to L) is third (left to right) exemplifies the combinations in Table 1:

TABLE 1
| n (1-3, N to L) | .m (1-6) | .n (1-3, N not to L) | | | |
|---|---|---|---|---|---|
| 1.1.1 | 1.1.2 | 1.1.3 | 1.2.1 | 1.2.2 | 1.2.3 |
| 1.3.1 | 1.3.2 | 1.3.3 | 1.4.1 | 1.4.2 | 1.4.3 |
| 1.5.1 | 1.5.2 | 1.5.3 | 1.6.1 | 1.6.2 | 1.6.3 |
| 2.1.1 | 2.1.2 | 2.1.3 | 2.2.1 | 2.2.2 | 2.2.3 |
| 2.3.1 | 2.3.2 | 2.3.3 | 2.4.1 | 2.4.2 | 2.4.3 |
| 2.5.1 | 2.5.2 | 2.5.3 | 2.6.1 | 2.6.2 | 2.6.3 |
| 3.1.1 | 3.1.2 | 3.1.3 | 3.2.1 | 3.2.2 | 3.2.3 |
| 3.3.1 | 3.3.2 | 3.3.3 | 3.4.1 | 3.4.2 | 3.4.3 |
| 3.5.1 | 3.5.2 | 3.5.3 | 3.6.1 | 3.6.2 | 3.6.3 |
The same combinatorial set of embodiments for drug moiety IIb where the linker (L) is covalently attached through an aryl carbon atom of a 1,8 naphthalimide group, are included in the compounds of the invention.
Exemplary embodiments of the bis-amino alkyl group where Y is N, and $R^a$ and $R^b$ are H include the drug moiety IIa structures:
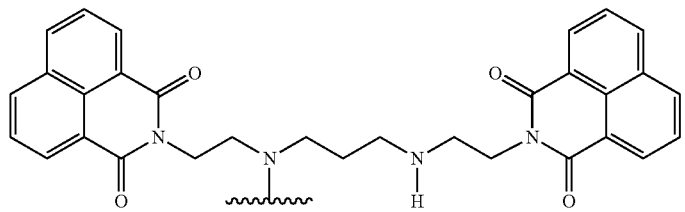
2.3.2
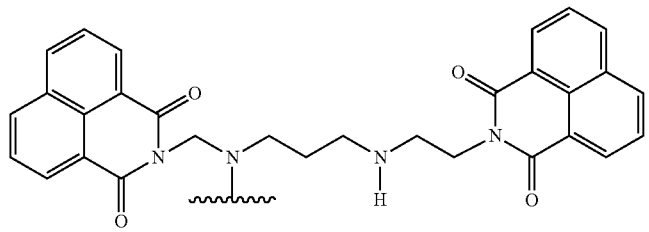
1.3.2
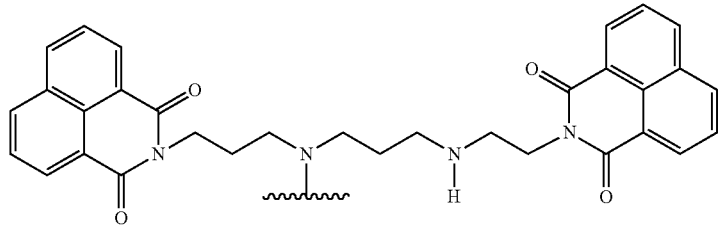
3.3.2
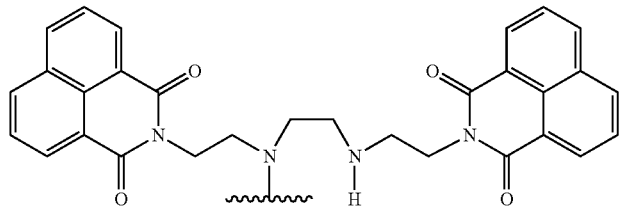
2.2.2
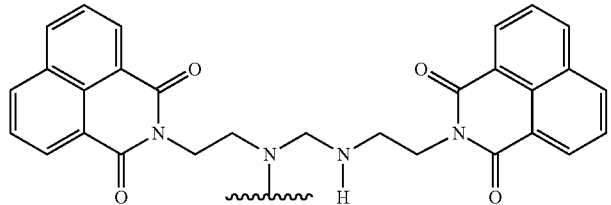
2.1.2

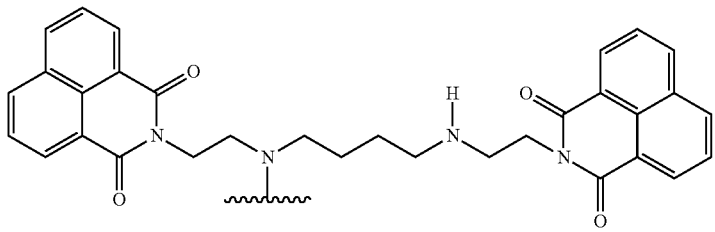

2.4.2

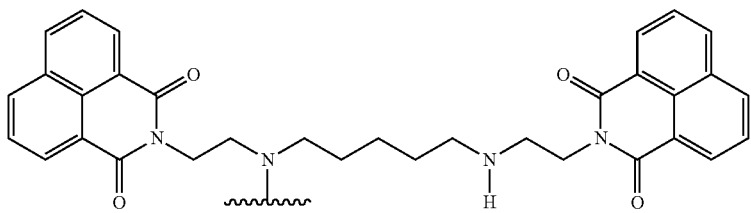

2.5.2

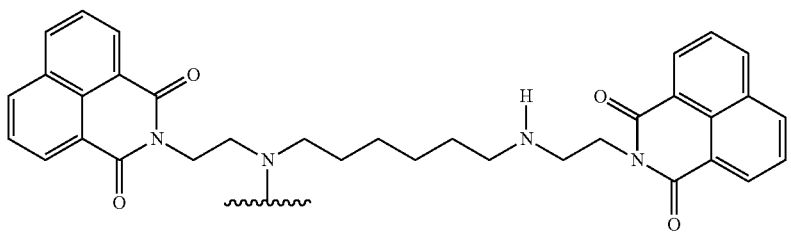

2.6.2

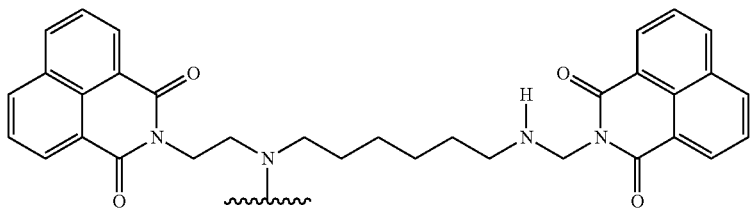

2.6.1

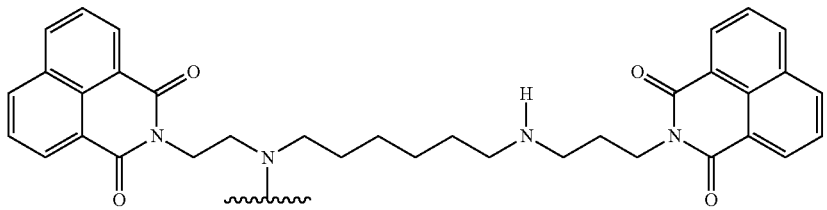

2.6.3

Exemplary embodiments of IIb where the two 1,8 naphthalimide groups are the same ($X^1$, $X^2$, $Z^3$, $X^4$=H) n is 2, m is 3, Y is N($R^b$), and $R^a$ and $R^b$ are H, include the exemplary structures:

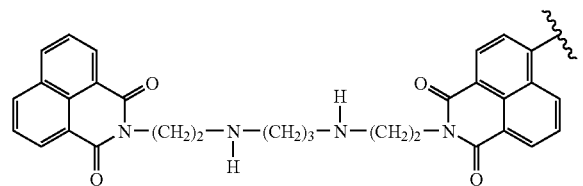

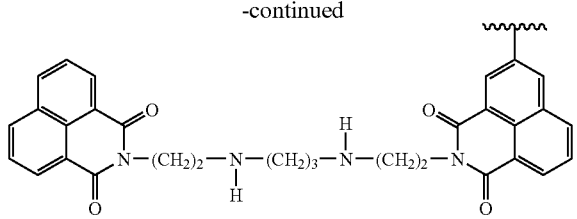

Exemplary embodiments of IIb where the linker (L) is attached through one of the 1,8 naphthalimide groups, the two 1,8 naphthalimide groups are different, n is 2, m is 3, and $R^a$ are H, include the exemplary structures:

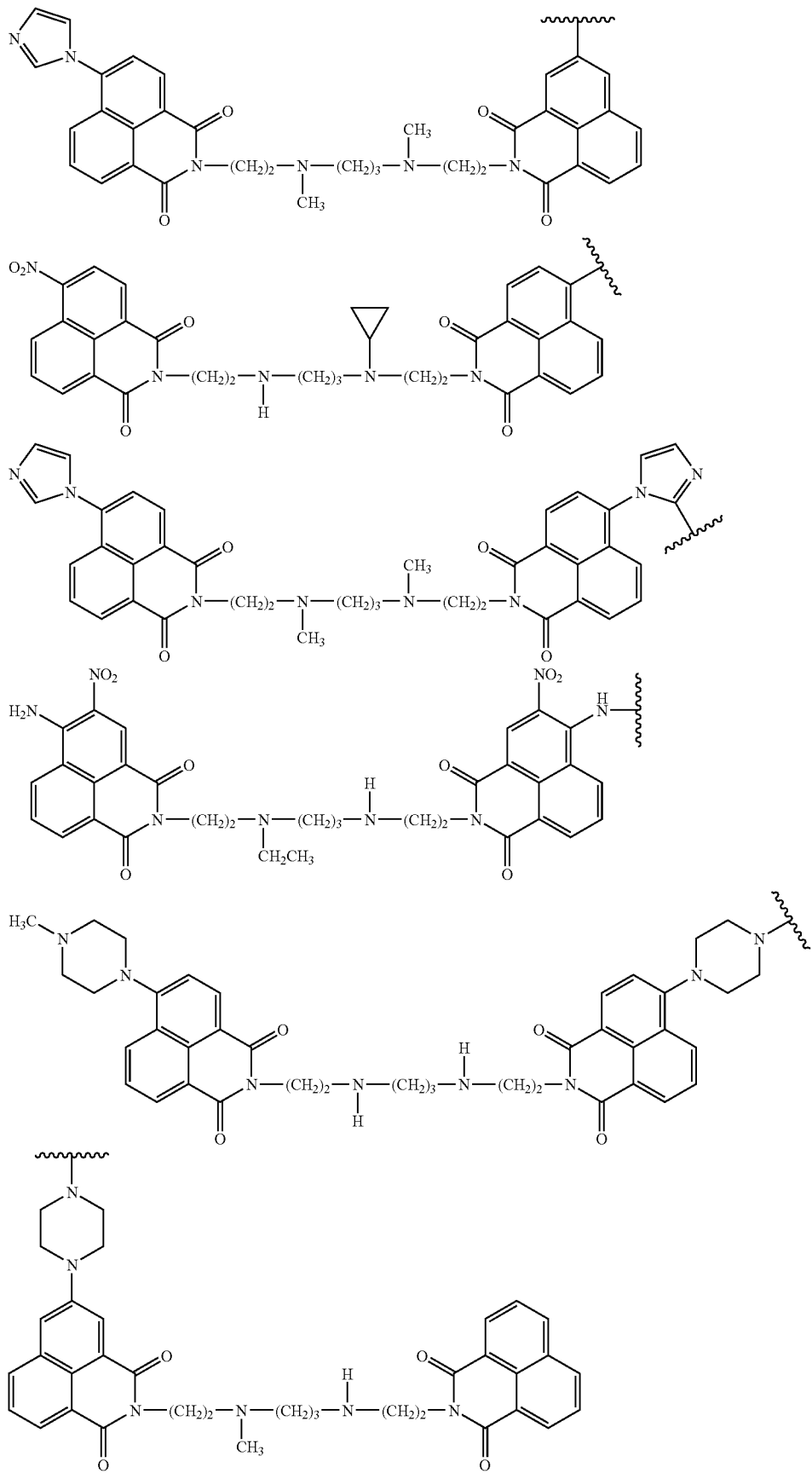

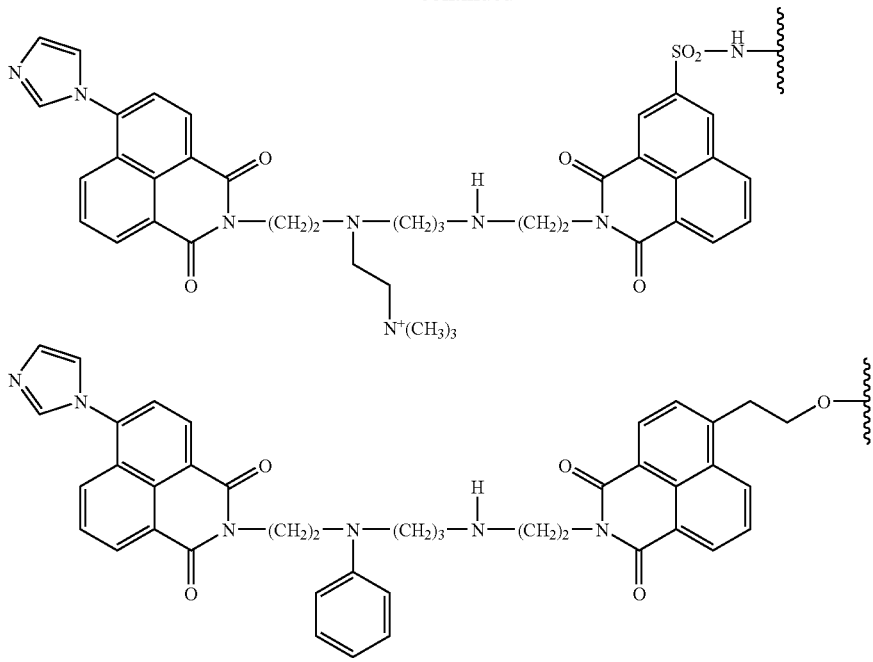

Exemplary embodiments of IIa and IIb where Y is O or S include the following structures:

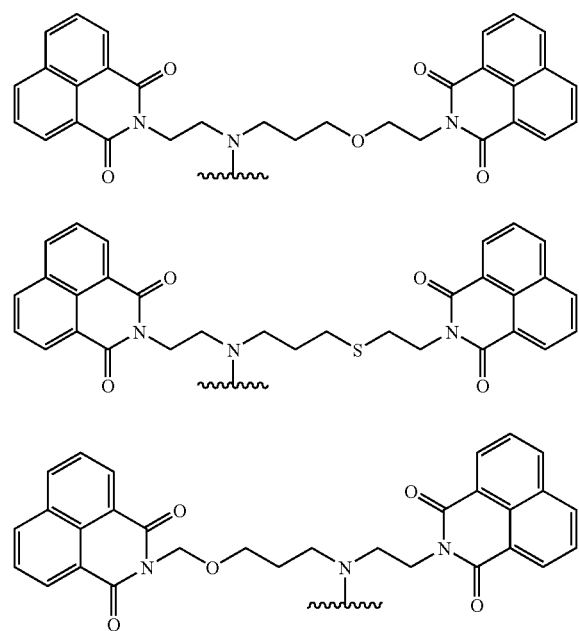

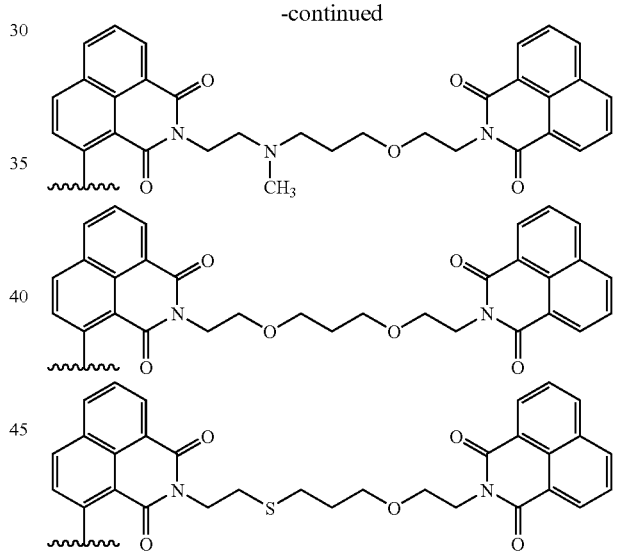

Synthesis of Bis 1,8 Naphthalimide Drug Moieties

Bis 1,8 naphthalimide drug moieties were prepared according to Brana et al (2004) J. Med. Chem. 47:1391-1399; Brana et al (2003) Org. Biomol. Chem. 1:648-654; Brana, M. F. and Ramos, A. (2001) Current Med. Chem.—Anti-Cancer Agents 1:237-255, as well as conventional organic chemistry methodology.

Generally, 1,8 naphthalimide intermediates may be prepared from 1,8-naphthalic anhydride compounds (Chem. Rev. (1970) 70:439-469; U.S. Pat. Nos. 4,146,720; 5,616,589; 5,416,089; 5,585,382; 5,552,544). Various substituted 1,8-naphthalic anhydride compounds are commercially available, such as 4-Bromo-1,8-naphthalic anhydride (Aldrich, Milwaukee, Wis.). Reaction of a 1,8-naphthalic anhydride compound with a primary amine gives the 1,8 naphthalimide (U.S. Pat. No. 5,329,048). Displacement of bromine from the 4 position occurs with various nucleophilic reagents.

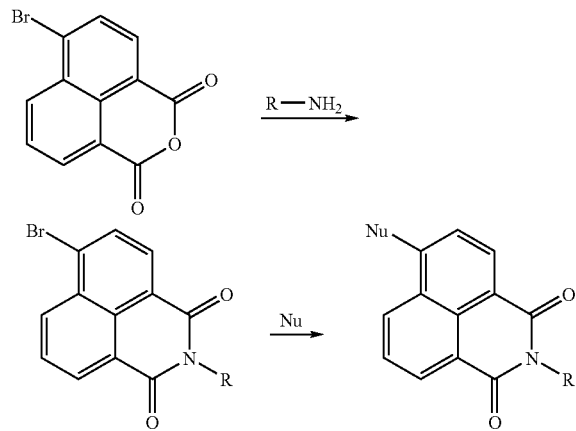

Where the amine reagent is a bis-amino compound, two 1,8-naphthalic anhydride react to form bis 1,8 naphthalimide intermediates (Brana, M. F. and Ramos, A. (2001) Current Med. Chem.—Anti-Cancer Agents 1:237-255; Brana et al (1993) Anticancer Drug Des. 8:257; Brana et al (1996) Anticancer Drug Des. 11:297; WO 94/02466; and U.S. Pat. Nos. 4,874,863; 5,206,249; 5,329,048; 5,416,089; 5,488,110; 5,981,753; 6,177,570). For example, two equivalents of an anhydride in toluene are treated with one equivalent of the corresponding polyamine in ethanol. The mixture is heated at reflux until the reaction is complete. The bis 1,8 naphthalimide is isolated, e.g. by filtration and crystallization, as the free base and converted to a salt, such as the mesylate (methanesulfonate) with methanesulfonic acid, or as the trifluoroacetate with trifluoroacetic acid (TFA), and washed with an organic solvent, according to the method of Brana et al (2004) J. Med. Chem. 47:1391-1399.

Alternatively, the 1,8 naphthalimide groups may be attached to the polyamine unit sequentially (WO 94/02466) by protecting one of the terminal amino groups of the polyamine reagent during reaction with the first 1,8 naphthalic anhydride reagent. After deprotection of the terminal amino group of the mono 1,8 naphthalimide intermediate, a second 1,8 naphthalic anhydride reagent may be reacted to form the bis 1,8 naphthalimide product. By this route, asymmetric bis 1,8 naphthalimide compounds can be prepared, i.e. where $X^1$ and $X^2$ are different than $X^3$ and $X^4$. Suitable amino protecting groups include mesitylenesulfonyl, dinitrobenzenesulfonyl, BOC (tert-butyloxycarbonyl), CBz (carbobenzoxy), or those detailed in *Protective Groups in Organic Chemistry*, Theodora W. Greene (1991) John Wiley & Sons, Inc., New York, or later editions thereto. Alternatively, the terminal amino group for coupling to the second 1,8 naphthalic anhydride reagent may be generated by reductive amination of a carbonyl group such as aldehyde or ester, or by reduction of a nitrile group.

Linker

The linker (L) is a bifunctional or multifunctional moiety which is covalently attached to one or more Drug moieties (D) and an antibody unit (Ab) to form Antibody Drug Conjugates (ADC) of the invention.

In one embodiment, the linker L of an ADC has the formula:

$$-A_a-W_w-SP_y-$$

wherein:
-A- is a Stretcher unit;
a is 0 or 1;
each —W— is independently an Amino Acid unit;
w is independently an integer ranging from 0 to 12;
—SP— is a Spacer unit; and
y is 0, 1 or 2.

In this embodiment, the ADC may be represented by Formula Ia:

$$\text{Ab-}(A_a-W_w-SP_y-D)_p \quad \text{Ia}$$

The linker may be a dendritic type linker for covalent attachment of more than one drug moiety through a branching, multifunctional linker moiety to an antibody (Sun et al (2002) Bioorganic & Medicinal Chemistry Letters 12:2213-2215; Sun et al (2003) Bioorganic & Medicinal Chemistry 11:1761-1768). Dendritic linkers can increase the molar ratio of drug to antibody, i.e. loading, which is related to the potency of the ADC. Thus, where an antibody bears only one reactive group, e.g. a lysine amino or a cysteine thiol, a multitude of drug moieties may be attached through a dendritic linker.

The following exemplary embodiments of dendritic linker reagents allow up to nine nucleophilic drug moiety reagents to be conjugated by reaction with the chloroethyl nitrogen mustard functional groups:

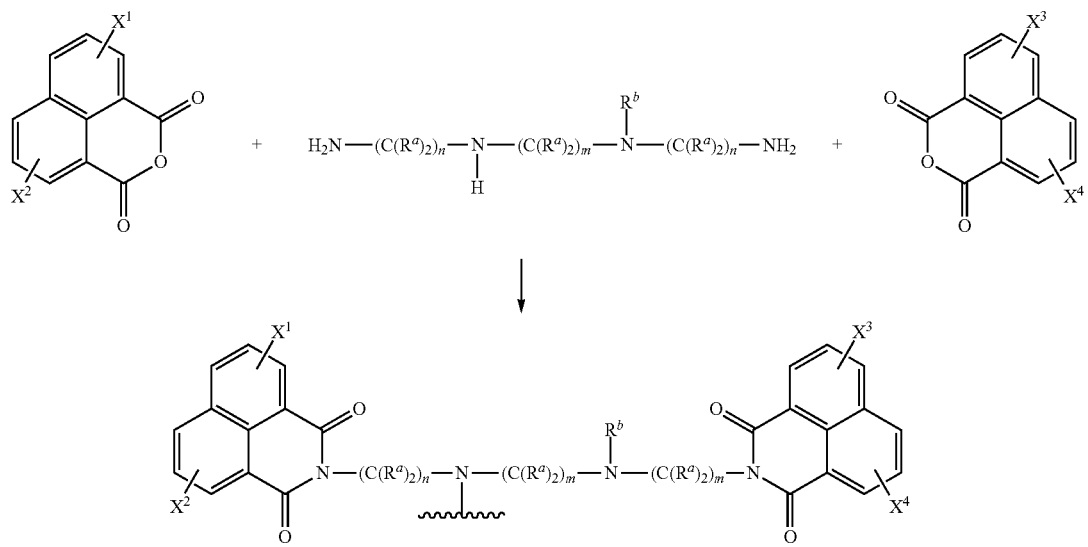

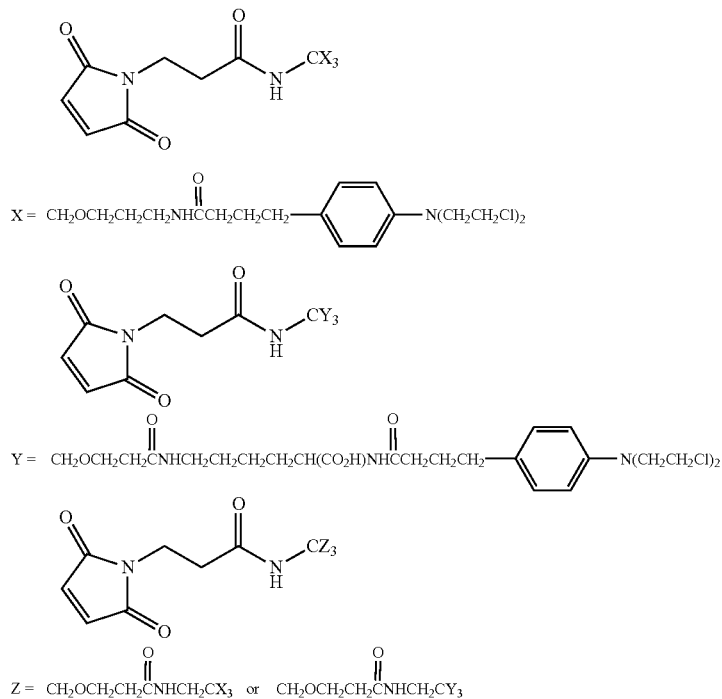

Stretcher Unit

The Stretcher unit (-A-), when present, is capable of linking an antibody (Ab) to an amino acid unit (—W—). In this regard an antibody (Ab) has a functional group that can form a bond with a functional group of a Stretcher. Useful functional groups that can be present on an antibody, either naturally or via chemical manipulation include, but are not limited to, sulfhydryl (—SH), amino, hydroxyl, carboxy, the anomeric hydroxyl group of a carbohydrate, and carboxyl. In one aspect, the reactive functional groups on the antibody are sulfhydryl and amino. Sulfhydryl groups can be generated by reduction of an intramolecular cysteine disulfide bond of an antibody. Alternatively, sulfhydryl groups can be generated by reaction of an amino group of a lysine moiety of an antibody using 2-iminothiolane (Traut's reagent) or another sulfhydryl generating reagent.

In one embodiment, the Stretcher unit forms a bond with a sulfur atom, e.g. a cysteine amino acid residue, of the Antibody unit. The sulfur atom can be derived from a sulfhydryl group of an antibody. Representative Stretcher units of this embodiment are depicted in Formulas IIIa and IIIb, wherein Ab-, —W—, —SP—, -D, w and y are as defined above and wherein $R^{17}$ is selected from $(CH_2)_r$, $C_3$-$C_8$ carbocyclyl, O—$(CH_2)_r$, arylene, $(CH_2)_r$-arylene, -arylene-$(CH_2)_r$—, $(CH_2)_r$—($C_3$-$C_8$ carbocyclyl), ($C_3$-$C_8$ carbocyclyl)-$(CH_2)_r$, $C_3$-$C_8$ heterocyclyl, $(CH_2)_r$($C_3$-$C_8$ heterocyclyl), —($C_3$-$C_8$ heterocyclyl)-$(CH_2)_r$—, —$(CH_2)_rC(O)NR^b(CH_2)_r$—, —$(CH_2CH_2O)_r(CH_2)_r$—, —$(CH_2)_rO(CH_2CH_2O)_r$ $(CH_2)_r$—, —$(CH_2)_rC(O)NR^b(CH_2CH_2O)_r(CH_2)_r$—, —$(CH_2)_rC(O)NR^b(CH_2CH_2O)_r$—$CH_2$—, —$(CH_2CH_2O)_rC(O)NR^b(CH_2CH_2O)_r(CH_2)_r$—, —$(CH_2CH_2O)_rC(O)NR^b$ $(CH_2CH_2O)_r$—$CH_2$—, and —$(CH_2CH_2O)_rC(O)NR^b$ $(CH_2)_r$—; where r is independently an integer ranging from 1-10.

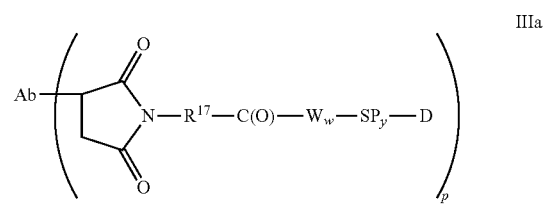

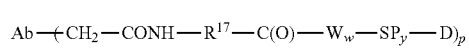

An illustrative Stretcher unit is that of Formula IIIa is derived from maleimido-caproyl (MC) wherein $R^{17}$ is —$(CH_2)_5$—:

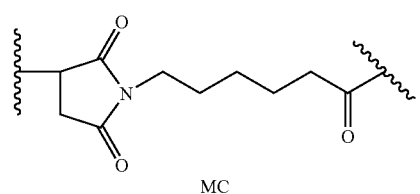

An illustrative Stretcher unit is that of Formula IIIa is derived from maleimido-propanoyl (MP) wherein $R^{17}$ is —$(CH_2)_2$—:

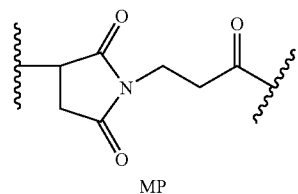

Another illustrative Stretcher unit is that of Formula IIIa wherein $R^{17}$ is —(CH$_2$CH$_2$O)$_r$—CH$_2$— and r is 2:

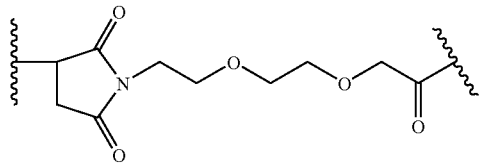

Another illustrative Stretcher unit is that of Formula IIIa wherein $R^{17}$ is —(CH$_2$)$_r$C(O)NR$^b$(CH$_2$CH$_2$O)$_r$—CH$_2$— where $R^b$ is H and each r is 2:

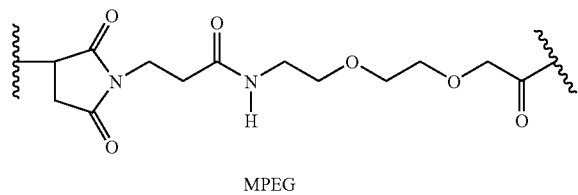

MPEG

Another illustrative Stretcher unit is that of Formula IIIa wherein $R^{17}$ is —(CH$_2$)$_5$—:

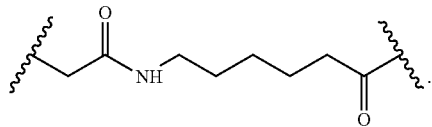

In another embodiment, the Stretcher unit is linked to the Antibody unit via a disulfide bond between a sulfur atom of the Antibody unit and a sulfur atom of the Stretcher unit. A representative Stretcher unit of this embodiment is depicted within the square brackets of Formula IV, wherein $R^{17}$, Ab-, —W—, —SP—, -D, w and y are as defined above.

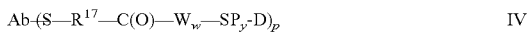
Ab—(S—R$^{17}$—C(O)—W$_w$—SP$_y$-D)$_p$  IV

In yet another embodiment, the reactive group of the Stretcher contains a reactive site that can form a bond with a primary or secondary amino group of an antibody. Example of these reactive sites include, but are not limited to, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Representative Stretcher units of this embodiment are depicted within the square brackets of Formulas Va, Vb and Vc, wherein —R$^{17}$—, Ab-, —W—, —SP—, -D, w and y are as defined above;

Ab—(C(O)NH—R$^{17}$—C(O)—W$_w$—SP$_y$-D)$_p$  Va

Ab—(C(S)NH—R$^{17}$—C(O)—W$_w$—SP$_y$-D)$_p$  Vb

Ab—(C(O)—R$^{17}$—C(O)—W$_w$—SP$_y$-D)$_p$  Vc

In yet another aspect, the reactive group of the Stretcher is reactive with an aldehyde, acetal, or ketal group on a sugar (carbohydrate) of a glycosylated antibody. For example, a carbohydrate can be mildly oxidized using a reagent such as sodium periodate and the resulting (—CHO) unit of the oxidized carbohydrate can be condensed with a Stretcher that contains a functionality such as a hydrazide, an oxime, a primary or secondary amine, a hydrazine, a thiosemicarbazone, a hydrazine carboxylate, and an arylhydrazide such as those described by Kaneko, T. et al (1991) Bioconjugate Chem 2:133-41. Representative Stretcher units of this embodiment are depicted within the square brackets of Formulas VIa, VIb, and VIc, wherein —R$^{17}$—, Ab-, —W—, —SP—, -D, w and y are as defined above.

Ab—(N—NH—R$^{17}$—C(O)—W$_w$—SP$_y$-D)$_p$  VIa

Ab—(N—O—R$^{17}$—C(O)—W$_w$—SP$_y$-D)$_p$  VIb

Ab—(N—NH—C(O)—R$^{17}$—C(O)—W$_w$—SP$_y$-D)$_p$  VIc

Amino Acid Unit

The Amino Acid unit (—W—), when present: (i) links the Stretcher unit to the Spacer unit if the Spacer unit is present, (ii) links the Stretcher unit to the Drug unit if the Spacer unit is absent, and (iii) links the antibody unit to the Drug unit if the Stretcher unit and Spacer unit are absent.

Amino Acid unit —W$_w$— is a dipeptide, tripeptide, tetrapeptide, pentapeptide, hexapeptide, heptapeptide, octapeptide, nonapeptide, decapeptide, undecapeptide or dodecapeptide unit. Each —W— unit independently has the formula denoted below in the square brackets, and w is an integer ranging from 0 to 12:

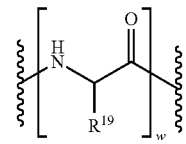

wherein $R^{19}$ includes all naturally occurring amino acid side chains, and analogs thereof. $R^{19}$ is selected from hydrogen, methyl, isopropyl, isobutyl, sec-butyl, benzyl, p-hydroxybenzyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl-, phenyl, cyclohexyl, and

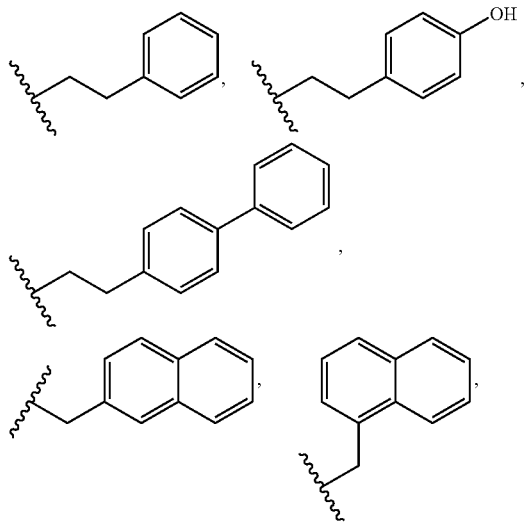

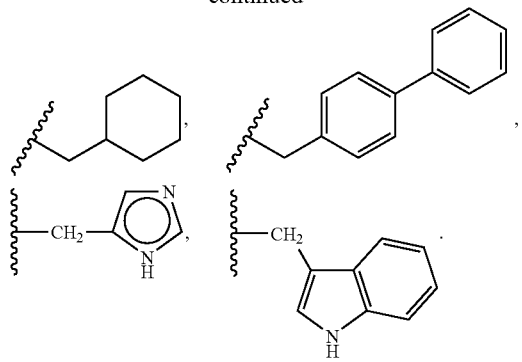

The Amino Acid unit can be enzymatically cleaved by one or more enzymes, including a tumor-associated protease or apoptotic-related enzyme such as cathepsin B, C, and D, or a plasmin protease, to liberate the drug moiety (-D).

Illustrative $W_w$ units are represented by Formulas (VII)-(IX):

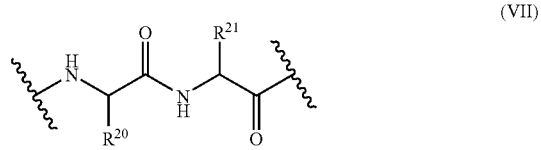
(VII)

wherein $R^{20}$ is methyl, isopropyl, isobutyl, sec-butyl, 3-methyl-1H-indole, or benzyl; and $R^{21}$ is $(CH_2)_4NH_2$, benzyl, $(CH_2)_3NHCONH_2$, or $(CH_2)_3NHC(=NH)NH_2$.

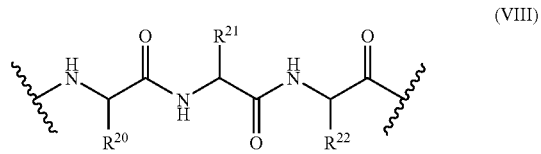
(VIII)

wherein $R^{20}$ is H, benzyl, or isopropyl; $R^{21}$ is benzyl; and $R^{22}$ is $(CH_2)_4NH_2$.

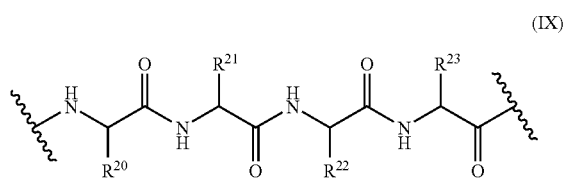
(IX)

wherein $R^{20}$ is H or methyl; $R^{21}$ is benzyl or isobutyl; $R^{22}$ is isobutyl or methyl; and $R^{23}$ is H or isobutyl.

Exemplary Amino Acid units include, but are not limited to, units of Formula (VII) where: $R^{20}$ is benzyl and $R^{21}$ is —$(CH_2)_4NH_2$; $R^{20}$ isopropyl and $R^{21}$ is —$(CH_2)_4NH_2$; $R^{20}$ isopropyl and $R^{21}$ is —$(CH_2)_3NHCONH_2$. Another exemplary Amino Acid unit is a unit of Formula (VIII) wherein $R^{20}$ is benzyl, $R^{21}$ is benzyl, and $R^{22}$ is —$(CH_2)_4NH_2$.

Exemplary —$W_w$— Amino Acid units include a dipeptide, a tripeptide, a tetrapeptide or a pentapeptide. Exemplary dipeptides include: valine-citrulline (vc or val-cit), alanine-phenylalanine (af or ala-phe). Exemplary tripeptides include: glycine-valine-citrulline and glycine-glycine-glycine.

When $R^{19}$, $R^{20}$, $R^{21}$, $R^{22}$ or $R^{23}$ is other than hydrogen, the carbon atom to which $R^{19}$, $R^{20}$, $R^{21}$, $R^{22}$ or $R^{23}$ is attached is chiral.

Each carbon atom to which $R^{19}$, $R^{20}$, $R^{21}$, $R^{22}$ or $R^{23}$ is attached independently in the (S) or (R) configuration, or a racemic mixture. Amino acid units may thus be enantiomerically pure, racemic, or diastereomeric.

Spacer Unit

The Spacer unit (—SP—), when present: (i) links an Amino Acid unit to the Drug unit when an Amino Acid unit is present, (ii) links the Stretcher unit to the Drug moiety when the Amino Acid unit is absent, or (iii) links the Drug moiety to the antibody unit when both the Amino Acid unit and Stretcher unit are absent. Spacer units are of two general types: self-immolative and non self-immolative. A non self-immolative Spacer unit is one in which part or all of the Spacer unit remains bound to the Drug moiety after cleavage, particularly enzymatic, of an Amino Acid unit from the Drug-Linker-antibody Conjugate or the Drug-Linker Compound. Examples of a non self-immolative Spacer unit include, but are not limited to a (glycine-glycine) Spacer unit and a glycine Spacer unit. When an Exemplary Compound containing a glycine-glycine Spacer unit or a glycine Spacer unit undergoes enzymatic cleavage via a tumor-cell associated-protease, a cancer-cell-associated protease or a lymphocyte-associated protease, a glycine-glycine-Drug moiety or a glycine-Drug moiety is cleaved from Ab-$A_a$-Ww-. In one embodiment, an independent hydrolysis reaction takes place within the target cell, cleaving the glycine-Drug moiety bond and liberating the Drug.

In another embodiment, —$SP_y$— is a para-aminobenzyloxycarbonyl (PAB) unit whose phenylene portion is substituted with $Q_m$ wherein Q is —$C_1$-$C_8$ alkyl, —O—($C_1$-$C_8$ alkyl), -halogen, -nitro or -cyano; and m is an integer ranging from 0-4.

Exemplary embodiments of a non self-immolative Spacer unit (—SP—) are: -Gly-Gly-; -Gly-; -Ala-Phe-; -Val-Cit-.

In one embodiment, a Drug moiety-linker or an ADC is provided in which the Spacer unit is absent (y=0), or a pharmaceutically acceptable salt or solvate thereof.

Alternatively, an ADC containing a self-immolative Spacer unit can release -D. In one embodiment, —SP— is a PAB group that is linked to —$W_w$— via the amino nitrogen atom of the PAB group, and connected directly to -D via a carbonate, carbamate or ether group, where the ADC has the exemplary structure:

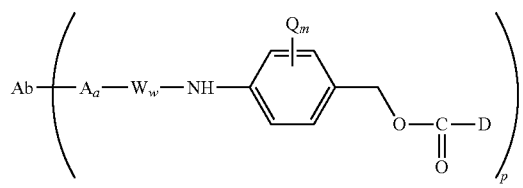

wherein Q is —$C_1$-$C_8$ alkyl, —O—($C_1$-$C_8$ alkyl), -halogen, -nitro or -cyano; m is an integer ranging from 0-4; and p ranges from 1 to 4.

Other examples of self-immolative spacers include, but are not limited to, aromatic compounds that are electronically similar to the PAB group such as 2-aminoimidazol-5-methanol derivatives (Hay et al. (1999) Bioorg. Med. Chem. Lett. 9:2237) and ortho or para-aminobenzylacetals. Self-immolative spacers also include where the PAB group is substituted by a heterocyclic group (WO 2005/082023). Spacers can be used that undergo cyclization upon amide bond hydrolysis, such as substituted and unsubstituted 4-aminobutyric acid amides (Rodrigues et al (1995) Chemistry Biology 2:223), appropriately substituted bicyclo[2.2.1] and bicyclo[2.2.2] ring systems (Storm et al (1972) J. Amer. Chem. Soc. 94:5815) and 2-aminophenylpropionic acid amides (Amsberry et al (1990) J. Org. Chem., 55:5867). Elimination of amine-containing drugs that are substituted at glycine (Kingsbury et al (1984) J. Med. Chem., 27, 1447) are also examples of self-immolative spacer useful in ADCs.

In one embodiment, the Spacer unit is a branched bis(hydroxymethyl)styrene (BHMS), which can be used to incorporate and release multiple drugs, having the structure:

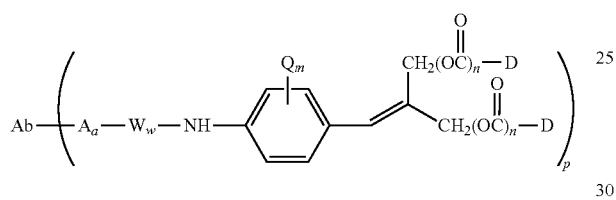

wherein Q is —$C_1$-$C_8$ alkyl, —O—($C_1$-$C_8$ alkyl), -halogen, -nitro or -cyano; m is an integer ranging from 0-4; n is 0 or 1; and p ranges raging from 1 to 4.

In another embodiment, the -D moieties are the same.

In yet another embodiment, the -D moieties are different.

in one aspect, Spacer units (—$SP_y$—) are represented by Formulas (X)-(XII):

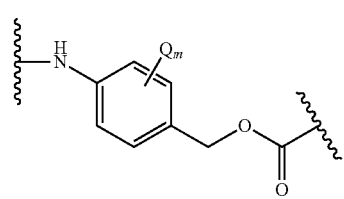

X wherein Q is —$C_1$-$C_8$ alkyl, —O—($C_1$-$C_8$ alkyl), -halogen, -nitro or -cyano; and m is an integer ranging from 0-4;

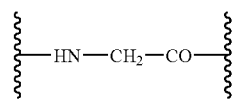

XI

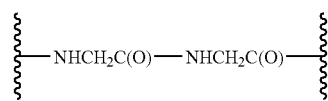

XII

Embodiments of the Formula I antibody-drug conjugate compounds include XIIIa (val-cit), XIIIb (MC-val-cit), XIIIc (MC-val-cit-PAB):

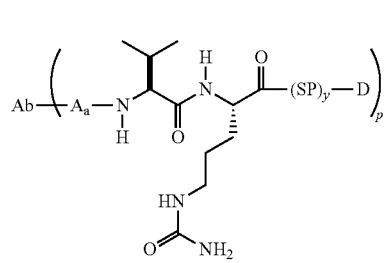

XIIIa

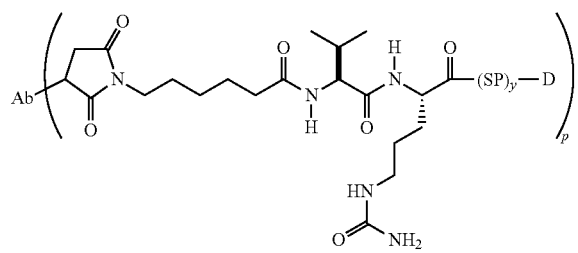

XIIIb

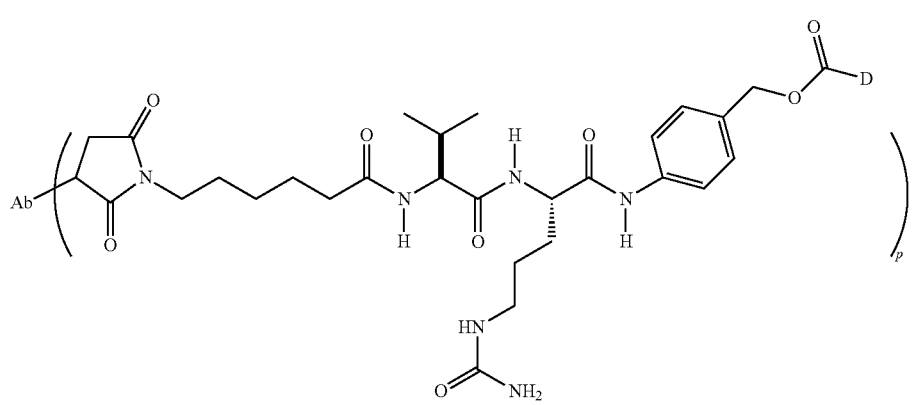

XIIIc

Other exemplary embodiments of the Formula Ia antibody-drug conjugate compounds include XIVa-h:

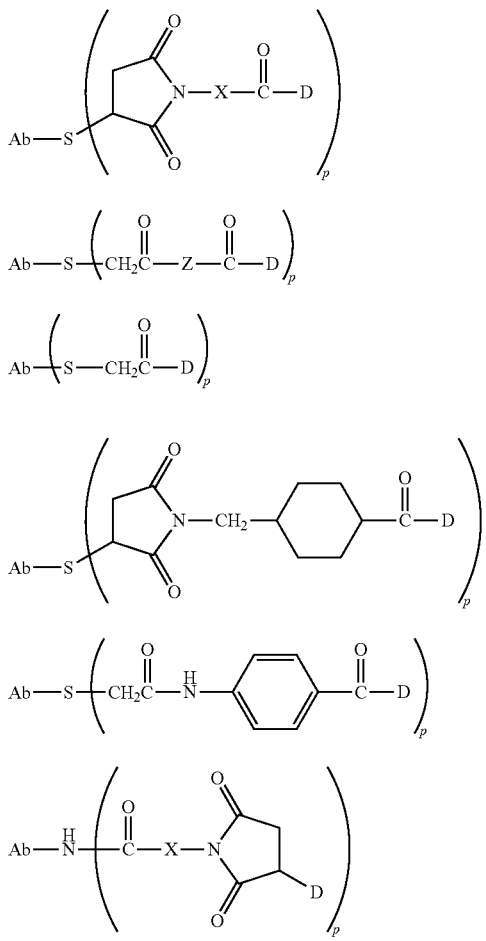

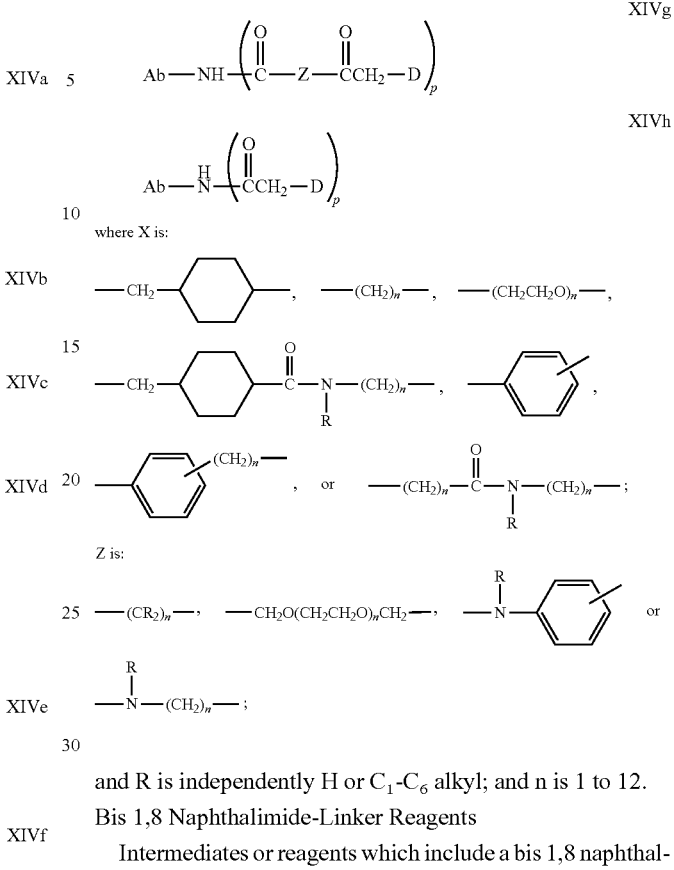

where X is:

—CH$_2$—⟨cyclohexyl⟩—, —(CH$_2$)$_n$—, —(CH$_2$CH$_2$O)$_n$—,

—CH$_2$—⟨cyclohexyl⟩—C(O)—N(R)—(CH$_2$)$_n$—, —⟨phenyl⟩—,

—⟨phenyl⟩—(CH$_2$)$_n$—, or —(CH$_2$)$_n$—C(O)—N(R)—(CH$_2$)$_n$—;

Z is:

—(CR$_2$)$_n$—, —CH$_2$O(CH$_2$CH$_2$O)$_n$CH$_2$—, —N(R)—⟨phenyl⟩— or

—N(R)—(CH$_2$)$_n$—;

and R is independently H or C$_1$-C$_6$ alkyl; and n is 1 to 12.

Bis 1,8 Naphthalimide-Linker Reagents

Intermediates or reagents which include a bis 1,8 naphthalimide drug moiety and a reactive Bis 1,8 naphthalimide-linker reagents bear functionality which is reactive with an antibody so as to allow covalent attachment, i.e. conjugation, of the reagent to the antibody to prepare an antibody drug conjugate (ADC) of the invention. Exemplary embodiments include the following bis 1,8 naphthalimide-linker reagents:

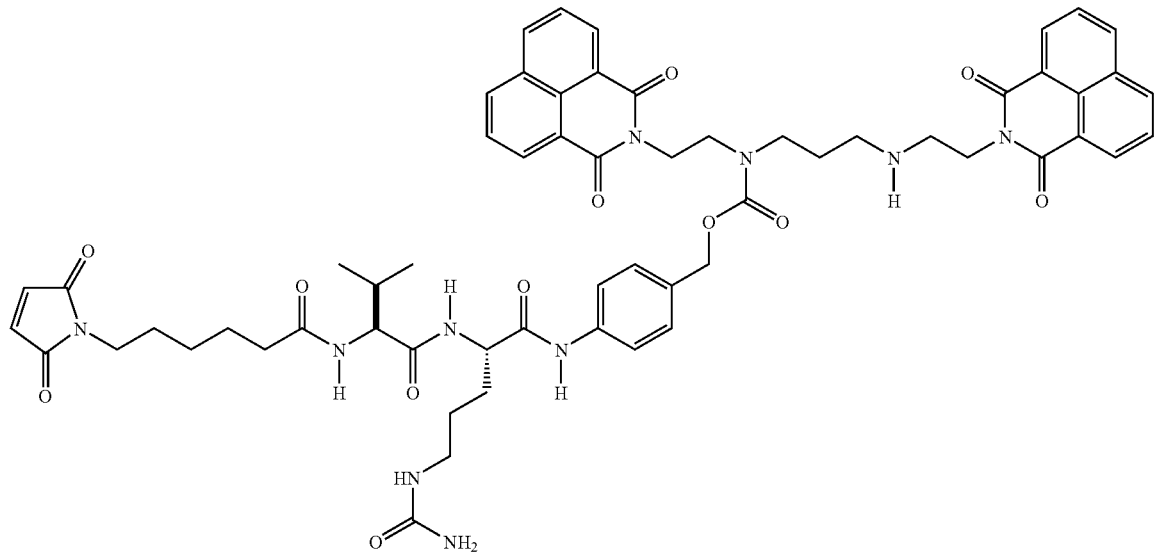

MC-vc-PAB-E where MC is maleimido-caproyl, vc is the valine-citrulline amino acid subunit, PAB is para-aminobenzyloxycarbonyl, and E is the bis 1,8 naphthalimide drug moiety IIa where $X^1$, $X^2$, $X^3$, and $X^4$ are H, $R^b$ is H, m is 3, and n is 2.

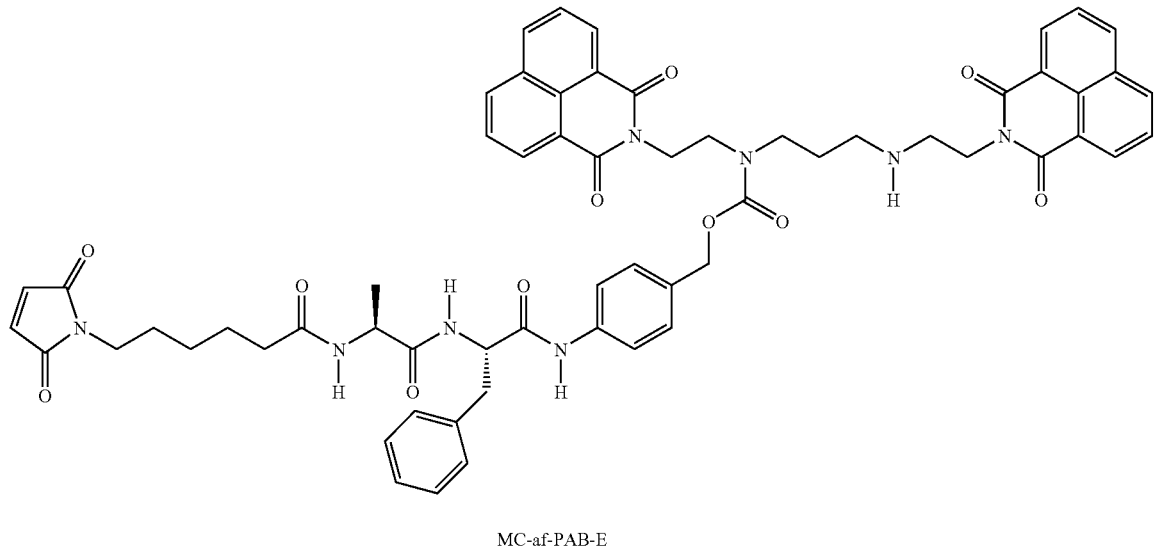

MC-af-PAB-E where af is the alanine-phenylalanine amino acid subunit.

Another exemplary bis 1,8 naphthalimide drug-linker reagent is MC-vc-PAB-(N, N'-(bis-aminoethyl-1,3-propanediamine)-bis-(4-N-imidazolyl)-1,8 naphthalimide) 111a:

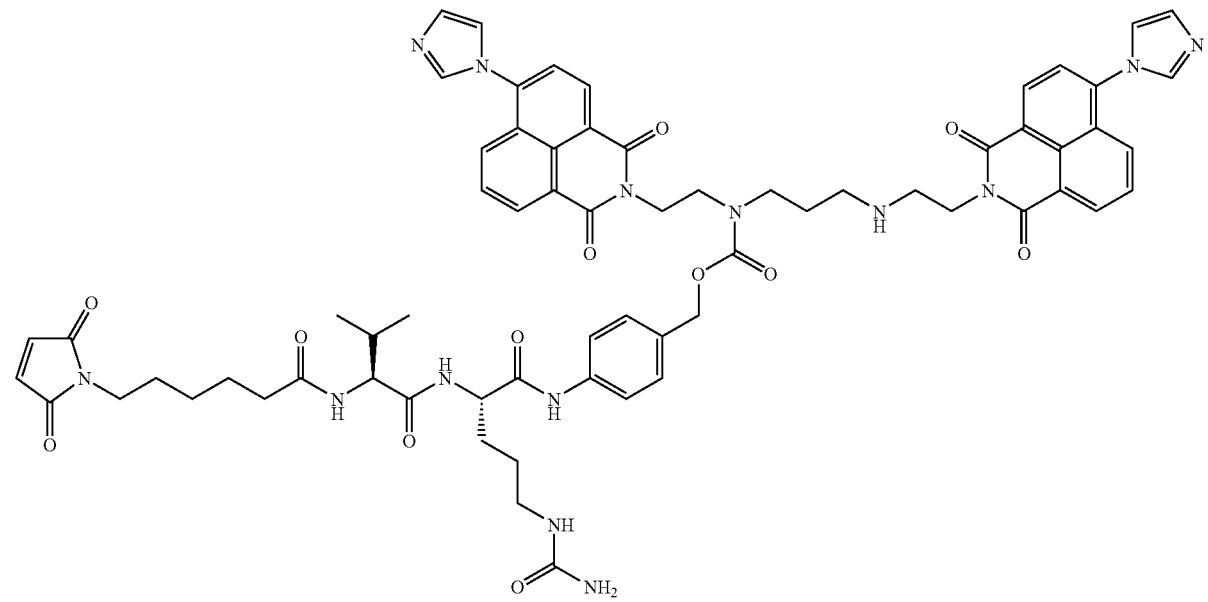

sought to be therapeutically or otherwise biologically modified. In one aspect, the antibody unit acts to deliver the Drug unit to the particular target cell population with which the antibody unit reacts. Such antibodies include, but are not limited to, large molecular weight proteins such as, for example, full-length antibodies, antibody fragments.

An antibody unit can form a bond to either a linker, a Stretcher unit, an Amino Acid unit, a Spacer Unit, or a Drug moiety directly. An antibody unit can form a bond to a Linker unit via a heteroatom of the antibody. The linking heteroatoms of the antibody may be a reactive nucleophilic group on any amino acid side chain, such as a cysteine thiol, a lysine amine, an aspartic acid or glutamic acid carboxyl, a serine, threonine, or tyrosine hydroxyl, or an arginine. Heteroatoms that may be present on an antibody unit include sulfur (in one embodiment, from a sulfhydryl group of an antibody such as Antibodies The antibody unit (Ab-) includes within its scope any unit of an antibody (Ab) that binds or reactively associates or complexes with a receptor, antigen or other receptive moiety associated with a given target-cell population. An antibody can be any protein or protein-like molecule that binds to, complexes with, or reacts with a moiety of a cell population a cysteine thiol), oxygen (in one embodiment, from a carbonyl, carboxyl or hydroxyl group of an antibody) and nitrogen (in one embodiment, from a primary or secondary amino group of an antibody). These heteroatoms can be present on the antibody in the antibody's natural state, for example a naturally occurring antibody, or can be introduced into the antibody via chemical modification.

In another embodiment, the antibody has one or more lysine residues that can be chemically modified to introduce one or more sulfhydryl groups. The antibody unit then may bond to a linker reagent or drug-linker moiety via the sulfhydryl group's sulfur atom. The reagents that can be used to modify lysines include, but are not limited to, N-succinimidyl S-acetylthioacetate (SATA) and 2-Iminothiolane hydrochloride (Traut's Reagent).

In another embodiment, the antibody can have one or more carbohydrate groups that can be chemically modified to have one or more sulfhydryl groups. The antibody unit bonds to the linker reagent or drug-linker moiety, such as the Stretcher Unit, via the sulfhydryl group's sulfur atom.

In yet another embodiment, the antibody can have one or more carbohydrate groups that can be oxidized to provide an aldehyde (—CHO) group suitable for conjugation with a linker reagent or drug-linker moiety (see, for e.g., Laguzza, et al., *J. Med. Chem.* 1989, 32 (3), 548-55). Suitable oxidizing reagents include periodate reagents. The corresponding aldehyde can form a bond with a Reactive Site on a Stretcher. The reaction may proceed through a Schiff's base intermediate and undergo subsequent reduction to a stable amine linkage. Reactive sites on a Stretcher that can react with a carbonyl group on an antibody include, but are not limited to, hydrazine and hydroxylamine. Other protocols for the modification of proteins for the attachment or association of Drug Units are described in Coligan et al., *Current Protocols in Protein Science*, vol. 2, John Wiley & Sons (2002), incorporated herein by reference.

In yet another embodiment, a tyrosine residue of the antibody may undergo diazotization by electrophilici aromatic substitution to form a diazo linkage with a linker reagent or drug-linker moiety.

In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Antibodies which comprise Ab in Formula I antibody drug conjugates (ADC) and which may be useful in the treatment of cancer include, but are not limited to, antibodies against tumor-associated antigens (TAA). Such tumor-associated antigens are known in the art, and can prepared for use in generating antibodies using methods and information which are well known in the art. Examples of TAA include (1)-(35), but are not limited to TAA (1)-(36) listed below. For convenience, information relating to these antigens, all of which are known in the art, is listed below and includes names, alternative names, Genbank accession numbers and primary reference(s). Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure specifically recited herein are expressly incorporated by reference.

Figure 4:
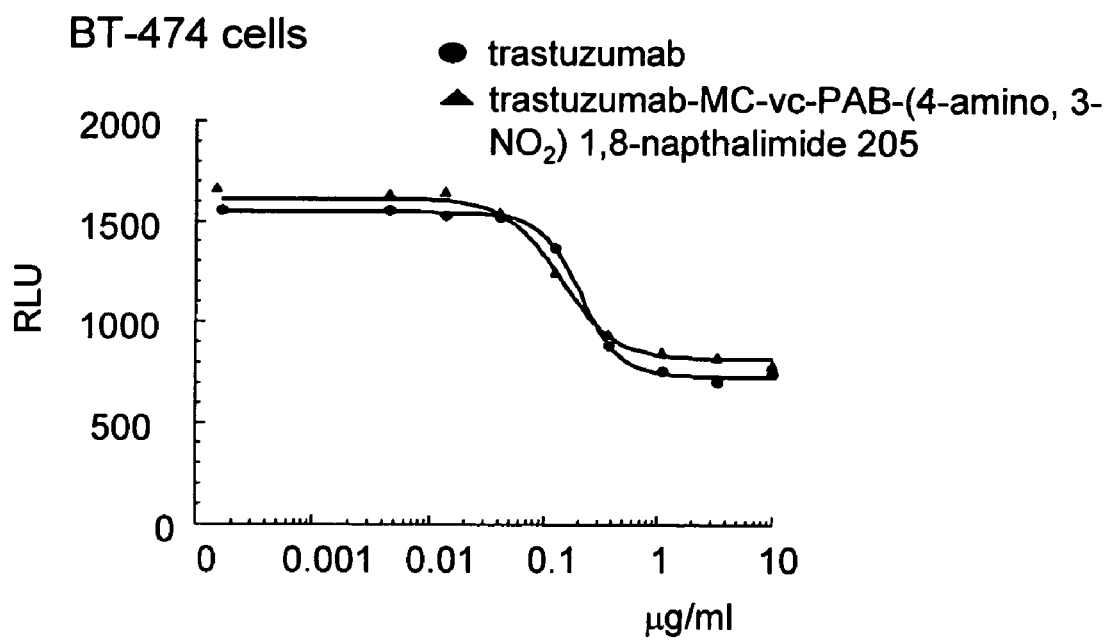
FIG. 4 shows an in vitro, cell proliferation assay with BT-474 cells treated with: -●-trastuzumab, and -▲-trastuzumab-(MC-val-cit-PAB-(N, N'-(N, N'-(bis-aminoethyl-1,3-propanediamine)-3-nitro, 4-amino-1,8 naphthalimide) 205, measured in Relative Fluorescence Units (RLU, ×1000) versus μg/ml concentration of antibody or ADC. trastuzumab is linked via a cysteine [cys].

Tumor-Associated Antigens (1)-(36):

(1) BMPR1B (bone morphogenetic protein receptor-type IB, Genbank accession no. NM_001203)
ten Dijke, P., et al Science 264 (5155):101-104 (1994), Oncogene 14 (11):1377-1382 (1997)); WO2004063362 (claim 2); WO2003042661 (claim 12); US2003134790-A1 (Page 38-39); WO2002102235 (claim 13; Page 296); WO2003055443 (Page 91-92); WO200299122 (Example 2; Page 528-530); WO2003029421 (claim 6); WO2003024392 (claim 2; FIG. 112); WO200298358 (claim 1; Page 183); WO200254940 (Page 100-101); WO200259377 (Page 349-350); WO200230268 (claim 27; Page 376); WO200148204 (Example; FIG. 4) NP_001194 bone morphogenetic protein receptor, type IB/pid=NP_001194.1-Cross-references: MIM:603248; NP_001194.1; NM_001203_1
SEQ ID NO:1

Figure 3:
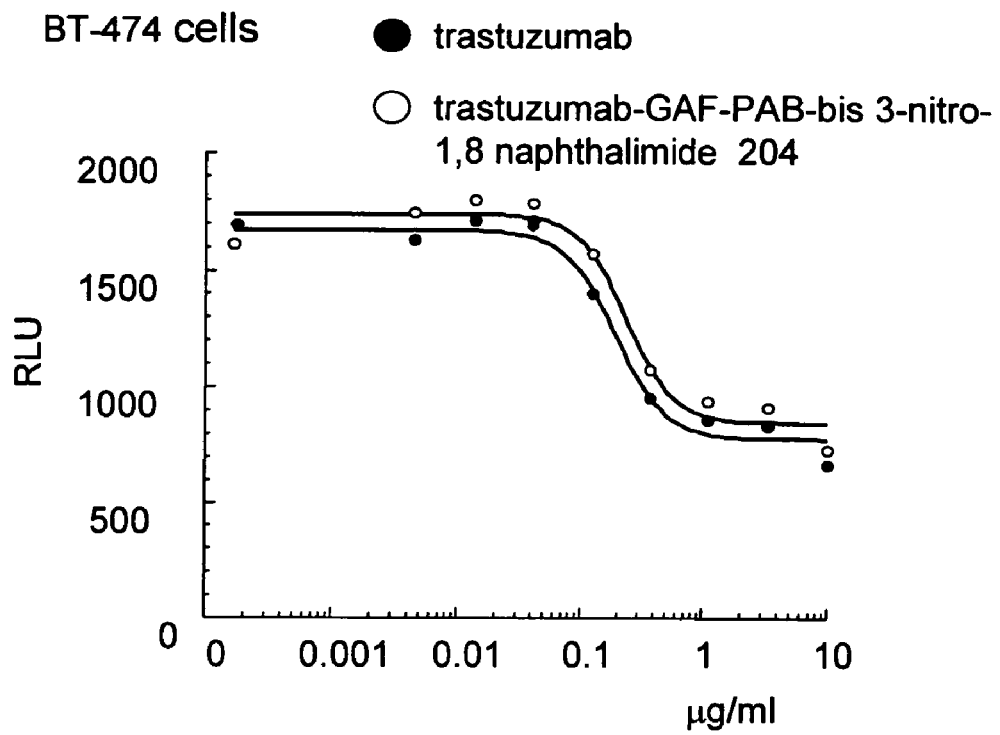
FIG. 3 shows an in vitro, cell proliferation assay with BT-474 cells treated with: -●-trastuzumab, and -o-trastuzumab-(succinate-gly-ala-phe)-(N, N'-(bis-aminoethyl-1,3-propanediamine)-bis 3-nitro-1,8 naphthalimide) 204, measured in Relative Fluorescence Units (RLU, ×1000) versus μg/ml concentration of antibody or ADC. trastuzumab is linked via an amino group.

(2) E16 (LAT1, SLC7A5, Genbank accession no. NM_003486) Biochem. Biophys. Res. Commun. 255 (2), 283-288 (1999), Nature 395 (6699):288-291 (1998), Gaugitsch, H. W., et al (1992) J. Biol. Chem. 267 (16): 11267-11273); WO2004048938 (Example 2); WO2004032842 (Example IV); WO2003042661 (claim 12); WO2003016475 (claim 1); WO200278524 (Example 2); WO200299074 (claim 19; Page 127-129); WO200286443 (claim 27; Pages 222, 393); WO2003003906 (claim 10; Page 293); WO200264798 (claim 33; Page 93-95); WO200014228 (claim 5; Page 133-136); US2003224454 (FIG. 3); WO2003025138 (claim 12; Page 150);
NP_003477 solute carrier family 7 (cationic amino acid transporter, y+system), member 5/pid=NP_003477.3—*Homo sapiens*
Cross-references: MIM:600182; NP_003477.3; NM_015923; NM_003486_1
SEQ ID NO:2

Figure 2:
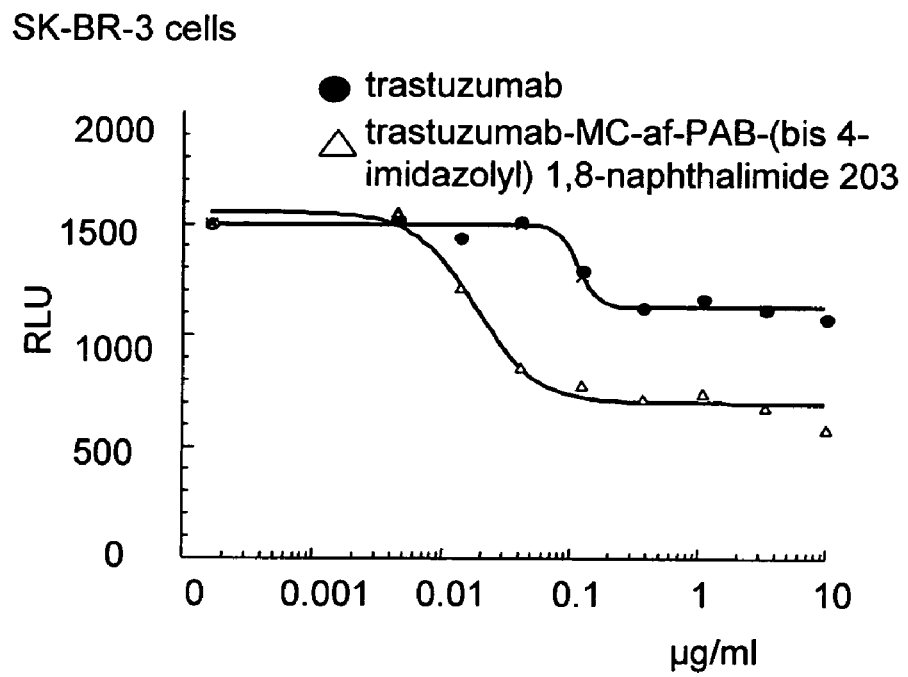
FIG. 2 shows an in vitro, cell proliferation assay with SK-BR-3 cells treated with: -●-trastuzumab and -Δ-trastuzumab-MC-ala-phe-PAB-(N, N'-(bis-aminoethyl-1,3-propanediamine)-bis-(4-N-imidazolyl)-1,8 naphthalimide) 203, measured in Relative Fluorescence Units (RLU, ×1000) versus μg/ml concentration of antibody or ADC. trastuzumab is linked via a cysteine [cys].

(3) STEAP1 (six transmembrane epithelial antigen of prostate, Genbank accession no. NM_012449)
Cancer Res. 61 (15), 5857-5860 (2001), Hubert, R. S., et al (1999) Proc. Natl. Acad. Sci. U.S.A. 96 (25):14523-14528); WO2004065577 (claim 6); WO2004027049 (FIG. 1L); EP1394274 (Example 11); WO2004016225 (claim 2); WO2003042661 (claim 12); US2003157089 (Example 5); US2003185830 (Example 5); US2003064397 (FIG. 2); WO200289747 (Example 5; Page 618-619); WO2003022995 (Example 9; FIG. 13A, Example 53; Page 173, Example 2; FIG. 2A);
NP_036581 six transmembrane epithelial antigen of the prostate
Cross-references: MIM:604415; NP_036581.1; NM_012449_1
SEQ ID NO:3

(4) 0772P (CA125, MUC16, Genbank accession no. AF361486)
J. Biol. Chem. 276 (29):27371-27375 (2001)); WO2004045553 (claim 14); WO200292836 (claim 6; FIG. 12); WO200283866 (claim 15; Page 116-121); US2003124140 (Example 16); US2003091580 (claim 6); WO200206317 (claim 6; Page 400-408);

Cross-references: GI:34501467; AAK74120.3; AF361486_1
SEQ ID NO:4

(5) MPF (MPF, MSLN, SMR, megakaryocyte potentiating factor, mesothelin, Genbank accession no. NM_005823) Yamaguchi, N., et al Biol. Chem. 269 (2), 805-808 (1994), Proc. Natl. Acad. Sci. U.S.A. 96 (20):11531-11536 (1999), Proc. Natl. Acad. Sci. U.S.A. 93 (1):136-140 (1996), J. Biol. Chem. 270 (37):21984-21990 (1995)); WO2003101283 (claim 14); (WO2002102235 (claim 13; Page 287-288); WO2002101075 (claim 4; Page 308-309); WO200271928 (Page 320-321); WO9410312 (Page 52-57);
Cross-references: MIM:601051; NP_005814.2; NM_005823_1
SEQ ID NO:5

(6) Napi3b (NAPI-3B, NPTIIb, SLC34A2, solute carrier family 34 (sodium phosphate), member 2, type II sodium-dependent phosphate transporter 3b, Genbank accession no. NM_006424) J. Biol. Chem. 277 (22):19665-19672 (2002), Genomics 62 (2):281-284 (1999), Feild, J. A., et al (1999) Biochem. Biophys. Res. Commun. 258 (3):578-582); WO2004022778 (claim 2); EP1394274 (Example 11); WO2002102235 (claim 13; Page 326); EP875569 (claim 1; Page 17-19); WO200157188 (claim 20; Page 329); WO2004032842 (Example IV); WO200175177 (claim 24; Page 139-140);
Cross-references: MIM:604217; NP_006415.1; NM_006424_1
SEQ ID NO:6

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878) Nagase T., et al (2000) DNA Res. 7 (2):143-150); WO2004000997 (claim 1); WO2003003984 (claim 1); WO200206339 (claim 1; Page 50); WO200188133 (claim 1; Page 41-43, 48-58); WO2003054152 (claim 20); WO2003101400 (claim 11);
Accession: Q9P283; EMBL; AB040878; BAA95969.1. Genew; HGNC:10737;
SEQ ID NO:7

(8) PSCA hlg (2700050C12Rik, C530008O16Rik, RIKEN cDNA 2700050C12, RIKEN cDNA 2700050C12 gene, Genbank accession no. AY358628);
US2003129192 (claim 2); US2004044180 (claim 12); US2004044179 (claim 11); US2003096961 (claim 11); US2003232056 (Example 5); WO2003105758 (claim 12); US2003206918 (Example 5); EP1347046 (claim 1); WO2003025148 (claim 20); Cross-references: GI:37182378; AAQ88991.1; AY358628_1
SEQ ID NO:8

Figure 6:
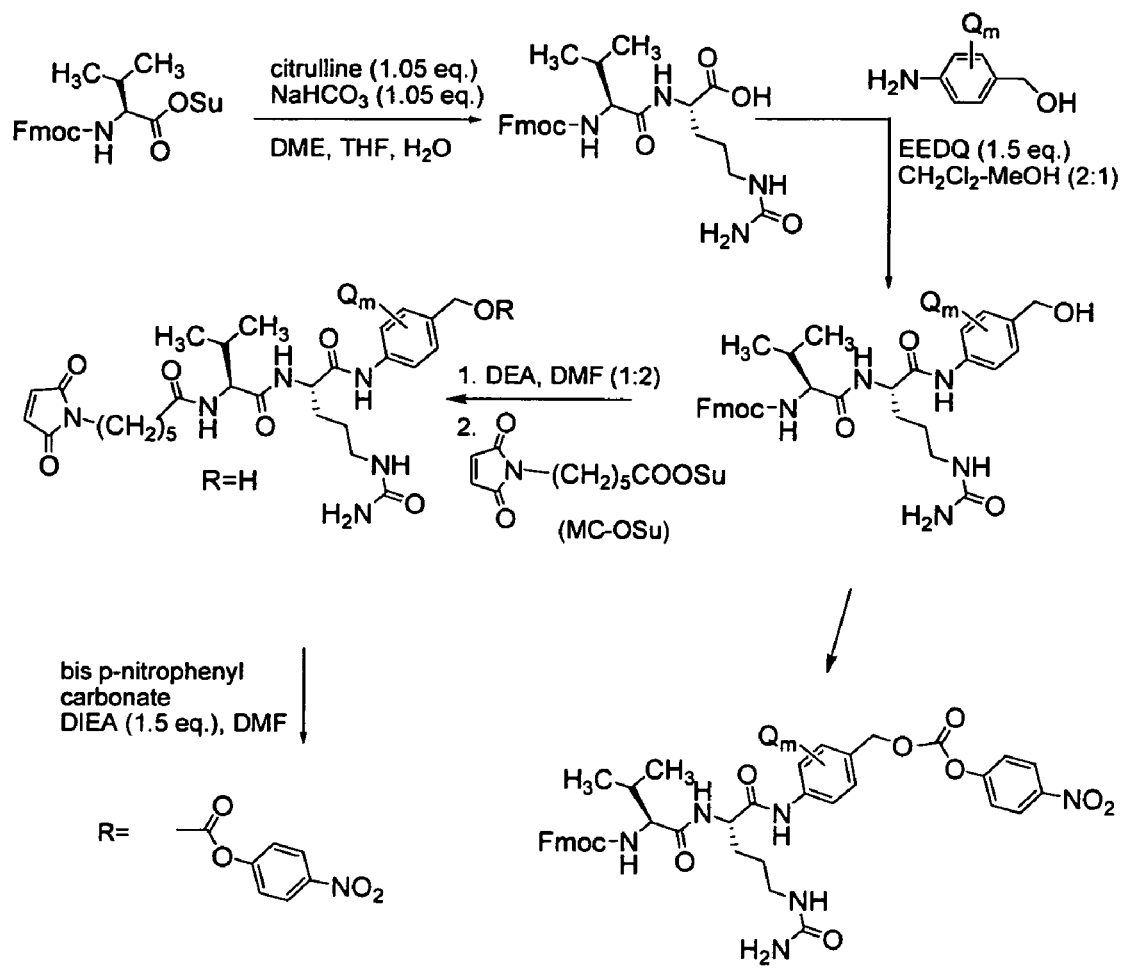
FIG. 6 shows a method for preparing a valine-citrulline (val-cit or vc) dipeptide Linker having a maleimide Stretcher and optionally a p-aminobenzyloxycarbonyl (PAB) self-immolative Spacer where Q is —$C_1$-$C_8$ alkyl, —O—($C_1$-$C_8$ alkyl), -halogen, -nitro or -cyano; and m is an integer ranging from 0-4.

(9) ETBR (Endothelin type B receptor, Genbank accession no. AY275463);
Nakamuta M., et al Biochem. Biophys. Res. Commun. 177, 34-39, 1991; Ogawa Y., et al Biochem. Biophys. Res. Commun. 178, 248-255, 1991; Arai H., et al Jpn. Circ. J. 56, 1303-1307, 1992; Arai H., et al J. Biol. Chem. 268, 3463-3470, 1993; Sakamoto A., Yanagisawa M., et al Biochem. Biophys. Res. Commun. 178, 656-663, 1991; Elshourbagy N. A., et al J. Biol. Chem. 268, 3873-3879, 1993; Haendler B., et al J. Cardiovasc. Pharmacol. 20, s1-S4, 1992; Tsutsumi M., et al Gene 228, 43-49, 1999; Strausberg R. L., et al Proc. Natl. Acad. Sci. U.S.A. 99, 16899-16903, 2002; Bourgeois C., et al J. Clin. Endocrinol. Metab. 82, 3116-3123, 1997; Okamoto Y., et al Biol. Chem. 272, 21589-21596, 1997; Verheij J. B., et al Am. J. Med. Genet. 108, 223-225, 2002; Hofstra R. M. W., et al Eur. J. Hum. Genet. 5, 180-185, 1997; Puffenberger E. G., et al Cell 79, 1257-1266, 1994; Attie T., et al, Hum Mol. Genet. 4, 2407-2409, 1995; Auricchio A., et al Hum. Mol. Genet. 5:351-354, 1996; Amiel J., et al Hum. Mol. Genet. 5, 355-357, 1996; Hofstra R. M. W., et al Nat. Genet. 12, 445-447, 1996; Svensson P. J., et al Hum. Genet. 103, 145-148, 1998; Fuchs S., et al Mol. Med. 7, 115-124, 2001; Pingault V., et al (2002) Hum. Genet. 111, 198-206; WO2004045516 (claim 1); WO2004048938 (Example 2); WO2004040000 (claim 151); WO2003087768 (claim 1); WO2003016475 (claim 1); WO2003016475 (claim 1); WO200261087 (FIG. 1); WO2003016494 (FIG. 6); WO2003025138 (claim 12; Page 144); WO200198351 (claim 1; Page 124-125); EP522868 (claim 8; FIG. 2); WO200177172 (claim 1; Page 297-299); US2003109676; U.S. Pat. No. 6,518,404 (FIG. 3); U.S. Pat. No. 5,773,223 (Claim 1a; Col 31-34); WO2004001004;
SEQ ID NO:9

(10) MSG783 (RNF124, hypothetical protein FLJ20315, Genbank accession no. NM_017763); WO2003104275 (claim 1); WO2004046342 (Example 2); WO2003042661 (claim 12); WO2003083074 (claim 14; Page 61); WO2003018621 (claim 1); WO2003024392 (claim 2; FIG. 93); WO200166689 (Example 6);
Cross-references: LocusID:54894; NP_060233.2; NM_017763_1
SEQ ID NO:10

Figure 10:
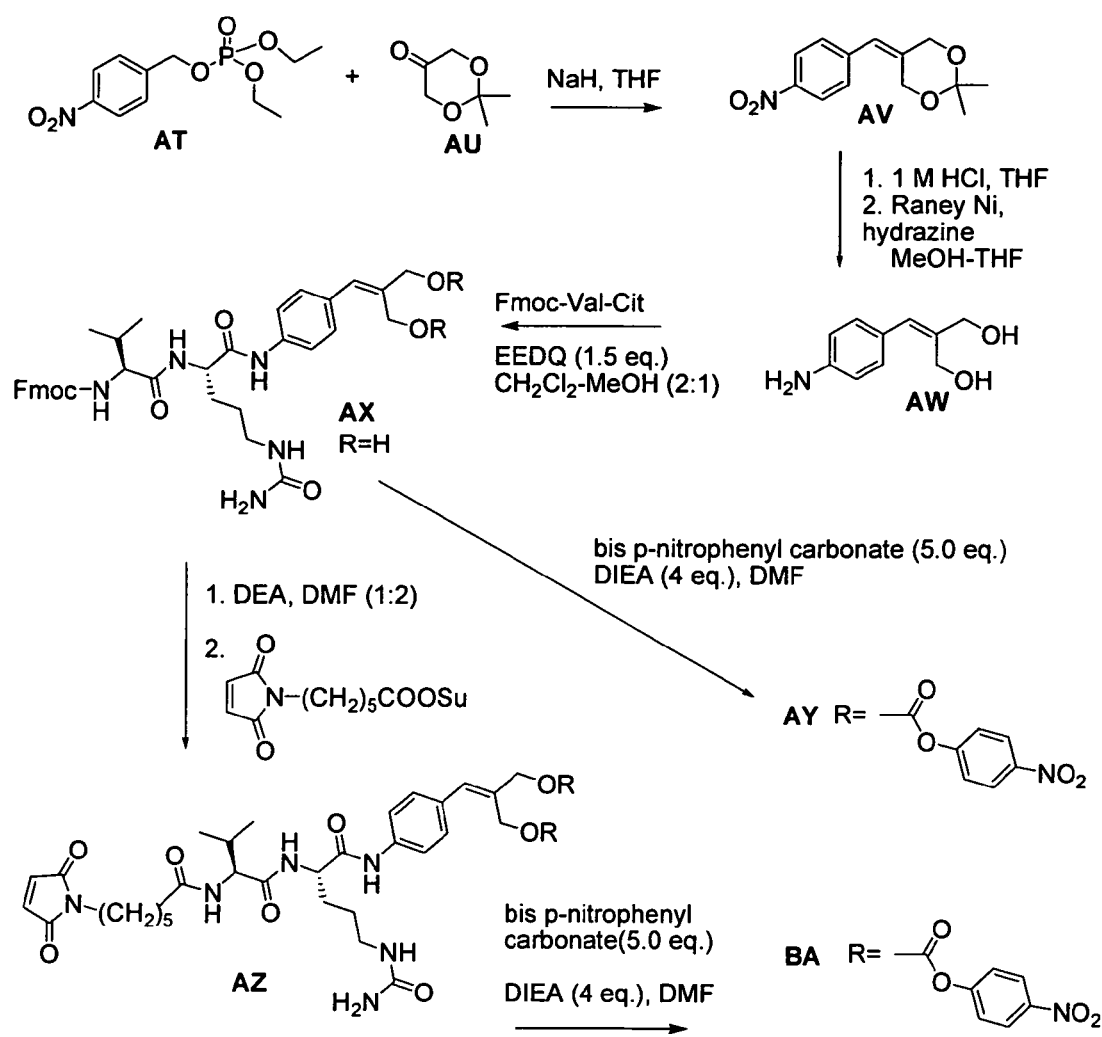
FIG. 10 shows a method for the synthesis of a branched linker reagent containing a BHMS group.

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138) Lab. Invest. 82 (11):1573-1582 (2002)); WO2003087306; US2003064397 (claim 1; FIG. 1); WO200272596 (claim 13; Page 54-55); WO200172962 (claim 1; FIG. 4B); WO2003104270 (claim 11); WO2003104270 (claim 16); US2004005598 (claim 22); WO2003042661 (claim 12); US2003060612 (claim 12; FIG. 10); WO200226822 (claim 23; FIG. 2); WO200216429 (claim 12; FIG. 10);
Cross-references: GI:22655488; AAN04080.1; AF455138_1
SEQ ID NO:11

(12) TrpM4 (BR22450, FLJ20041, TRPM4, TRPM4B, transient receptor potential cation channel, subfamily M, member 4, Genbank accession no. NM_017636) Xu, X. Z., et al Proc. Natl. Acad. Sci. U.S.A. 98 (19):10692-10697 (2001), Cell 109 (3):397-407 (2002), J. Biol. Chem. 278 (33): 30813-30820 (2003)); US2003143557 (claim 4); WO200040614 (claim 14; Page 100-103); WO200210382 (claim 1; FIG. 9A); WO2003042661 (claim 12); WO200230268 (claim 27; Page 391); US2003219806 (claim 4); WO200162794 (claim 14; FIG. 1A-D);
Cross-references: MIM:606936; NP_060106.2; NM_017636_1
SEQ ID NO:12

(13) CRIPTO (CR, CR1, CRGF, CRIPTO, TDGF1, teratocarcinoma-derived growth factor, Genbank accession no. NP_003203 or NM_003212)
Ciccodicola, A., et al EMBO J. 8 (7):1987-1991 (1989), Am. J. Hum. Genet. 49 (3):555-565 (1991)); US2003224411 (claim 1); WO2003083041 (Example 1); WO2003034984 (claim 12); WO200288170 (claim 2; Page 52-53); WO2003024392 (claim 2; FIG. 58); WO200216413

(claim 1; Page 94-95, 105); WO200222808 (claim 2; FIG. 1); U.S. Pat. No. 5,854,399 (Example 2; Col 17-18); U.S. Pat. No. 5,792,616 (FIG. 2);
Cross-references: MIM:187395; NP_003203.1; NM_003212_1
SEQ ID NO:13

Figure 9:
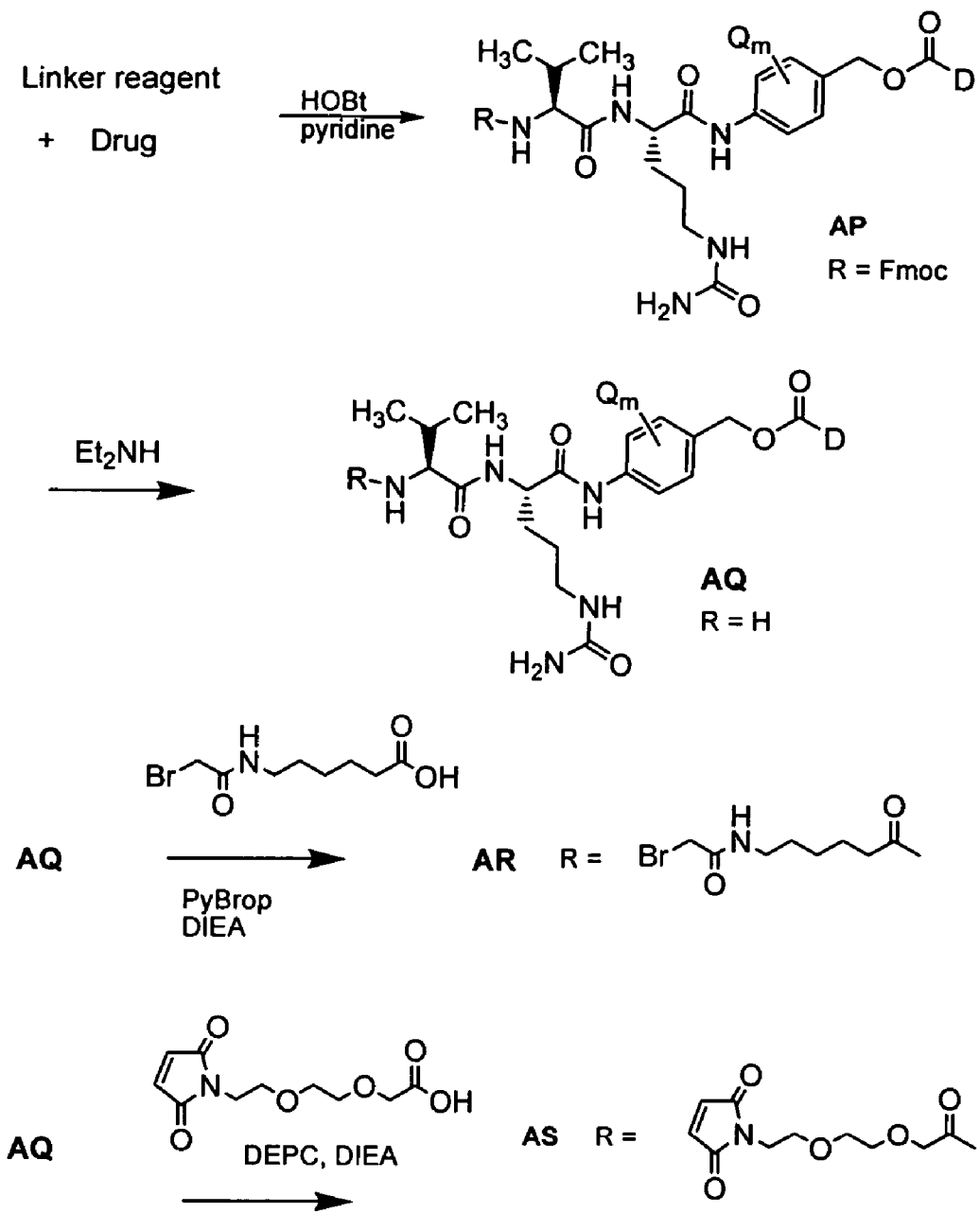
FIG. 9 shows a method for synthesis of a bis 1,8 naphthalimide-linker reagent.

(14) CD21 (CR2 (Complement receptor 2) or C3DR (C3d/Epstein Barr virus receptor) or Hs.73792 Genbank accession no. M26004)
Fujisaku et al (1989) J. Biol. Chem. 264 (4):2118-2125); Weis J. J., et al J. Exp. Med. 167, 1047-1066, 1988; Moore M., et al Proc. Natl. Acad. Sci. U.S.A. 84, 9194-9198, 1987; Bard M., et al Mol. Immunol. 35, 1025-1031, 1998; Weis J. J., et al Proc. Natl. Acad. Sci. U.S.A. 83, 5639-5643, 1986; Sinha S. K., et al (1993) J. Immunol. 150, 5311-5320; WO2004045520 (Example 4); US2004005538 (Example 1); WO2003062401 (claim 9); WO2004045520 (Example 4); WO9102536 (FIG. 9.1-9.9); WO2004020595 (claim 1);
Accession: P20023; Q13866; Q14212; EMBL; M26004; AAA35786.1.
SEQ ID NO:14

(15) CD79b (CD79B, CD79β, IGb (immunoglobulin-associated beta), B29, Genbank accession no. NM_000626 or 11038674)
Proc. Natl. Acad. Sci. U.S.A. (2003) 100 (7):4126-4131, Blood (2002) 100 (9):3068-3076, Muller et al (1992) Eur. J. Immunol. 22 (6):1621-1625); WO2004016225 (claim 2, FIG. 140); WO2003087768, US2004101874 (claim 1, page 102); WO2003062401 (claim 9); WO200278524 (Example 2); US2002150573 (claim 5, page 15); U.S. Pat. No. 5,644,033; WO2003048202 (claim 1, pages 306 and 309); WO 99/558658, U.S. Pat. No. 6,534,482 (claim 13, FIG. 17A/B); WO200055351 (claim 11, pages 1145-1146);
Cross-references: MIM:147245; NP_000617.1; NM_000626_1
SEQ ID NO:15

(16) FcRH2 (IFGP4, IRTA4, SPAP1A (SH2 domain containing phosphatase anchor protein 1a), SPAP1B, SPAP1C, Genbank accession no. NM_030764)
Genome Res. 13 (10):2265-2270 (2003), Immunogenetics 54 (2):87-95 (2002), Blood 99 (8):2662-2669 (2002), Proc. Natl. Acad. Sci. U.S.A. 98 (17):9772-9777 (2001), Xu, M. J., et al (2001) Biochem. Biophys. Res. Commun. 280 (3):768-775; WO2004016225 (claim 2); WO2003077836; WO200138490 (claim 5; FIGS. 18D-1-18D-2); WO2003097803 (claim 12); WO2003089624 (claim 25);
Cross-references: MIM:606509; NP_110391.2; NM_030764_1
SEQ ID NO:16

Figure 7:
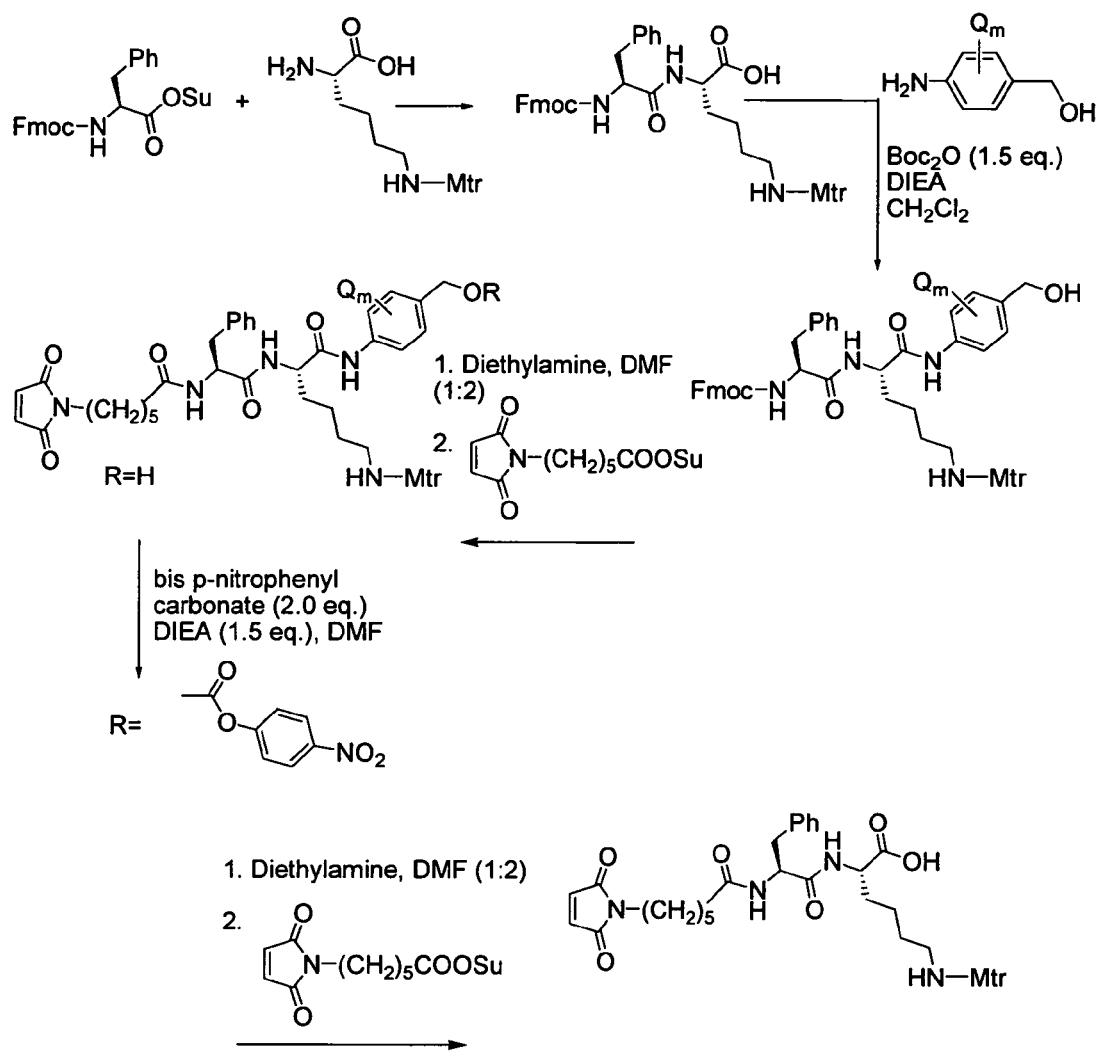
FIG. 7 shows a method for preparing a phe-lys(Mtr) dipeptide linker reagent having a maleimide Stretcher unit and a p-aminobenzyl self-immolative Spacer unit, where Q is —$C_1$-$C_8$ alkyl, —O—($C_1$-$C_8$ alkyl), -halogen, -nitro or -cyano; and m is an integer ranging from 0-4.

(17) HER2 (ErbB2, Genbank accession no. M11730)
Coussens L., et al Science (1985) 230(4730):1132-1139); Yamamoto T., et al Nature 319, 230-234, 1986; Semba K., et al Proc. Natl. Acad. Sci. U.S.A. 82, 6497-6501, 1985; Swiercz J. M., et al J. Cell Biol. 165, 869-880, 2004; Kuhns J. J., et al J. Biol. Chem. 274, 36422-36427, 1999; Cho H.-S., et al Nature 421, 756-760, 2003; Ehsani A., et al (1993) Genomics 15, 426-429; WO2004048938 (Example 2); WO2004027049 (FIG. 1I); WO2004009622; WO2003081210; WO2003089904 (claim 9); WO2003016475 (claim 1); US2003118592; WO2003008537 (claim 1); WO2003055439 (claim 29; FIG. 1A-B); WO2003025228 (claim 37; FIG. 5C); WO200222636 (Example 13; Page 95-107); WO200212341 (claim 68; FIG. 7); WO200213847 (Page 71-74); WO200214503 (Page 114-117); WO200153463 (claim 2; Page 41-46); WO200141787 (Page 15); WO200044899 (claim 52; FIG. 7); WO200020579 (claim 3; FIG. 2); U.S. Pat. No. 5,869,445 (claim 3; Col 31-38); WO9630514 (claim 2; Page 56-61); EP1439393 (claim 7); WO2004043361 (claim 7); WO2004022709; WO200100244 (Example 3; FIG. 4);
Accession: P04626; EMBL; M11767; AAA35808.1. EMBL; M11761; AAA35808.1.
SEQ ID NO:17

(18) NCA (CEACAM6, Genbank accession no. M18728); Barnett T., et al Genomics 3, 59-66, 1988; Tawaragi Y., et al Biochem. Biophys. Res. Commun. 150, 89-96, 1988; Strausberg R. L., et al Proc. Natl. Acad. Sci. U.S.A. 99:16899-16903, 2002; WO2004063709; EP1439393 (claim 7); WO2004044178 (Example 4); WO2004031238; WO2003042661 (claim 12); WO200278524 (Example 2); WO200286443 (claim 27; Page 427); WO200260317 (claim 2);
Accession: P40199; Q14920; EMBL; M29541; AAA59915.1. EMBL; M18728;
SEQ ID NO:18

Figure 8:
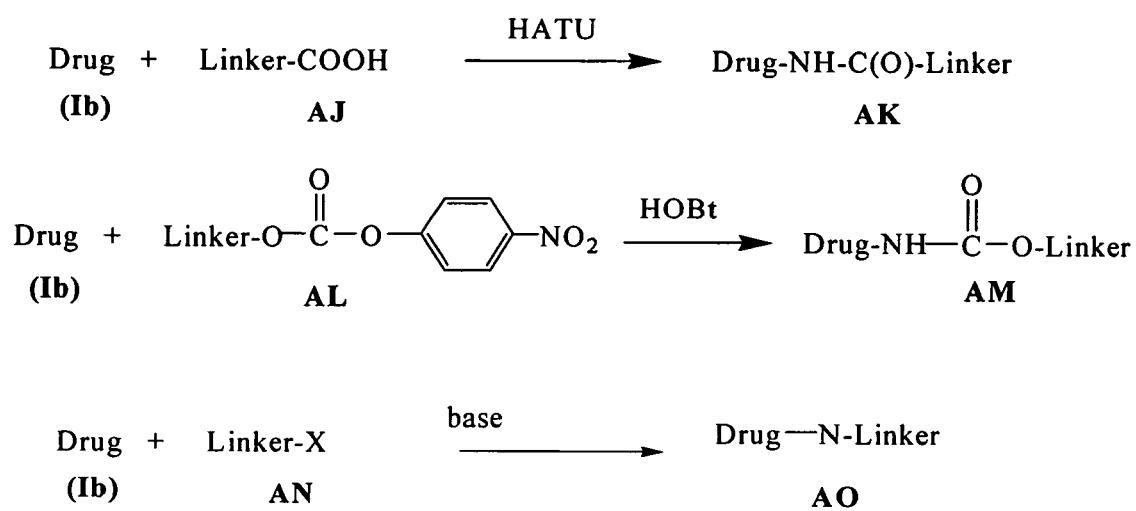
FIG. 8 shows three exemplary strategies for covalent attachment of the amino group of a drug moiety to a linker reagent to form a bis 1,8 naphthalimide-linker reagent.

(19) MDP (DPEP1, Genbank accession no. BC017023)
Proc. Natl. Acad. Sci. U.S.A. 99 (26):16899-16903 (2002)); WO2003016475 (claim 1); WO200264798 (claim 33; Page 85-87); JP05003790 (FIGS. 6-8); WO9946284 (FIG. 9);
Cross-references: MIM:179780; AAH17023.1; BC017023_1
SEQ ID NO:19

(20) IL20Rα (IL20Ra, ZCYTOR7, Genbank accession no. AF184971);
Clark H. F., et al Genome Res. 13, 2265-2270, 2003; Mungall A. J., et al Nature 425, 805-811, 2003; Blumberg H., et al Cell 104, 9-19, 2001; Dumoutier L., et al J. Immunol. 167, 3545-3549, 2001; Parrish-Novak J., et al J. Biol. Chem. 277, 47517-47523, 2002; Pletnev S., et al (2003) Biochemistry 42:12617-12624; Sheikh F., et al (2004) J. Immunol. 172, 2006-2010; EP1394274 (Example 11); US2004005320 (Example 5); WO2003029262 (Page 74-75); WO2003002717 (claim 2; Page 63); WO200222153 (Page 45-47); US2002042366 (Page 20-21); WO200146261 (Page 57-59); WO200146232 (Page 63-65); WO9837193 (claim 1; Page 55-59);
Accession: Q9UHF4; Q6UWA9; Q96SH8; EMBL; AF184971; AAF01320.1.
SEQ ID NO:20

(21) Brevican (BCAN, BEHAB, Genbank accession no. AF229053)
Gary S. C., et al Gene 256, 139-147, 2000; Clark H. F., et al Genome Res. 13, 2265-2270, 2003; Strausberg R. L., et al Proc. Natl. Acad. Sci. U.S.A. 99, 16899-16903, 2002; US2003186372 (claim 11); US2003186373 (claim 11); US2003119131 (claim 1; FIG. 52); US2003119122 (claim 1; FIG. 52); US2003119126 (claim 1); US2003119121 (claim 1; FIG. 52); US2003119129 (claim 1); US2003119130 (claim 1); US2003119128 (claim 1; FIG. 52); US2003119125 (claim 1); WO2003016475 (claim 1); WO200202634 (claim 1);
SEQ NO:21

(22) EphB2R (DRT, ERK, HekS, EPHT3, Tyro5, Genbank accession no. NM_004442) Chan, J. and Watt, V. M., Oncogene 6 (6), 1057-1061 (1991) Oncogene 10 (5):897-905 (1995), Annu. Rev. Neurosci. 21:309-345 (1998), Int. Rev. Cytol. 196:177-244 (2000)); WO2003042661 (claim 12); WO200053216 (claim 1; Page 41); WO2004065576 (claim 1); WO2004020583 (claim 9); WO2003004529 (Page 128-132); WO200053216 (claim 1; Page 42);

Cross-references: MIM:600997; NP_004433.2; NM_004442_1
SEQ ID NO:22

(23) ASLG659 (B7h, Genbank accession no. AX092328)
US20040101899 (claim 2); WO2003104399 (claim 11); WO2004000221 (FIG. 3); US2003165504 (claim 1); US2003124140 (Example 2); US2003065143 (FIG. 60); WO2002102235 (claim 13; Page 299); US2003091580 (Example 2); WO200210187 (claim 6; FIG. 10); WO200194641 (claim 12; FIG. 7b); WO200202624 (claim 13; FIGS. 1A-1B); US2002034749 (claim 54; Page 45-46); WO200206317 (Example 2; Page 320-321, claim 34; Page 321-322); WO200271928 (Page 468-469); WO200202587 (Example 1; FIG. 1); WO200140269 (Example 3; Pages 190-192); WO200036107 (Example 2; Page 205-207); WO2004053079 (claim 12); WO2003004989 (claim 1); WO200271928 (Page 233-234, 452-453); WO 0116318;
SEQ ID NO:23

(24) PSCA (Prostate stem cell antigen precursor, Genbank accession no. AJ297436) Reiter R. E., et al Proc. Natl. Acad. Sci. U.S.A. 95, 1735-1740, 1998; Gu Z., et al Oncogene 19, 1288-1296, 2000; Biochem. Biophys. Res. Commun. (2000) 275 (3):783-788; WO2004022709; EP1394274 (Example 11); US2004018553 (claim 17); WO2003008537 (claim 1); WO200281646 (claim 1; Page 164); WO2003003906 (claim 10; Page 288); WO200140309 (Example 1; FIG. 17); US2001055751 (Example 1; FIG. 1b); WO200032752 (claim 18; FIG. 1); WO9851805 (claim 17; Page 97); WO9851824 (claim 10; Page 94); WO9840403 (claim 2; FIG. 1B);
Accession: O43653; EMBL; AF043498; AAC39607.1.
SEQ ID NO:24

(25) GEDA (Genbank accession No. AY260763);
AAP14954 lipoma HMGIC fusion-partner-like protein/pid=AAP14954.1—Homo sapiens Species: Homo sapiens (human)
WO2003054152 (claim 20); WO2003000842 (claim 1); WO2003023013 (Example 3, claim 20); US2003194704 (claim 45);
Cross-references: GI:30102449; AAP14954.1; AY260763_1
SEQ ID NO:25

(26) BAFF-R (B cell-activating factor receptor, BLyS receptor 3, BR3, Genbank accession No. NP_443177.1);
NP_443177 BAFF receptor/pid=NP_443177.1—Homo sapiens Thompson, J. S., et al Science 293 (5537), 2108-2111 (2001); WO2004058309; WO2004011611; WO2003045422 (Example; Page 32-33); WO2003014294 (claim 35; FIG. 6B); WO2003035846 (claim 70; Page 615-616); WO200294852 (Col 136-137); WO200238766 (claim 3; Page 133); WO200224909 (Example 3; FIG. 3);
Cross-references: MIM:606269; NP_443177.1; NM_052945_1
SEQ ID NO:26

(27) CD22 (B-cell receptor CD22-B isoform, Genbank accession No. NP-001762.1); Stamenkovic, I. and Seed, B., Nature 345 (6270), 74-77 (1990); US2003157113; US2003118592; WO2003062401 (claim 9); WO2003072036 (claim 1; FIG. 1); WO200278524 (Example 2); Cross-references: MIM:107266; NP_001762.1; NM_001771_1
SEQ ID NO:27

(28) CD79a (CD79A, CD79a, immunoglobulin-associated alpha, a B cell-specific protein that covalently interacts with Ig beta (CD79B) and forms a complex on the surface with Ig M molecules, transduces a signal involved in B-cell differentiation) 226 aa, pI: 4.84, MW: 25028 TM: 2 [P] Gene Chromosome: 19q13.2, Genbank accession No. NP_001774.10) WO2003088808, US20030228319; WO2003062401 (claim 9); US2002150573 (claim 4, pages 13-14); WO9958658 (claim 13, FIG. 16); WO9207574 (FIG. 1); U.S. Pat. No. 5,644,033; Ha et al (1992) J. Immunol. 148(5):1526-1531; Mueller et al (1992) Eur. J. Biochem. 22:1621-1625; Hashimoto et al (1994) Immunogenetics 40(4):287-295; Preud'homme et al (1992) Clin. Exp. Immunol. 90(1):141-146; Yu et al (1992) J. Immunol. 148 (2) 633-637; Sakaguchi et al (1988) EMBO J. 7 (11):3457-3464;
SEQ ID NO:28

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia) 372 aa, pI: 8.54 MW: 41959 TM: 7 [P] Gene Chromosome: 11q23.3, Genbank accession No. NP_001707.1)
WO2004040000; WO2004015426; US2003105292 (Example 2); U.S. Pat. No. 6,555,339 (Example 2); WO200261087 (FIG. 1); WO200157188 (claim 20, page 269); WO200172830 (pages 12-13); WO200022129 (Example 1, pages 152-153, Example 2, pages 254-256); WO9928468 (claim 1, page 38); U.S. Pat. No. 5,440,021 (Example 2, col 49-52); WO9428931 (pages 56-58); WO9217497 (claim 7, FIG. 5); Dobner et al (1992) Eur. J. Immunol. 22:2795-2799; Barella et al (1995) Biochem. J. 309:773-779;
SEQ ID NO:29

(30) HLA-DOB (Beta subunit of MHC class II molecule (Ia antigen) that binds peptides and presents them to CD4+ T lymphocytes) 273 aa, pI: 6.56 MW: 30820 TM: 1 [P] Gene Chromosome: 6p21.3, Genbank accession No. NP_002111.1)
Tonnelle et al (1985) EMBO J. 4 (11):2839-2847; Jonsson et al (1989) Immunogenetics 29 (6):411-413; Beck et al (1992) J. Mol. Biol. 228:433-441; Strausberg et al (2002) Proc. Natl. Acad. Sci. USA 99:16899-16903; Servenius et al (1987) J. Biol. Chem. 262:8759-8766; Beck et al (1996) J. Mol. Biol. 255:1-13; Naruse et al (2002) Tissue Antigens 59:512-519; WO9958658 (claim 13, FIG. 15); U.S. Pat. No. 6,153,408 (Col 35-38); U.S. Pat. No. 5,976,551 (col 168-170); US6011146 (col 145-146); Kasahara et al (1989) Immunogenetics 30 (1):66-68; Larhammar et al (1985) J. Biol. Chem. 260 (26):14111-14119;
SEQ ID NO:30

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability) 422 aa, pI: 7.63, MW: 47206 TM: 1 [P] Gene Chromosome: 17p13.3, Genbank accession No. NP_002552.2)
Le et al (1997) FEBS Lett. 418 (1-2):195-199; WO2004047749; WO2003072035 (claim 10); Touchman et al (2000) Genome Res. 10:165-173; WO200222660 (claim 20); WO2003093444 (claim 1); WO2003087768 (claim 1); WO2003029277 (page 82);
SEQ ID NO:31

(32) CD72 (B-cell differentiation antigen CD72, Lyb-2) 359 aa, pI: 8.66, MW: 40225 TM: 1 [P] Gene Chromosome: 9p13.3, Genbank accession No. NP_001773.1)
WO2004042346 (claim 65); WO2003026493 (pages 51-52, 57-58); WO200075655 (pages 105-106); Von Hoegen et al (1990) J. Immunol. 144 (12):4870-4877; Strausberg et al (2002) Proc. Natl. Acad. Sci. USA 99:16899-16903;

SEQ ID NO:32

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis) 661 aa, pI: 6.20, MW: 74147 TM: 1 [α] Gene Chromosome: 5q12, Genbank accession No. NP_005573.1) US2002193567; WO9707198 (claim 11, pages 39-42); Miura et al (1996) Genomics 38 (3):299-304; Miura et al (1998) Blood 92:2815-2822; WO2003083047; WO9744452 (claim 8, pages 57-61); WO200012130 (pages 24-26);

SEQ ID NO:33

(34) FCRH1 (Fc receptor-like protein 1, a putative receptor for the immunoglobulin Fc domain that contains C2 type Ig-like and ITAM domains, may have a role in B-lymphocyte differentiation) 429 aa, pI: 5.28, MW: 46925 TM: 1 [P] Gene Chromosome: 1q21-1q22, Genbank accession No. NP_443170.1)

WO2003077836; WO200138490 (claim 6, FIGS. 18E-1-18-E-2); Davis et al (2001) Proc. Natl. Acad. Sci. USA 98 (17):9772-9777; WO2003089624 (claim 8); EP1347046 (claim 1); WO2003089624 (claim 7);

SEQ ID NO:34

(35) IRTA2 (Immunoglobulin superfamily receptor translocation associated 2, a putative immunoreceptor with possible roles in B cell development and lymphomagenesis; deregulation of the gene by translocation occurs in some B cell malignancies) 977 aa, pI: 6.88 MW: 106468 TM: 1 [P] Gene Chromosome: 1q21, Genbank accession No. NP_112571.1) WO2003024392 (claim 2, FIG. 97); Nakayama et al (2000) Biochem. Biophys. Res. Commun. 277 (1):124-127; WO2003077836; WO200138490 (claim 3, FIGS. 18B-1-18B-2);

SEQ ID NO:35

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436

WO2004074320; JP2004113151; WO2003042661; WO2003009814; EP1295944 (pages 69-70); WO200230268 (page 329); WO200190304; US2004249130; US2004022727; WO2004063355; US2004197325; US2003232350; US2004005563; US2003124579; Horie et al (2000) Genomics 67:146-152; Uchida et al (1999) Biochem. Biophys. Res. Commun. 266:593-602; Liang et al (2000) Cancer Res. 60:4907-12; Glynne-Jones et al (2001) Int J Cancer. October 15; 94 (2):178-84.

SEQ ID NO:36

For other tumor-associated antigens and specific antibodies thereto, see also: WO04/045516 (3 Jun. 2004); WO03/000113 (3 Jan. 2003); WO02/016429 (28 Feb. 2002); WO02/16581 (28 Feb. 2002); WO03/024392 (27 Mar. 2003); WO04/016225 (26 Feb. 2004); WO01/40309 (7 Jun. 2001); US 20050238650 A1; all of which are incorporated herein by reference in their entirety.

Production of Recombinant Antibodies

Antibodies of the invention can be produced using any method known in the art to be useful for the synthesis of antibodies, in particular, by chemical synthesis or by recombinant expression techniques.

Recombinant expression of antibodies, or fragment, derivative or analog thereof, may be conducted by assembling a nucleic acid encoding the antibody, if the nucleotide sequence of the antibody is known, from chemically synthesized oligonucleotides (e.g., as described in Kutmeier et al., 1994, BioTechniques 17:242). This method involves the synthesis of overlapping oligonucleotides containing portions of the sequence encoding the antibody, annealing and ligation of those oligonucleotides, and then amplification of the ligated oligonucleotides by PCR.

Alternatively, a nucleic acid molecule encoding an antibody can be generated from a suitable source. If a clone containing the nucleic acid encoding the particular antibody is not available, but the sequence of the antibody is known, a nucleic acid encoding the antibody can be obtained from a suitable source (e.g., an antibody cDNA library, or cDNA library generated from any tissue or cells expressing the immunoglobulin) by PCR amplification using synthetic primers hybridizable to the 3' and 5' ends of the sequence or by cloning using an oligonucleotide probe specific for the particular gene sequence.

If an antibody that specifically recognizes a particular antigen is not commercially available (or a source for a cDNA library for cloning a nucleic acid encoding such an immunoglobulin), antibodies specific for a particular antigen can be generated by any method known in the art, for example, by immunizing a patient, such as a rabbit, to generate polyclonal antibodies or, by generating monoclonal antibodies, e.g., as described by Kohler and Milstein (1975, Nature 256:495-497) or, as described by Kozbor et al. (1983, Immunology Today 4:72) or Cole et al. (1985 in *Monoclonal Antibodies and Cancer Therapy*, Alan R. Liss, Inc., pp. 77-96). Alternatively, a clone encoding at least the Fab portion of the antibody can be obtained by screening Fab expression libraries (e.g., as described in Huse et al., 1989, Science 246:1275-1281) for clones of Fab fragments that bind the specific antigen or by screening antibody libraries (See, e.g., Clackson et al., 1991, Nature 352:624; Hane et al., 1997 Proc. Natl. Acad. Sci. USA 94:4937).

Once a nucleic acid sequence encoding at least the variable domain of the antibody is obtained, it can be introduced into a vector containing the nucleotide sequence encoding the constant regions of the antibody (see, e.g., WO 86/05807; WO 89/01036; and U.S. Pat. No. 5,122,464). Vectors containing the complete light or heavy chain that allow for the expression of a complete antibody molecule are available. Then, the nucleic acid encoding the antibody can be used to introduce the nucleotide substitutions or deletion necessary to substitute (or delete) the one or more variable region cysteine residues participating in an intrachain disulfide bond with an amino acid residue that does not contain a sulfhydyl group. Such modifications can be carried out by any method known in the art for the introduction of specific mutations or deletions in a nucleotide sequence, for example, but not limited to, chemical mutagenesis and in vitro site directed mutagenesis (Hutchinson et al., 1978, *J. Biol. Chem.* 253:6551).

In addition, techniques developed for the production of "chimeric antibodies" (Morrison et al., 1984, *Proc. Natl. Acad. Sci.* 81:851-855; Neuberger et al., 1984, *Nature* 312: 604-608; Takeda et al., 1985, *Nature* 314:452-454) by splicing genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine monoclonal antibody and a human immunoglobulin constant region, e.g., humanized antibodies.

Alternatively, techniques described for the production of single chain antibodies (U.S. Pat. No. 4,694,778; Bird, 1988, Science 242:423-42; Huston et al., 1988, Proc. Natl. Acad. Sci. USA 85:5879-5883; and Ward et al., 1989, Nature 334: 544-54) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., 1988, Science 242:1038-1041).

Antibody fragments that recognize specific epitopes can be generated by known techniques. For example, such fragments include, but are not limited to, the F(ab')2 fragments that can be produced by pepsin digestion of the antibody molecule and the Fab fragments that can be generated by reducing the disulfide bridges of the F(ab')2 fragments.

Once a nucleic acid sequence encoding an antibody has been obtained, the vector for the production of the antibody can be produced by recombinant DNA technology using techniques well known in the art. Methods that are well known to those skilled in the art can be used to construct expression vectors containing the antibody coding sequences and appropriate transcriptional and translational control signals. These methods include, for example, in vitro recombinant DNA techniques, synthetic techniques, and in vivo genetic recombination. See, for example, the techniques described in Sambrook et al. (1990, *Molecular Cloning, A Laboratory Manual*, $2^{nd}$ Ed., Cold Spring Harbor Laboratory, Cold Spring Harbor, N.Y.) and Ausubel et al. (eds., 1998, *Current Protocols in Molecular Biology*, John Wiley & Sons, NY).

Polyclonal antibodies may be raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies. For example, the monoclonal antibodies may be made using the hybridoma method first described by Kohler et al., *Nature*, 256:495 (1975), or may be made by recombinant DNA methods (U.S. Pat. No. 4,816,567). Lymphocytes then are fused with myeloma cells using a suitable fusing agent, such as polyethylene glycol, to form a hybridoma cell (Goding, *Monoclonal Antibodies: Principles and Practice*, pp. 59-103, Academic Press, 1986). Review articles on recombinant expression in bacteria of DNA encoding the antibody include Skerra et al., *Curr. Opinion in Immunol.*, 5:256-262 (1993) and Plückthun, *Immunol. Revs.*, 130:151-188 (1992).

Monoclonal antibodies or antibody fragments can be isolated from antibody phage libraries generated using the techniques described in McCafferty et al (1990) Nature 348:552-554; Clackson et al (1991) Nature, 352:624-628; and Marks et al (1991) J. Mol. Biol. 222:581-597. Subsequent publications describe the production of high affinity (nm range) human antibodies by chain shuffling (Marks et al (1992) Bio/Technology, 10:779-783) as well as combinatorial infection and in vivo recombination as a strategy for constructing very large phage libraries (Waterhouse et al (1993) Nuc. Acids. Res., 21:2265-2266). Thus, these techniques are viable alternatives to traditional monoclonal antibody hybridoma techniques for isolation of monoclonal antibodies.

The DNA also may be modified, for example, by substituting the coding sequence for human heavy chain and light chain constant domains in place of the homologous murine sequences (U.S. Pat. No. 4,816,567; and Morrison, et al (1984) Proc. Natl Acad. Sci. USA 81:6851), or by covalently joining to the immunoglobulin coding sequence all or part of the coding sequence for a non-immunoglobulin polypeptide.

Humanization can be performed by substituting hypervariable region sequences for the corresponding sequences of a human antibody (Jones et al (1986) Nature 321:522-525; Riechmann et al (1988) Nature 332:323-327; Verhoeyen et al (1988) Science 239:1534-1536). Accordingly, such "humanized" antibodies are chimeric antibodies (U.S. Pat. No. 4,816, 567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies (Sims et al (1993) J. Immunol., 151:2296; Chothia et al (1987) J. Mol. Biol., 196:901; Carter et al (1992) Proc. Natl. Acad. Sci. USA, 89:4285; Presta et al., (1993) J. Immunol., 151:2623).

Various forms of the humanized antibody are contemplated. For example, the humanized antibody may be an antibody fragment, such as a Fab. Alternatively, the humanized antibody may be an intact antibody, such as an intact IgG1 antibody. The murine monoclonal antibody 4D5 which specifically binds the extracellular domain of ErbB2 is produced, as described in Fendly et al (1990) Cancer Research 50:1550-1558, from NIH 3T3/HER2-$3_{400}$ cells (expressing approximately $1\times10^5$ ErbB2 molecules/cell), as described in Hudziak et al (1987) Proc. Natl. Acad. Sci. (USA) 84:7158-7163 and harvested with phosphate buffered saline (PBS) containing 25 mM EDTA and used to immunize BALB/c mice. Hybridoma supernatants were screened for ErbB2-binding by ELISA and radioimmunoprecipitation.

As an alternative to humanization, human antibodies can be generated (Jakobovits et al (1993) Proc. Natl. Acad. Sci. USA, 90:2551; Jakobovits et al (1993) Nature, 362:255-258; Bruggermann et al (1993) Year in Immuno. 7:33; and U.S. Pat. No. 5,591,669, U.S. Pat. No. 5,589,369, U.S. Pat. No. 5,545,807).

Alternatively, phage display technology (McCafferty et al., (1990) Nature 348:552-553) can be used to produce human antibodies and antibody fragments in vitro, from immunoglobulin variable (V) domain gene repertoires from unimmunized donors (Johnson, Kevin S. and Chiswell, David J., (1993) Current Opinion in Structural Biology 3:564-571; Clackson et al (1991) Nature, 352:624-628). Human antibodies may also be generated by in vitro activated B cells (see U.S. Pat. No. 5,567,610 and U.S. Pat. No. 5,229,275). Human anti-ErbB2 antibodies are described in U.S. Pat. No. 5,772, 997 and WO 97/00271.

Various techniques have been developed for the production of antibody fragments (Morimoto et al (1992) Journal of Biochem. and Biophys. Methods 24:107-117; and Brennan et al (1985) Science, 229:81; Carter et al (1992) Bio/Technology 10:163-167; WO 93/16185; U.S. Pat. No. 5,571,894; U.S. Pat. No. 5,587,458; U.S. Pat. No. 5,641,870).

Amino acid sequence modification(s) of the antibodies described herein are contemplated. For example, it may be desirable to improve the binding affinity and/or other biological properties of the antibody. Amino acid sequence variants are prepared by introducing appropriate nucleotide changes into the antibody expressing nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid changes also may alter post-translational processes of the antibody, such as changing the number or position of glycosylation sites.

A useful method for identification of certain residues or regions of an antibody that are preferred locations for mutagenesis is called "alanine scanning mutagenesis" (Cunningham and Wells (1989) Science, 244:1081-1085. Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an N-terminal methionyl residue or the antibody fused to a cytotoxic polypeptide. Other insertional variants include the fusion to the N- or C-terminus of the antibody to an enzyme (e.g. for ADEPT) or a polypeptide which increases the serum half-life of the antibody.

Peptide sequences which specifically bind to albumin may be fused or conjugated to the antibody which comprises the antibody drug conjugates (ADC). Plasma-protein binding can be an effective means of improving the pharmacokinetic properties of short lived molecules, such as antibodies or ADC. Serum albumin binding peptides (ABP) can alter the pharmacodynamics of fused active domain proteins, including alteration of tissue uptake, clearance, penetration, and diffusion, and increase serum half life. These pharmacodynamic parameters can be modulated by specific selection of the appropriate serum albumin binding peptide sequence (US 20040001827 at [0076]). A series of albumin binding peptides were identified by phage display screening (Dennis et al. (2002) J Biol Chem. 277:35035-35043 at Tables III and IV, page 35038; WO 01/45746); and WO 01/45746 at pages 12-13, all of which are incorporated herein by reference.

Another type of variant is an amino acid substitution variant. The sites of greatest interest for substitutional mutagenesis include the hypervariable regions, but FR alterations are also contemplated.

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

It may be desirable to modify the antibody of the invention with respect to effector function, e.g. so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al J. Exp Med. 176:1191-1195 (1992) and Shopes, B. J. Immunol. 148:2918-2922 (1992). Homodimeric antibodies with enhanced anti-tumor activity may also be prepared using heterobifunctional cross-linkers as described in Wolff et al. Cancer Research 53:2560-2565 (1993). Alternatively, an antibody can be engineered which has dual Fc regions and may thereby have enhanced complement lysis and ADCC capabilities. See Stevenson et al. Anti-Cancer Drug Design 3:219-230 (1989).

To increase the serum half life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

Some antibodies are glycosylated at conserved positions in their constant regions (Jefferis and Lund, (1997) Chem. Immunol. 65:111-128; Wright and Morrison, (1997) TibTECH 15:26-32). The oligosaccharide side chains of the immunoglobulins affect protein function (Boyd et al., (1996) Mol. Immunol. 32:1311-1318; Wittwe and Howard, (1990) Biochem. 29:4175-4180), and the intramolecular interaction between portions of the glycoprotein which can affect the conformation and presented three-dimensional surface of the glycoprotein (Hefferis and Lund, supra; Wyss and Wagner, (1996) Current Opin. Biotech. 7:409-416; Malhotra et al., (1995) Nature Med. 1:237-243; Hse et al., (1997) J. Biol. Chem. 272:9062-9070; U.S. Pat. No. 5,047,335; U.S. Pat. No. 5,510,261; U.S. Pat. No. 5,278,299).

Synthesis of Antibody Drug Conjugates

The Antibody Drug Conjugates (ADC) of the Invention can be made using the synthetic procedures outlined below. ADC can be conveniently prepared using a Linker having a reactive site for binding to the Drug and Antibody. In one aspect, a Linker has a reactive site which has an electrophilic group that is reactive to a nucleophilic group present on an antibody. Useful nucleophilic groups on an antibody include but are not limited to, sulfhydryl, hydroxyl and amino groups. The heteroatom of the nucleophilic group of an antibody is reactive to an electrophilic group on a Linker and forms a covalent bond to a Linker unit. Useful electrophilic groups include, but are not limited to, maleimide and haloacetamide groups. The electrophilic group provides a convenient site for Antibody attachment.

In another embodiment, a Linker has a reactive site which has a nucleophilic group that is reactive to an electrophilic group present on an antibody. Useful electrophilic groups on an antibody include, but are not limited to, aldehyde and ketone carbonyl groups. The heteroatom of a nucleophilic group of a Linker can react with an electrophilic group on an antibody and form a covalent bond to an antibody unit. Useful nucleophilic groups on a Linker include, but are not limited to, hydrazide, oxime, amino, hydrazine, thiosemicarbazone, hydrazine carboxylate, and arylhydrazide. The electrophilic group on an antibody provides a convenient site for attachment to a Linker.

Carboxylic acid functional groups and chloroformate functional groups are also useful reactive sites for a Linker because they can react with secondary amino groups of a Drug to form an amide linkage. Also useful as a reactive site is a carbonate functional group on a Linker, such as but not limited to p-nitrophenyl carbonate, which can react with an amino group of a Drug, such as but not limited to N-methyl valine, to form a carbamate linkage. Typically, peptide-based Drugs can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, 1965, Academic Press) that is well known in the field of peptide chemistry.

As described in more detail below, the ADC of the Invention are conveniently prepared using a Linker having two or more reactive functional groups for binding to the Drug and Antibody. In one aspect of the invention, a Linker has an electrophilic group that is reactive with a nucleophilic group present on an antibody. Useful nucleophilic groups on a Antibody include but are not limited to, sulfhydryl, hydroxyl and amino groups. The heteroatom of the nucleophilic group of an antibody is reactive to an electrophilic group on a Linker and forms a covalent bond to a Linker unit. Useful electrophilic groups include, but are not limited to, maleimide, carbonate, and haloacetamide groups. The electrophilic group provides a convenient site for Antibody attachment.

In another embodiment, a Linker has a reactive functional group which has a nucleophilic group that is reactive to an electrophilic group present on an antibody. Useful electrophilic groups on an Antibody include, but are not limited to, aldehyde and ketone carbonyl groups. The heteroatom of a nucleophilic group of a Linker can react with an electrophilic group on an antibody and form a covalent bond to an antibody unit. Useful nucleophilic groups on a Linker include, but are not limited to, hydrazide, oxime, amino, hydrazine, thiosemicarbazone, hydrazine carboxylate, and arylhydrazide. The electrophilic group on an antibody provides a convenient site for attachment to a Linker.

Typically, peptide-type Linkers can be prepared by forming a peptide bond between two or more amino acids and/or peptide fragments. Such peptide bonds can be prepared, for example, according to the liquid phase synthesis method (see E. Schröder and K. Lübke, "The Peptides", volume 1, pp 76-136, (1965), Academic Press) that is well known in the field of peptide chemistry.

Linker intermediates may be assembled with any combination or sequence of reactions including Spacer, Stretcher, and Amino Acid units. The Spacer, Stretcher, and Amino Acid units may employ reactive functional groups which are electrophilic, nucleophilic, free radical in nature. Reactive functional groups include, but are not limited to:

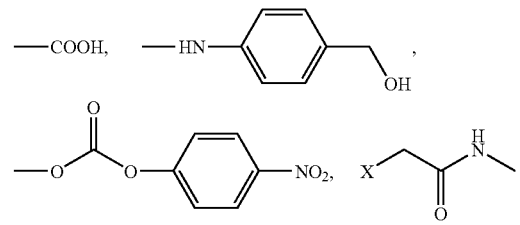

where X is a leaving group, e.g. O-mesyl, O-tosyl, —Cl, —Br, —I, an alkyldisulfide or aryldisulfide (RSS—), or a maleimide group.

In another embodiment, the Linker may be substituted with groups which modulated solubility or reactivity. For example, a sulfonate substituent may increase water solubility of the reagent and facilitate the coupling reaction of the linker reagent with the antibody or the drug moiety, or facilitate the coupling reaction of Ab-L with D, or D-L with Ab, depending on the synthetic route employed to prepare the ADC.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available from Pierce Biotechnology, Inc., Rockford, Ill. 61105 U.S.A. See pages 467-498, 2003-2004 Applications Handbook and Catalog.

Useful Linkers can also be obtained from other commercial sources, such as Molecular Biosciences Inc. (Boulder, Colo.), or synthesized in accordance with procedures described in U.S. Pat. No. 6,214,345 to Firestone et al, *J. Org. Chem.* 1995, 60, 5352-5), Frisch, et al., (1996) *Bioconjugate Chem.*, 7, 180-186.

Useful Stretchers may be incorporated into a Linker using the commercially available intermediates from Molecular Biosciences (Boulder, Colo.) described below by utilizing known techniques of organic synthesis.

Stretchers of formula (IIIa) can be introduced into a Linker by reacting the following intermediates with the N-terminus of an Amino Acid unit:

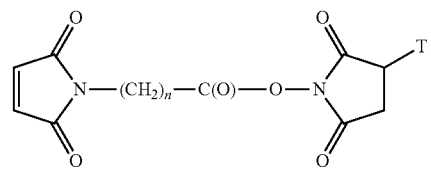

where n is an integer ranging from 1-10 and T is —H or —SO$_3$Na;

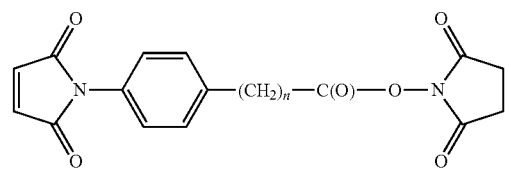

where n is an integer ranging from 0-3;

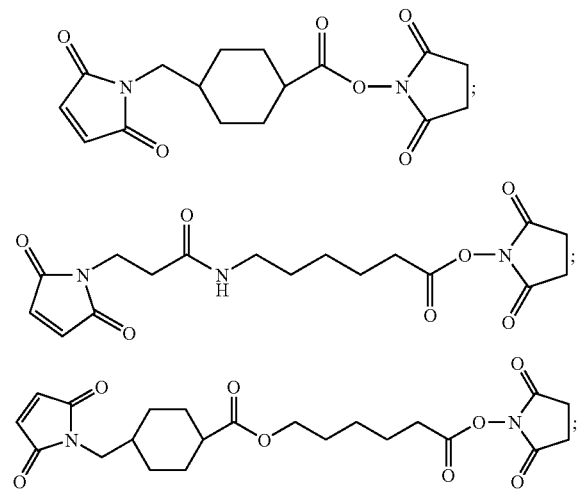

and

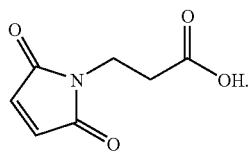

Stretcher units of can be introduced into a Linker by reacting the following bifunctional reagents with the N-terminus of an Amino Acid unit:

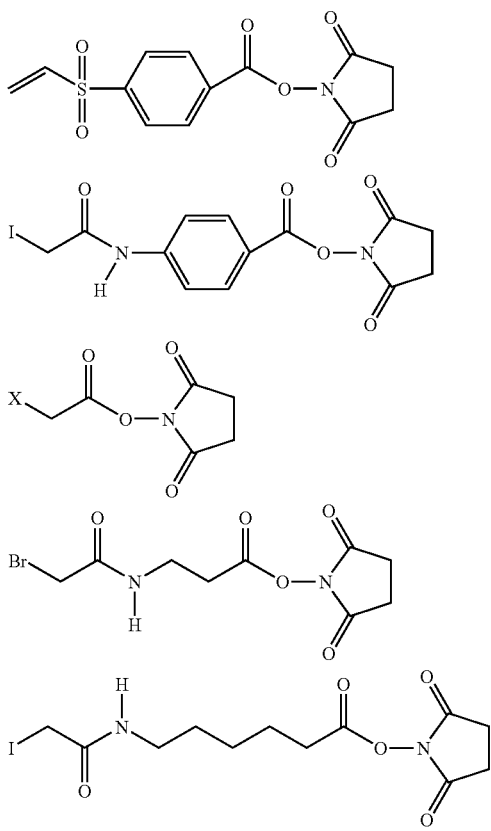

where X is Br or I. Stretcher units of Formula IIIa and IIIb can also be introduced into a Linker by reacting the following bifunctional reagents with the N-terminus of an Amino Acid unit:

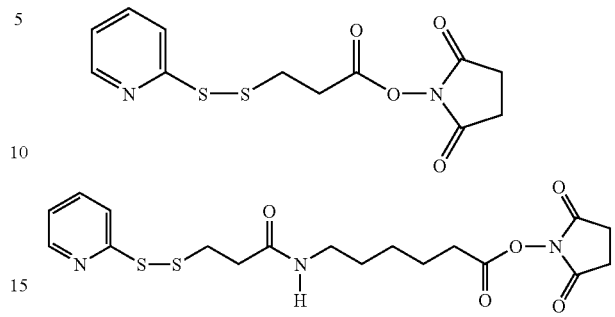

Stretcher units of formula (Va) can be introduced into a Linker by reacting the following intermediates with the N-terminus of an Amino Acid unit:

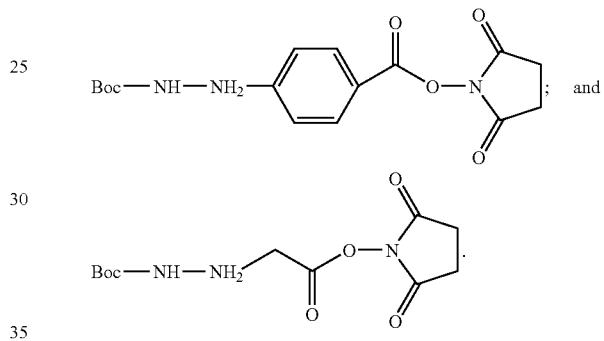

Other useful Stretchers may be synthesized according to known procedures. Aminooxy Stretchers ($H_2N-O-R^{17}-C(O)-$) can be prepared by treating alkyl halides with N-Boc-hydroxylamine according to procedures described in Jones, D. S. et al., *Tetrahedron Letters*, 2000, 41(10), 1531-1533; and Gilon, C. et al., *Tetrahedron*, 1967, 23(11), 4441-4447, wherein $-R^{17}-$ is selected from $-C_1-C_{10}$ alkylene-, $-C_3-C_8$ carbocyclo-, $-O-(C_1-C_8$ alkyl)-, -arylene-, $-C_1-C_{10}$ alkylene-arylene-, -arylene-$C_1-C_{10}$ alkylene-, $-C_1-C_{10}$ alkylene-$(C_3-C_8$ carbocyclo)-, $-(C_3-C_8$ carbocyclo)-$C_1-C_{10}$ alkylene-, $-C_3-C_8$ heterocyclo-, $-C_1-C_{10}$alkylene-$(C_3-C_8$ heterocyclo)-, $-(C_3-C_8$ heterocyclo)-$C_1-C_{10}$alkylene-, $-(CH_2CH_2O)_r-$, $-(CH_2CH_2O)_r-CH_2-$; and r is an integer ranging from 1-10. Isothiocyanate Stretchers ($S=C=N-R^{17}-C(O)-$) may be prepared from isothiocyanatocarboxylic acid chlorides as described in *Angew. Chem.*, 1975, 87(14), 517.

FIG. 6 shows a method for preparing a valine-citrulline (val-cit or vc) dipeptide Linker having a maleimide Stretcher and optionally a p-aminobenzyloxycarbonyl (PAB) self-immolative Spacer where Q is $-C_1-C_8$ alkyl, $-O-(C_1-C_8$ alkyl), -halogen, -nitro or -cyano; and m is an integer ranging from 0-4.

FIG. 7 illustrates the synthesis of a phe-lys(Mtr) dipeptide Linker unit having a maleimide Stretcher unit and a p-aminobenzyloxycarbonyl self-immolative Spacer unit, where Q is $-C_1-C_8$ alkyl, $-O-(C_1-C_8$ alkyl), -halogen, -nitro or -cyano; and m is an integer ranging from 0-4. Starting material, lys(Mtr), is commercially available (Bachem, Torrance, Calif.) or can be prepared according to Dubowchik, et al. (1997) *Tetrahedron Letters*, 38:5257-60.

FIG. 8 shows a Linker reacted with an amino group of a Drug moiety to form an ADC that contains an amide or carbamate group, linking the Drug unit to the Linker unit. When a linker intermediate has a carboxylic acid group, as in Linker AJ, the coupling reaction can be performed using HATU or PyBrop and an appropriate amine base, resulting in a Drug-Linker Compound AK, containing an amide bond between the Drug unit and the Linker unit. When the functional group is a carbonate, as in Linker AL, the Linker can be coupled to the Drug using HOBt in a mixture of DMF/pyridine to provide a Drug-Linker Compound AM, containing a carbamate bond between the Drug unit and the Linker unit. Alternately, when the reactive functional group is a good leaving group, such as halide in Linker AN, the Linker can be coupled with an amine group of a Drug via a nucleophilic substitution process to provide a Drug-Linker Compound having an amine linkage (AO) between the Drug unit and the Linker unit. Illustrative methods useful for linking a Drug to an antibody to form a Drug-Linker Compound are depicted in FIG. 8 and are outlined in General Procedures G-H.

General Procedure G: Amide formation using HATU. A Drug (Ib) (1.0 eq.) and an N-protected Linker containing a carboxylic acid group (1.0 eq.) are diluted with a suitable organic solvent, such as dichloromethane, and the resulting solution is treated with HATU (1.5 eq.) and an organic base, such as pyridine (1.5 eq.). The reaction mixture is allowed to stir under an inert atmosphere, such as argon, for 6 h, during which time the reaction mixture is monitored using HPLC. The reaction mixture is concentrated and the resulting residue is purified using HPLC to yield the amide of formula AK.

General Procedure H: Carbamate formation using HOBt. A mixture of a Linker AL having a p-nitrophenyl carbonate (1.1 eq.) and Drug (Ib) (1.0 eq.) are diluted with an aprotic organic solvent, such as DMF, to provide a solution having a concentration of 50-100 mM, and the resulting solution is treated with HOBt (2.0 eq.) and placed under an inert atmosphere, such as argon. The reaction mixture is allowed to stir for 15 min, then an organic base, such as pyridine (1/4 v/v), is added and the reaction progress is monitored using HPLC. The Linker is typically consumed within 16 h. The reaction mixture is then concentrated in vacuo and the resulting residue is purified using, for example, HPLC to yield the carbamate AM.

An alternate method of preparing Drug-Linker Compounds is outlined in FIG. 8 where a drug moiety D is reacted with a Linker reagent, which does not have a Stretcher unit attached. This provides intermediate AP, which has an Amino Acid unit having an Fmoc-protected N-terminus. The Fmoc group is then removed and the resulting amine intermediate AQ is then attached to a Stretcher unit via a coupling reaction catalyzed using PyBrop or DEPC. The construction of Drug-Linker Compounds containing either a bromoacetamide Stretcher AR or a PEG maleimide Stretcher AS is illustrated in FIG. 9 where Q is —$C_1$-$C_8$ alkyl, —O—($C_1$-$C_8$ alkyl), -halogen, -nitro or -cyano; and m is an integer ranging from 0-4.

FIG. 10 shows the preparation of a Linker unit containing a branched spacer is shown in, which illustrates the synthesis of a val-cit dipeptide linker having a maleimide Stretcher unit and a bis(4-hydroxymethyl)styrene (BHMS) unit. The synthesis of the BHMS intermediate (AW) has been improved from previous literature procedures (see WO 98/13059 and Crozet, et al (1985) *Tetrahedron Lett.*, 26:5133-5134) and utilizes as starting materials, commercially available diethyl (4-nitrobenzyl)phosphonate (AT) and commercially available 2,2-dimethyl-1,3-dioxan-5-one (AU). Linkers AY and BA can be prepared from intermediate AW.

Conjugation of Drug Moieties to Antibodies

One exemplary method of preparing an antibody for conjugation with a bis 1,8 naphthalimide drug moiety of the invention entails treating the antibody with a reducing agent, such as dithiothreitol (DTT) to reduce some or all of the cysteine disulfide residues to form highly nucleophilic cysteine thiol groups (—$CH_2SH$). The partially reduced antibody thus reacts with bis 1,8 naphthalimide drug-linker compounds, or linker reagents with electrophilic functional groups such as maleimide or α-halo carbonyl, according to the conjugation method at page 766 of Klussman, et al (2004), Bioconjugate Chemistry 15 (4):765-773.

For example, an antibody, e.g. trastuzumab, dissolved in 500 mM sodium borate and 500 mM sodium chloride at pH 8.0 is treated with an excess of 100 mM dithiothreitol (DTT). After incubation at 37° C. for about 30 minutes, the buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm. The reduced antibody dissolved in PBS is chilled on ice. The drug linker, e.g. MC-val-cit-PAB-bis 1,8 naphthalimide in DMSO, dissolved in acetonitrile and water at known concentration, is added to the chilled reduced antibody in PBS. After about one hour, an excess of maleimide is added to quench the reaction and cap any unreacted antibody thiol groups. The reaction mixture is concentrated by centrifugal ultrafiltration and the ADC, e.g. trastuzumab-MC-vc-PAB-bis 1,8 naphthalimide, is purified and desalted by elution through G25 resin in PBS, filtered through 0.2 μm filters under sterile conditions, and frozen for storage.

1,8 bis-naphthalimide Compounds

Heterocyclic-substituted 1,8 bis-naphthalimide have structures according to Formula XV:

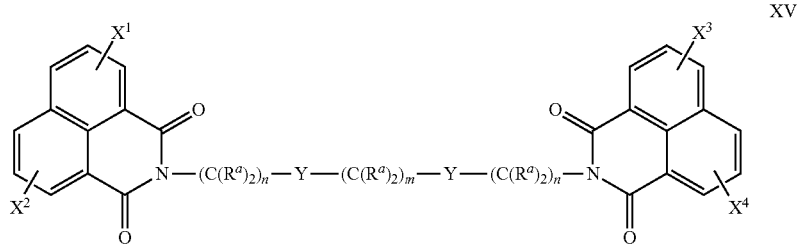

XV or a pharmaceutically acceptable salt or solvate thereof, wherein

Y is N($R^b$), C($R^a$)$_2$, O, or S;

$R^a$ is independently selected from H, F, Cl, Br, I, OH, —N($R^b$)$_2$, —N($R^b$)$_3^+$, $C_1$-$C_8$ alkylhalide, carboxylate, sulfate, sulfamate, sulfonate, —$SO_2R^b$, —S(=O)$R^b$, —$SR^b$, —$SO_2N(R^b)_2$, —C(=O)$R^b$, —$CO_2R^b$, —C(=O)N($R^b$)$_2$, —CN, —$N_3$, —$NO_2$, $C_1$-$C_8$ alkoxy, $C_1$-$C_8$ trifluoroalkyl, polyethyleneoxy, phosphonate, phosphate, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_1$-$C_{20}$ heterocycle, and $C_1$-$C_{20}$ substituted heterocycle; or when taken together, two $R^a$ groups on the same carbon atom form a carbonyl (=O), or on different carbon atoms form a carbocyclic, heterocyclic, or aryl ring of 3 to 7 carbon atoms;

$R^b$ is independently selected from H, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_1$-$C_{20}$ heterocycle, and $C_1$-$C_{20}$ substituted heterocycle;

where $C_1$-$C_8$ substituted alkyl, $C_2$-$C_8$ substituted alkenyl, $C_2$-$C_8$ substituted alkynyl, $C_6$-$C_{20}$ substituted aryl, and $C_2$-$C_{20}$ substituted heterocycle are independently substituted with one or more substituents selected from F, Cl, Br, I, OH, —N($R^b$)$_2$, —N($R^b$)$_3^+$, $C_1$-$C_8$ alkylhalide, carboxylate, sulfate, sulfamate, sulfonate, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, —SO$_2R^b$, —S(=O)$R^b$, —S$R^b$, —SO$_2$N($R^b$)$_2$, —C(=O)$R^b$, —CO$_2R^b$, —C(=O)N($R^b$)$_2$, —CN, —N$_3$, —NO$_2$, $C_1$-$C_8$ alkoxy, $C_1$-$C_8$ trifluoroalkyl, $C_1$-$C_8$ alkyl, $C_3$-$C_{12}$ carbocyclyl, $C_6$-$C_{20}$ aryl, $C_1$-$C_{20}$ heterocyclyl, polyethyleneoxy, phosphonate, and phosphate;

m is 1, 2, 3, 4, 5, or 6;

n is independently selected from 1, 2, and 3;

$X^1$, $X^2$, $X^3$, and $X^4$ are independently selected from F, Cl, Br, I, OH, —N($R^b$)$_2$, —N($R^b$)$_3^+$, —N($R^b$)C(=O)$R^b$, —N($R^b$)C(=O)N($R^b$)$_2$, —N($R^b$)SO$_2$N($R^b$)$_2$, —N($R^b$)SO$_2R^b$, OR, OC(=O)$R^b$, OC(=O)N($R^b$)$_2$, $C_1$-$C_8$ alkylhalide, carboxylate, sulfate, sulfamate, sulfonate, —SO$_2R^b$, —SO$_2$Ar, —SOAr, —SAr, —SO$_2$N($R^b$)$_2$, —SOR$^b$, CO$_2R^b$, —C(=O)N($R^b$)$_2$, —CN, —N$_3$, —NO$_2$, $C_1$-$C_8$ alkoxy, $C_1$-$C_8$ trifluoroalkyl, polyethyleneoxy, phosphonate, phosphate, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_1$-$C_{20}$ heterocyclyl, and $C_1$-$C_{20}$ substituted heterocyclyl; or $X^1$ and $X^2$ together, and $X^3$ and $X^4$ together, independently form —CH$_2$CH$_2$— or —CH$_2$CH$_2$CH$_2$—; and at least one of $X^1$, $X^2$, $X^3$, and $X^4$ is nitrogen-linked $C_1$-$C_{20}$ heterocyclyl having the structure:

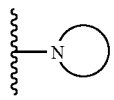

where the wavy line indicates the site of attachment to a 1,8 naphthalimide carbon;

with the proviso that when at least one of $X^1$, $X^2$, $X^3$, and $X^4$ is nitrogen-linked $C_1$-$C_{20}$ heterocyclyl at the 3 position of the 1,8 naphthalimide, and each of $R^a$ is H or $C_1$-$C_8$ alkyl, then Y is not N($R^b$).

For descriptive purposes herein, each of the 1,8 naphthalimide aromatic carbon atoms are numbered according to the structure:

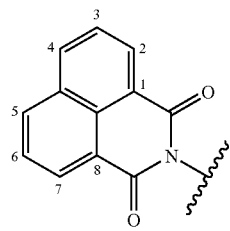

The nitrogen-linked $C_1$-$C_{20}$ heterocyclyl substituents include at least one nitrogen atom. A nitrogen atom of the nitrogen-linked $C_1$-$C_{20}$ heterocyclyl substituent is bonded directly to an aryl carbon of one of the 1,8 naphthalimide groups of a Formula XV compound. The nitrogen-linked $C_1$-$C_{20}$ heterocyclyl substituents include, but are not limited to: aziridinyl, azetidinyl, pyrrole, pyrrolidinyl, 2-pyrroline, 3-pyrroline, imidazolyl, imidazolidinyl, 2-imidazoline, 3-imidazoline, pyrazole, pyrazoline, 2-pyrazoline, 3-pyrazoline, piperidine, piperazinyl, indole, indoline, 1H-indazole, position 2 of a isoindole, or isoindoline, position 4 of a morpholine, and 9 carbazolyl (β-carbolinyl).

Exemplary nitrogen-linked $C_1$-$C_{20}$ heterocyclyl substituents include, but are not limited to the following structures, where the wavy line indicates the covalent attachment to a 1,8 naphthalimide group:

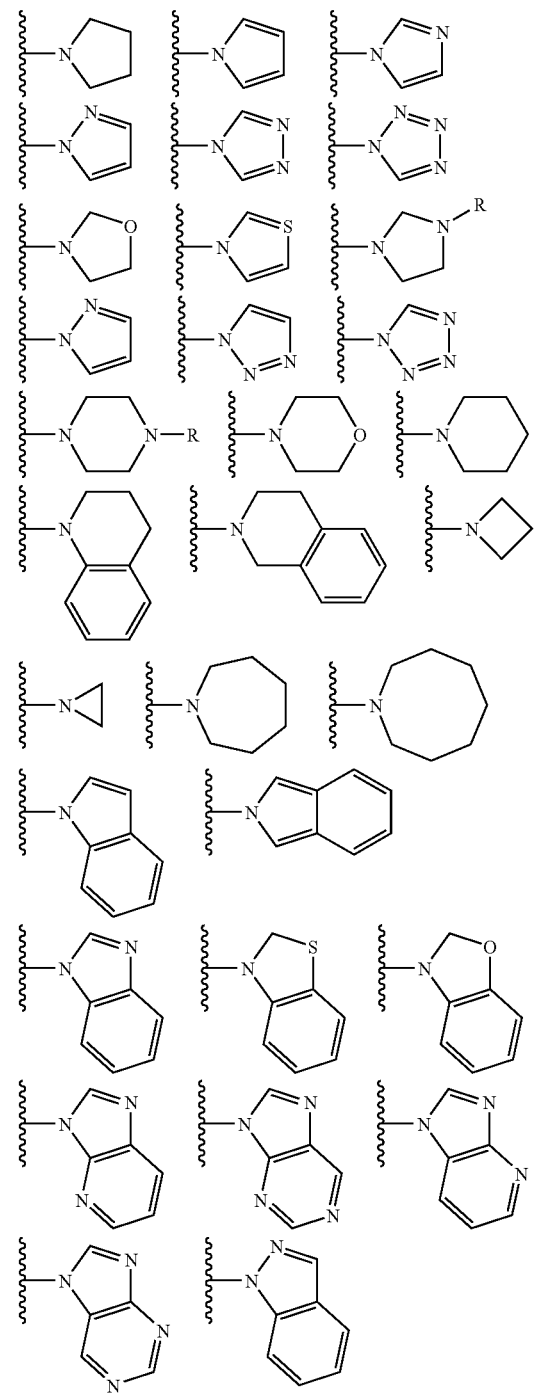

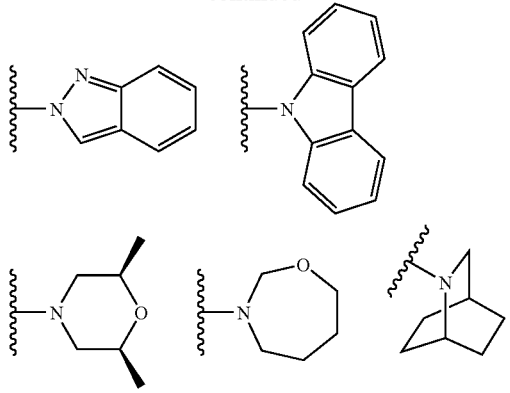
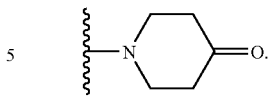
The 1,8 naphthalimide aromatic carbon atoms may be independently substituted with a range of substituents ($X^1$-$X^4$) besides H at the 2-7 positions. Exemplary embodiments of I where the two 1,8 naphthalimide groups are the same, and where Y is $N(R^b)$, n is 2, m is 3, $R^a$ and $R^b$ are H, include the exemplary structures:
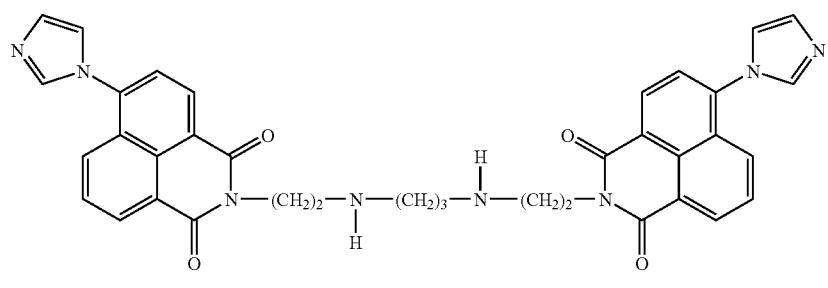
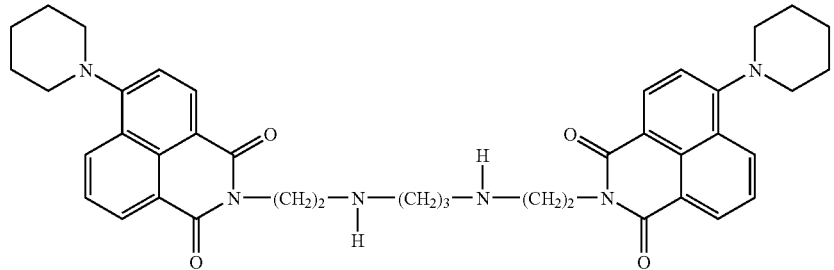
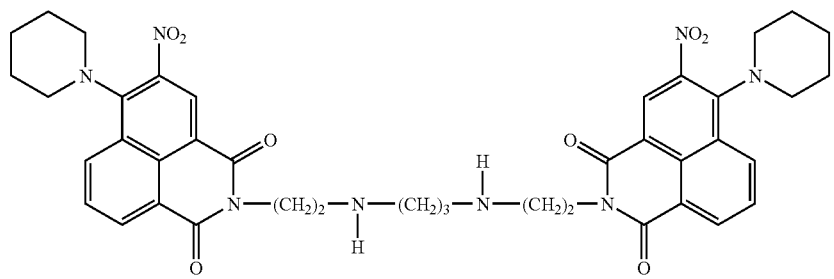
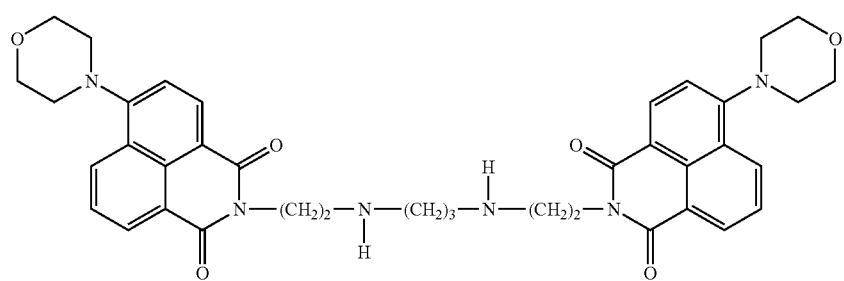

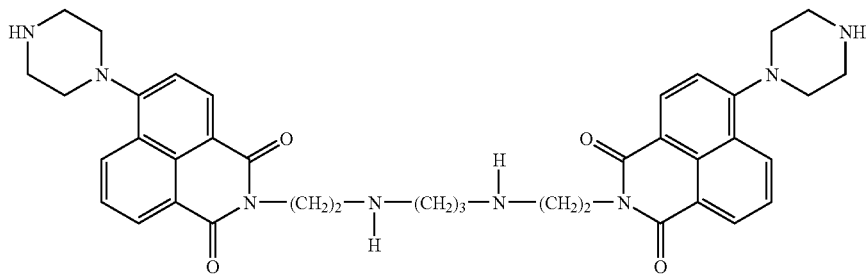
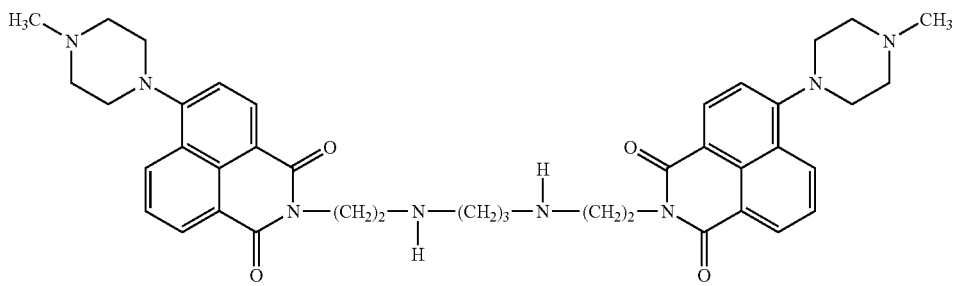
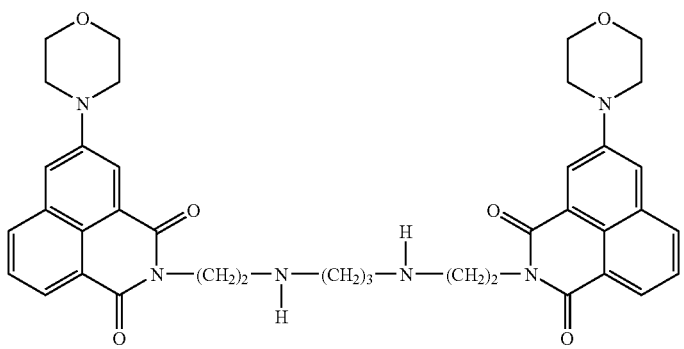
Exemplary embodiment where the two 1,8 naphthalimide groups are not the same, and where Y is N(R$^b$), n is 2, m is 3, R$^a$ and R$^b$ are H, include the structures:
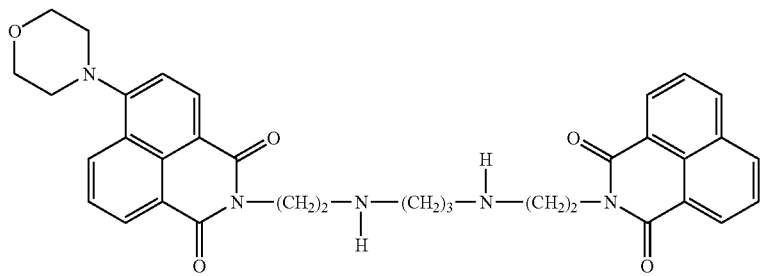
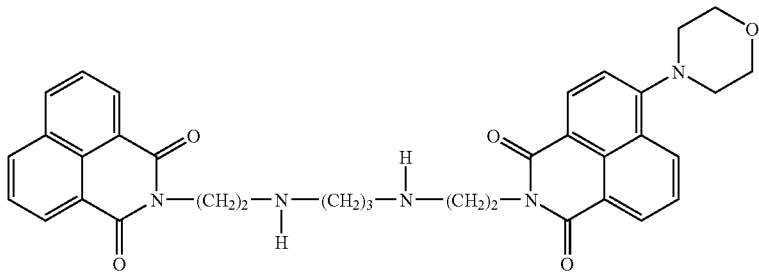

-continued
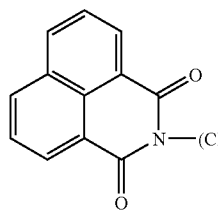
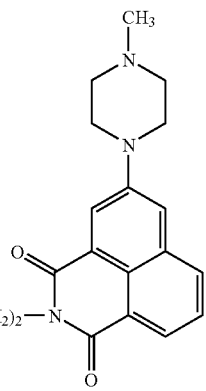
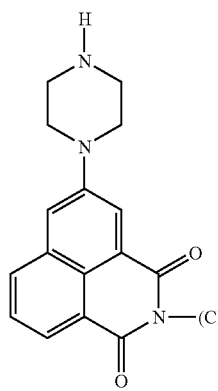
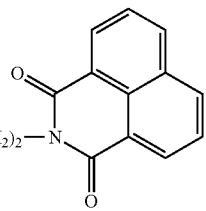
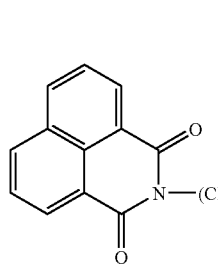
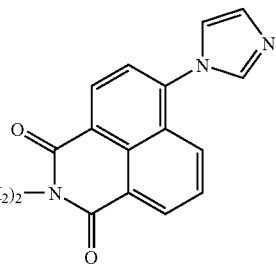
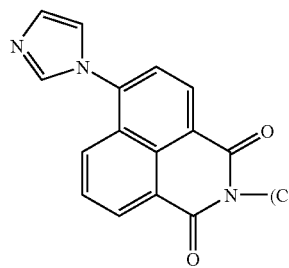
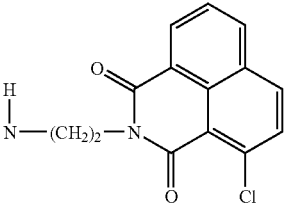
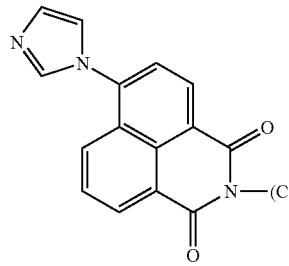
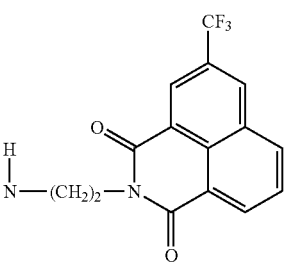

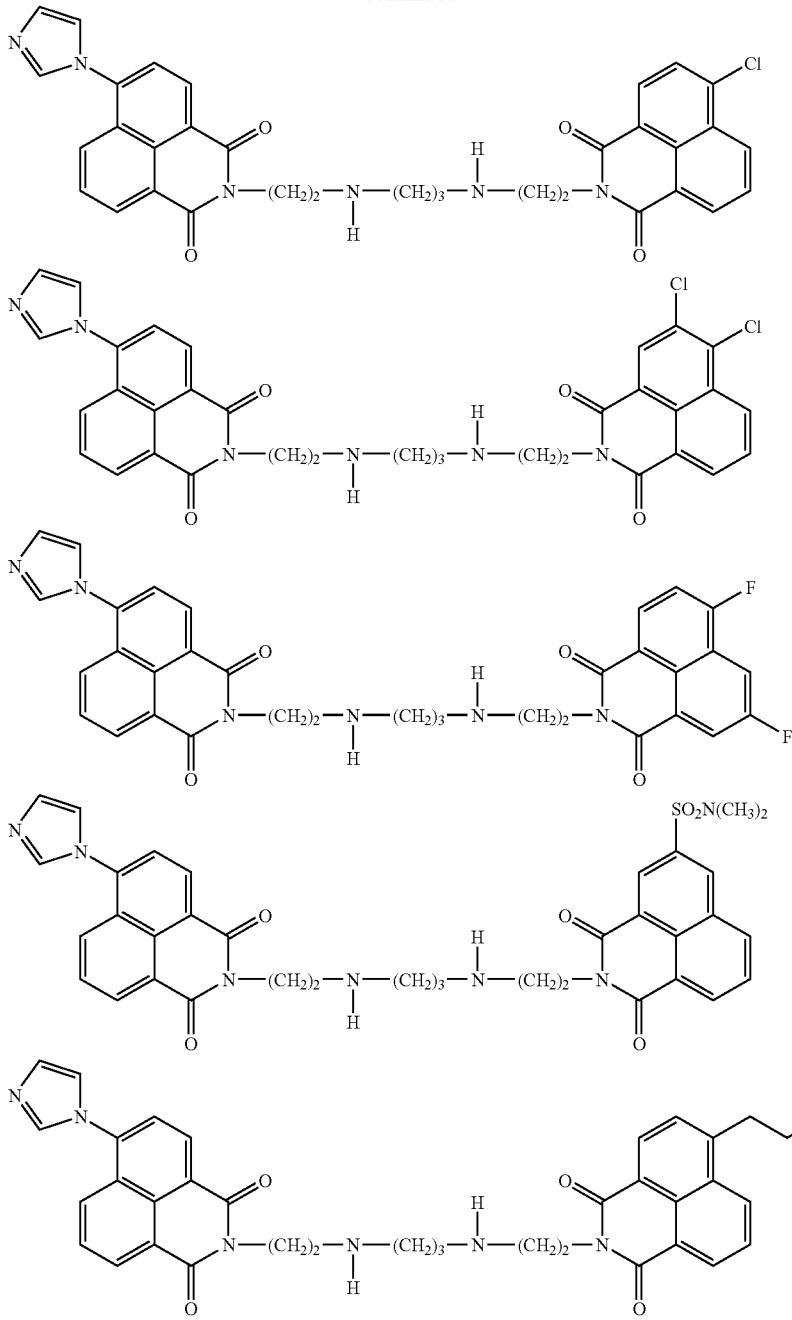
$X^1$ and $X^2$ together, or $X^3$ and $X^4$ together, independently may form —$CH_2CH_2$— or —$CH_2CH_2CH_2$—. Exemplary embodiments of such, and where Y is $N(R^b)$, n is 2, m is 3, $R^a$ and $R^b$ are H, include the structures:
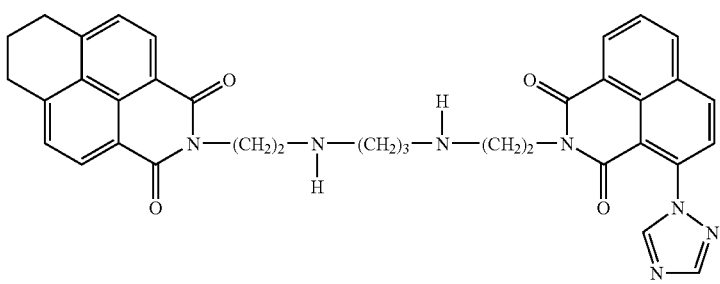

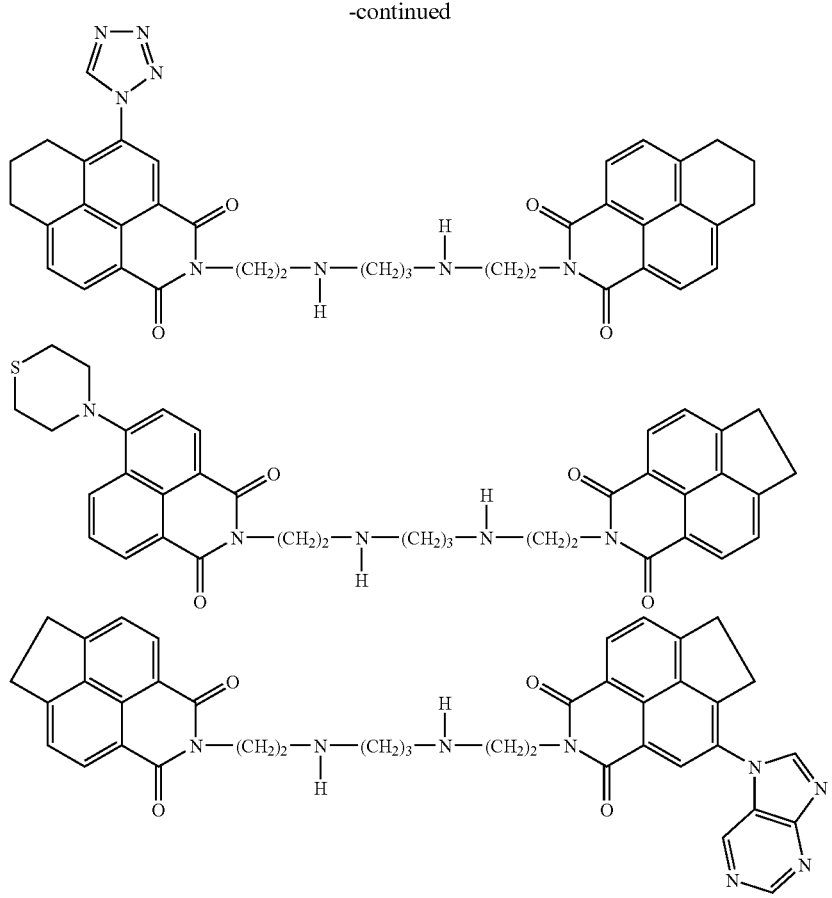
Two $X^1$, $X^2$, $X^3$, or $X^4$ on adjacent carbon atoms may form a fused $C_6$-$C_{20}$ aryl, $C_6$-$C_{20}$ substituted aryl, $C_1$-$C_{20}$ heterocycle, or $C_1$-$C_{20}$ substituted heterocycle. Exemplary embodiments of such, and where Y is $N(R^b)$, n is 2, m is 3, $R^a$ and $R^b$ are H, include the structures:
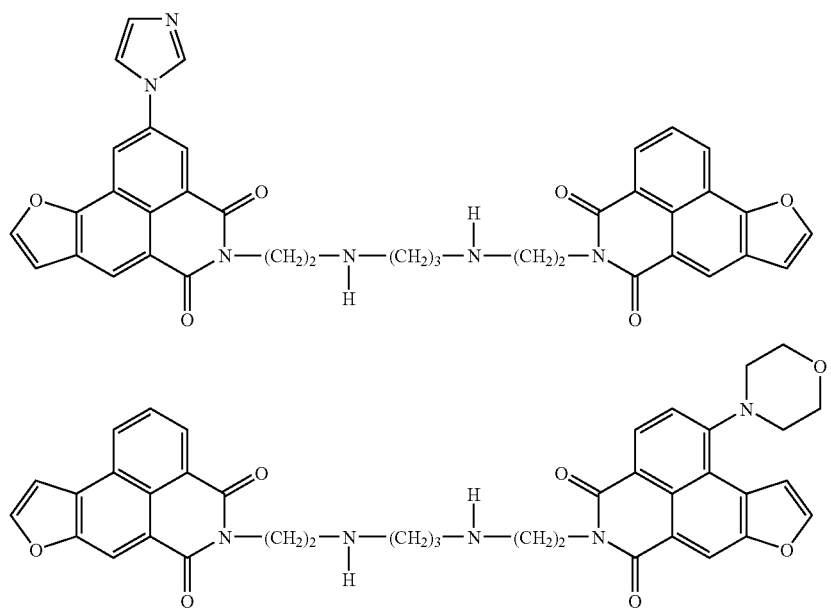

-continued
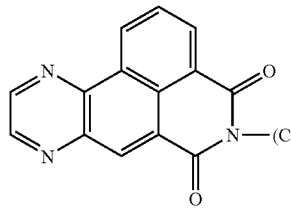 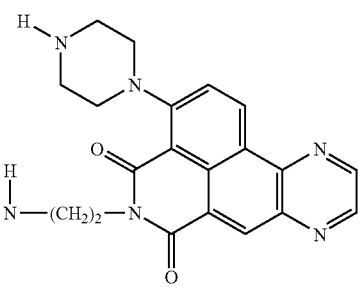
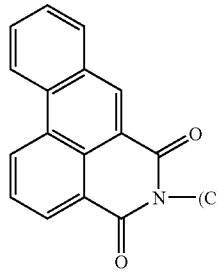 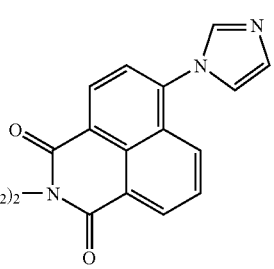
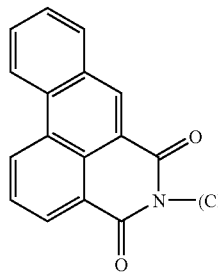 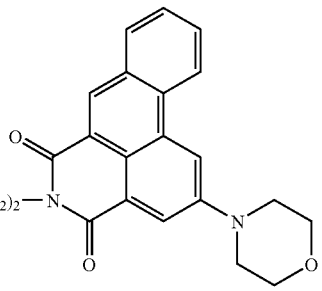
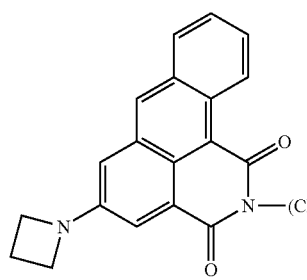 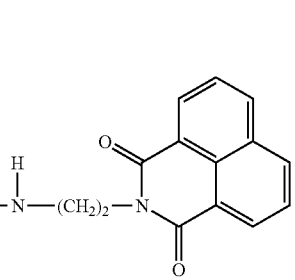
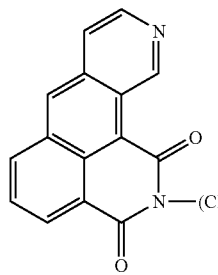 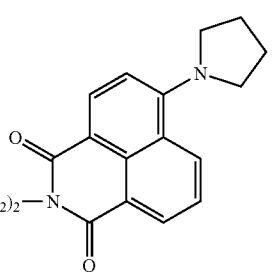
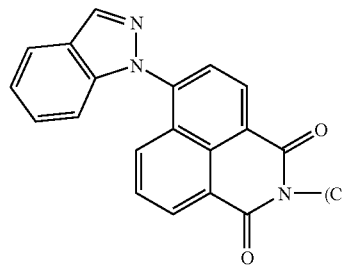 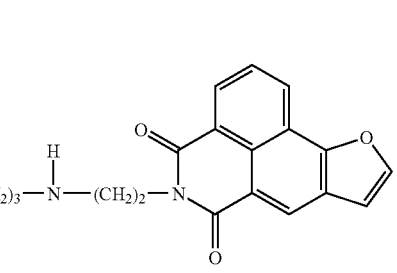

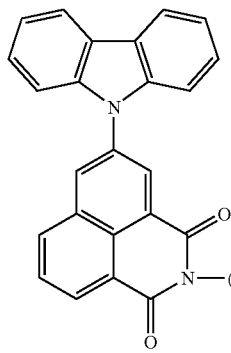
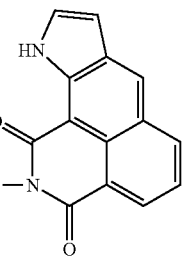
The bis-amino alkyl group that attaches the two 1,8 naphthalimide groups may bear a range of substituents besides H on the carbon atoms ($R^a$) and the nitrogen atom not linked to L ($R^b$). Exemplary embodiments of D where Y is N($R^b$), m is 3 and n is 2 in the bis-amino alkyl group include the structures:
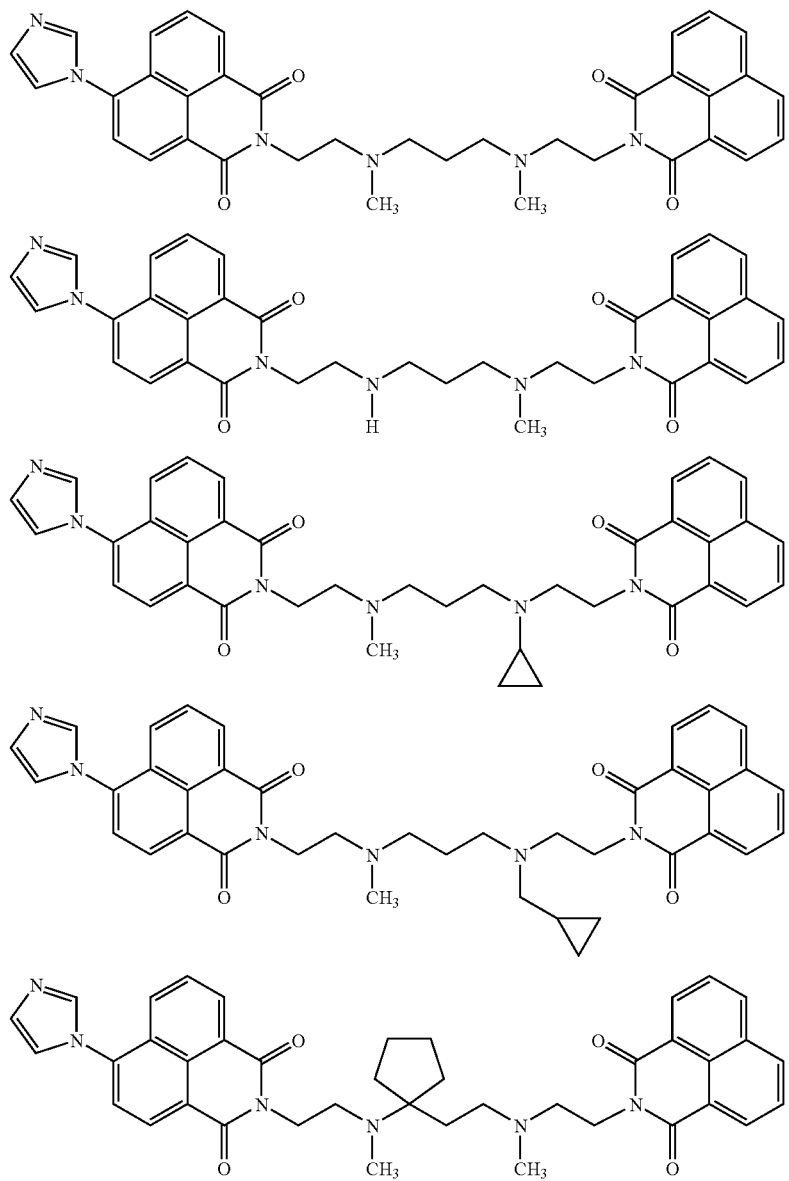

-continued
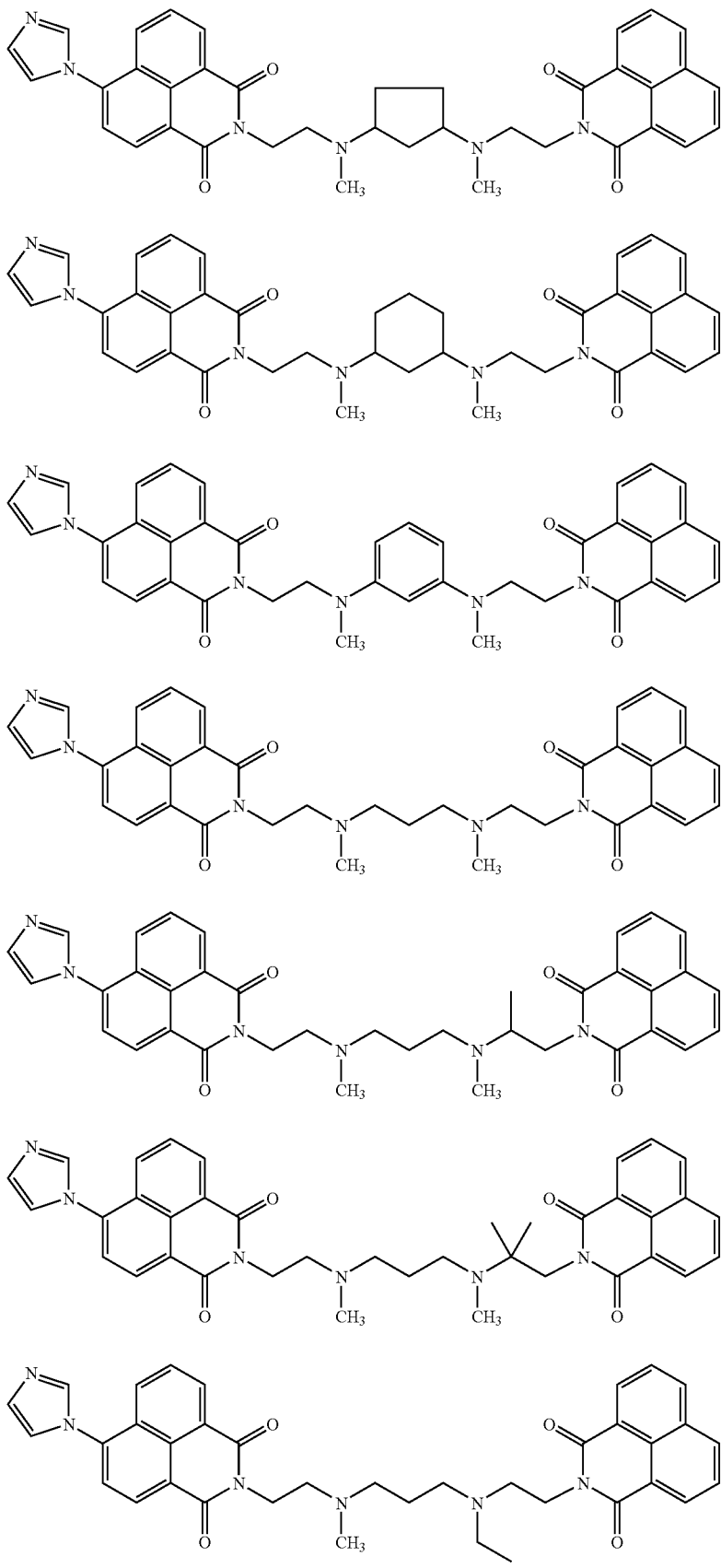

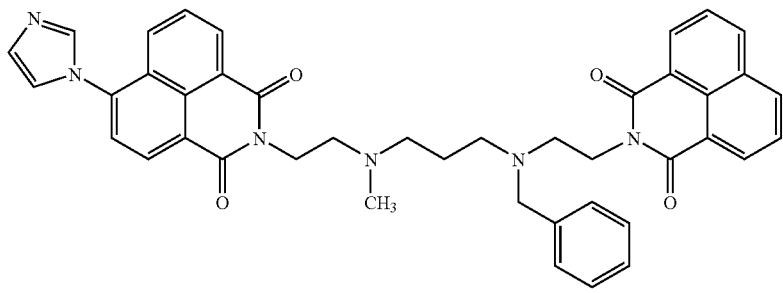
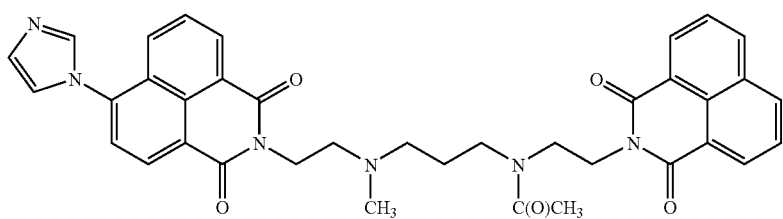
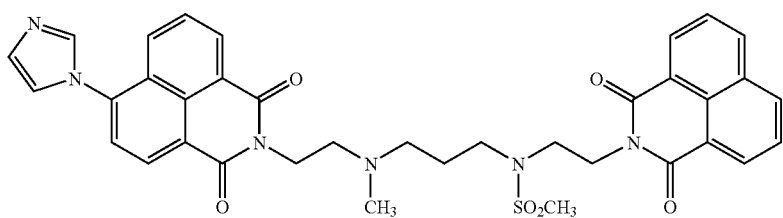
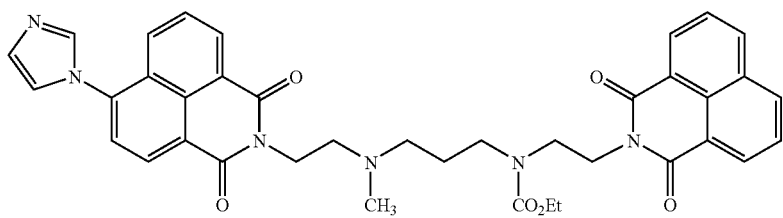
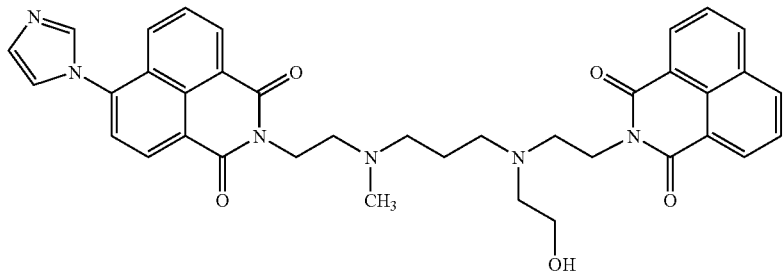
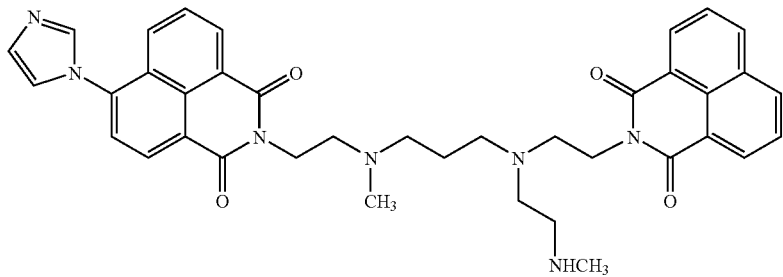

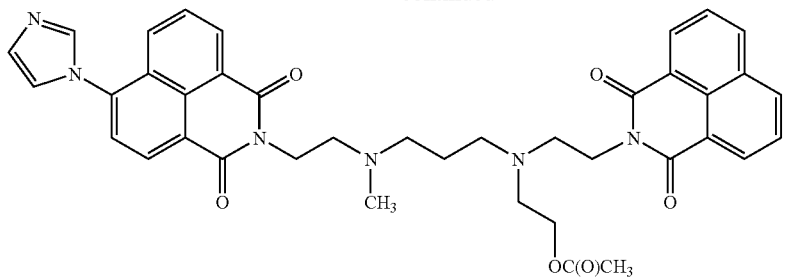
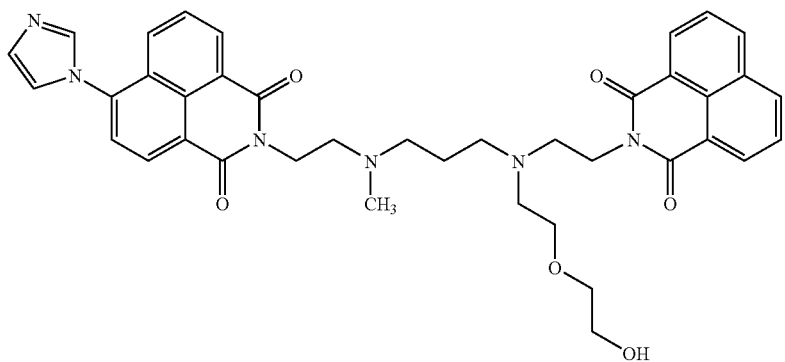
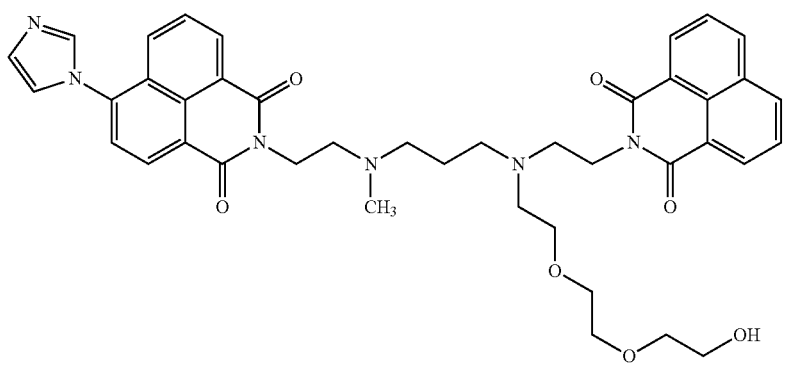
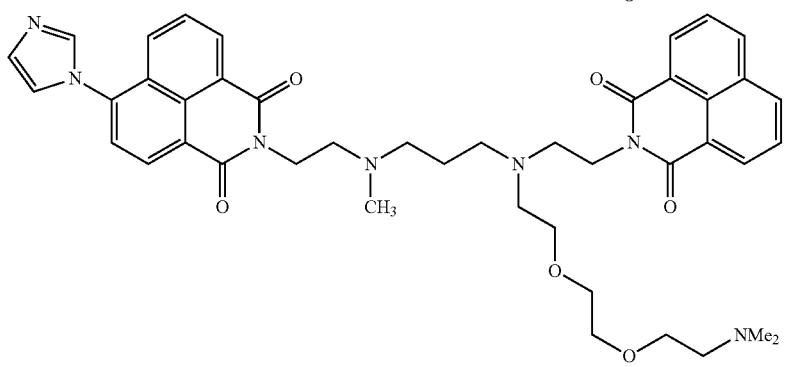
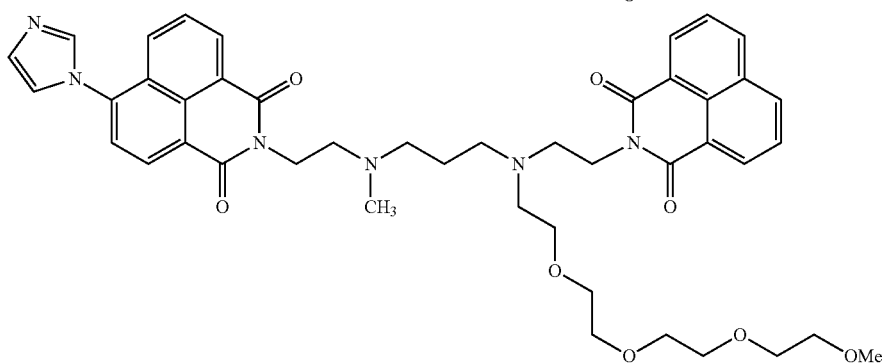

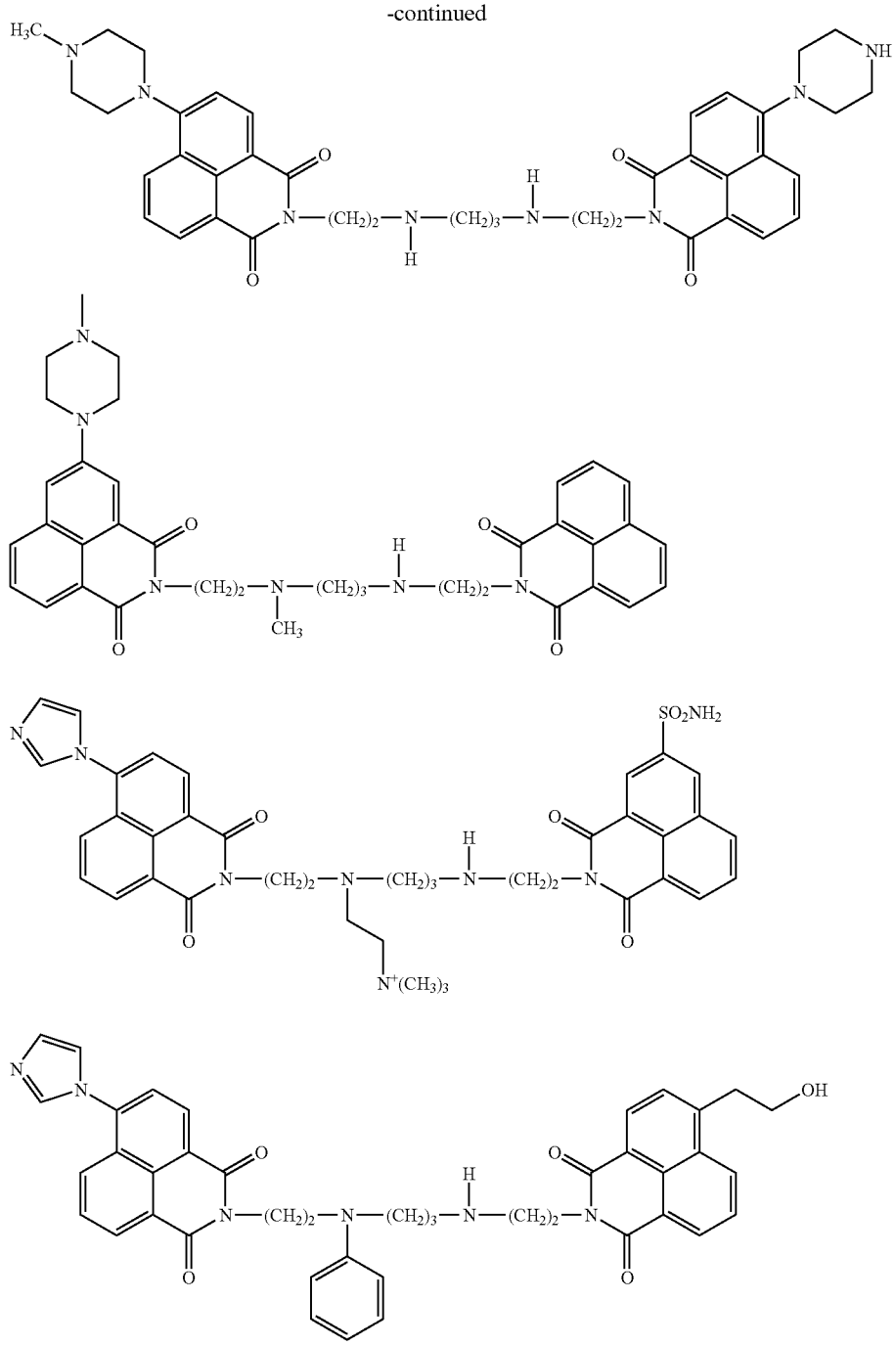

The three alkylene groups of the bis-amino alkyl group that attaches the two 1,8 naphthalimide groups may independently be of different lengths and bear a range of substituents besides H on the carbon atoms ($R^a$) and nitrogen atom ($Y=NR^b$). The two non-equivalent alkylene groups between each 1,8 naphthalimide group and a nitrogen atom (n) are independently 1, 2, or 3 carbons in length. The alkylene group between the nitrogen atoms (m) is 1, 2, 3, 4, 5, or 6 carbons in length. The compounds of the invention thus include all 54 possible combinations of lengths of the three alkylene groups.

Exemplary embodiments of compounds of the invention where at least one of Y is O or S include the following structures:

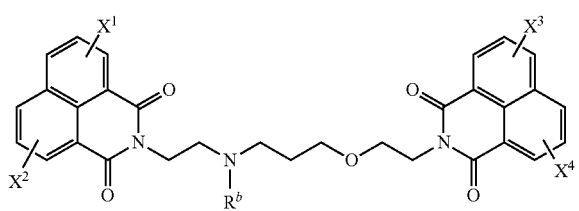

125
-continued

126
-continued

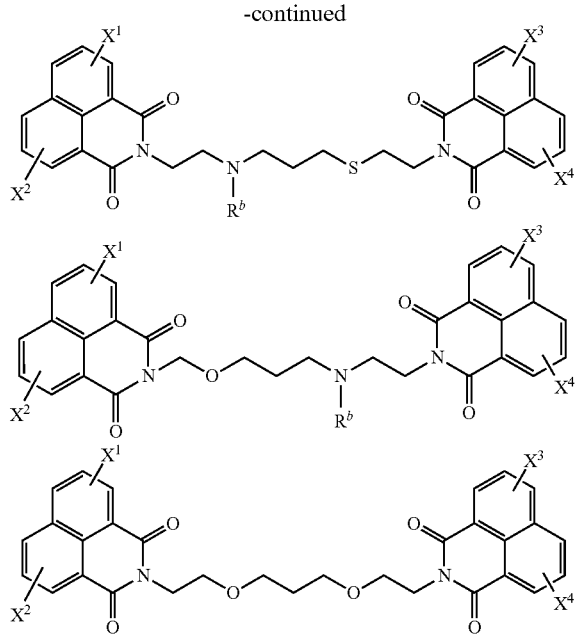

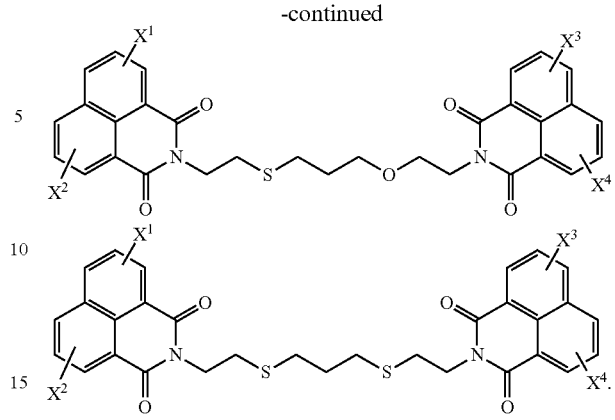

Compounds listed in Table 2 were prepared, characterized, and assayed for their in vitro activity against tumor cells. It was found generally that the heterocyclic-substituted 1,8 bis-naphthalimide compounds in Table 2 had dramatically improved solubility, e.g. greater than 1 mg/ml, in neutral aqueous solutions, relative to analogs with hydrogen at the 1,8 positions or other non-heterocyclic substituents, e.g. nitro, halo, or alkoxy, e.g. less than 0.1 mg/ml.

TABLE 2

| No. | Structure | Name |
| --- | --- | --- |
| 20 | 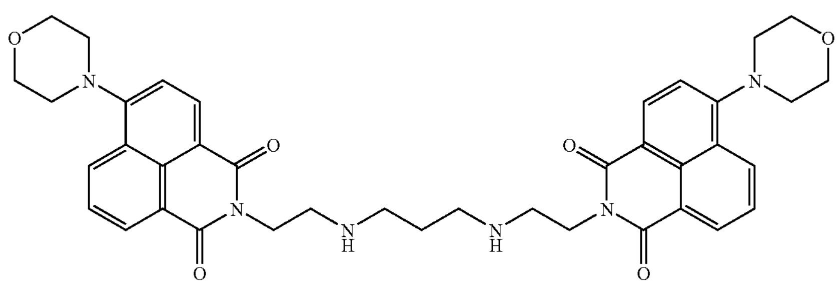 | N, N'-(bis-aminoethyl-1,3-propanediamine)-bis-4-morpholino-1,8 naphthalimide |
| 30a | 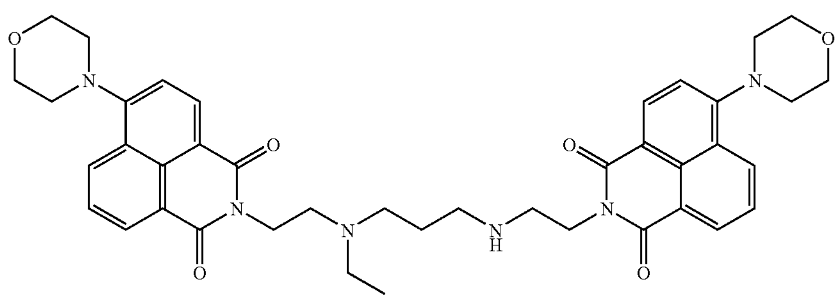 | N, N'-(N-ethyl, bis-aminoethyl-1,3-propanediamine)-bis-4-morpholino-1,8 naphthalimide |
| 34 | 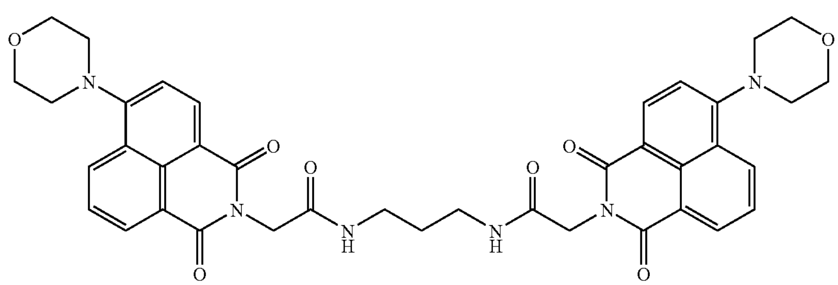 | N, N'-(bis-2-acetamido-1,3-propanediamine)-bis-4-morpholino-1,8 naphtbalimide |

TABLE 2-continued

| No. | Structure | Name |
| --- | --- | --- |
| 35 | 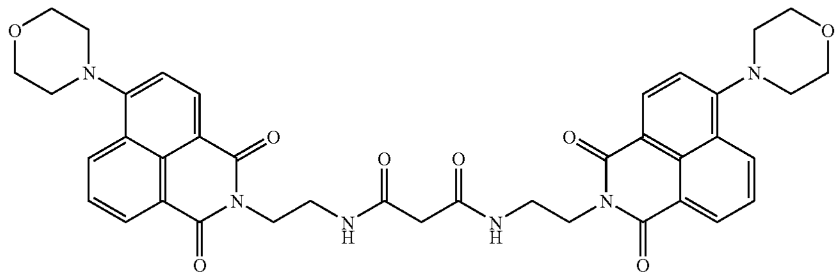 | N, N'-(bis-ethyl, malondiamide)-bis-4-morpholino-1,8 naphthalimide |
| 54a | 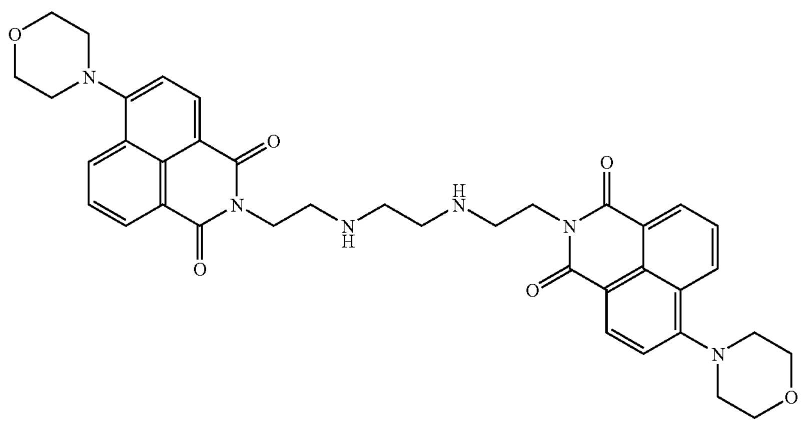 | N, N'-(bis-aminoethyl-1,2-ethanediamine)-bis-4-morpholino-1,8 naphthalimide |
| 54b | 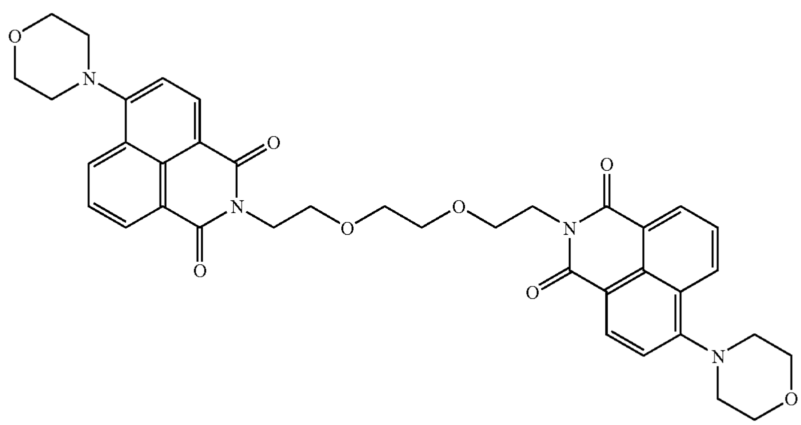 | N, N'-(3,6-dioxaoctanylene)-bis-4-morpholino-1,8 naphthalimide |
| 54c | 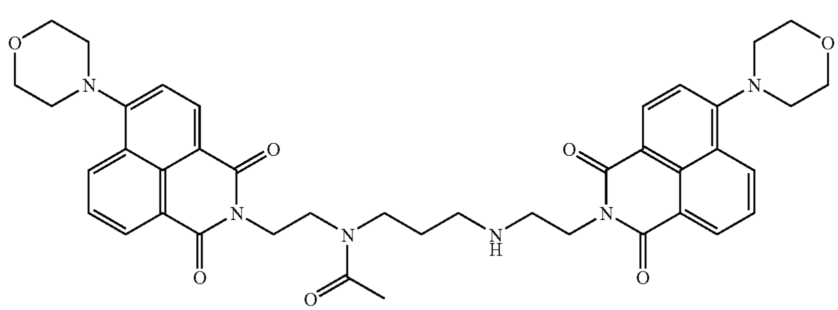 | N, N'-(N-acetyl, bis-aminoethyl-1,3-propanediamine)-bis-4-morpholino-1,8 naphthalimide |

TABLE 2-continued

| No. | Structure | Name |
|---|---|---|
| 54d | 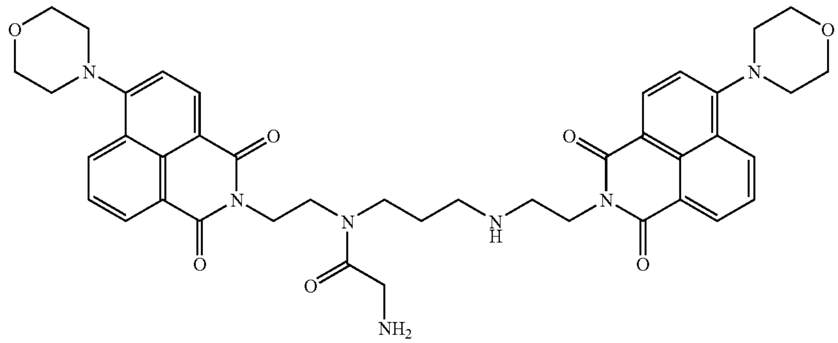 | N, N'-(N-glycyl, bis-aminoethyl-1,3-propanediamine)-bis-4-morpholino-1,8 naphthalimide |
| 54e | 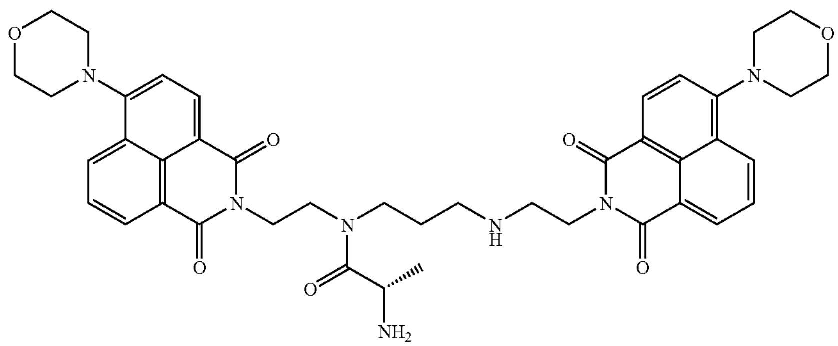 | N, N'-(N-alanyl, bis-aminoethyl-1,3-propanediamine)-bis-4-morpholino-1,8 naphthalimide |
| 54f | 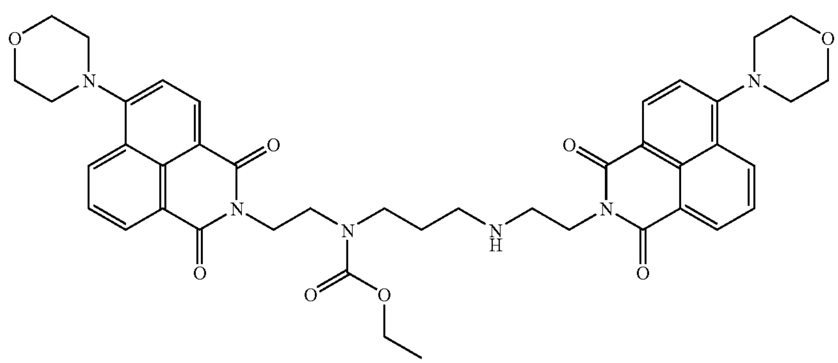 | N, N'-(N-carboethoxy, bis-aminoethyl-1,3-propanediamine)-bis-4-morpholino-1,8 naphthalimide |
| 54g | 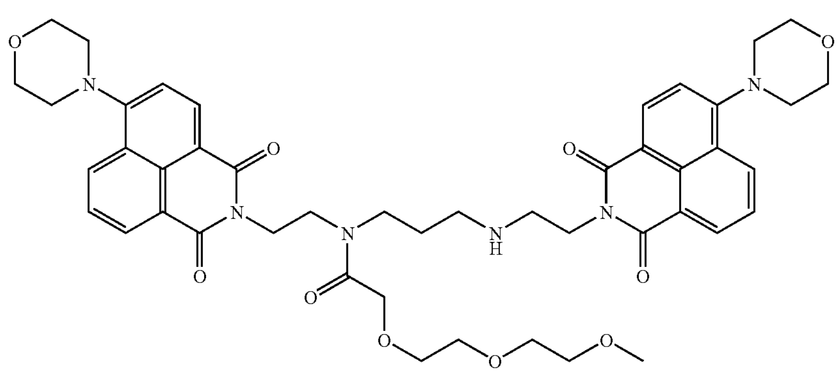 | N, N'-(N-methylethoxyethoxyacetyloxy, bis-aminoethyl-1,3-propanediamine)-bis-4-morpholino-1,8 naphthalimide |

TABLE 2-continued

| No. | Structure | Name |
|---|---|---|
| 54h | 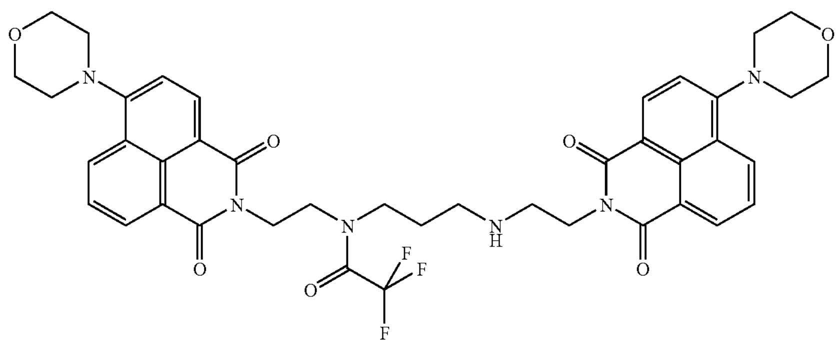 | N, N'-(N-trifluoromethylacetyl, bis-aminoethyl-1,3-propanediamine)-bis-4-morpholino-1,8 naphthalimide |
| 38 | 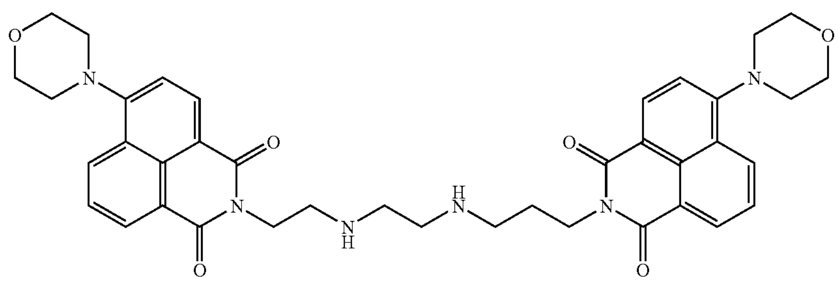 | N, N'-2-acetamido-1,2-ethanediamine-propyl)-bis-4-morpholino-1,8 naphthalimide |
| 55a | 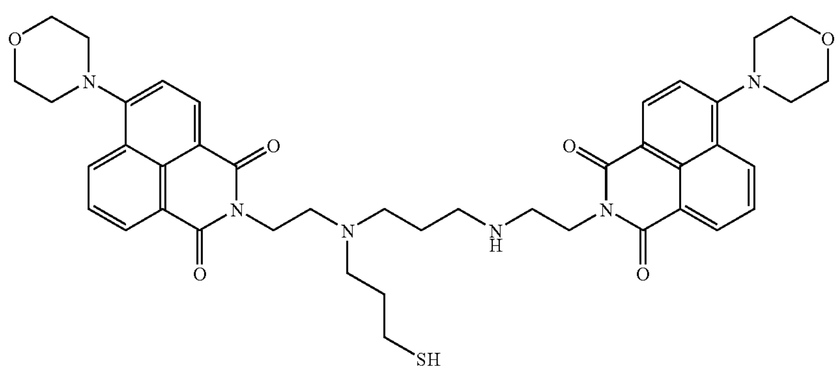 | N, N'-(N-3-mercaptopropyl, bis-aminoethyl-1,3-propanediamine)-bis-4-morpholino-1,8 naphthalimide |
| 55b | 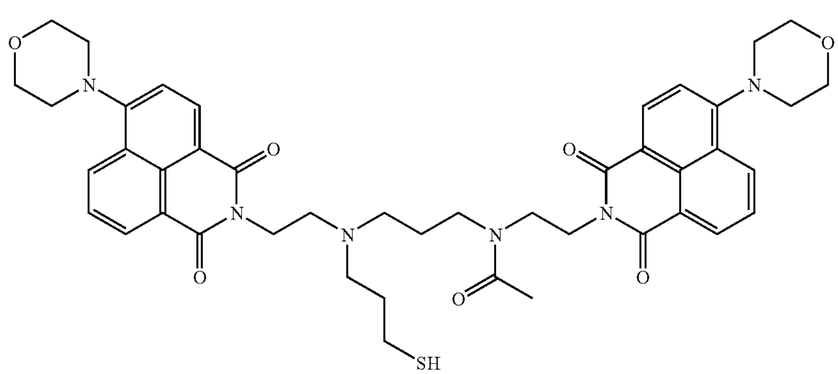 | N, N'-(1-N-acetyl, 3-N-trifluoromethylacetyl, bis-aminoethyl-1,3-propanediamine)-bis-4-morpholino-1,8 naphthalimide |

TABLE 2-continued

| No. | Structure | Name |
|---|---|---|
| 41 | 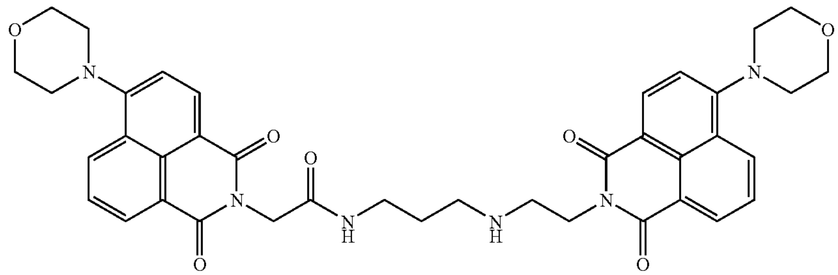 | N, N'-2-acetamido-1,2-propanediamine-ethyl)-bis-4-morpholino-1,8 naphthalimide |
| 55c | 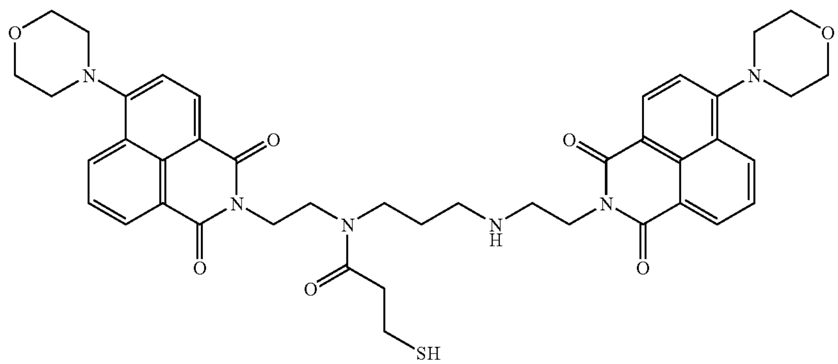 | N, N'-(N-3-mercaptopropionyl, bis-aminoethyl-1,3-propanediamine)-bis-4-morpholino-1,8 naphthalimide |
| 55d | 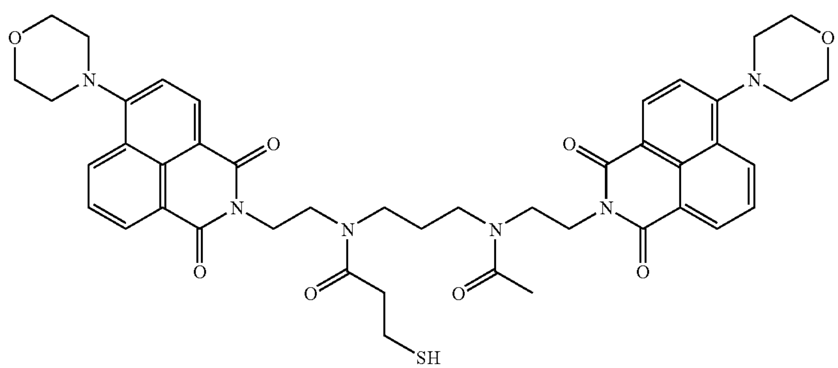 | N, N'-(1-N-(3-mercaptopropionyl), 3-N-acetyl, bis-aminoethyl-1,3-propanediamine)-bis-4-morpholino-1,8 naphthalimide |
| 56a | 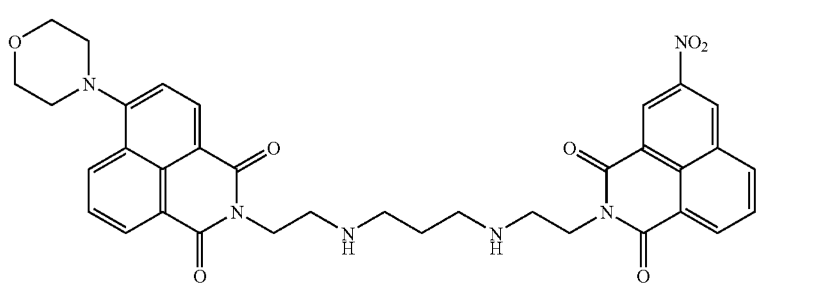 | N, N'-(bis-aminoethyl-1,3-propanediamine)-3-nitro, 4-morpholino-1,8 naphthalimide |
| 56b | 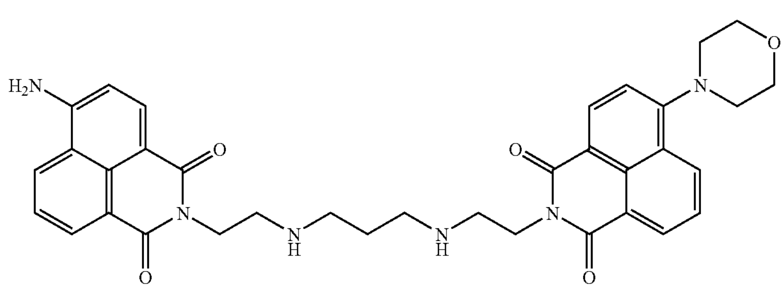 | N, N'-(bis-aminoethyl-1,3-propanediamine)-4-amino, 4-morpholino-1,8 naphthalimide |

| No. | Structure | Name |
|---|---|---|
| 57 | 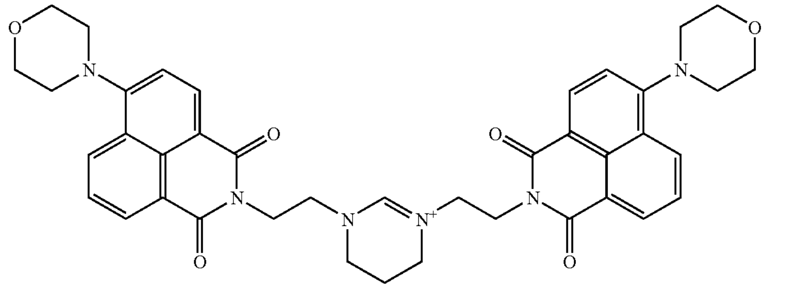 | N, N'-(bis-aminoethyl-1,4,5,6-tetrahydropyrimidinium)-bis-4-morpholino-1,8 naphthalimide |
| 58a | 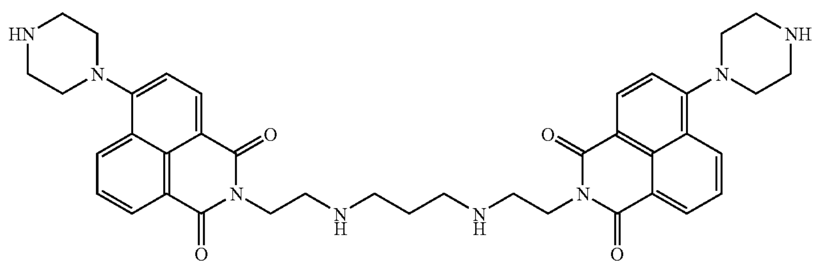 | N, N'-(bis-aminoethyl-1,3-propanediamine)-bis-4-piperazino-1,8 naphthalimide |
| 59 | 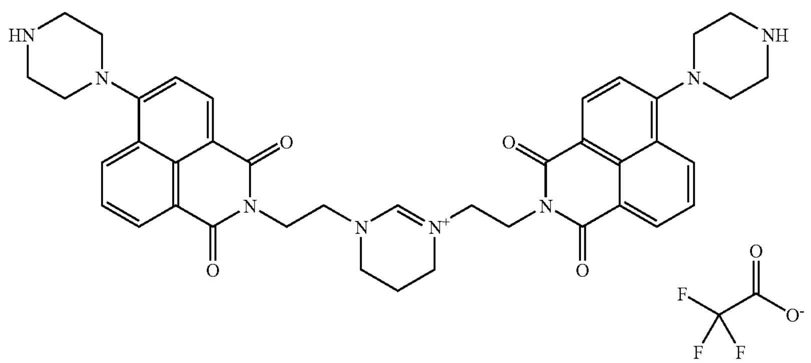 | N, N'-(bis-aminoetbyl-1,4,5,6-tetrahydropyrimidinium)-bis-4-piperazino-1,8 naphthalimide trifluoroacetate salt |
| 60 | 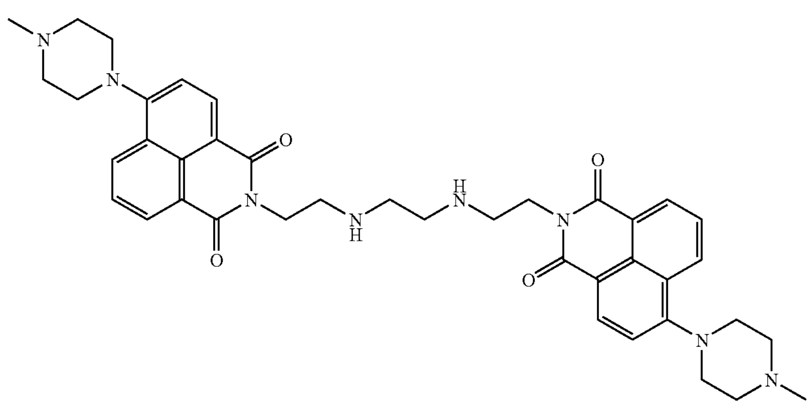 | N, N'-(bis-aminoethyl-1,2-ethanediamrne)-bis-4-(4-methylpiperazino)-1,8 naphthalimide |

TABLE 2-continued

| No. | Structure | Name |
|---|---|---|
| 58b | 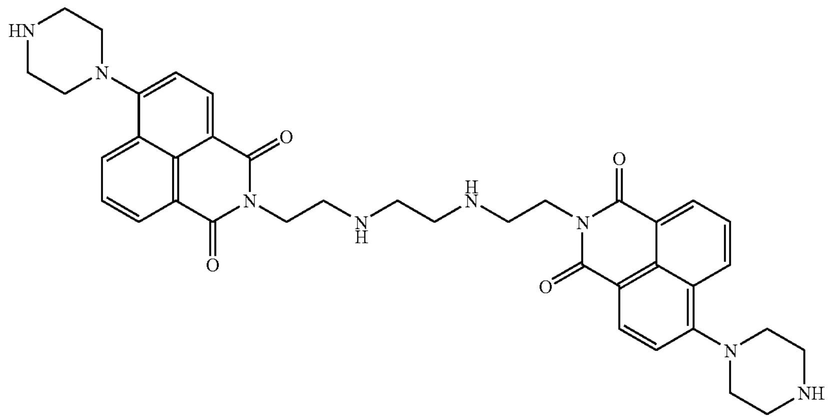 | N, N'-(bis-aminoethyl-1,2-ethanediamine)-bis-4-piperazino-1,8 naphthalimide |
| 45 | 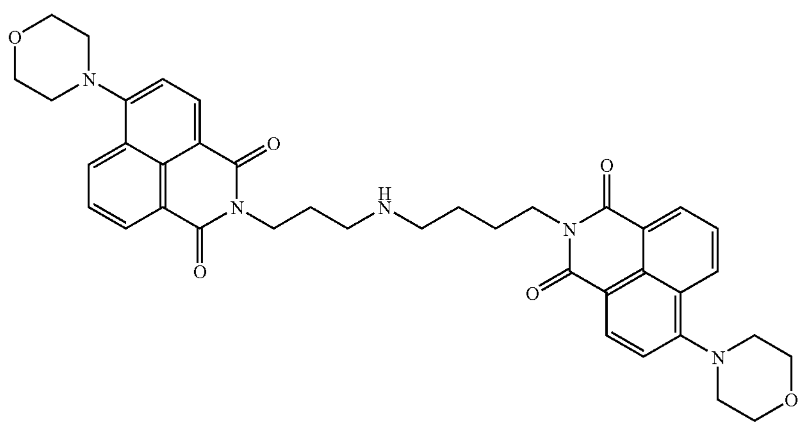 | N, N'-(4-aza-octanyl)-bis-4-morpholino-1,8 naphthalimide |
| 24a | 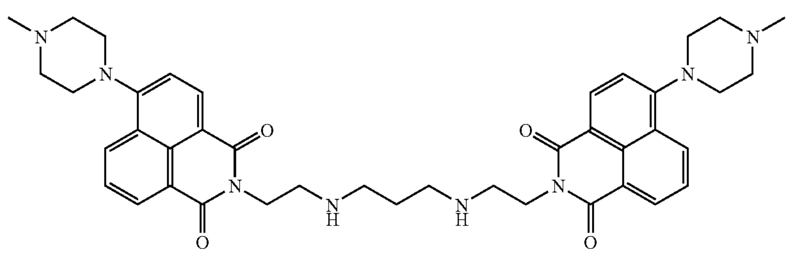 | N, N'-(bis-aminoethyl-1,2-propanediamine)-bis-(4-N-methylpiperazine)-1,8 naphthalimide |
| 61 | 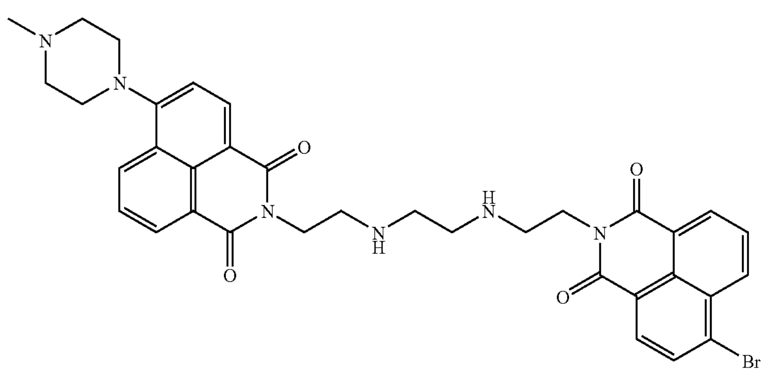 | N, N'-(bis-aminoethyl-1,2-ethanediamine)-4-piperazino,4-bromo-1,8 naphthalimide |

TABLE 2-continued

| No. | Structure | Name |
|---|---|---|
| 62 | 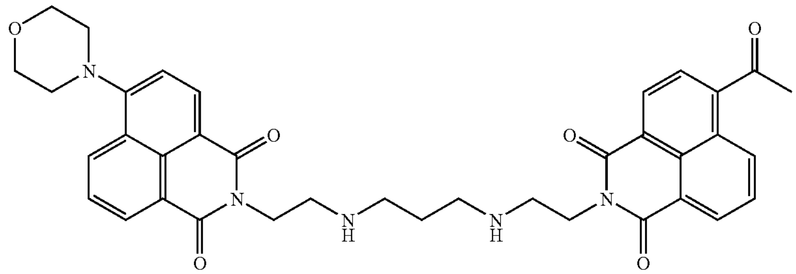 | N, N'-(bis-aminoethyl-1,3-propanediamine)-4-acetyl,4-morpholino-1,8 naphthalimide |
| 63a | 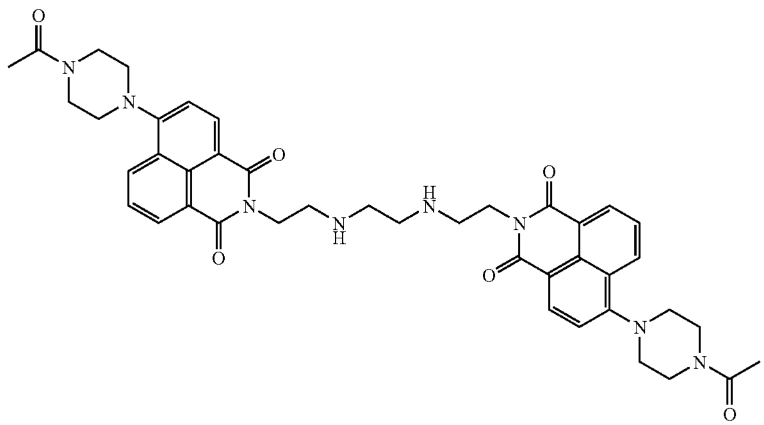 | N, N'-(bis-aminoethyl-1,2-ethanediamine)-bis 4-(4-acetylpiperazino)-1,8 naphthalimide |
| 24b | 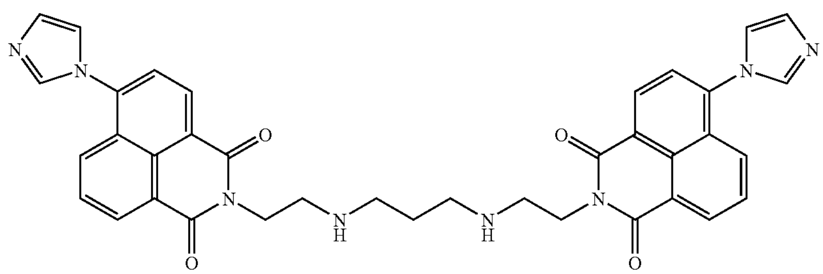 | N, N'-(bis-aminoethyl-1,3-propanediamine)-bis-(4-N-imidazolyl)-1,8 naphthalimide |
| 63b | 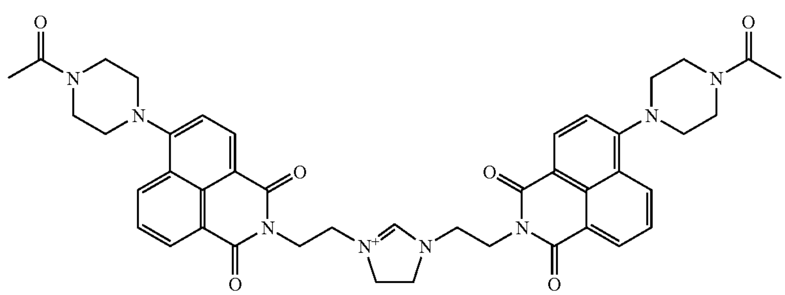 | N, N'-(bis-aminoethy-4,5-dihydro-imidazolium)-bis 4-(4-acetylpiperazino)-1,8 naphthaliinide |
| 63c | 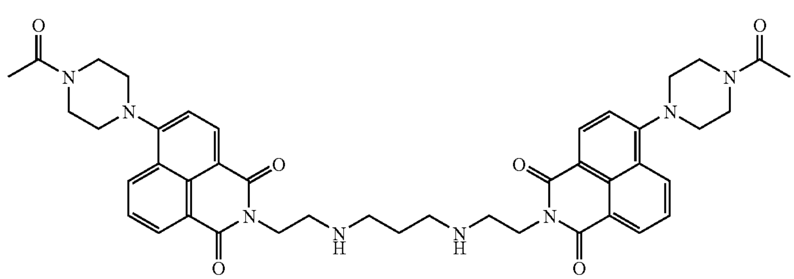 | N, N'-(bis-aminoethyl-1,3-propanediamine)-bis-4-(4-acetylpiperazino)-1,8 naphthalimide |

TABLE 2-continued

| No. | Structure | Name |
|---|---|---|
| 64 | 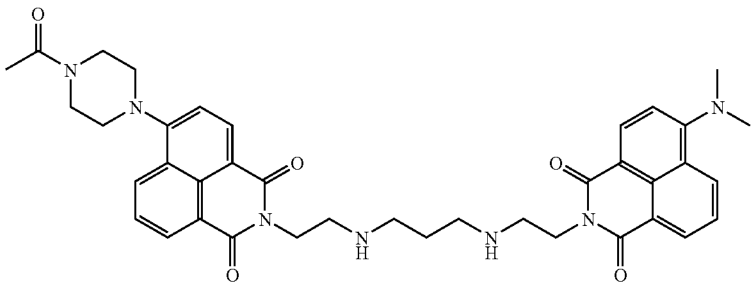 | N, N'-(bis-aminoethyl-1,3-propanediamine)-4-(4-acetylpiperazino)-4-dimethylamino-1,8 naphthalimide |
| 65 | 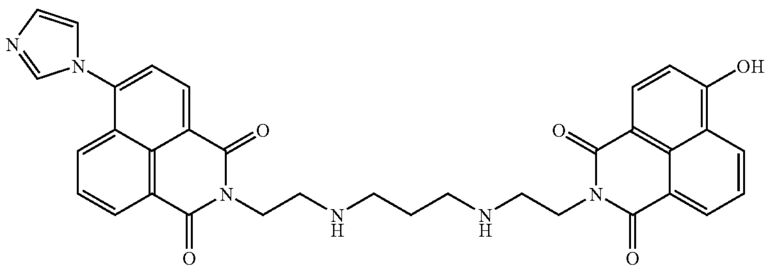 | N, N'-(bis-aminoethyl-1,3-propanediamine)-4-(N-imidazolyl)-4-hydroxyl-1,8 naphthalimide |
| 66 | 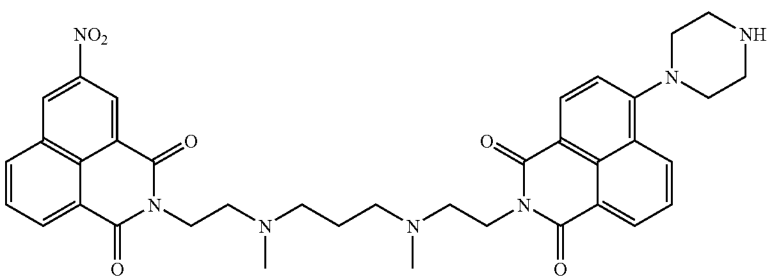 | $N^1,N^2$ bis methyl, N, N'-(bis-aminoethyl-1,3-propanediamine)-3-nitro-4-N-piperazinyl 1,8 naphthalimide |
| 67 | 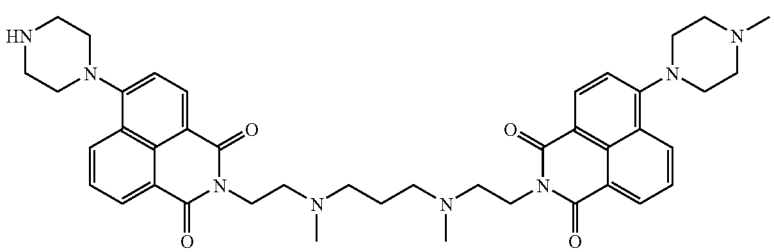 | $N^1,N^2$ bis methyl, N, N'-(bis-aminoethyl-1,3-propanediamine)-4-N-(4-methylpiperazinyl),4-N-piperazinyl 1,8 naphthalimide |
| 68 | 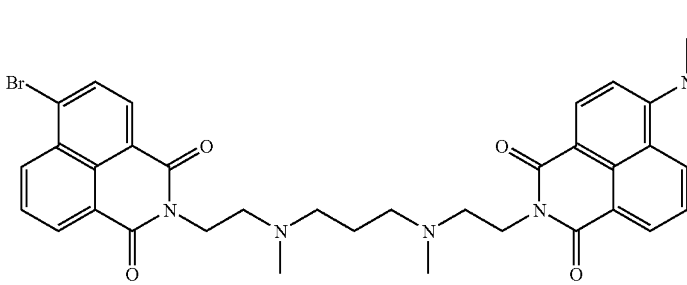 | $N^1,N^2$ bis methyl, N, N'-(bis-aminoethyl-1,3-propanediamine)-4-bromo,4-N-imidazolyl 1,8 naphthalimide |

TABLE 2-continued

| No. | Structure | Name |
|---|---|---|
| 69 | 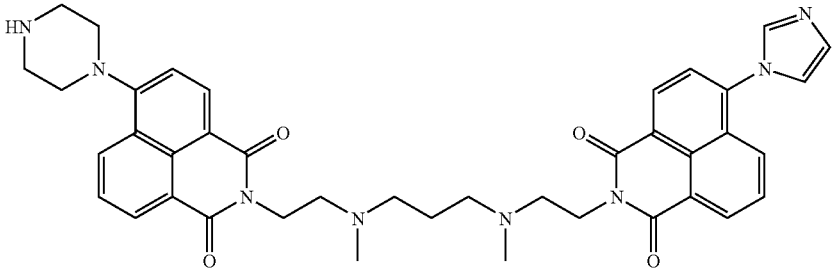 | $N^1, N^2$ bis methyl, N, N'-(bis-aminoethyl-1,3-propanediamine)-4-N-imidazoly,4-piperazinyl 1,8 naphthalimide |
| 24c | 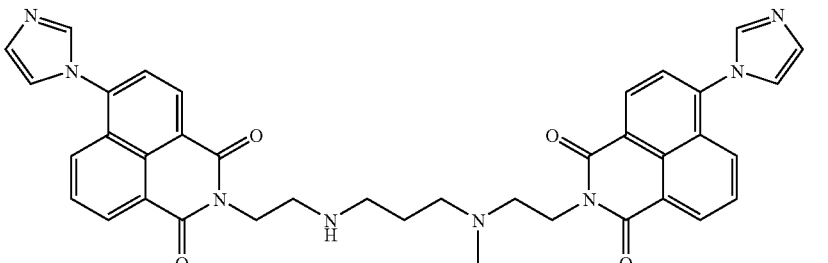 | $N^1$—H, $N^2$ -methyl, N, N'-(bis-aminoethyl-1,3-propanediamine)-bis-(4-N-imidazolyl)-1,8 naphthalimide |
| 70a | 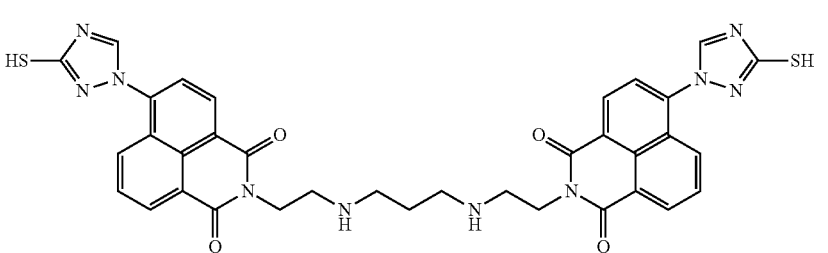 | N, N'-(bis-aminoethyl-1,3-propanediamine)-bis-(4-1N-(3-thio, 1,2,4 triazolyl)-1,8 naphthalimide |
| 70b | 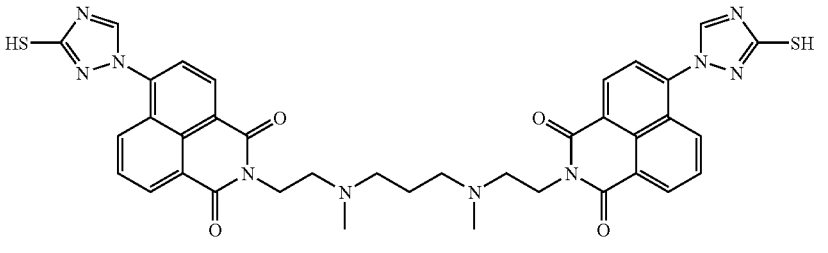 | $N^1, N^2$ bis methyl, N, N'-(bis-aminoethyl-1,3-propanediamine)-bis-(4-1N-(3-thio,1,2,4 triazolyl)-1,8 naphthalimide |
| 140 | 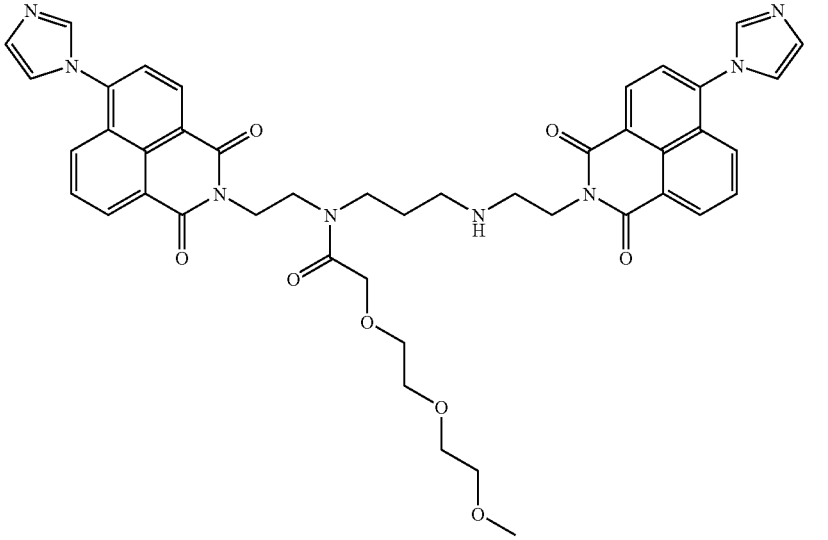 | $N^1$—H, $N^2$ -(methoxyethoxyethoxyacetamide)-(N, N'-(bis-aminoethyl-1,3-propanediamine)-bis 4-N-imidazolyl-1,8 naphthalimide) |

TABLE 2-continued

| No. | Structure | Name |
|---|---|---|
| 33b | 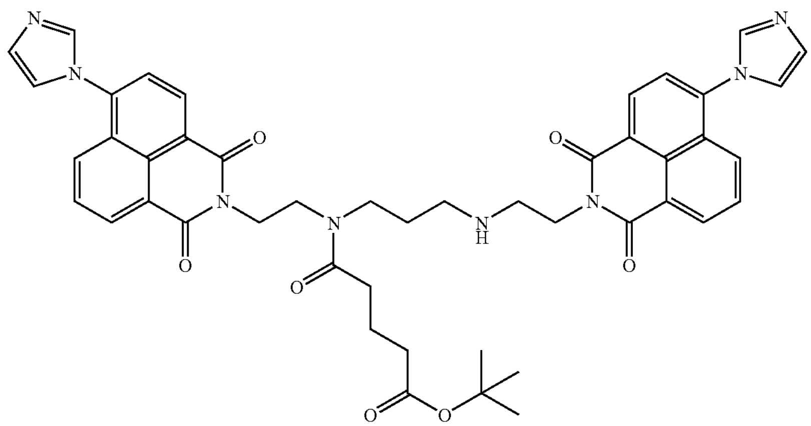 | N-(tert-butylglutaramide), bis-aminoethyl-1,3-propanediamine)-bis-4-N-imidazolyl-1,8 naphthalimide |
| 30b | 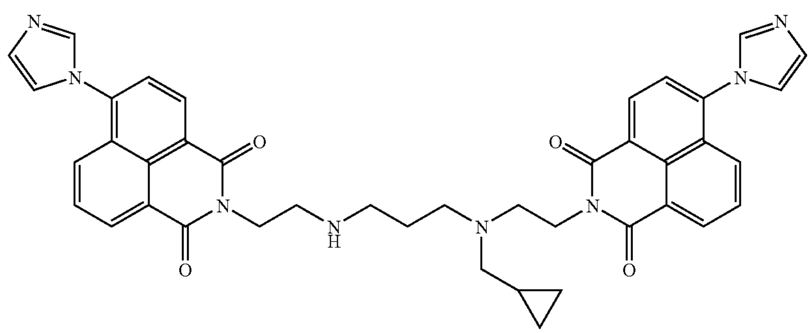 | N, N'-(N-cyclopropylmethyl, bis-aminoethyl-1,3-propanediamine)-bis-4-N-imidazolyl-1,8 naphthalimide |
| 139 | 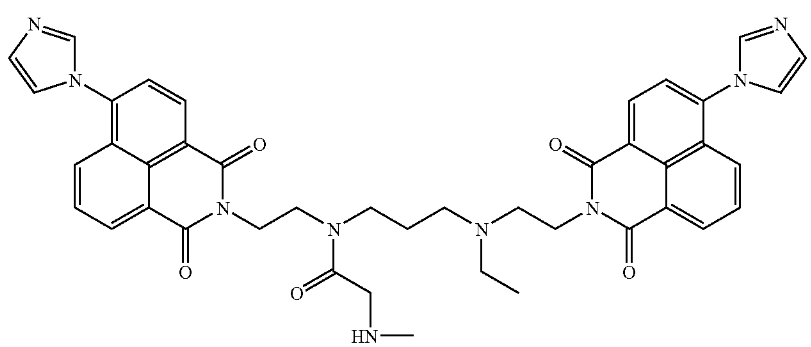 | $N^1$-methyl, $N^2$-(N-methylglycyl)-N,N'-(bis-aminoethyl-1,3-propanediamine)-bis 4-N-imidazolyl-1,8 naphthalimide |
| 50 | 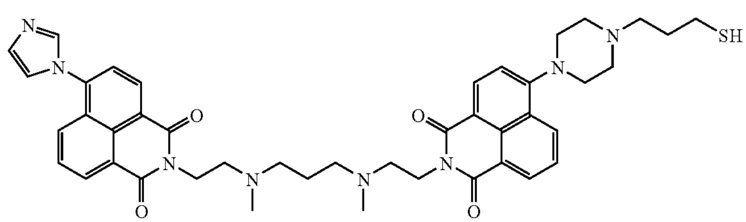 | $N^1,N^2$ bis methyl, N, N'-(bis-aminoethyl-1,3-propanediamine)-4-N-imidazolyl,4-(4-mercaptopropylpiperazinyl)-1,8 naphthalimide |

TABLE 2-continued

| No. | Structure | Name |
|---|---|---|
| 71a | 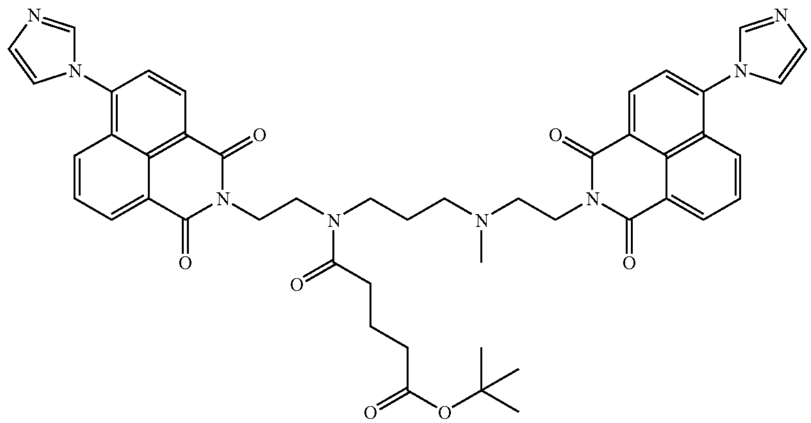 | $N^1$-methyl, $N^2$-tert-butylglutaramide)-N, N'-(bis-aminoethyl-1,3-propanediamine)-bis 4-N-imidazolyl-1,8 naphtbalimide |
| 71b | 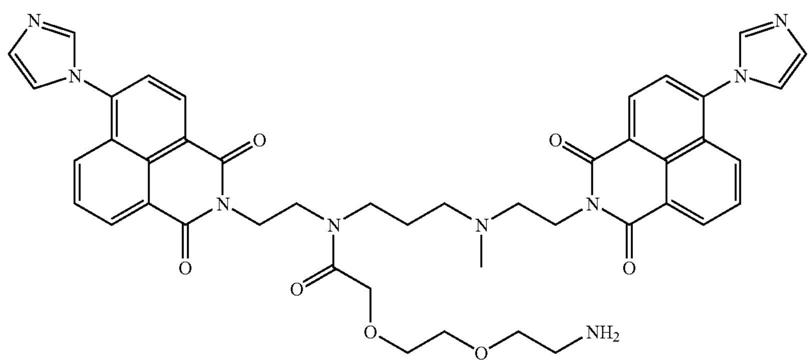 | $N^1$-methyl, $N^2$-(2-(2-(2-aminoethoxy)ethoxy)acetamido)-N, N'-(bis-aminoethyl-1,3-propanediamine)-bis 4-N-imidazolyl-1,8 naphthalimide |
| 71c | 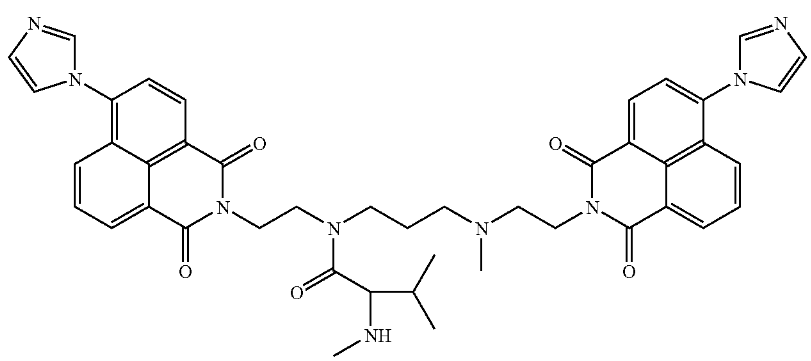 | $N^1$-methyl, $N^2$-(N-methylvaline)-N, N'-(bis-aminoethyl-1,3-propanediamine)-bis 4-N-imidazolyl-1,8 naphthalimide |
| 51 | 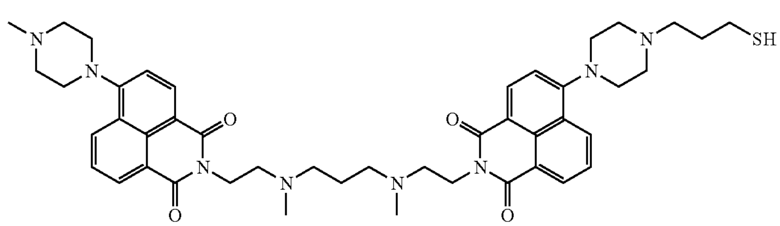 | N, N'-(Bis-2-acetamido-1,3-propanediamine)-4-piperazinyl, 4-(4N-(3-mercaptopropyl)-piperazinyl-1,8 naphthalimide |

TABLE 2-continued

| No. | Structure | Name |
|---|---|---|
| 71d | 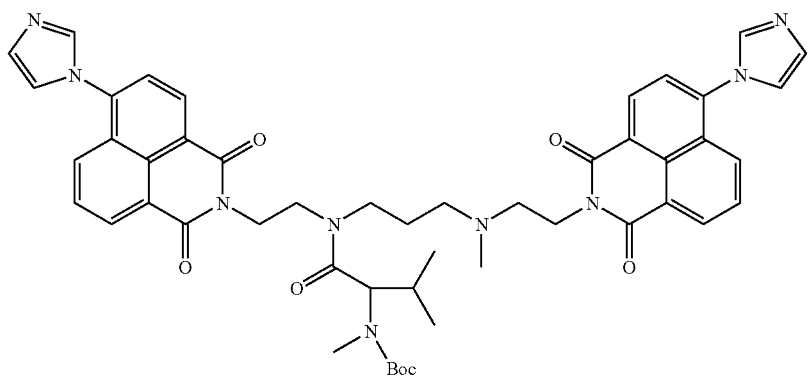 | N¹-methyl, N²-(N-methyl, N-tertbuytyloxy valine)-N, N'-(bis-aminoethyl-1,3-propanediamine)-bis 4-N-imidazolyl-1,8 naphthalimide |
| 71e | 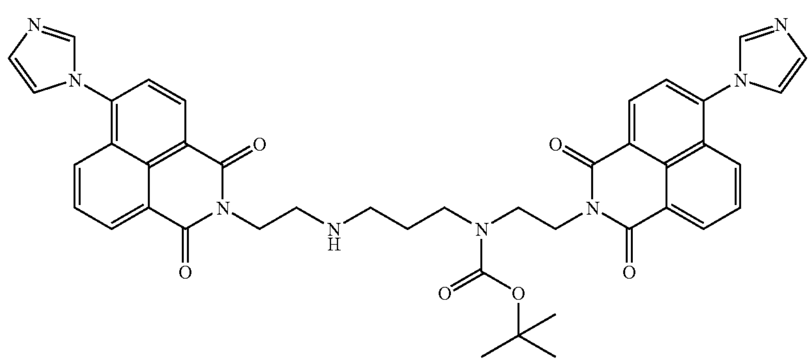 | N¹—H, N²-tertbuytyloxycarbonyl)-N, N'-(bis-aminoethyl-1,3-propanediamine)-bis 4-N-imidazolyl-1,8 naphthalimide |
| 71f | 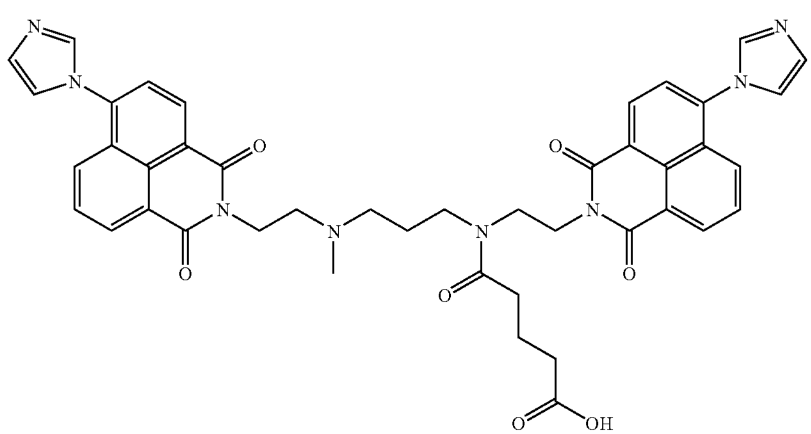 | N¹-methyl, N²-glutaramide)-N, N'-(bis-aminoethyl-1,3-propanediamine)-bis 4-N-imidazolyl-1,8 naphthalimide |
| 72 | 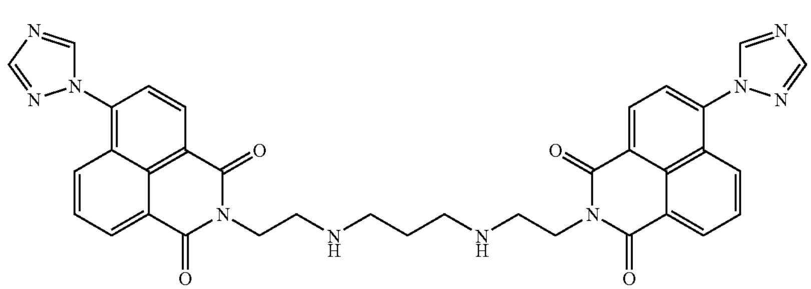 | N, N'-(bis-aminoethyl-1,3-propanediamine)-bis 4-1N-(1,2,4-triazolyl)-1,8 naphthalimide |

TABLE 2-continued

| No. | Structure | Name |
|---|---|---|
| 73a | 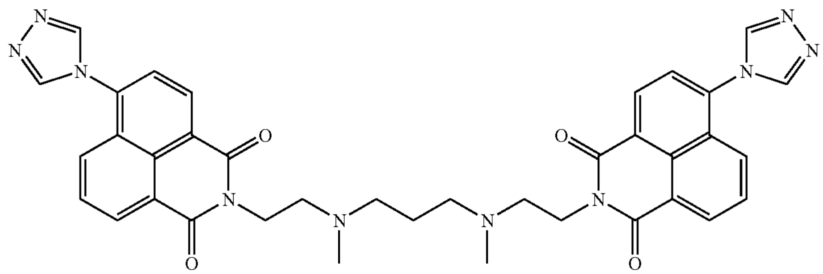 | $N^1,N^2$ bis methyl, N, N'-(bis-aminoethyl-1,3-propanediamine)-bis 4-1N-(1,3,4-triazolyl)-1,8 naphthalimide |
| 73b | 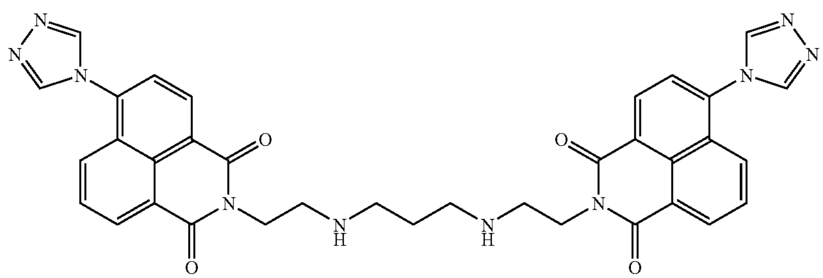 | N, N'-(bis-aminoethyl-1,3-propanediamine)-bis 4-1N-(1,3,4-triazolyl)-1,8 naphthalimide |
| 73c | 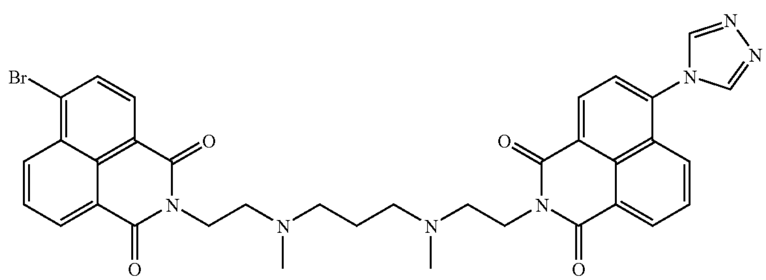 | $N^1,N^2$ bis methyl, N, N'-(bis-aminoethyl-1,3-propanediamine)-4-bromo, 4-1N-(1,3,4-triazolyl)-1,8 naphthalimide |
| 74 | 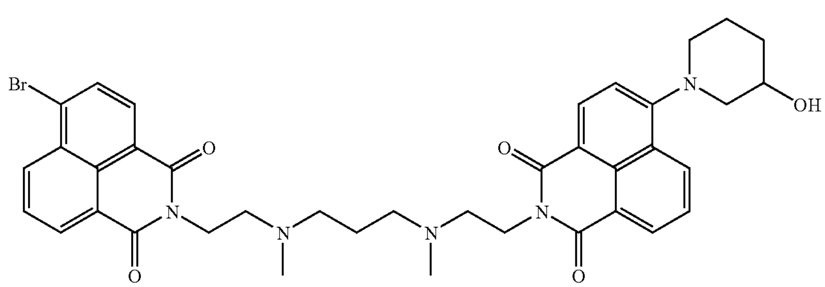 | $N^1,N^2$ bis methyl, N, N'-(bis-aminoetbyl-1,3-propanediamine)-4-bromo, 4-N-(3-hydroxypiperidmyl)-1,8 naphthalimide |
| 75 | 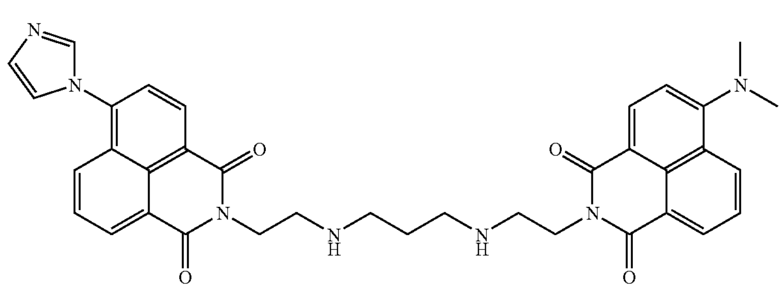 | N, N'-(bis-aminoethyl-1,3-propanediamine)4-dimethylamino, 4-N-imidazolyl-1,8 naphtbalimide |

TABLE 2-continued

| No. | Structure | Name |
|---|---|---|
| 58c | 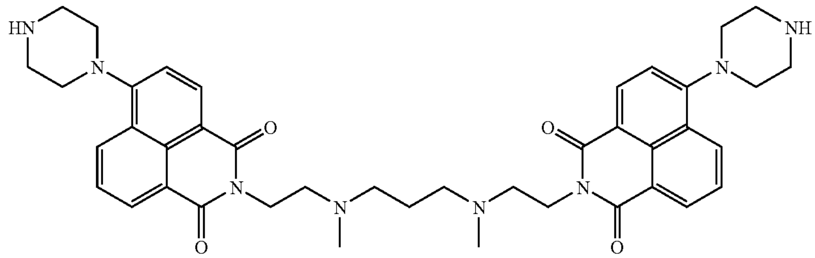 | $N^1,N^2$ bis methyl, N, N'-(bis-aminoethyl-1,3-propanediamine)-bis 4-N-(piperazinyl)-1,8 naphthalimide |
| 71g | 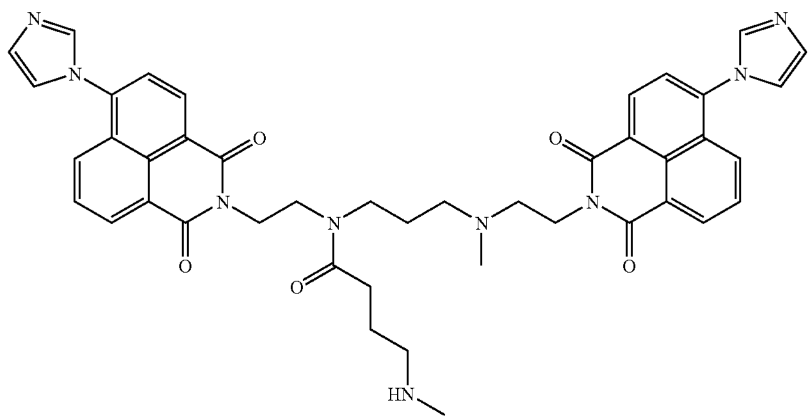 | $N^1$-methyl, $N^2$-(3-(N-methyl)-butyramide, N, N'-(bis-aminoethyl-1,3-propanediamine)-bis 4-N-(piperazinyl)-1,8 naphthalimide |
| 76a | 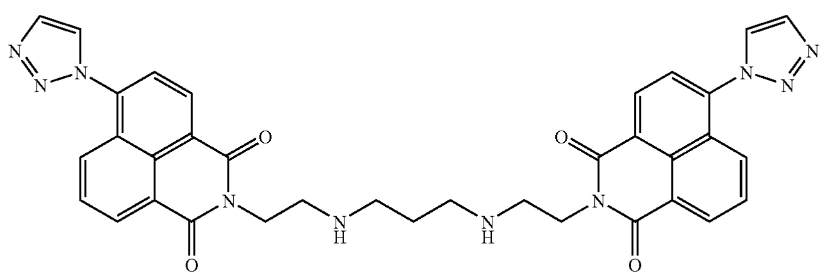 | N, N'-(bis-aminoethyl-1,3-propanediamine)-bis 4-1N-(1,2,3-triazolyl)-1,8 naphthalimide |
| 77a | 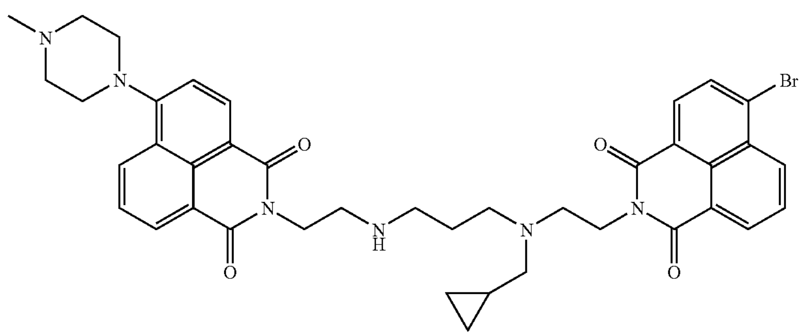 | $N^1$—H, $N^2$-cyclopropylmethyl, N, N'-(bis-aminoethyl-1,3-propanediamine)-4-bromo,4-N-(4-methylpiperazinyl)-1,8 naphthalimide |
| 77b | 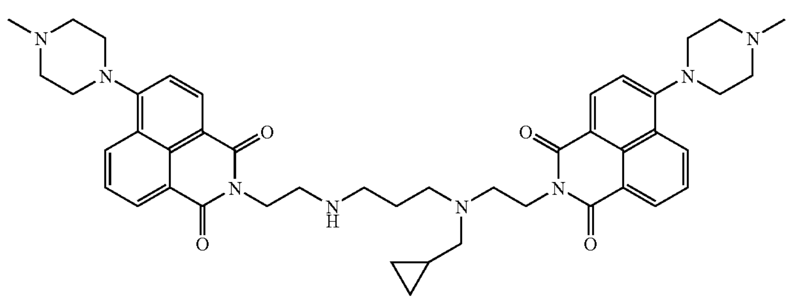 | $N^1$—H, $N^2$-cyclopropylmethyl, N, N'-(bis-aminoethyl-1,3-propanediamine)-bis 4-N-(4-methylpiperazinyl)-1,8 naphthalimide |

TABLE 2-continued

| No. | Structure | Name |
|---|---|---|
| 78 | 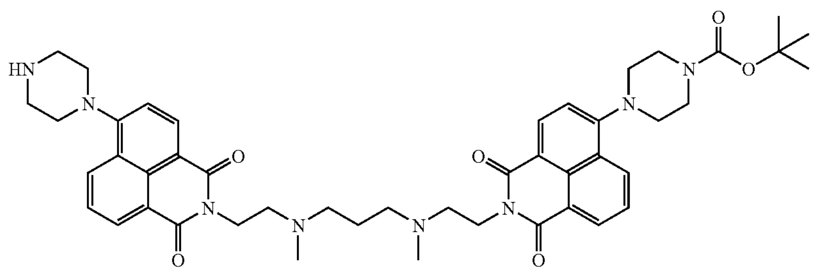 | $N^1, N^2$ bis methyl, N, N'-(bis-aminoethyl-1,3-propanediamine)-4-N-(piperazinyl), 4-N-(4-Boc-piperazinyl)-1,8 naphthalimide |
| 79a | 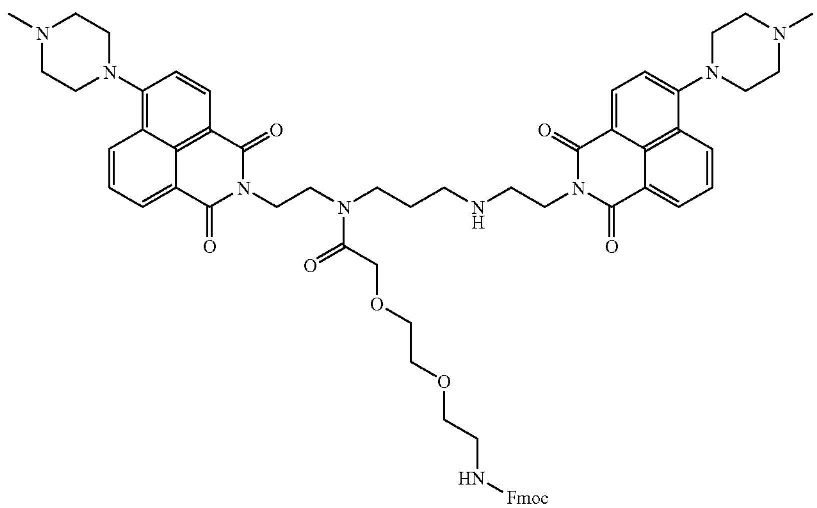 | $N^1$—H, $N^2$-(2-(2-(2-(N-Fmoc)aminoethoxy)ethoxy)acet-amido)-N, N'-(bis-aminoethyl-1,3-propanediamine)-bis 4-N-(4-methyl piperazinyl-1,8 naphthalimide |
| 79b | 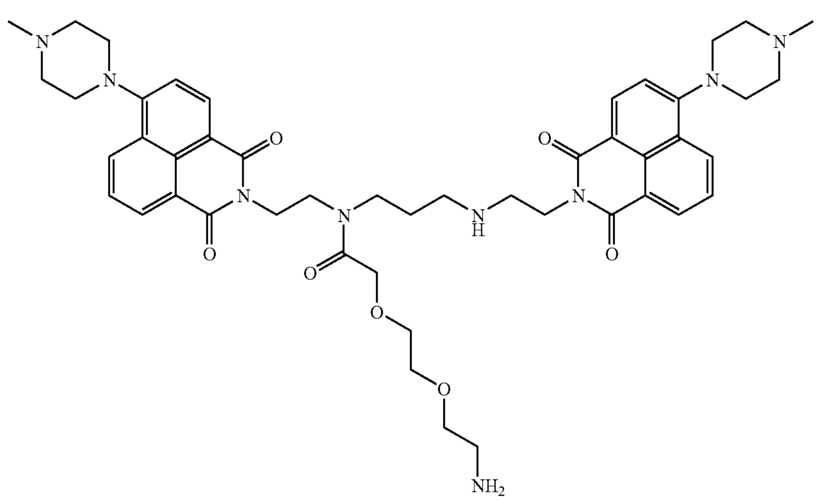 | $N^1$—H, $N^2$-(2-(2-(2-aminoethoxy)ethoxy)acetamido)-N, N'-(bis-aminoethyl-1,3-propanediamine)-bis 4-N-(4-methyl piperazinyl-1,8 naphthalimide |

TABLE 2-continued

| No. | Structure | Name |
|---|---|---|
| 79c | 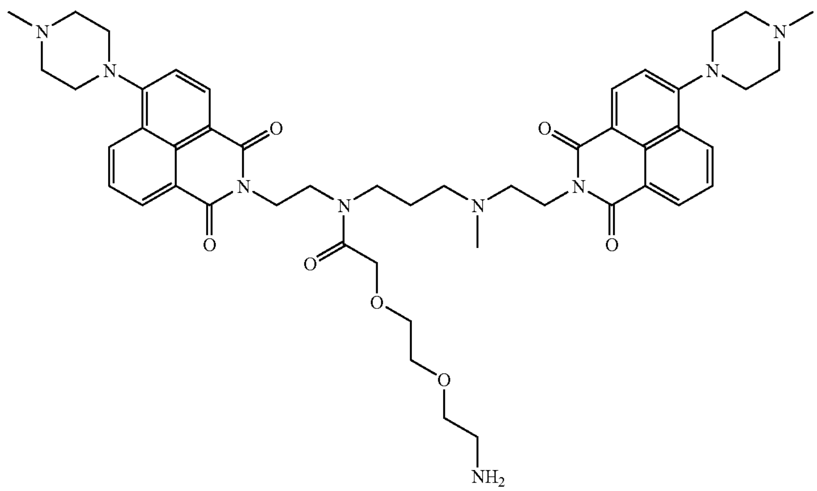 | $N^1$-methyl, $N^2$-(2-(2-(2-aminoethoxy)ethoxy)acetamido)-N, N'-(bis-aminoethyl-1,3-propanediamine)-bis 4-N-(4-methyl piperazinyl-1,8 naphthalimide |
| 71h | 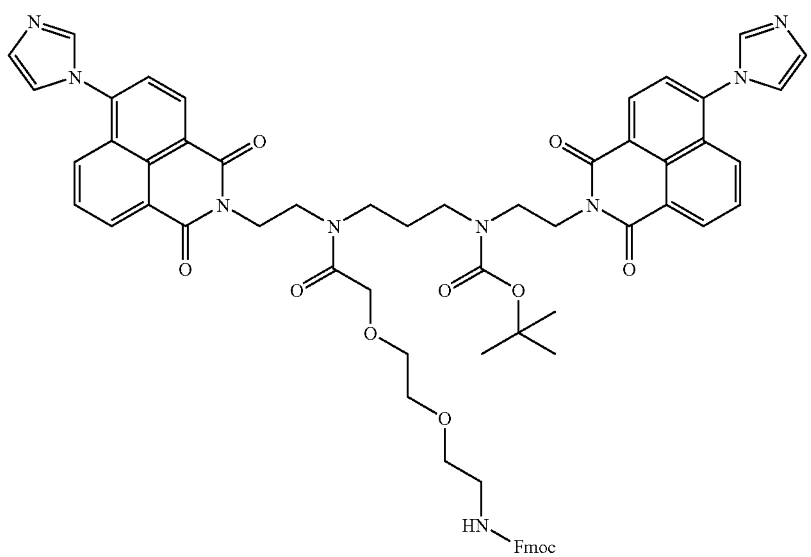 | $N^1$-Boc, $N^2$-(2-(2-(2-(N-Fmoc)aminoethoxy)ethoxy)acetamido)-N, N'-(bis-aminoethyl-1,3-propanediamine)-bis 4-N-imidazolyl-1,8 naphthalimide |
| 71i | 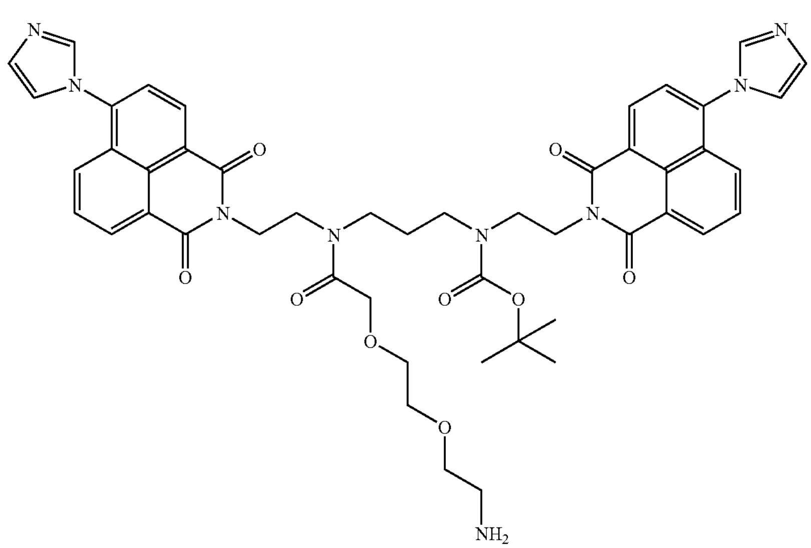 | $N^1$-Boc, $N^2$-(2-(2-(2-aminoethoxy)ethoxy)acetamido)-N, N'-(bis-aminoethyl-1,3-propanediamine)-bis 4-N-imidazolyl-1,8 naphthalimide |

TABLE 2-continued

| No. | Structure | Name |
|---|---|---|
| 79d | 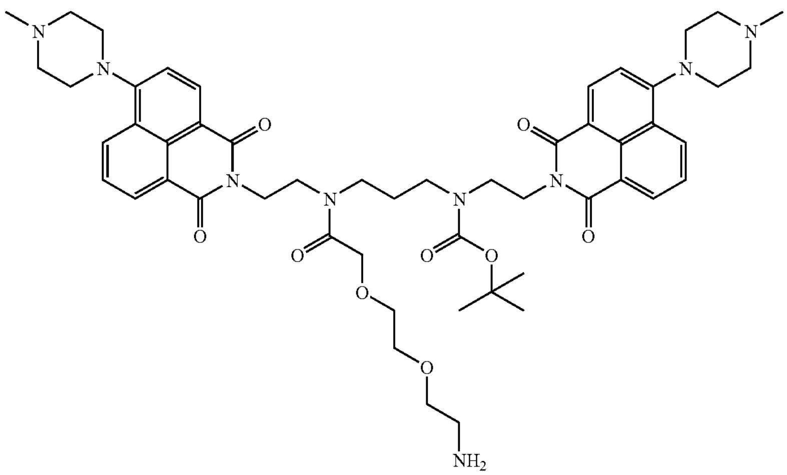 | $N^1$-Boc, $N^2$-(2-(2-(2-aminoethoxy)ethoxy)acetamido)-N, N'-(bis-aminoethyl-1,3-propanediamine)-bis 4-N-(4-methyl piperazinyl-1,8 naphthalimide |
| 76b | 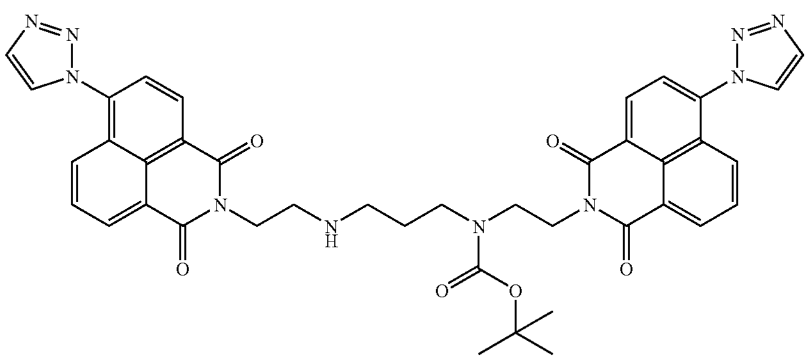 | $N^1$—H, $N^2$-Boc, N, N'-(bis-aminoethyl-1,3-propanediamine)-bis 4-1N-(1,2,3-triazolyl)-1,8 naphthalimide |
| 49 | 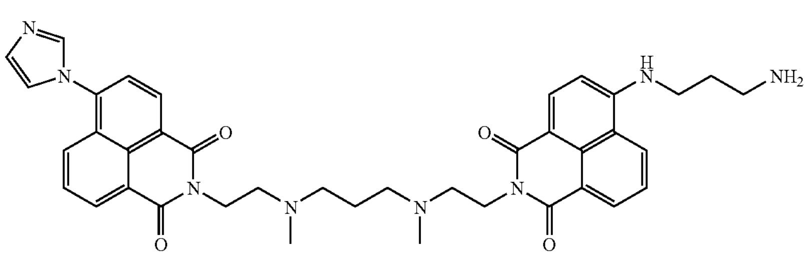 | $N^1,N^2$ bis methyl, N, N'-(bis-aminoethyl-1,3-propanediamine)-4-N-imidazolyl, 4-(3-aminopropyl)amino)-1,8 naphthalimide |
| 80a | 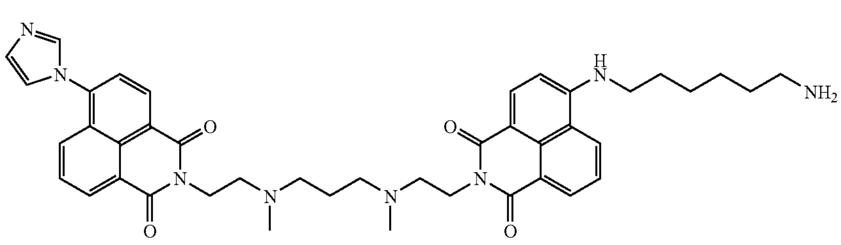 | $N^1,N^2$ bis methyl, N, N'-(bis-aminoethyl-1,3-propanediamine)-4-N-imidazolyl, 4-(6-aminohexyl)amino)-1,8 naphthalimide |

TABLE 2-continued

| No. | Structure | Name |
|---|---|---|
| 80b | 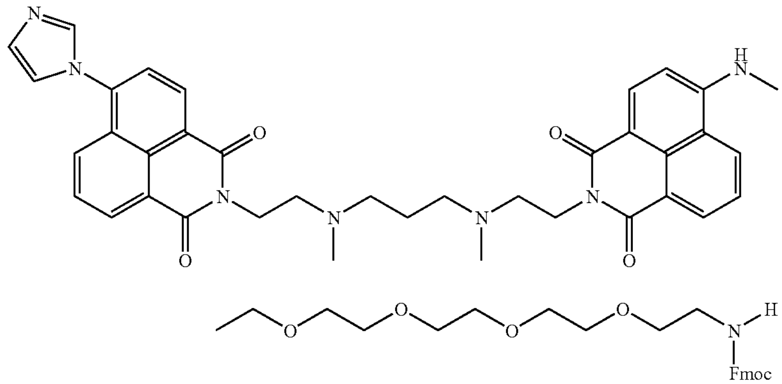 | $N^1,N^2$ bis methyl, N, N'-(bis-aminoetiiyl-1,3-propanediamine)-4-N-imidazolyl, 4-N-(2-(N-Fmoc)aminoethoxy-tetraethoxy)-1,8 naphthalimide |
| 80c | 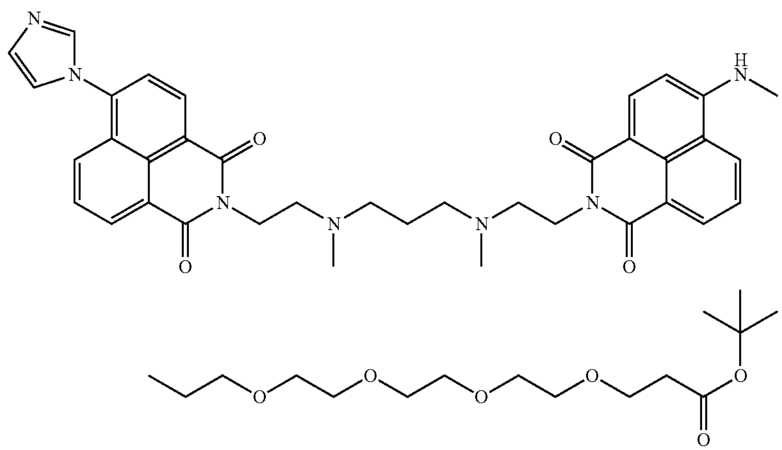 | $N^1,N^2$ bis methyl, N, N'-(bis-aminoethyl-1,3-propanediamine)-4-N-imidazolyl, 4-N-(3-tertbutylpropionate-tetraethoxy)-1,8 naphthalimide |
| 81a | 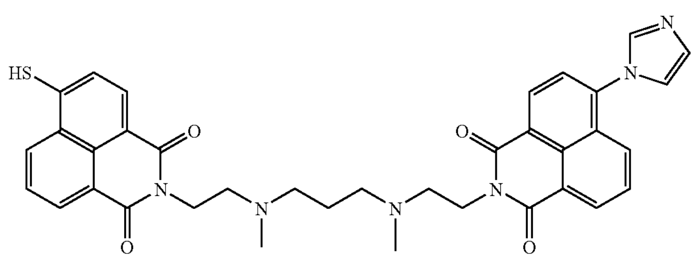 | $N^1,N^2$ bis methyl, N, N'-(bis-aminoethyl-1,3-propanediamine)-4-thiol, 4-N-imidazolyl-1,8 naphthalimide |
| 81b | 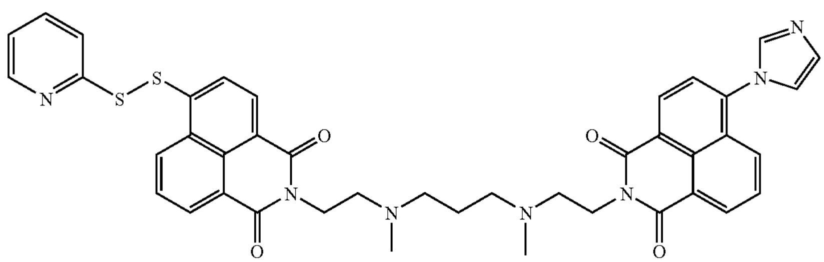 | $N^1,N^2$ bis methyl, N, N'-(bis-aminoethyl-1,3-propanediamine)-4-dithio-(2-pyridyl), 4-N-imidazolyl-1,8 naphthalimide |
| 81c | 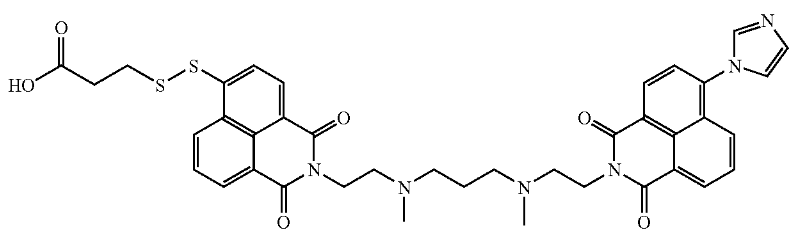 | $N^1,N^2$ bis methyl, N, N'-(bis-aminoethyl-1,3-propanediamine)-4-dithio-(3-propionic acid), 4-N-imidazolyl-1,8 naphthalimide |

| No. | Structure | Name |
|---|---|---|
| 71j | 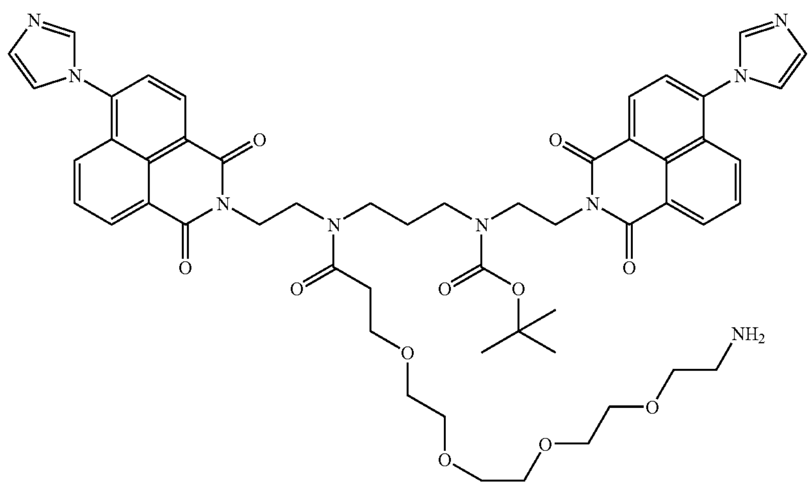 | N'-Boc, N²-(2-(2-(2-aminoethoxy)triethoxy)propion-amido)-N, N'-(bis-aminoethyl-1,3-propanediamine)-bis 4-N-imidazolyl-1,8 naphthalimide |
| 71k | 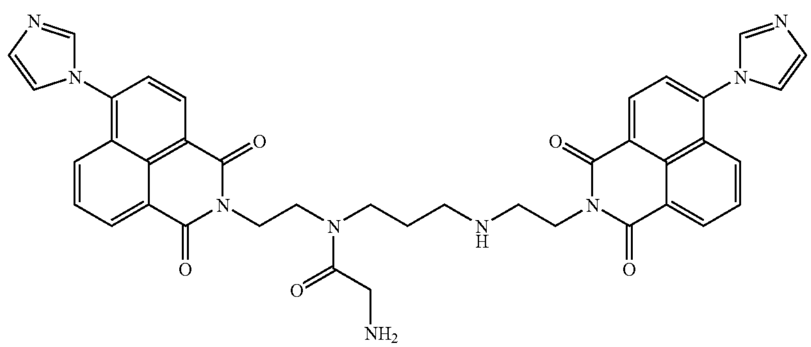 | N¹—H, N²-glycyl, N, N'-(bis-aminoethyl-1,3-propanediamine)-bis 4-N-imidazolyl-1,8 naphthalimide |
| 71l | 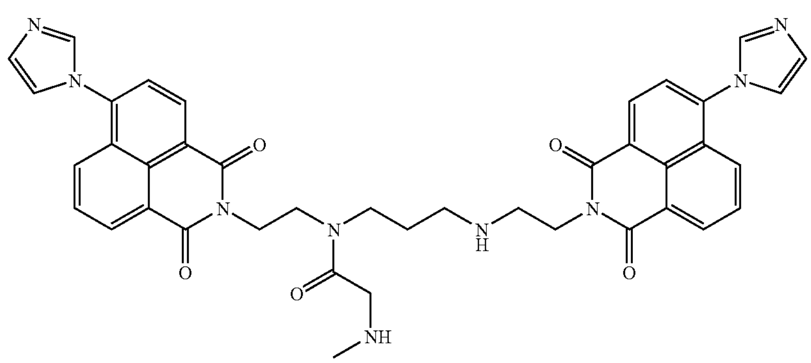 | N¹—H, N²-(N-methyl) glycyl, N, N'-(bis-aminoethyl-1,3-propanediamine)-bis 4-N-imidazolyl-1,8 naphthalimide |
| 71m | 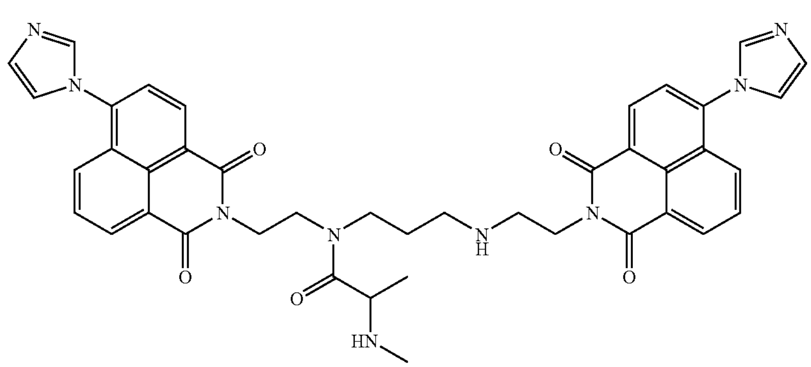 | N¹—H, N²-(N-methyl) alanyl, N, N'-(bis-aminoetbyl-1,3-propanediamine)-bis 4-N-imidazolyl-1,8 naphthalimide |

TABLE 2-continued

| No. | Structure | Name |
|---|---|---|
| 71n | 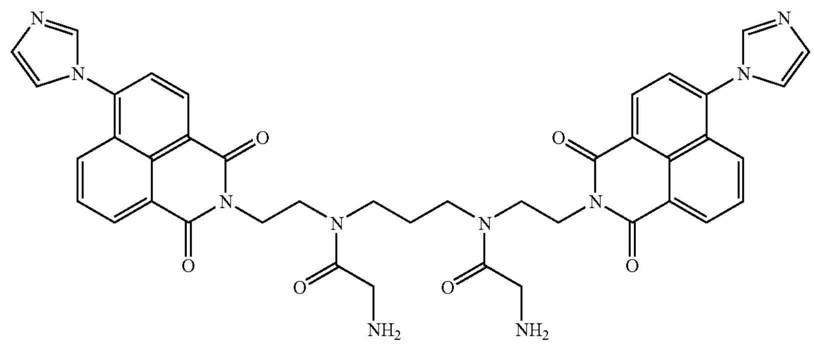 | $N^1$, $N^2$ bis glycyl, N, N'-(bis-aminoethyl-1,3-propanediamine)-bis 4-N-imidazolyl-1,8 naphthalimide |
| 71o | 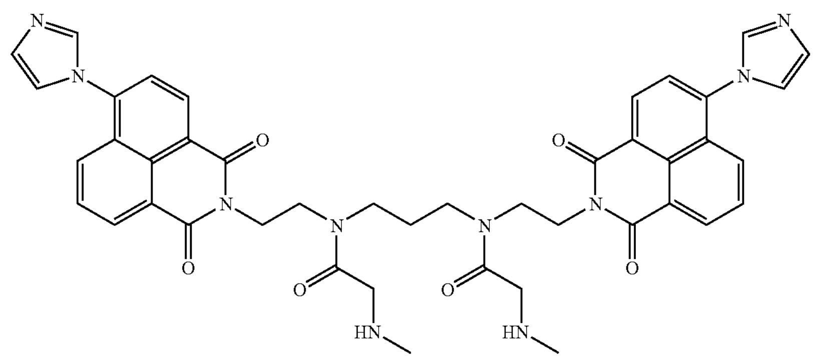 | $N^1$, $N^2$ bis (N-methyl glycyl), N, N'-(bis-aminoethyl-1,3-propanediamine)-bis 4-N-imidazolyl-1,8 naphthalimide |
| 71p | 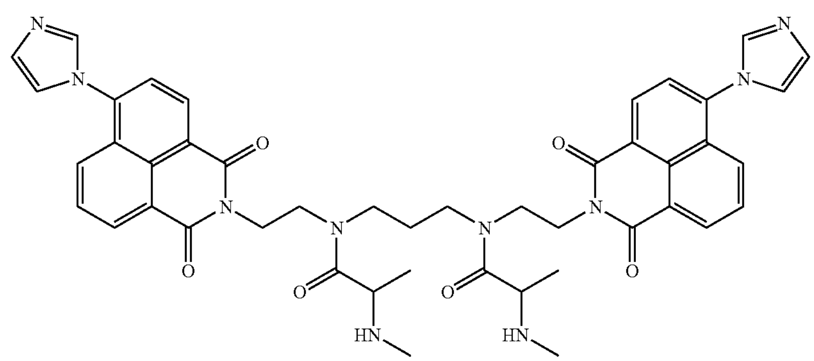 | $N^1$, $N^2$ bis (N-methyl alanyl), N, N'-(bis-aminoethyl-1,3-propanediamine)-bis 4-N-imidazolyl-1,8 naphthalimide |

Synthesis of bis 1,8 naphthalimide Compounds

Bis 1,8 naphthalimide compounds were prepared according to Brana et al (2004) J. Med. Chem. 47:1391-1399; Brana et al (2003) Org. Biomol. Chem. 1:648-654; Brana, M. F. and Ramos, A. (2001) Current Med. Chem.—Anti-Cancer Agents 1:237-255, as well as conventional organic chemistry methodology.

Generally, 1,8 naphthalimide intermediates may be prepared from 1,8-naphthalic anhydride compounds (Chem. Rev. (1970) 70:439-469; U.S. Pat. Nos. 4,146,720; 5,616,589; 5,416,089; 5,585,382; 5,552,544). Various substituted 1,8-naphthalic anhydride compounds are commercially available, such as 4-Bromo-1,8-naphthalic anhydride (Aldrich, Milwaukee, Wis.). Reaction of a 1,8-naphthalic anhydride compound with a primary amine gives the 1,8 naphthalimide. Displacement of bromine from the 4 position occurs with various nucleophilic reagents.

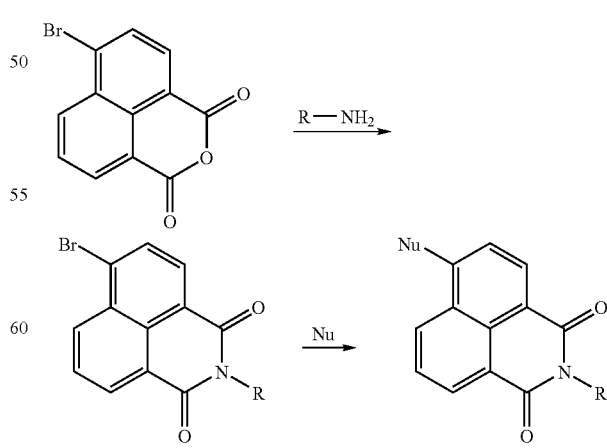

Where the amine reagent is a bis-amino compound, two 1,8-naphthalic anhydride molecules react with an amine to form bis 1,8 naphthalimide intermediates (Brana, M. F. and Ramos, A. (2001) Current Med. Chem.—Anti-Cancer Agents 1:237-255; Brana et al (1993) Anticancer Drug Des. 8:257; Brana et al (1996) Anticancer Drug Des. 11:297; WO 94/02466; and U.S. Pat. Nos. 4,874,863; 5,206,249; 5,416,089; 5,488,110; 5,981,753; 6,177,570). For example, two equivalents of an anhydride in toluene are treated with one equivalent of the corresponding polyamine in ethanol. The mixture is heated at reflux until the reaction is complete. The bis 1,8 naphthalimide is isolated, e.g. by filtration and crystallization, as the free base and converted to a salt, such as the mesylate with methanesulfonic acid, or as the trifluoroacetate with trifluoroacetic acid (TFA), and washed with an organic solvent, according to the method of Brana et al (2004) J. Med. Chem. 47:1391-1399.

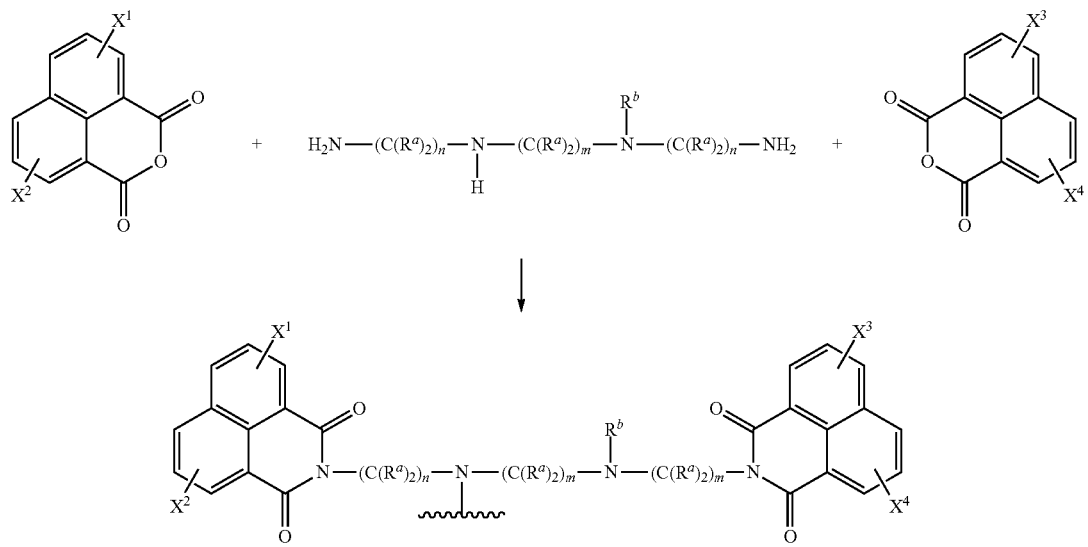

Alternatively, the 1,8 naphthalimide groups may be attached to the polyamine unit sequentially (WO 94/02466) by protecting one of the terminal amino groups of the polyamine reagent during reaction with the first 1,8 naphthalic anhydride reagent. After deprotection of the terminal amino group of the mono 1,8 naphthalimide intermediate, a second 1,8 naphthalic anhydride reagent may be reacted to form the bis 1,8 naphthalimide product. By this route, asymmetric bis 1,8 naphthalimide compounds can be prepared, i.e. where $X^1$ and $X^2$ are different than $X^3$ and $X^4$. Suitable amino protecting groups include mesitylenesulfonyl, dinitrobenzenesulfonyl, BOC (tert-butyloxycarbonyl), CBz (carbobenzoxy), or those detailed in *Protective Groups in Organic Chemistry*, Theodora W. Greene (1991) John Wiley & Sons, Inc., New York, or later editions thereto. Alternatively, the terminal amino group for coupling to the second 1,8 naphthalic anhydride reagent may be generated by reductive amination of a carbonyl group such as aldehyde or ester, or by reduction of a nitrile group.

In vitro Cell Proliferation Assays

Generally, the cytotoxic or cytostatic activity of a compound of the invention is measured by: exposing mammalian cells having receptor proteins, e.g. HER2, to the antibody of the ADC in a cell culture medium; culturing the cells for a period from about 6 hours to about 5 days; and measuring cell viability. Cell-based in vitro assays were used to measure viability (proliferation), cytotoxicity, and induction of apoptosis (caspase activation) of the ADC of the invention.

The in vitro potency of antibody drug conjugates was measured by a cell proliferation assay (FIGS. 1-5). The CellTiter-Glo® Luminescent Cell Viability Assay is a commercially available (Promega Corp., Madison, Wis.), homogeneous assay method based on the recombinant expression of *Coleoptera* luciferase (U.S. Pat. No. 5,583,024; U.S. Pat. No. 5,674,713 and U.S. Pat. No. 5,700,670). This cell proliferation assay determines the number of viable cells in culture based on quantitation of the ATP present, an indicator of metabolically active cells (Crouch et al (1993) J. Immunol. Meth. 160:81-88, U.S. Pat. No. 6,602,677). The CellTiter-Glo® Assay was conducted in 96 well format, making it amenable to automated high-throughput screening (HTS) (Cree et al (1995) AntiCancer Drugs 6:398-404). The homogeneous assay procedure involves adding the single reagent (CellTiter-Glo® Reagent) directly to cells cultured in serum-supplemented medium. Cell washing, removal of medium and multiple pipetting steps are not required. The system detects as few as 15 cells/well in a 384-well format in 10 minutes after adding reagent and mixing. The cells may be treated continuously with ADC, or they may be treated and separated from ADC. Generally, cells treated briefly, i.e. 3 hours, showed the same potency effects as continuously treated cells.

The homogeneous "add-mix-measure" format results in cell lysis and generation of a luminescent signal proportional to the amount of ATP present. The amount of ATP is directly proportional to the number of cells present in culture. The CellTiter-Glo® Assay generates a "glow-type" luminescent signal, produced by the luciferase reaction, which has a half-life generally greater than five hours, depending on cell type and medium used. Viable cells are reflected in relative luminescence units (RLU). The substrate, Beetle Luciferin, is oxidatively decarboxylated by recombinant firefly luciferase with concomitant conversion of ATP to AMP and generation of photons. The extended half-life eliminates the need to use reagent injectors and provides flexibility for continuous or batch mode processing of multiple plates. This cell proliferation assay can be used with various multiwell formats, e.g. 96 or 384 well format. Data can be recorded by luminometer or CCD camera imaging device. The luminescence output is presented as relative light units (RLU), measured over time.

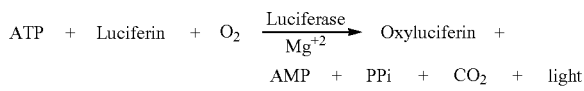

$$ATP + Luciferin + O_2 \xrightarrow[Mg^{+2}]{Luciferase} Oxyluciferin +$$
$$AMP + PPi + CO_2 + light$$

The anti-proliferative effects of antibody drug conjugates were measured by the cell proliferation, in vitro cell killing assay above against two breast tumor cell lines (FIGS. 1-5).

FIG. 1 shows an in vitro, cell proliferation assay with SK-BR-3 cells treated with: -o-trastuzumab and -●-trastuzumab-MC-vc-PAB-(N,N'-(bis-aminoethyl-1,3-propanediamine)-bis-(4-N-imidazolyl)-1,8 naphthalimide) 202, measured in Relative Fluorescence Units (RLU, ×1000) versus µg/ml concentration of antibody or ADC. Trastuzumab is linked via a cysteine.

FIG. 2 shows an in vitro, cell proliferation assay with SK-BR-3 cells treated with: -●-trastuzumab and -Δ-trastuzumab-MC-ala-phe-PAB-(N,N'-(bis-aminoethyl-1,3-propanediamine)-bis-(4-N-imidazolyl)-1,8 naphthalimide) 203, measured in Relative Fluorescence Units (RLU, ×1000) versus µg/ml concentration of antibody or ADC. Trastuzumab is linked via a cysteine.

FIG. 3 shows an in vitro, cell proliferation assay with BT-474 cells treated with: -●-trastuzumab, and -o-trastuzumab-(succinate-gly-ala-phe)-(N,N'-(bis-aminoethyl-1,3-propanediamine)-bis 3-nitro-1,8 naphthalimide) 204, measured in Relative Fluorescence Units (RLU, ×1000) versus µg/ml concentration of antibody or ADC. Trastuzumab is linked via an amino group.

FIG. 4 shows an in vitro, cell proliferation assay with BT474 cells treated with: -●-trastuzumab, and -▲-trastuzumab-(MC-val-cit-PAB-(N,N'—(N,N'-(bis-aminoethyl-1, 3-propanediamine)-3-nitro, 4-amino-1,8 naphthalimide) 205, measured in Relative Fluorescence Units (RLU) versus µg/ml concentration of antibody or ADC. Trastuzumab is linked via a cysteine.

Figure 5:
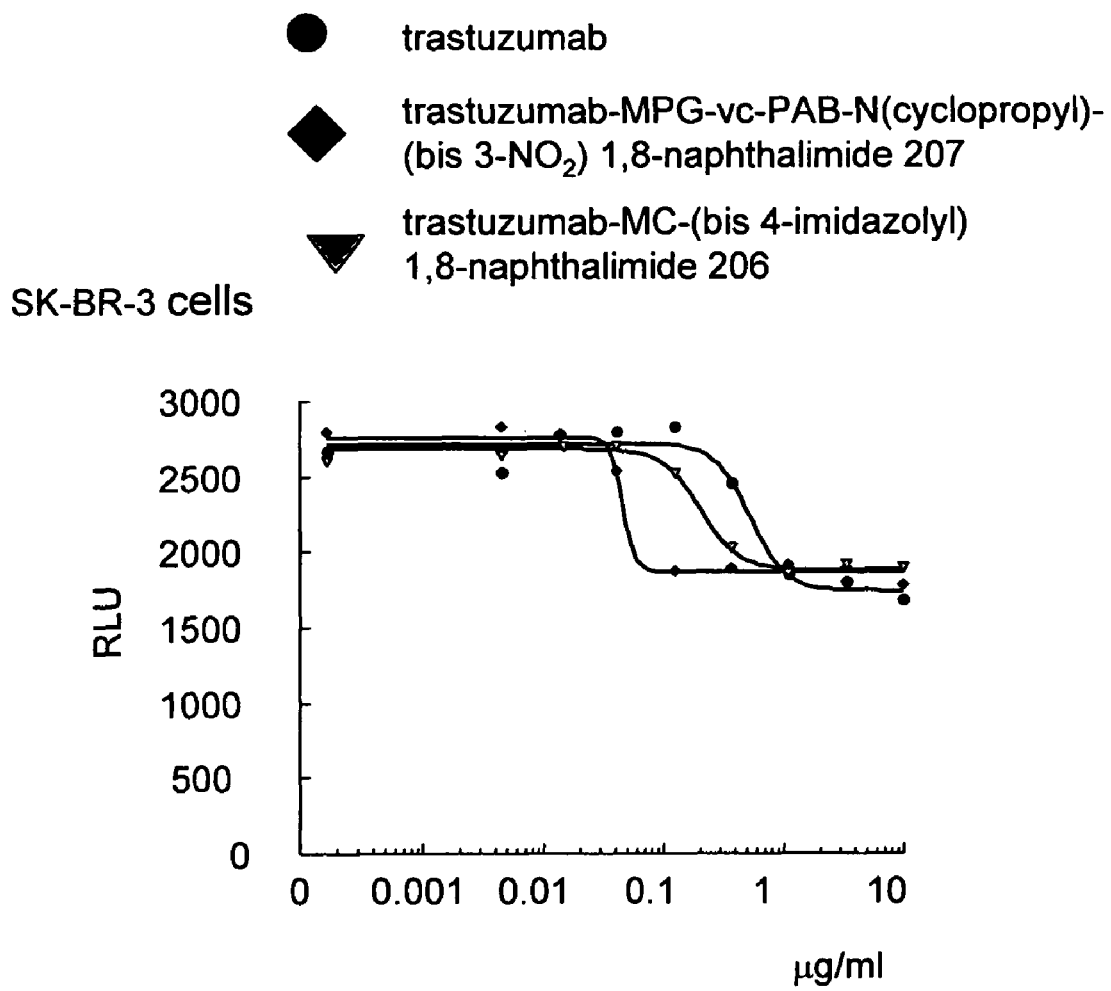
FIG. 5 shows an in vitro, cell proliferation assay with SK-BR-3 cells treated with: -●-trastuzumab, -♦-trastuzumab-MC-(N,N'-(bis-aminoethyl-1,3-propanediamine)-bis-(4-N-imidazolyl)-1,8 naphthalimide) 206, and -▼-trastuzumab-$N^1$-cyclopropylmethyl, $N^2$-maleimidopropyl-gly-val-cit-PAB-(N,N'-(bis-aminoethyl-1,3-propanediamine)-bis 3-nitro-1,8 naphthalimide) 207, measured in Relative Fluorescence Units (RLU, ×1000) versus μg/ml concentration of antibody or ADC. trastuzumab is linked via a cysteine [cys].

FIG. 5 shows an in vitro, cell proliferation assay with SK-BR-3 cells treated with: -●-trastuzumab, -♦-trastuzumab-MC-(N,N'-(bis-aminoethyl-1,3-propanediamine)-bis-(4-N-imidazolyl)-1,8 naphthalimide) 206, and -▼-trastuzumab-$N^1$-cyclopropylmethyl, $N^2$-maleimidopropyl-gly-val-cit-PAB-(N,N'-(bis-aminoethyl-1,3-propanediamine)-bis 3-nitro-1,8 naphthalimide) 207, measured in Relative Fluorescence Units (RLU, ×1000) versus µg/ml concentration of antibody or ADC. Trastuzumab is linked via a cysteine.

The antibody drug conjugates of Table 3 were prepared and tested. $IC_{50}$ values of the ADC were established for invitro cell killing potency against SK-BR-3 and BT-474 (Table 3), which are known to over-express HER2 receptor protein.

TABLE 3

| Antibody Bis 1,8 naphthalimide Drug Conjugate | $IC_{50}$ (µg ADC/ml) SK-BR-3 cells | $IC_{50}$ (µg ADC/ml) BT-474 cells |
|---|---|---|
| H-MC-vc-PAB-(bis 4-imidazolyl E) 202 | 0.04 | 0.021 |
| H-MPG-vc-PAB-(bis 4-imidazolyl E) | 0.018 | 0.012 |
| H-MPEG-vc-PAB-(bis 4-imidazolyl E) | 0.018-0.030 | 0.012-0.033 |
| H-MC-gg-PAB-(bis 4 imidazolyl E) | 0.045 | NSA |
| H-MC-af-PAB-(bis 4-imidazolyl E) 203 | 0.22 | 0.013 |
| H-MC-(bis 4-imidazolyl E) 206 | 0.045 | NSA |
| H-MC-hydrazone-E | NSA | NSA |
| H-MC-hydrazone-1-E | NSA | 0.39 |
| H-MC-hydrazone-2-E | NSA | NSA |

TABLE 3-continued

| Antibody Bis 1,8 naphthalimide Drug Conjugate | $IC_{50}$ (µg ADC/ml) SK-BR-3 cells | $IC_{50}$ (µg ADC/ml) BT-474 cells |
|---|---|---|
| H-succinate-gaf-PAB-(bis 3-nitro E) 204 H is linked via an amino group | 0.18 | 0.22 |
| H-MC-vc-PAB-N(Me)val, N'-ethyl (bis 3-nitro E) | NSA | NSA |
| H-MPG-vc-PAB-N(Me)val-N'-ethyl (3-nitro E) | NSA | 0.25 |
| H-MC-vc-PAB-(bis 4-morpholino E) | 0.085 | 0.33 |
| H-MC-hydrazone-(bis 3-nitro E) | NSA | NSA |
| H-MPG-vc-PAB-N(cyclopropylmethyl)-(bis 3 nitro E) 207 | 0.20 | 0.12 |
| H-MC-hydrazone-(bis 3-morpholino E) | NSA | NSA |
| H-MC-vc-PAB-(4-amino, 3-nitro E) 205 | 0.17 | 0.15 |
| H-MC-vc-PAB-(bis 4-piperidine E) | NSA | NSA |
| H-MPG-vc-PAB-(bis 4-piperidine E) | 0.19 | 0.45 |
| H-MC-(4(4-Me-Piperidine E) | NSA | NSA |
| H-MPG-af-PAB-(bis 4-pip, 3-nitro E) | NSA | NSA |
| H-SMCC-E | NSA | NSA |
| H-SPP-E (trastuzumab) | NSA (0.10-0.20) | 1.1 (0.10-0.30) |
| 2H9 (anti-EphB2R)-MC-vc-PAB-(bis 4-imidazolyl E) 202 | — | 0.42 |

H = trastuzumab linked via a cysteine [cys] except where noted.
E = bis 1,8 naphthalimide
NSA = no significant activity Antibody drug conjugates of Formula I were prepared where Ab included anti-EphB2R and anti-CD22 antibodies. These conjugates also showed in vitro cytotoxic or cytostatic activity.

Heterocyclic-substituted bis-1,8-naphthalimide compounds of Formula XV in Table 2 were prepared and tested for in vitro activity against a panel of tumor cells (Example 110). The $IC_{50}$ (µg ADC/ml) activities ranged from about 1 nM to about 100 µM, or no significant activity, in BT474, H460, HCT116, HUVEC, LNCAP, MCF7, and PC3 cells. The average log and linear IC50 (nM) of some of the compounds, across the 7 tumor cell panel is shown in Table 4.

TABLE 4

| Compound No. | Avg. (log IC50) | Avg. (nM) |
|---|---|---|
| 20 | −8.59 | 2.57 |
| 30a | −8.4 | 3.98 |
| 34 | −5.66 | 2188 |
| 35 | NSA | NSA |
| 54a | −7.64 | 22.91 |
| 54b | NSA | NSA |
| 54c | −6.72 | 191 |
| 54d | −6.49 | 324 |
| 54e | −6.9 | 126 |
| 54f | −6.16 | 692 |
| 54g | −6.16 | 692 |
| 54h | −6.51 | 309 |
| 38 | −5.74 | 1820 |
| 55a | −7.24 | 57.54 |
| 55b | −5.54 | 2884 |
| 41 | −8.47 | 3.39 |
| 55c | −5.43 | 3715 |
| 56a | −8.79 | 1.62 |
| 56b | −7.73 | 18.62 |
| 57 | −6.33 | 468 |
| 58a | −8.77 | 1.7 |
| 59 | −8.82 | 1.51 |
| 60 | −8.98 | 1.05 |
| 58b | −7.57 | 26.92 |
| 45 | −5.82 | 1514 |
| 24a | −9.15 | 0.71 |
| 61 | −7.39 | 40.74 |

TABLE 4-continued

| Compound No. | Avg. (log IC50) | Avg. (nM) |
|---|---|---|
| 62 | −8.34 | 4.57 |
| 63a | −8.35 | 4.47 |
| 24b | −9.39 | 0.41 |
| 63b | −6.6 | 251 |
| 63c | −8.96 | 1.1 |
| 64 | −8.74 | 1.82 |
| 65 | −6.54 | 288 |

NSA = no significant activity

In vivo Serum Clearance and Stability in Mice

Serum clearance and stability of ADC may be investigated in nude, naive (without tumors received by exogenous grafts) mice. A difference in the amount of total antibody and ADC indicates cleavage of the linker and separation of the antibody from its drug moiety.

In vivo Efficacy

Efficacy of the antibody-drug conjugates of the invention was measured in vivo by implanting allografts or xenografts of cancer cells in rodents and treating the tumors with ADC. Variable results are to be expected depending on the cell line, the specificity of antibody binding of the ADC to receptors present on the cancer cells, dosing regimen, and other factors. For example, the in vivo efficacy of anti-HER2 ADC was measured by a high expressing HER2 transgenic explant mouse model. An allograft may be propagated from the Fo5 MMTV transgenic mouse which does not respond to, or responds poorly to, HERCEPTIN therapy. Subjects were treated once with ADC and monitored over 3-6 weeks to measure the time to tumor doubling, log cell kill, and tumor shrinkage. The ADC of the invention showed only modest efficacy in slowing the progression of tumor growth. For example, an IV administration of 10 mg H-MC-af-PAB-(bis 4-imidazolyl E) 203 per kg animal showed only a slight increase in the time for mean MMTV—HER2 Fo5 tumor volume doubling in athymic nude mice relative to control (injection vehicle, PBS buffer). Follow up dose-response and multi-dose experiments may be conducted.

Rodent Toxicity

Antibody-drug conjugates and an ADC-minus control, "Vehicle", may be evaluated in an acute toxicity rat model (Brown et al (2002) Cancer Chemother. Pharmacol. 50:333-340). Toxicity of ADC may be investigated by treatment of rats with the ADC and subsequent inspection and analysis of the effects on various organs. Based on gross observations (body weights), clinical pathology parameters (serum chemistry and hematology) and histopathology, the toxicity of ADC may be observed, characterized, and measured. Clinical chemistry, serum enzymes and hematology analysis may also be conducted periodically; concluding with complete necropsy with histopathological assessment. Toxicity signals included the clinical observation of weight loss, considering that weight loss, or weight change relative to animals dosed only with Vehicle in animals after dosing with ADC, is a gross and general indicator of systemic or localized toxicity. Hepatotoxicity may be measured by: (i) elevated liver enzymes such as AST (aspartate aminotransferase), ALT (alanine aminotransferase), GGT (g-glutamyl transferase); (ii) increased numbers of mitotic and apoptotic figures; and (iii) hepatocyte necrosis. Hematolymphoid toxicity is observed by depletion of leukocytes, primarily granuloctyes (neutrophils), and/or platelets, and lymphoid organ involvement, i.e. atrophy or apoptotic activity. Toxicity is also noted by gastrointestinal tract lesions such as increased numbers of mitotic and apoptotic figures and degenerative entercolitis.

Administration of bis 1,8-naphthalimide Drug Compounds, Antibody Drug Conjugates and Pharmaceutical Formulations The compounds of the invention may be administered by any route appropriate to the condition to be treated. The ADC will typically be administered parenterally, i.e. infusion, subcutaneous, intramuscular, intravenous, intradermal, intrathecal and epidural. The heterocyclic-substituted bis 1,8-naphthalimide compounds may be administered parenterally or orally.

Pharmaceutical formulations of therapeutic antibody drug conjugates (ADC) of the invention are typically prepared for parenteral administration, i.e. bolus, intravenous, intratumor injection with a pharmaceutically acceptable parenteral vehicle and in a unit dosage injectable form. An antibody-drug conjugate (ADC) having the desired degree of purity is optionally mixed with pharmaceutically acceptable diluents, carriers, excipients or stabilizers (Remington's Pharmaceutical Sciences (1980) 16th edition, Osol, A. Ed.), in the form of a lyophilized formulation or an aqueous solution.

Acceptable diluents, carriers, excipients, and stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). For example, lyophilized anti-ErbB2 antibody formulations are described in WO 97/04801, expressly incorporated herein by reference.

The active pharmaceutical ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be prepared. Suitable examples of sustained-release preparations include semipermeable matrices of solid hydrophobic polymers containing the ADC, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid.

The formulations to be used for in vivo administration must be sterile, which is readily accomplished by filtration through sterile filtration membranes.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Aqueous suspensions of the invention contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxybenzoate, one or more coloring agents, one or more flavoring agents and one or more sweetening agents, such as sucrose or saccharin.

The pharmaceutical compositions of ADC may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such as a solution in 1,3-butane-diol or prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

The amount of active ingredient that may be combined with the carrier material to produce a single dosage form will vary depending upon the host treated and the particular mode of administration. For example, an aqueous solution intended for intravenous infusion may contain from about 3 to 500 µg of the active ingredient per milliliter of solution in order that infusion of a suitable volume at a rate of about 30 mL/hr can occur.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

Although oral administration of protein therapeutics are disfavored due to hydrolysis or denaturation in the gut, formulations of ADC suitable for oral administration may be prepared as discrete units such as capsules, cachets or tablets each containing a predetermined amount of the ADC.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Exemplary unit dosage formulations include a daily dose or unit daily sub-dose, as herein above recited, or an appropriate fraction thereof, of the active ingredient.

The invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered parenterally, orally or by any other desired route.

Treatments

It is contemplated that the compounds of the present invention may be used to treat various diseases or disorders, e.g. characterized by the overexpression of a tumor antigen. Exemplary conditions or disorders include benign or malignant tumors; leukemia and lymphoid malignancies; other disorders such as neuronal, glial, astrocytal, hypothalamic, glandular, macrophagal, epithelial, stromal, blastocoelic, inflammatory, angiogenic and immunologic disorders.

The compounds which are identified in the animal models and cell-based assays can be further tested in tumor-bearing higher primates and human clinical trials. Human clinical trials can be designed similar to the clinical trials testing the efficacy of the anti-HER2 monoclonal antibody HERCEPTIN in patients with HER2 overexpressing metastatic breast cancers that had received extensive prior anti-cancer therapy as reported by Baselga et al. (1996) J. Clin. Oncol. 14:737-744. The clinical trial may be designed to evaluate the efficacy of an ADC in combinations with known therapeutic regimens, such as radiation and/or chemotherapy involving known chemotherapeutic and/or cytotoxic agents.

Generally, the disease or disorder to be treated is cancer. Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The cancer will generally comprise HER2-expressing cells, such that the ADC of the present invention are able to bind to the cancer cells. To determine ErbB2 expression in the cancer, various diagnostic/prognostic assays are available. In one embodiment, ErbB2 overexpression may be analyzed by IHC, e.g. using the HERCEPTEST (Dako). Parrafin embedded tissue sections from a tumor biopsy may be subjected to the IHC assay and accorded a ErbB2 protein staining intensity criteria as follows: Score 0, no staining is observed or membrane staining is observed in less than 10% of tumor cells; Score 1+, a faint/barely perceptible membrane staining is detected in more than 10% of the tumor cells, the cells are only stained in part of their membrane; Score 2+, a weak to moderate complete membrane staining is observed in more than 10% of the tumor cells; Score 3+, a moderate to strong complete membrane staining is observed in more than 10% of the tumor cells.

Those tumors with 0 or 1+ scores for ErbB2 overexpression assessment may be characterized as not overexpressing ErbB2, whereas those tumors with 2+ or 3+ scores may be characterized as overexpressing ErbB2.

Alternatively, or additionally, FISH assays such as the INFORM™ (Ventana Co., Ariz.) or PATHVISION™ (Vysis, Ill.) may be carried out on formalin-fixed, paraffin-embedded tumor tissue to determine the extent (if any) of ErbB2 overexpression in the tumor.

The cancer to be treated herein may be one characterized by excessive activation of an ErbB receptor, e.g. HER2. Such excessive activation may be attributable to overexpression or increased production of the ErbB receptor or an ErbB ligand. In one embodiment of the invention, a diagnostic or prognostic assay will be performed to determine whether the patient's cancer is characterized by excessive activation of an ErbB receptor. For example, ErbB gene amplification and/or overexpression of an ErbB receptor in the cancer may be determined. Various assays for determining such amplification/overexpression are available in the art and include the IHC, FISH and shed antigen assays described above. Alternatively, or additionally, levels of an ErbB ligand, such as TGF-alpha., in or associated with the tumor may be determined according to known procedures. Such assays may detect protein and/or nucleic acid encoding it in the sample to be tested. In one embodiment, ErbB ligand levels in the tumor may be determined using immunohistochemistry (IHC); see, for example, Scher et al. (1995) Clin. Cancer Research 1:545-550. Alternatively, or additionally, one may evaluate levels of ErbB ligand-encoding nucleic acid in the sample to be tested; e.g. via FISH, southern blotting, or PCR techniques.

Moreover, ErbB receptor or ErbB ligand overexpression or amplification may be evaluated using an in vivo diagnostic assay, e.g. by administering a molecule (such as an antibody) which binds the molecule to be detected and is tagged with a detectable label (e.g. a radioactive isotope) and externally scanning the patient for localization of the label.

For the prevention or treatment of disease, the appropriate dosage of an ADC will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 μg/kg to 15 mg/kg (e.g. 0.1-20 mg/kg) of molecule is an initial candidate dosage for administration to the patient, whether, for example, by one or more separate administrations, or by continuous infusion. A typical daily dosage might range from about 1 μg/kg to 100 mg/kg or more, depending on the factors mentioned above. An exemplary dosage of ADC to be administered to a patient is in the range of about 0.1 to about 10 mg/kg of patient weight.

For repeated administrations over several days or longer, depending on the condition, the treatment is sustained until a desired suppression of disease symptoms occurs. An exemplary dosing regimen comprises administering an initial loading dose of about 4 mg/kg, followed by a weekly maintenance dose of about 2 mg/kg of the anti-ErbB2 antibody. Other dosage regimens may be useful. The progress of this therapy is easily monitored by conventional techniques and assays.

Combination Therapy

A compound of the invention may be combined in a pharmaceutical combination formulation, or dosing regimen as combination therapy, with a second compound having anti-cancer properties. The second compound of the pharmaceutical combination formulation or dosing regimen may have complementary activities to the ADC of the combination such that they do not adversely affect each other.

The second compound may be a chemotherapeutic agent, cytotoxic agent, cytokine, growth inhibitory agent, anti-hormonal agent, and/or cardioprotectant. Such molecules are suitably present in combination in amounts that are effective for the purpose intended. A pharmaceutical composition containing an ADC of the invention may also have a therapeutically effective amount of a chemotherapeutic agent such as a tubulin-forming inhibitor, a topoisomerase inhibitor, or a DNA binder.

Alternatively, or additionally, the second compound may be an antibody which binds ErbB2 and blocks ligand activation of an ErbB receptor. The second antibody may be monoclonal antibody 2C4 or humanized 2C4. The second antibody may be conjugated with a cytotoxic or chemotherapeutic agent, e.g., a 1,8 bis-naphthalimide moiety. For example, it may be desirable to further provide antibodies which bind to EGFR, ErbB2, ErbB3, ErbB4, or vascular endothelial factor (VEGF) in the one formulation or dosing regimen. An exemplary combination therapy of the invention is a Formula I ADC and bevacizumab (Avastin™, Genentech, South San Francisco, Calif.).

Other therapeutic regimens may be combined with the administration of an anticancer agent identified in accordance with this invention. The combination therapy may be administered as a simultaneous or sequential regimen. When administered sequentially, the combination may be administered in two or more administrations. The combined administration includes coadministration, using separate formulations or a single pharmaceutical formulation, and consecutive administration in either order, wherein there is a time period while both (or all) active agents simultaneously exert their biological activities.

In one embodiment, treatment with an ADC of the present invention involves the combined administration of an anti-cancer agent identified herein, and one or more chemotherapeutic agents or growth inhibitory agents, including coadministration of cocktails of different chemotherapeutic agents, optionally along with treatment with an anti-ErbB2 antibody, such as trastuzumab. Chemotherapeutic agents include taxanes (such as paclitaxel and doxetaxel) and/or anthracycline antibiotics. Preparation and dosing schedules for such chemotherapeutic agents may be used according to manufacturers instructions or as determined empirically by the skilled practitioner. Preparation and dosing schedules for such chemotherapy are also described in Chemotherapy Service Ed., M. C. Perry, Williams & Wilkins, Baltimore, Md. (1992).

The anticancer agent may be combined with an anti-hormonal compound; e.g., an anti-estrogen compound such as tamoxifen; an anti-progesterone such as onapristone (EP 616812); or an anti-androgen such as flutamide, in dosages known for such molecules. Where the cancer to be treated is hormone independent cancer, the patient may previously have been subjected to anti-hormonal therapy and, after the cancer becomes hormone independent, the anti-ErbB2 antibody (and optionally other agents as described herein) may be administered to the patient. It may be beneficial to also coadminister a cardioprotectant (to prevent or reduce myocardial dysfunction associated with the therapy) or one or more cytokines to the patient. In addition to the above therapeutic regimes, the patient may be subjected to surgical removal of cancer cells and/or radiation therapy.

Suitable dosages for any of the above coadministered agents are those presently used and may be lowered due to the combined action (synergy) of the newly identified agent and other chemotherapeutic agents or treatments.

The combination therapy may provide "synergy" and prove "synergistic", i.e. the effect achieved when the active ingredients used together is greater than the sum of the effects that results from using the compounds separately. A synergistic effect may be attained when the active ingredients are: (1) co-formulated and administered or delivered simultaneously in a combined, unit dosage formulation; (2) delivered by alternation or in parallel as separate formulations; or (3) by some other regimen. When delivered in alternation therapy, a synergistic effect may be attained when the compounds are administered or delivered sequentially, e.g. by different injections in separate syringes. In general, during alternation therapy, an effective dosage of each active ingredient is administered sequentially, i.e. serially, whereas in combination therapy, effective dosages of two or more active ingredients are administered together.

Metabolites of the Compounds

Also falling within the scope of this invention are the in vivo metabolic products of the compounds described herein, to the extent such products are novel and unobvious over the prior art. Such products may result for example from the oxidation, reduction, hydrolysis, amidation, esterification, enzymatic cleavage, and the like, of the administered compound. Accordingly, the invention includes novel and unobvious compounds produced by a process comprising contacting a compound of this invention with a mammal for a period of time sufficient to yield a metabolic product thereof.

Metabolite products typically may be identified by preparing a radiolabelled (e.g. $C^{14}$ or $H^3$) ADC, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS, LC/MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the ADC compounds of the invention.

Articles of Manufacture

In another embodiment of the invention, an article of manufacture, or "kit", containing materials useful for the treatment of the disorders described above is provided. The article of manufacture comprises a container and a label or package insert on or associated with the container. Suitable containers include, for example, bottles, vials, syringes, blister pack, etc. The containers may be formed from a variety of materials such as glass or plastic. The container holds an antibody-drug conjugate (ADC) composition which is effective for treating the condition and may have a sterile access port (for example the container may be an intravenous solution bag or a vial having a stopper pierceable by a hypodermic injection needle). At least one active agent in the composition is an ADC. The label or package insert indicates that the composition is used for treating the condition of choice, such as cancer.

The article of manufacture may comprise (a) a first container with a compound contained therein, wherein the compound comprises an ADC of the present invention in which the antibody of the ADC is a first antibody inhibits growth of cancer cells; and (b) a second container with a compound contained therein, wherein the compound comprises a second compound, composition, or formulation having biological activity. The article of manufacture in this embodiment of the invention may further comprise a package insert indicating that the first and second compounds can be used to treat cancer, or other disorder. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

Example 1

Synthesis of 4-morpholino-naphthoic anhydride 1

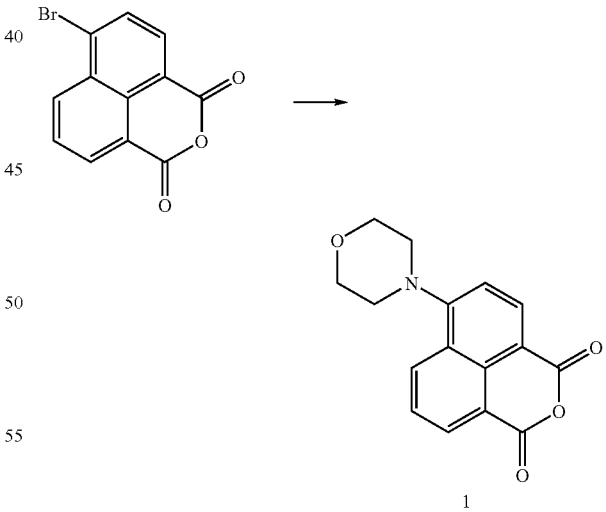

1

A mixture of 4-bromo, naphthalic anhydride (0.21 gm, 0.74 mmoles), morpholine (0.61 ml, 0.70 mmoles), and 5 ml ethanol was heated for 4.5 hr at 160° C. in a 15 ml sealed tube. After cooling, the mixture was concentrated under vacuum, dissolved in 30 ml dichloromethane, washed with 1 M citric acid, dried and concentrated. The orange solid was triturated with toluene to an orange solid, 4-morpholino-1,8-naphthalic anhydride 1 (0.089 gm, 51% yield). LC/MS −283 MW. $^1$H NMR (300 MHz, CDCl$_3$): δ 8.61 (1H, d, J=7.3 Hz), 8.55 (1H, d, J=8.4 Hz), 8.48 (1H, d, J=8.5 Hz), 7.75 (1H, t, J=8.1 Hz); 7.27 (1H, dd, J=8.1 Hz); 4.31 (4H, m); 3.31 (4H, m).

Example 2

Synthesis of 1,3-bis glycyl-1,3 diaminopropane 2

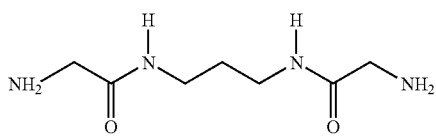

Carbonyl diimidazole (CDI, 0.71 gm, 4.40 mmoles) was added to a mixture of 10 ml dichloromethane and BOC-glycine (0.73 gm, 4.19 mmoles) at 0° C. under nitrogen. After 2 hr at 0° C., 1,3 propanediamine (0.18 ml, 2.0 mmoles) was added and the mixture was warmed to room temperature and stirred overnight. The mixture was diluted with dichloromethane and extracted with sat. NaHCO$_3$. The aqueous phase was extracted 2× with dichloromethane. The combined organic phases were washed with sat. NaCl, dried over MgSO$_4$, and concentrated under vacuum to give the 1,3 bis BOC glycyl-1,3 diaminopropane intermediate as a white sticky solid. $^1$H NMR (300 MHz, CDCl$_3$): δ 6.76 (2H, s, br); 5.30 (2H, s, br); 3.77 (4H, d, J=5.7 Hz); 3.31 (4H, m); 1.66 (2H, m); 1.4 (9H, m). This intermediate was taken up with 16 ml 1M HCl in AcOH and stirred under nitrogen at room temperature for 2 hours. The mixture was concentrated under vacuum to a white solid which was triturated with diethyl ether to give the bis hydrochloride salt of 1,3-bis glycyl-1,3 diaminopropane 2 as a yellow oil. $^1$H NMR (300 MHz, D$_2$O): δ 3.78 (4H, s), 3.26 (4H, t, J=5.7 Hz); 1.66 (2H, m).

Example 3

Synthesis of N$^1$,N$^3$-bis(2-aminoethyl)malonamide 3

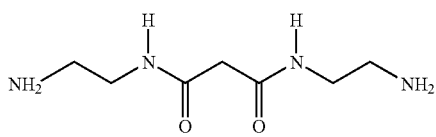

A solution of malonyl chloride (0.5 ml, 5.0 mmoles) in 4 ml dichloromethane under nitrogen was stirred at 0° C., then added dropwise over 30 minutes to a stirred solution of mono BOC-1,2-diaminoethane (1.6 ml, 10.0 mmoles) and triethylamine (1.67 ml, 12 mmoles) in 5 ml dichloromethane at 0° C. The solution was allowed to warm to room temperature and stir overnight. The cloudy orange mixture was diluted with 90 ml dichloromethane, washed with 30 ml each of 2N HCl, sat NaHCO$_3$, and sat. NaCl, then dried over MgSO$_4$ and concentrated under vacuum to give the bis BOC intermediate as a sticky orange solid $^1$H NMR (300 MHz, CDCl$_3$): δ 7.27 (2H, m); 5.01 (4H, s, br); 3.38 (4H, m); 3.28 (4H, m); 3.16 (s, 2H). The BOC groups were removed to give N$^1$,N$^3$-bis(2-aminoethyl)malonamide 3.

Example 4

Synthesis of N-glycyl-3-nitro-1,8 naphthalimide 4

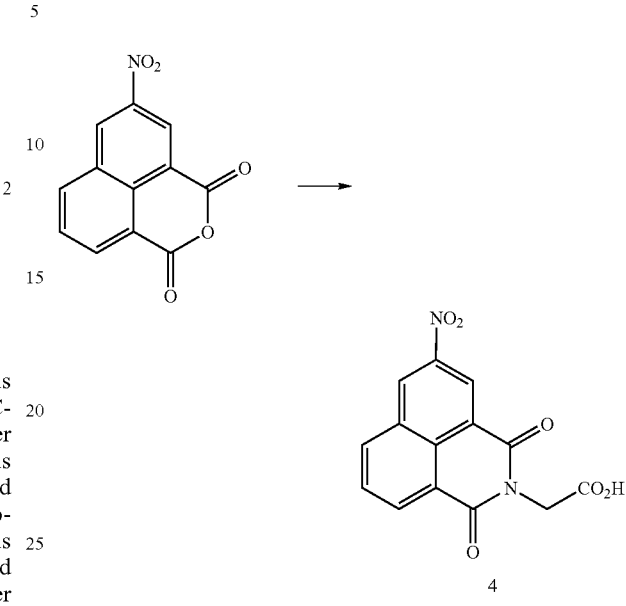

A mixture of 3-nitro-1,8-naphthalic anhydride (0.155 gm, 0.64 mmole) and glycine (0.048 gm, 0.64 mmole) in 1.5 ml dimethylformamide (DMF) was heated at 100° C. under nitrogen for about 12 hours. The mixture was diluted with ethylacetate and washed with 1.0M citric acid, dried over MgSO$_4$, and concentrated under vacuum to give N-glycyl-3-nitro-1,8 naphthalimide 4. $^1$H NMR (300 MHz, DMSO-d$_6$): δ 9.54 (1H, J=2.2 Hz); 8.99 (1H, d, J=2.2 Hz); 8.84 (1H, d, J=7.4 Hz); 8.72 (1H, d, J=7.3 Hz); 8.09 (1H, t, J=8.2 Hz); 4.76 (s, 2H).

Example 5

Synthesis of N-glycyl-4-amino-1,8 naphthalimide 5

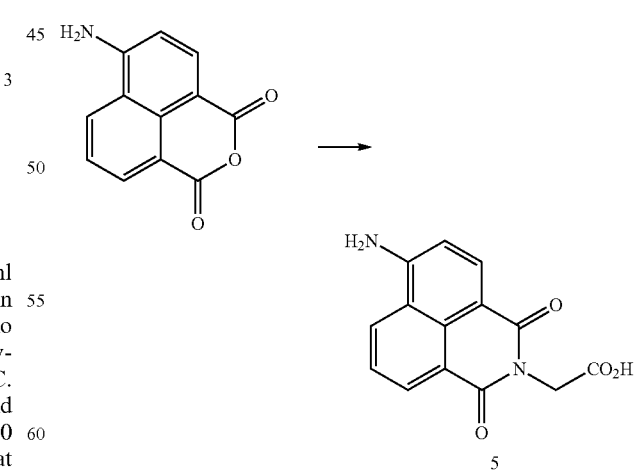

A mixture of 4-amino-1,8-naphthalic anhydride (0.230 gm, 1.03 mmole) and glycine (0.239 gm, 3.19 mmoles) in 3 ml dimethylformamide (DMF) was heated by microwave treatment at 200° C. for 10 minutes. LC/MS analysis of the mixture showed conversion of starting anhydride to be complete.

The mixture was cooled, filtered and the precipitate was dried to give N-glycyl-4-amino-1,8 naphthalimide 5. ¹H NMR (300 MHz, DMSO-d$_6$): δ 8.65 (1H, d, J=8.7 Hz); 8.44 (1H, d, J=6.9 Hz); 8.19 (1H, d, J=8.4 Hz); 7.67 (1H, t, J=7.5 Hz); 6.85 (1H, d, J=8.1 Hz); 4.67 (s, 2H).

Example 6

Synthesis of N-glycyl-4-morpholino, 1,8 naphthalimide 6

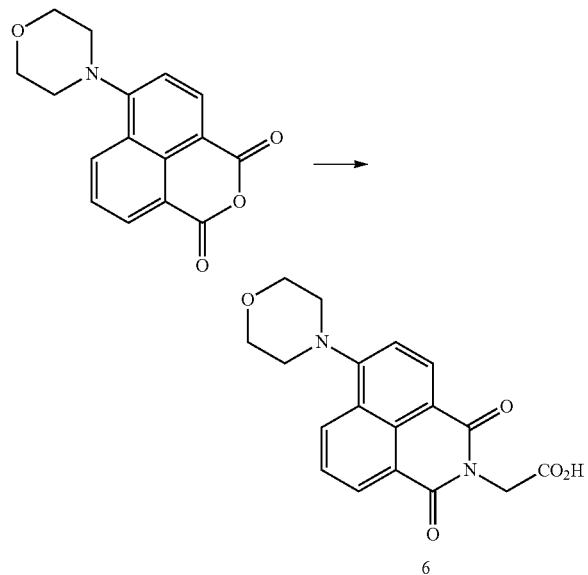

6

A mixture of 4-morpholino-1,8-naphthalic anhydride (0.163 gm, 0.63 mmole) and glycine (0.10 gm, 1.33 mmole) in 3 ml dimethylformamide (DMF) was heated at 200° C. with microwave treatment for 10 minutes. The mixture was diluted with ethylacetate and washed with 1.0M citric acid, dried over MgSO4, and concentrated under vacuum to give N-glycyl-4-morpholino-1,8 naphthalimide 6. ¹H NMR (300 MHz, DMSO-d$_6$): δ 8.63 (2H, m), 8.55 (1H, d, J=8.2 Hz); 7.95 (1H, t, J=8.0 Hz); 7.50 (1H, d, J=8.0 Hz); 4.82 (2H, s); 4.20 (4H, m); 3.36 (4H, m).

Example 7

Synthesis of N-aminoethylethoxy-3-nitro-1,8 naphthalimide 7

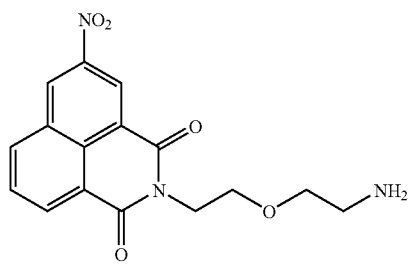

7

A suspension of 0.2 M 2,2'-oxydiethylamine dihydrochloride (0.247 gm, 1.35 mmole) and 0.4 M DIEA (0.47 ml, 2.7 mmole) in 4.5 DMF was added to 3-nitro-1,8-naphthalic anhydride (0.018 gm, 0.073 mmole) and heated at 150° C. with microwave treatment for 5 minutes. The mixture was cooled, treated with 25 ml 1.3 M aqueous TFA, and concentrated to about 2 ml. The residue was diluted with dichloromethane, washed with sat. NaCl, dried over MgSO$_4$, and concentrated under vacuum to give N-aminoethylethoxy-3-nitro-1,8 naphthalimide 7. MS m/z 330 (M+H)⁺.

Example 8

Synthesis of N-aminoethylethoxy-4-amino-1,8 naphthalimide 8

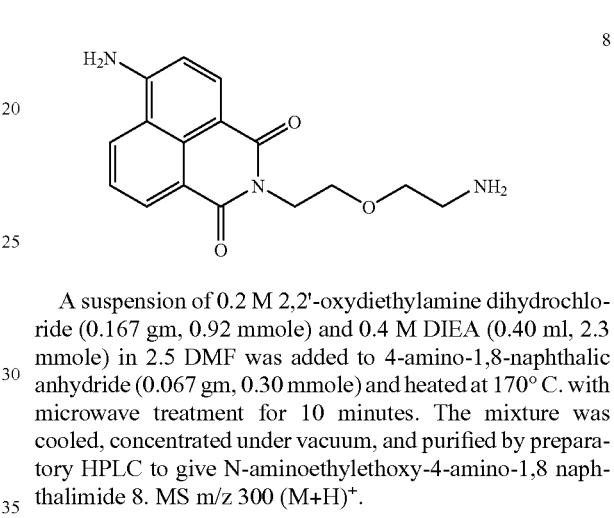

8

A suspension of 0.2 M 2,2'-oxydiethylamine dihydrochloride (0.167 gm, 0.92 mmole) and 0.4 M DIEA (0.40 ml, 2.3 mmole) in 2.5 DMF was added to 4-amino-1,8-naphthalic anhydride (0.067 gm, 0.30 mmole) and heated at 170° C. with microwave treatment for 10 minutes. The mixture was cooled, concentrated under vacuum, and purified by preparatory HPLC to give N-aminoethylethoxy-4-amino-1,8 naphthalimide 8. MS m/z 300 (M+H)⁺.

Example 9

Synthesis of N aminoethylethoxy-4-morpholino-1,8 naphthalimide 9

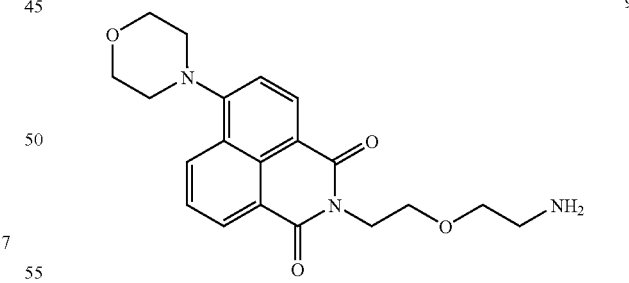

9

A suspension of 0.2 M 2,2'-oxydiethylamine dihydrochloride (0.135 gm, 0.74 mmole) and 0.4 M DIEA (0.32 ml, 1.85 mmole) in 2.5 DMF was added to 4-morpholino-1,8-naphthalic anhydride (0.068 gm, 0.24 mmole) and heated at 150° C. with microwave treatment for 12 minutes. The mixture was cooled, diluted with dichloromethane, washed with sat. NaHCO$_3$, dried over MgSO$_4$, and concentrated under vacuum to give N-aminoethylethoxy-4-morpholino-1,8 naphthalimide 9. ¹H NMR (300 MHz, CDCl$_3$): δ 8.59 (1H, d, J=7.2 Hz); 8.53 (1H, d, J=7.8 Hz); 8.42 (1H, d, J=8.4 Hz); 7.70 (1H, t, J=7.2 Hz); 7.25 (d, 1H, J=8.1 Hz); 4.43 (2H, t, J=5.8 Hz); 4.02 (4H, m); 3.80 (2H, t, J=6.0 Hz); 3.54 (2H, t, J=5.2 Hz); 3.26 (4H, m); 2.81 (2H, t, J=5.7 Hz).

Example 10

Synthesis of N-aminopropylethylamine-3-nitro-1,8 naphthalimide 10a and N-aminoethylpropylamine-3-nitro-1,8 naphthalimide 10b

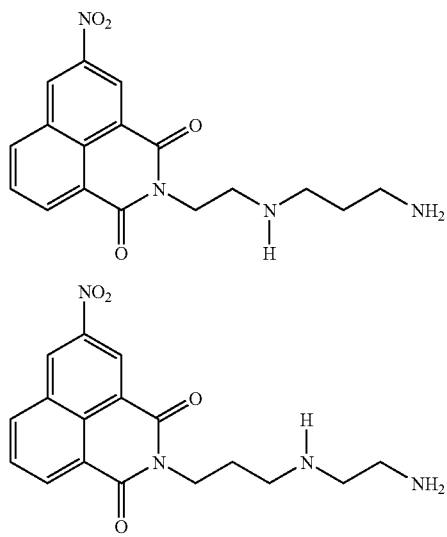

10a

10b

A mixture of 3-nitro-1,8-naphthalic anhydride (0.641 gm, 2.64 mmole), 2-aminoethyl-1,3-propanediamine (1 ml, 7.68 mmole) and 2.5 ml ethanol was heated from 0° C. to 100° C. over 30 minutes then at 100° C. for 2 hours. LC/MS analysis showed the reaction was complete and the products were formed in a 2:1 ratio. The mixture was cooled, concentrated under vacuum, and purified by prep. HPLC which separated the products N-aminopropylethylamine-3-nitro-1,8 naphthalimide 10a $^1$H NMR (300 MHz, CF$_3$CO$_2$D): δ 9.38 (1H, d, J=2.1 Hz); 9.32 (1H, d, J=2.1 Hz); 8.85 (1H, d, J=7.5 Hz); 8.61 (1H, d, J=8.6 Hz); 8.04 (1H, t, J=7.8 Hz); 4.57 (2H, m); 3.79 (m, 2H); 3.50 (2H, m); 3.40 (2H, m); 2.42 (m, 2H), and N-aminoethylpropylamine-3-nitro-1,8 naphthalimide 10b in about 85-91% purity.

Example 11

Synthesis of N-aminopropylethylamine-4-amino-1,8 naphthalimide 11a and N-aminoethylpropylamine-4-amino-1,8 naphthalimide 11b

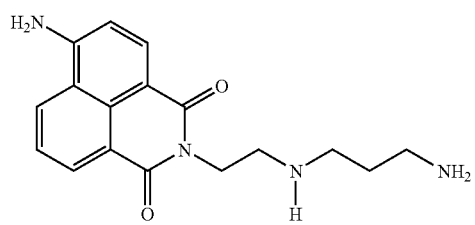

11a

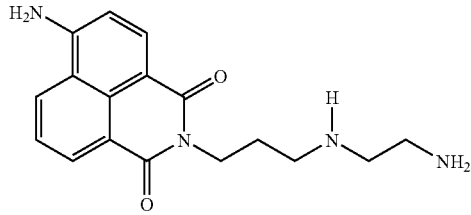

11b

A mixture of 4-amino-1,8-naphthalic anhydride (0.477 gm, 2.13 mmole), 2-aminoethyl-1,3-propanediamine (0.83 ml, 6.38 mmole) and 2.5 ml ethanol was heated from 0° C. to 100° C. over 30 minutes then at 100° C. for 2 hours with microwave treatment. LC/MS analysis showed the reaction was complete and the products were formed in a 2:1 ratio. The mixture was cooled, concentrated under vacuum, and purified by prep. HPLC which separated the products N-aminopropylethylamine-4-amino-1,8 naphthalimide 11a $^1$H NMR (300 MHz, CF$_3$CO$_2$D): δ 8.82 (1H, d, J=7.5 Hz); 8.61 (1H, d, J=8.4 Hz); 8.07 (1H, t, J=8.2 Hz); 4.75 (2H, m); 3.80 (2H, m); 3.49 (2H, m); 3.41 (2H, m); 3.34 (2H, m), and N-aminoethylpropylamine-4-amino-1,8 naphthalimide 11b, each in about 98% purity.

Example 12

Synthesis of N'-aminopropylethylamine-4-morpholino-1,8 naphthalimide 12a and N-aminoethylpropylamine-4-morpholino-1,8 naphthalimide 12b

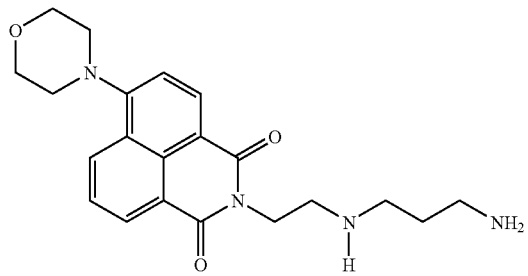

12a

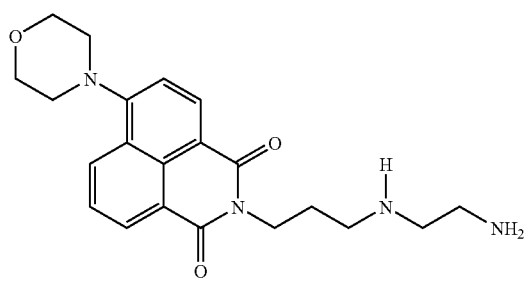

12b

A mixture of 4-morpholino-1,8-naphthalic anhydride (0.317 gm, 1.06 mmole), 2-aminoethyl-1,3-propanediamine (0.44 ml, 3.38 mmole) and 2.5 ml ethanol was heated from 0° C. to 100° C. over 30 minutes then at 100° C. for 2 hours. LC/MS analysis showed the reaction was complete and the products were formed in a 3:1 ratio. The mixture was cooled, concentrated under vacuum, and purified by prep. HPLC which separated the products N-aminopropylethylamine-(4-morpholino)-1,8 naphthalimide 12a $^1$H NMR (300 MHz, CF$_3$CO$_2$D): δ 8.80 (2H, m); 8.69 (1H, d, J=8.4 Hz); 8.19 (1H, d, J=8.2 Hz); 8.07 (1H, t, J=8.4 Hz); 4.74 (2H, m); 4.54 (2H, m); 4.21 (2H, m); 3.79 (2H, m); 3.44 (2H, m); 3.34 (m, 2H); 2.36 (2H, m), and N-aminoethylpropylamine-(4-morpholino-1,8 naphthalimide 12b each in about 93-99% purity.

Example 13

Synthesis of N-methanesulfonyloxyethyl-(3-nitro-1,8 naphthalimide 13

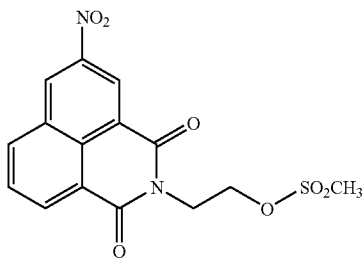

13

N-hydoxyethyl-3-nitro-1,8 naphthalimide was prepared from 3-nitro-1,8 naphthalimide and ethanolamine in ethanol by microwave heating at 150° C. for 5 minutes, and precipitation from boiling toluene. Methanesulfonyl chloride (1.05 ml, 13 mmole) was added to a solution of N-hydoxyethyl-3-nitro-1,8 naphthalimide (1.70 gm, 5.94 mmole) and 100 ml pyridine. After several hours stirring at room temperature under nitrogen, one liter of water was added, and the precipitate was filtered to give N-methanesulfonyloxyethyl-(3-nitro)-1,8 naphthalimide 13 (2.0 gm, 92% yield). $^1$H NMR (300 MHz, DMSO-d$_6$): δ 9.51 (1H, d, J=2.0 Hz); 8.98 (1H, d, J=2.0 Hz); 8.81 (1H, J=8.2 Hz); 8.71 (1H, d, J=7.4 Hz); 8.07 (1H, t, J=7.5 Hz); 4.46 (4H, m); 3.15 (3H, s).

Example 14

Synthesis of N-iodoethyl-(3-nitro)-1,8 naphthalimide 14

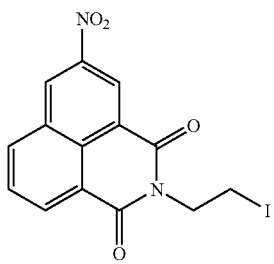

14

N-methanesulfonyloxyethyl-(3-nitro)-1,8 naphthalimide 13 (2.0 gm, 5.49 mmole) was dissolved in 250 ml 2-butanone and treated with sodium iodide (5.15 gm, 33.9 mmole) and stirred overnight at room temperature under nitrogen. The precipitate was filtered and the eluate washed with sat. NaCl, dried over MgSO$_4$, and concentrated under vacuum to give N-iodoethyl-(3-nitro)-1,8 naphthalimide 14. $^1$H NMR (300 MHz, DMSO-d$_6$): δ 9.51 (1H, d, J=2.1 Hz); 8.97 (1H, d, J=2.1 Hz); 8.80 (1H, d, J=8.3 Hz); 8.71 (1H, d, J=6.9 Hz); 8.07 (1H, t, J=7.4 Hz); 4.40 (2H, t, J=7.4 Hz); 3.41 (2H, t, J=7.4 Hz).

Example 15

Synthesis of N-(2,4-dinitrophenylaminoethylethoxy)-3-nitro-1,8 naphthalimide 15

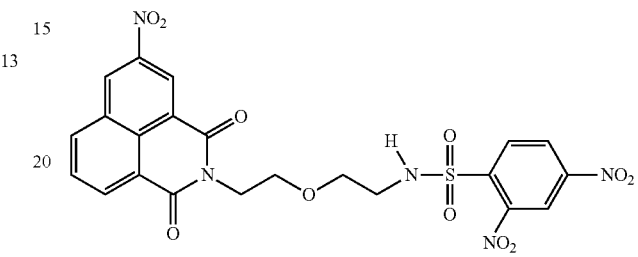

15

A solution of N-aminoethylethoxy-3-nitro-1,8 naphthalimide 7 (TFA salt, 0.190 gm, 0.043 mmole), triethylamine (0.18 ml, 1.29 mmole), and 5 ml DMF was cooled to 0° C. 2,4-Dinitrobenzenesulfonyl chloride (0.128 gm, 0.47 mmole) was added and the solution was allowed to warm to room temperature and stir under nitrogen for an hour. LC/MS analysis showed that sulfonation was virtually complete. A slight excess of sodium ethoxide in 1 ml ethanol was added to quench remaining 2,4-dinitrobenzenesulfonyl chloride. The mixture was filtered through celite, rinsed with 15 ml DMF and 20 ml ethanol. The filtrate was concentrated under vacuum, and purified by prep. HPLC to give N-(2,4-dinitrophenylaminoethylethoxy)-3-nitro-1,8 naphthalimide 15 in 61% yield. $^1$H NMR (300 MHz, CDCl$_3$): δ 9.32 (1H, d, J=2.4 Hz); 9.16 (1H, d, J=2.1 Hz); 8.80 (1H, d, J=7.8 Hz); 8.63 (1H, d, J=2.1 Hz); 8.48 (m, 2H); 8.33 (1H, d, J=8.4 Hz); 7.98 (1H, t, J=7.8 Hz); 5.92 (1H, m); 4.35 (2H, t, J=5.4 Hz); 3.70 (2H, t, J=5.4 Hz); 3.62 (2H, t, J=5.0 Hz); 3.32 (2H, m).

Example 16a

Synthesis of N,N'-(bis-aminoethyl-1,3-propanediamine)-bis-4-nitro-1,8 naphthalimide 16a

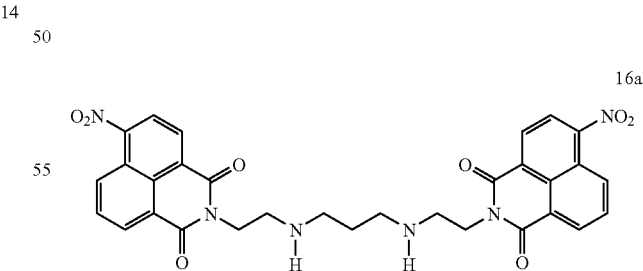

16a

A solution of N,N-bis(aminoethyl)-1,3-propanediamine (0.91 gm, 5.29 mmole) in 5 ml N-methylmorpholine (NMM) was added to a solution of 4-nitro-1,8-naphthalic anhydride (2.54 gm, 9.92 mmole) in 10 ml NMM. The reaction was stirred at room temperature under nitrogen for 5 minutes, then heated at 38° C. for one hour, then at 120° C. (reflux) for 2 hours. The mixture was filtered hot, concentrated under vacuum, dissolved in a minimum of dichloromethane, and purified by silica gel chromatography to give N,N'-(bis-aminoethyl-1,3-propanediamine)-bis-4-nitro-1,8 naphthalimide 16a. MS m/z 611 (M+H)+.

Example 16b

Synthesis of N,N'-(bis-aminoethyl-1,3-propanediamine)-bis-4-nitro-1,8 naphthalimide 16b

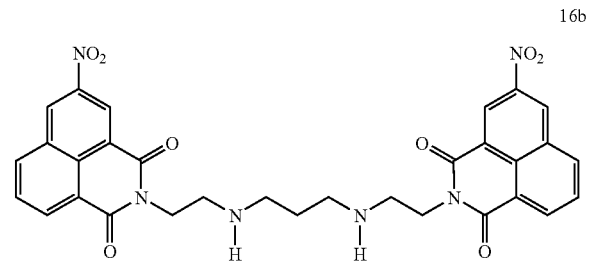

16b

Following the same procedure as Example 16a, N,N'-(bis-aminoethyl-1,3-propanediamine)-bis-3-nitro-1,8 naphthalimide 16b was prepared from 3-nitro-1,8-naphthalic anhydride (1.00 gm, 3.91 mmole) and N,N-bis(aminoethyl)-1,3-propanediamine (11.7 mmole, 3 equiv) in 3 ml, at 100° C. for 5 minutes.

Example 17

Synthesis of N,N'-(bis-aminoethyl-1,3-propanediamine)-bis-4-chloro-1,8 naphthalimide 17

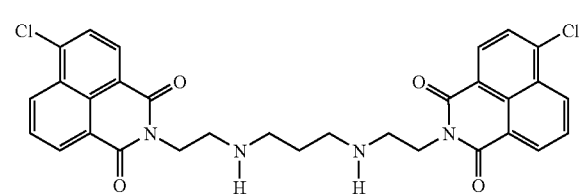

17

A solution of N,N-bis(aminoethyl)-1,3-propanediamine (also: 1,4,8,11-tetraazaundecane, 0.87 ml, 5.03 mmole) in 2 ml ethanol was slowly added to a solution of 4-chloro-1,8-naphthalic anhydride (2.35 gm, 10.10 mmole) in 12 ml NMM. The reaction was stirred at room temperature under nitrogen for 5 minutes, then heated at 38° C. for 45 minutes, the heat was increased slowly to 115° C. and held for 1.5 hours. The mixture was cooled, filtered, concentrated under vacuum, dissolved in a minimum of dichloromethane, and purified by silica gel chromatography to give the bis TFA salt of N,N'-(bis-aminoethyl-1,3-propanediamine)-bis-4-chloro-1,8 naphthalimide 17 as a bright yellow solid. MS m/z 589 (M+).

Example 18

Synthesis of N,N'-(bis-aminoethyl-1,3-propanediamine)-bis-3-bromo-1,8 naphthalimide 18

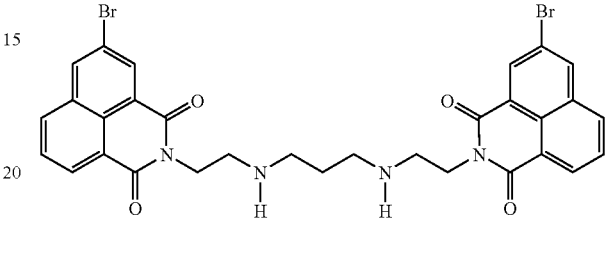

18

A solution of N,N-bis(aminoethyl)-1,3-propanediamine (also: 1,4,8,11-tetraazaundecane, 0.081 ml, 0.47 mmole) in 5 ml dioxane was slowly added to a solution of 3-bromo-1,8-naphthalic anhydride (0.267 gm, 0.93 mmole) in 1.2 ml NMM. The reaction was stirred at room temperature under nitrogen for 5 minutes, then heated at 38° C. for 45 minutes, the heat was increased slowly to 115° C. and held for 1.5 hours. The mixture was cooled, filtered, concentrated under vacuum, dissolved in a minimum of dichloromethane, and purified by silica gel chromatography to give the bis TFA salt of N,N'-(bis-aminoethyl-1,3-propanediamine)-bis-3-bromo-1,8 naphthalimide 18 as a white solid. MS m/z 679 (M+H)+.

Example 19

Synthesis of N,N'-(bis-aminoethyl-1,3-propanediamine)-bis-4-amino-1,8 naphthalimide 19

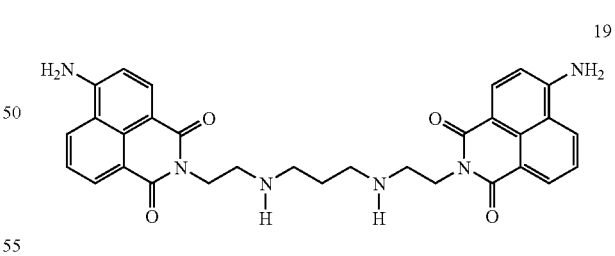

19

Palladium on carbon (10% Pd/C, 76 mg) was added to a solution of N,N'-(bis-aminoethyl-1,3-propanediamine)-bis-4-nitro-1,8 naphthalimide 16a (about 60% pure, 0.12 gm, 0.12 mmole) and 20 ml DMF. The flask was flushed with hydrogen gas and the reaction was stirred at room temperature overnight. The mixture was filtered though celite, rinsing with DMF, concentrated, and purified by prep. HPLC to give N N,N'-(bis-aminoethyl-1,3-propanediamine)-bis-4-amino-1,8 naphthalimide 19 as a red solid. MS m/z 551 (M+H)+.

Example 20

Synthesis of N,N'-(bis-aminoethyl-1,3-propanediamine)-bis-4-morpholino-1,8 naphthalimide 20

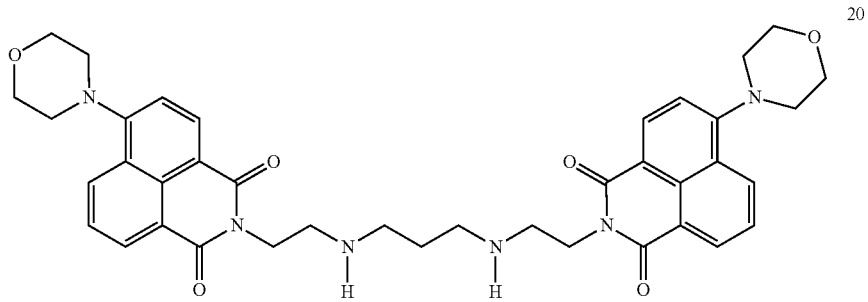

A solution of N,N'-(bis-aminoethyl-1,3-propanediamine)-bis-4-bromo-1,8 naphthalimide (19 mg, 0.021 mmole) and 1 ml N-methylmorpholine (NMM) was heated in a sealed tube to 70° C. and held for 3 hours, then increased to 100° C. and held for 2 hours. The mixture was cooled, and purified by prep. HPLC to give N,N'-(bis-aminoethyl-1,3-propanediamine)-bis-4-morpholino-1,8 naphthalimide 20 as the bis-TFA salt. MS m/z 691 (M+H)$^+$.

Example 21

Synthesis of N,N'-(bis-aminoethyl-1,3-propanediamine)-bis-4-dimethylamino-1,8 naphthalimide 21

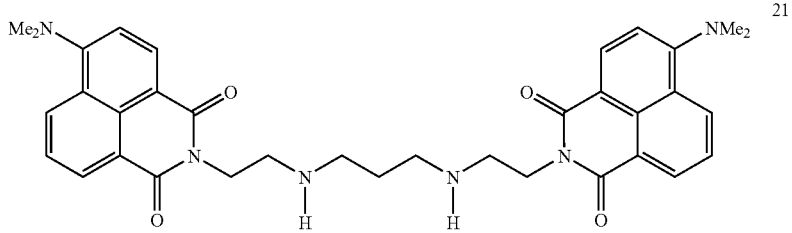

A solution of N,N'-(bis-aminoethyl-1,3-propanediamine)-bis-4-bromo-1,8 naphthalimide (16 mg, 0.017 mmole) and 1.5 ml 40% aqueous dimethylamine was placed in a sealed tube for one hour at room temperature, then heated to 60° C. and held for 1 hour, then increased to 70° C. and held for 30 minutes. Dimethylformamide (0.75 ml) was added and heating at 70° C. was continued for 1.5 hours, then let stand at room temperature for 48 hours. The mixture was cooled, and purified by prep. HPLC to give the bright orange solid N,N'-(bis-aminoethyl-1,3-propanediamine)-bis-4-dimethylamino-1,8 naphthalimide 21 as the bis-TFA salt. MS m/z 607 (M+H)$^+$.

Example 22

Synthesis of N,N'-(bis-aminoethyl-1,3-propanediamine)-bis-(4-N-methoxyethyl)-1,8 naphthalimide 22

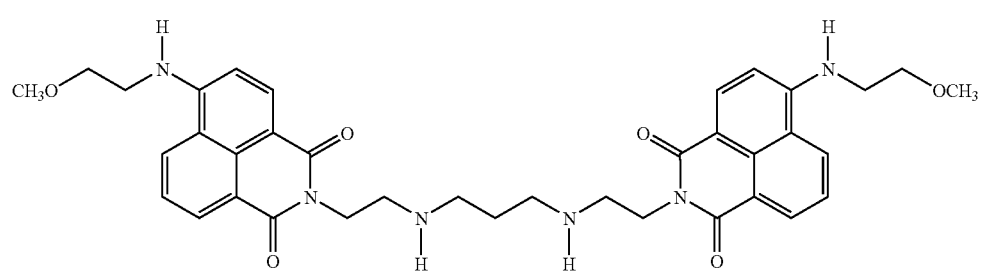

A solution of N,N'-(bis-aminoethyl-1,3-propanediamine)-bis-4-bromo-1,8 naphthalimide (26 mg, 0.028 mmole) and 4 ml of 2-methoxyethylamine was placed in a sealed tube and the temperature was raised to 80° C. over 15 minutes and held for 3.5 hours. The mixture was cooled, concentrated, and purified by prep. HPLC to give the orange solid N,N'-(bis-aminoethyl-1,3-propanediamine)-bis-(4-N-methoxyethyl)-1,8 naphthalimide 22 as the bis-TFA salt. MS m/z 667 (M+H)$^+$.

Example 23

Synthesis of N,N'-(bis-aminoethyl-1,3-propanediamine)-bis-(4-N-hydroxyethyl)-1,8 naphthalimide 23

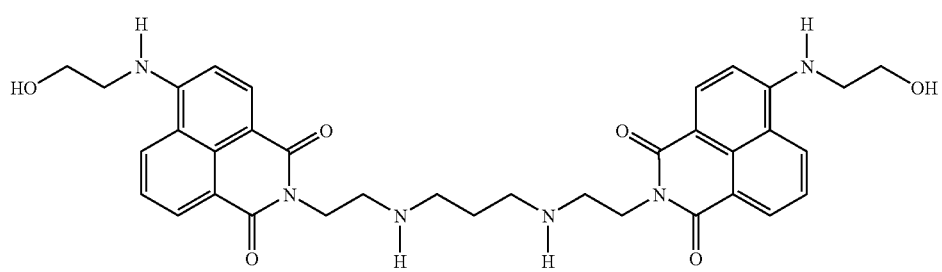

A solution of N,N'-(bis-aminoethyl-1,3-propanediamine)-bis-4-bromo-1,8 naphthalimide (36 mg, 0.040 mmole) and 2 ml of ethanolamine was placed in a sealed tube and the temperature was raised to 80° C. over 15 minutes and held overnight. The mixture was cooled, concentrated, and purified by prep. HPLC to give the bright red solid N,N'-(bis-aminoethyl-1,3-propanediamine)-bis-(4-N-hydroxyethyl)-1,8 naphthalimide 23 as the bis-TFA salt. MS m/z 639 (M+H)$^+$.

Example 24a

Synthesis of N,N'-(bis-aminoethyl-1,3-propanediamine)-bis-(4-N-methylpiperazine)-1,8 naphthalimide 24a

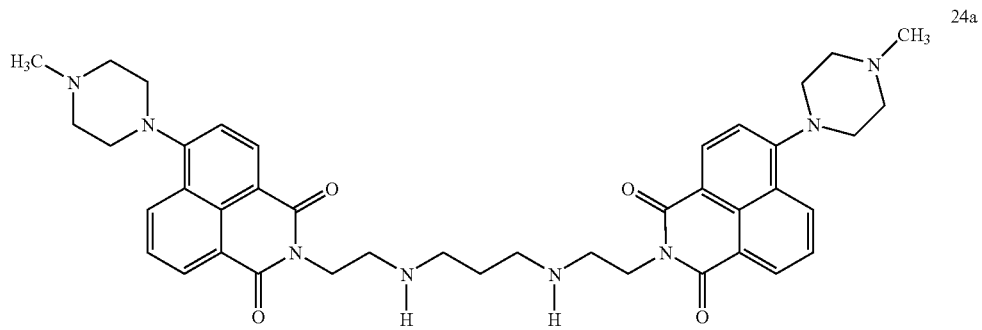

A solution of N,N'-(bis-aminoethyl-1,3-propanediamine)-bis-4-bromo-1,8 naphthalimide (0.112 gm, 0.12 mmole) and 7 ml of 1-methylpiperazine was placed in a 15 ml sealed tube and the temperature was raised to 80° C. over 15 minutes and held 15 hours. The mixture was cooled, concentrated, and purified by prep. HPLC to give N,N'-(bis-aminoethyl-1,3-propanediamine)-bis-(4-N-methylpiperidine)-1,8 naphthalimide 24a as the tetra-TFA salt. MS m/z 717 (M+H)$^+$.

Example 24b

Synthesis of N,N'-(bis-aminoethyl-1,3-propanediamine)-bis-(4-N-imidazolyl)-1,8 naphthalimide 24b

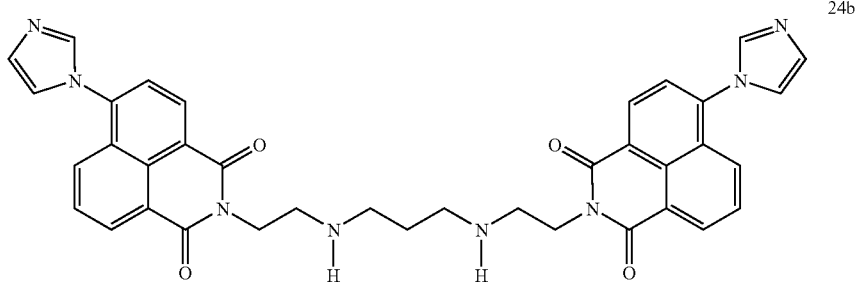

Following the same protocol as Example 24a, N,N'-(bis-aminoethyl-1,3-propanediamine)-bis-(4-N-imidazolyl)-1,8 naphthalimide 24b was prepared from N,N'-(bis-aminoethyl-1,3-propanediamine)-bis-4-bromo-1,8 naphthalimide, imidazole, potassium carbonate, in DMF with heating.

Example 24c

Synthesis of N$^1$-methyl, N,N'-(bis-aminoethyl-1,3-propanediamine)-bis-(4-N-imidazolyl)-1,8 naphthalimide 24c Also following the same protocol as Example 24a, N$^1$-methyl, N,N'-(bis-aminoethyl-1,3-propanediamine)-bis-(4-N-imidazolyl)-1,8 naphthalimide 24c was prepared from N$^1$-methyl, N,N'-(bis-aminoethyl-1,3-propanediamine)-bis-4-bromo-1,8 naphthalimide and imidazole.

Example 24d

Synthesis of N,N'-(bis-aminoethyl-1,3-propanediamine)-bis-(4-azido)-1,8 naphthalimide 24d Also following the same protocol as Example 24a, N,N'-(bis-aminoethyl-1,3-propanediamine)-bis-(4-azido)-1,8 naphthalimide 24d was prepared from N,N'-(bis-aminoethyl-1,3-propanediamine)-bis-4-bromo-1,8 naphthalimide, sodium azide, potassium carbonate, in DMF with heating at 150° C. for 5 minutes.

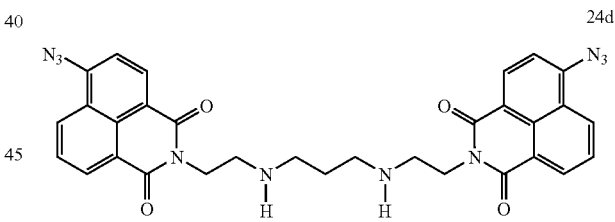

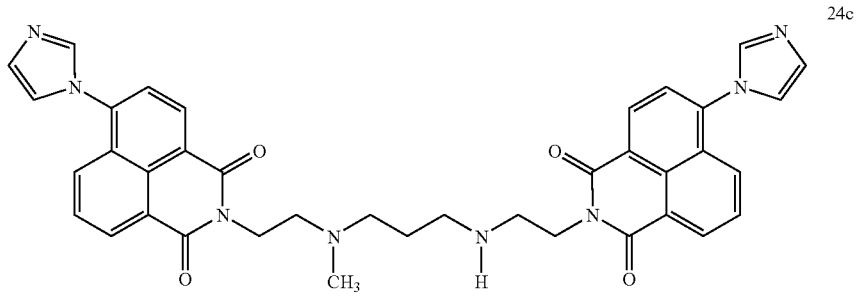

Example 25

Synthesis of N,N'-(bis-N-formyl-aminoethyl-1,3-propanediamine)-bis-3-nitro-1,8 naphthalimide 25a and enamminium 25b

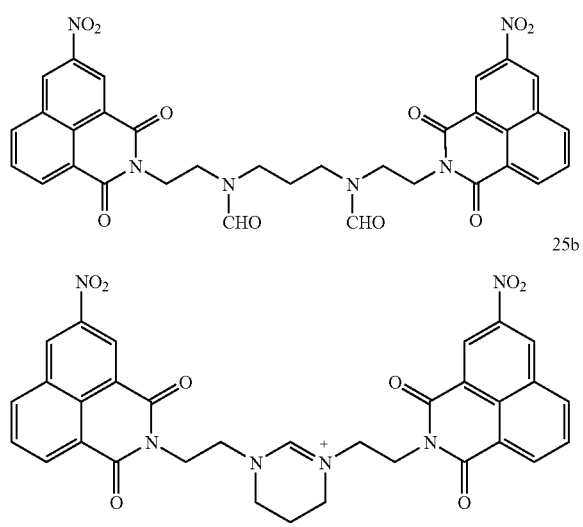

25a

25b

A solution of N,N'-(bis-aminoethyl-1,3-propanediamine)-bis-3-nitro-1,8 naphthalimide (0.029 gm, 0.047 mmole), 5 ml ethylformate, and 2 ml DMF was refluxed under nitrogen for 3.5 hours. The mixture was cooled, concentrated, and purified by prep. HPLC to separate N,N'-(bis-N-formyl-aminoethyl-1,3-propanediamine)-bis-3-nitro-1,8 naphthalimide 25a (minor product), and the cyclized enamminium salt 25b (major product) $^1$H NMR (300 MHz, DMSO-d6): δ 9.77 (d, 2H, J=2.4 Hz); 8.89 (d, 2H, J=2.4 Hz); 8.75 (2H, d, J=7.5 Hz); 8.59 (2H, d, J=7.2 Hz); 8.30 (s, 1H); 8.00 (2H, t, J=7.2 Hz); 4.16 (m, 4H); 3.58 (m, 8H); 2.09 (m, 2H).

Example 26

Synthesis of N,N'—(N-benzyl-aminoethyl-1,3-propanediamine)-bis-3-nitro-1,8 naphthalimide 26a and N,N'-(bis-N-benzyl-aminoethyl-1,3-propanediamine)-bis-3-nitro-1,8 naphthalimide 26b

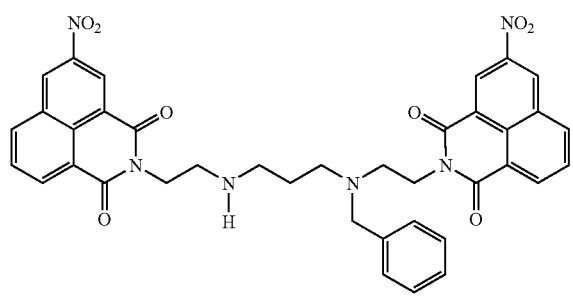

26a

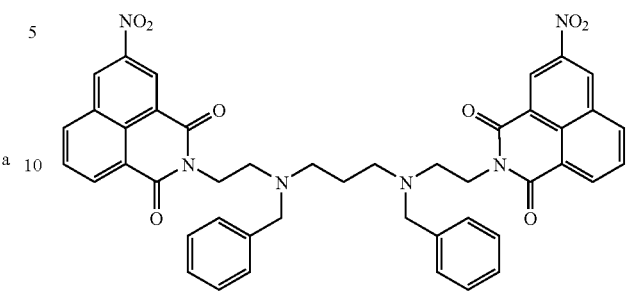

26b

Benzylbromide (0.27 ml, 0.22 mmole), followed by 0.5 N NaOH (0.44 ml, 0.22 mmole) was added to a solution of N,N'-(bis-aminoethyl-1,3-propanediamine)-bis-3-nitro-1,8 naphthalimide (0.112 gm, 0.18 mmole) in 20 ml DMF under nitrogen and stirred overnight. The mixture was filtered and the filtrate was purified by prep. HPLC to separate N,N'—(N-benzyl-aminoethyl-1,3-propanediamine)-bis-3-nitro-1,8 naphthalimide 26a MS m/z 701 (M+H)$^+$ and N,N'-(bis-N-benzyl-aminoethyl-1,3-propanediamine)-bis-3-nitro-1,8 naphthalimide 26b MS m/z 791 (M+H)$^+$, each as the bis TFA salt.

Example 27

Synthesis of N,N'—(N-allyl-aminoethyl-1,3-propanediamine)-bis-3-nitro-1,8 naphthalimide 27a and N,N'-(bis-N-allyl-aminoethyl-1,3-propanediamine)-bis-3-nitro-1,8 naphthalimide 27b

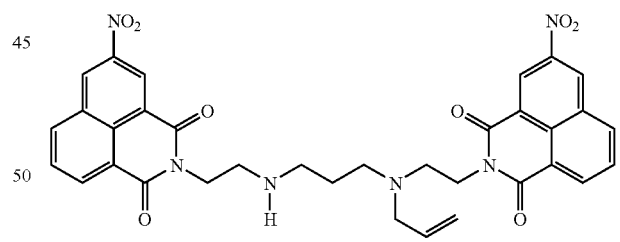

27a

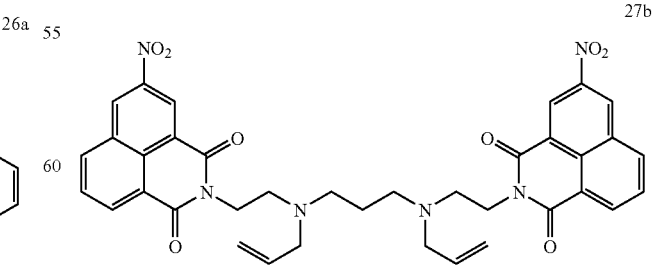

27b

Allylbromide (0.12 ml, 0.14 mmole), followed by 0.5 N NaOH (0.27 ml, 0.14 mmole) was added to a solution of N,N'-(bis-aminoethyl-1,3-propanediamine)-bis-3-nitro-1,8 naphthalimide (0.040 gm, 0.065 mmole) in 15 ml DMF under nitrogen and stirred overnight. The mixture was filtered and the filtrate was purified by prep. HPLC to separate N,N'—(N-allyl-aminoethyl-1,3-propanediamine)-bis-3-nitro-1,8 naphthalimide 27a MS m/z 651 (M+H)$^+$, and N,N'-(bis-N-allyl-aminoethyl-1,3-propanediamine)-bis-3-nitro-1,8 naphthalimide 27b MS m/z 691 (M+H)$^+$, each as the bis TFA salt.

Example 28

Synthesis of N,N'-(bis-N-acetamidomethyl-aminoethyl-1,3-propanediamine)-bis-3-nitro-1,8 naphthalimide 28

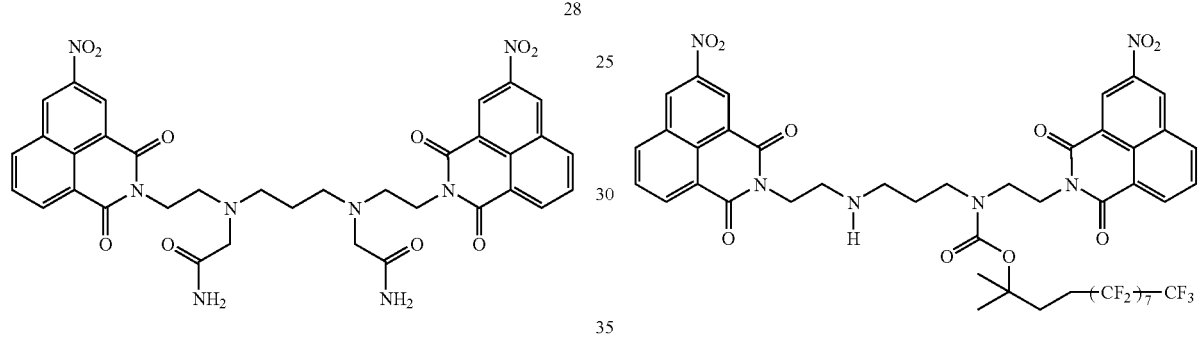

28

A mixture of N,N'-(bis-aminoethyl-1,3-propanediamine)-bis-3-nitro-1,8 naphthalimide (0.040 gm, 0.065 mmole), 2-bromoacetamide (0.045 gm, 0.32 mmole), cesium carbonate (CsCO$_3$, 0.022 gm, 0.067 mmole) and 3 ml DMF was stirred under nitrogen overnight at room temperature. LC/MS analysis showed starting N,N'-(bis-aminoethyl-1,3-propanediamine)-bis-3-nitro-1,8 naphthalimide and N,N'-(bis-N-acetamidomethyl-aminoethyl-1,3-propanediamine)-bis-3-nitro-1,8 naphthalimide 28. MS m/z 725 (M+H)$^+$.

Example 29

Synthesis of N,N'—(N-acetyl-aminoethyl-1,3-propanediamine)-bis-3-nitro-1,8 naphthalimide 29

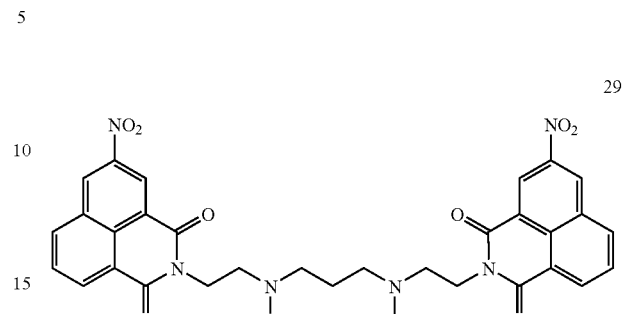

29

A mixture of N,N'—(N—F$_{17}$BOC-aminoethyl-1,3-propanediamine)-bis-3-nitro-1,8 naphthalimide (14 mg, 0.010 mmole), having the structure:

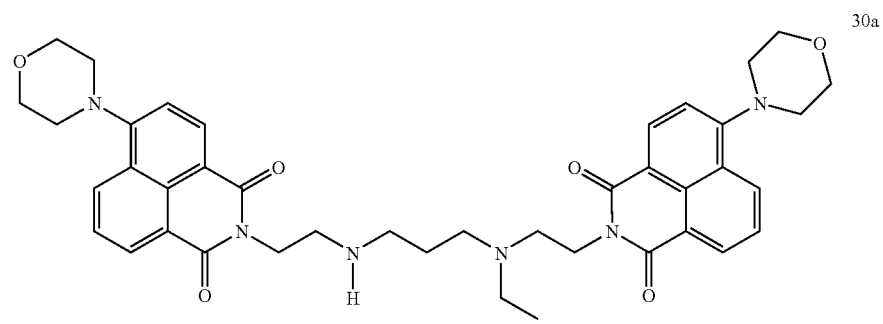

and 3 ml acetic anhydride was refluxed (110° C.) for one hour, then cooled. Several drops of water was added and the solution was concentrated to a white solid. One ml of TFA was added, mixed and let stand for an hour at room temperature. Concentration under vacuum gave the TFA salt as a yellow solid, N,N'—(N-acetyl-aminoethyl-1,3-propanediamine)-bis-3-nitro-1,8 naphthalimide 29. MS m/z 653 (M+H)$^+$.

Example 30a

Synthesis of N,N'—(N-ethyl, bis-aminoethyl-1,3-propanediamine)-bis-4-morpholino-1,8 naphthalimide 30a A mixture of the bis-TFA salt of N,N'-(bis-aminoethyl-1,3-propanediamine)-bis-4-morpholino-1,8 naphthalimide 20 (32 mg, 0.035 mmole), cesium carbonate (36 mg, 0.11 mmole), 5 ml acetonitrile, and 5 ml DMF was stirred at room temperature under nitrogen. Ethyl iodide (0.031 ml, 0.038 mmole) was added and stirred overnight. After 2 ml 10% TFA was added, the mixture was concentrated under vacuum, and purified by prep. HPLC column to give N,N'—(N-ethyl, bis-aminoethyl-1,3-propanediamine)-bis-4-morpholino-1,8 naphthalimide 30a MS m/z 719 (M+H)$^+$, as well as a small amount of the bis-ethyl compound.

Example 30b

Synthesis of N,N'—(N-cyclopropylmethyl, bis-aminoethyl-1,3-propanediamine)-bis-4-N-imidazolyl-1,8 naphthalimide 30b

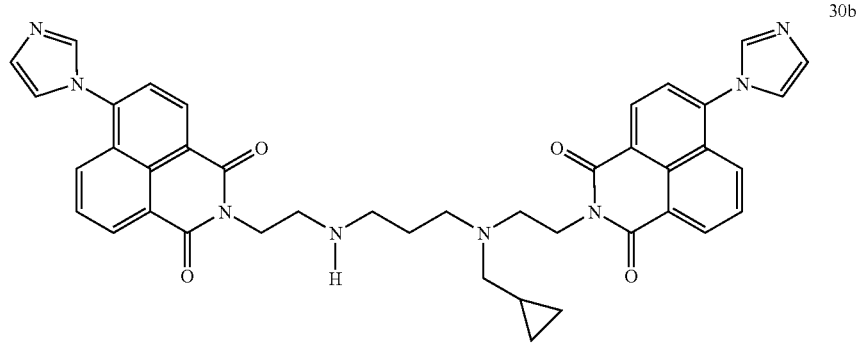

30b

Following Example 30a, N,N'—(N-cyclopropylmethyl, bis-aminoethyl-1,3-propanediamine)-bis-4-N-imidazolyl-1,8 naphthalimide 30b was prepared from (bromomethyl)cyclopropane and N,N'-(bis-aminoethyl-1,3-propanediamine)-bis-4-N-imidazolyl-1,8 naphthalimide 24b.

Example 30c

Synthesis of N,N'—(N-cyclopropylmethyl, bis-aminoethyl-1,3-propanediamine)-bis-3-nitro-1,8 naphthalimide 30c

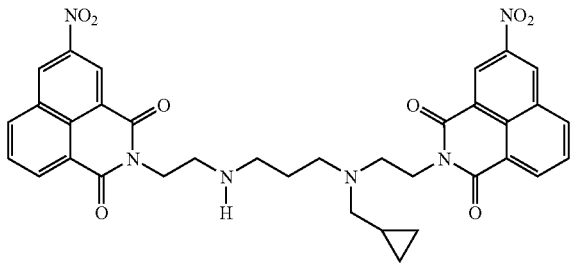

30c

Following Example 30a, N,N'—(N-cyclopropylmethyl, bis-aminoethyl-1,3-propanediamine)-bis-3-nitro-1,8 naphthalimide 30c was prepared from (bromomethyl)cyclopropane and N,N'-(bis-aminoethyl-1,3-propanediamine)-bis-3-nitro-1,8 naphthalimide 16b.

Example 31

Synthesis of N,N'—(N-(4-acetylbenzamide), bis-aminoethyl-1,3-propanediamine)-bis-3-nitro-1,8 naphthalimide 31a and N,N'-(bis-N-(4-acetylbenzamide), bis-aminoethyl-1,3-propanediamine)-bis-3-nitro-1,8 naphthalimide 31b

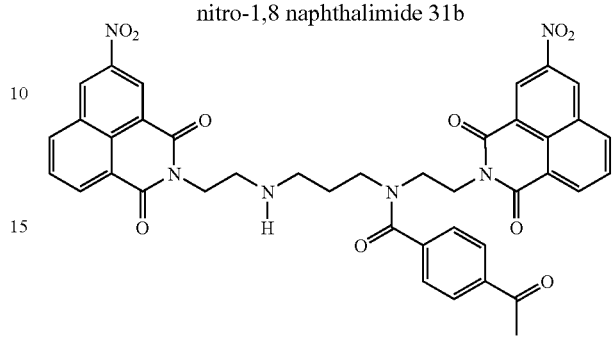

31a

-continued

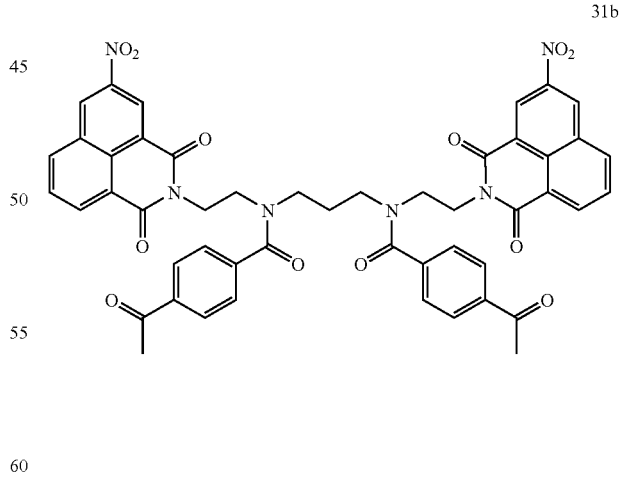

31b

4-Acetylbenzoic acid (0.061 gm 0.36 mmole), diisopropylethylamine (0.13 ml, 0.72 mmole), 2-(7-aza-1H-benzotriazole-1-yl)-1,1,3,3-tetramethyluronium hexafluorophosphate (HATU, 0.133 gm, 0.35 mmole), and 3 ml DMF were stirred under nitrogen for 15 minutes at room temperature. A solution of N,N'-(bis-aminoethyl-1,3-propanediamine)-bis-3-nitro-1,8 naphthalimide (0.212 gm, 0.35 mmole) and 12 ml DMF was added. After 30 minutes, LC/MS analysis showed the presence of reactant, and products 31a and 31b. The reaction was stirred overnight at room temperature, quenched with aqueous TFA, concentrated, and purified by prep. HPLC to give separated and purified N,N'—(N-(4-acetylbenzamide), bis-aminoethyl-1,3-propanediamine)-bis-3-nitro-1,8 naphthalimide 31a MS m/z 757 (M+H)$^+$, and N,N'-(bis-N-(4-acetylbenzamide), bis-aminoethyl-1,3-propanediamine)-bis-3-nitro-1,8 naphthalimide 31b.

Example 32

Synthesis of N,N'—(N-(3-benzoylpropionamide), bis-aminoethyl-1,3-propanediamine)-bis-3-nitro-1,8 naphthalimide 32

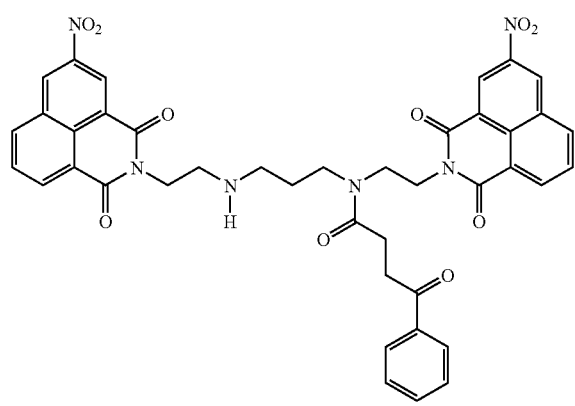

32

3-Benzoylpropionic acid (0.037 gm, 0.20 mmole), diisopropylethylamine (0.07 ml, 0.40 mmole), HATU (0.077 gm, 0.20 mmole), and 2 ml DMF were stirred under nitrogen for 10 minutes at room temperature, then it was added to a solution of N,N'-(bis-aminoethyl-1,3-propanediamine)-bis-3-nitro-1,8 naphthalimide (0.162 gm, 0.35 mmole), diisopropylethylamine (0.17 ml, 0.90 mmole) and 6 ml DMF was added. After 30 minutes, LC/MS analysis showed the presence of reactant and product 33a. The reaction was stirred overnight at room temperature, quenched with aqueous TFA, concentrated, and purified by prep. HPLC to give N,N'—(N-(3-benzoylpropionamide), bis-aminoethyl-1,3-propanediamine)-bis-3-nitro-1,8 naphthalimide 32. MS m/z 771 (M+H)$^+$.

Example 33a

Synthesis of N,N'—(N-(levulinamide), bis-aminoethyl-1,3-propanediamine)-bis-3-nitro-1,8 naphthalimide 33a

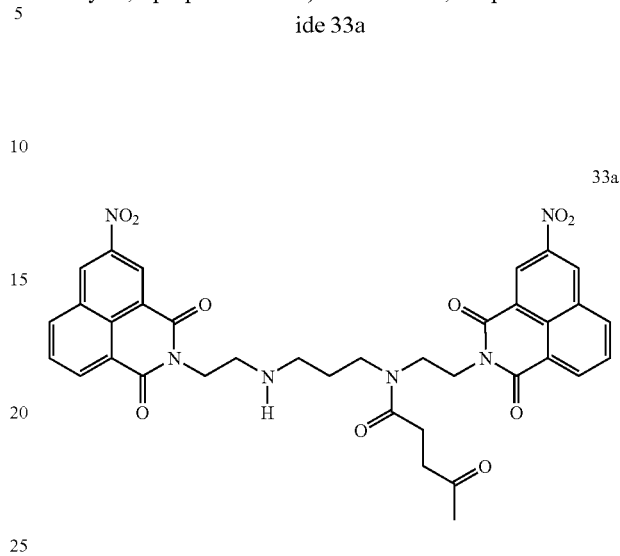

33a

Levulinic acid (0.015 ml, 0.15 mmole), diisopropylethylamine (0.04 ml, 0.25 mmole), HATU (0.054 gm, 0.15 mmole), and 1 ml DMF were stirred under nitrogen for 15 minutes at room temperature, then it was added to a solution of N,N'—(N—F$_{17}$BOC-aminoethyl-1,3-propanediamine)-bis-3-nitro-1,8 naphthalimide (62 mg, 0.049 mmole), having the structure:

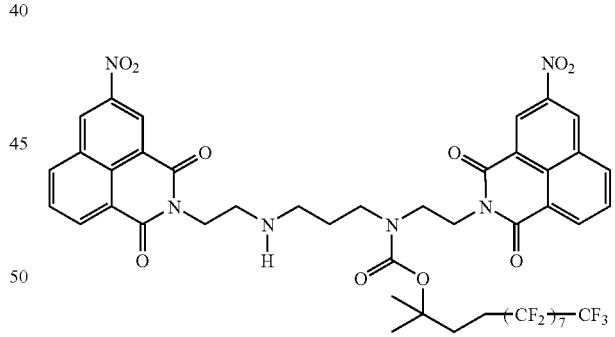

diisopropylethylamine (DIEA, 0.02 ml), and 1 ml DMF at room temperature. LC/MS analysis showed the presence of reactant and product 32. The reaction was stirred overnight at room temperature, quenched with aqueous TFA to hydrolyze the fluorocarbamate protecting group, concentrated, dissolved in acetic acid and DMF and purified by prep. HPLC to give N,N'—(N-(levulinamide), bis-aminoethyl-1,3-propanediamine)-bis-3-nitro-1,8 naphthalimide 33a. MS m/z 709 (M+H)$^+$.

Example 33b

Synthesis of N,N'—(N-(tert-butylglutaramide), bis-aminoethyl-1,3-propanediamine)-bis-4-N-imidazolyl-1,8 naphthalimide 33b

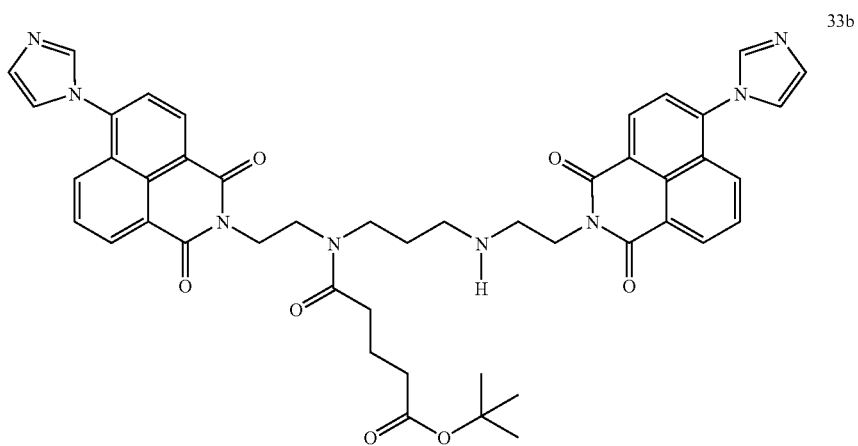

Following the same protocol as Example 33a, N-(tert-butylglutaramide), bis-aminoethyl-1,3-propanediamine)-bis-4-N-imidazolyl-1,8 naphthalimide 33b was prepared from mono-tert-butyl malonic acid and N,N'—(N—$F_{17}$BOC-aminoethyl-1,3-propanediamine)-bis-4-N-imidazolyl-1,8 naphthalimide, followed by hydrolysis of the N—$F_{17}$BOC group.

Example 34

Synthesis of N,N'-(bis-2-acetamido-1,3-propanediamine)-bis-4-morpholino-1,8 naphthalimide 34

The bis TFA salt of 1,3-bisglycyl-1,3 diaminopropane 2 (22 mg, 0.53 mmole) and DIEA (0.046 ml, 0.26 mmole) were dissolved in 0.5 ml DMF at room temperature under nitrogen. 4-Morpholino-1,8-naphthalic anhydride 1 (31 mg, 0.11 mmole) was added. The mixture was microwave heated at 150° C. for 5 minutes, then heating was increased to 200° C. for 10 minutes. The reaction was quenched with 4 ml 1.3M aqueous TFA and purified by prep. HPLC to give N,N'-(bis-2-acetamido-1,3-propanediamine)-bis-4-morpholino-1,8 naphthalimide 34. MS m/z 719 (M+H)$^+$.

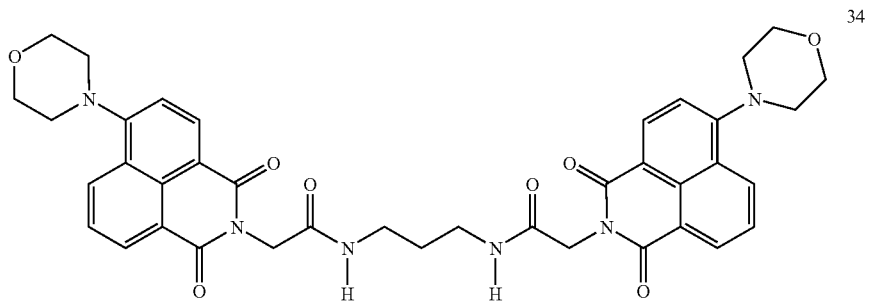

Example 35

Synthesis of N,N'-(bis-ethyl, malondiamide)-bis-4-morpholino-1,8 naphthalimide 35

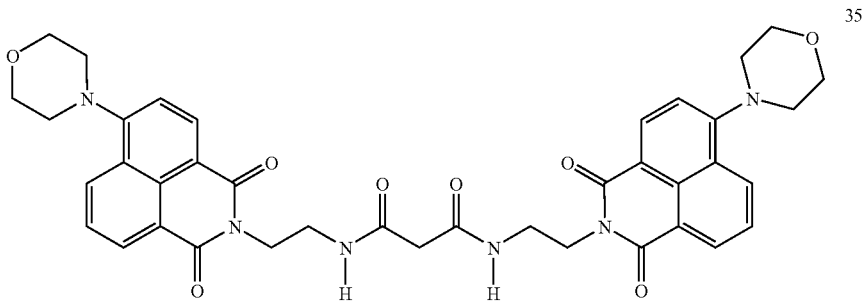

The TFA salt of N¹,N³-bis(2-aminoethyl)malonamide 3 (0.041 mmole) and DIEA (0.058 ml, 0.33 mmole) were dissolved in 0.5 ml DMF at room temperature under nitrogen. 4-Morpholino-1,8-naphthalic anhydride 1 (23 mg, 0.082 mmole) was added. The mixture was microwave heated at 180° C. for 10 minutes, then heating was increased to 200° C. for 5 minutes. The reaction was quenched with 4 ml 1.3M aqueous TFA and purified by prep. HPLC to give N,N'-(bis-ethyl, malondiamide)-bis-4-morpholino-1,8 naphthalimide 35. MS m/z 719 (M+H)$^+$.

Example 36

Synthesis of N,N'-(bis-ethyl, malondiamide)-bis-3-nitro-1,8 naphthalimide 36

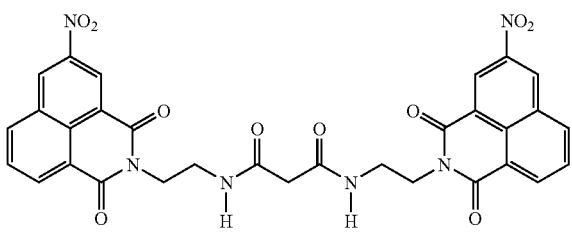

The TFA salt of N¹,N³-bis(2-aminoethyl)malonamide 3 (0.074 mmole) and DIEA (0.10 ml, 0.59 mmole) were dissolved in 1 ml DMF at room temperature under nitrogen. 3-Nitro-1,8-naphthalic anhydride (36 mg, 0.148 mmole) was added. The mixture was microwave heated at 150° C. for 5 minutes. The reaction was quenched with 4 ml 1.3M aqueous TFA and purified by prep. HPLC to give N,N'-(bis-ethyl, malondiamide)-bis-3-nitro-1,8 naphthalimide 36. MS m/z 639 (M+H)$^+$.

Example 37

Synthesis of N,N'-2-acetamido-1,3-propanediamine-ethyl)-bis-4-amino-1,8 naphthalimide 37

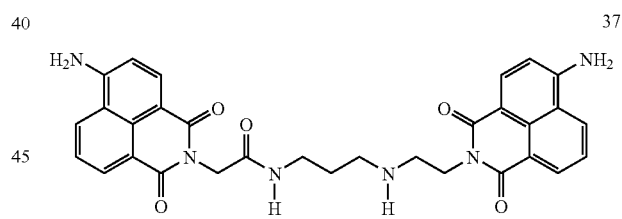

A solution of N-glycyl-4-amino-1,8 naphthalimide 5 (25 mg, 0.10 mmole), DIEA (0.043 ml, 0.25 mmole), Benzotriazole-1-yl-oxy-tris-pyrrolidino-phosphonium hexafluorophosphate (PyBOP, 52 mg, 0.10 mmole), and 0.5 ml DMF was stirred under nitrogen at room temperature for 75 minutes. A solution of the TFA salt of N-aminopropylethylamine-4-amino-1,8 naphthalimide 11a (57 mg, 0.103 mmole) and DIEA (0.070 ml, 0.40 mmole), and 1 ml DMF was stirred under nitrogen at room temperature for 40 minutes. The two solutions were mixed and stirred overnight. The mixture was concentrated under vacuum, diluted with aqueous TFA, and purified by prep. HPLC to give N,N'-2-acetamido-1,3-propanediamine-ethyl)-bis-4-amino-1,8 naphthalimide 37. MS m/z 565 (M+H)$^+$.

Example 38

Synthesis of N,N'-2-acetamido-1,2-ethanediamine-propyl)-bis-4-morpholino-1,8 naphthalimide 38

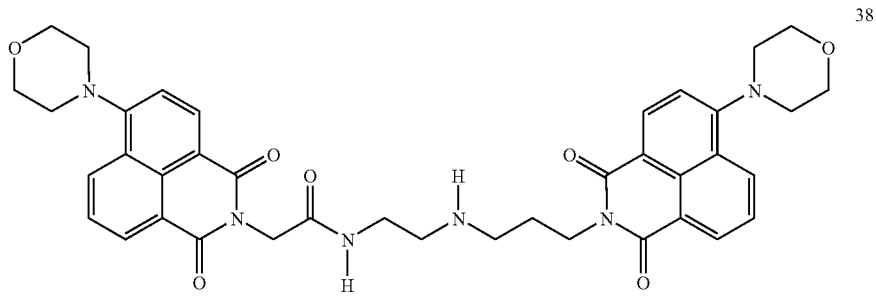

A solution of N-glycyl-4-morpholino-1,8 naphthalimide 6 (25 mg, 0.10 mmole), DIEA (0.043 ml, 0.25 mmole), benzotriazole-1-yl-oxy-tris-pyrrolidino-phosphonium hexafluorophosphate (PyBOP, 52 mg, 0.10 mmole), and 0.5 ml DMF was stirred under nitrogen at room temperature for 75 minutes. A solution of the TFA salt of N-aminoethylpropylamine-4-morpholino-1,8 naphthalimide 12b (57 mg, 0.103 mmole) and DIEA (0.070 ml, 0.40 mmole), and 1 ml DMF was stirred under nitrogen at room temperature for 40 minutes. The two solutions were mixed and stirred overnight. The mixture was concentrated under vacuum, diluted with aqueous TFA, and purified by prep. HPLC to give the TFA salt of N,N'-2-acetamido-1,3-ethanediamine-propyl)-bis-4-morpholino-1,8 naphthalimide 38. MS m/z 705 (M+H)$^+$.

Example 39

Synthesis of N,N'-2-acetamido-1,2-ethanediamine-propyl)-bis-4-amino-1,8 naphthalimide 39

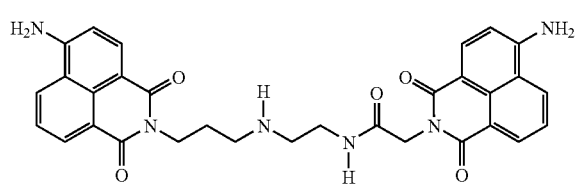

A first solution of N-glycyl-4-amino-1,8 naphthalimide 5 (31 mg, 0.114 mmole), DIEA (0.040 ml, 0.23 mmole), benzotriazole-1-yl-oxy-tris-pyrrolidino-phosphonium hexafluorophosphate (PyBOP, 61 mg, 0.12 mmole), and 1 ml DMF was stirred under nitrogen at room temperature for 75 minutes. A second solution of the TFA salt of N-aminoethylpropylamine-4-amino-1,8 naphthalimide 11b (63 mg, 0.115 mmole) and DIEA (0.070 ml, 0.40 mmole), and 1 ml DMF was stirred under nitrogen at room temperature for 40 minutes. The first solution was added slowly to the second solution and the resultant mixture was stirred overnight. The mixture was quenched with 10% aqueous TFA, concentrated under vacuum, and purified by prep. HPLC to give the TFA salt of N,N'-2-acetamido-1,3-ethanediamine-propyl)-bis-4-amino-1,8 naphthalimide 39. MS m/z 565 (M+H)$^+$.

Example 40

Synthesis of N,N'-2-acetamido-1,2-ethanediamine-propyl)-bis-3-nitro-1,8 naphthalimide 40

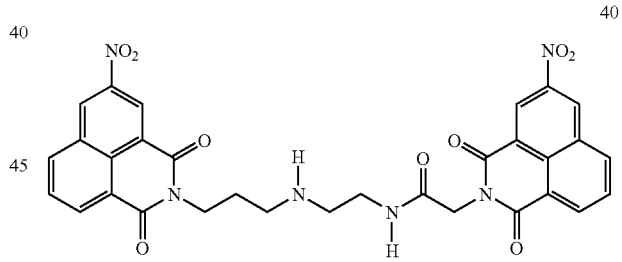

A first solution of N-glycyl-3-nitro-1,8 naphthalimide 4 (47 mg, 0.145 mmole), DIEA (0.038 ml, 0.21 mmole), benzotriazole-1-yl-oxy-tris-pyrrolidino-phosphonium hexafluorophosphate (PyBOP, 111 mg, 0.23 mmole), and 1 ml DMF was stirred under nitrogen at room temperature for 75 minutes. A second solution of the TFA salt of N-aminoethylpropylamine-3-nitro-1,8 naphthalimide 10b (106 mg, 0.177 mmole) and DIEA (0.092 ml, 0.53 mmole), and 1 ml DMF was stirred under nitrogen at room temperature for 40 minutes. The first solution was added slowly to the second solution and the resultant mixture was stirred overnight. The mixture was quenched with 10% aqueous TFA, concentrated under vacuum, and purified by prep. HPLC to give the TFA salt of N,N'-2-acetamido-1,2-ethanediamine-propyl)-bis-3-nitro-1,8 naphthalimide 40. MS m/z 625 (M+H)$^+$.

Example 41

Synthesis of N,N'-2-acetamido-1,2-propanediamine-ethyl)-bis-4-morpholino-1,8 naphthalimide 41

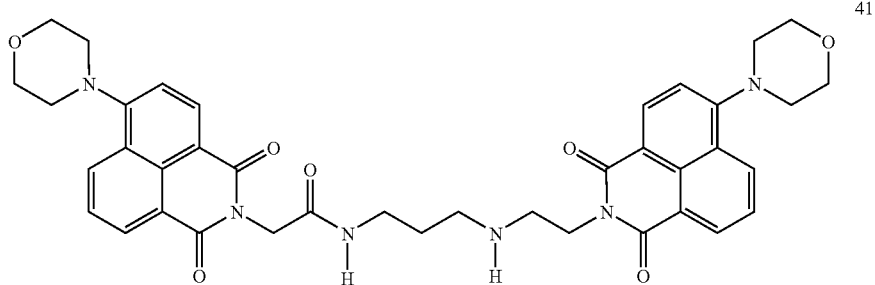

A first solution of N-glycyl-4-morpholino-1,8 naphthalimide 6 (31 mg, 0.092 mmole), DIEA (0.038 ml, 0.21 mmole), benzotriazole-1-yl-oxy-tris-pyrrolidino-phosphonium hexafluorophosphate (PyBOP, 57 mg, 0.11 mmole), and 1 ml DMF was stirred under nitrogen at room temperature for 75 minutes. A second solution of the TFA salt of N-aminopropylethylamine-4-morpholino-1,8 naphthalimide 12a (57 mg, 0.092 mmole) and DIEA (0.050 ml, 0.53 mmole), and 1 ml DMF was stirred under nitrogen at room temperature for 40 minutes. The first solution was added slowly to the second solution and the resultant mixture was stirred overnight. The mixture was quenched with 10% aqueous TFA, concentrated under vacuum, and purified by prep. HPLC to give the TFA salt of N,N'-2-acetamido-1,2-propanediamine-ethyl)-bis-4-morpholino-1,8 naphthalimide 41. MS m/z 705 (M+H)$^+$.

Example 42

Synthesis of N,N'-2-acetamido-1,2-propanediamine-ethyl)-bis-3-nitro-1,8 naphthalimide 42

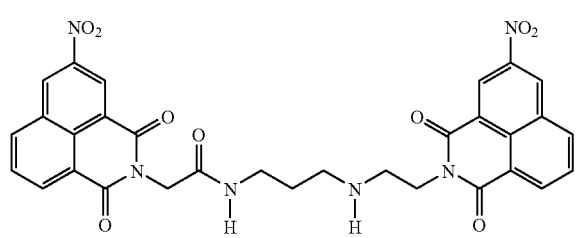

A first solution of N-glycyl-3-nitro-1,8 naphthalimide 4 (37 mg, 0.114 mmole), DIEA (0.040 ml, 0.23 mmole), benzotriazole-1-yl-oxy-tris-pyrrolidino-phosphonium hexafluorophosphate (PyBOP, 78 mg, 0.16 mmole), and 1 ml DMF was stirred under nitrogen at room temperature for 75 minutes. A second solution of the TFA salt of N-aminopropylethylamine-3-nitro-1,8 naphthalimide 10a (66 mg, 0.105 mmole) and DIEA (0.055 ml, 0.31 mmole), and 1 ml DMF was stirred under nitrogen at room temperature for 40 minutes. The first solution was added slowly to the second solution and the resultant mixture was stirred overnight. The mixture was quenched with 10% aqueous TFA, concentrated under vacuum, and purified by prep. HPLC to give the TFA salt of N,N'-2-acetamido-1,2-propanediamine-ethyl)-bis-3-nitro-1,8 naphthalimide 42. MS m/z 625 (M+H)$^+$.

Example 43

Synthesis of N,N'-2-acetamido-2-ethyleneoxyethyl)-bis-3-nitro-1,8 naphthalimide 43

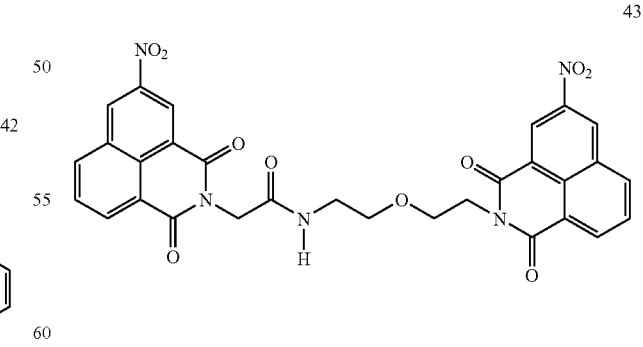

A first solution of N-glycyl-3-nitro-1,8 naphthalimide 4 (18 mg, 0.052 mmole), DIEA (0.030 ml, 0.17 mmole), benzotriazole-1-yl-oxy-tris-pyrrolidino-phosphonium hexafluorophosphate (PyBOP, 28 mg, 0.054 mmole), and 0.2 ml DMF was mixed under nitrogen at room temperature for 30 minutes. A second solution of the TFA salt of N-aminoethyl-ethoxy-3-nitro-1,8 naphthalimide 7 (25 mg, 0.052 mmole) and DIEA (0.020 ml, 0.12 mmole), and 0.5 ml DMF was mixed under nitrogen at room temperature for 40 minutes. The first solution was added slowly to the second solution and the resultant mixture was stirred overnight. The mixture was quenched with 10% aqueous TFA, concentrated under vacuum, and purified by prep. HPLC to give the TFA salt of N,N'-2-acetamido-2-ethyleneoxyethyl)-bis-3-nitro-1,8 naphthalimide 43. MS m/z 612 (M+H)$^+$.

Example 44

Synthesis of N,N'-(4-aza-octanyl)-bis-4-bromo-1,8 naphthalimide 44

A solution of 3-bromo-1,8-naphthalic anhydride (0.409 gm, 1.40 mmole), N'-(3-aminopropyl)butane-1,4-diamine (spermidine, 0.11 ml, 0.70 mmole), and 4 ml ethanol was microwave heated at 150° C. for 5 minutes. The mixture was cooled, filtered, concentrated under vacuum, dissolved in 1 ml acetic acid and 0.5 ml DMF, and purified by prep. HPLC to give the TFA salt of N,N'-(4-aza-octanyl)-bis-4-bromo-1,8 naphthalimide 44. MS m/z 664 (M+H)$^+$.

Example 45

Synthesis of N,N'-(4-aza-octanyl)-bis-4-morpholino-1,8 naphthalimide 45

A solution of N,N'-(4-aza-octanyl)-bis-4-bromo-1,8 naphthalimide 44 (0.029 gm, 0.031 mmole) and 3 ml morpholine was heated at 80° C. for 16 hours. LC/MS analysis showed the reaction was complete. The mixture was cooled, concentrated, dissolved in 2.5 ml acetic acid and 0.5 ml 0.1% aqueous TFA, and purified by prep. HPLC to give N,N'-(4-aza-octanyl)-bis-4-morpholino-1,8 naphthalimide 45. MS m/z 676 (M+H)$^+$.

Example 46

Synthesis of N,N'-(2-ethoxy-N-(2,4-dinitrobenzensulfonyl)-ethylethanamine)-bis-3-nitro-1,8 naphthalimide 46

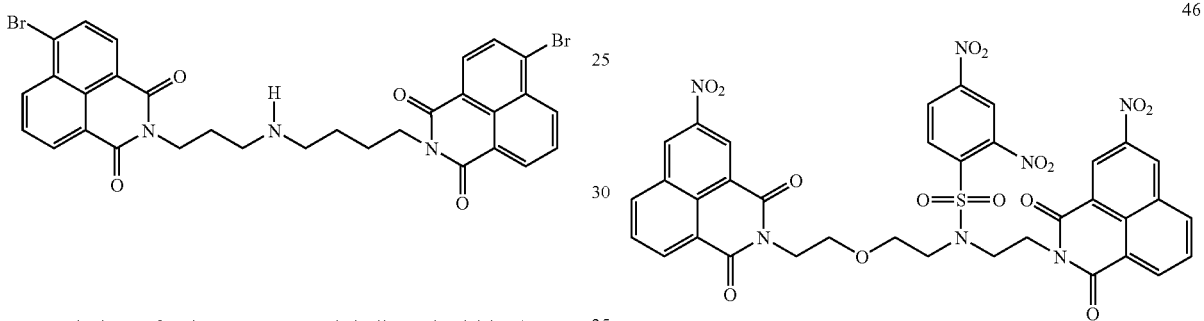

Cesium carbonate (0.144 gm, 0.442 mmole) was added to N-(2,4-dinitrophenylaminoethylethoxy)-3-nitro-1,8 naphthalimide 15 (79 mg, 0.14 mmole) in 1.5 ml DMF under nitrogen at room temperature. N-Iodoethyl-(3-nitro-1,8 naphthalimide 14 (0.11 gm, 0.28 mmole) in 7.5 ml was added, and the mixture was stirred overnight at 40° C. The mixture was concentrated, and purified by prep. HPLC to give N,N'-(2-ethoxy-N-(2,4-dinitrobenzensulfonyl)-ethylethanamine)-bis-3-nitro-1,8 naphthalimide 46. MS m/z 827 (M$^+$).

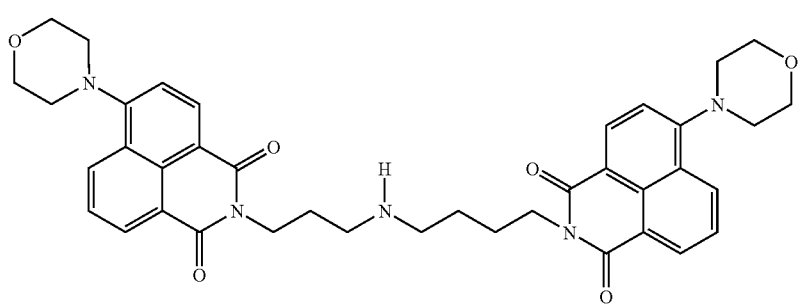

Example 47

Synthesis of N,N'-(2-ethoxy-N-ethylethanamine)-bis-3-nitro-1,8 naphthalimide 47

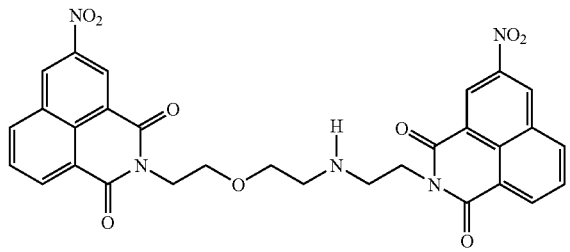

A solution of N,N'-(2-ethoxy-N-(2,4-dinitrobenzensulfonyl)-ethylethanamine)-bis-3-nitro-1,8 naphthalimide 46 (36 mg, 0.043 mmole), cesium carbonate (0.045 gm, 0.14 mmole). thiophenol (0.045 ml, 0.043 mmole) and 2 ml DMF was stirred under nitrogen at room temperature for 20 minutes. The mixture was concentrated, and purified by prep. HPLC to give N,N'-(2-ethoxy-N-ethylethanamine)-bis-3-nitro-1,8 naphthalimide 47. MS m/z 598 (M+H)$^+$.

Example 48

Synthesis of N,N'-(bis-2-acetamido-1,3-propanediamine)-bis-4-amino-1,8 naphthalimide 48

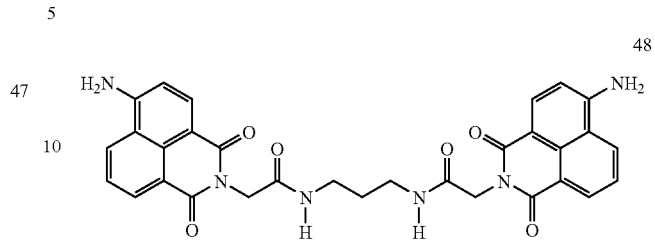

The bis HCl salt of 1,3-bis glycyl-1,3 diaminopropane 2 (37 mg, 0.141 mmole) and DIEA (0.058 ml, 0.33 mmole) were dissolved in 2 ml ethanol at room temperature under nitrogen. 4-Amino-1,8-naphthalic anhydride (63 mg, 0.28 mmole) and DIEA (0.045 ml, 0.26 mmole) in 1 ml ethanol was added. The mixture was microwave heated at 150° C. for 5 minutes. The reaction was quenched with 4 ml 1.3M aqueous TFA and purified by prep. HPLC to give N,N'-(bis-2-acetamido-1,3-propanediamine)-bis-4-amino-1,8 naphthalimide 48.

Example 49

Synthesis of $N^1,N^2$ bis methyl, N,N'-(bis-aminoethyl-1,3-propanediamine)-4-N-imidazolyl, 4-(3-aminopropyl)amino)-1,8 naphthalimide 49

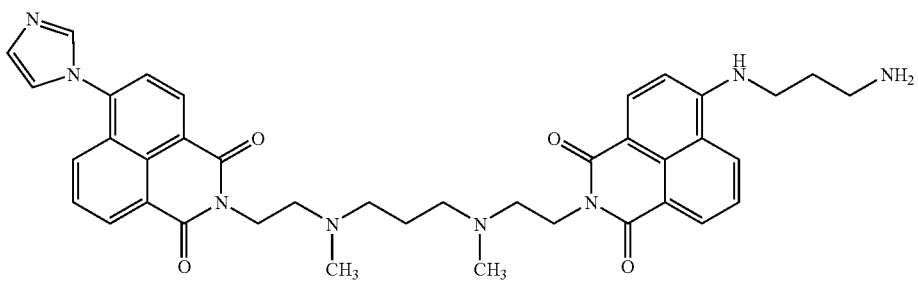

A solution of the trifluoroacetate salt of $N^1,N^2$ bis methyl, N,N'-(bis-aminoethyl-1,3-propanediamine)-4-N-imidazolyl, 4-bromo-1,8 naphthalimide (0.050 gm, 0.048 mmole), 1,3 propanediamine (0.18 ml, 2.4 mmole), ethanol, DMF, and N-methylmorpholine (NMM) was heated at 150° C. for 5 minutes. Preparatory HPLC gave $N^1,N^2$ bis methyl, N,N'-(bis-aminoethyl-1,3-propanediamine)-4-N-imidazolyl, 4-(3-aminopropyl)amino)-1,8 naphthalimide 49.

Example 50

Synthesis of $N^1,N^2$ bis methyl, N,N'-(bis-aminoethyl-1,3-propanediamine)-4-N-imidazolyl, 4-(4-mercaptopropylpiperazinyl)-1,8 naphthalimide 50

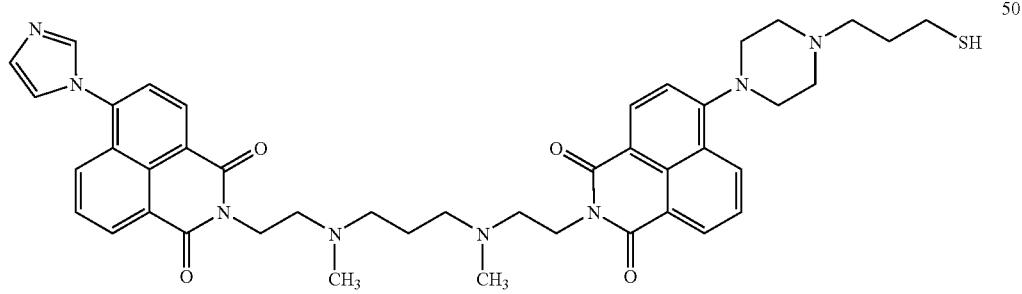

A solution of the trifluoroacetate salt of N¹,N² bis methyl, N,N'-(bis-aminoethyl-1,3-propanediamine)-4-N-imidazolyl, 4-bromo-1,8 naphthalimide, an excess of piperazine, ethanol, DMF, and N-methylmorpholine (NMM) was heated. The piperazinyl adduct was isolated and treated with an excess of ethylene sulfide. Preparatory HPLC gave N¹,N² bis methyl, N,N'-(bis-aminoethyl-1,3-propanediamine)-4-N-imidazolyl, 4-(4-mercaptopropylpiperazinyl)-1,8 naphthalimide 50.

Example 51

Synthesis of N,N'-(bis-2-acetamido-1,3-propanediamine)-4-piperazinyl, 4-(4N-(3-mercaptopropyl)-piperazinyl-1,8 naphthalimide 51

2-Fluoro-1-ethyl-pyridinium tetrafluoroborate (FEP, 0.079 gm), N-Methyl, N—BOC glycine (0.070 gm, 0.37 mmole), DIEA (0.071 ml), and 1 ml DMF were mixed and stirred under nitrogen at room temperature then added to a solution of N,N'—(N¹-ethyl, N²—H, bis-aminoethyl-1,3-propanediamine)-bis-2-nitro-1,8 naphthalimide (0.31 gm, 0.37 mmole), DIEA (0.81 mmole) in 3 ml DMF, to give N,N'—(N¹-ethyl, N²—(N-methyl, N—BOC glycyl), bis-aminoethyl-1,3-propanediamine)-bis-2-nitro-1,8 naphthalimide 52: MS m/z 852.4 (M+H)⁺.

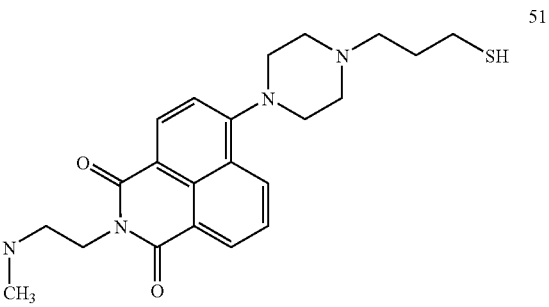

51

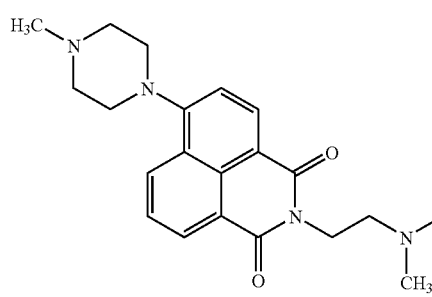

N,N'-(Bis-2-acetamido-1,3-propanediamine)-4-piperazinyl, 4-(4N-(3-mercaptopropyl)-piperazinyl-1,8 naphthalimide 51 was prepared following the protocol of Example 50.

Example 52

Synthesis of N,N'—(N¹-ethyl, N²—(N-methyl, N—BOC glycyl), bis-aminoethyl-1,3-propanediamine)-bis-2-nitro-1,8 naphthalimide 52

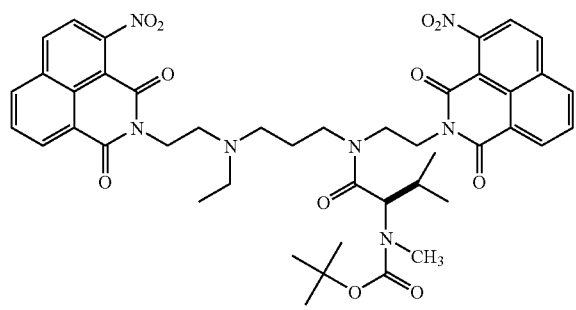

52

Example 53

Synthesis of N,N'—(N¹-ethyl,N²—(N-methyl glycyl), bis-aminoethyl-1,3-propanediamine)-bis-2-nitro-1,8 naphthalimide 53

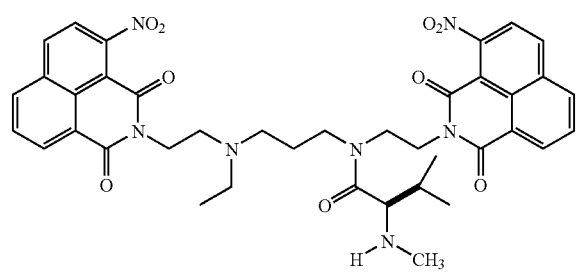

53

The BOC group was removed with acid to give N,N'—(N¹-ethyl, N²—(N-methyl glycyl), bis-aminoethyl-1,3-propanediamine)-bis-2-nitro-1,8 naphthalimide 53. MS m/z 752.1 (M+H)⁺.

Example 54

Synthesis of MC-vc-PAB-(N,N'-2-acetamido-1,3-propanediamine-ethyl)-bis-4-amino-1,8 naphthalimide) 101

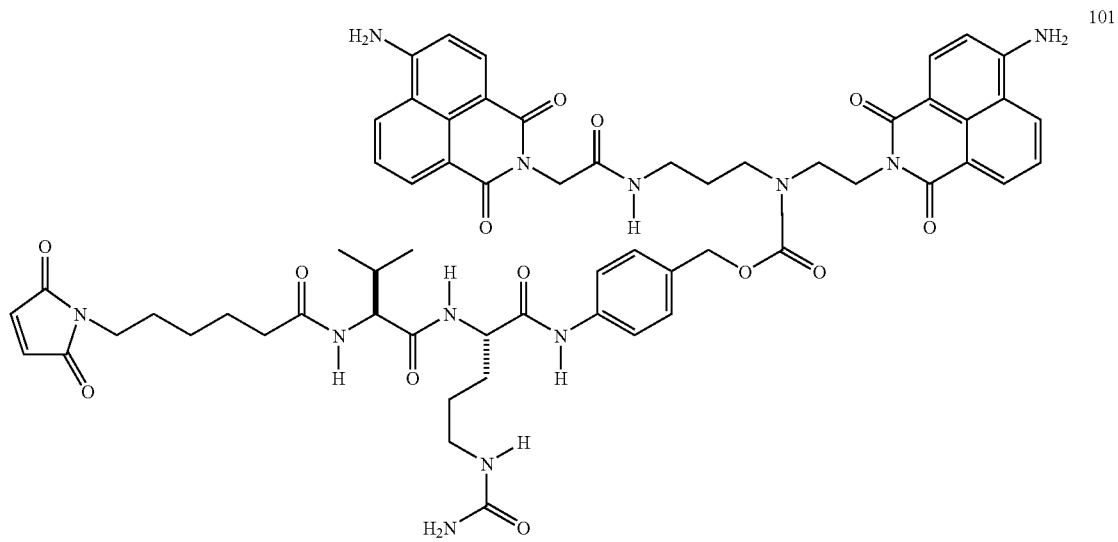

A mixture of N,N'-2-acetamido-1,3-propanediamine-ethyl)-bis-4-amino-1,8 naphthalimide 37 (18 mg, 0.025 mmole), DIEA (0.0044 ml, 0.05 mmole) and 1.2 ml DMF was stirred at room temperature under nitrogen for 10 minutes, then maleimido-caproyl-valine-citrulline-para-aminobenzyl-4-nitrophenylcarbonate (MC-vc-PAB-OPNP, 19 mg, 0.025 mmole) having the structure:

and DIEA (0.005 ml) were added, and the mixture was stirred at room temperature overnight. The mixture was quenched with 0.20 ml 1.3M aqueous TFA and 0.30 ml acetic acid, and purified by prep. HPLC to give MC-vc-PAB-(N,N'-2-acetamido-1,3-propanediamine-ethyl)-bis-4-amino-1,8 naphthalimide) 101. MS m/z 1164 (M+H)$^+$.

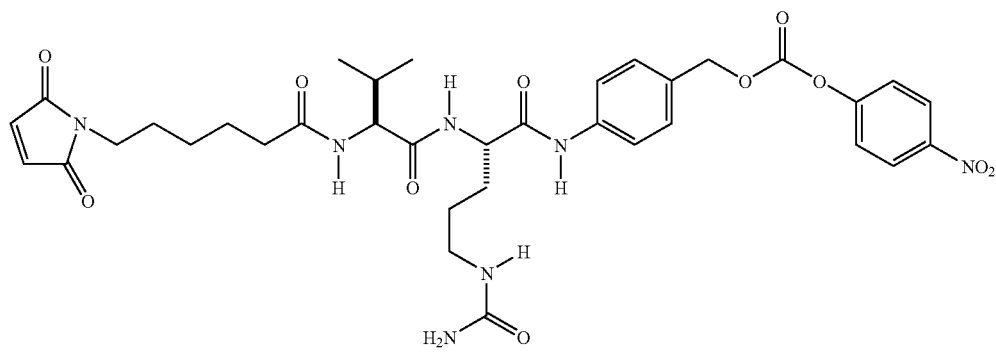

MC-vc-PAB-OPNP

Example 55
Synthesis of MC-vc-PAB-(N,N'-2-acetamido-1,3-ethanediamine-propyl)-bis-4-morpholino-1,8 naphthalimide) 102

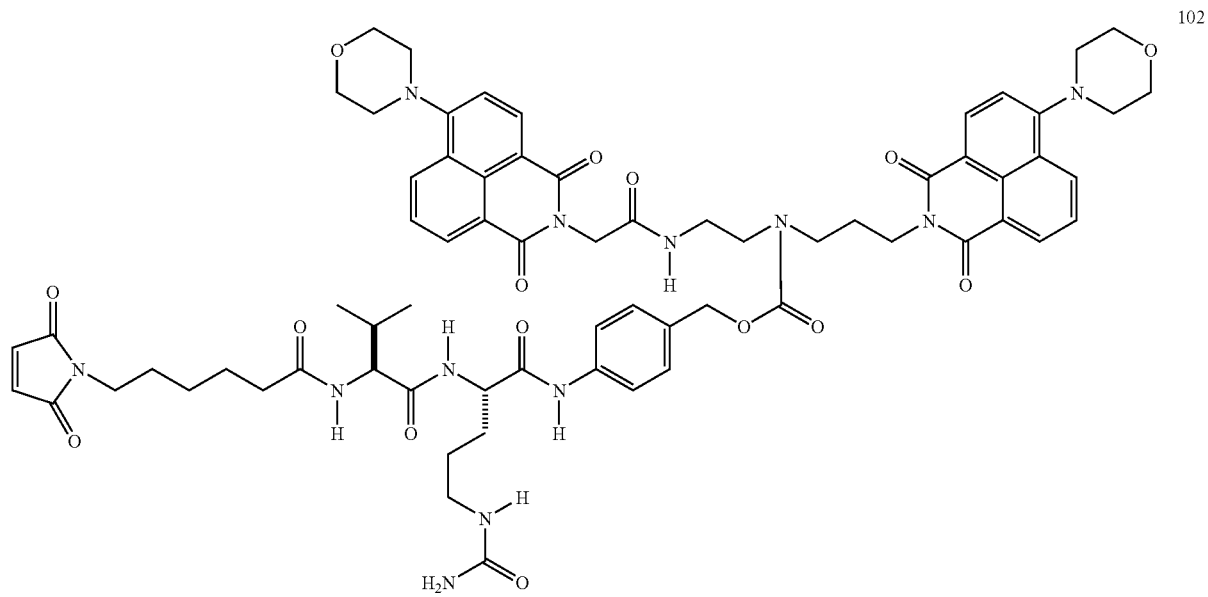

A mixture of N,N'-2-acetamido-1,3-ethanediamine-propyl)-bis-4-morpholino-1,8 naphthalimide 38 (9 mg, 0.011 mmole), DIEA (0.0044 ml, 0.05 mmole) and 1.2 ml DMF was stirred at room temperature under nitrogen for 10 minutes, then maleimido-caproyl-valine-citrulline-para-aminobenzyl-4-nitrophenylcarbonate (MC-vc-PAB-OPNP, 18 mg, 0.025 mmole) and DIEA (0.005 ml) were added, and the mixture was stirred at room temperature overnight. The mixture was quenched with 0.20 ml 1.3M aqueous TFA and 0.30 ml acetic acid, and purified by prep. HPLC to give MC-vc-PAB-(N,N'-2-acetamido-1,3-ethanediamine-propyl)-bis-4-morpholino-1,8 naphthalimide) 102. MS m/z 1304 (M+H)$^+$.

Example 56
Synthesis of MC-vc-PAB-(N,N'-2-acetamido-1,2-propanediamine-ethyl)-bis-4-morpholino-1,8 naphthalimide) 103

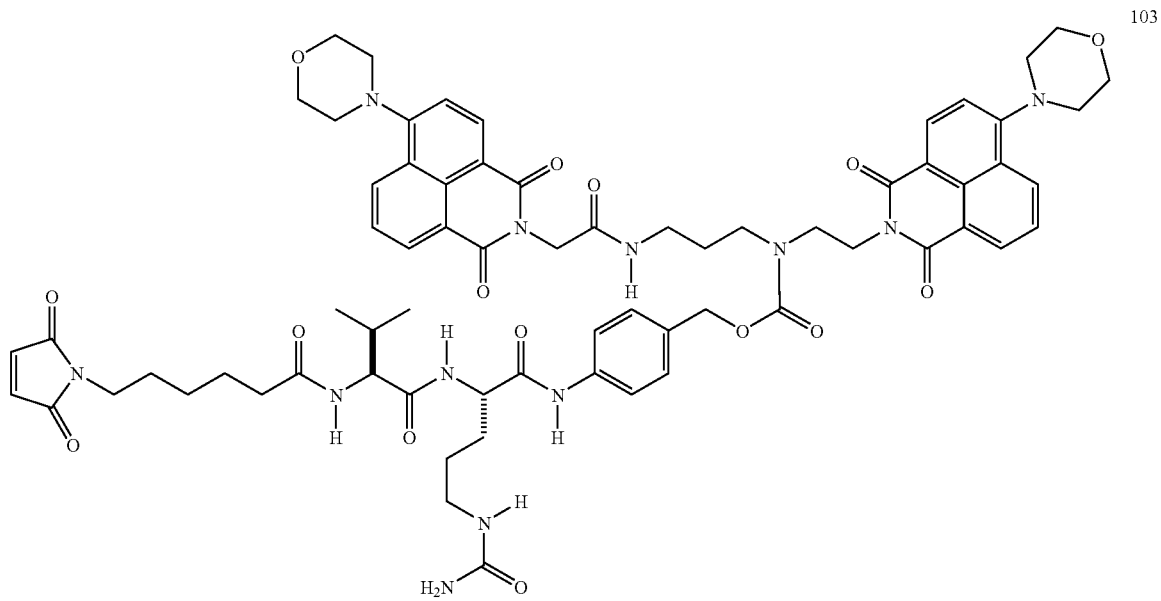

A mixture of N,N'-2-acetamido-1,2-propanediamine-ethyl)-bis-4-morpholino-1,8 naphthalimide 41 (9 mg, 0.011 mmole), DIEA (0.0044 ml, 0.05 mmole) and 1.2 ml DMF was stirred at room temperature under nitrogen for 10 minutes, then maleimido-caproyl-valine-citrulline-para-aminobenzyl-4-nitrophenylcarbonate (MC-vc-PAB-OPNP, 7 mg, 0.011 mmole) and DIEA (0.005 ml) were added, and the mixture was stirred at room temperature overnight. The mixture was quenched with 0.20 ml 1.3M aqueous TFA and 0.30 ml acetic acid, and purified by prep. HPLC to give MC-vc-PAB-(N,N'-2-acetamido-1,3-propanediamine-ethyl)-bis-4-morpholino-1,8 naphthalimide) 103. MS m/z 1304 (M+H)$^+$.

Example 57

Synthesis of MC-vc-PAB-(N,N'-2-acetamido-1,3-ethanediamine-propyl)-bis-4-amino-1,8 naphthalimide) 104 mmole), DIEA (0.003 ml, 0.03 mmole) and 0.7 ml DMF was stirred at room temperature under nitrogen for 10 minutes, then maleimido-caproyl-valine-citrulline-para-aminobenzyl-4-nitrophenylcarbonate (MC-vc-PAB-OPNP, 10 mg, 0.013 mmole) and DIEA (0.005 ml) were added, and the mixture was stirred at room temperature overnight. The mixture was quenched with 0.10 ml 1.3M aqueous TFA and 0.30 ml acetic acid, and purified by prep. HPLC to give MC-vc-PAB-(N,N'-2-acetamido-1,3-ethanediamine-propyl)-bis-4-amino-1,8 naphthalimide) 104. MS m/z 1164 (M+H)$^+$.

Example 58

Synthesis of MC-vc-PAB-(N,N'-2-acetamido-1,2-propanediamine-ethyl)-bis-3-nitro-1,8 naphthalimide) 105

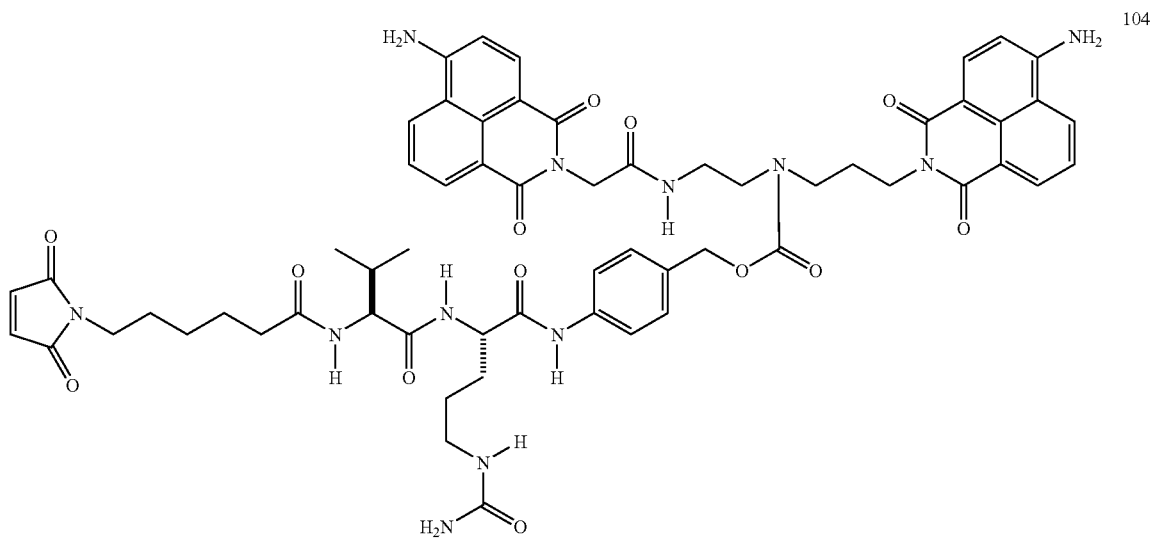

A mixture of N,N'-2-acetamido-1,3-ethanediamine-propyl)-bis-4-amino-1,8 naphthalimide 39 (10 mg, 0.013

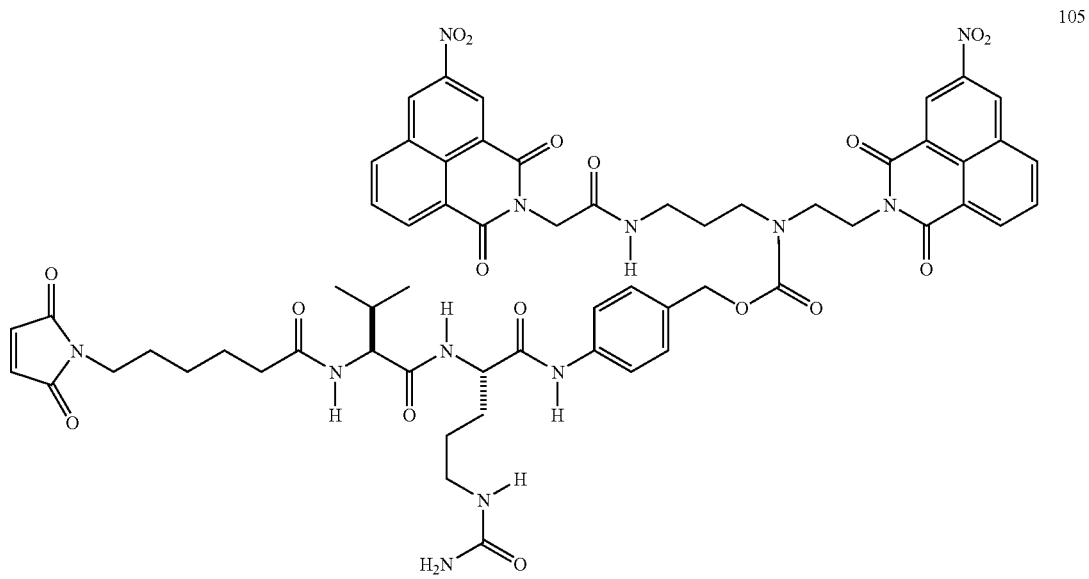

A mixture of N,N'-2-acetamido-1,2-propanediamine-ethyl)-bis-3-nitro-1,8 naphthalimide 42 (21 mg, 0.026 mmole), DIEA (0.016 ml, 0.092 mmole) and 0.2 ml DMF was stirred at room temperature under nitrogen for 10 minutes, then maleimido-caproyl-valine-citrulline-para-aminobenzyl-4-nitrophenylcarbonate (MC-vc-PAB-OPNP, 26 mg, 0.035 mmole) and DIEA (0.013 ml, 0.075 mmole) were added, and the mixture was stirred at room temperature overnight. The mixture was quenched with 0.50 ml 1.3M aqueous TFA and purified by prep. HPLC to give MC-vc-PAB-(N,N'-2-acetamido-1,3-propanediamine-ethyl)-bis-3-nitro-1,8 naphthalimide) 105. MS m/z 1223 (M+).

DIEA (0.004 ml, 0.023 mmole) and 0.7 ml DMF was stirred at room temperature under nitrogen for 10 minutes, then maleimido-caproyl-valine-citrulline-para-aminobenzyl-4-nitrophenylcarbonate (MC-vc-PAB-OPNP, 9 mg, 0.012 mmole) and DIEA (0.005 ml) were added, and the mixture was stirred at room temperature overnight. The mixture was quenched with 0.10 ml 1.3M aqueous TFA and 0.30 ml acetic acid, and purified by prep. HPLC to give MC-vc-PAB-(N,N'-2-acetamido-1,3-ethanediamine-propyl)-bis-3-nitro-1,8 naphthalimide) 106. MS m/z 1224 (M+H)+.

Example 59

Synthesis of MC-vc-PAB-(N,N'-2-acetamido-1,3-ethanediamine-propyl)-bis-3-nitro-1,8 naphthalimide) 106

Example 60

Synthesis of MC-vc-PAB-(N,N'-(4-aza-octanyl)-bis-3-nitro-1,8 naphthalimide) 107

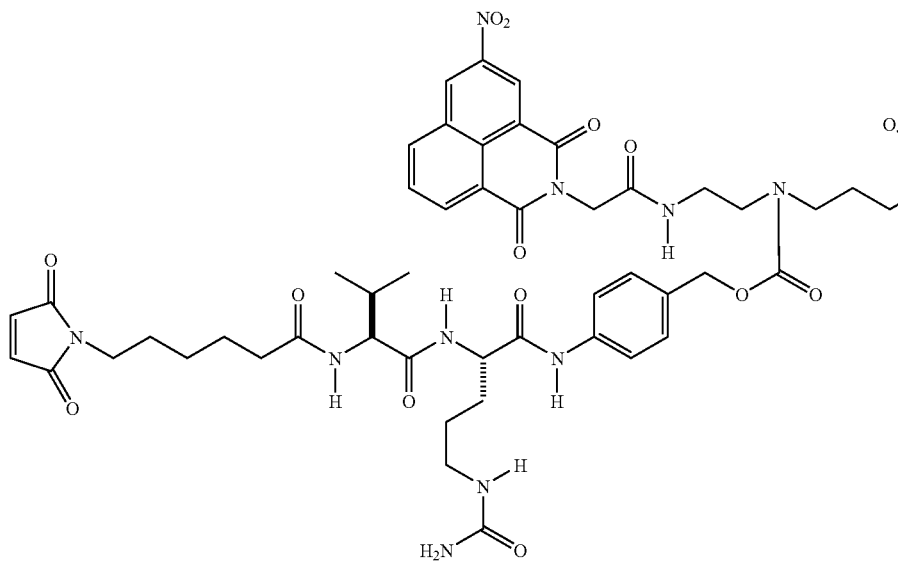

A mixture of N,N'-2-acetamido-1,2-ethanediamine-propyl)-bis-3-nitro-1,8 naphthalimide 40 (9 mg, 0.012 mmole),

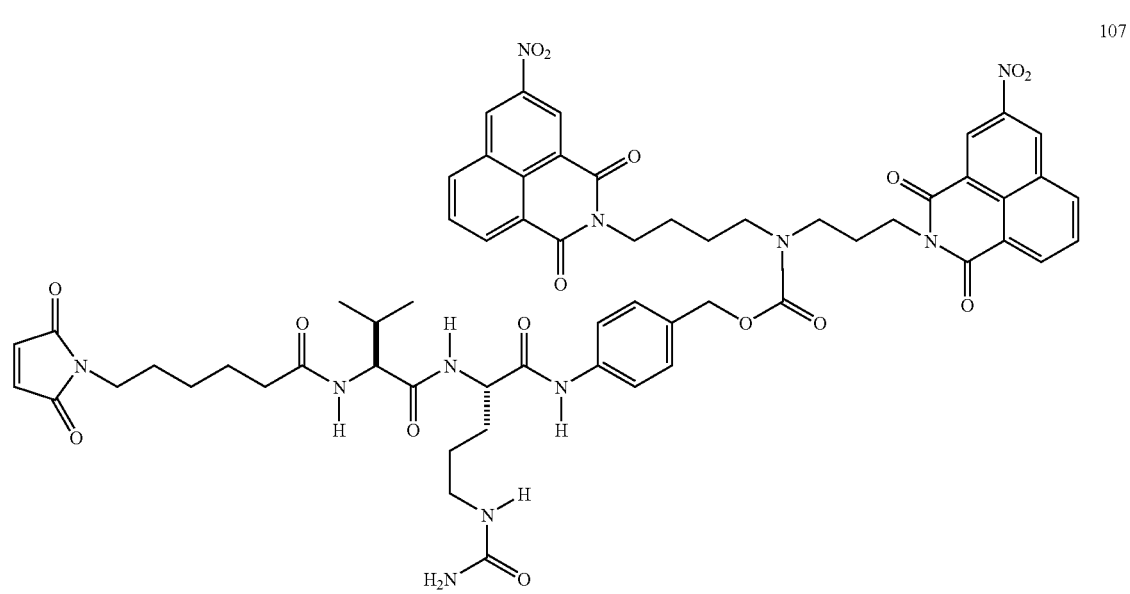

A mixture of N,N'-(4-aza-octanyl)-bis-3-nitro-1,8 naphthalimide (15 mg, 0.021 mmole), DIEA (0.010 ml, 0.057 mmole) and 0.2 ml DMF was stirred at room temperature under nitrogen for 10 minutes, then maleimido-caproyl-valine-citrulline-para-aminobenzyl-4-nitrophenylcarbonate (MC-vc-PAB-OPNP, 15 mg, 0.021 mmole) N-hydroxybenzotriazole (HOBt, (0.002 mmole) and DIEA (0.005 ml) in 0.8 ml DMF were added, and the mixture was stirred at 35° C. for 1.5 hours. The mixture was filtered and purified by prep. HPLC to give MC-vc-PAB-(N,N'-(4-aza-octanyl)-bis-3-nitro-1,8 naphthalimide) 107. MS m/z 1195 (M+H)$^+$.

Example 61

Synthesis of MC-vc-PAB-(N,N'-(2-ethoxy-N-ethylethanamine)-bis-3-nitro-1,8 naphthalimide) 108

A mixture of N,N'-(2-ethoxy-N-ethylethanamine)-bis-3-nitro-1,8 naphthalimide 47 (7 mg, 0.009 mmole), DIEA (0.004 ml, 0.023 mmole) and 0.7 ml DMF was stirred at room temperature under nitrogen for 10 minutes, then maleimido-caproyl-valine-citrulline-para-aminobenzyl-4-nitrophenylcarbonate (MC-vc-PAB-OPNP, 7 mg, 0.009 mmole) and DIEA (0.005 ml) were added, and the mixture was stirred at room temperature overnight. The mixture was filtered, and purified by prep. HPLC to give MC-vc-PAB-(N,N'-(2-ethoxy-N-ethylethanamine)-bis-3-nitro-1,8 naphthalimide) 108. MS m/z 1196 (M$^+$).

Example 62

Synthesis of MC-hydrazone-(N,N'—(N-(levulinamide), bis-aminoethyl-1,3-propanediamine)-bis-3-nitro-1,8 naphthalimide) 109

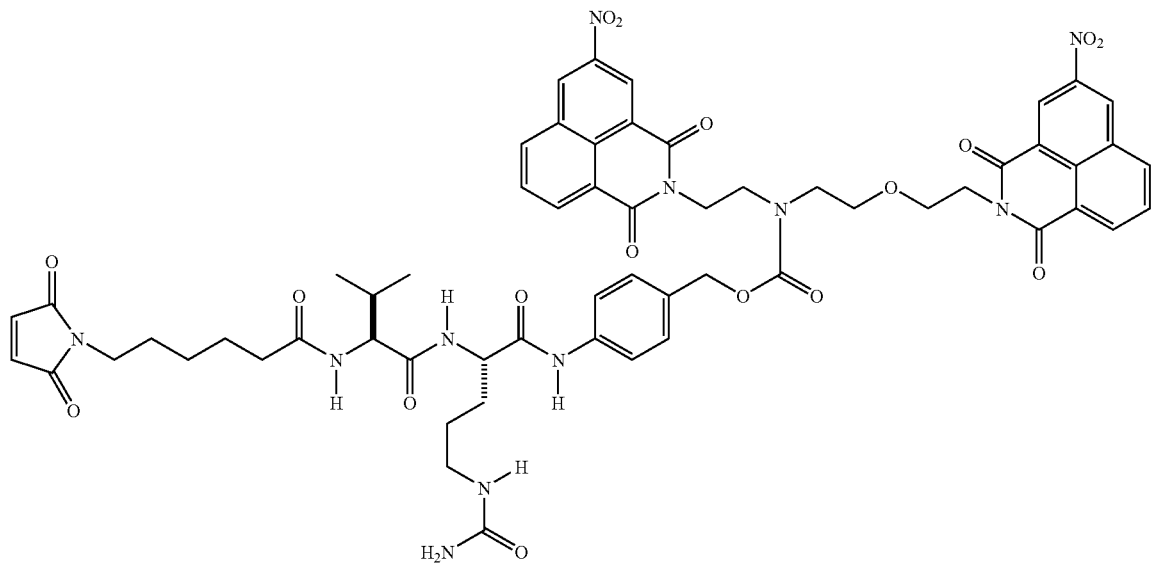

108

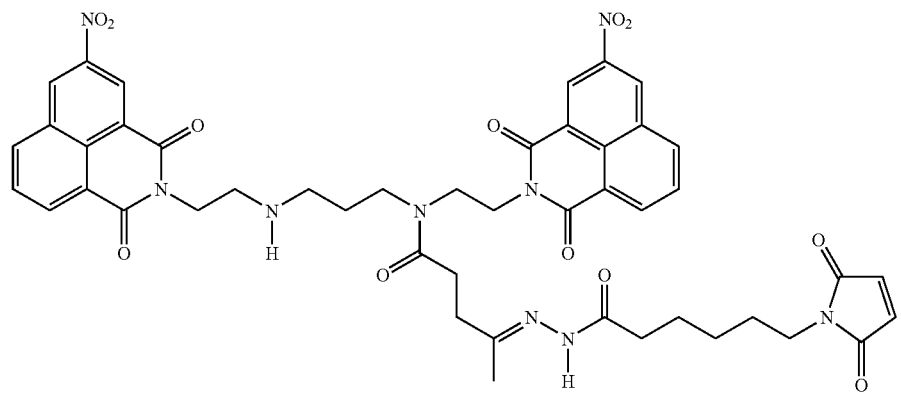

109

The TFA salt of N,N'—(N-(levulinamide), bis-aminoethyl-1,3-propanediamine)-bis-3-nitro-1,8 naphthalimide 33a (15 mg, 0.018 mmole), N-[6-maleimidocaproic acid]hydrazide (EMCH, Pierce Biotechnology, 20 mg, 0.088 mmole), acetic acid (0.010 ml, 0.002 mmole), and 3 ml DMF were stirred at room temperature for about 48 hours. The mixture was filtered, and purified by prep. HPLC to give MC-hydrazone-(N,N'—(N-(levulinamide), bis-aminoethyl-1,3-propanediamine)-bis-3-nitro-1,8 naphthalimide) 109. MS m/z 916 (M+H)$^+$.

Example 63

Synthesis of MC-hydrazone-(N,N'—(N-(levulinamide), bis-aminoethyl-1,3-propanediamine)-bis-3-nitro-1,8 naphthalimide) 110

The TFA salt of N,N'—(N-(4-acetylbenzamide), bis-aminoethyl-1,3-propanediamine)-bis-3-nitro-1,8 naphthalimide 31a (34 mg, 0.039 mmole), EMCH (Pierce Biotechnology, 28 mg, 0.124 mmole), acetic acid (0.011 ml, 0.002 mmole), 5 ml ethanol, and 1 ml DMF were stirred at room temperature overnight. The mixture was filtered and purified by prep. HPLC to give MC-hydrazone-(N,N'—(N-(levulinamide), bis-aminoethyl-1,3-propanediamine)-bis-3-nitro-1,8 naphthalimide) 110. MS m/z 964 (M+H)$^+$.

Example 64

Synthesis of MC-vc-PAB-(N,N'-(bis-aminoethyl-1,3-propanediamine)-bis-(4-N-methylpiperidine)-1,8 naphthalimide) 111

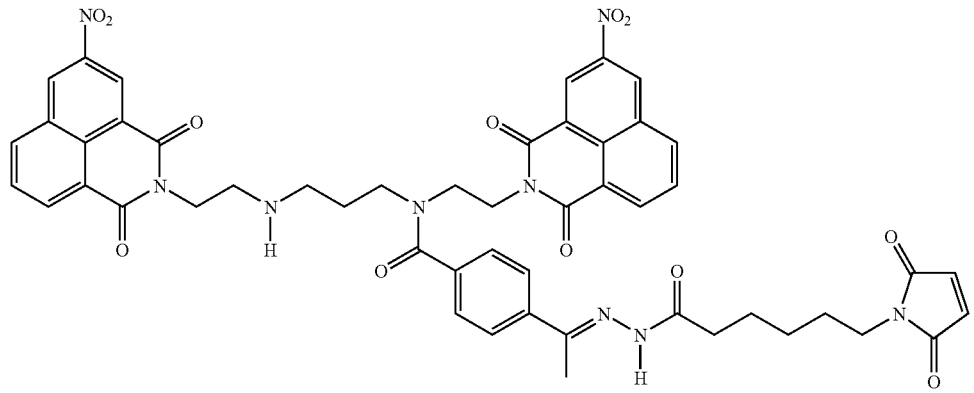

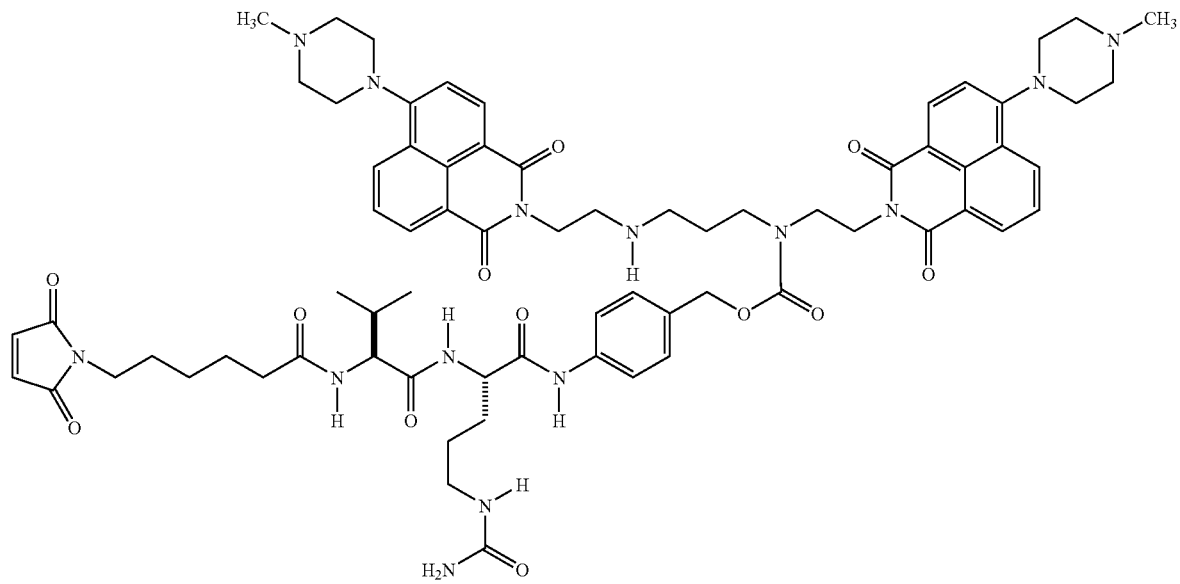

A mixture of the tetra-TFA salt of N,N'-(bis-aminoethyl-1,3-propanediamine)-bis-(4-N-methylpiperidine)-1,8 naphthalimide 24 (11 mg, 0.009 mmole), DIEA (0.008 ml, 0.092 mmole) and 0.2 ml DMF was stirred at room temperature under nitrogen for 10 minutes, then maleimido-caproyl-valine-citrulline-para-aminobenzyl-4-nitrophenylcarbonate (MC-vc-PAB-OPNP, 7 mg, 0.009 mmole), HOBt (0.002 mmole), DIEA (0.013 ml, 0.075 mmole) in 3 ml DMF were added, and the mixture was stirred at room temperature overnight. The mixture was quenched with 0.50 ml 1.3M aqueous TFA and purified by prep. HPLC to give MC-vc-PAB-(N,N'-(bis-aminoethyl-1,3-propanediamine)-bis-(4-N-methylpiperidine)-1,8 naphthalimide) 111. MS m/z 1315 (M)$^+$.

Example 64a

Synthesis of MC-vc-PAB-(N,N'-(bis-aminoethyl-1,3-propanediamine)-bis-(4-N-imidazolyl)-1,8 naphthalimide) 111a

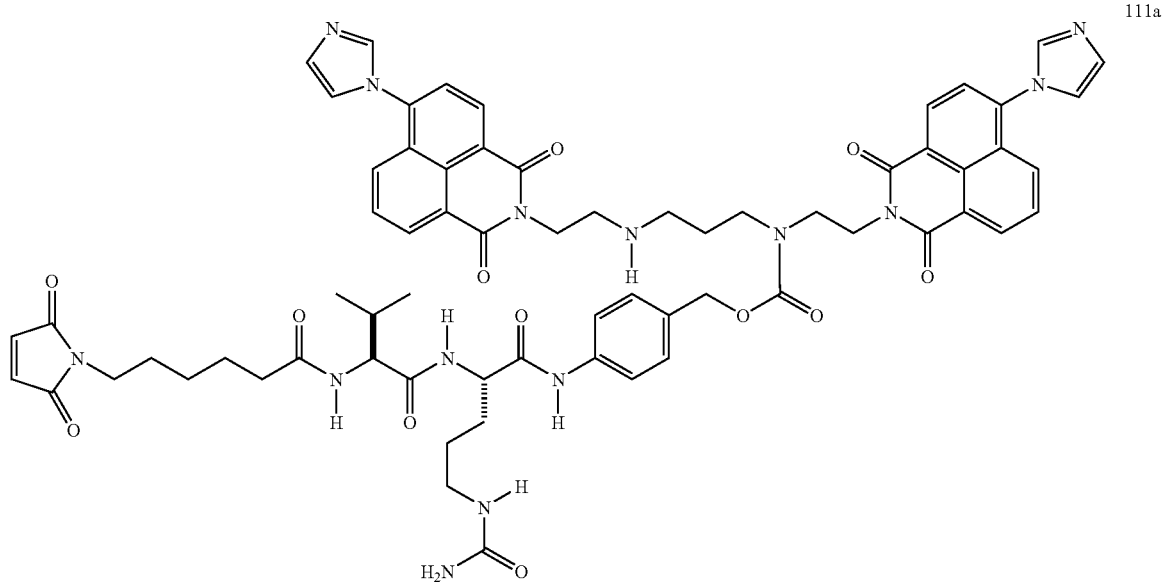

Following the protocol of Example 64, MC-val-cit-PAB-OPNP and N,N'-(bis-aminoethyl-1,3-propanediamine)-bis-(4-N-imidazolyl)-1,8 naphthalimide 24b were reacted to give MC-vc-PAB-(N,N'-(bis-aminoethyl-1,3-propanediamine)-bis-(4-N-imidazolyl)-1,8 naphthalimide) 111a.

Example 64b

Synthesis of MC-ala-phe-PAB-(N,N'-(bis-aminoethyl-1,3-propanediamine)-bis-(4-N-imidazolyl)-1,8 naphthalimide) 111b

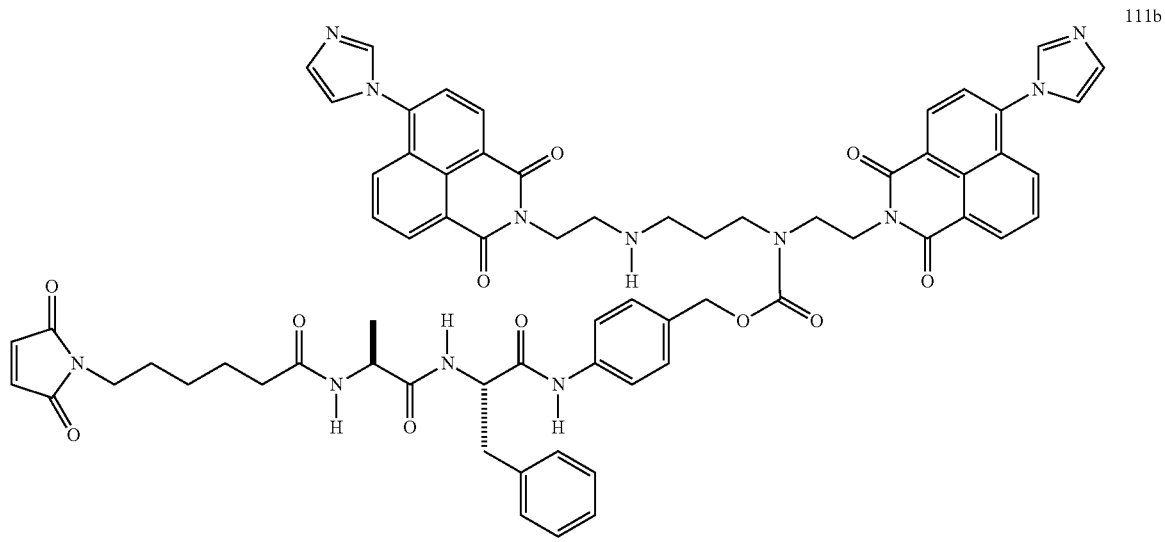

Following the protocol of Example 64, MC-ala-phe-PAB-OPNP and N,N'-(bis-aminoethyl-1,3-propanediamine)-bis-(4-N-imidazolyl)-1,8 naphthalimide 24b were reacted to give MC-ala-phe-PAB-(N,N'-(bis-aminoethyl-1,3-propanediamine)-bis-(4-N-imidazolyl)-1,8 naphthalimide) 111b.

Example 65

Synthesis of MP-vc-PAB-(N,N'-(bis-aminoethyl-1,3-propanediamine)-bis-(4-N-methylpiperidine)-1,8 naphthalimide) 112

0.075 mmole) in 3 ml DMF were added, and the mixture was stirred at room temperature overnight. The mixture was quenched with 0.50 ml 1.3M aqueous TFA and purified by prep. HPLC to give MP-vc-PAB-(N,N'-(bis-aminoethyl-1,3-propanediamine)-bis-(4-N-methylpiperidine)-1,8 naphthalimide) 112. MS m/z 1331 (M+H)$^+$.

Example 67

Synthesis of MC—(N,N'-(bis-aminoethyl-1,3-propanediamine)-bis-(4-N-methylpiperidine)-1,8 naphthalimide) 113

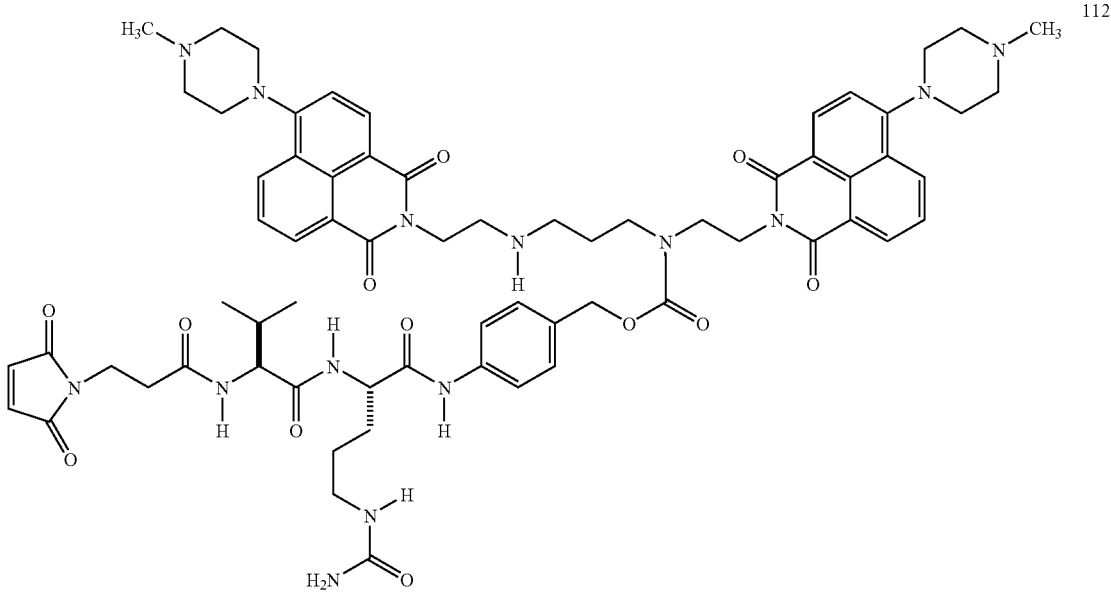

A mixture of the tetra-TFA salt of N,N'-(bis-aminoethyl-1,3-propanediamine)-bis-(4-N-methylpiperidine)-1,8 naphthalimide 24 (23 mg, 0.020 mmole), DIEA (0.017 ml, 0.098 mmole) and 0.2 ml DMF was stirred at room temperature under nitrogen for 10 minutes, then maleimido-propanoyl-valine-citrulline-para-aminobenzyl-4-nitrophenylcarbonate (MP-vc-PAB-OPNP, 9 mg, 0.012 mmole), DIEA (0.013 ml,

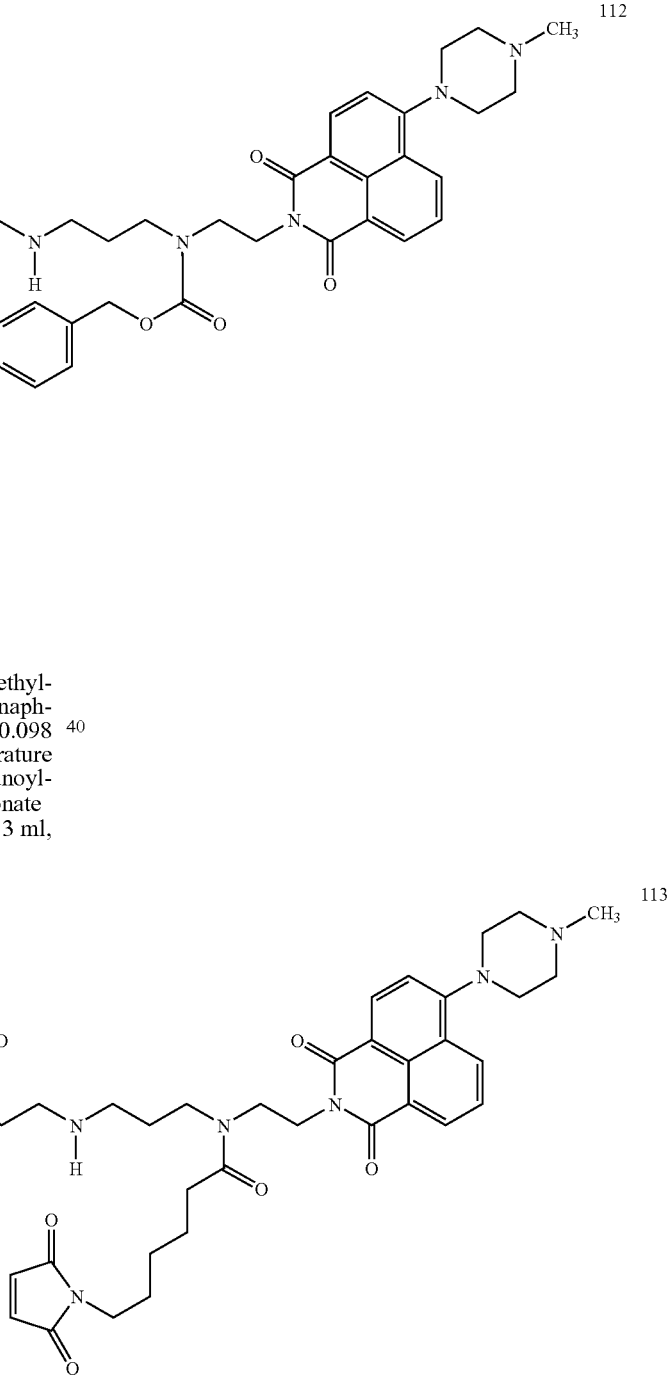

A mixture of 6-maleimidocaproic acid (3.3 mg, 0.015 mmole), PyBOP (7 mg, 0.014 mmole), DIEA (0.004 ml, 0.024 mmole), HOBt (2 mg, 0.013 mmole) and 0.2 ml DMF was stirred at room temperature under nitrogen for 5 minutes, then added to a solution of the tetra-TFA salt of N,N'-(bis-aminoethyl-1,3-propanediamine)-bis-(4-N-methylpiperidine)-1,8 naphthalimide 24 (14 mg, 0.012 mmole), DIEA (0.010 ml, 0.059 mmole) in 0.2 ml DMF. The mixture was stirred at room temperature for 2 hours, quenched with 7 ml 0.1% aqueous TFA and 2 ml acetic acid, and purified by prep. HPLC to give MC—(N,N'-(bis-aminoethyl-1,3-propanediamine)-bis-(4-N-methylpiperidine)-1,8 naphthalimide) 113. MS m/z 910 (M+).

Example 68

Synthesis of MC—(N,N'-(bis-aminoethyl-1,3-propanediamine)-bis-(4-N-imidazolyl)-1,8 naphthalimide) 113a

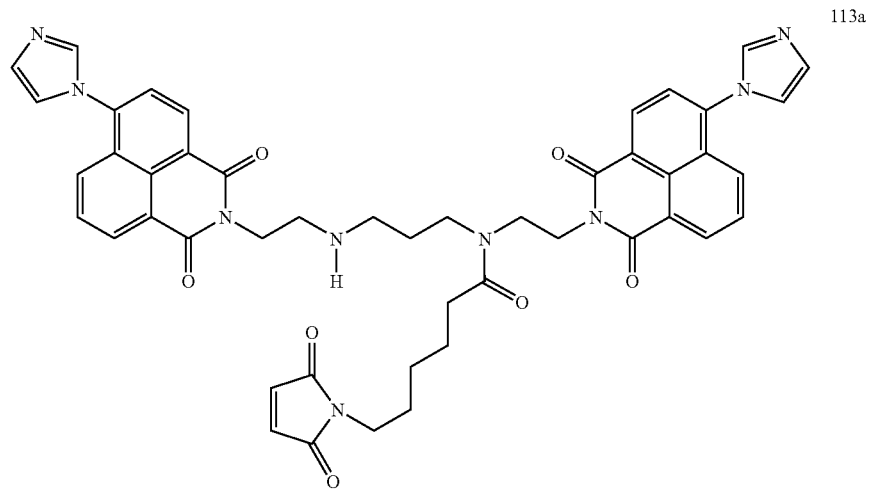

Following the procedure of Example 67, N,N'-(bis-aminoethyl-1,3-propanediamine)-bis-(4-N-imidazolyl)-1,8 naphthalimide 24b was converted to the maleimidocaproyl amide, MC—(N,N'-(bis-aminoethyl-1,3-propanediamine)-bis-(4-N-imidazolyl)-1,8 naphthalimide) 113a.

Example 69

Synthesis of tBu-Adip-vc-PAB-(N,N'-(bis-aminoethyl-1,3-propanediamine)-bis-(4-N-methylpiperidine)-1,8 naphthalimide) 114

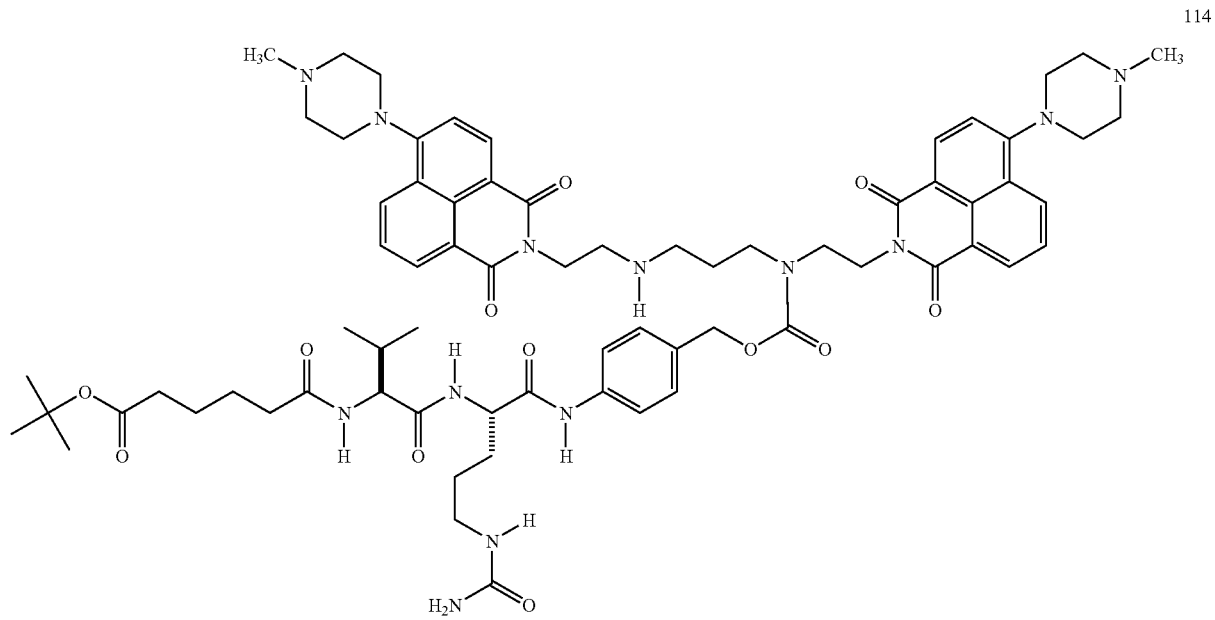

A mixture of the tetra-TFA salt of N,N'-(bis-aminoethyl-1,3-propanediamine)-bis-(4-N-methylpiperidine)-1,8 naphthalimide 24 (10 mg, 0.009 mmole), DIEA (0.012 ml, 0.070 mmole) and 0.2 ml DMF was stirred at room temperature under nitrogen for 10 minutes, then tert-butyladipate-valine-citrulline-para-aminobenzyl-4-nitrophenylcarbonate (tBuAdip-vc-PAB-OPNP, 6.4 mg, 0.009 mmole), DIEA (0.013 ml, 0.075 mmole) in 3 ml DMF were added, and the mixture was stirred at room temperature overnight. The mixture was quenched with 0.050 ml 1.3M aqueous TFA and purified by prep. HPLC to give tBu-Adip-vc-PAB-(N,N'-(bis-aminoethyl-1,3-propanediamine)-bis-(4-N-methylpiperidine)-1,8 naphthalimide) 114. MS m/z 1306 (M)$^+$.

Example 70

Synthesis of N$^1$-acetyl, N$^2$-Adip-vc-PAB-(N,N'-(bis-aminoethyl-1,3-propanediamine)-bis-(4-N-methylpiperidine)-1,8 naphthalimide) 115

A mixture of the TFA salt of tBu-Adip-vc-PAB-(N,N'-(bis-aminoethyl-1,3-propanediamine)-bis-(4-N-methylpiperidine)-1,8 naphthalimide) 114 (2 mg, 0.001 mmole), acetic anhydride (0.013 mmole), triethylamine (0.013 mmole) and 0.5 ml dichloromethane were stirred at room temperature for about 25 minutes, then one drop of water was added and concentrated under vacuum to give N$^1$-acetyl, N$^2$-t-BuAdip-vc-PAB-(N,N'-(bis-aminoethyl-1,3-propanediamine)-bis-(4-N-methylpiperidine)-1,8 naphthalimide). A solution of 10% TFA (2 ml) was added and stirred for 2.5 hours and concentrated to give N$^1$-acetyl, N$^2$-Adip-vc-PAB-(N,N'-(bis-aminoethyl-1,3-propanediamine)-bis-(4-N-methylpiperidine)-1,8 naphthalimide) 115.

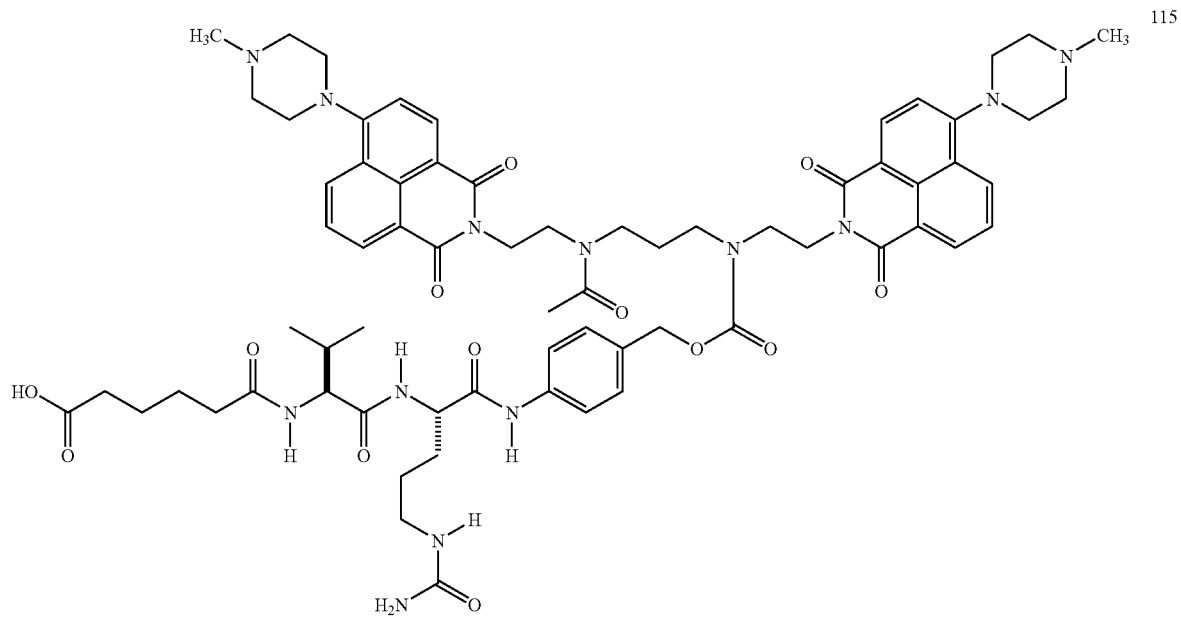

Example 71

Synthesis of N¹-acetyl, N²—NHS-Adip-vc-PAB-(N, N'-(bis-aminoethyl-1,3-propanediamine)-bis-(4-N-methylpiperidine)-1,8 naphthalimide) 116

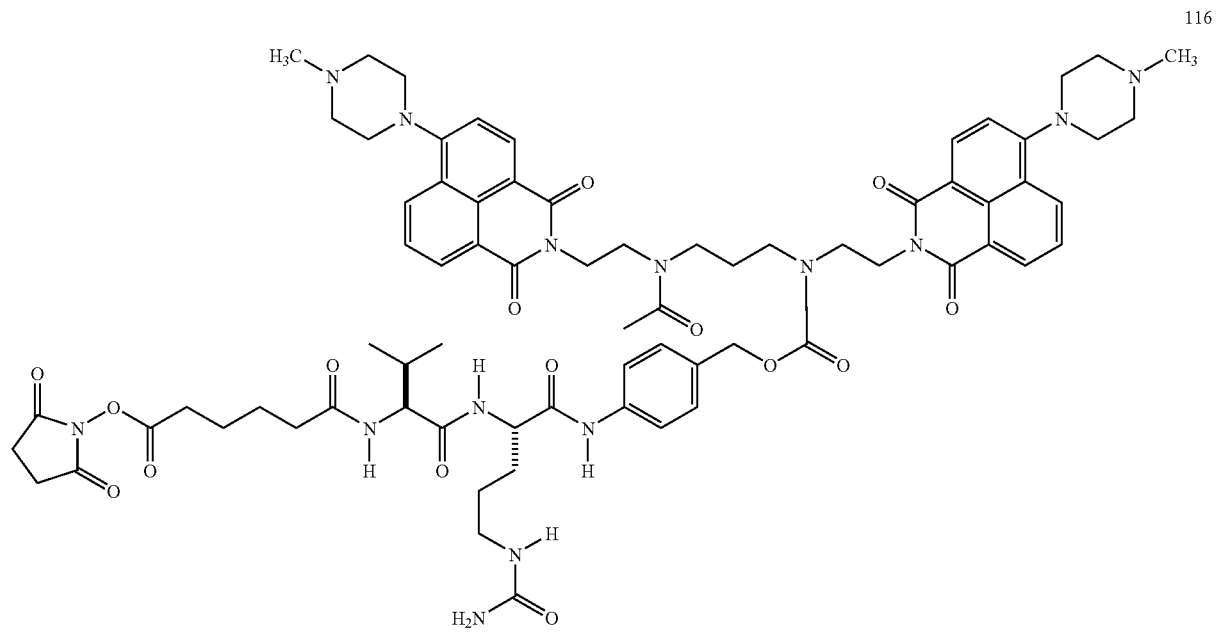

A mixture of N¹-acetyl, N²-Adip-vc-PAB-(N,N'-(bis-aminoethyl-1,3-propanediamine)-bis-(4-N-methylpiperidine)-1,8 naphthalimide) 115 (about 2 mg, 0.001 mmole), N,N'-disuccinimidyl carbonate (DSC, 10 mg, 0.037 mmole), 0.1 ml acetonitrile, and 0.1 ml DMF was stirred at room temperature for about 1.5 hours, then quenched with acetic acid and dilute aqueous TFA, concentrated under vacuum, and purified by prep. HPLC to give N¹-acetyl, N²—NHS-Adip-vc-PAB-(N, N'-(bis-aminoethyl-1,3-propanediamine)-bis-(4-N-methylpiperidine)-1,8 naphthalimide) 116. MS m/z 1391 (M+H)⁺.

Example 72

Synthesis of N¹-methyl, N²-MC-af-PAB-(N,N'-(bis-aminoethyl-1,3-propanediamine)-bis-(4-N-imidazolyl)-1,8 naphthalimide) 117

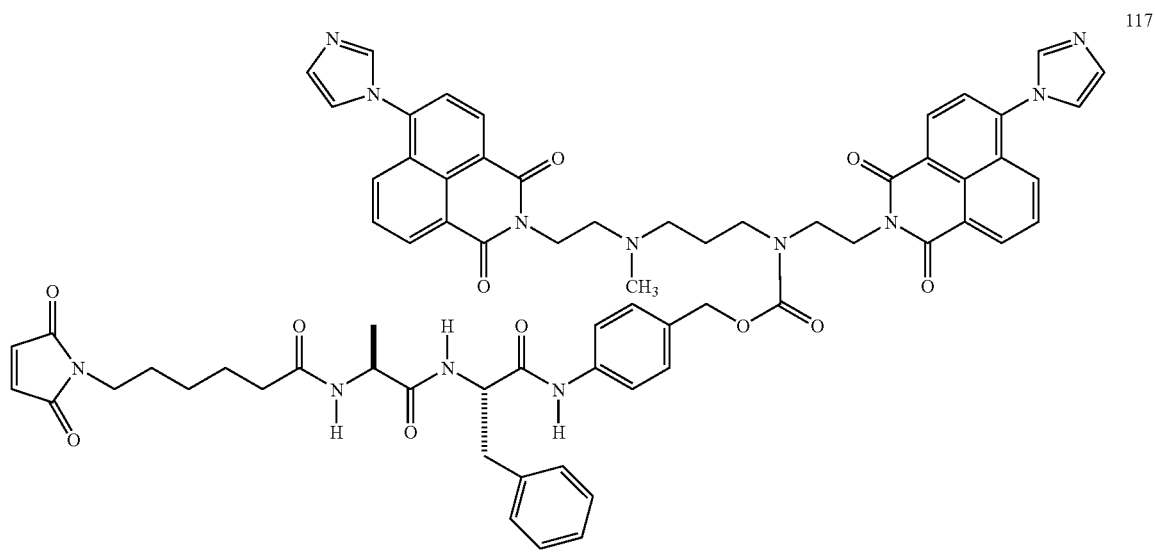

Following the protocols of the foregoing Examples, N[1]-methyl, N[2]-MC-af-PAB-(N,N'-(bis-aminoethyl-1,3-propanediamine)-bis-(4-N-imidazolyl)-1,8 naphthalimide) 117 was prepared.

Example 73

Synthesis of N[1]-methyl, N[2]-(MC-vc-PAB-N-methylglycyl)-(N,N'-(bis-aminoethyl-1,3-propanediamine)-bis-(4-N-imidazolyl)-1,8 naphthalimide) 118

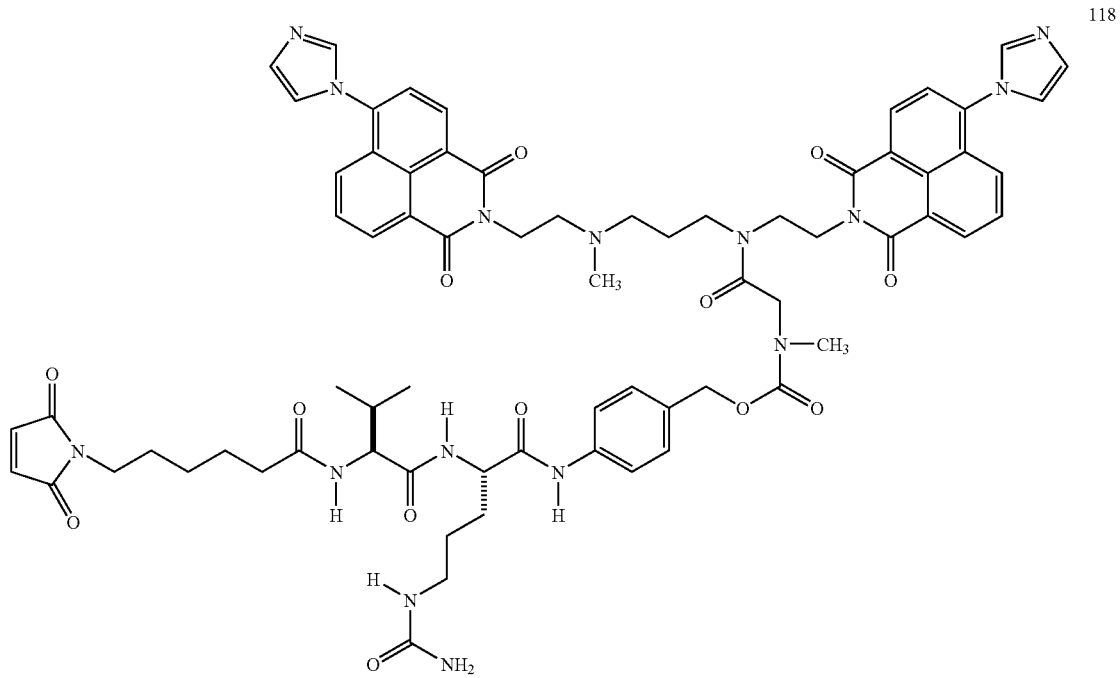

Following the protocols of the foregoing Examples, N[1]-methyl, N[2]-(MC-vc-PAB-N-methylglycyl)-(N,N'-(bis-aminoethyl-1,3-propanediamine)-bis-(4-N-imidazolyl)-1,8 naphthalimide) 118 was prepared.

Example 74

Synthesis of N[1]-methyl, N[2]-(MC-af-PAB-N-methylglycyl)-(N,N'-(bis-aminoethyl-1,3-propanediamine)-bis-(4-N-imidazolyl)-1,8 naphthalimide) 119

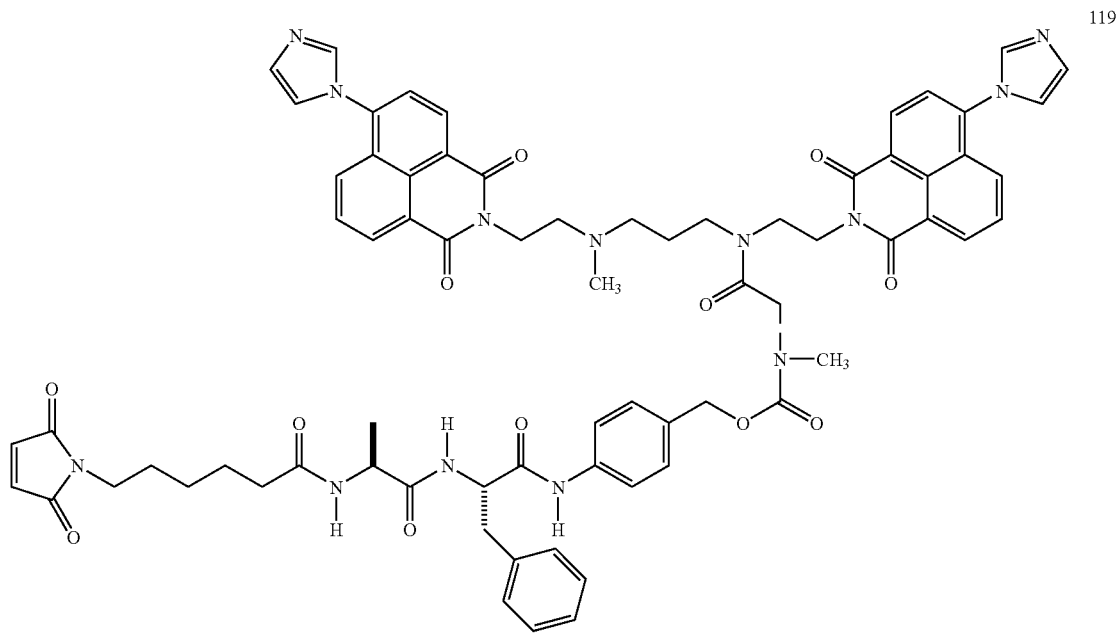

241

Following the protocols of the foregoing Examples, N$^1$-methyl, N$^2$-(MC-af-PAB-N-methylglycyl)-(N,N'-(bis-aminoethyl-1,3-propanediamine)-bis-(4-N-imidazolyl)-1,8 naphthalimide) 119 was prepared.

242

Example 75

Synthesis of N$^1$-methyl, N$^2$-(MC-vc-PAB-(3-N-methylpropanamide))-(N,N'-(bis-aminoethyl-1,3-propanediamine)-bis-(4-N-imidazolyl)-1,8 naphthalimide) 120

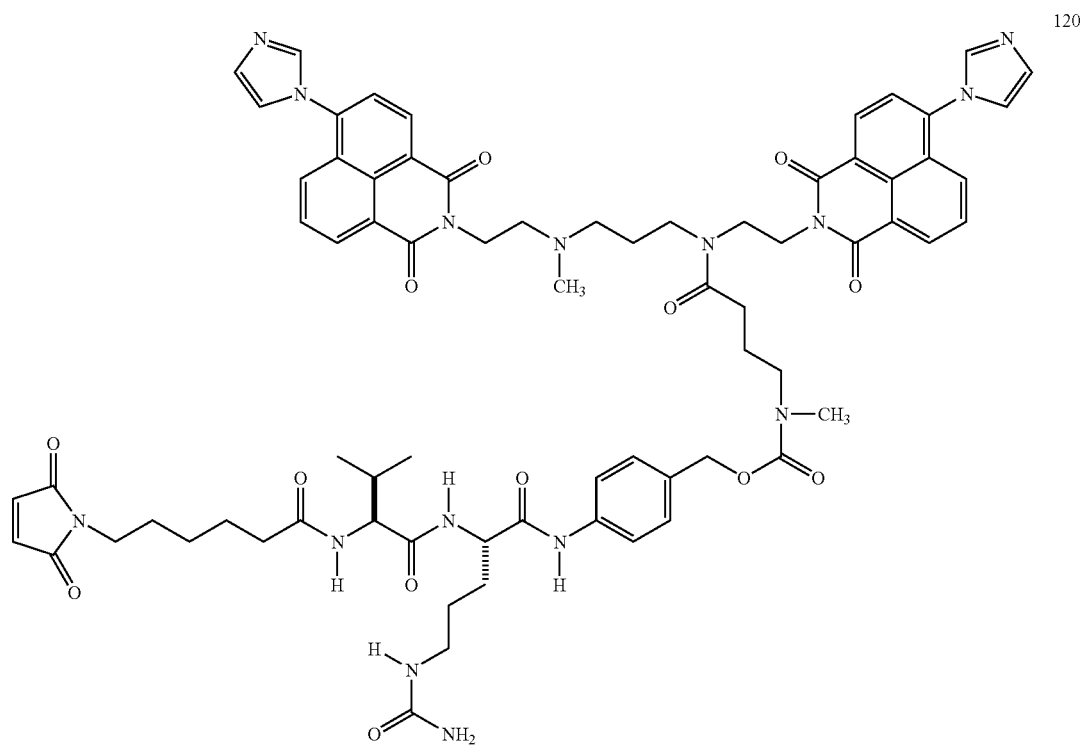

Following the protocols of the foregoing Examples, N$^1$-methyl, N$^2$-(MC-vc-PAB-(3-N-methylpropanamide))-(N,N'-(bis-aminoethyl-1,3-propanediamine)-bis-(4-N-imidazolyl)-1,8 naphthalimide) 120 was prepared.

Example 76

Synthesis of N¹-methyl, N²-(MC-af-PAB-(3-N-methylpropanamide))-(N,N'-(bis-aminoethyl-1,3-propanediamine)-bis-(4-N-imidazolyl)-1,8 naphthalimide) 121

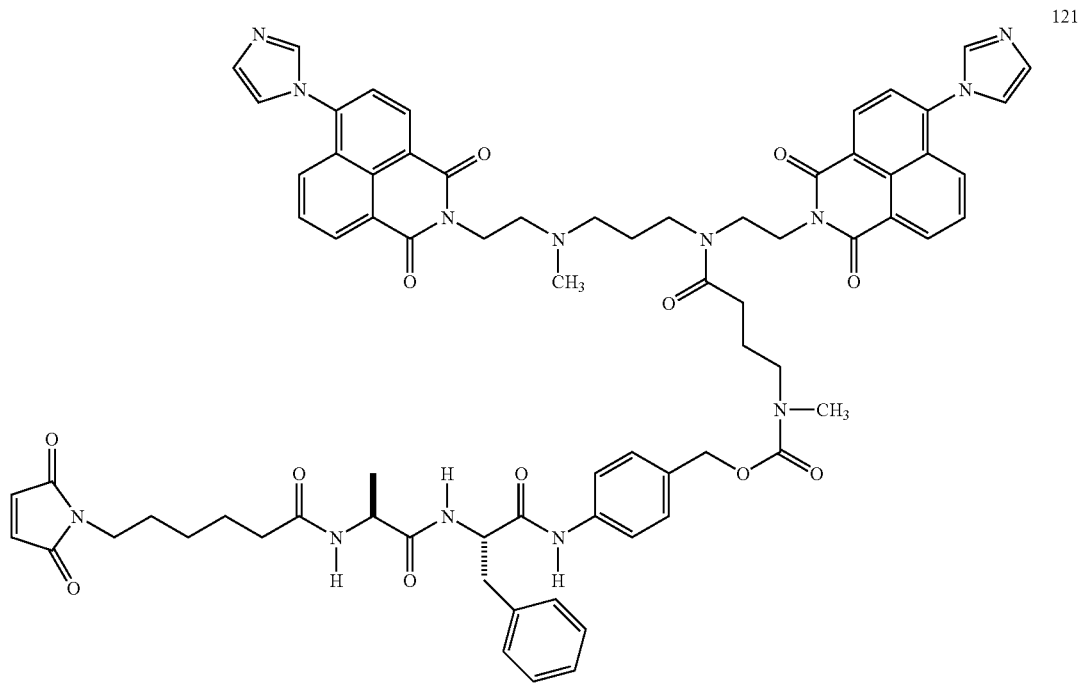

Following the protocols of the foregoing Examples, N¹-methyl, N²-(MC-af-PAB-(3-N-methylpropanamide))-(N,N'-(bis-aminoethyl-1,3-propanediamine)-bis-(4-N-imidazolyl)-1,8 naphthalimide) 121 was prepared.

Example 77

Synthesis of N,N'-(bis-aminoethyl-1,3-bis N-methyl-propanediamine)-(4-N-imidazolyl, 4-N-(MC-vc-PAB)-1,8 naphthalimide) 122

Following the protocols of the foregoing Examples, N,N'-(bis-aminoethyl-1,3-bis N-methyl-propanediamine)-(4-N-imidazolyl, 4-N-(MC-vc-PAB)-1,8 naphthalimide) 122 was prepared.

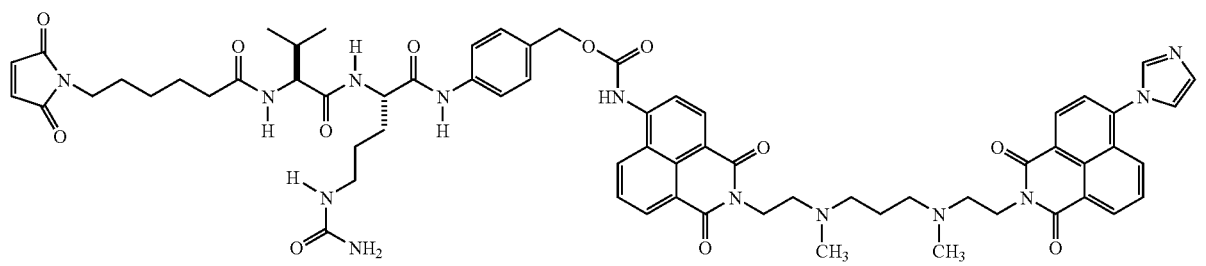

Example 78

Synthesis of N,N'-(bis-aminoethyl-1,3-bis N-methyl-propanediamine)-(4-N-imidazolyl, 4-N-(MC-af-PAB)-1,8 naphthalimide) 122a

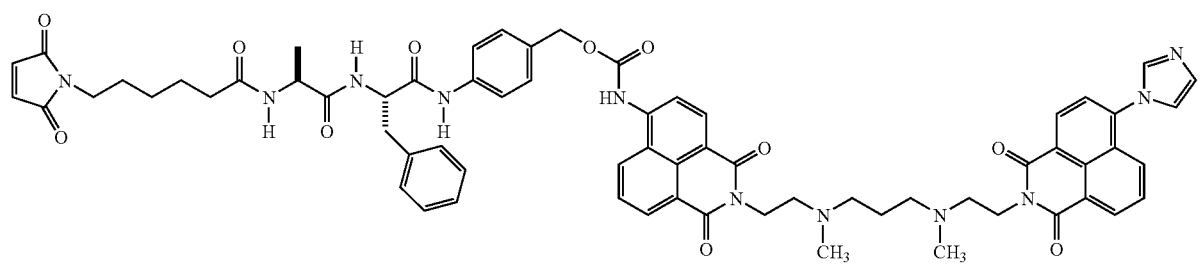

Following the protocols of the foregoing Examples, N,N'-(bis-aminoethyl-1,3-bis N-methyl-propanediamine)-(4-N-imidazolyl, 4-N-(maleimidocaproyl-af-PAB)-1,8 naphthalimide) 122a was prepared.

Example 79

Synthesis of N,N'-(bis-aminoethyl-1,3-bis N-methyl-propanediamine)-(4-N-imidazolyl, 4-N-(MC-vc)-1,8 naphthalimide) 123

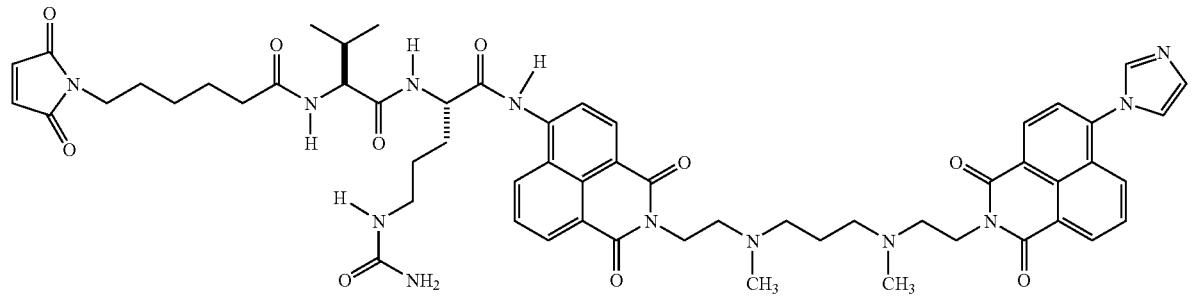

Following the protocols of the foregoing Examples, N,N'-(bis-aminoethyl-1,3-bis N-methyl-propanediamine)-(4-N-imidazolyl, 4-N-(maleimidocaproyl-valine-citrulline)-1,8 naphthalimide) 123 was prepared.

Example 80

Synthesis of N,N'-(bis-aminoethyl-1,3-bis N-methyl-propanediamine)-3-nitro, 4-N-(MP-gly-val-cit)-4-PAB-4-piperazinyl-1,8 naphthalimide) 123a Following the protocols of the foregoing Examples, N,N'-(bis-aminoethyl-1,3-bis N-methyl-propanediamine)-3-nitro, 4-N-(3-maleimidopropanoyl-gly-val-cit)-4-PAB-4-piperazinyl-1,8 naphthalimide) 123a was prepared.

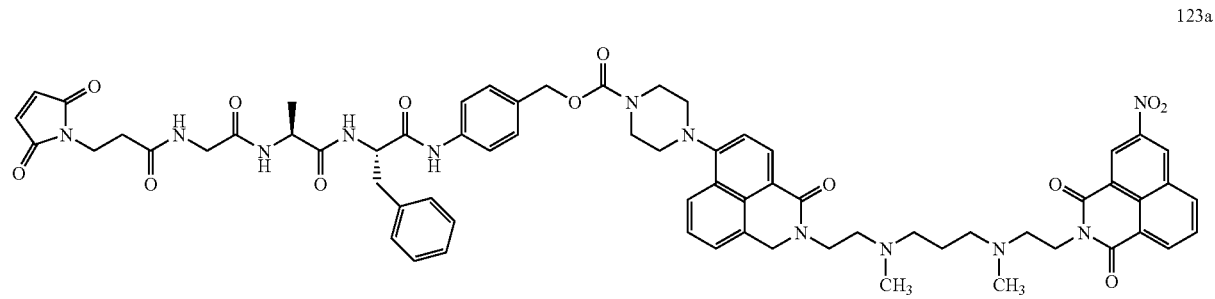

Example 81

Synthesis of N¹-ethyl, N²-MC-af-PAB-(N,N'-(bis-aminoethyl-1,3-propanediamine)-bis 3-nitro-1,8 naphthalimide) 124

Following the protocols of the foregoing Examples, N¹-ethyl, N²-MC-ala-phe-PAB-(N-methylvaline)-(N,N'-(bis-aminoethyl-1,3-propanediamine)-bis 3-nitro-1,8 naphthalimide) 125 was prepared.

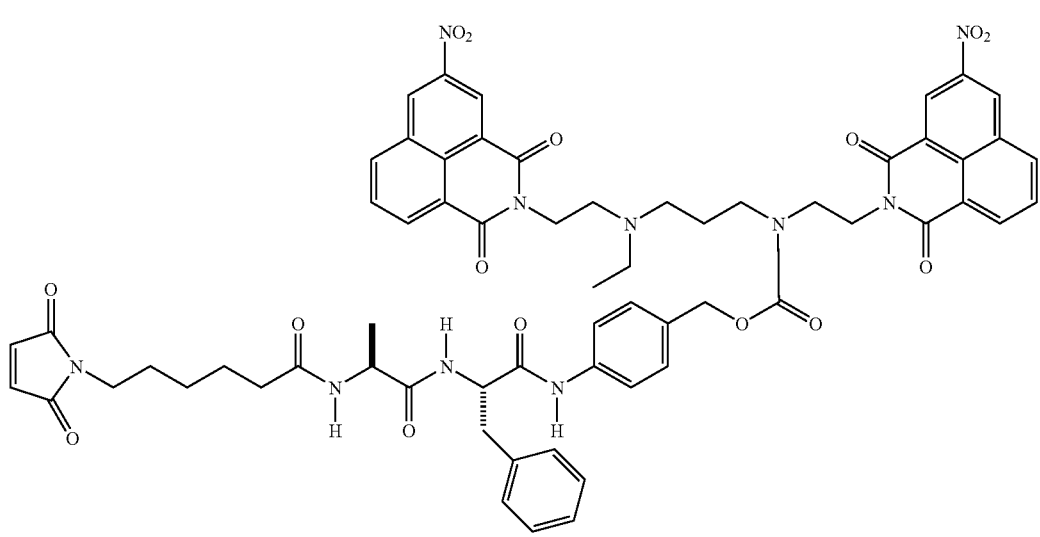

Following the protocols of the foregoing Examples, N¹-ethyl, N²-MC-af-PAB-(N,N'-(bis-aminoethyl-1,3-propanediamine)-bis 3-nitro-1,8 naphthalimide) 124 was prepared.

Example 82

Synthesis of N¹-ethyl, N²-MC-ala-phe-PAB-(N-methylvaline)-(N,N'-(bis-aminoethyl-1,3-propanediamine)-bis 3-nitro-1,8 naphthalimide) 125

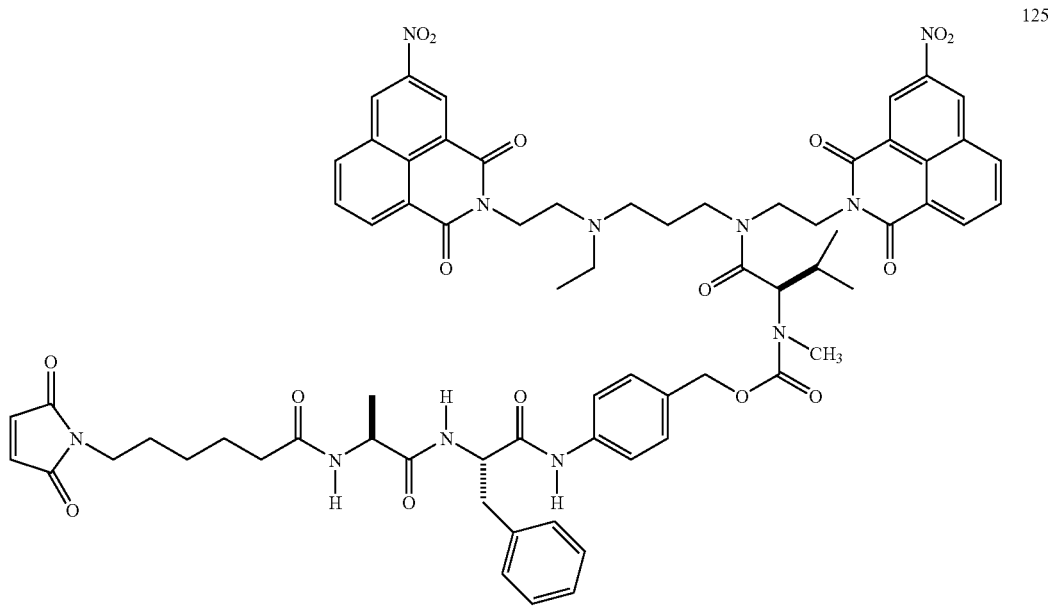

Example 83

Synthesis of N¹—H, N²-MC-vc-PAB-(N,N'-(bis-aminoethyl-1,3-propanediamine)-bis 3-nitro-1,8 naphthalimide) 126

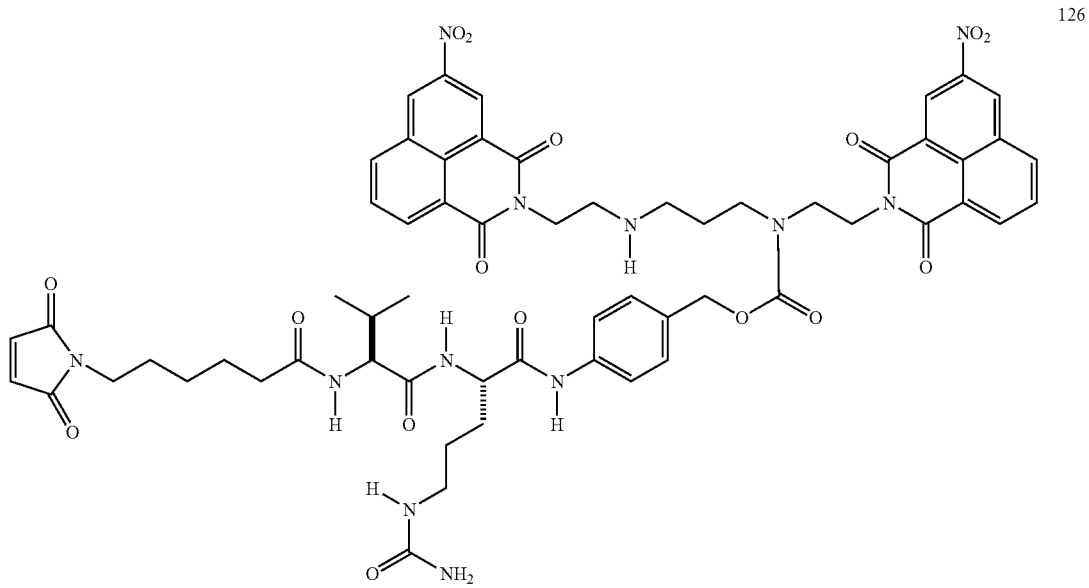

Following the protocols of the foregoing Examples, N¹—H, N²-MC-vc-PAB-(N,N'-(bis-aminoethyl-1,3-propanediamine)-bis 3-nitro-1,8 naphthalimide) 126 was prepared.

Example 84

Synthesis of N¹—H, N²-MC-Vc-PAB-(N,N'-(bis-aminoethyl-1,3-propanediamine)-3-nitro, 4-amino-1,8 naphthalimide) 126a Following the protocols of the foregoing Examples, N¹—H, N²-MC-vc-PAB-(N,N'-(bis-aminoethyl-1,3-propanediamine)-3-nitro, 4-amino-1,8 naphthalimide) 126a was prepared.

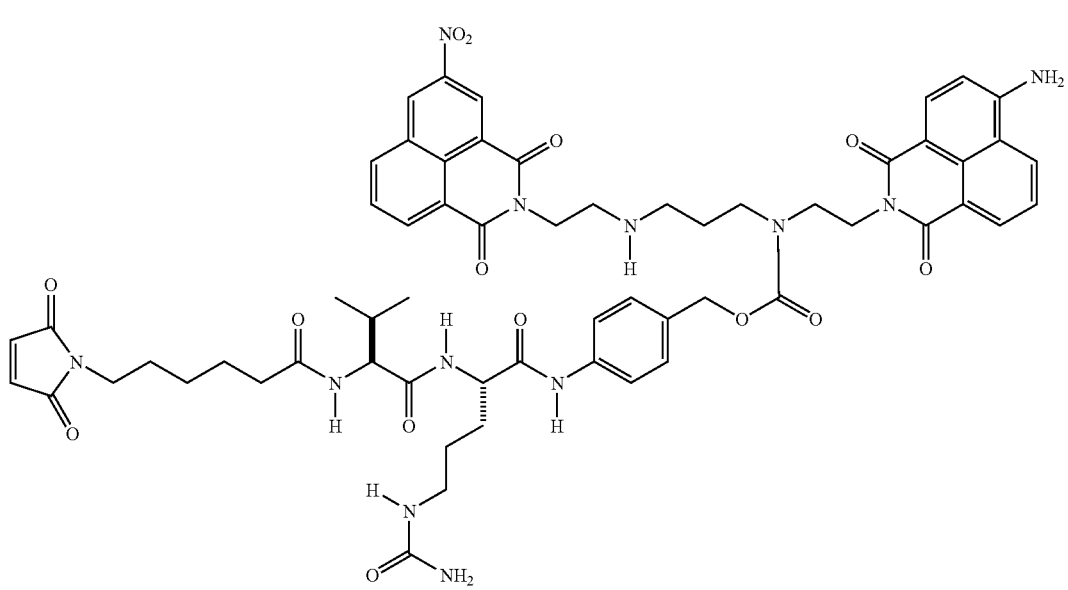

Example 85

Synthesis of $N^1$—H, $N^2$-MC-af-PAB-(N,N'-(bis-aminoethyl-1,3-propanediamine)-bis 3-nitro-1,8 naphthalimide) 127

Following the protocols of the foregoing Examples, $N^1$—H, $N^2$-(tert-butyladipate-gly-gly-gly-PAB)-(N,N'-(bis-aminoethyl-1,3-propanediamine)-bis 3-nitro-1,8 naphthalimide) 128 was prepared.

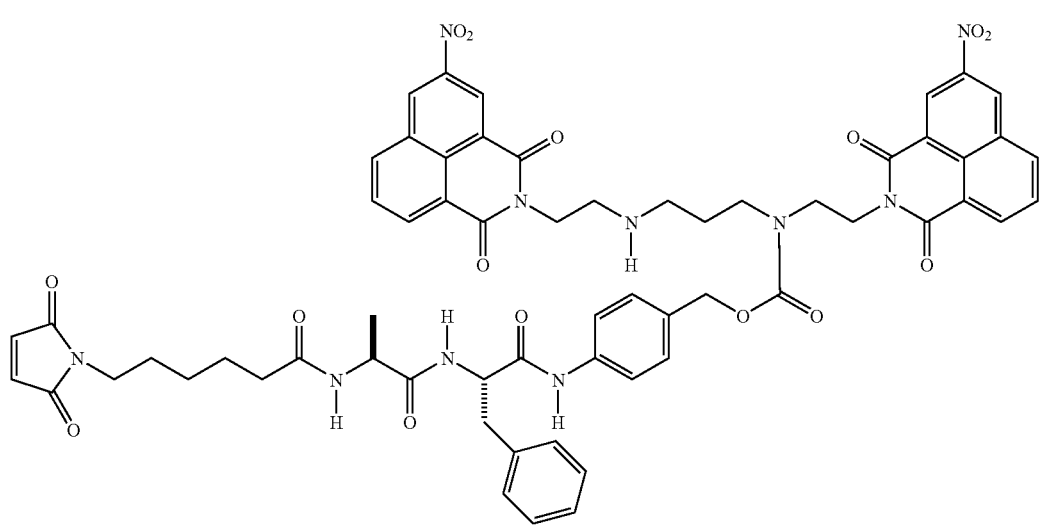

Following the protocols of the foregoing Examples, $N^1$—H, $N^2$-MC-af-PAB-(N,N'-(bis-aminoethyl-1,3-propanediamine)-bis 3-nitro-1,8 naphthalimide) 127 was prepared.

Example 86

Synthesis of $N^1$—H, $N^2$-(tert-butyladipate-gly-gly-gly-PAB)-(N,N'-(bis-aminoethyl-1,3-propanediamine)-bis 3-nitro-1,8 naphthalimide) 128

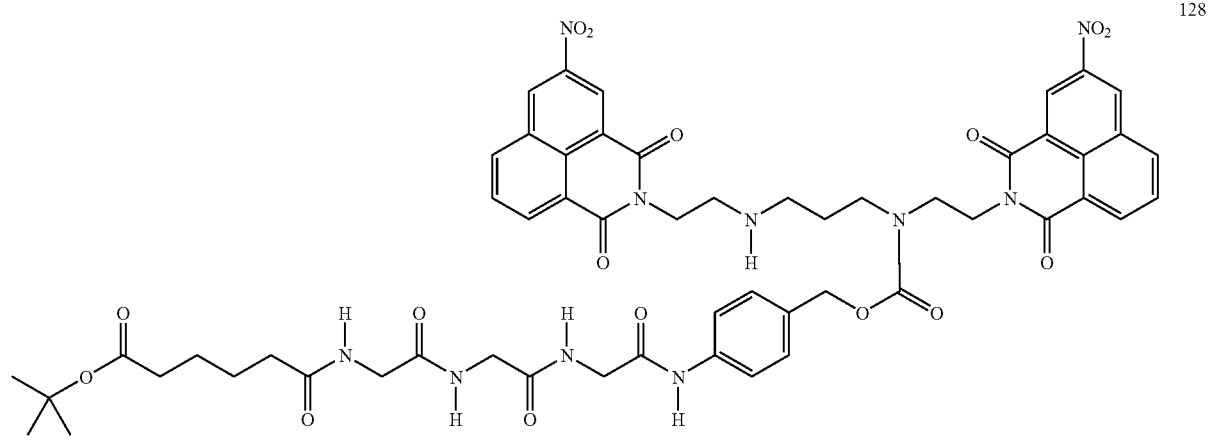

Example 87

Synthesis of $N^1$—H, $N^2$-(MC-val-cit)-(N,N'-(bis-aminoethyl-1,3-propanediamine)-bis 3-nitro-1,8 naphthalimide) 129

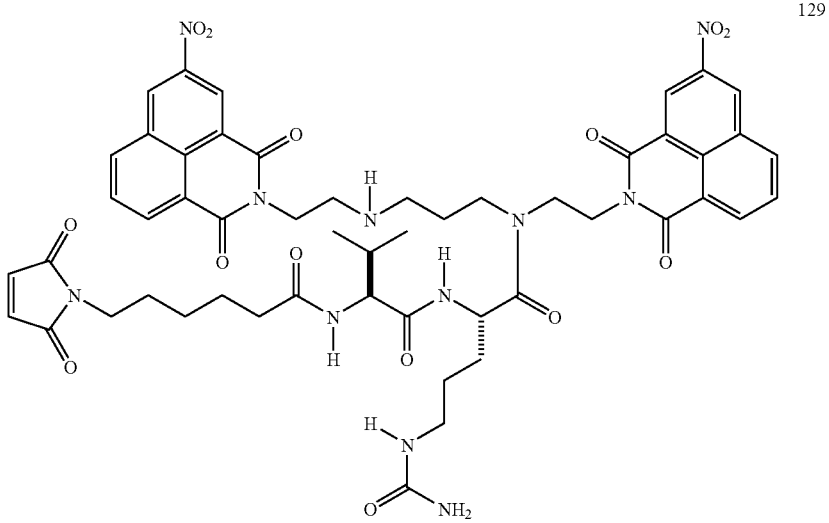

Following the protocols of the foregoing Examples, $N^1$—H, $N^2$-(MC-val-cit)-(N,N'-(bis-aminoethyl-1,3-propanediamine)-bis 3-nitro-1,8 naphthalimide) 129 was prepared.

Example 88

Synthesis of $N^1$—H. $N^2$-(MC-vc-gly)-(N,N'-(bis-aminoethyl-1,3-propanediamine)-bis 3-nitro-1,8 naphthalimide) 130

Following the protocols of the foregoing Examples, $N^1$—H, $N^2$-(MC-vc-gly)-(N,N'-(bis-aminoethyl-1,3-propanediamine)-bis 3-nitro-1,8 naphthalimide) 130 was prepared.

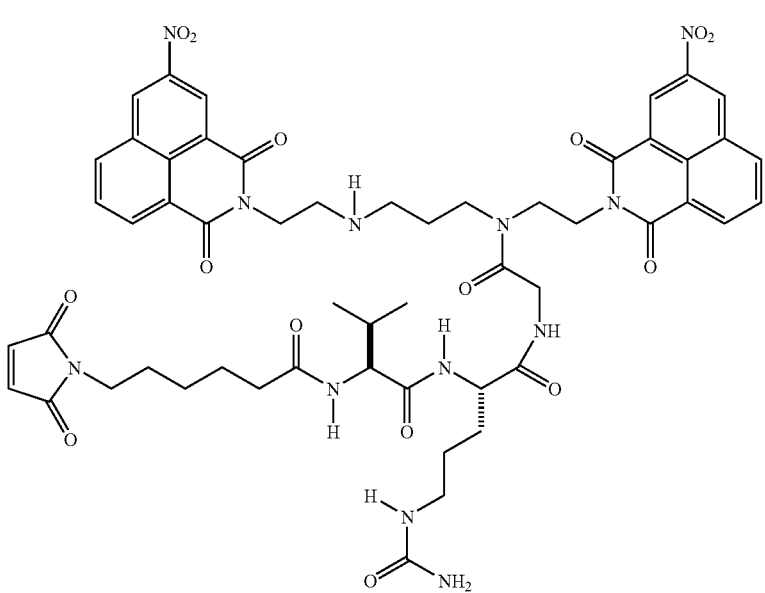

Example 89

Synthesis of $N^1$—H, $N^2$-(MC-af)-(N,N'-(bis-aminoethyl-1,3-propanediamine)-bis 3-nitro-1,8 naphthalimide) 131

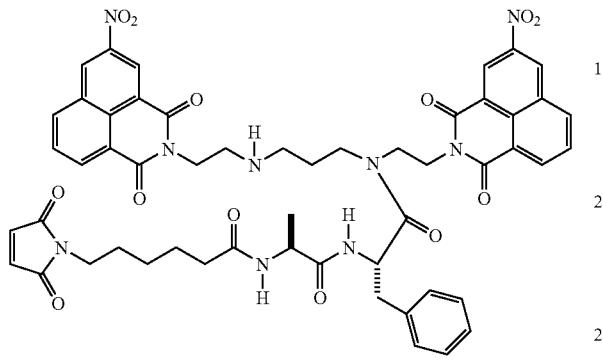

Following the protocols of the foregoing Examples, $N^1$—H, $N^2$-(MC-ala-phe)-(N,N'-(bis-aminoethyl-1,3-propanediamine)-bis 3-nitro-1,8 naphthalimide) 131 was prepared.

Example 90

Synthesis of $N^1$—H, $N^2$-(MC-ala-phe-gly)-(N,N'-(bis-aminoethyl-1,3-propanediamine)-bis 3-nitro-1,8 naphthalimide) 132

Following the protocols of the foregoing Examples, $N^1$—H, $N^2$-(MC-ala-phe-gly)-(N,N'-(bis-aminoethyl-1,3-propanediamine)-bis 3-nitro-1,8 naphthalimide) 132 was prepared.

Example 91

Synthesis of $N^1$—H, $N^2$-(succinic-gly-val-cit)-(N,N'-(bis-aminoethyl-1,3-propanediamine)-bis 3-nitro-1,8 naphthalimide) 133

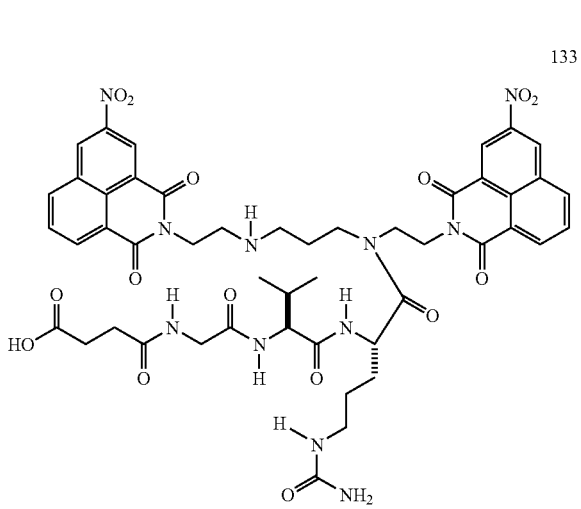

Following the protocols of the foregoing Examples, $N^1$—H, $N^2$-(succinic-gly-val-cit)-(N,N'-(bis-aminoethyl-1,3-propanediamine)-bis 3-nitro-1,8 naphthalimide) 133 was prepared.

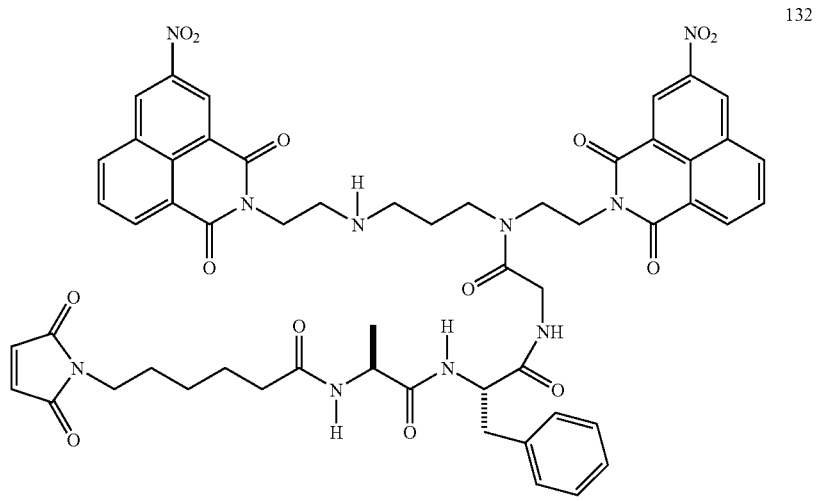

Example 92

Synthesis of N¹—H, N²-(succinic-gly-val-cit-gly)-(N,N'-(bis-aminoethyl-1,3-propanediamine)-bis3-nitro-1,8 naphthalimide) 134

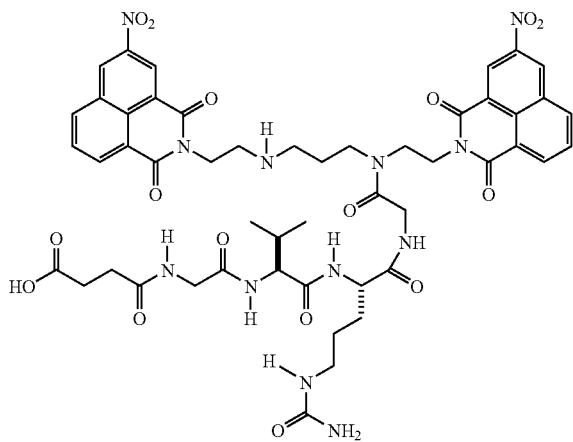

Following the protocols of the foregoing Examples, N¹—H, N²-(succinic-gly-val-cit-gly)-(N,N'-(bis-aminoethyl-1,3-propanediamine)-bis 3-nitro-1,8 naphthalimide) 134 was prepared.

Example 93

Synthesis of N¹—H, N²-(succinic-gly-ala-phe)-(N,N'-(bis-aminoethyl-1,3-propanediamine)-bis 3-nitro-1,8 naphthalimide) 135

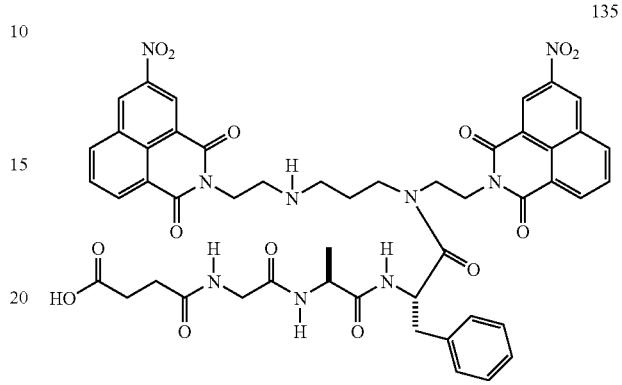

Following the protocols of the foregoing Examples, N¹—H, N²-(succinic-gly-ala-phe)-(N,N'-(bis-aminoethyl-1,3-propanediamine)-bis 3-nitro-1,8 naphthalimide) 135 was prepared.

Example 94

Synthesis of N¹—H, N²—(N-hydroxysuccinimide-succinic-gly-ala-phe)-(N,N'-(bis-aminoethyl-1,3-propanediamine)-bis 3-nitro-1,8 naphthalimide) 135a Following the protocol of Example 69, acid 135 from Example 89 was converted to the NHS ester, N¹—H, N²—(N-hydroxysuccinimide-succinate-gly-ala-phe)-(N,N'-(bis-aminoethyl-1,3-propanediamine)-bis 3-nitro-1,8 naphthalimide) 135a.

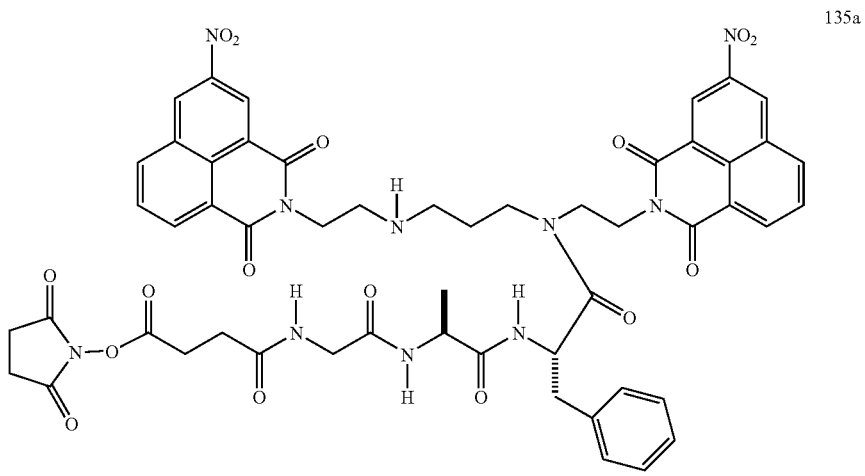

Example 95

Synthesis of N¹—H, N²-(succinic-gly-ala-phe-gly)-(N,N'-(bis-aminoethyl-1,3-propanediamine)-bis 3-nitro-1,8 naphthalimide) 136

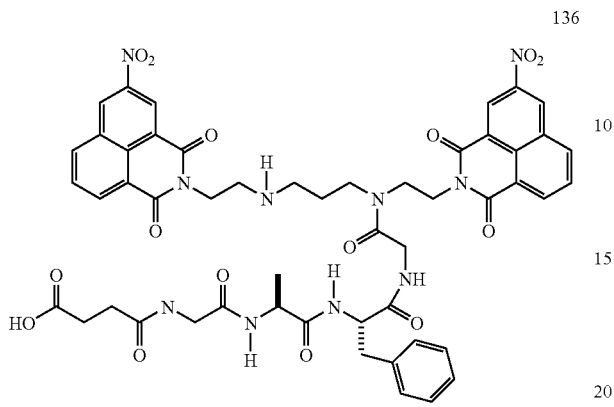

Following the protocols of the foregoing Examples, N¹—H, N²-(succinic-gly-ala-phe-gly)-(N,N'-(bis-aminoethyl-1,3-propanediamine)-bis 3-nitro-1,8 naphthalimide) 136 was prepared.

Example 96

Synthesis of N¹-ethyl, N²-(MC-vc-PAB-N-methylvaline)-(N,N'-(bis-aminoethyl-1,3-propanediamine)-bis 2-nitro-1,8 naphthalimide) 137

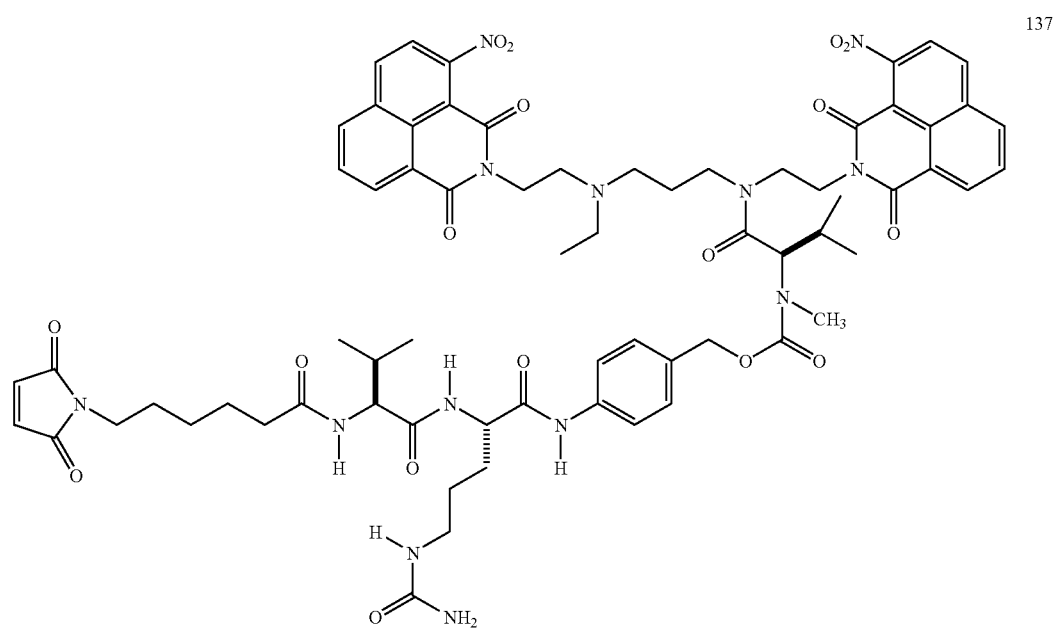

Following the protocols of the foregoing Examples, N$^1$-ethyl, N$^2$-(MC-vc-PAB-N-methylvaline)-(N,N'-(bis-aminoethyl-1,3-propanediamine)-bis 2-nitro-1,8 naphthalimide) 137 was prepared.

Example 97

Synthesis of N$^1$-ethyl, N$^2$-(maleimido-4-oxo-caproyl-vc-PAB-N-methylvaline)-(N,N'-(bis-aminoethyl-1,3-propanediamine)-bis 2-nitro-1,8 naphthalimide) 138

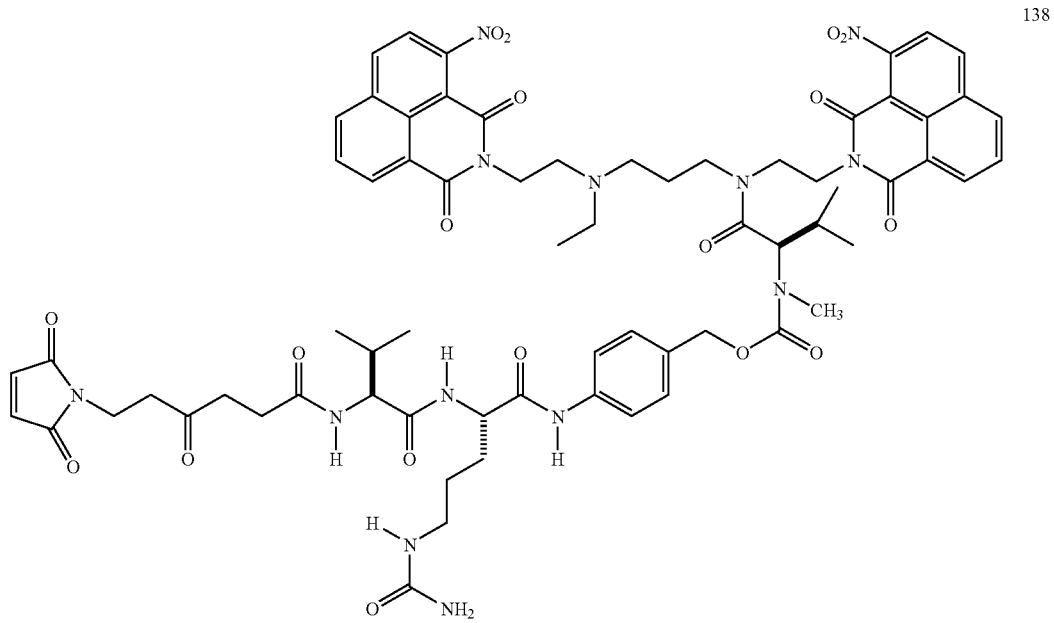

138

Following the protocols of the foregoing Examples, N$^1$-ethyl, N$^2$-(maleimido-4-oxo-caproyl-vc-PAB-N-methylvaline)-(N,N'-(bis-aminoethyl-1,3-propanediamine)-bis 2-nitro-1,8 naphthalimide) 138 was prepared.

Example 98

Synthesis of N$^1$-methyl, N$^2$—(N-methylglycyl)-(N,N'-(bis-aminoethyl-1,3-propanediamine)-bis 4-N-imidazolyl-1,8 naphthalimide) 139

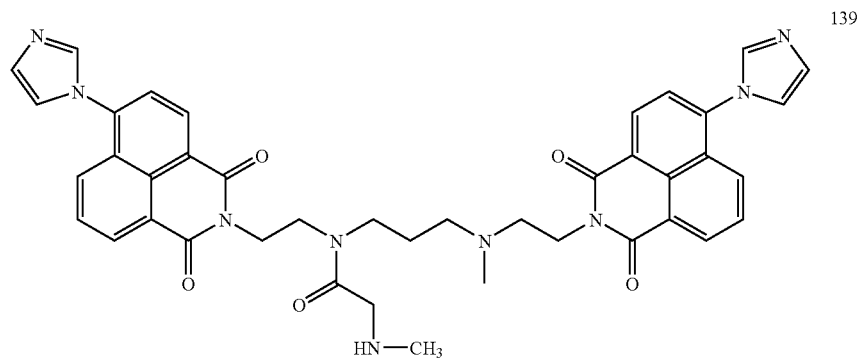

139

Following the protocols of the foregoing Examples, N¹-methyl, N²—(N-methylglycyl)-N,N'-(bis-aminoethyl-1,3-propanediamine)-bis 4-N-imidazolyl-1,8 naphthalimide 139 was prepared.

Example 99

Synthesis of N¹—H, N²-(methoxyethoxyethoxyacetamide)-(N,N'-(bis-aminoethyl-1,3-propanediamine)-bis 4-N-imidazolyl-1,8 naphthalimide) 140

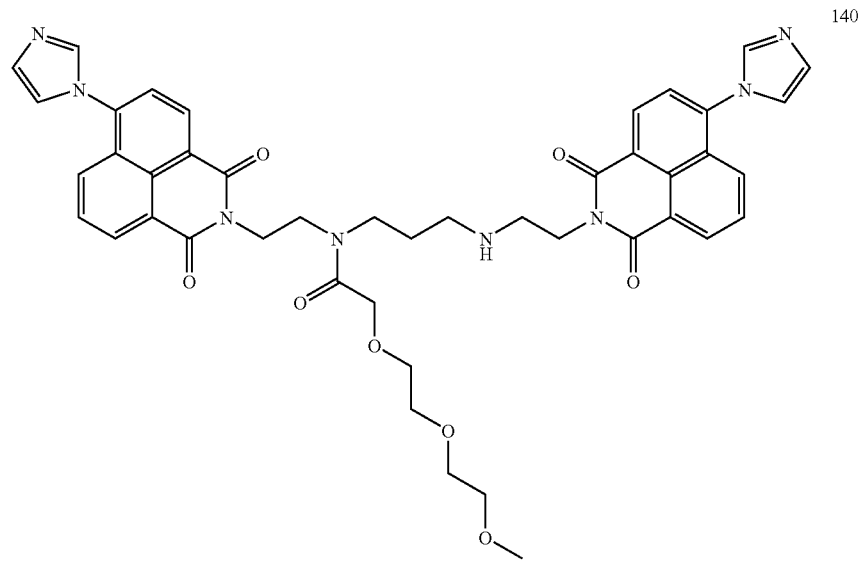

Following the protocols of the foregoing Examples, N¹—H, N²-(methoxyethoxyethoxyacetamide)-(N,N'-(bis-aminoethyl-1,3-propanediamine)-bis 4-N-imidazolyl-1,8 naphthalimide) 140 was prepared.

Example 100

Synthesis of N¹-(MC-vc-PAB), N²-(methoxyethoxyethoxyacetamide)-(N,N'-(bis-aminoethyl-1,3-propanediamine)-bis 4-N-imidazolyl-1,8 naphthalimide) 141

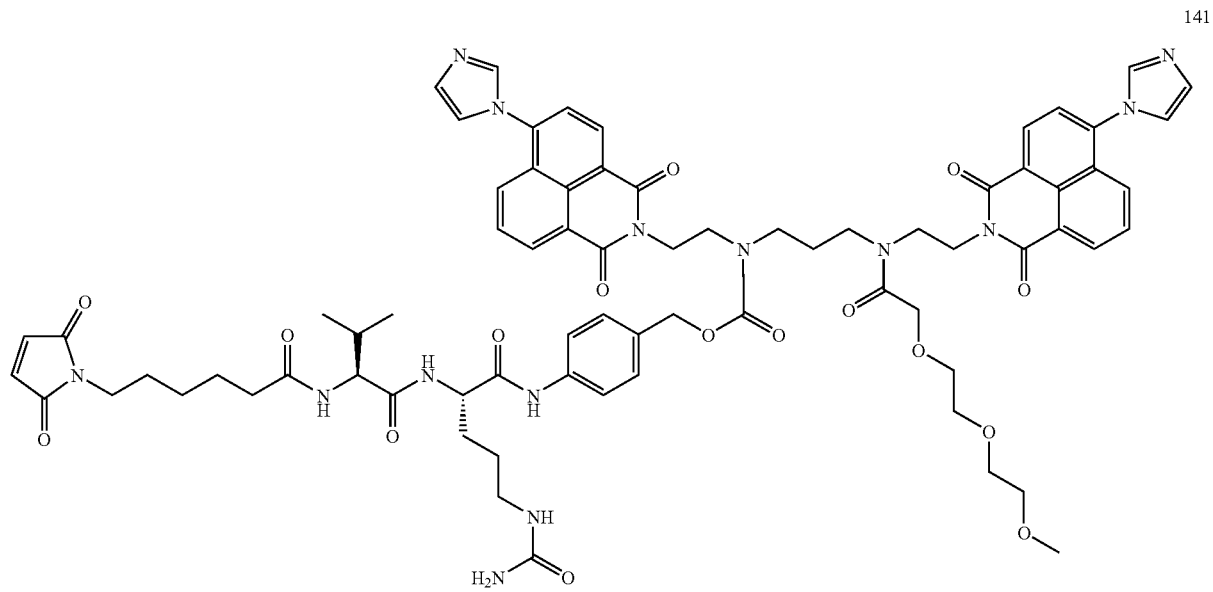

Following the protocols of the foregoing Examples, N¹-(maleimidio-valine-citrulline-PAB), N²-(methoxyethoxyethoxyacetamide)-(N,N'-(bis-aminoethyl-1,3-propanediamine)-bis 4-N-imidazolyl-1,8 naphthalimide) 141 was prepared.

Example 101

Synthesis of N¹-(MC-af-PAB), N²-(methoxyethoxyethoxyacetamide)-(N,N'-(bis-aminoethyl-1,3-propanediamine)-bis 4-N'-imidazolyl-1,8 naphthalimide) 142

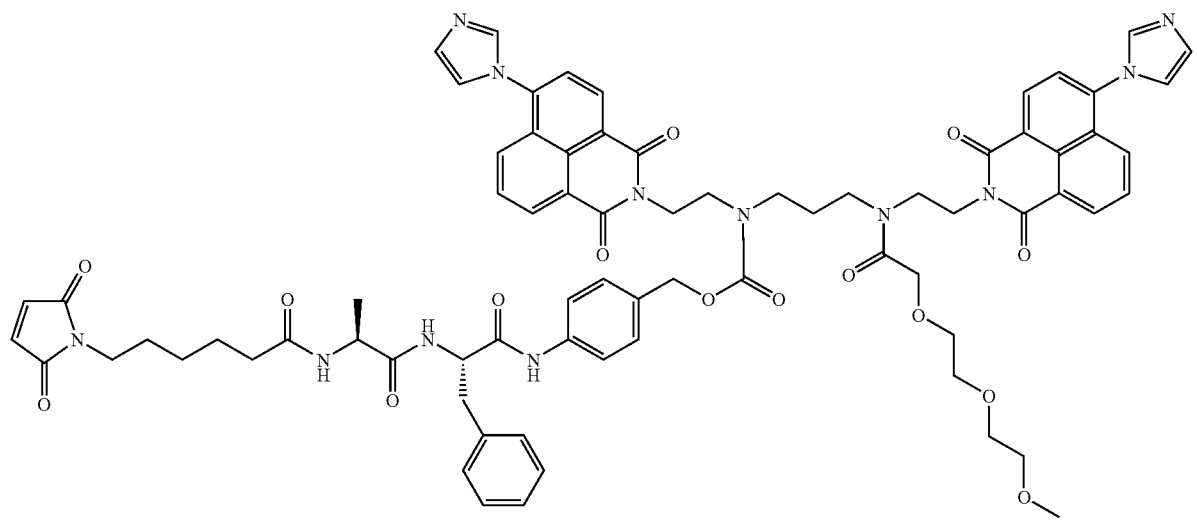

142

Following the protocols of the foregoing Examples, N¹-(MC-af-PAB), N²-(methoxyethoxyethoxyacetamide)-(N,N'-(bis-aminoethyl-1,3-propanediamine)-bis 4-N-imidazolyl-1,8 naphthalimide) 142 was prepared.

Example 102

Synthesis of N¹-cyclopropylmethyl, N²-MP-gly-val-cit-PAB-(N,N'-(bis-aminoethyl-1,3-propanediamine)-bis 3-nitro-1,8 naphthalimide) 143

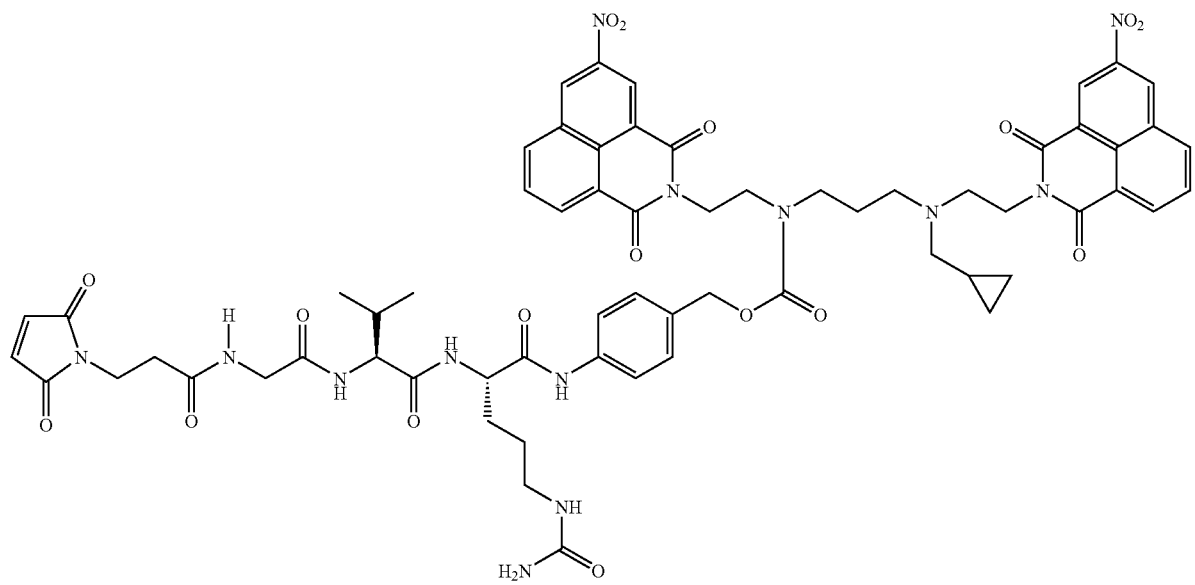

143

267

Following the protocols of the foregoing Examples, MP-gvc-PAB-OPNP and N,N'—(N-cyclopropylmethyl, bis-aminoethyl-1,3-propanediamine)-bis-3-nitro-1,8 naphthalimide 30c were reacted to give $N^1$-cyclopropylmethyl, $N^2$-maleimidopropyl-gly-val-cit-PAB-(N,N'-(bis-aminoethyl-1,3-propanediamine)-bis 3-nitro-1,8 naphthalimide) 143.

Example 103

Preparation of trastuzumab-MC-vc-PAB-(N,N'-2-acetamido-1,3-ethanediamine-propyl)-bis-4-morpholino-1,8 naphthalimide) 201 by conjugation of trastuzumab and 102

One vial containing 440 mg HERCEPTIN® (huMAb4D5-8, rhuMAb HER2, U.S. Pat. No. 5,821,337) antibody was dissolved in 50 mL MES buffer (25 mM MES, 50 mM NaCl, pH 5.6) and loaded on a cation exchange column (Sepharose S, 15 cm×1.7 cm) that had been equilibrated in the same buffer. The column was then washed with the same buffer (5 column volumes). Trastuzumab was eluted by raising the NaCl concentration of the buffer to 200 mM. Fractions containing the antibody were pooled, diluted to 10 mg/mL, and dialyzed into a buffer containing 50 mM potassium phosphate, 50 mM NaCl, 2 mM EDTA, pH 6.5.

Trastuzumab, dissolved in 500 mM sodium borate and 500 mM sodium chloride at pH 8.0 is treated with an excess of 100 mM dithiothreitol (DTT). After incubation at 37° C. for about 30 minutes, the buffer is exchanged by elution over Sephadex G25 resin and eluted with PBS with 1 mM DTPA. The thiol/Ab value is checked by determining the reduced antibody concentration from the absorbance at 280 nm of the solution and the thiol concentration by reaction with DTNB (Aldrich, Milwaukee, Wis.) and determination of the absorbance at 412 nm. The reduced antibody dissolved in PBS is chilled on ice.

The drug linker reagent, maleimidocaproyl-(valine-citrulline)-(para-aminobenzyloxycarbonyl)-(N,N'-2-acetamido-1, 3-ethanediamine-propyl)-bis-4-morpholino-1,8 naphthalimide) 102, dissolved in DMSO, is diluted in acetonitrile and water at known concentration, and added to the chilled reduced antibody trastuzumab in PBS. After about one hour, an excess of maleimide is added to quench the reaction and cap any unreacted antibody thiol groups. The reaction mixture is concentrated by centrifugal ultrafiltration and 201 is purified and desalted by elution through G25 resin in PBS, filtered through 0.2 μm filters under sterile conditions, and frozen for storage.

Example 104

Preparation of trastuzumab-MC-vc-PAB-(N,N'-(bis-aminoethyl-1,3-propanediamine)-bis-(4-N-imidazolyl)-1,8 naphthalimide) 202

Following the protocol of Example 103, antibody drug conjugate, trastuzumab-MC-vc-PAB-(N,N'-(bis-aminoethyl-1,3-propanediamine)-bis-(4-N-imidazolyl)-1,8 naphthalimide) 202, was prepared by conjugation of trastuzumab and MC-vc-PAB-(N,N'-(bis-aminoethyl-1,3-propanediamine)-bis-(4-N-imidazolyl)-1,8 naphthalimide) 111a.

Example 105

Preparation of trastuzumab-MC-ala-phe-PAB-(N,N'-(bis-aminoethyl-1,3-propanediamine)-bis-(4-N-imidazolyl)-1,8 naphthalimide) 203

Following the protocol of Example 103, antibody drug conjugate, trastuzumab-MC-ala-phe-PAB-(N,N'-(bis-ami-

268 noethyl-1,3-propanediamine)-bis-(4-N-imidazolyl)-1,8 naphthalimide) 203, was prepared by conjugation of trastuzumab and MC-ala-phe-PAB-(N,N'-(bis-aminoethyl-1,3-propanediamine)-bis-(4-N-imidazolyl)-1,8 naphthalimide) 111b.

Example 106

Preparation of trastuzumab-(succinate-gly-ala-phe)-(N,N'-(bis-aminoethyl-1,3-propanediamine)-bis 3-nitro-1,8 naphthalimide) 204

Following the protocol of Example 103 for isolating trastuzumab, antibody drug conjugate, trastuzumab-(succinate-gly-ala-phe)-(N,N'-(bis-aminoethyl-1,3-propanediamine)-bis 3-nitro-1,8 naphthalimide) 204, was prepared by conjugation of trastuzumab and $N^1$—H, $N^2$—(N-hydroxysuccinimide-succinate-gly-ala-phe)-(N,N'-(bis-aminoethyl-1,3-propanediamine)-bis 3-nitro-1,8 naphthalimide) 135a.

Example 107

Preparation of trastuzumab-MC-val-cit-PAB-(N,N'-(bis-aminoethyl-1,3-propanediamine)-3-nitro, 4-amino-1,8 naphthalimide) 205

Following the protocol of Example 103, antibody drug conjugate, trastuzumab-MC-val-cit-PAB-(N,N'-(bis-aminoethyl-1,3-propanediamine)-3-nitro, 4-amino-1,8 naphthalimide) 205, was prepared by conjugation of trastuzumab and ($N^1$—H, $N^2$-MC-vc-PAB-(N,N'-(bis-aminoethyl-1,3-propanediamine)-3-nitro, 4-amino-1,8 naphthalimide) 126a.

Example 108

Preparation of trastuzumab-MC—(N,N'-(bis-aminoethyl-1,3-propanediamine)-bis-(4-N-imidazolyl)-1,8 naphthalimide) 206

Following the protocol of Example 103, antibody drug conjugate, trastuzumab-MC—(N,N'-(bis-aminoethyl-1,3-propanediamine)-bis-(4-N-imidazolyl)-1,8 naphthalimide) 206, was prepared by conjugation of trastuzumab and MC—(N,N'-(bis-aminoethyl-1,3-propanediamine)-bis-(4-N-imidazolyl)-1,8 naphthalimide) 113a.

Example 109

Preparation of trastuzumab-MC—(N,N'-(bis-aminoethyl-1,3-propanediamine)-bis-3-nitro-1,8 naphthalimide) 207

Following the protocol of Example 103, antibody drug conjugate, trastuzumab-$N^1$-cyclopropylmethyl, $N^2$-maleimidopropyl-gly-val-cit-PAB-(N,N'-(bis-aminoethyl-1,3-propanediamine)-bis 3-nitro-1,8 naphthalimide) 207, was prepared by conjugation of trastuzumab and $N^1$-cyclopropylmethyl, $N^2$-maleimidopropyl-gly-val-cit-PAB-(N,N'-(bis-aminoethyl-1,3-propanediamine)-bis 3-nitro-1,8 naphthalimide) 143.

Example 110

In Vitro Cell Proliferation Assay

Efficacy of compounds of the invention were measured by a cell proliferation assay employing the following protocol (Promega Corp. Technical Bulletin TB288; Mendoza et al (2002) Cancer Res. 62:5485-5488):

1. An aliquot of 100 µl of cell culture containing about $10^4$ cells (SKBR-3, BT474, MCF7 or MDA-MB-468) in medium was deposited in each well of a 96-well, opaque-walled plate.
2. Control wells were prepared containing medium and without cells.
3. Test compound was added to the experimental wells and incubated for 3-5 days.
4. The plates were equilibrated to room temperature for approximately 30 minutes.
5. A volume of CellTiter-Glo Reagent equal to the volume of cell culture medium present in each well was added.
6. The contents were mixed for 2 minutes on an orbital shaker to induce cell lysis.
7. The plate was incubated at room temperature for 10 minutes to stabilize the luminescence signal.
8. Luminescence was recorded and reported in graphs as RLU=relative luminescence units.

Alternatively, the efficacy of compounds of the invention can be assayed by the following free test compound cell-based assay protocol Day 1:
1. Prepare each cell line (BT474, H460, HCT116, HUVEC, LNCaP, MCF7, and PC3) at 1 k cells/well in separate plates with Complete Media (CM): RPM1 1460+10% FBS (Fetal Bovine Serum)+1% of 200 mM L-Glutamine. Plate number depends on test compounds provided by submitter.
2. Detach prospective cell lines by first removing the media. When the flask is empty of media, begin rinsing out individual flasks with 5 mL sterile PBS. Move the PBS around within the flask to rinse well. Decant the PBS and add aseptically 5 mL of Accutase/flask. Make sure the Accutase covers the entire flask.
3. Immediately place the flask(s) into a 37° C. incubator to allow cells to detach for 5-7 minutes.
4. Post 5-7 minutes, remove flask(s) from the incubator and begin harvesting the detached cells using a serological pipette. Pipette up and down along the back of the flask to facilitate cell detachment. Pipette the Accutase containing cells into a sterile 50 mL conical tube/cell line. Pipette 10 mL of sterile PBS and re-rinse the flask to obtain remaining cells and dispense it into the same 50 mL conical tube/cell line for a total volume of 15 mL/tube/cell line.
5. After each cell line has been allocated to a designated tube, take out 100 µL/tube/cell line for the cell counts. While the cell counts are being calculated, centrifuge the 50 mL tubes at 1000 rpm at 4° C. with a high brake.
6. When centrifugation and cell calculations are completed, decant excess liquid and resuspend the cell pellet(s) using 5 mL CM, depending on calculations.
7. Using a 5 mL syringe and an 18 G ½ needle, strain the cells to help prevent aggregation. Further strain by using a 70 µM cell filter to block out any huge aggregates not broken down by the needle.
8. After cell straining and filtering, take out calculated amount for a 1 k cells/well into fresh media. Take the media containing cells and load 100 µL/well into a bottom tissue culture treated flat 96 well plate.
9. Immediately place in a 37° C. incubator overnight to allow the cells to adhere to the tissue culture treated 96 well plates.

Day 2:
1. Test compounds are submitted at 10 mM in sterile DMSO.
2. DMSO as negative control and a positive standard are used in every assay!
3. Prepare a 1:1000 fold dilution for each test compound, control, and standard for a 10e-5 M starting point. Do a 1:100 first, then a 1:10.
4. Prior to diluting samples, vortex the samples and the controls for a homogeneous mixture. Note any sample that will not solubilize and/or stay in suspension.
5. When the samples are at 10e-5 M, vortex each tube well and spin down fluid to ensure sample remains in tacked.

Manual Dilution Protocol:
1. After the tubes are at a final 1:1000 (10e-5 M) dilution, load the first column of the microtube box with the prospective sample. Load DMSO and positive control in singlets. The test compounds are loaded in duplicates. Load the remaining empty microtube racks with 540 µL of media to prepare for a serial dilution of 1:10.
2. Agitate and transfer 60 µL from column 1 into successive wells containing 540 µL of media (1:10). Therefore, transfer 60 µL of column 1 into 540 µL of column 2. Resuspend column 2 about 10-15×'s then transfer 60 µL from column 2 to column 3 etc.

Automated Dilution Protocol:
1. Once the tubes are at a final 1:1000 (10e-5 M), load the first column of the microtube box with the prospective sample. Load DMSO and positive control in singlets. The compounds are loaded in duplicates. Load the remaining empty microtube racks manually with 540 µL of media to prepare for the automated serial dilution of 1:10 (see above diagram).
2. Place the prepared microtube box(es) on the tray within the front plate stage of the Precision 2000 (Biotek). Set a sterile box of P100 tips directly behind each microtube box.
3. The Precision is programmed to do a 1:10 serial dilution up to 3 microtube boxes, if needed. If 2-3 microtube box dilutions are selected, the Precision 2000 will treat each box separately. It will resuspend the first column containing samples then take out another set of sterile tips to transfer 60 µL into the 540 µL of CM etc. to column 12.

Automated and Manual Protocol:
1. Take the cell lines that had been incubating overnight, aspirate the media SLOWLY, and load 100 µL of each sample/row using a multichannel pipette into it's prospective wells. Tilting the 96 well plates vertically while loading will prevent significant amounts of cells washing off.
2. When the entire plate(s) have been loaded, re-incubate the plate(s) for 4.5 days to permit the test compounds to take effect.
3. Take a day 0 reading by reverse pipetting a 100 µL/well of Cell Glo (CellTiter-Glo Luminescent cell viability assay kit reagent, Promega, Cat. #G7571/2/3) and let sit for 10 minutes before reading the luminescence. Reverse pipetting prevents the Wallac (Perkin Elmer's Victor V, 1420 Wallac Manager Program, luminescence 96 reader, C700 Filter) from reading the bubbles formed from regular pipetting. Also, a day 0 reading is used to measure the cell doubling time from the start of the assay.

Day 4-5:
1. On day 4-5, stop the assay by applying 100 ul/well of Cell Glo to all of the wells and plates.
2. After 10 minutes, read the luminescence and document the assay number for exporting the data.
3. Analyze the data and provide it for the submitter.

Tumor Cell lines:
BT-474 (ATCC: HTB-20) Human, breast, epithelial, mammary gland ductal carcinoma (HER2 expression: 3+)
H460 (ATCC: HTB-177) Human, lung, epithelial, large cell, metastatic site: pleural effusion carcinoma HCT 116 (ATCC: CCL-247) Human, colon, epithelial, colorectal carcinoma HUVEC (ATCC: CRL-1730) Human, umbilical vein, endothelial, normal LNCaP (ATCC: CRL-1740) Human, prostate, epithelial, metastatic site: left supraclavicular lymph node carcinoma MCF7 (ATCC: HTB-22) Human, breast, epithelial, mammary gland, metastatic site: pleural effusion adenocarcinoma (HER2 expression: 0)

PC-3, (ATCC: CRL-1435) Human, prostate, epithelial, metastatic site: bone adenocarcinoma The present invention is not to be limited in scope by the specific embodiments disclosed in the examples which are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims.

All references cited herein are incorporated by reference in their entirety and for all purposes to the same extent as if each individual publication or patent or patent application was specifically and individually indicated to be incorporated by reference in its entirety for all purposes.

We claim:

1. A compound having Formula XV

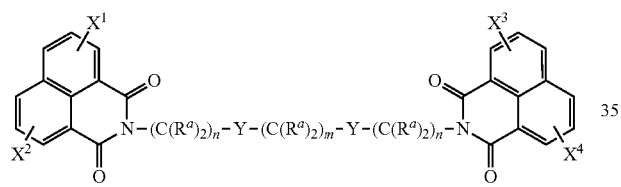

or a pharmaceutically acceptable salt thereof, wherein

Y is independently selected from $N(R^b)$, $C(R^a)_2$, O, and S;

$R^a$ is independently selected from H, F, Cl, Br, I, OH, $-N(R^b)_2$, $-N(R^b)_3^+$, $C_1$-$C_8$ alkylhalide, carboxylate, sulfate, sulfamate, sulfonate, $-SO_2R^b$, $-S(=O)R^b$, $-SR^b$, $-SO_2N(R^b)_2$, $-C(=O)R^b$, $-CO_2R^b$, $-C(=O)N(R^b)_2$, $-CN$, $-N_3$, $-NO_2$, $C_1$-$C_8$ alkoxy, $C_1$-$C_8$ trifluoroalkyl, polyethyleneoxy, phosphonate, phosphate, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_1$-$C_{20}$ heterocycle, and $C_1$-$C_{20}$ substituted heterocycle; or when taken together, two $R^a$ groups on the same carbon atom form a carbonyl (=O), or on different carbon atoms form a carbocyclic, heterocyclic, or aryl ring of 3 to 7 carbon atoms;

$R^b$ is independently selected from H, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_1$-$C_{20}$ heterocycle, and $C_1$-$C_{20}$ substituted heterocycle;

where $C_1$-$C_8$ substituted alkyl, $C_2$-$C_8$ substituted alkenyl, $C_2$-$C_8$ substituted alkynyl, $C_6$-$C_{20}$ substituted aryl, and $C_2$-$C_{20}$ substituted heterocycle are independently substituted with one or more substituents selected from F, Cl, Br, I, OH, $-N(R^b)_2$, $-N(R^b)_3^+$, $C_1$-$C_8$ alkylhalide, carboxylate, sulfate, sulfamate, sulfonate, $C_1$-$C_8$ alkylsulfonate, $C_1$-$C_8$ alkylamino, 4-dialkylaminopyridinium, $C_1$-$C_8$ alkylhydroxyl, $C_1$-$C_8$ alkylthiol, $-SO_2R^b$, $-S(=O)R^b$, $-SR^b$, $-SO_2N(R^b)_2$, $-C(=O)R^b$, $-CO_2R^b$, $-C(=O)N(R^b)_2$, $-CN$, $-N_3$, $-NO_2$, $C_1$-$C_8$ alkoxy, $C_1$-$C_8$ trifluoroalkyl, $C_1$-$C_8$ alkyl, $C_3$-$C_{12}$ carbocyclyl, $C_6$-$C_{20}$ aryl, $C_1$-$C_{20}$ heterocyclyl, polyethyleneoxy, phosphonate, and phosphate;

m is 3;

n is independently selected from 1, 2, and 3;

$X^1$, $X^2$, $X^3$, and $X^4$ are independently selected from F, Cl, Br, I, OH, $-N(R^b)_2$, $-N(R^b)_3^+$, $-N(R^b)C(=O)R^b$, $-N(R^b)C(=O)N(R^b)_2$, $-N(R^b)SO_2N(R^b)_2$, $-N(R^b)SO_2R^b$, OR, $OC(=O)R^b$, $OC(=O)N(R^b)_2$, $C_1$-$C_8$ alkylhalide, carboxylate, sulfate, sulfamate, sulfonate, $-SO_2R^b$, $-SO_2Ar$, $-SOAr$, $-SAr$, $-SO_2N(R^b)_2$, $-SOR^b$, $-CO_2R^b$, $-C(=O)N(R^b)_2$, $-CN$, $-N_3$, $-NO_2$, $C_1$-$C_8$ alkoxy, $C_1$-$C_8$ trifluoroalkyl, polyethyleneoxy, phosphonate, phosphate, $C_1$-$C_8$ alkyl, $C_1$-$C_8$ substituted alkyl, $C_2$-$C_8$ alkenyl, $C_2$-$C_8$ substituted alkenyl, $C_2$-$C_8$ alkynyl, $C_2$-$C_8$ substituted alkynyl, $C_6$-$C_{20}$ aryl, $C_6$-$C_{20}$ substituted aryl, $C_1$-$C_{20}$ heterocyclyl, and $C_1$-$C_{20}$ substituted heterocyclyl; or $X^1$ and $X^2$ together, and $X^3$ and $X^4$ together, independently form $-CH_2CH_2-$ or $-CH_2CH_2CH_2-$; and at least one of $X^1$, $X^2$, $X^3$, and $X^4$ is nitrogen-linked imidazolyl.

2. The compound of claim 1 where n is 2.

3. The compound of claim 1 where each $R^a$ is H.

4. The compound of claim 1 wherein Y is $N(R^b)$; n is 2; and $R^a$ and $R^b$ are H.

5. The compound of claim 4 having the structure:
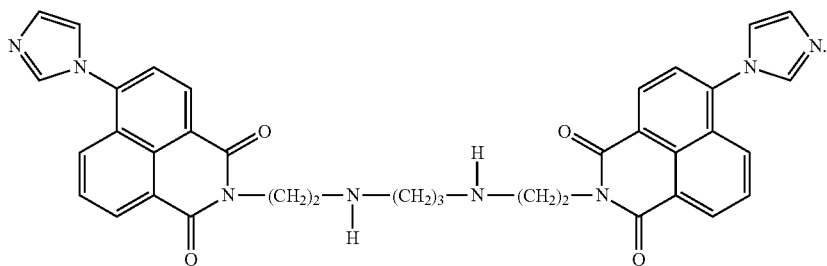
6. The compound of claim 4 selected from the structures:
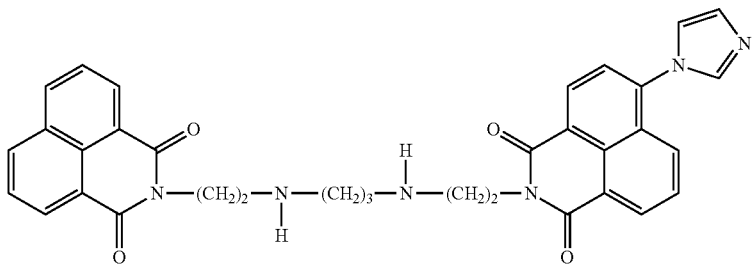
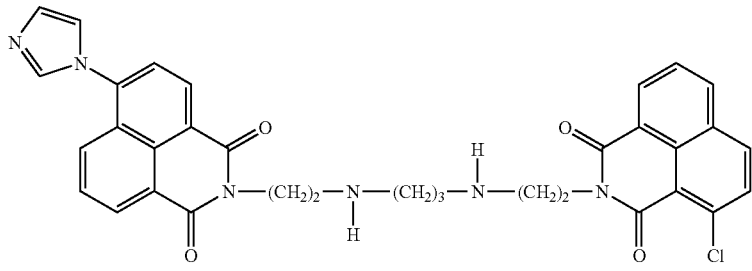
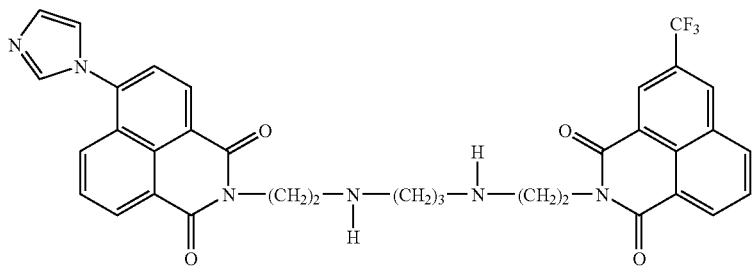
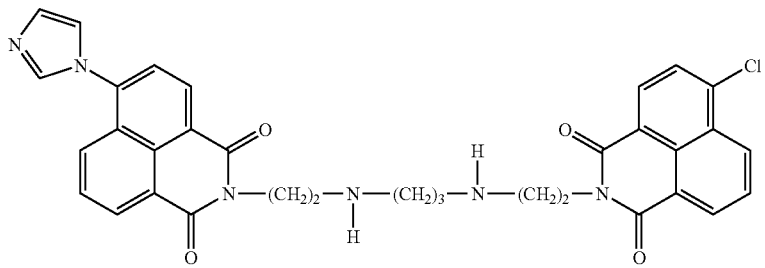

-continued

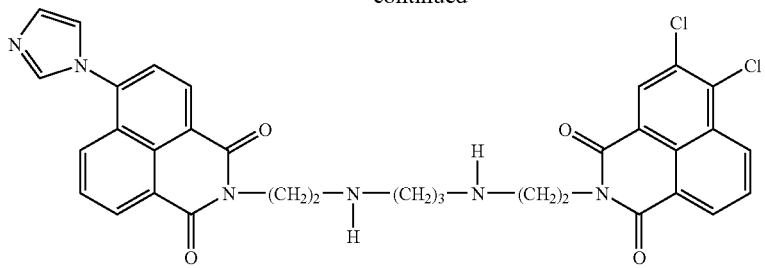

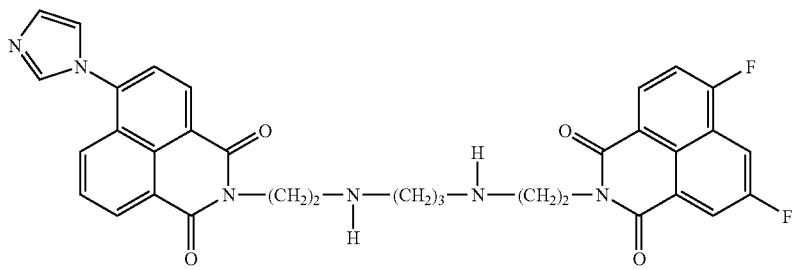

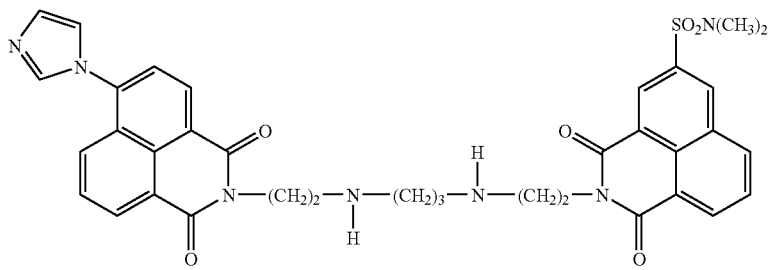

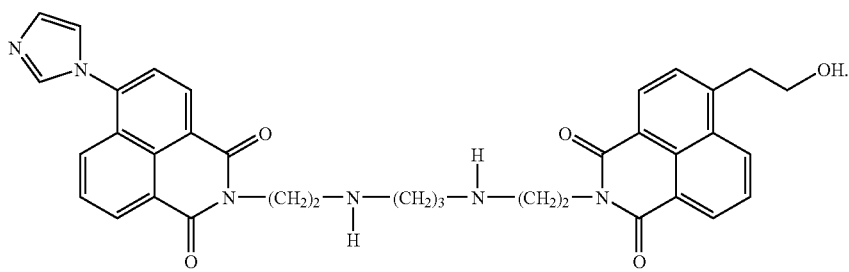

7. The compound of claim 1 wherein $X^1$ and $X^2$ together, or $X^3$ and $X^4$ together, independently form —CH$_2$CH$_2$— or —CH$_2$CH$_2$CH$_2$—.

8. The compound of claim 1 wherein two $X^1$, $X^2$, $X^3$, or $X^4$ on adjacent carbon atoms form a fused $C_6$-$C_{20}$ aryl, $C_6$-$C_{20}$ substituted aryl, $C_1$-$C_{20}$ heterocycle, or $C_1$-$C_{20}$ substituted heterocycle.

9. The compound of claim 8 selected from the structures:

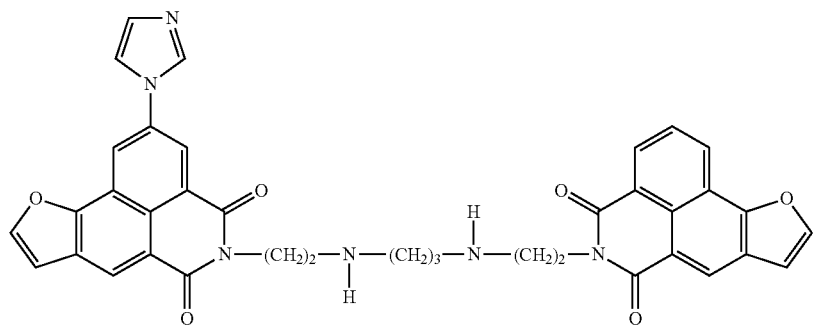

-continued
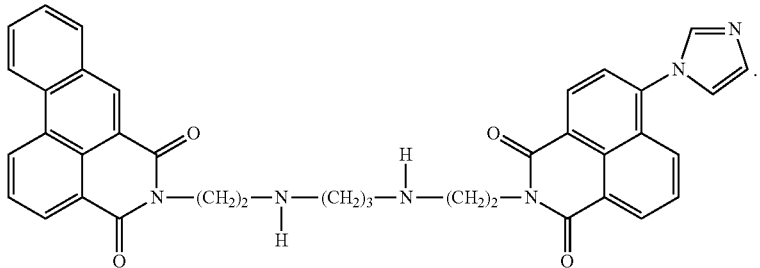
10. The compound of claim 1 selected from the structures:
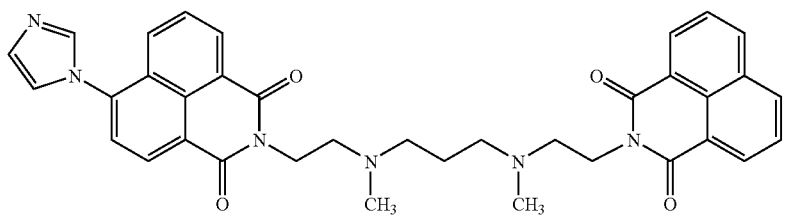
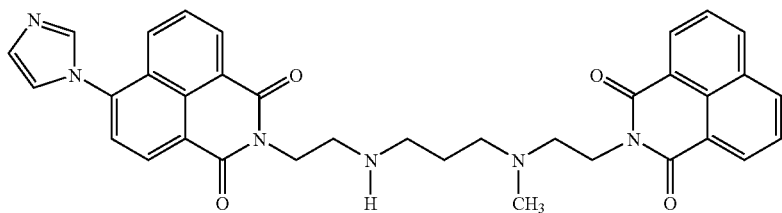
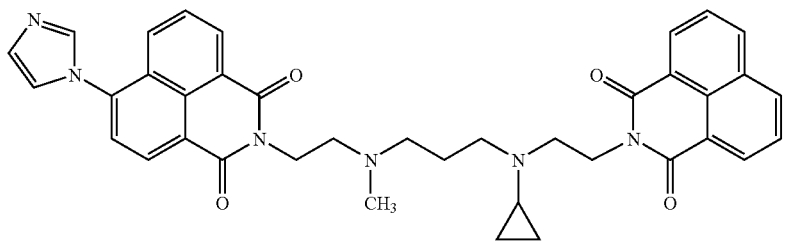
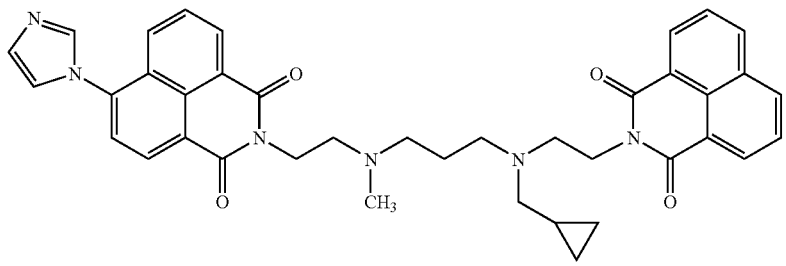
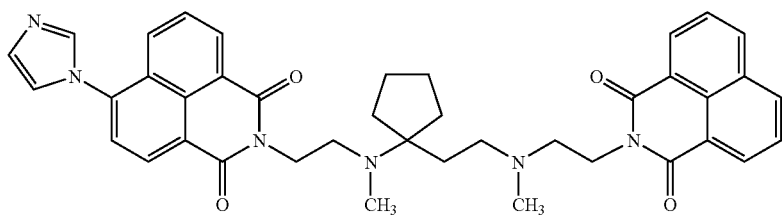

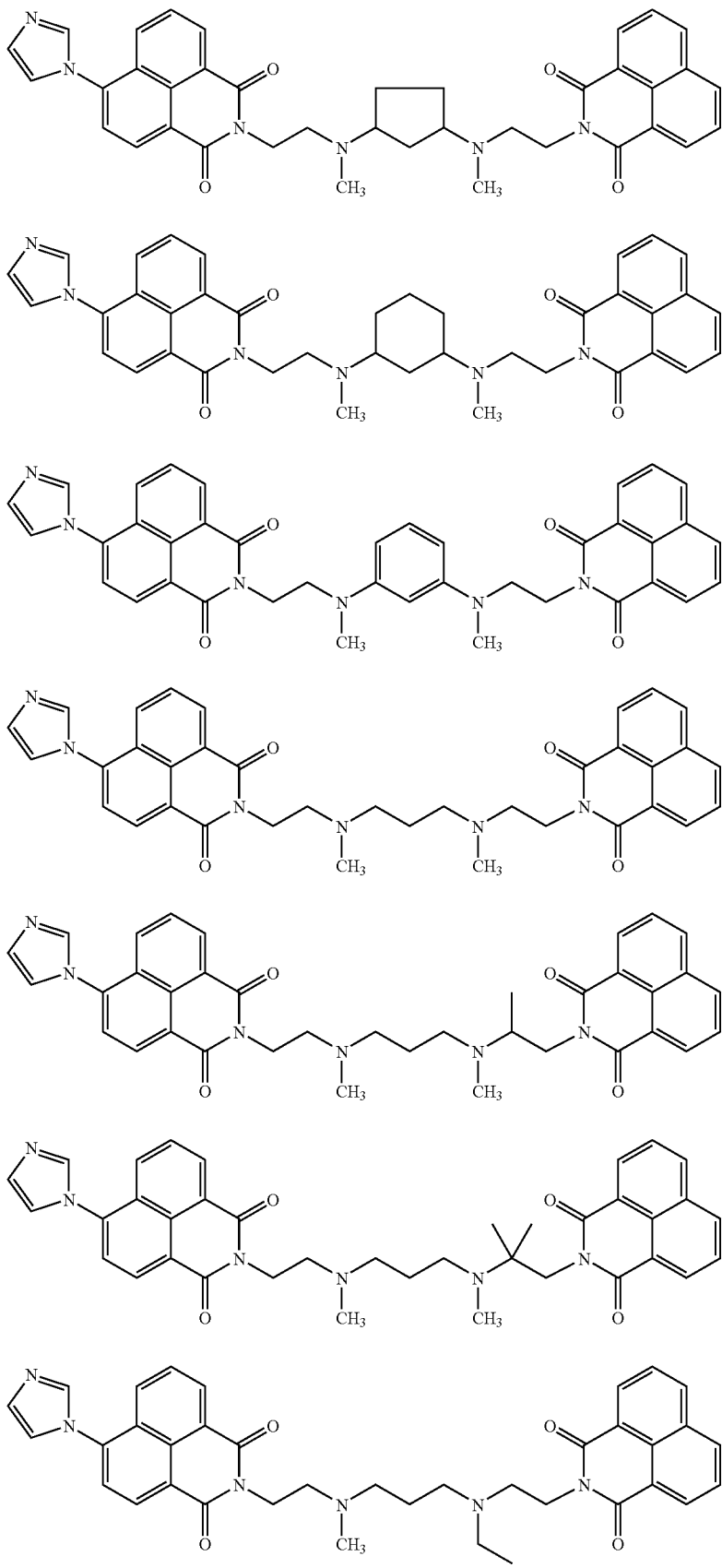

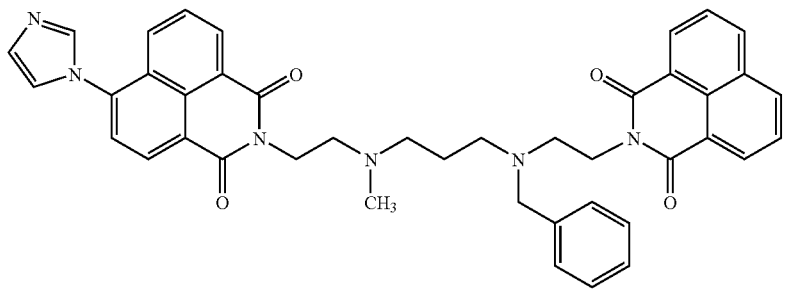
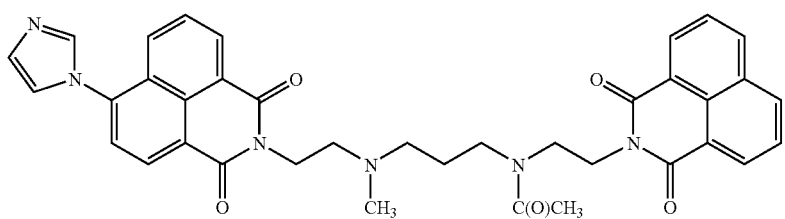
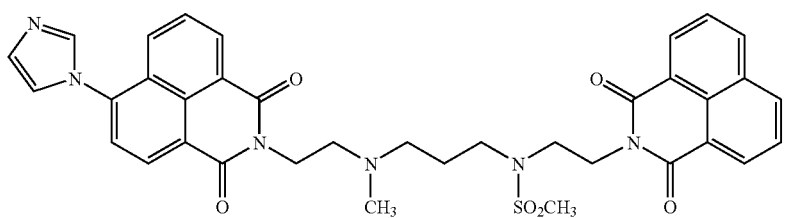
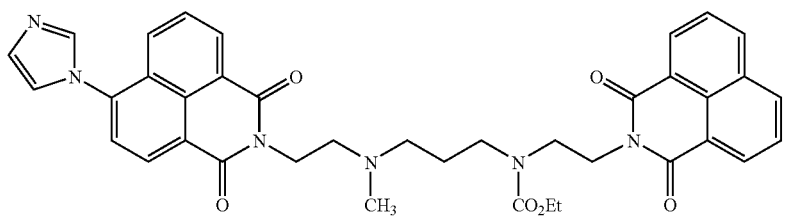
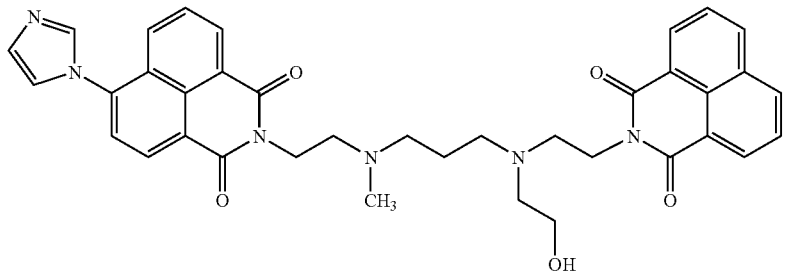
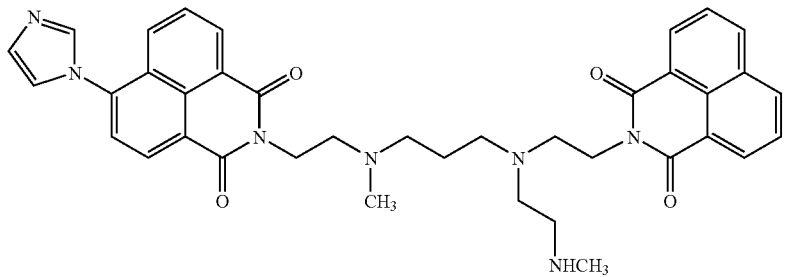

-continued
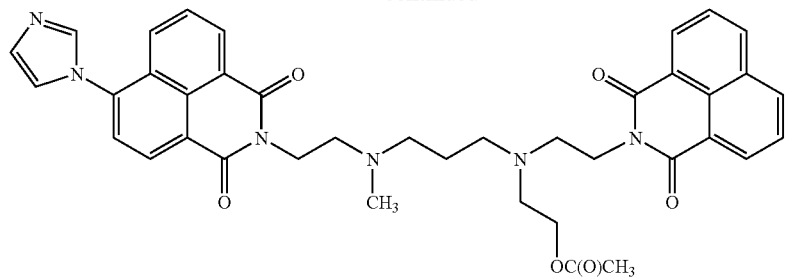
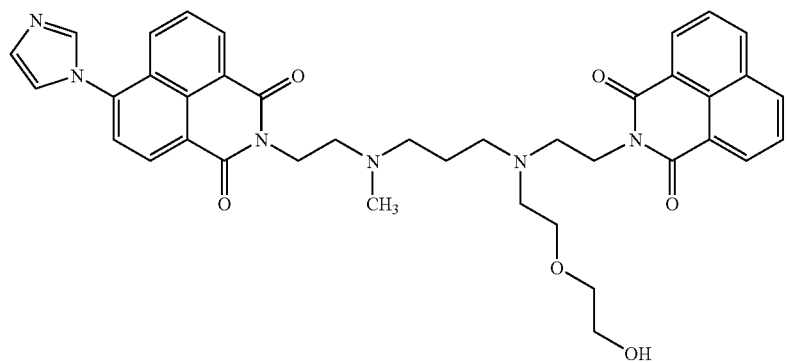
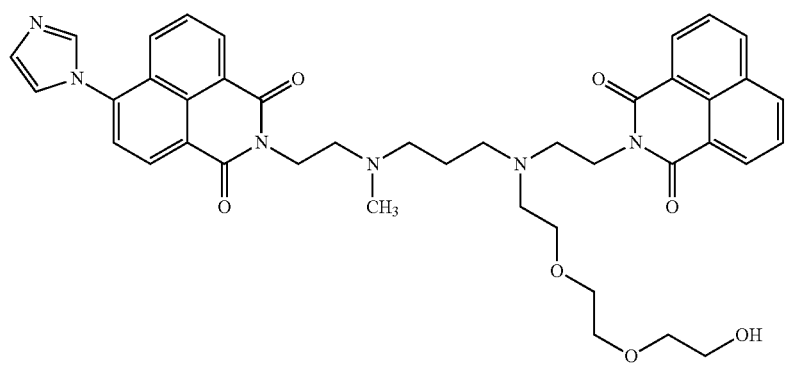
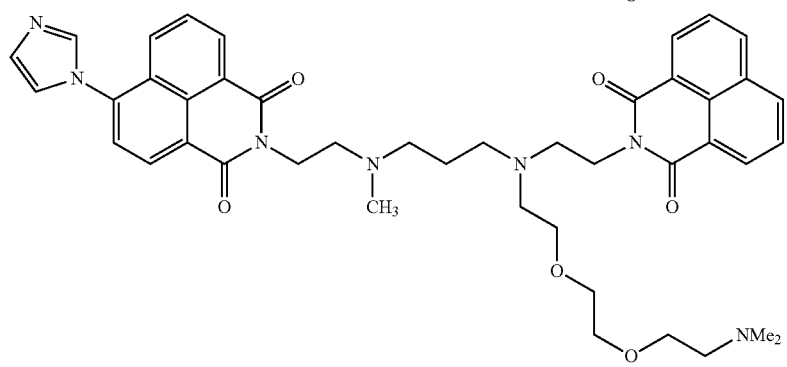
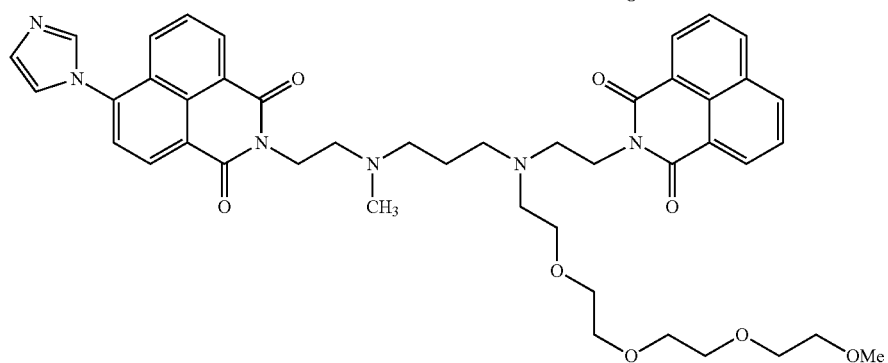

-continued

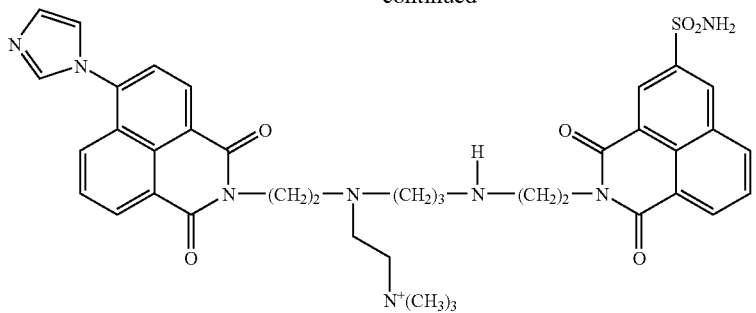

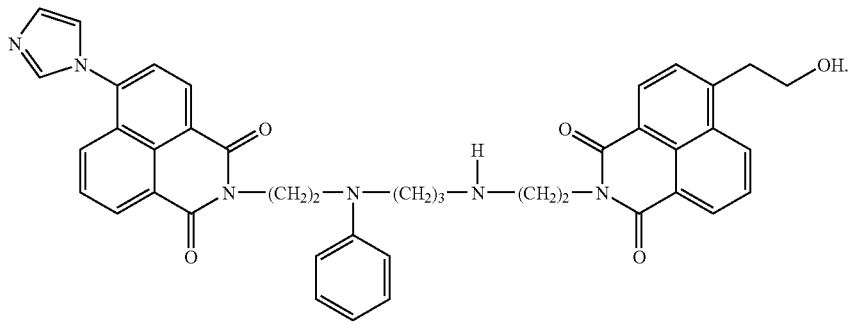

11. The compound of claim 1 selected from the structures:

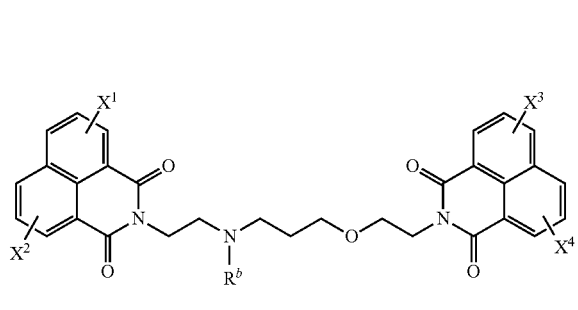

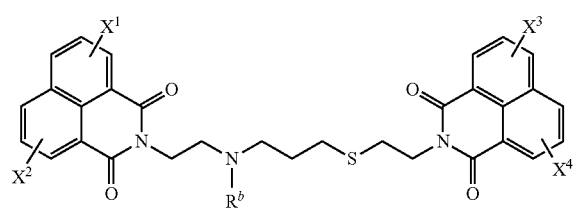

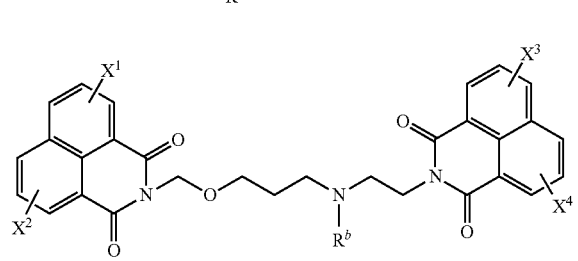

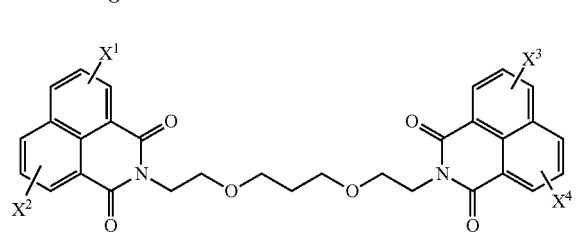

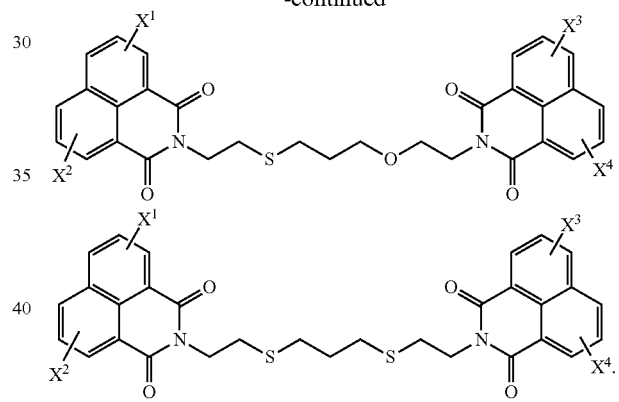

12. The compound of claim 1 selected from
N,N'-(bis-aminoethyl-1,3-propanediamine)-bis-(4-N-imidazolyl)-1,8 naphthalimide;
N,N'-(bis-aminoethyl-1,3-propanediamine)-4-(N-imidazolyl)-4-hydroxyl-1,8 naphtalimide;
$N^1, N^2$ bis methyl, N,N'-(bis-aminoethyl-1,3-propanediamine)-4-bromo, 4-N-imidazolyl 1,8 naphthalimide;
$N^1, N^2$ bis methyl, N,N'-(bis-aminoethyl-1,3-propanediamine)-4-N-imidazoly, 4-piperazinyl 1,8 naphthalimide;
$N^1$—H, $N^2$-methyl, N,N'-(bis-aminoethyl-1,3-propanediamine)-bis-(4-N-imidazolyl)-1,8 naphthalimide;
$N^1$—H, $N^2$-(methoxyethoxyethoxyacetamide)-(N,N'-(bis-aminoethyl-1,3-propanediamine)-bis 4-N-imidazolyl-1,8 naphthalimide);
N-(tert-butylglutaramide), bis-aminoethyl-1,3-propanediamine)-bis-4-N-imidazolyl-1,8 naphthalimide;
N,N'-(N-cyclopropylmethyl, bis-aminoethyl-1,3-propanediamine)-bis-4-N-imidazolyl-1,8 naphthalimide;
$N^1$-methyl, $N^2$—(N-methylglycyl)-N,N'-(bis-aminoethyl-1,3-propanediamine)-bis 4-N-imidazolyl-1,8 naphthalimide;

$N^1,N^2$ bis methyl, N,N'-(bis-aminoethyl-1,3-propanediamine)-4-N-imidazolyl, 4-(4-mercaptopropylpiperazinyl)-1,8 naphthalimide;

$N^1$-methyl, $N^2$-(tert-butylglutaramide)-N,N'-(bis-aminoethyl-1,3-propanediamine)-bis 4-N-imidazolyl-1,8 naphthalimide;

$N^1$-methyl, $N^2$-(2-(2-(2-aminoethoxy)ethoxy)acetamido)-N,N'-(bis-aminoethyl-1,3-propanediamine)-bis 4-N-imidazolyl-1,8 naphthalimide;

$N^1$-methyl, $N^2$—(N-methylvaline)-N,N'-(bis-aminoethyl-1,3-propanediamine)-bis 4-N-imidazolyl-1,8 naphthalimide;

$N^1$-methyl, $N^2$—(N-methyl, N-tertbuytyloxy valine)-N,N'-(bis-aminoethyl-1,3-propanediamine)-bis 4-N-imidazolyl-1,8 naphthalimide;

$N^1$—H, $N^2$-tertbuytyloxycarbonyl)-N,N'-(bis-aminoethyl-1,3-propanediamine)-bis 4-N-imidazolyl-1,8 naphthalimide;

$N^1$-methyl, $N^2$-glutaramide)-N,N'-(bis-aminoethyl-1,3-propanediamine)-bis 4-N-imidazolyl-1,8 naphthalimide;

N,N'-(bis-aminoethyl-1,3-propanediamine)-4-dimethylamino, 4-N-imidazolyl-1,8 naphthalimide;

$N^1$-Boc, $N^2$-(2-(2-(2-(N-Fmoc)aminoethoxy)ethoxy)acetamido)-N,N'-(bis-aminoethyl-1,3-propanediamine)-bis 4-N-imidazolyl-1,8 naphthalimide;

$N^1$-Boc, $N^2$-(2-(2-(2-aminoethoxy)ethoxy)acetamido)-N,N'-(bis-aminoethyl-1,3-propanediamine)-bis 4-N-imidazolyl-1,8 naphthalimide;

$N^1,N^2$ bis methyl, N,N'-(bis-aminoethyl-1,3-propanediamine)-4-N-imidazolyl, 4-(3-aminopropyl)amino)-1,8 naphthalimide;

$N^1,N^2$ bis methyl, N,N'-(bis-aminoethyl-1,3-propanediamine)-4-N-imidazolyl, 4-(6-aminohexyl)amino)-1,8 naphthalimide;

$N^1,N^2$ bis methyl, N,N'-(bis-aminoethyl-1,3-propanediamine)-4-N-imidazolyl, 4-N-(2-(N-Fmoc)aminoethoxy-tetraethoxy)-1,8 naphthalimide;

$N^1,N^2$ bis methyl, N,N'-(bis-aminoethyl-1,3-propanediamine)-4-N-imidazolyl, 4-N-(3-tertbutylpropionate-tetraethoxy)-1,8 naphthalimide;

$N^1,N^2$ bis methyl, N,N'-(bis-aminoethyl-1,3-propanediamine)-4-thiol, 4-N-imidazolyl-1,8 naphthalimide;

$N^1,N^2$ bis methyl, N,N'-(bis-aminoethyl-1,3-propanediamine)-4-dithio-(2-pyridyl), 4-N-imidazolyl-1,8 naphthalimide;

$N^1,N^2$ bis methyl, N,N'-(bis-aminoethyl-1,3-propanediamine)-4-dithio-(3-propionic acid), 4-N-imidazolyl-1,8 naphthalimide;

$N^1$-Boc, $N^2$-(2-(2-(2-aminoethoxy)triethoxy)propionamido)-N,N'-(bis-aminoethyl-1,3-propanediamine)-bis 4-N-imidazolyl-1,8 naphthalimide;

$N^1$—H, $N^2$-glycyl, N,N'-(bis-aminoethyl-1,3-propanediamine)-bis 4-N-imidazolyl-1,8 naphthalimide;

$N^1$—H, $N^2$—(N-methyl)glycyl, N,N'-(bis-aminoethyl-1,3-propanediamine)-bis 4-N-imidazolyl-1,8 naphthalimide;

$N^1$—H, $N^2$—(N-methyl)alanyl, N,N'-(bis-aminoethyl-1,3-propanediamine)-bis 4-N-imidazolyl-1,8 naphthalimide;

$N^1$, $N^2$ bis glycyl, N,N'-(bis-aminoethyl-1,3-propanediamine)-bis 4-N-imidazolyl-1,8 naphthalimide;

$N^1$, $N^2$ bis(N-methyl glycyl), N,N'-(bis-aminoethyl-1,3-propanediamine)-bis 4-N-imidazolyl-1,8 naphthalimide; and $N^1$, $N^2$ bis(N-methyl alanyl), N,N'-(bis-aminoethyl-1,3-propanediamine)-bis 4-N-imidazolyl-1,8 naphthalimide.

13. A pharmaceutical composition comprising an effective amount of the compound of claim 1, and a pharmaceutically acceptable diluent, carrier or excipient.

14. An article of manufacture comprising
a compound of claim 1;
a container; and
a package insert or a label affixed to the container indicating that the compound can be used to treat cancer.

15. The article of manufacture of claim 14 wherein said package insert of label indicates that the compound can be used to treat cancer characterized by the overexpression of an ErbB2 receptor.

16. The article of manufacture of claim 14 wherein the cancer is breast cancer.

* * * * *

SEQUENCE LISTING

<160> NUMBER OF SEQ ID NOS: 36

<210> SEQ ID NO 1
<211> LENGTH: 502
<212> TYPE: PRT
<213> ORGANISM: Homo sapiens

<400> SEQUENCE: 1

```
Met Leu Leu Arg Ser Ala Gly Lys Leu Asn Val Gly Thr Lys Lys
  1               5                  10                  15

Glu Asp Gly Glu Ser Thr Ala Pro Thr Pro Arg Pro Lys Val Leu
                 20                  25                  30

Arg Cys Lys Cys His His His Cys Pro Glu Asp Ser Val Asn Asn
                 35                  40                  45

Ile Cys Ser Thr Asp Gly Tyr Cys Phe Thr Met Ile Glu Glu Asp
                 50                  55                  60

Asp Ser Gly Leu Pro Val Val Thr Ser Gly Cys Leu Gly Leu Glu
                 65                  70                  75

Gly Ser Asp Phe Gln Cys Arg Asp Thr Pro Ile Pro His Gln Arg
                 80                  85                  90

Arg Ser Ile Glu Cys Cys Thr Glu Arg Asn Glu Cys Asn Lys Asp
                 95                 100                 105

Leu His Pro Thr Leu Pro Pro Leu Lys Asn Arg Asp Phe Val Asp
                110                 115                 120

Gly Pro Ile His His Arg Ala Leu Leu Ile Ser Val Thr Val Cys
                125                 130                 135

Ser Leu Leu Leu Val Leu Ile Ile Leu Phe Cys Tyr Phe Arg Tyr
                140                 145                 150

Lys Arg Gln Glu Thr Arg Pro Arg Tyr Ser Ile Gly Leu Glu Gln
                155                 160                 165

Asp Glu Thr Tyr Ile Pro Pro Gly Glu Ser Leu Arg Asp Leu Ile
                170                 175                 180

Glu Gln Ser Gln Ser Ser Gly Ser Gly Ser Gly Leu Pro Leu Leu
                185                 190                 195

Val Gln Arg Thr Ile Ala Lys Gln Ile Gln Met Val Lys Gln Ile
                200                 205                 210

Gly Lys Gly Arg Tyr Gly Glu Val Trp Met Gly Lys Trp Arg Gly
                215                 220                 225

Glu Lys Val Ala Val Lys Val Phe Phe Thr Thr Glu Glu Ala Ser
                230                 235                 240

Trp Phe Arg Glu Thr Glu Ile Tyr Gln Thr Val Leu Met Arg His
                245                 250                 255
```

-continued

Glu Asn Ile Leu Gly Phe Ile Ala Ala Asp Ile Lys Gly Thr Gly
            260                 265                 270

Ser Trp Thr Gln Leu Tyr Leu Ile Thr Asp Tyr His Glu Asn Gly
            275                 280                 285

Ser Leu Tyr Asp Tyr Leu Lys Ser Thr Thr Leu Asp Ala Lys Ser
            290                 295                 300

Met Leu Lys Leu Ala Tyr Ser Ser Val Ser Gly Leu Cys His Leu
            305                 310                 315

His Thr Glu Ile Phe Ser Thr Gln Gly Lys Pro Ala Ile Ala His
            320                 325                 330

Arg Asp Leu Lys Ser Lys Asn Ile Leu Val Lys Lys Asn Gly Thr
            335                 340                 345

Cys Cys Ile Ala Asp Leu Gly Leu Ala Val Lys Phe Ile Ser Asp
            350                 355                 360

Thr Asn Glu Val Asp Ile Pro Pro Asn Thr Arg Val Gly Thr Lys
            365                 370                 375

Arg Tyr Met Pro Pro Glu Val Leu Asp Glu Ser Leu Asn Arg Asn
            380                 385                 390

His Phe Gln Ser Tyr Ile Met Ala Asp Met Tyr Ser Phe Gly Leu
            395                 400                 405

Ile Leu Trp Glu Val Ala Arg Arg Cys Val Ser Gly Gly Ile Val
            410                 415                 420

Glu Glu Tyr Gln Leu Pro Tyr His Asp Leu Val Pro Ser Asp Pro
            425                 430                 435

Ser Tyr Glu Asp Met Arg Glu Ile Val Cys Ile Lys Lys Leu Arg
            440                 445                 450

Pro Ser Phe Pro Asn Arg Trp Ser Ser Asp Glu Cys Leu Arg Gln
            455                 460                 465

Met Gly Lys Leu Met Thr Glu Cys Trp Ala His Asn Pro Ala Ser
            470                 475                 480

Arg Leu Thr Ala Leu Arg Val Lys Lys Thr Leu Ala Lys Met Ser
            485                 490                 495

Glu Ser Gln Asp Ile Lys Leu
            500

<210> SEQ ID NO 2
<211> LENGTH: 507
<212> TYPE: PRT
<213> ORGANISM: Homo sapiens

<400> SEQUENCE: 2

Met Ala Gly Ala Gly Pro Lys Arg Arg Ala Leu Ala Ala Pro Ala
  1               5                  10                  15

Ala Glu Glu Lys Glu Glu Ala Arg Glu Lys Met Leu Ala Ala Lys
            20                  25                  30

Ser Ala Asp Gly Ser Ala Pro Ala Gly Glu Gly Glu Gly Val Thr
            35                  40                  45

Leu Gln Arg Asn Ile Thr Leu Leu Asn Gly Val Ala Ile Ile Val
            50                  55                  60

Gly Thr Ile Ile Gly Ser Gly Ile Phe Val Thr Pro Thr Gly Val
            65                  70                  75

Leu Lys Glu Ala Gly Ser Pro Gly Leu Ala Leu Val Val Trp Ala
            80                  85                  90

Ala Cys Gly Val Phe Ser Ile Val Gly Ala Leu Cys Tyr Ala Glu
            95                 100                 105

```
Leu Gly Thr Thr Ile Ser Lys Ser Gly Gly Asp Tyr Ala Tyr Met
            110                 115                 120

Leu Glu Val Tyr Gly Ser Leu Pro Ala Phe Lys Leu Trp Ile
            125                 130                 135

Glu Leu Leu Ile Ile Arg Pro Ser Ser Gln Tyr Ile Val Ala Leu
            140                 145                 150

Val Phe Ala Thr Tyr Leu Leu Lys Pro Leu Phe Pro Thr Cys Pro
            155                 160                 165

Val Pro Glu Glu Ala Ala Lys Leu Val Ala Cys Leu Cys Val Leu
            170                 175                 180

Leu Leu Thr Ala Val Asn Cys Tyr Ser Val Lys Ala Ala Thr Arg
            185                 190                 195

Val Gln Asp Ala Phe Ala Ala Ala Lys Leu Leu Ala Leu Ala Leu
            200                 205                 210

Ile Ile Leu Leu Gly Phe Val Gln Ile Gly Lys Gly Val Val Ser
            215                 220                 225

Asn Leu Asp Pro Asn Phe Ser Phe Glu Gly Thr Lys Leu Asp Val
            230                 235                 240

Gly Asn Ile Val Leu Ala Leu Tyr Ser Gly Leu Phe Ala Tyr Gly
            245                 250                 255

Gly Trp Asn Tyr Leu Asn Phe Val Thr Glu Glu Met Ile Asn Pro
            260                 265                 270

Tyr Arg Asn Leu Pro Leu Ala Ile Ile Ile Ser Leu Pro Ile Val
            275                 280                 285

Thr Leu Val Tyr Val Leu Thr Asn Leu Ala Tyr Phe Thr Thr Leu
            290                 295                 300

Ser Thr Glu Gln Met Leu Ser Ser Glu Ala Val Ala Val Asp Phe
            305                 310                 315

Gly Asn Tyr His Leu Gly Val Met Ser Trp Ile Ile Pro Val Phe
            320                 325                 330

Val Gly Leu Ser Cys Phe Gly Ser Val Asn Gly Ser Leu Phe Thr
            335                 340                 345

Ser Ser Arg Leu Phe Phe Val Gly Ser Arg Glu Gly His Leu Pro
            350                 355                 360

Ser Ile Leu Ser Met Ile His Pro Gln Leu Leu Thr Pro Val Pro
            365                 370                 375

Ser Leu Val Phe Thr Cys Val Met Thr Leu Leu Tyr Ala Phe Ser
            380                 385                 390

Lys Asp Ile Phe Ser Val Ile Asn Phe Phe Ser Phe Phe Asn Trp
            395                 400                 405

Leu Cys Val Ala Leu Ala Ile Ile Gly Met Ile Trp Leu Arg His
            410                 415                 420

Arg Lys Pro Glu Leu Glu Arg Pro Ile Lys Val Asn Leu Ala Leu
            425                 430                 435

Pro Val Phe Phe Ile Leu Ala Cys Leu Phe Leu Ile Ala Val Ser
            440                 445                 450

Phe Trp Lys Thr Pro Val Glu Cys Gly Ile Gly Phe Thr Ile Ile
            455                 460                 465

Leu Ser Gly Leu Pro Val Tyr Phe Phe Gly Val Trp Trp Lys Asn
            470                 475                 480

Lys Pro Lys Trp Leu Leu Gln Gly Ile Phe Ser Thr Thr Val Leu
            485                 490                 495

Cys Gln Lys Leu Met Gln Val Val Pro Gln Glu Thr
            500                 505
```

<210> SEQ ID NO 3
<211> LENGTH: 339
<212> TYPE: PRT
<213> ORGANISM: Homo sapiens

<400> SEQUENCE: 3

```
Met Glu Ser Arg Lys Asp Ile Thr Asn Gln Glu Leu Trp Lys
 1               5                  10                  15
Met Lys Pro Arg Arg Asn Leu Glu Glu Asp Asp Tyr Leu His Lys
             20                  25                  30
Asp Thr Gly Glu Thr Ser Met Leu Lys Arg Pro Val Leu Leu His
         35                  40                  45
Leu His Gln Thr Ala His Ala Asp Glu Phe Asp Cys Pro Ser Glu
     50                  55                  60
Leu Gln His Thr Gln Glu Leu Phe Pro Gln Trp His Leu Pro Ile
 65                  70                  75
Lys Ile Ala Ala Ile Ile Ala Ser Leu Thr Phe Leu Tyr Thr Leu
                 80                  85                  90
Leu Arg Glu Val Ile His Pro Leu Ala Thr Ser His Gln Gln Tyr
             95                 100                 105
Phe Tyr Lys Ile Pro Ile Leu Val Ile Asn Lys Val Leu Pro Met
        110                 115                 120
Val Ser Ile Thr Leu Leu Ala Leu Val Tyr Leu Pro Gly Val Ile
    125                 130                 135
Ala Ala Ile Val Gln Leu His Asn Gly Thr Lys Tyr Lys Lys Phe
140                 145                 150
Pro His Trp Leu Asp Lys Trp Met Leu Thr Arg Lys Gln Phe Gly
                155                 160                 165
Leu Leu Ser Phe Phe Phe Ala Val Leu His Ala Ile Tyr Ser Leu
            170                 175                 180
Ser Tyr Pro Met Arg Arg Ser Tyr Arg Tyr Lys Leu Leu Asn Trp
        185                 190                 195
Ala Tyr Gln Gln Val Gln Gln Asn Lys Glu Asp Ala Trp Ile Glu
    200                 205                 210
His Asp Val Trp Arg Met Glu Ile Tyr Val Ser Leu Gly Ile Val
215                 220                 225
Gly Leu Ala Ile Leu Ala Leu Ala Val Thr Ser Ile Pro Ser
                230                 235                 240
Val Ser Asp Ser Leu Thr Trp Arg Glu Phe His Tyr Ile Gln Ser
            245                 250                 255
Lys Leu Gly Ile Val Ser Leu Leu Leu Gly Thr Ile His Ala Leu
        260                 265                 270
Ile Phe Ala Trp Asn Lys Trp Ile Asp Ile Lys Gln Phe Val Trp
    275                 280                 285
Tyr Thr Pro Pro Thr Phe Met Ile Ala Val Phe Leu Pro Ile Val
290                 295                 300
Val Leu Ile Phe Lys Ser Ile Leu Phe Leu Pro Cys Leu Arg Lys
                305                 310                 315
Lys Ile Leu Lys Ile Arg His Gly Trp Glu Asp Val Thr Lys Ile
            320                 325                 330
Asn Lys Thr Glu Ile Cys Ser Gln Leu
        335
```

<210> SEQ ID NO 4

```
<211> LENGTH: 6995
<212> TYPE: PRT
<213> ORGANISM: Homo sapiens

<400> SEQUENCE: 4

Pro Val Thr Ser Leu Leu Thr Pro Gly Leu Val Ile Thr Thr Asp
  1               5                  10                  15

Arg Met Gly Ile Ser Arg Glu Pro Gly Thr Ser Ser Thr Ser Asn
                 20                  25                  30

Leu Ser Ser Thr Ser His Glu Arg Leu Thr Thr Leu Glu Asp Thr
                 35                  40                  45

Val Asp Thr Glu Ala Met Gln Pro Ser Thr His Thr Ala Val Thr
                 50                  55                  60

Asn Val Arg Thr Ser Ile Ser Gly His Glu Ser Gln Ser Ser Val
                 65                  70                  75

Leu Ser Asp Ser Glu Thr Pro Lys Ala Thr Ser Pro Met Gly Thr
                 80                  85                  90

Thr Tyr Thr Met Gly Glu Thr Ser Val Ser Ile Ser Thr Ser Asp
                 95                 100                 105

Phe Phe Glu Thr Ser Arg Ile Gln Ile Glu Pro Thr Ser Ser Leu
                110                 115                 120

Thr Ser Gly Leu Arg Glu Thr Ser Ser Glu Arg Ile Ser Ser
                125                 130                 135

Ala Thr Glu Gly Ser Thr Val Leu Ser Glu Val Pro Ser Gly Ala
                140                 145                 150

Thr Thr Glu Val Ser Arg Thr Glu Val Ile Ser Ser Arg Gly Thr
                155                 160                 165

Ser Met Ser Gly Pro Asp Gln Phe Thr Ile Ser Pro Asp Ile Ser
                170                 175                 180

Thr Glu Ala Ile Thr Arg Leu Ser Thr Ser Pro Ile Met Thr Glu
                185                 190                 195

Ser Ala Glu Ser Ala Ile Thr Ile Glu Thr Gly Ser Pro Gly Ala
                200                 205                 210

Thr Ser Glu Gly Thr Leu Thr Leu Asp Thr Ser Thr Thr Thr Phe
                215                 220                 225

Trp Ser Gly Thr His Ser Thr Ala Ser Pro Gly Phe Ser His Ser
                230                 235                 240

Glu Met Thr Thr Leu Met Ser Arg Thr Pro Gly Asp Val Pro Trp
                245                 250                 255

Pro Ser Leu Pro Ser Val Glu Glu Ala Ser Ser Val Ser Ser Ser
                260                 265                 270

Leu Ser Ser Pro Ala Met Thr Ser Thr Ser Phe Phe Ser Thr Leu
                275                 280                 285

Pro Glu Ser Ile Ser Ser Ser Pro His Pro Val Thr Ala Leu Leu
                290                 295                 300

Thr Leu Gly Pro Val Lys Thr Thr Asp Met Leu Arg Thr Ser Ser
                305                 310                 315

Glu Pro Glu Thr Ser Ser Pro Pro Asn Leu Ser Ser Thr Ser Ala
                320                 325                 330

Glu Ile Leu Ala Thr Ser Glu Val Thr Lys Asp Arg Glu Lys Ile
                335                 340                 345

His Pro Ser Ser Asn Thr Pro Val Val Asn Val Gly Thr Val Ile
                350                 355                 360

Tyr Lys His Leu Ser Pro Ser Ser Val Leu Ala Asp Leu Val Thr
                365                 370                 375
```

```
Thr Lys Pro Thr Ser Pro Met Ala Thr Ser Thr Leu Gly Asn
            380                 385                 390
Thr Ser Val Ser Thr Ser Thr Pro Ala Phe Pro Glu Thr Met Met
            395                 400                 405
Thr Gln Pro Thr Ser Ser Leu Thr Ser Gly Leu Arg Glu Ile Ser
            410                 415                 420
Thr Ser Gln Glu Thr Ser Ser Ala Thr Glu Arg Ser Ala Ser Leu
            425                 430                 435
Ser Gly Met Pro Thr Gly Ala Thr Thr Lys Val Ser Arg Thr Glu
            440                 445                 450
Ala Leu Ser Leu Gly Arg Thr Ser Thr Pro Gly Pro Ala Gln Ser
            455                 460                 465
Thr Ile Ser Pro Glu Ile Ser Thr Glu Thr Ile Thr Arg Ile Ser
            470                 475                 480
Thr Pro Leu Thr Thr Thr Gly Ser Ala Glu Met Thr Ile Thr Pro
            485                 490                 495
Lys Thr Gly His Ser Gly Ala Ser Ser Gln Gly Thr Phe Thr Leu
            500                 505                 510
Asp Thr Ser Ser Arg Ala Ser Trp Pro Gly Thr His Ser Ala Ala
            515                 520                 525
Thr His Arg Ser Pro His Ser Gly Met Thr Thr Pro Met Ser Arg
            530                 535                 540
Gly Pro Glu Asp Val Ser Trp Pro Ser Arg Pro Ser Val Glu Lys
            545                 550                 555
Thr Ser Pro Pro Ser Ser Leu Val Ser Leu Ser Ala Val Thr Ser
            560                 565                 570
Pro Ser Pro Leu Tyr Ser Thr Pro Ser Glu Ser Ser His Ser Ser
            575                 580                 585
Pro Leu Arg Val Thr Ser Leu Phe Thr Pro Val Met Met Lys Thr
            590                 595                 600
Thr Asp Met Leu Asp Thr Ser Leu Glu Pro Val Thr Thr Ser Pro
            605                 610                 615
Pro Ser Met Asn Ile Thr Ser Asp Glu Ser Leu Ala Thr Ser Lys
            620                 625                 630
Ala Thr Met Glu Thr Glu Ala Ile Gln Leu Ser Glu Asn Thr Ala
            635                 640                 645
Val Thr Gln Met Gly Thr Ile Ser Ala Arg Gln Glu Phe Tyr Ser
            650                 655                 660
Ser Tyr Pro Gly Leu Pro Glu Pro Ser Lys Val Thr Ser Pro Val
            665                 670                 675
Val Thr Ser Ser Thr Ile Lys Asp Ile Val Ser Thr Thr Ile Pro
            680                 685                 690
Ala Ser Ser Glu Ile Thr Arg Ile Glu Met Glu Ser Thr Ser Thr
            695                 700                 705
Leu Thr Pro Thr Pro Arg Glu Thr Ser Thr Ser Gln Glu Ile His
            710                 715                 720
Ser Ala Thr Lys Pro Ser Thr Val Pro Tyr Lys Ala Leu Thr Ser
            725                 730                 735
Ala Thr Ile Glu Asp Ser Met Thr Gln Val Met Ser Ser Ser Arg
            740                 745                 750
Gly Pro Ser Pro Asp Gln Ser Thr Met Ser Gln Asp Ile Ser Thr
            755                 760                 765
Glu Val Ile Thr Arg Leu Ser Thr Ser Pro Ile Lys Thr Glu Ser
```

```
                    770                 775                 780
Thr Glu Met Thr Ile Thr Thr Gln Thr Gly Ser Pro Gly Ala Thr
                785                 790                 795
Ser Arg Gly Thr Leu Thr Leu Asp Thr Ser Thr Thr Phe Met Ser
                800                 805                 810
Gly Thr His Ser Thr Ala Ser Gln Gly Phe Ser His Ser Gln Met
                815                 820                 825
Thr Ala Leu Met Ser Arg Thr Pro Gly Glu Val Pro Trp Leu Ser
                830                 835                 840
His Pro Ser Val Glu Glu Ala Ser Ser Ala Ser Phe Ser Leu Ser
                845                 850                 855
Ser Pro Val Met Thr Ser Ser Pro Val Ser Ser Thr Leu Pro
                860                 865                 870
Asp Ser Ile His Ser Ser Leu Pro Val Thr Ser Leu Leu Thr
                875                 880                 885
Ser Gly Leu Val Lys Thr Thr Glu Leu Leu Gly Thr Ser Ser Glu
                890                 895                 900
Pro Glu Thr Ser Ser Pro Pro Asn Leu Ser Ser Thr Ser Ala Glu
                905                 910                 915
Ile Leu Ala Thr Thr Glu Val Thr Thr Asp Thr Glu Lys Leu Glu
                920                 925                 930
Met Thr Asn Val Val Thr Ser Gly Tyr Thr His Glu Ser Pro Ser
                935                 940                 945
Ser Val Leu Ala Asp Ser Val Thr Thr Lys Ala Thr Ser Ser Met
                950                 955                 960
Gly Ile Thr Tyr Pro Thr Gly Asp Thr Asn Val Leu Thr Ser Thr
                965                 970                 975
Pro Ala Phe Ser Asp Thr Ser Arg Ile Gln Thr Lys Ser Lys Leu
                980                 985                 990
Ser Leu Thr Pro Gly Leu Met Glu Thr Ser Ile Ser Glu Glu Thr
                995                 1000                1005
Ser Ser Ala Thr Glu Lys Ser Thr Val Leu Ser Ser Val Pro Thr
                1010                1015                1020
Gly Ala Thr Thr Glu Val Ser Arg Thr Glu Ala Ile Ser Ser Ser
                1025                1030                1035
Arg Thr Ser Ile Pro Gly Pro Ala Gln Ser Thr Met Ser Ser Asp
                1040                1045                1050
Thr Ser Met Glu Thr Ile Thr Arg Ile Ser Thr Pro Leu Thr Arg
                1055                1060                1065
Lys Glu Ser Thr Asp Met Ala Ile Thr Pro Lys Thr Gly Pro Ser
                1070                1075                1080
Gly Ala Thr Ser Gln Gly Thr Phe Thr Leu Asp Ser Ser Thr
                1085                1090                1095
Ala Ser Trp Pro Gly Thr His Ser Ala Thr Thr Gln Arg Phe Pro
                1100                1105                1110
Arg Ser Val Val Thr Thr Pro Met Ser Arg Gly Pro Glu Asp Val
                1115                1120                1125
Ser Trp Pro Ser Pro Leu Ser Val Glu Lys Asn Ser Pro Pro Ser
                1130                1135                1140
Ser Leu Val Ser Ser Ser Ser Val Thr Ser Pro Ser Pro Leu Tyr
                1145                1150                1155
Ser Thr Pro Ser Gly Ser Ser His Ser Ser Pro Val Pro Val Thr
                1160                1165                1170
```

```
Ser Leu Phe Thr Ser Ile Met Met Lys Ala Thr Asp Met Leu Asp
              1175                1180                1185

Ala Ser Leu Glu Pro Glu Thr Thr Ser Ala Pro Asn Met Asn Ile
        1190                1195                1200

Thr Ser Asp Glu Ser Leu Ala Ala Ser Lys Ala Thr Thr Glu Thr
            1205                1210                1215

Glu Ala Ile His Val Phe Glu Asn Thr Ala Ala Ser His Val Glu
        1220                1225                1230

Thr Thr Ser Ala Thr Glu Glu Leu Tyr Ser Ser Ser Pro Gly Phe
            1235                1240                1245

Ser Glu Pro Thr Lys Val Ile Ser Pro Val Thr Ser Ser Ser
        1250                1255                1260

Ile Arg Asp Asn Met Val Ser Thr Thr Met Pro Gly Ser Ser Gly
        1265                1270                1275

Ile Thr Arg Ile Glu Ile Glu Ser Met Ser Ser Leu Thr Pro Gly
            1280                1285                1290

Leu Arg Glu Thr Arg Thr Ser Gln Asp Ile Thr Ser Ser Thr Glu
            1295                1300                1305

Thr Ser Thr Val Leu Tyr Lys Met Pro Ser Gly Ala Thr Pro Glu
            1310                1315                1320

Val Ser Arg Thr Glu Val Met Pro Ser Ser Arg Thr Ser Ile Pro
            1325                1330                1335

Gly Pro Ala Gln Ser Thr Met Ser Leu Asp Ile Ser Asp Glu Val
            1340                1345                1350

Val Thr Arg Leu Ser Thr Ser Pro Ile Met Thr Glu Ser Ala Glu
            1355                1360                1365

Ile Thr Ile Thr Thr Gln Thr Gly Tyr Ser Leu Ala Thr Ser Gln
            1370                1375                1380

Val Thr Leu Pro Leu Gly Thr Ser Met Thr Phe Leu Ser Gly Thr
            1385                1390                1395

His Ser Thr Met Ser Gln Gly Leu Ser His Ser Glu Met Thr Asn
            1400                1405                1410

Leu Met Ser Arg Gly Pro Glu Ser Leu Ser Trp Thr Ser Pro Arg
            1415                1420                1425

Phe Val Glu Thr Thr Arg Ser Ser Ser Ser Leu Thr Ser Leu Pro
            1430                1435                1440

Leu Thr Thr Ser Leu Ser Pro Val Ser Ser Thr Leu Leu Asp Ser
            1445                1450                1455

Ser Pro Ser Ser Pro Leu Pro Val Thr Ser Leu Ile Leu Pro Gly
            1460                1465                1470

Leu Val Lys Thr Thr Glu Val Leu Asp Thr Ser Ser Glu Pro Lys
            1475                1480                1485

Thr Ser Ser Ser Pro Asn Leu Ser Ser Thr Ser Val Glu Ile Pro
            1490                1495                1500

Ala Thr Ser Glu Ile Met Thr Asp Thr Glu Lys Ile His Pro Ser
            1505                1510                1515

Ser Asn Thr Ala Val Ala Lys Val Arg Thr Ser Ser Ser Val His
            1520                1525                1530

Glu Ser His Ser Ser Val Leu Ala Asp Ser Glu Thr Thr Ile Thr
            1535                1540                1545

Ile Pro Ser Met Gly Ile Thr Ser Ala Val Glu Asp Thr Thr Val
            1550                1555                1560

Phe Thr Ser Asn Pro Ala Phe Ser Glu Thr Arg Arg Ile Pro Thr
            1565                1570                1575
```

```
Glu Pro Thr Phe Ser Leu Thr Pro Gly Phe Arg Glu Thr Ser Thr
            1580                1585                1590

Ser Glu Glu Thr Thr Ser Ile Thr Glu Thr Ser Ala Val Leu Phe
            1595                1600                1605

Gly Val Pro Thr Ser Ala Thr Thr Glu Val Ser Met Thr Glu Ile
            1610                1615                1620

Met Ser Ser Asn Arg Thr His Ile Pro Asp Ser Asp Gln Ser Thr
            1625                1630                1635

Met Ser Pro Asp Ile Ile Thr Glu Val Ile Thr Arg Leu Ser Ser
            1640                1645                1650

Ser Ser Met Met Ser Glu Ser Thr Gln Met Thr Ile Thr Thr Gln
            1655                1660                1665

Lys Ser Ser Pro Gly Ala Thr Ala Gln Ser Thr Leu Thr Leu Ala
            1670                1675                1680

Thr Thr Thr Ala Pro Leu Ala Arg Thr His Ser Thr Val Pro Pro
            1685                1690                1695

Arg Phe Leu His Ser Glu Met Thr Thr Leu Met Ser Arg Ser Pro
            1700                1705                1710

Glu Asn Pro Ser Trp Lys Ser Ser Pro Phe Val Glu Lys Thr Ser
            1715                1720                1725

Ser Ser Ser Ser Leu Leu Ser Leu Pro Val Thr Thr Ser Pro Ser
            1730                1735                1740

Val Ser Ser Thr Leu Pro Gln Ser Ile Pro Ser Ser Ser Phe Ser
            1745                1750                1755

Val Thr Ser Leu Leu Thr Pro Gly Met Val Lys Thr Thr Asp Thr
            1760                1765                1770

Ser Thr Glu Pro Gly Thr Ser Leu Ser Pro Asn Leu Ser Gly Thr
            1775                1780                1785

Ser Val Glu Ile Leu Ala Ala Ser Glu Val Thr Thr Asp Thr Glu
            1790                1795                1800

Lys Ile His Pro Ser Ser Ser Met Ala Val Thr Asn Val Gly Thr
            1805                1810                1815

Thr Ser Ser Gly His Glu Leu Tyr Ser Ser Val Ser Ile His Ser
            1820                1825                1830

Glu Pro Ser Lys Ala Thr Tyr Pro Val Gly Thr Pro Ser Ser Met
            1835                1840                1845

Ala Glu Thr Ser Ile Ser Thr Ser Met Pro Ala Asn Phe Glu Thr
            1850                1855                1860

Thr Gly Phe Glu Ala Glu Pro Phe Ser His Leu Thr Ser Gly Leu
            1865                1870                1875

Arg Lys Thr Asn Met Ser Leu Asp Thr Ser Ser Val Thr Pro Thr
            1880                1885                1890

Asn Thr Pro Ser Ser Pro Gly Ser Thr His Leu Leu Gln Ser Ser
            1895                1900                1905

Lys Thr Asp Phe Thr Ser Ser Ala Lys Thr Ser Ser Pro Asp Trp
            1910                1915                1920

Pro Pro Ala Ser Gln Tyr Thr Glu Ile Pro Val Asp Ile Ile Thr
            1925                1930                1935

Pro Phe Asn Ala Ser Pro Ser Ile Thr Glu Ser Thr Gly Ile Thr
            1940                1945                1950

Ser Phe Pro Glu Ser Arg Phe Thr Met Ser Val Thr Glu Ser Thr
            1955                1960                1965

His His Leu Ser Thr Asp Leu Leu Pro Ser Ala Glu Thr Ile Ser
```

-continued

```
                1970                1975                1980
Thr Gly Thr Val Met Pro Ser Leu Ser Glu Ala Met Thr Ser Phe
                1985                1990                1995
Ala Thr Thr Gly Val Pro Arg Ala Ile Ser Gly Ser Gly Ser Pro
                2000                2005                2010
Phe Ser Arg Thr Glu Ser Gly Pro Gly Asp Ala Thr Leu Ser Thr
                2015                2020                2025
Ile Ala Glu Ser Leu Pro Ser Ser Thr Pro Val Pro Phe Ser Ser
                2030                2035                2040
Ser Thr Phe Thr Thr Thr Asp Ser Ser Thr Ile Pro Ala Leu His
                2045                2050                2055
Glu Ile Thr Ser Ser Ser Ala Thr Pro Tyr Arg Val Asp Thr Ser
                2060                2065                2070
Leu Gly Thr Glu Ser Ser Thr Thr Glu Gly Arg Leu Val Met Val
                2075                2080                2085
Ser Thr Leu Asp Thr Ser Ser Gln Pro Gly Arg Thr Ser Ser Ser
                2090                2095                2100
Pro Ile Leu Asp Thr Arg Met Thr Glu Ser Val Glu Leu Gly Thr
                2105                2110                2115
Val Thr Ser Ala Tyr Gln Val Pro Ser Leu Ser Thr Arg Leu Thr
                2120                2125                2130
Arg Thr Asp Gly Ile Met Glu His Ile Thr Lys Ile Pro Asn Glu
                2135                2140                2145
Ala Ala His Arg Gly Thr Ile Arg Pro Val Lys Gly Pro Gln Thr
                2150                2155                2160
Ser Thr Ser Pro Ala Ser Pro Lys Gly Leu His Thr Gly Gly Thr
                2165                2170                2175
Lys Arg Met Glu Thr Thr Thr Ala Leu Lys Thr Thr Thr Thr
                2180                2185                2190
Ala Leu Lys Thr Thr Ser Arg Ala Thr Leu Thr Thr Ser Val Tyr
                2195                2200                2205
Thr Pro Thr Leu Gly Thr Leu Thr Pro Leu Asn Ala Ser Met Gln
                2210                2215                2220
Met Ala Ser Thr Ile Pro Thr Glu Met Met Ile Thr Thr Pro Tyr
                2225                2230                2235
Val Phe Pro Asp Val Pro Glu Thr Thr Ser Ser Leu Ala Thr Ser
                2240                2245                2250
Leu Gly Ala Glu Thr Ser Thr Ala Leu Pro Arg Thr Thr Pro Ser
                2255                2260                2265
Val Phe Asn Arg Glu Ser Glu Thr Thr Ala Ser Leu Val Ser Arg
                2270                2275                2280
Ser Gly Ala Glu Arg Ser Pro Val Ile Gln Thr Leu Asp Val Ser
                2285                2290                2295
Ser Ser Glu Pro Asp Thr Thr Ala Ser Trp Val Ile His Pro Ala
                2300                2305                2310
Glu Thr Ile Pro Thr Val Ser Lys Thr Thr Pro Asn Phe Phe His
                2315                2320                2325
Ser Glu Leu Asp Thr Val Ser Ser Thr Ala Thr Ser His Gly Ala
                2330                2335                2340
Asp Val Ser Ser Ala Ile Pro Thr Asn Ile Ser Pro Ser Glu Leu
                2345                2350                2355
Asp Ala Leu Thr Pro Leu Val Thr Ile Ser Gly Thr Asp Thr Ser
                2360                2365                2370
```

```
Thr Thr Phe Pro Thr Leu Thr Lys Ser Pro His Glu Thr Glu Thr
            2375                2380                2385

Arg Thr Thr Trp Leu Thr His Pro Ala Glu Thr Ser Ser Thr Ile
            2390                2395                2400

Pro Arg Thr Ile Pro Asn Phe Ser His His Glu Ser Asp Ala Thr
            2405                2410                2415

Pro Ser Ile Ala Thr Ser Pro Gly Ala Glu Thr Ser Ser Ala Ile
            2420                2425                2430

Pro Ile Met Thr Val Ser Pro Gly Ala Glu Asp Leu Val Thr Ser
            2435                2440                2445

Gln Val Thr Ser Ser Gly Thr Asp Arg Asn Met Thr Ile Pro Thr
            2450                2455                2460

Leu Thr Leu Ser Pro Gly Glu Pro Lys Thr Ile Ala Ser Leu Val
            2465                2470                2475

Thr His Pro Glu Ala Gln Thr Ser Ser Ala Ile Pro Thr Ser Thr
            2480                2485                2490

Ile Ser Pro Ala Val Ser Arg Leu Val Thr Ser Met Val Thr Ser
            2495                2500                2505

Leu Ala Ala Lys Thr Ser Thr Thr Asn Arg Ala Leu Thr Asn Ser
            2510                2515                2520

Pro Gly Glu Pro Ala Thr Thr Val Ser Leu Val Thr His Ser Ala
            2525                2530                2535

Gln Thr Ser Pro Thr Val Pro Trp Thr Thr Ser Ile Phe Phe His
            2540                2545                2550

Ser Lys Ser Asp Thr Thr Pro Ser Met Thr Thr Ser His Gly Ala
            2555                2560                2565

Glu Ser Ser Ser Ala Val Pro Thr Pro Thr Val Ser Thr Glu Val
            2570                2575                2580

Pro Gly Val Val Thr Pro Leu Val Thr Ser Ser Arg Ala Val Ile
            2585                2590                2595

Ser Thr Thr Ile Pro Ile Leu Thr Leu Ser Pro Gly Glu Pro Glu
            2600                2605                2610

Thr Thr Pro Ser Met Ala Thr Ser His Gly Glu Glu Ala Ser Ser
            2615                2620                2625

Ala Ile Pro Thr Pro Thr Val Ser Pro Gly Val Pro Gly Val Val
            2630                2635                2640

Thr Ser Leu Val Thr Ser Ser Arg Ala Val Thr Ser Thr Thr Ile
            2645                2650                2655

Pro Ile Leu Thr Phe Ser Leu Gly Glu Pro Glu Thr Thr Pro Ser
            2660                2665                2670

Met Ala Thr Ser His Gly Thr Glu Ala Gly Ser Ala Val Pro Thr
            2675                2680                2685

Val Leu Pro Glu Val Pro Gly Met Val Thr Ser Leu Val Ala Ser
            2690                2695                2700

Ser Arg Ala Val Thr Ser Thr Leu Pro Thr Leu Thr Leu Ser
            2705                2710                2715

Pro Gly Glu Pro Glu Thr Thr Pro Ser Met Ala Thr Ser His Gly
            2720                2725                2730

Ala Glu Ala Ser Ser Thr Val Pro Thr Val Ser Pro Glu Val Pro
            2735                2740                2745

Gly Val Val Thr Ser Leu Val Thr Ser Ser Ser Gly Val Asn Ser
            2750                2755                2760

Thr Ser Ile Pro Thr Leu Ile Leu Ser Pro Gly Glu Leu Glu Thr
            2765                2770                2775
```

```
Thr Pro Ser Met Ala Thr Ser His Gly Ala Glu Ala Ser Ser Ala
            2780                2785                2790

Val Pro Thr Pro Thr Val Ser Pro Gly Val Ser Gly Val Val Thr
            2795                2800                2805

Pro Leu Val Thr Ser Ser Arg Ala Val Thr Ser Thr Thr Ile Pro
            2810                2815                2820

Ile Leu Thr Leu Ser Ser Ser Glu Pro Glu Thr Thr Pro Ser Met
            2825                2830                2835

Ala Thr Ser His Gly Val Glu Ala Ser Ser Ala Val Leu Thr Val
            2840                2845                2850

Ser Pro Glu Val Pro Gly Met Val Thr Phe Leu Val Thr Ser Ser
            2855                2860                2865

Arg Ala Val Thr Ser Thr Thr Ile Pro Thr Leu Thr Ile Ser Ser
            2870                2875                2880

Asp Glu Pro Glu Thr Thr Thr Ser Leu Val Thr His Ser Glu Ala
            2885                2890                2895

Lys Met Ile Ser Ala Ile Pro Thr Leu Gly Val Ser Pro Thr Val
            2900                2905                2910

Gln Gly Leu Val Thr Ser Leu Val Thr Ser Ser Gly Ser Glu Thr
            2915                2920                2925

Ser Ala Phe Ser Asn Leu Thr Val Ala Ser Ser Gln Pro Glu Thr
            2930                2935                2940

Ile Asp Ser Trp Val Ala His Pro Gly Thr Glu Ala Ser Ser Val
            2945                2950                2955

Val Pro Thr Leu Thr Val Ser Thr Gly Glu Pro Phe Thr Asn Ile
            2960                2965                2970

Ser Leu Val Thr His Pro Ala Glu Ser Ser Ser Thr Leu Pro Arg
            2975                2980                2985

Thr Thr Ser Arg Phe Ser His Ser Glu Leu Asp Thr Met Pro Ser
            2990                2995                3000

Thr Val Thr Ser Pro Glu Ala Glu Ser Ser Ser Ala Ile Ser Thr
            3005                3010                3015

Thr Ile Ser Pro Gly Ile Pro Gly Val Leu Thr Ser Leu Val Thr
            3020                3025                3030

Ser Ser Gly Arg Asp Ile Ser Ala Thr Phe Pro Thr Val Pro Glu
            3035                3040                3045

Ser Pro His Glu Ser Glu Ala Thr Ala Ser Trp Val Thr His Pro
            3050                3055                3060

Ala Val Thr Ser Thr Thr Val Pro Arg Thr Thr Pro Asn Tyr Ser
            3065                3070                3075

His Ser Glu Pro Asp Thr Thr Pro Ser Ile Ala Thr Ser Pro Gly
            3080                3085                3090

Ala Glu Ala Thr Ser Asp Phe Pro Thr Ile Thr Val Ser Pro Asp
            3095                3100                3105

Val Pro Asp Met Val Thr Ser Gln Val Thr Ser Ser Gly Thr Asp
            3110                3115                3120

Thr Ser Ile Thr Ile Pro Thr Leu Thr Leu Ser Ser Gly Glu Pro
            3125                3130                3135

Glu Thr Thr Thr Ser Phe Ile Thr Tyr Ser Glu Thr His Thr Ser
            3140                3145                3150

Ser Ala Ile Pro Thr Leu Pro Val Ser Pro Asp Ala Ser Lys Met
            3155                3160                3165

Leu Thr Ser Leu Val Ile Ser Ser Gly Thr Asp Ser Thr Thr Thr
```

```
                    3170            3175            3180
Phe Pro Thr Leu Thr Glu Thr Pro Tyr Glu Pro Glu Thr Thr Ala
                3185            3190            3195
Ile Gln Leu Ile His Pro Ala Glu Thr Asn Thr Met Val Pro Arg
                3200            3205            3210
Thr Thr Pro Lys Phe Ser His Ser Lys Ser Asp Thr Leu Pro
            3215            3220            3225
Val Ala Ile Thr Ser Pro Gly Pro Glu Ala Ser Ser Ala Val Ser
                3230            3235            3240
Thr Thr Thr Ile Ser Pro Asp Met Ser Asp Leu Val Thr Ser Leu
                3245            3250            3255
Val Pro Ser Ser Gly Thr Asp Thr Ser Thr Thr Phe Pro Thr Leu
                3260            3265            3270
Ser Glu Thr Pro Tyr Glu Pro Glu Thr Thr Ala Thr Trp Leu Thr
                3275            3280            3285
His Pro Ala Glu Thr Ser Thr Val Ser Gly Thr Ile Pro Asn
            3290            3295            3300
Phe Ser His Arg Gly Ser Asp Thr Ala Pro Ser Met Val Thr Ser
                3305            3310            3315
Pro Gly Val Asp Thr Arg Ser Gly Val Pro Thr Thr Ile Pro
            3320            3325            3330
Pro Ser Ile Pro Gly Val Val Thr Ser Gln Val Thr Ser Ser Ala
                3335            3340            3345
Thr Asp Thr Ser Thr Ala Ile Pro Thr Leu Thr Pro Ser Pro Gly
                3350            3355            3360
Glu Pro Glu Thr Thr Ala Ser Ser Ala Thr His Pro Gly Thr Gln
                3365            3370            3375
Thr Gly Phe Thr Val Pro Ile Arg Thr Val Pro Ser Ser Glu Pro
                3380            3385            3390
Asp Thr Met Ala Ser Trp Val Thr His Pro Pro Gln Thr Ser Thr
                3395            3400            3405
Pro Val Ser Arg Thr Thr Ser Ser Phe Ser His Ser Ser Pro Asp
                3410            3415            3420
Ala Thr Pro Val Met Ala Thr Ser Pro Arg Thr Glu Ala Ser Ser
                3425            3430            3435
Ala Val Leu Thr Thr Ile Ser Pro Gly Ala Pro Glu Met Val Thr
                3440            3445            3450
Ser Gln Ile Thr Ser Ser Gly Ala Ala Thr Ser Thr Thr Val Pro
                3455            3460            3465
Thr Leu Thr His Ser Pro Gly Met Pro Glu Thr Thr Ala Leu Leu
                3470            3475            3480
Ser Thr His Pro Arg Thr Glu Thr Ser Lys Thr Phe Pro Ala Ser
                3485            3490            3495
Thr Val Phe Pro Gln Val Ser Glu Thr Thr Ala Ser Leu Thr Ile
                3500            3505            3510
Arg Pro Gly Ala Glu Thr Ser Thr Ala Leu Pro Thr Gln Thr Thr
                3515            3520            3525
Ser Ser Leu Phe Thr Leu Leu Val Thr Gly Thr Ser Arg Val Asp
                3530            3535            3540
Leu Ser Pro Thr Ala Ser Pro Gly Val Ser Ala Lys Thr Ala Pro
                3545            3550            3555
Leu Ser Thr His Pro Gly Thr Glu Thr Ser Thr Met Ile Pro Thr
                3560            3565            3570
```

-continued

Ser Thr Leu Ser Leu Gly Leu Leu Glu Thr Thr Gly Leu Leu Ala
         3575                3580                3585

Thr Ser Ser Ser Ala Glu Thr Ser Thr Ser Thr Leu Thr Leu Thr
         3590                3595                3600

Val Ser Pro Ala Val Ser Gly Leu Ser Ser Ala Ser Ile Thr Thr
         3605                3610                3615

Asp Lys Pro Gln Thr Val Thr Ser Trp Asn Thr Glu Thr Ser Pro
         3620                3625                3630

Ser Val Thr Ser Val Gly Pro Pro Glu Phe Ser Arg Thr Val Thr
         3635                3640                3645

Gly Thr Thr Met Thr Leu Ile Pro Ser Glu Met Pro Thr Pro Pro
         3650                3655                3660

Lys Thr Ser His Gly Glu Gly Val Ser Pro Thr Thr Ile Leu Arg
         3665                3670                3675

Thr Thr Met Val Glu Ala Thr Asn Leu Ala Thr Thr Gly Ser Ser
         3680                3685                3690

Pro Thr Val Ala Lys Thr Thr Thr Phe Asn Thr Leu Ala Gly
         3695                3700                3705

Ser Leu Phe Thr Pro Leu Thr Thr Pro Gly Met Ser Thr Leu Ala
         3710                3715                3720

Ser Glu Ser Val Thr Ser Arg Thr Ser Tyr Asn His Arg Ser Trp
         3725                3730                3735

Ile Ser Thr Thr Ser Ser Tyr Asn Arg Arg Tyr Trp Thr Pro Ala
         3740                3745                3750

Thr Ser Thr Pro Val Thr Ser Thr Phe Ser Pro Gly Ile Ser Thr
         3755                3760                3765

Ser Ser Ile Pro Ser Ser Thr Ala Ala Thr Val Pro Phe Met Val
         3770                3775                3780

Pro Phe Thr Leu Asn Phe Thr Ile Thr Asn Leu Gln Tyr Glu Glu
         3785                3790                3795

Asp Met Arg His Pro Gly Ser Arg Lys Phe Asn Ala Thr Glu Arg
         3800                3805                3810

Glu Leu Gln Gly Leu Leu Lys Pro Leu Phe Arg Asn Ser Ser Leu
         3815                3820                3825

Glu Tyr Leu Tyr Ser Gly Cys Arg Leu Ala Ser Leu Arg Pro Glu
         3830                3835                3840

Lys Asp Ser Ser Ala Thr Ala Val Asp Ala Ile Cys Thr His Arg
         3845                3850                3855

Pro Asp Pro Glu Asp Leu Gly Leu Asp Arg Glu Arg Leu Tyr Trp
         3860                3865                3870

Glu Leu Ser Asn Leu Thr Asn Gly Ile Gln Glu Leu Gly Pro Tyr
         3875                3880                3885

Thr Leu Asp Arg Asn Ser Leu Tyr Val Asn Gly Phe Thr His Arg
         3890                3895                3900

Ser Ser Met Pro Thr Thr Ser Thr Pro Gly Thr Ser Thr Val Asp
         3905                3910                3915

Val Gly Thr Ser Gly Thr Pro Ser Ser Ser Pro Ser Pro Thr Thr
         3920                3925                3930

Ala Gly Pro Leu Leu Met Pro Phe Thr Leu Asn Phe Thr Ile Thr
         3935                3940                3945

Asn Leu Gln Tyr Glu Glu Asp Met Arg Arg Thr Gly Ser Arg Lys
         3950                3955                3960

Phe Asn Thr Met Glu Ser Val Leu Gln Gly Leu Leu Lys Pro Leu
         3965                3970                3975

```
Phe Lys Asn Thr Ser Val Gly Pro Leu Tyr Ser Gly Cys Arg Leu
            3980                3985                3990

Thr Leu Leu Arg Pro Glu Lys Asp Gly Ala Ala Thr Gly Val Asp
            3995                4000                4005

Ala Ile Cys Thr His Arg Leu Asp Pro Lys Ser Pro Gly Leu Asn
            4010                4015                4020

Arg Glu Gln Leu Tyr Trp Glu Leu Ser Lys Leu Thr Asn Asp Ile
            4025                4030                4035

Glu Glu Leu Gly Pro Tyr Thr Leu Asp Arg Asn Ser Leu Tyr Val
            4040                4045                4050

Asn Gly Phe Thr His Gln Ser Ser Val Ser Thr Thr Ser Thr Pro
            4055                4060                4065

Gly Thr Ser Thr Val Asp Leu Arg Thr Ser Gly Thr Pro Ser Ser
            4070                4075                4080

Leu Ser Ser Pro Thr Ile Met Ala Ala Gly Pro Leu Leu Val Pro
            4085                4090                4095

Phe Thr Leu Asn Phe Thr Ile Thr Asn Leu Gln Tyr Gly Glu Asp
            4100                4105                4110

Met Gly His Pro Gly Ser Arg Lys Phe Asn Thr Thr Glu Arg Val
            4115                4120                4125

Leu Gln Gly Leu Leu Gly Pro Ile Phe Lys Asn Thr Ser Val Gly
            4130                4135                4140

Pro Leu Tyr Ser Gly Cys Arg Leu Thr Ser Leu Arg Ser Glu Lys
            4145                4150                4155

Asp Gly Ala Ala Thr Gly Val Asp Ala Ile Cys Ile His His Leu
            4160                4165                4170

Asp Pro Lys Ser Pro Gly Leu Asn Arg Glu Arg Leu Tyr Trp Glu
            4175                4180                4185

Leu Ser Gln Leu Thr Asn Gly Ile Lys Glu Leu Gly Pro Tyr Thr
            4190                4195                4200

Leu Asp Arg Asn Ser Leu Tyr Val Asn Gly Phe Thr His Arg Thr
            4205                4210                4215

Ser Val Pro Thr Thr Ser Thr Pro Gly Thr Ser Thr Val Asp Leu
            4220                4225                4230

Gly Thr Ser Gly Thr Pro Phe Ser Leu Pro Ser Pro Ala Thr Ala
            4235                4240                4245

Gly Pro Leu Leu Val Leu Phe Thr Leu Asn Phe Thr Ile Thr Asn
            4250                4255                4260

Leu Lys Tyr Glu Glu Asp Met His Arg Pro Gly Ser Arg Lys Phe
            4265                4270                4275

Asn Thr Thr Glu Arg Val Leu Gln Thr Leu Val Gly Pro Met Phe
            4280                4285                4290

Lys Asn Thr Ser Val Gly Leu Leu Tyr Ser Gly Cys Arg Leu Thr
            4295                4300                4305

Leu Leu Arg Ser Glu Lys Asp Gly Ala Ala Thr Gly Val Asp Ala
            4310                4315                4320

Ile Cys Thr His Arg Leu Asp Pro Lys Ser Pro Gly Val Asp Arg
            4325                4330                4335

Glu Gln Leu Tyr Trp Glu Leu Ser Gln Leu Thr Asn Gly Ile Lys
            4340                4345                4350

Glu Leu Gly Pro Tyr Thr Leu Asp Arg Asn Ser Leu Tyr Val Asn
            4355                4360                4365

Gly Phe Thr His Trp Ile Pro Val Pro Thr Ser Ser Thr Pro Gly
```

```
                        4370            4375            4380
Thr Ser Thr Val Asp Leu Gly Ser Gly Thr Pro Ser Ser Leu Pro
                4385            4390            4395
Ser Pro Thr Ser Ala Thr Ala Gly Pro Leu Leu Val Pro Phe Thr
                4400            4405            4410
Leu Asn Phe Thr Ile Thr Asn Leu Lys Tyr Glu Glu Asp Met His
                4415            4420            4425
Cys Pro Gly Ser Arg Lys Phe Asn Thr Thr Glu Arg Val Leu Gln
                4430            4435            4440
Ser Leu Leu Gly Pro Met Phe Lys Asn Thr Ser Val Gly Pro Leu
                4445            4450            4455
Tyr Ser Gly Cys Arg Leu Thr Leu Leu Arg Ser Glu Lys Asp Gly
                4460            4465            4470
Ala Ala Thr Gly Val Asp Ala Ile Cys Thr His Arg Leu Asp Pro
                4475            4480            4485
Lys Ser Pro Gly Val Asp Arg Glu Gln Leu Tyr Trp Glu Leu Ser
                4490            4495            4500
Gln Leu Thr Asn Gly Ile Lys Glu Leu Gly Pro Tyr Thr Leu Asp
                4505            4510            4515
Arg Asn Ser Leu Tyr Val Asn Gly Phe Thr His Gln Thr Ser Ala
                4520            4525            4530
Pro Asn Thr Ser Thr Pro Gly Thr Ser Thr Val Asp Leu Gly Thr
                4535            4540            4545
Ser Gly Thr Pro Ser Ser Leu Pro Ser Pro Thr Ser Ala Gly Pro
                4550            4555            4560
Leu Leu Val Pro Phe Thr Leu Asn Phe Thr Ile Thr Asn Leu Gln
                4565            4570            4575
Tyr Glu Glu Asp Met His His Pro Gly Ser Arg Lys Phe Asn Thr
                4580            4585            4590
Thr Glu Arg Val Leu Gln Gly Leu Leu Gly Pro Met Phe Lys Asn
                4595            4600            4605
Thr Ser Val Gly Leu Leu Tyr Ser Gly Cys Arg Leu Thr Leu Leu
                4610            4615            4620
Arg Pro Glu Lys Asn Gly Ala Ala Thr Gly Met Asp Ala Ile Cys
                4625            4630            4635
Ser His Arg Leu Asp Pro Lys Ser Pro Gly Leu Asn Arg Glu Gln
                4640            4645            4650
Leu Tyr Trp Glu Leu Ser Gln Leu Thr His Gly Ile Lys Glu Leu
                4655            4660            4665
Gly Pro Tyr Thr Leu Asp Arg Asn Ser Leu Tyr Val Asn Gly Phe
                4670            4675            4680
Thr His Arg Ser Ser Val Ala Pro Thr Ser Thr Pro Gly Thr Ser
                4685            4690            4695
Thr Val Asp Leu Gly Thr Ser Gly Thr Pro Ser Ser Leu Pro Ser
                4700            4705            4710
Pro Thr Thr Ala Val Pro Leu Leu Val Pro Phe Thr Leu Asn Phe
                4715            4720            4725
Thr Ile Thr Asn Leu Gln Tyr Gly Glu Asp Met Arg His Pro Gly
                4730            4735            4740
Ser Arg Lys Phe Asn Thr Thr Glu Arg Val Leu Gln Gly Leu Leu
                4745            4750            4755
Gly Pro Leu Phe Lys Asn Ser Ser Val Gly Pro Leu Tyr Ser Gly
                4760            4765            4770
```

-continued

Cys Arg Leu Ile Ser Leu Arg Ser Glu Lys Asp Gly Ala Ala Thr
                4775                4780                4785

Gly Val Asp Ala Ile Cys Thr His His Leu Asn Pro Gln Ser Pro
                4790                4795                4800

Gly Leu Asp Arg Glu Gln Leu Tyr Trp Gln Leu Ser Gln Met Thr
                4805                4810                4815

Asn Gly Ile Lys Glu Leu Gly Pro Tyr Thr Leu Asp Arg Asn Ser
                4820                4825                4830

Leu Tyr Val Asn Gly Phe Thr His Arg Ser Ser Gly Leu Thr Thr
                4835                4840                4845

Ser Thr Pro Trp Thr Ser Thr Val Asp Leu Gly Thr Ser Gly Thr
                4850                4855                4860

Pro Ser Pro Val Pro Ser Pro Thr Thr Ala Gly Pro Leu Leu Val
                4865                4870                4875

Pro Phe Thr Leu Asn Phe Thr Ile Thr Asn Leu Gln Tyr Glu Glu
                4880                4885                4890

Asp Met His Arg Pro Gly Ser Arg Lys Phe Asn Ala Thr Glu Arg
                4895                4900                4905

Val Leu Gln Gly Leu Leu Ser Pro Ile Phe Lys Asn Ser Ser Val
                4910                4915                4920

Gly Pro Leu Tyr Ser Gly Cys Arg Leu Thr Ser Leu Arg Pro Glu
                4925                4930                4935

Lys Asp Gly Ala Ala Thr Gly Met Asp Ala Val Cys Leu Tyr His
                4940                4945                4950

Pro Asn Pro Lys Arg Pro Gly Leu Asp Arg Glu Gln Leu Tyr Trp
                4955                4960                4965

Glu Leu Ser Gln Leu Thr His Asn Ile Thr Glu Leu Gly Pro Tyr
                4970                4975                4980

Ser Leu Asp Arg Asp Ser Leu Tyr Val Asn Gly Phe Thr His Gln
                4985                4990                4995

Asn Ser Val Pro Thr Thr Ser Thr Pro Gly Thr Ser Thr Val Tyr
                5000                5005                5010

Trp Ala Thr Thr Gly Thr Pro Ser Ser Phe Pro Gly His Thr Glu
                5015                5020                5025

Pro Gly Pro Leu Leu Ile Pro Phe Thr Phe Asn Phe Thr Ile Thr
                5030                5035                5040

Asn Leu His Tyr Glu Glu Asn Met Gln His Pro Gly Ser Arg Lys
                5045                5050                5055

Phe Asn Thr Thr Glu Arg Val Leu Gln Gly Leu Leu Lys Pro Leu
                5060                5065                5070

Phe Lys Asn Thr Ser Val Gly Pro Leu Tyr Ser Gly Cys Arg Leu
                5075                5080                5085

Thr Leu Leu Arg Pro Glu Lys Gln Glu Ala Ala Thr Gly Val Asp
                5090                5095                5100

Thr Ile Cys Thr His Arg Val Asp Pro Ile Gly Pro Gly Leu Asp
                5105                5110                5115

Arg Glu Arg Leu Tyr Trp Glu Leu Ser Gln Leu Thr Asn Ser Ile
                5120                5125                5130

Thr Glu Leu Gly Pro Tyr Thr Leu Asp Arg Asp Ser Leu Tyr Val
                5135                5140                5145

Asn Gly Phe Asn Pro Trp Ser Ser Val Pro Thr Thr Ser Thr Pro
                5150                5155                5160

Gly Thr Ser Thr Val His Leu Ala Thr Ser Gly Thr Pro Ser Ser
                5165                5170                5175

```
Leu Pro Gly His Thr Ala Pro Val Pro Leu Leu Ile Pro Phe Thr
                5180                5185                5190
Leu Asn Phe Thr Ile Thr Asn Leu His Tyr Glu Glu Asn Met Gln
                5195                5200                5205
His Pro Gly Ser Arg Lys Phe Asn Thr Thr Glu Arg Val Leu Gln
                5210                5215                5220
Gly Leu Leu Lys Pro Leu Phe Lys Ser Thr Ser Val Gly Pro Leu
                5225                5230                5235
Tyr Ser Gly Cys Arg Leu Thr Leu Leu Arg Pro Glu Lys His Gly
                5240                5245                5250
Ala Ala Thr Gly Val Asp Ala Ile Cys Thr Leu Arg Leu Asp Pro
                5255                5260                5265
Thr Gly Pro Gly Leu Asp Arg Glu Arg Leu Tyr Trp Glu Leu Ser
                5270                5275                5280
Gln Leu Thr Asn Ser Val Thr Glu Leu Gly Pro Tyr Thr Leu Asp
                5285                5290                5295
Arg Asp Ser Leu Tyr Val Asn Gly Phe Thr His Arg Ser Ser Val
                5300                5305                5310
Pro Thr Thr Ser Ile Pro Gly Thr Ser Ala Val His Leu Glu Thr
                5315                5320                5325
Ser Gly Thr Pro Ala Ser Leu Pro Gly His Thr Ala Pro Gly Pro
                5330                5335                5340
Leu Leu Val Pro Phe Thr Leu Asn Phe Thr Ile Thr Asn Leu Gln
                5345                5350                5355
Tyr Glu Glu Asp Met Arg His Pro Gly Ser Arg Lys Phe Asn Thr
                5360                5365                5370
Thr Glu Arg Val Leu Gln Gly Leu Leu Lys Pro Leu Phe Lys Ser
                5375                5380                5385
Thr Ser Val Gly Pro Leu Tyr Ser Gly Cys Arg Leu Thr Leu Leu
                5390                5395                5400
Arg Pro Glu Lys Arg Gly Ala Ala Thr Gly Val Asp Thr Ile Cys
                5405                5410                5415
Thr His Arg Leu Asp Pro Leu Asn Pro Gly Leu Asp Arg Glu Gln
                5420                5425                5430
Leu Tyr Trp Glu Leu Ser Lys Leu Thr Arg Gly Ile Ile Glu Leu
                5435                5440                5445
Gly Pro Tyr Leu Leu Asp Arg Gly Ser Leu Tyr Val Asn Gly Phe
                5450                5455                5460
Thr His Arg Asn Phe Val Pro Ile Thr Ser Thr Pro Gly Thr Ser
                5465                5470                5475
Thr Val His Leu Gly Thr Ser Glu Thr Pro Ser Ser Leu Pro Arg
                5480                5485                5490
Pro Ile Val Pro Gly Pro Leu Leu Val Pro Phe Thr Leu Asn Phe
                5495                5500                5505
Thr Ile Thr Asn Leu Gln Tyr Glu Glu Ala Met Arg His Pro Gly
                5510                5515                5520
Ser Arg Lys Phe Asn Thr Thr Glu Arg Val Leu Gln Gly Leu Leu
                5525                5530                5535
Arg Pro Leu Phe Lys Asn Thr Ser Ile Gly Pro Leu Tyr Ser Ser
                5540                5545                5550
Cys Arg Leu Thr Leu Leu Arg Pro Glu Lys Asp Lys Ala Ala Thr
                5555                5560                5565
Arg Val Asp Ala Ile Cys Thr His His Pro Asp Pro Gln Ser Pro
```

```
                        5570              5575              5580
Gly Leu Asn Arg Glu Gln Leu Tyr Trp Glu Leu Ser Gln Leu Thr
                        5585              5590              5595
His Gly Ile Thr Glu Leu Gly Pro Tyr Thr Leu Asp Arg Asp Ser
                        5600              5605              5610
Leu Tyr Val Asp Gly Phe Thr His Trp Ser Pro Ile Pro Thr Thr
                        5615              5620              5625
Ser Thr Pro Gly Thr Ser Ile Val Asn Leu Gly Thr Ser Gly Ile
                        5630              5635              5640
Pro Pro Ser Leu Pro Glu Thr Thr Ala Thr Gly Pro Leu Leu Val
                        5645              5650              5655
Pro Phe Thr Leu Asn Phe Thr Ile Thr Asn Leu Gln Tyr Glu Glu
                        5660              5665              5670
Asn Met Gly His Pro Gly Ser Arg Lys Phe Asn Ile Thr Glu Ser
                        5675              5680              5685
Val Leu Gln Gly Leu Leu Lys Pro Leu Phe Lys Ser Thr Ser Val
                        5690              5695              5700
Gly Pro Leu Tyr Ser Gly Cys Arg Leu Thr Leu Leu Arg Pro Glu
                        5705              5710              5715
Lys Asp Gly Val Ala Thr Arg Val Asp Ala Ile Cys Thr His Arg
                        5720              5725              5730
Pro Asp Pro Lys Ile Pro Gly Leu Asp Arg Gln Gln Leu Tyr Trp
                        5735              5740              5745
Glu Leu Ser Gln Leu Thr His Ser Ile Thr Glu Leu Gly Pro Tyr
                        5750              5755              5760
Thr Leu Asp Arg Asp Ser Leu Tyr Val Asn Gly Phe Thr Gln Arg
                        5765              5770              5775
Ser Ser Val Pro Thr Thr Ser Thr Pro Gly Thr Phe Thr Val Gln
                        5780              5785              5790
Pro Glu Thr Ser Glu Thr Pro Ser Ser Leu Pro Gly Pro Thr Ala
                        5795              5800              5805
Thr Gly Pro Val Leu Leu Pro Phe Thr Leu Asn Phe Thr Ile Ile
                        5810              5815              5820
Asn Leu Gln Tyr Glu Glu Asp Met His Arg Pro Gly Ser Arg Lys
                        5825              5830              5835
Phe Asn Thr Thr Glu Arg Val Leu Gln Gly Leu Leu Met Pro Leu
                        5840              5845              5850
Phe Lys Asn Thr Ser Val Ser Ser Leu Tyr Ser Gly Cys Arg Leu
                        5855              5860              5865
Thr Leu Leu Arg Pro Glu Lys Asp Gly Ala Ala Thr Arg Val Asp
                        5870              5875              5880
Ala Val Cys Thr His Arg Pro Asp Pro Lys Ser Pro Gly Leu Asp
                        5885              5890              5895
Arg Glu Arg Leu Tyr Trp Lys Leu Ser Gln Leu Thr His Gly Ile
                        5900              5905              5910
Thr Glu Leu Gly Pro Tyr Thr Leu Asp Arg His Ser Leu Tyr Val
                        5915              5920              5925
Asn Gly Phe Thr His Gln Ser Ser Met Thr Thr Thr Arg Thr Pro
                        5930              5935              5940
Asp Thr Ser Thr Met His Leu Ala Thr Ser Arg Thr Pro Ala Ser
                        5945              5950              5955
Leu Ser Gly Pro Thr Thr Ala Ser Pro Leu Leu Val Leu Phe Thr
                        5960              5965              5970
```

-continued

```
Ile Asn Phe Thr Ile Thr Asn Leu Arg Tyr Glu Glu Asn Met His
            5975                5980                5985

His Pro Gly Ser Arg Lys Phe Asn Thr Thr Glu Arg Val Leu Gln
            5990                5995                6000

Gly Leu Leu Arg Pro Val Phe Lys Asn Thr Ser Val Gly Pro Leu
            6005                6010                6015

Tyr Ser Gly Cys Arg Leu Thr Leu Leu Arg Pro Lys Lys Asp Gly
            6020                6025                6030

Ala Ala Thr Lys Val Asp Ala Ile Cys Thr Tyr Arg Pro Asp Pro
            6035                6040                6045

Lys Ser Pro Gly Leu Asp Arg Glu Gln Leu Tyr Trp Glu Leu Ser
            6050                6055                6060

Gln Leu Thr His Ser Ile Thr Glu Leu Gly Pro Tyr Thr Leu Asp
            6065                6070                6075

Arg Asp Ser Leu Tyr Val Asn Gly Phe Thr Gln Arg Ser Ser Val
            6080                6085                6090

Pro Thr Thr Ser Ile Pro Gly Thr Pro Thr Val Asp Leu Gly Thr
            6095                6100                6105

Ser Gly Thr Pro Val Ser Lys Pro Gly Pro Ser Ala Ala Ser Pro
            6110                6115                6120

Leu Leu Val Leu Phe Thr Leu Asn Phe Thr Ile Thr Asn Leu Arg
            6125                6130                6135

Tyr Glu Glu Asn Met Gln His Pro Gly Ser Arg Lys Phe Asn Thr
            6140                6145                6150

Thr Glu Arg Val Leu Gln Gly Leu Leu Arg Ser Leu Phe Lys Ser
            6155                6160                6165

Thr Ser Val Gly Pro Leu Tyr Ser Gly Cys Arg Leu Thr Leu Leu
            6170                6175                6180

Arg Pro Glu Lys Asp Gly Thr Ala Thr Gly Val Asp Ala Ile Cys
            6185                6190                6195

Thr His His Pro Asp Pro Lys Ser Pro Arg Leu Asp Arg Glu Gln
            6200                6205                6210

Leu Tyr Trp Glu Leu Ser Gln Leu Thr His Asn Ile Thr Glu Leu
            6215                6220                6225

Gly Pro Tyr Ala Leu Asp Asn Asp Ser Leu Phe Val Asn Gly Phe
            6230                6235                6240

Thr His Arg Ser Ser Val Ser Thr Thr Ser Thr Pro Gly Thr Pro
            6245                6250                6255

Thr Val Tyr Leu Gly Ala Ser Lys Thr Pro Ala Ser Ile Phe Gly
            6260                6265                6270

Pro Ser Ala Ala Ser His Leu Leu Ile Leu Phe Thr Leu Asn Phe
            6275                6280                6285

Thr Ile Thr Asn Leu Arg Tyr Glu Glu Asn Met Trp Pro Gly Ser
            6290                6295                6300

Arg Lys Phe Asn Thr Thr Glu Arg Val Leu Gln Gly Leu Leu Arg
            6305                6310                6315

Pro Leu Phe Lys Asn Thr Ser Val Gly Pro Leu Tyr Ser Gly Cys
            6320                6325                6330

Arg Leu Thr Leu Leu Arg Pro Glu Lys Asp Gly Glu Ala Thr Gly
            6335                6340                6345

Val Asp Ala Ile Cys Thr His Arg Pro Asp Pro Thr Gly Pro Gly
            6350                6355                6360

Leu Asp Arg Glu Gln Leu Tyr Leu Glu Leu Ser Gln Leu Thr His
            6365                6370                6375
```

```
Ser Ile Thr Glu Leu Gly Pro Tyr Thr Leu Asp Arg Asp Ser Leu
            6380                6385                6390

Tyr Val Asn Gly Phe Thr His Arg Ser Ser Val Pro Thr Thr Ser
            6395                6400                6405

Thr Gly Val Val Ser Glu Glu Pro Phe Thr Leu Asn Phe Thr Ile
            6410                6415                6420

Asn Asn Leu Arg Tyr Met Ala Asp Met Gly Gln Pro Gly Ser Leu
            6425                6430                6435

Lys Phe Asn Ile Thr Asp Asn Val Met Gln His Leu Leu Ser Pro
            6440                6445                6450

Leu Phe Gln Arg Ser Ser Leu Gly Ala Arg Tyr Thr Gly Cys Arg
            6455                6460                6465

Val Ile Ala Leu Arg Ser Val Lys Asn Gly Ala Glu Thr Arg Val
            6470                6475                6480

Asp Leu Leu Cys Thr Tyr Leu Gln Pro Leu Ser Gly Pro Gly Leu
            6485                6490                6495

Pro Ile Lys Gln Val Phe His Glu Leu Ser Gln Gln Thr His Gly
            6500                6505                6510

Ile Thr Arg Leu Gly Pro Tyr Ser Leu Asp Lys Asp Ser Leu Tyr
            6515                6520                6525

Leu Asn Gly Tyr Asn Glu Pro Gly Pro Asp Glu Pro Pro Thr Thr
            6530                6535                6540

Pro Lys Pro Ala Thr Thr Phe Leu Pro Pro Leu Ser Glu Ala Thr
            6545                6550                6555

Thr Ala Met Gly Tyr His Leu Lys Thr Leu Thr Leu Asn Phe Thr
            6560                6565                6570

Ile Ser Asn Leu Gln Tyr Ser Pro Asp Met Gly Lys Gly Ser Ala
            6575                6580                6585

Thr Phe Asn Ser Thr Glu Gly Val Leu Gln His Leu Leu Arg Pro
            6590                6595                6600

Leu Phe Gln Lys Ser Ser Met Gly Pro Phe Tyr Leu Gly Cys Gln
            6605                6610                6615

Leu Ile Ser Leu Arg Pro Glu Lys Asp Gly Ala Ala Thr Gly Val
            6620                6625                6630

Asp Thr Thr Cys Thr Tyr His Pro Asp Pro Val Gly Pro Gly Leu
            6635                6640                6645

Asp Ile Gln Gln Leu Tyr Trp Glu Leu Ser Gln Leu Thr His Gly
            6650                6655                6660

Val Thr Gln Leu Gly Phe Tyr Val Leu Asp Arg Asp Ser Leu Phe
            6665                6670                6675

Ile Asn Gly Tyr Ala Pro Gln Asn Leu Ser Ile Arg Gly Glu Tyr
            6680                6685                6690

Gln Ile Asn Phe His Ile Val Asn Trp Asn Leu Ser Asn Pro Asp
            6695                6700                6705

Pro Thr Ser Ser Glu Tyr Ile Thr Leu Leu Arg Asp Ile Gln Asp
            6710                6715                6720

Lys Val Thr Thr Leu Tyr Lys Gly Ser Gln Leu His Asp Thr Phe
            6725                6730                6735

Arg Phe Cys Leu Val Thr Asn Leu Thr Met Asp Ser Val Leu Val
            6740                6745                6750

Thr Val Lys Ala Leu Phe Ser Ser Asn Leu Asp Pro Ser Leu Val
            6755                6760                6765

Glu Gln Val Phe Leu Asp Lys Thr Leu Asn Ala Ser Phe His Trp
```

-continued

```
                6770                6775                6780
Leu Gly Ser Thr Tyr Gln Leu Val Asp Ile His Val Thr Glu Met
                6785                6790                6795

Glu Ser Ser Val Tyr Gln Pro Thr Ser Ser Ser Thr Gln His
                6800                6805                6810

Phe Tyr Leu Asn Phe Thr Ile Thr Asn Leu Pro Tyr Ser Gln Asp
                6815                6820                6825

Lys Ala Gln Pro Gly Thr Thr Asn Tyr Gln Arg Asn Lys Arg Asn
                6830                6835                6840

Ile Glu Asp Ala Leu Asn Gln Leu Phe Arg Asn Ser Ser Ile Lys
                6845                6850                6855

Ser Tyr Phe Ser Asp Cys Gln Val Ser Thr Phe Arg Ser Val Pro
                6860                6865                6870

Asn Arg His His Thr Gly Val Asp Ser Leu Cys Asn Phe Ser Pro
                6875                6880                6885

Leu Ala Arg Arg Val Asp Arg Val Ala Ile Tyr Glu Glu Phe Leu
                6890                6895                6900

Arg Met Thr Arg Asn Gly Thr Gln Leu Gln Asn Phe Thr Leu Asp
                6905                6910                6915

Arg Ser Ser Val Leu Val Asp Gly Tyr Ser Pro Asn Arg Asn Glu
                6920                6925                6930

Pro Leu Thr Gly Asn Ser Asp Leu Pro Phe Trp Ala Val Ile Leu
                6935                6940                6945

Ile Gly Leu Ala Gly Leu Leu Gly Leu Ile Thr Cys Leu Ile Cys
                6950                6955                6960

Gly Val Leu Val Thr Thr Arg Arg Arg Lys Lys Glu Gly Glu Tyr
                6965                6970                6975

Asn Val Gln Gln Gln Cys Pro Gly Tyr Tyr Gln Ser His Leu Asp
                6980                6985                6990

Leu Glu Asp Leu Gln
                6995

<210> SEQ ID NO 5
<211> LENGTH: 622
<212> TYPE: PRT
<213> ORGANISM: Homo sapiens

<400> SEQUENCE: 5

Met Ala Leu Pro Thr Ala Arg Pro Leu Leu Gly Ser Cys Gly Thr
  1               5                  10                 15

Pro Ala Leu Gly Ser Leu Leu Phe Leu Leu Phe Ser Leu Gly Trp
                 20                  25                 30

Val Gln Pro Ser Arg Thr Leu Ala Gly Glu Thr Gly Gln Glu Ala
                 35                  40                 45

Ala Pro Leu Asp Gly Val Leu Ala Asn Pro Pro Asn Ile Ser Ser
                 50                  55                 60

Leu Ser Pro Arg Gln Leu Leu Gly Phe Pro Cys Ala Glu Val Ser
                 65                  70                 75

Gly Leu Ser Thr Glu Arg Val Arg Glu Leu Ala Val Ala Leu Ala
                 80                  85                 90

Gln Lys Asn Val Lys Leu Ser Thr Glu Gln Leu Arg Cys Leu Ala
                 95                 100                105

His Arg Leu Ser Glu Pro Pro Glu Asp Leu Asp Ala Leu Pro Leu
                110                 115                120

Asp Leu Leu Leu Phe Leu Asn Pro Asp Ala Phe Ser Gly Pro Gln
```

```
                    125                 130                 135
Ala Cys Thr Arg Phe Phe Ser Arg Ile Thr Lys Ala Asn Val Asp
                140                 145                 150

Leu Leu Pro Arg Gly Ala Pro Glu Arg Gln Arg Leu Leu Pro Ala
                155                 160                 165

Ala Leu Ala Cys Trp Gly Val Arg Gly Ser Leu Leu Ser Glu Ala
                170                 175                 180

Asp Val Arg Ala Leu Gly Gly Leu Ala Cys Asp Leu Pro Gly Arg
                185                 190                 195

Phe Val Ala Glu Ser Ala Glu Val Leu Leu Pro Arg Leu Val Ser
                200                 205                 210

Cys Pro Gly Pro Leu Asp Gln Asp Gln Gln Glu Ala Ala Arg Ala
                215                 220                 225

Ala Leu Gln Gly Gly Gly Pro Pro Tyr Gly Pro Ser Thr Trp
                230                 235                 240

Ser Val Ser Thr Met Asp Ala Leu Arg Gly Leu Leu Pro Val Leu
                245                 250                 255

Gly Gln Pro Ile Ile Arg Ser Ile Pro Gln Gly Ile Val Ala Ala
                260                 265                 270

Trp Arg Gln Arg Ser Ser Arg Asp Pro Ser Trp Arg Gln Pro Glu
                275                 280                 285

Arg Thr Ile Leu Arg Pro Arg Phe Arg Arg Glu Val Glu Lys Thr
                290                 295                 300

Ala Cys Pro Ser Gly Lys Lys Ala Arg Glu Ile Asp Glu Ser Leu
                305                 310                 315

Ile Phe Tyr Lys Lys Trp Glu Leu Glu Ala Cys Val Asp Ala Ala
                320                 325                 330

Leu Leu Ala Thr Gln Met Asp Arg Val Asn Ala Ile Pro Phe Thr
                335                 340                 345

Tyr Glu Gln Leu Asp Val Leu Lys His Lys Leu Asp Glu Leu Tyr
                350                 355                 360

Pro Gln Gly Tyr Pro Glu Ser Val Ile Gln His Leu Gly Tyr Leu
                365                 370                 375

Phe Leu Lys Met Ser Pro Glu Asp Ile Arg Lys Trp Asn Val Thr
                380                 385                 390

Ser Leu Glu Thr Leu Lys Ala Leu Leu Glu Val Asn Lys Gly His
                395                 400                 405

Glu Met Ser Pro Gln Val Ala Thr Leu Ile Asp Arg Phe Val Lys
                410                 415                 420

Gly Arg Gly Gln Leu Asp Lys Asp Thr Leu Asp Thr Leu Thr Ala
                425                 430                 435

Phe Tyr Pro Gly Tyr Leu Cys Ser Leu Ser Pro Glu Glu Leu Ser
                440                 445                 450

Ser Val Pro Pro Ser Ser Ile Trp Ala Val Arg Pro Gln Asp Leu
                455                 460                 465

Asp Thr Cys Asp Pro Arg Gln Leu Asp Val Leu Tyr Pro Lys Ala
                470                 475                 480

Arg Leu Ala Phe Gln Asn Met Asn Gly Ser Glu Tyr Phe Val Lys
                485                 490                 495

Ile Gln Ser Phe Leu Gly Gly Ala Pro Thr Glu Asp Leu Lys Ala
                500                 505                 510

Leu Ser Gln Gln Asn Val Ser Met Asp Leu Ala Thr Phe Met Lys
                515                 520                 525
```

-continued

```
Leu Arg Thr Asp Ala Val Leu Pro Leu Thr Val Ala Glu Val Gln
            530                 535                 540

Lys Leu Leu Gly Pro His Val Glu Gly Leu Lys Ala Glu Glu Arg
            545                 550                 555

His Arg Pro Val Arg Asp Trp Ile Leu Arg Gln Arg Gln Asp Asp
            560                 565                 570

Leu Asp Thr Leu Gly Leu Gly Leu Gln Gly Gly Ile Pro Asn Gly
            575                 580                 585

Tyr Leu Val Leu Asp Leu Ser Met Gln Glu Ala Leu Ser Gly Thr
            590                 595                 600

Pro Cys Leu Leu Gly Pro Gly Pro Val Leu Thr Val Leu Ala Leu
            605                 610                 615

Leu Leu Ala Ser Thr Leu Ala
            620

<210> SEQ ID NO 6
<211> LENGTH: 690
<212> TYPE: PRT
<213> ORGANISM: Homo sapiens

<400> SEQUENCE: 6

Met Ala Pro Trp Pro Glu Leu Gly Asp Ala Gln Pro Asn Pro Asp
  1               5                  10                  15

Lys Tyr Leu Glu Gly Ala Ala Gly Gln Gln Pro Thr Ala Pro Asp
             20                  25                  30

Lys Ser Lys Glu Thr Asn Lys Thr Asp Asn Thr Glu Ala Pro Val
             35                  40                  45

Thr Lys Ile Glu Leu Leu Pro Ser Tyr Ser Thr Ala Thr Leu Ile
             50                  55                  60

Asp Glu Pro Thr Glu Val Asp Asp Pro Trp Asn Leu Pro Thr Leu
             65                  70                  75

Gln Asp Ser Gly Ile Lys Trp Ser Glu Arg Asp Thr Lys Gly Lys
             80                  85                  90

Ile Leu Cys Phe Phe Gln Gly Ile Gly Arg Leu Ile Leu Leu Leu
             95                 100                 105

Gly Phe Leu Tyr Phe Phe Val Cys Ser Leu Asp Ile Leu Ser Ser
            110                 115                 120

Ala Phe Gln Leu Val Gly Gly Lys Met Ala Gly Gln Phe Phe Ser
            125                 130                 135

Asn Ser Ser Ile Met Ser Asn Pro Leu Leu Gly Leu Val Ile Gly
            140                 145                 150

Val Leu Val Thr Val Leu Val Gln Ser Ser Thr Ser Thr Ser Ser
            155                 160                 165

Ile Val Val Ser Met Val Ser Ser Leu Leu Thr Val Arg Ala
            170                 175                 180

Ala Ile Pro Ile Ile Met Gly Ala Asn Ile Gly Thr Ser Ile Thr
            185                 190                 195

Asn Thr Ile Val Ala Leu Met Gln Val Gly Asp Arg Ser Glu Phe
            200                 205                 210

Arg Arg Ala Phe Ala Gly Ala Thr Val His Asp Phe Phe Asn Trp
            215                 220                 225

Leu Ser Val Leu Val Leu Leu Pro Val Glu Val Ala Thr His Tyr
            230                 235                 240

Leu Glu Ile Ile Thr Gln Leu Ile Val Glu Ser Phe His Phe Lys
            245                 250                 255
```

-continued

```
Asn Gly Glu Asp Ala Pro Asp Leu Leu Lys Val Ile Thr Lys Pro
            260                 265                 270
Phe Thr Lys Leu Ile Val Gln Leu Asp Lys Lys Val Ile Ser Gln
        275                 280                 285
Ile Ala Met Asn Asp Glu Lys Ala Lys Asn Lys Ser Leu Val Lys
        290                 295                 300
Ile Trp Cys Lys Thr Phe Thr Asn Lys Thr Gln Ile Asn Val Thr
        305                 310                 315
Val Pro Ser Thr Ala Asn Cys Thr Ser Pro Ser Leu Cys Trp Thr
        320                 325                 330
Asp Gly Ile Gln Asn Trp Thr Met Lys Asn Val Thr Tyr Lys Glu
        335                 340                 345
Asn Ile Ala Lys Cys Gln His Ile Phe Val Asn Phe His Leu Pro
        350                 355                 360
Asp Leu Ala Val Gly Thr Ile Leu Leu Ile Leu Ser Leu Leu Val
        365                 370                 375
Leu Cys Gly Cys Leu Ile Met Ile Val Lys Ile Leu Gly Ser Val
        380                 385                 390
Leu Lys Gly Gln Val Ala Thr Val Ile Lys Lys Thr Ile Asn Thr
        395                 400                 405
Asp Phe Pro Phe Pro Phe Ala Trp Leu Thr Gly Tyr Leu Ala Ile
        410                 415                 420
Leu Val Gly Ala Gly Met Thr Phe Ile Val Gln Ser Ser Ser Val
        425                 430                 435
Phe Thr Ser Ala Leu Thr Pro Leu Ile Gly Ile Gly Val Ile Thr
        440                 445                 450
Ile Glu Arg Ala Tyr Pro Leu Thr Leu Gly Ser Asn Ile Gly Thr
        455                 460                 465
Thr Thr Thr Ala Ile Leu Ala Ala Leu Ala Ser Pro Gly Asn Ala
        470                 475                 480
Leu Arg Ser Ser Leu Gln Ile Ala Leu Cys His Phe Phe Phe Asn
        485                 490                 495
Ile Ser Gly Ile Leu Leu Trp Tyr Pro Ile Pro Phe Thr Arg Leu
        500                 505                 510
Pro Ile Arg Met Ala Lys Gly Leu Gly Asn Ile Ser Ala Lys Tyr
        515                 520                 525
Arg Trp Phe Ala Val Phe Tyr Leu Ile Ile Phe Phe Leu Ile
        530                 535                 540
Pro Leu Thr Val Phe Gly Leu Ser Leu Ala Gly Trp Arg Val Leu
        545                 550                 555
Val Gly Val Gly Val Pro Val Val Phe Ile Ile Leu Val Leu
        560                 565                 570
Cys Leu Arg Leu Leu Gln Ser Arg Cys Pro Arg Val Leu Pro Lys
        575                 580                 585
Lys Leu Gln Asn Trp Asn Phe Leu Pro Leu Trp Met Arg Ser Leu
        590                 595                 600
Lys Pro Trp Asp Ala Val Val Ser Lys Phe Thr Gly Cys Phe Gln
        605                 610                 615
Met Arg Cys Cys Tyr Cys Cys Arg Val Cys Cys Arg Ala Cys Cys
        620                 625                 630
Leu Leu Cys Gly Cys Pro Lys Cys Cys Arg Cys Ser Lys Cys Cys
        635                 640                 645
Glu Asp Leu Glu Glu Ala Gln Glu Gly Gln Asp Val Pro Val Lys
        650                 655                 660
```

```
Ala Pro Glu Thr Phe Asp Asn Ile Thr Ile Ser Arg Glu Ala Gln
            665                 670                 675

Gly Glu Val Pro Ala Ser Asp Ser Lys Thr Glu Cys Thr Ala Leu
            680                 685                 690

<210> SEQ ID NO 7
<211> LENGTH: 1093
<212> TYPE: PRT
<213> ORGANISM: Homo sapiens

<400> SEQUENCE: 7

Met Val Leu Ala Gly Pro Leu Ala Val Ser Leu Leu Leu Pro Ser
  1               5                  10                  15

Leu Thr Leu Leu Val Ser His Leu Ser Ser Ser Gln Asp Val Ser
             20                  25                  30

Ser Glu Pro Ser Ser Glu Gln Gln Leu Cys Ala Leu Ser Lys His
             35                  40                  45

Pro Thr Val Ala Phe Glu Asp Leu Gln Pro Trp Val Ser Asn Phe
             50                  55                  60

Thr Tyr Pro Gly Ala Arg Asp Phe Ser Gln Leu Ala Leu Asp Pro
             65                  70                  75

Ser Gly Asn Gln Leu Ile Val Gly Ala Arg Asn Tyr Leu Phe Arg
             80                  85                  90

Leu Ser Leu Ala Asn Val Ser Leu Leu Gln Ala Thr Glu Trp Ala
             95                 100                 105

Ser Ser Glu Asp Thr Arg Arg Ser Cys Gln Ser Lys Gly Lys Thr
            110                 115                 120

Glu Glu Glu Cys Gln Asn Tyr Val Arg Val Leu Ile Val Ala Gly
            125                 130                 135

Arg Lys Val Phe Met Cys Gly Thr Asn Ala Phe Ser Pro Met Cys
            140                 145                 150

Thr Ser Arg Gln Val Gly Asn Leu Ser Arg Thr Thr Glu Lys Ile
            155                 160                 165

Asn Gly Val Ala Arg Cys Pro Tyr Asp Pro Arg His Asn Ser Thr
            170                 175                 180

Ala Val Ile Ser Ser Gln Gly Glu Leu Tyr Ala Ala Thr Val Ile
            185                 190                 195

Asp Phe Ser Gly Arg Asp Pro Ala Ile Tyr Arg Ser Leu Gly Ser
            200                 205                 210

Gly Pro Pro Leu Arg Thr Ala Gln Tyr Asn Ser Lys Trp Leu Asn
            215                 220                 225

Glu Pro Asn Phe Val Ala Ala Tyr Asp Ile Gly Leu Phe Ala Tyr
            230                 235                 240

Phe Phe Leu Arg Glu Asn Ala Val Glu His Asp Cys Gly Arg Thr
            245                 250                 255

Val Tyr Ser Arg Val Ala Arg Val Cys Lys Asn Asp Val Gly Gly
            260                 265                 270

Arg Phe Leu Leu Glu Asp Thr Trp Thr Thr Phe Met Lys Ala Arg
            275                 280                 285

Leu Asn Cys Ser Arg Pro Gly Glu Val Pro Phe Tyr Tyr Asn Glu
            290                 295                 300

Leu Gln Ser Ala Phe His Leu Pro Glu Gln Asp Leu Ile Tyr Gly
            305                 310                 315

Val Phe Thr Thr Asn Val Asn Ser Ile Ala Ala Ser Ala Val Cys
            320                 325                 330
```

```
Ala Phe Asn Leu Ser Ala Ile Ser Gln Ala Phe Asn Gly Pro Phe
            335                 340                 345

Arg Tyr Gln Glu Asn Pro Arg Ala Ala Trp Leu Pro Ile Ala Asn
        350                 355                 360

Pro Ile Pro Asn Phe Gln Cys Gly Thr Leu Pro Glu Thr Gly Pro
    365                 370                 375

Asn Glu Asn Leu Thr Glu Arg Ser Leu Gln Asp Ala Gln Arg Leu
380                 385                 390

Phe Leu Met Ser Glu Ala Val Gln Pro Val Thr Pro Glu Pro Cys
            395                 400                 405

Val Thr Gln Asp Ser Val Arg Phe Ser His Leu Val Val Asp Leu
        410                 415                 420

Val Gln Ala Lys Asp Thr Leu Tyr His Val Leu Tyr Ile Gly Thr
    425                 430                 435

Glu Ser Gly Thr Ile Leu Lys Ala Leu Ser Thr Ala Ser Arg Ser
440                 445                 450

Leu His Gly Cys Tyr Leu Glu Glu Leu His Val Leu Pro Pro Gly
            455                 460                 465

Arg Arg Glu Pro Leu Arg Ser Leu Arg Ile Leu His Ser Ala Arg
        470                 475                 480

Ala Leu Phe Val Gly Leu Arg Asp Gly Val Leu Arg Val Pro Leu
    485                 490                 495

Glu Arg Cys Ala Ala Tyr Arg Ser Gln Gly Ala Cys Leu Gly Ala
500                 505                 510

Arg Asp Pro Tyr Cys Gly Trp Asp Gly Lys Gln Gln Arg Cys Ser
            515                 520                 525

Thr Leu Glu Asp Ser Ser Asn Met Ser Leu Trp Thr Gln Asn Ile
        530                 535                 540

Thr Ala Cys Pro Val Arg Asn Val Thr Arg Asp Gly Gly Phe Gly
    545                 550                 555

Pro Trp Ser Pro Trp Gln Pro Cys Glu His Leu Asp Gly Asp Asn
560                 565                 570

Ser Gly Ser Cys Leu Cys Arg Ala Arg Ser Cys Asp Ser Pro Arg
            575                 580                 585

Pro Arg Cys Gly Gly Leu Asp Cys Leu Gly Pro Ala Ile His Ile
        590                 595                 600

Ala Asn Cys Ser Arg Asn Gly Ala Trp Thr Pro Trp Ser Ser Trp
    605                 610                 615

Ala Leu Cys Ser Thr Ser Cys Gly Ile Gly Phe Gln Val Arg Gln
620                 625                 630

Arg Ser Cys Ser Asn Pro Ala Pro Arg His Gly Gly Arg Ile Cys
            635                 640                 645

Val Gly Lys Ser Arg Glu Glu Arg Phe Cys Asn Glu Asn Thr Pro
        650                 655                 660

Cys Pro Val Pro Ile Phe Trp Ala Ser Trp Gly Ser Trp Ser Lys
    665                 670                 675

Cys Ser Ser Asn Cys Gly Gly Gly Met Gln Ser Arg Arg Arg Ala
680                 685                 690

Cys Glu Asn Gly Asn Ser Cys Leu Gly Cys Val Glu Phe Lys
            695                 700                 705

Thr Cys Asn Pro Glu Gly Cys Pro Glu Val Arg Arg Asn Thr Pro
        710                 715                 720

Trp Thr Pro Trp Leu Pro Val Asn Val Thr Gln Gly Gly Ala Arg
```

```
                    725                 730                 735
Gln Glu Gln Arg Phe Arg Phe Thr Cys Arg Ala Pro Leu Ala Asp
            740                 745                 750
Pro His Gly Leu Gln Phe Gly Arg Arg Thr Glu Thr Arg Thr
            755                 760                 765
Cys Pro Ala Asp Gly Ser Gly Ser Cys Asp Thr Asp Ala Leu Val
            770                 775                 780
Glu Asp Leu Leu Arg Ser Gly Ser Thr Ser Pro His Thr Val Ser
            785                 790                 795
Gly Gly Trp Ala Ala Trp Gly Pro Trp Ser Ser Cys Ser Arg Asp
            800                 805                 810
Cys Glu Leu Gly Phe Arg Val Arg Lys Arg Thr Cys Thr Asn Pro
            815                 820                 825
Glu Pro Arg Asn Gly Gly Leu Pro Cys Val Gly Asp Ala Ala Glu
            830                 835                 840
Tyr Gln Asp Cys Asn Pro Gln Ala Cys Pro Val Arg Gly Ala Trp
            845                 850                 855
Ser Cys Trp Thr Ser Trp Ser Pro Cys Ser Ala Ser Cys Gly Gly
            860                 865                 870
Gly His Tyr Gln Arg Thr Arg Ser Cys Thr Ser Pro Ala Pro Ser
            875                 880                 885
Pro Gly Glu Asp Ile Cys Leu Gly Leu His Thr Glu Glu Ala Leu
            890                 895                 900
Cys Ala Thr Gln Ala Cys Pro Glu Gly Trp Ser Pro Trp Ser Glu
            905                 910                 915
Trp Ser Lys Cys Thr Asp Asp Gly Ala Gln Ser Arg Ser Arg His
            920                 925                 930
Cys Glu Glu Leu Leu Pro Gly Ser Ser Ala Cys Ala Gly Asn Ser
            935                 940                 945
Ser Gln Ser Arg Pro Cys Pro Tyr Ser Glu Ile Pro Val Ile Leu
            950                 955                 960
Pro Ala Ser Ser Met Glu Glu Ala Thr Gly Cys Ala Gly Phe Asn
            965                 970                 975
Leu Ile His Leu Val Ala Thr Gly Ile Ser Cys Phe Leu Gly Ser
            980                 985                 990
Gly Leu Leu Thr Leu Ala Val Tyr Leu Ser Cys Gln His Cys Gln
            995                 1000                1005
Arg Gln Ser Gln Glu Ser Thr Leu Val His Pro Ala Thr Pro Asn
            1010                1015                1020
His Leu His Tyr Lys Gly Gly Thr Pro Lys Asn Glu Lys Tyr
            1025                1030                1035
Thr Pro Met Glu Phe Lys Thr Leu Asn Lys Asn Asn Leu Ile Pro
            1040                1045                1050
Asp Asp Arg Ala Asn Phe Tyr Pro Leu Gln Gln Thr Asn Val Tyr
            1055                1060                1065
Thr Thr Thr Tyr Tyr Pro Ser Pro Leu Asn Lys His Ser Phe Arg
            1070                1075                1080
Pro Glu Ala Ser Pro Gly Gln Arg Cys Phe Pro Asn Ser
            1085                1090

<210> SEQ ID NO 8
<211> LENGTH: 141
<212> TYPE: PRT
<213> ORGANISM: Homo sapiens
```

```
<400> SEQUENCE: 8

Met Trp Val Leu Gly Ile Ala Ala Thr Phe Cys Gly Leu Phe Leu
  1               5                  10                  15

Leu Pro Gly Phe Ala Leu Gln Ile Gln Cys Tyr Gln Cys Glu Glu
                 20                  25                  30

Phe Gln Leu Asn Asn Asp Cys Ser Ser Pro Glu Phe Ile Val Asn
                 35                  40                  45

Cys Thr Val Asn Val Gln Asp Met Cys Gln Lys Glu Val Met Glu
                 50                  55                  60

Gln Ser Ala Gly Ile Met Tyr Arg Lys Ser Cys Ala Ser Ser Ala
                 65                  70                  75

Ala Cys Leu Ile Ala Ser Ala Gly Tyr Gln Ser Phe Cys Ser Pro
                 80                  85                  90

Gly Lys Leu Asn Ser Val Cys Ile Ser Cys Cys Asn Thr Pro Leu
                 95                 100                 105

Cys Asn Gly Pro Arg Pro Lys Lys Arg Gly Ser Ser Ala Ser Ala
                110                 115                 120

Leu Arg Pro Gly Leu Arg Thr Thr Ile Leu Phe Leu Lys Leu Ala
                125                 130                 135

Leu Phe Ser Ala His Cys
                140

<210> SEQ ID NO 9
<211> LENGTH: 442
<212> TYPE: PRT
<213> ORGANISM: Homo sapiens

<400> SEQUENCE: 9

Met Gln Pro Pro Pro Ser Leu Cys Gly Arg Ala Leu Val Ala Leu
  1               5                  10                  15

Val Leu Ala Cys Gly Leu Ser Arg Ile Trp Gly Glu Glu Arg Gly
                 20                  25                  30

Phe Pro Pro Asp Arg Ala Thr Pro Leu Leu Gln Thr Ala Glu Ile
                 35                  40                  45

Met Thr Pro Pro Thr Lys Thr Leu Trp Pro Lys Gly Ser Asn Ala
                 50                  55                  60

Ser Leu Ala Arg Ser Leu Ala Pro Ala Glu Val Pro Lys Gly Asp
                 65                  70                  75

Arg Thr Ala Gly Ser Pro Pro Arg Thr Ile Ser Pro Pro Pro Cys
                 80                  85                  90

Gln Gly Pro Ile Glu Ile Lys Glu Thr Phe Lys Tyr Ile Asn Thr
                 95                 100                 105

Val Val Ser Cys Leu Val Phe Val Leu Gly Ile Ile Gly Asn Ser
                110                 115                 120

Thr Leu Leu Arg Ile Ile Tyr Lys Asn Lys Cys Met Arg Asn Gly
                125                 130                 135

Pro Asn Ile Leu Ile Ala Ser Leu Ala Leu Gly Asp Leu Leu His
                140                 145                 150

Ile Val Ile Asp Ile Pro Ile Asn Val Tyr Lys Leu Leu Ala Glu
                155                 160                 165

Asp Trp Pro Phe Gly Ala Glu Met Cys Lys Leu Val Pro Phe Ile
                170                 175                 180

Gln Lys Ala Ser Val Gly Ile Thr Val Leu Ser Leu Cys Ala Leu
                185                 190                 195

Ser Ile Asp Arg Tyr Arg Ala Val Ala Ser Trp Ser Arg Ile Lys
```

-continued

```
                   200                 205                 210
Gly Ile Gly Val Pro Lys Trp Thr Ala Val Glu Ile Val Leu Ile
               215                 220                 225
Trp Val Val Ser Val Val Leu Ala Val Pro Glu Ala Ile Gly Phe
               230                 235                 240
Asp Ile Ile Thr Met Asp Tyr Lys Gly Ser Tyr Leu Arg Ile Cys
               245                 250                 255
Leu Leu His Pro Val Gln Lys Thr Ala Phe Met Gln Phe Tyr Lys
               260                 265                 270
Thr Ala Lys Asp Trp Trp Leu Phe Ser Phe Tyr Phe Cys Leu Pro
               275                 280                 285
Leu Ala Ile Thr Ala Phe Phe Tyr Thr Leu Met Thr Cys Glu Met
               290                 295                 300
Leu Arg Lys Lys Ser Gly Met Gln Ile Ala Leu Asn Asp His Leu
               305                 310                 315
Lys Gln Arg Arg Glu Val Ala Lys Thr Val Phe Cys Leu Val Leu
               320                 325                 330
Val Phe Ala Leu Cys Trp Leu Pro Leu His Leu Ser Arg Ile Leu
               335                 340                 345
Lys Leu Thr Leu Tyr Asn Gln Asn Asp Pro Asn Arg Cys Glu Leu
               350                 355                 360
Leu Ser Phe Leu Leu Val Leu Asp Tyr Ile Gly Ile Asn Met Ala
               365                 370                 375
Ser Leu Asn Ser Cys Ile Asn Pro Ile Ala Leu Tyr Leu Val Ser
               380                 385                 390
Lys Arg Phe Lys Asn Cys Phe Lys Ser Cys Leu Cys Cys Trp Cys
               395                 400                 405
Gln Ser Phe Glu Glu Lys Gln Ser Leu Glu Glu Lys Gln Ser Cys
               410                 415                 420
Leu Lys Phe Lys Ala Asn Asp His Gly Tyr Asp Asn Phe Arg Ser
               425                 430                 435
Ser Asn Lys Tyr Ser Ser Ser
               440

<210> SEQ ID NO 10
<211> LENGTH: 783
<212> TYPE: PRT
<213> ORGANISM: Homo sapiens

<400> SEQUENCE: 10

Met Ser Gly Gly His Gln Leu Gln Leu Ala Ala Leu Trp Pro Trp
  1               5                  10                  15
Leu Leu Met Ala Thr Leu Gln Ala Gly Phe Gly Arg Thr Gly Leu
                 20                  25                  30
Val Leu Ala Ala Ala Val Glu Ser Glu Arg Ser Ala Glu Gln Lys
                 35                  40                  45
Ala Ile Ile Arg Val Ile Pro Leu Lys Met Asp Pro Thr Gly Lys
                 50                  55                  60
Leu Asn Leu Thr Leu Glu Gly Val Phe Ala Gly Val Ala Glu Ile
                 65                  70                  75
Thr Pro Ala Glu Gly Lys Leu Met Gln Ser His Pro Leu Tyr Leu
                 80                  85                  90
Cys Asn Ala Ser Asp Asp Asp Asn Leu Glu Pro Gly Phe Ile Ser
                 95                 100                 105
Ile Val Lys Leu Glu Ser Pro Arg Arg Ala Pro Arg Pro Cys Leu
```

-continued

```
                110                 115                 120
Ser Leu Ala Ser Lys Ala Arg Met Ala Gly Glu Arg Gly Ala Ser
                125                 130                 135
Ala Val Leu Phe Asp Ile Thr Glu Asp Arg Ala Ala Ala Glu Gln
                140                 145                 150
Leu Gln Gln Pro Leu Gly Leu Thr Trp Pro Val Val Leu Ile Trp
                155                 160                 165
Gly Asn Asp Ala Glu Lys Leu Met Glu Phe Val Tyr Lys Asn Gln
                170                 175                 180
Lys Ala His Val Arg Ile Glu Leu Lys Glu Pro Pro Ala Trp Pro
                185                 190                 195
Asp Tyr Asp Val Trp Ile Leu Met Thr Val Val Gly Thr Ile Phe
                200                 205                 210
Val Ile Ile Leu Ala Ser Val Leu Arg Ile Arg Cys Arg Pro Arg
                215                 220                 225
His Ser Arg Pro Asp Pro Leu Gln Gln Arg Thr Ala Trp Ala Ile
                230                 235                 240
Ser Gln Leu Ala Thr Arg Arg Tyr Gln Ala Ser Cys Arg Gln Ala
                245                 250                 255
Arg Gly Glu Trp Pro Asp Ser Gly Ser Ser Cys Ser Ser Ala Pro
                260                 265                 270
Val Cys Ala Ile Cys Leu Glu Glu Phe Ser Glu Gly Gln Glu Leu
                275                 280                 285
Arg Val Ile Ser Cys Leu His Glu Phe His Arg Asn Cys Val Asp
                290                 295                 300
Pro Trp Leu His Gln His Arg Thr Cys Pro Leu Cys Val Phe Asn
                305                 310                 315
Ile Thr Glu Gly Asp Ser Phe Ser Gln Ser Leu Gly Pro Ser Arg
                320                 325                 330
Ser Tyr Gln Glu Pro Gly Arg Arg Leu His Leu Ile Arg Gln His
                335                 340                 345
Pro Gly His Ala His Tyr His Leu Pro Ala Ala Tyr Leu Leu Gly
                350                 355                 360
Pro Ser Arg Ser Ala Val Ala Arg Pro Arg Pro Gly Pro Phe
                365                 370                 375
Leu Pro Ser Gln Glu Pro Gly Met Gly Pro Arg His His Arg Phe
                380                 385                 390
Pro Arg Ala Ala His Pro Arg Ala Pro Gly Glu Gln Gln Arg Leu
                395                 400                 405
Ala Gly Ala Gln His Pro Tyr Ala Gln Gly Trp Gly Met Ser His
                410                 415                 420
Leu Gln Ser Thr Ser Gln His Pro Ala Ala Cys Pro Val Pro Leu
                425                 430                 435
Arg Arg Ala Arg Pro Pro Asp Ser Ser Gly Ser Gly Glu Ser Tyr
                440                 445                 450
Cys Thr Glu Arg Ser Gly Tyr Leu Ala Asp Gly Pro Ala Ser Asp
                455                 460                 465
Ser Ser Ser Gly Pro Cys His Gly Ser Ser Ser Asp Ser Val Val
                470                 475                 480
Asn Cys Thr Asp Ile Ser Leu Gln Gly Val His Gly Ser Ser Ser
                485                 490                 495
Thr Phe Cys Ser Ser Leu Ser Ser Asp Phe Asp Pro Leu Val Tyr
                500                 505                 510
```

-continued

```
Cys Ser Pro Lys Gly Asp Pro Gln Arg Val Asp Met Gln Pro Ser
            515                 520                 525

Val Thr Ser Arg Pro Arg Ser Leu Asp Ser Val Val Pro Thr Gly
            530                 535                 540

Glu Thr Gln Val Ser Ser His Val His Tyr His Arg His Arg His
            545                 550                 555

His His Tyr Lys Lys Arg Phe Gln Trp His Gly Arg Lys Pro Gly
            560                 565                 570

Pro Glu Thr Gly Val Pro Gln Ser Arg Pro Pro Ile Pro Arg Thr
            575                 580                 585

Gln Pro Gln Pro Glu Pro Pro Ser Pro Asp Gln Gln Val Thr Gly
            590                 595                 600

Ser Asn Ser Ala Ala Pro Ser Gly Arg Leu Ser Asn Pro Gln Cys
            605                 610                 615

Pro Arg Ala Leu Pro Glu Pro Ala Pro Gly Pro Val Asp Ala Ser
            620                 625                 630

Ser Ile Cys Pro Ser Thr Ser Ser Leu Phe Asn Leu Gln Lys Ser
            635                 640                 645

Ser Leu Ser Ala Arg His Pro Gln Arg Lys Arg Arg Gly Gly Pro
            650                 655                 660

Ser Glu Pro Thr Pro Gly Ser Arg Pro Gln Asp Ala Thr Val His
            665                 670                 675

Pro Ala Cys Gln Ile Phe Pro His Tyr Thr Pro Ser Val Ala Tyr
            680                 685                 690

Pro Trp Ser Pro Glu Ala His Pro Leu Ile Cys Gly Pro Pro Gly
            695                 700                 705

Leu Asp Lys Arg Leu Leu Pro Glu Thr Pro Gly Pro Cys Tyr Ser
            710                 715                 720

Asn Ser Gln Pro Val Trp Leu Cys Leu Thr Pro Arg Gln Pro Leu
            725                 730                 735

Glu Pro His Pro Pro Gly Glu Gly Pro Ser Glu Trp Ser Ser Asp
            740                 745                 750

Thr Ala Glu Gly Arg Pro Cys Pro Tyr Pro His Cys Gln Val Leu
            755                 760                 765

Ser Ala Gln Pro Gly Ser Glu Glu Leu Glu Glu Leu Cys Glu
            770                 775                 780

Gln Ala Val

<210> SEQ ID NO 11
<211> LENGTH: 490
<212> TYPE: PRT
<213> ORGANISM: Homo sapiens

<400> SEQUENCE: 11

Met Glu Ser Ile Ser Met Met Gly Ser Pro Lys Ser Leu Ser Glu
  1               5                  10                  15

Thr Val Leu Pro Asn Gly Ile Asn Gly Ile Lys Asp Ala Arg Lys
            20                  25                  30

Val Thr Val Gly Val Ile Gly Ser Gly Asp Phe Ala Lys Ser Leu
            35                  40                  45

Thr Ile Arg Leu Ile Arg Cys Gly Tyr His Val Val Ile Gly Ser
            50                  55                  60

Arg Asn Pro Lys Phe Ala Ser Glu Phe Phe Pro His Val Val Asp
            65                  70                  75

Val Thr His His Glu Asp Ala Leu Thr Lys Thr Asn Ile Ile Phe
```

```
                    80                  85                  90
Val Ala Ile His Arg Glu His Tyr Thr Ser Leu Trp Asp Leu Arg
                95                 100                 105
His Leu Leu Val Gly Lys Ile Leu Ile Asp Val Ser Asn Asn Met
               110                 115                 120
Arg Ile Asn Gln Tyr Pro Glu Ser Asn Ala Glu Tyr Leu Ala Ser
               125                 130                 135
Leu Phe Pro Asp Ser Leu Ile Val Lys Gly Phe Asn Val Val Ser
               140                 145                 150
Ala Trp Ala Leu Gln Leu Gly Pro Lys Asp Ala Ser Arg Gln Val
               155                 160                 165
Tyr Ile Cys Ser Asn Asn Ile Gln Ala Arg Gln Gln Val Ile Glu
               170                 175                 180
Leu Ala Arg Gln Leu Asn Phe Ile Pro Ile Asp Leu Gly Ser Leu
               185                 190                 195
Ser Ser Ala Arg Glu Ile Glu Asn Leu Pro Leu Arg Leu Phe Thr
               200                 205                 210
Leu Trp Arg Gly Pro Val Val Ala Ile Ser Leu Ala Thr Phe
               215                 220                 225
Phe Phe Leu Tyr Ser Phe Val Arg Asp Val Ile His Pro Tyr Ala
               230                 235                 240
Arg Asn Gln Gln Ser Asp Phe Tyr Lys Ile Pro Ile Glu Ile Val
               245                 250                 255
Asn Lys Thr Leu Pro Ile Val Ala Ile Thr Leu Leu Ser Leu Val
               260                 265                 270
Tyr Leu Ala Gly Leu Leu Ala Ala Ala Tyr Gln Leu Tyr Tyr Gly
               275                 280                 285
Thr Lys Tyr Arg Arg Phe Pro Pro Trp Leu Glu Thr Trp Leu Gln
               290                 295                 300
Cys Arg Lys Gln Leu Gly Leu Leu Ser Phe Phe Ala Met Val
               305                 310                 315
His Val Ala Tyr Ser Leu Cys Leu Pro Met Arg Arg Ser Glu Arg
               320                 325                 330
Tyr Leu Phe Leu Asn Met Ala Tyr Gln Gln Val His Ala Asn Ile
               335                 340                 345
Glu Asn Ser Trp Asn Glu Glu Val Trp Arg Ile Glu Met Tyr
               350                 355                 360
Ile Ser Phe Gly Ile Met Ser Leu Gly Leu Leu Ser Leu Leu Ala
               365                 370                 375
Val Thr Ser Ile Pro Ser Val Ser Asn Ala Leu Asn Trp Arg Glu
               380                 385                 390
Phe Ser Phe Ile Gln Ser Thr Leu Gly Tyr Val Ala Leu Leu Ile
               395                 400                 405
Ser Thr Phe His Val Leu Ile Tyr Gly Trp Lys Arg Ala Phe Glu
               410                 415                 420
Glu Glu Tyr Tyr Arg Phe Tyr Thr Pro Pro Asn Phe Val Leu Ala
               425                 430                 435
Leu Val Leu Pro Ser Ile Val Ile Leu Gly Lys Ile Ile Leu Phe
               440                 445                 450
Leu Pro Cys Ile Ser Gln Lys Leu Lys Arg Ile Lys Lys Gly Trp
               455                 460                 465
Glu Lys Ser Gln Phe Leu Glu Glu Gly Ile Gly Gly Thr Ile Pro
               470                 475                 480
```

His Val Ser Pro Glu Arg Val Thr Val Met
              485             490

<210> SEQ ID NO 12
<211> LENGTH: 1214
<212> TYPE: PRT
<213> ORGANISM: Homo sapiens

<400> SEQUENCE: 12

Met Val Val Pro Glu Lys Glu Gln Ser Trp Ile Pro Lys Ile Phe
 1               5                  10                  15

Lys Lys Lys Thr Cys Thr Thr Phe Ile Val Asp Ser Thr Asp Pro
                20                  25                  30

Gly Gly Thr Leu Cys Gln Cys Gly Arg Pro Arg Thr Ala His Pro
                35                  40                  45

Ala Val Ala Met Glu Asp Ala Phe Gly Ala Ala Val Val Thr Val
                50                  55                  60

Trp Asp Ser Asp Ala His Thr Thr Glu Lys Pro Thr Asp Ala Tyr
                65                  70                  75

Gly Glu Leu Asp Phe Thr Gly Ala Gly Arg Lys His Ser Asn Phe
                80                  85                  90

Leu Arg Leu Ser Asp Arg Thr Asp Pro Ala Ala Val Tyr Ser Leu
                95                 100                 105

Val Thr Arg Thr Trp Gly Phe Arg Ala Pro Asn Leu Val Val Ser
               110                 115                 120

Val Leu Gly Gly Ser Gly Gly Pro Val Leu Gln Thr Trp Leu Gln
               125                 130                 135

Asp Leu Leu Arg Arg Gly Leu Val Arg Ala Ala Gln Ser Thr Gly
               140                 145                 150

Ala Trp Ile Val Thr Gly Gly Leu His Thr Gly Ile Gly Arg His
               155                 160                 165

Val Gly Val Ala Val Arg Asp His Gln Met Ala Ser Thr Gly Gly
               170                 175                 180

Thr Lys Val Val Ala Met Gly Val Ala Pro Trp Gly Val Val Arg
               185                 190                 195

Asn Arg Asp Thr Leu Ile Asn Pro Lys Gly Ser Phe Pro Ala Arg
               200                 205                 210

Tyr Arg Trp Arg Gly Asp Pro Glu Asp Gly Val Gln Phe Pro Leu
               215                 220                 225

Asp Tyr Asn Tyr Ser Ala Phe Phe Leu Val Asp Asp Gly Thr His
               230                 235                 240

Gly Cys Leu Gly Gly Glu Asn Arg Phe Arg Leu Arg Leu Glu Ser
               245                 250                 255

Tyr Ile Ser Gln Gln Lys Thr Gly Val Gly Gly Thr Gly Ile Asp
               260                 265                 270

Ile Pro Val Leu Leu Leu Leu Ile Asp Gly Asp Glu Lys Met Leu
               275                 280                 285

Thr Arg Ile Glu Asn Ala Thr Gln Ala Gln Leu Pro Cys Leu Leu
               290                 295                 300

Val Ala Gly Ser Gly Gly Ala Ala Asp Cys Leu Ala Glu Thr Leu
               305                 310                 315

Glu Asp Thr Leu Ala Pro Gly Ser Gly Gly Ala Arg Gln Gly Glu
               320                 325                 330

Ala Arg Asp Arg Ile Arg Arg Phe Phe Pro Lys Gly Asp Leu Glu
               335                 340                 345

```
Val Leu Gln Ala Gln Val Glu Arg Ile Met Thr Arg Lys Glu Leu
            350                 355                 360

Leu Thr Val Tyr Ser Ser Glu Asp Gly Ser Glu Glu Phe Glu Thr
            365                 370                 375

Ile Val Leu Lys Ala Leu Val Lys Ala Cys Gly Ser Ser Glu Ala
            380                 385                 390

Ser Ala Tyr Leu Asp Glu Leu Arg Leu Ala Val Ala Trp Asn Arg
            395                 400                 405

Val Asp Ile Ala Gln Ser Glu Leu Phe Arg Gly Asp Ile Gln Trp
            410                 415                 420

Arg Ser Phe His Leu Glu Ala Ser Leu Met Asp Ala Leu Leu Asn
            425                 430                 435

Asp Arg Pro Glu Phe Val Arg Leu Leu Ile Ser His Gly Leu Ser
            440                 445                 450

Leu Gly His Phe Leu Thr Pro Met Arg Leu Ala Gln Leu Tyr Ser
            455                 460                 465

Ala Ala Pro Ser Asn Ser Leu Ile Arg Asn Leu Leu Asp Gln Ala
            470                 475                 480

Ser His Ser Ala Gly Thr Lys Ala Pro Ala Leu Lys Gly Gly Ala
            485                 490                 495

Ala Glu Leu Arg Pro Pro Asp Val Gly His Val Leu Arg Met Leu
            500                 505                 510

Leu Gly Lys Met Cys Ala Pro Arg Tyr Pro Ser Gly Gly Ala Trp
            515                 520                 525

Asp Pro His Pro Gly Gln Gly Phe Gly Glu Ser Met Tyr Leu Leu
            530                 535                 540

Ser Asp Lys Ala Thr Ser Pro Leu Ser Leu Asp Ala Gly Leu Gly
            545                 550                 555

Gln Ala Pro Trp Ser Asp Leu Leu Trp Ala Leu Leu Leu Asn
            560                 565                 570

Arg Ala Gln Met Ala Met Tyr Phe Trp Glu Met Gly Ser Asn Ala
            575                 580                 585

Val Ser Ser Ala Leu Gly Ala Cys Leu Leu Arg Val Met Ala
            590                 595                 600

Arg Leu Glu Pro Asp Ala Glu Ala Ala Arg Arg Lys Asp Leu
            605                 610                 615

Ala Phe Lys Phe Glu Gly Met Gly Val Asp Leu Phe Gly Glu Cys
            620                 625                 630

Tyr Arg Ser Ser Glu Val Arg Ala Ala Arg Leu Leu Leu Arg Arg
            635                 640                 645

Cys Pro Leu Trp Gly Asp Ala Thr Cys Leu Gln Leu Ala Met Gln
            650                 655                 660

Ala Asp Ala Arg Ala Phe Phe Ala Gln Asp Gly Val Gln Ser Leu
            665                 670                 675

Leu Thr Gln Lys Trp Trp Gly Asp Met Ala Ser Thr Thr Pro Ile
            680                 685                 690

Trp Ala Leu Val Leu Ala Phe Phe Cys Pro Pro Leu Ile Tyr Thr
            695                 700                 705

Arg Leu Ile Thr Phe Arg Lys Ser Glu Glu Pro Thr Arg Glu
            710                 715                 720

Glu Leu Glu Phe Asp Met Asp Ser Val Ile Asn Gly Glu Gly Pro
            725                 730                 735

Val Gly Thr Ala Asp Pro Ala Glu Lys Thr Pro Leu Gly Val Pro
            740                 745                 750
```

```
Arg Gln Ser Gly Arg Pro Gly Cys Cys Gly Arg Cys Gly Gly
            755                 760                 765
Arg Arg Cys Leu Arg Arg Trp Phe His Phe Trp Gly Ala Pro Val
            770                 775                 780
Thr Ile Phe Met Gly Asn Val Val Ser Tyr Leu Leu Phe Leu Leu
            785                 790                 795
Leu Phe Ser Arg Val Leu Leu Val Asp Phe Gln Pro Ala Pro Pro
            800                 805                 810
Gly Ser Leu Glu Leu Leu Leu Tyr Phe Trp Ala Phe Thr Leu Leu
            815                 820                 825
Cys Glu Glu Leu Arg Gln Gly Leu Ser Gly Gly Gly Ser Leu
            830                 835                 840
Ala Ser Gly Gly Pro Gly Pro Gly His Ala Ser Leu Ser Gln Arg
            845                 850                 855
Leu Arg Leu Tyr Leu Ala Asp Ser Trp Asn Gln Cys Asp Leu Val
            860                 865                 870
Ala Leu Thr Cys Phe Leu Leu Gly Val Gly Cys Arg Leu Thr Pro
            875                 880                 885
Gly Leu Tyr His Leu Gly Arg Thr Val Leu Cys Ile Asp Phe Met
            890                 895                 900
Val Phe Thr Val Arg Leu Leu His Ile Phe Thr Val Asn Lys Gln
            905                 910                 915
Leu Gly Pro Lys Ile Val Ile Val Ser Lys Met Met Lys Asp Val
            920                 925                 930
Phe Phe Phe Leu Phe Phe Leu Gly Val Trp Leu Val Ala Tyr Gly
            935                 940                 945
Val Ala Thr Glu Gly Leu Leu Arg Pro Arg Asp Ser Asp Phe Pro
            950                 955                 960
Ser Ile Leu Arg Arg Val Phe Tyr Arg Pro Tyr Leu Gln Ile Phe
            965                 970                 975
Gly Gln Ile Pro Gln Glu Asp Met Asp Val Ala Leu Met Glu His
            980                 985                 990
Ser Asn Cys Ser Ser Glu Pro Gly Phe Trp Ala His Pro Pro Gly
            995                 1000                1005
Ala Gln Ala Gly Thr Cys Val Ser Gln Tyr Ala Asn Trp Leu Val
            1010                1015                1020
Val Leu Leu Leu Val Ile Phe Leu Leu Val Ala Asn Ile Leu Leu
            1025                1030                1035
Val Asn Leu Leu Ile Ala Met Phe Ser Tyr Thr Phe Gly Lys Val
            1040                1045                1050
Gln Gly Asn Ser Asp Leu Tyr Trp Lys Ala Gln Arg Tyr Arg Leu
            1055                1060                1065
Ile Arg Glu Phe His Ser Arg Pro Ala Leu Ala Pro Pro Phe Ile
            1070                1075                1080
Val Ile Ser His Leu Arg Leu Leu Arg Gln Leu Cys Arg Arg
            1085                1090                1095
Pro Arg Ser Pro Gln Pro Ser Ser Pro Ala Leu Glu His Phe Arg
            1100                1105                1110
Val Tyr Leu Ser Lys Glu Ala Glu Arg Lys Leu Leu Thr Trp Glu
            1115                1120                1125
Ser Val His Lys Glu Asn Phe Leu Leu Ala Arg Ala Arg Asp Lys
            1130                1135                1140
Arg Glu Ser Asp Ser Glu Arg Leu Lys Arg Thr Ser Gln Lys Val
```

```
                    1145                1150                1155

Asp Leu Ala Leu Lys Gln Leu Gly His Ile Arg Glu Tyr Glu Gln
                1160                1165                1170

Arg Leu Lys Val Leu Glu Arg Glu Val Gln Gln Cys Ser Arg Val
                1175                1180                1185

Leu Gly Trp Val Ala Glu Ala Leu Ser Arg Ser Ala Leu Leu Pro
                1190                1195                1200

Pro Gly Gly Pro Pro Pro Asp Leu Pro Gly Ser Lys Asp
                1205                1210

<210> SEQ ID NO 13
<211> LENGTH: 188
<212> TYPE: PRT
<213> ORGANISM: Homo sapiens

<400> SEQUENCE: 13

Met Asp Cys Arg Lys Met Ala Arg Phe Ser Tyr Ser Val Ile Trp
  1               5                  10                  15

Ile Met Ala Ile Ser Lys Val Phe Glu Leu Gly Leu Val Ala Gly
                 20                  25                  30

Leu Gly His Gln Glu Phe Ala Arg Pro Ser Arg Gly Tyr Leu Ala
                 35                  40                  45

Phe Arg Asp Asp Ser Ile Trp Pro Gln Glu Pro Ala Ile Arg
                 50                  55                  60

Pro Arg Ser Ser Gln Arg Val Pro Pro Met Gly Ile Gln His Ser
                 65                  70                  75

Lys Glu Leu Asn Arg Thr Cys Cys Leu Asn Gly Gly Thr Cys Met
                 80                  85                  90

Leu Gly Ser Phe Cys Ala Cys Pro Pro Ser Phe Tyr Gly Arg Asn
                 95                 100                 105

Cys Glu His Asp Val Arg Lys Glu Asn Cys Gly Ser Val Pro His
                110                 115                 120

Asp Thr Trp Leu Pro Lys Lys Cys Ser Leu Cys Lys Cys Trp His
                125                 130                 135

Gly Gln Leu Arg Cys Phe Pro Gln Ala Phe Leu Pro Gly Cys Asp
                140                 145                 150

Gly Leu Val Met Asp Glu His Leu Val Ala Ser Arg Thr Pro Glu
                155                 160                 165

Leu Pro Pro Ser Ala Arg Thr Thr Thr Phe Met Leu Val Gly Ile
                170                 175                 180

Cys Leu Ser Ile Gln Ser Tyr Tyr
                185

<210> SEQ ID NO 14
<211> LENGTH: 1033
<212> TYPE: PRT
<213> ORGANISM: Homo sapiens

<400> SEQUENCE: 14

Met Gly Ala Ala Gly Leu Leu Gly Val Phe Leu Ala Leu Val Ala
  1               5                  10                  15

Pro Gly Val Leu Gly Ile Ser Cys Gly Ser Pro Pro Pro Ile Leu
                 20                  25                  30

Asn Gly Arg Ile Ser Tyr Tyr Ser Thr Pro Ile Ala Val Gly Thr
                 35                  40                  45

Val Ile Arg Tyr Ser Cys Ser Gly Thr Phe Arg Leu Ile Gly Glu
                 50                  55                  60
```

-continued

```
Lys Ser Leu Leu Cys Ile Thr Lys Asp Lys Val Asp Gly Thr Trp
                65                  70                  75
Asp Lys Pro Ala Pro Lys Cys Glu Tyr Phe Asn Lys Tyr Ser Ser
             80                  85                  90
Cys Pro Glu Pro Ile Val Pro Gly Gly Tyr Lys Ile Arg Gly Ser
         95                 100                 105
Thr Pro Tyr Arg His Gly Asp Ser Val Thr Phe Ala Cys Lys Thr
        110                 115                 120
Asn Phe Ser Met Asn Gly Asn Lys Ser Val Trp Cys Gln Ala Asn
        125                 130                 135
Asn Met Trp Gly Pro Thr Arg Leu Pro Thr Cys Val Ser Val Phe
        140                 145                 150
Pro Leu Glu Cys Pro Ala Leu Pro Met Ile His Asn Gly His His
        155                 160                 165
Thr Ser Glu Asn Val Gly Ser Ile Ala Pro Gly Leu Ser Val Thr
        170                 175                 180
Tyr Ser Cys Glu Ser Gly Tyr Leu Leu Val Gly Glu Lys Ile Ile
        185                 190                 195
Asn Cys Leu Ser Ser Gly Lys Trp Ser Ala Val Pro Pro Thr Cys
        200                 205                 210
Glu Glu Ala Arg Cys Lys Ser Leu Gly Arg Phe Pro Asn Gly Lys
        215                 220                 225
Val Lys Glu Pro Pro Ile Leu Arg Val Gly Val Thr Ala Asn Phe
        230                 235                 240
Phe Cys Asp Glu Gly Tyr Arg Leu Gln Gly Pro Pro Ser Ser Arg
        245                 250                 255
Cys Val Ile Ala Gly Gln Gly Val Ala Trp Thr Lys Met Pro Val
        260                 265                 270
Cys Glu Glu Ile Phe Cys Pro Ser Pro Pro Ile Leu Asn Gly
        275                 280                 285
Arg His Ile Gly Asn Ser Leu Ala Asn Val Ser Tyr Gly Ser Ile
        290                 295                 300
Val Thr Tyr Thr Cys Asp Pro Asp Pro Glu Glu Gly Val Asn Phe
        305                 310                 315
Ile Leu Ile Gly Glu Ser Thr Leu Arg Cys Thr Val Asp Ser Gln
        320                 325                 330
Lys Thr Gly Thr Trp Ser Gly Pro Ala Pro Arg Cys Glu Leu Ser
        335                 340                 345
Thr Ser Ala Val Gln Cys Pro His Pro Gln Ile Leu Arg Gly Arg
        350                 355                 360
Met Val Ser Gly Gln Lys Asp Arg Tyr Thr Tyr Asn Asp Thr Val
        365                 370                 375
Ile Phe Ala Cys Met Phe Gly Phe Thr Leu Lys Gly Ser Lys Gln
        380                 385                 390
Ile Arg Cys Asn Ala Gln Gly Thr Trp Glu Pro Ser Ala Pro Val
        395                 400                 405
Cys Glu Lys Glu Cys Gln Ala Pro Pro Asn Ile Leu Asn Gly Gln
        410                 415                 420
Lys Glu Asp Arg His Met Val Arg Phe Asp Pro Gly Thr Ser Ile
        425                 430                 435
Lys Tyr Ser Cys Asn Pro Gly Tyr Val Leu Val Gly Glu Glu Ser
        440                 445                 450
Ile Gln Cys Thr Ser Glu Gly Val Trp Thr Pro Pro Val Pro Gln
```

```
                       455                 460                 465
Cys Lys Val Ala Ala Cys Glu Ala Thr Gly Arg Gln Leu Leu Thr
                470                 475                 480
Lys Pro Gln His Gln Phe Val Arg Pro Asp Val Asn Ser Ser Cys
                485                 490                 495
Gly Glu Gly Tyr Lys Leu Ser Gly Ser Val Tyr Gln Glu Cys Gln
                500                 505                 510
Gly Thr Ile Pro Trp Phe Met Glu Ile Arg Leu Cys Lys Glu Ile
                515                 520                 525
Thr Cys Pro Pro Pro Val Ile Tyr Asn Gly Ala His Thr Gly
                530                 535                 540
Ser Ser Leu Glu Asp Phe Pro Tyr Gly Thr Thr Val Thr Tyr Thr
                545                 550                 555
Cys Asn Pro Gly Pro Glu Arg Gly Val Glu Phe Ser Leu Ile Gly
                560                 565                 570
Glu Ser Thr Ile Arg Cys Thr Ser Asn Asp Gln Glu Arg Gly Thr
                575                 580                 585
Trp Ser Gly Pro Ala Pro Leu Cys Lys Leu Ser Leu Leu Ala Val
                590                 595                 600
Gln Cys Ser His Val His Ile Ala Asn Gly Tyr Lys Ile Ser Gly
                605                 610                 615
Lys Glu Ala Pro Tyr Phe Tyr Asn Asp Thr Val Thr Phe Lys Cys
                620                 625                 630
Tyr Ser Gly Phe Thr Leu Lys Gly Ser Ser Gln Ile Arg Cys Lys
                635                 640                 645
Ala Asp Asn Thr Trp Asp Pro Glu Ile Pro Val Cys Glu Lys Glu
                650                 655                 660
Thr Cys Gln His Val Arg Gln Ser Leu Gln Glu Leu Pro Ala Gly
                665                 670                 675
Ser Arg Val Glu Leu Val Asn Thr Ser Cys Gln Asp Gly Tyr Gln
                680                 685                 690
Leu Thr Gly His Ala Tyr Gln Met Cys Gln Asp Ala Glu Asn Gly
                695                 700                 705
Ile Trp Phe Lys Lys Ile Pro Leu Cys Lys Val Ile His Cys His
                710                 715                 720
Pro Pro Pro Val Ile Val Asn Gly Lys His Thr Gly Met Met Ala
                725                 730                 735
Glu Asn Phe Leu Tyr Gly Asn Glu Val Ser Tyr Glu Cys Asp Gln
                740                 745                 750
Gly Phe Tyr Leu Leu Gly Glu Lys Lys Leu Gln Cys Arg Ser Asp
                755                 760                 765
Ser Lys Gly His Gly Ser Trp Ser Gly Pro Ser Pro Gln Cys Leu
                770                 775                 780
Arg Ser Pro Pro Val Thr Arg Cys Pro Asn Pro Glu Val Lys His
                785                 790                 795
Gly Tyr Lys Leu Asn Lys Thr His Ser Ala Tyr Ser His Asn Asp
                800                 805                 810
Ile Val Tyr Val Asp Cys Asn Pro Gly Phe Ile Met Asn Gly Ser
                815                 820                 825
Arg Val Ile Arg Cys His Thr Asp Asn Thr Trp Val Pro Gly Val
                830                 835                 840
Pro Thr Cys Ile Lys Lys Ala Phe Ile Gly Cys Pro Pro Pro Pro
                845                 850                 855
```

```
Lys Thr Pro Asn Gly Asn His Thr Gly Gly Asn Ile Ala Arg Phe
            860                 865                 870

Ser Pro Gly Met Ser Ile Leu Tyr Ser Cys Asp Gln Gly Tyr Leu
            875                 880                 885

Leu Val Gly Glu Ala Leu Leu Leu Cys Thr His Glu Gly Thr Trp
            890                 895                 900

Ser Gln Pro Ala Pro His Cys Lys Glu Val Asn Cys Ser Ser Pro
            905                 910                 915

Ala Asp Met Asp Gly Ile Gln Lys Gly Leu Glu Pro Arg Lys Met
            920                 925                 930

Tyr Gln Tyr Gly Ala Val Val Thr Leu Glu Cys Glu Asp Gly Tyr
            935                 940                 945

Met Leu Glu Gly Ser Pro Gln Ser Gln Cys Gln Ser Asp His Gln
            950                 955                 960

Trp Asn Pro Pro Leu Ala Val Cys Arg Ser Arg Ser Leu Ala Pro
            965                 970                 975

Val Leu Cys Gly Ile Ala Ala Gly Leu Ile Leu Leu Thr Phe Leu
            980                 985                 990

Ile Val Ile Thr Leu Tyr Val Ile Ser Lys His Arg Glu Arg Asn
            995                1000                1005

Tyr Tyr Thr Asp Thr Ser Gln Lys Glu Ala Phe His Leu Glu Ala
           1010                1015                1020

Arg Glu Val Tyr Ser Val Asp Pro Tyr Asn Pro Ala Ser
           1025                1030

<210> SEQ ID NO 15
<211> LENGTH: 229
<212> TYPE: PRT
<213> ORGANISM: Homo sapiens

<400> SEQUENCE: 15

Met Ala Arg Leu Ala Leu Ser Pro Val Pro Ser His Trp Met Val
  1               5                  10                  15

Ala Leu Leu Leu Leu Leu Ser Ala Glu Pro Val Pro Ala Ala Arg
             20                  25                  30

Ser Glu Asp Arg Tyr Arg Asn Pro Lys Gly Ser Ala Cys Ser Arg
             35                  40                  45

Ile Trp Gln Ser Pro Arg Phe Ile Ala Arg Lys Arg Gly Phe Thr
             50                  55                  60

Val Lys Met His Cys Tyr Met Asn Ser Ala Ser Gly Asn Val Ser
             65                  70                  75

Trp Leu Trp Lys Gln Glu Met Asp Glu Asn Pro Gln Gln Leu Lys
             80                  85                  90

Leu Glu Lys Gly Arg Met Glu Glu Ser Gln Asn Glu Ser Leu Ala
             95                 100                 105

Thr Leu Thr Ile Gln Gly Ile Arg Phe Glu Asp Asn Gly Ile Tyr
            110                 115                 120

Phe Cys Gln Gln Lys Cys Asn Asn Thr Ser Glu Val Tyr Gln Gly
            125                 130                 135

Cys Gly Thr Glu Leu Arg Val Met Gly Phe Ser Thr Leu Ala Gln
            140                 145                 150

Leu Lys Gln Arg Asn Thr Leu Lys Asp Gly Ile Ile Met Ile Gln
            155                 160                 165

Thr Leu Leu Ile Ile Leu Phe Ile Ile Val Pro Ile Phe Leu Leu
            170                 175                 180
```

-continued

Leu Asp Lys Asp Asp Ser Lys Ala Gly Met Glu Asp His Thr
              185                 190                 195

Tyr Glu Gly Leu Asp Ile Asp Gln Thr Ala Thr Tyr Glu Asp Ile
              200                 205                 210

Val Thr Leu Arg Thr Gly Glu Val Lys Trp Ser Val Gly Glu His
              215                 220                 225

Pro Gly Gln Glu

<210> SEQ ID NO 16
<211> LENGTH: 508
<212> TYPE: PRT
<213> ORGANISM: Homo sapiens

<400> SEQUENCE: 16

Met Leu Leu Trp Ser Leu Leu Val Ile Phe Asp Ala Val Thr Glu
  1               5                  10                  15

Gln Ala Asp Ser Leu Thr Leu Val Ala Pro Ser Ser Val Phe Glu
                 20                  25                  30

Gly Asp Ser Ile Val Leu Lys Cys Gln Gly Glu Gln Asn Trp Lys
                 35                  40                  45

Ile Gln Lys Met Ala Tyr His Lys Asp Asn Lys Glu Leu Ser Val
                 50                  55                  60

Phe Lys Lys Phe Ser Asp Phe Leu Ile Gln Ser Ala Val Leu Ser
                 65                  70                  75

Asp Ser Gly Asn Tyr Phe Cys Ser Thr Lys Gly Gln Leu Phe Leu
                 80                  85                  90

Trp Asp Lys Thr Ser Asn Ile Val Lys Ile Lys Val Gln Glu Leu
                 95                 100                 105

Phe Gln Arg Pro Val Leu Thr Ala Ser Ser Phe Gln Pro Ile Glu
                110                 115                 120

Gly Gly Pro Val Ser Leu Lys Cys Glu Thr Arg Leu Ser Pro Gln
                125                 130                 135

Arg Leu Asp Val Gln Leu Gln Phe Cys Phe Phe Arg Glu Asn Gln
                140                 145                 150

Val Leu Gly Ser Gly Trp Ser Ser Ser Pro Glu Leu Gln Ile Ser
                155                 160                 165

Ala Val Trp Ser Glu Asp Thr Gly Ser Tyr Trp Cys Lys Ala Glu
                170                 175                 180

Thr Val Thr His Arg Ile Arg Lys Gln Ser Leu Gln Ser Gln Ile
                185                 190                 195

His Val Gln Arg Ile Pro Ile Ser Asn Val Ser Leu Glu Ile Arg
                200                 205                 210

Ala Pro Gly Gly Gln Val Thr Glu Gly Gln Lys Leu Ile Leu Leu
                215                 220                 225

Cys Ser Val Ala Gly Gly Thr Gly Asn Val Thr Phe Ser Trp Tyr
                230                 235                 240

Arg Glu Ala Thr Gly Thr Ser Met Gly Lys Lys Thr Gln Arg Ser
                245                 250                 255

Leu Ser Ala Glu Leu Glu Ile Pro Ala Val Lys Glu Ser Asp Ala
                260                 265                 270

Gly Lys Tyr Tyr Cys Arg Ala Asp Asn Gly His Val Pro Ile Gln
                275                 280                 285

Ser Lys Val Val Asn Ile Pro Val Arg Ile Pro Val Ser Arg Pro
                290                 295                 300

Val Leu Thr Leu Arg Ser Pro Gly Ala Gln Ala Ala Val Gly Asp

```
                      305                 310                 315
Leu Leu Glu Leu His Cys Glu Ala Leu Arg Gly Ser Pro Pro Ile
                  320                 325                 330
Leu Tyr Gln Phe Tyr His Glu Asp Val Thr Leu Gly Asn Ser Ser
                  335                 340                 345
Ala Pro Ser Gly Gly Gly Ala Ser Phe Asn Leu Ser Leu Thr Ala
                  350                 355                 360
Glu His Ser Gly Asn Tyr Ser Cys Glu Ala Asn Asn Gly Leu Gly
                  365                 370                 375
Ala Gln Cys Ser Glu Ala Val Pro Val Ser Ile Ser Gly Pro Asp
                  380                 385                 390
Gly Tyr Arg Arg Asp Leu Met Thr Ala Gly Val Leu Trp Gly Leu
                  395                 400                 405
Phe Gly Val Leu Gly Phe Thr Gly Val Ala Leu Leu Leu Tyr Ala
                  410                 415                 420
Leu Phe His Lys Ile Ser Gly Glu Ser Ser Ala Thr Asn Glu Pro
                  425                 430                 435
Arg Gly Ala Ser Arg Pro Asn Pro Gln Glu Phe Thr Tyr Ser Ser
                  440                 445                 450
Pro Thr Pro Asp Met Glu Glu Leu Gln Pro Val Tyr Val Asn Val
                  455                 460                 465
Gly Ser Val Asp Val Asp Val Val Tyr Ser Gln Val Trp Ser Met
                  470                 475                 480
Gln Gln Pro Glu Ser Ser Ala Asn Ile Arg Thr Leu Leu Glu Asn
                  485                 490                 495
Lys Asp Ser Gln Val Ile Tyr Ser Ser Val Lys Lys Ser
                  500                 505

<210> SEQ ID NO 17
<211> LENGTH: 1255
<212> TYPE: PRT
<213> ORGANISM: Homo sapiens

<400> SEQUENCE: 17

Met Glu Leu Ala Ala Leu Cys Arg Trp Gly Leu Leu Leu Ala Leu
  1               5                  10                  15
Leu Pro Pro Gly Ala Ala Ser Thr Gln Val Cys Thr Gly Thr Asp
                  20                  25                  30
Met Lys Leu Arg Leu Pro Ala Ser Pro Glu Thr His Leu Asp Met
                  35                  40                  45
Leu Arg His Leu Tyr Gln Gly Cys Gln Val Val Gln Gly Asn Leu
                  50                  55                  60
Glu Leu Thr Tyr Leu Pro Thr Asn Ala Ser Leu Ser Phe Leu Gln
                  65                  70                  75
Asp Ile Gln Glu Val Gln Gly Tyr Val Leu Ile Ala His Asn Gln
                  80                  85                  90
Val Arg Gln Val Pro Leu Gln Arg Leu Arg Ile Val Arg Gly Thr
                  95                 100                 105
Gln Leu Phe Glu Asp Asn Tyr Ala Leu Ala Val Leu Asp Asn Gly
                 110                 115                 120
Asp Pro Leu Asn Asn Thr Thr Pro Val Thr Gly Ala Ser Pro Gly
                 125                 130                 135
Gly Leu Arg Glu Leu Gln Leu Arg Ser Leu Thr Glu Ile Leu Lys
                 140                 145                 150
Gly Gly Val Leu Ile Gln Arg Asn Pro Gln Leu Cys Tyr Gln Asp
```

```
                        155                 160                 165
Thr Ile Leu Trp Lys Asp Ile Phe His Lys Asn Asn Gln Leu Ala
                170                 175                 180
Leu Thr Leu Ile Asp Thr Asn Arg Ser Arg Ala Cys His Pro Cys
                185                 190                 195
Ser Pro Met Cys Lys Gly Ser Arg Cys Trp Gly Glu Ser Ser Glu
                200                 205                 210
Asp Cys Gln Ser Leu Thr Arg Thr Val Cys Ala Gly Cys Ala
                215                 220                 225
Arg Cys Lys Gly Pro Leu Pro Thr Asp Cys Cys His Glu Gln Cys
                230                 235                 240
Ala Ala Gly Cys Thr Gly Pro Lys His Ser Asp Cys Leu Ala Cys
                245                 250                 255
Leu His Phe Asn His Ser Gly Ile Cys Glu Leu His Cys Pro Ala
                260                 265                 270
Leu Val Thr Tyr Asn Thr Asp Thr Phe Glu Ser Met Pro Asn Pro
                275                 280                 285
Glu Gly Arg Tyr Thr Phe Gly Ala Ser Cys Val Thr Ala Cys Pro
                290                 295                 300
Tyr Asn Tyr Leu Ser Thr Asp Val Gly Ser Cys Thr Leu Val Cys
                305                 310                 315
Pro Leu His Asn Gln Glu Val Thr Ala Glu Asp Gly Thr Gln Arg
                320                 325                 330
Cys Glu Lys Cys Ser Lys Pro Cys Ala Arg Val Cys Tyr Gly Leu
                335                 340                 345
Gly Met Glu His Leu Arg Glu Val Arg Ala Val Thr Ser Ala Asn
                350                 355                 360
Ile Gln Glu Phe Ala Gly Cys Lys Lys Ile Phe Gly Ser Leu Ala
                365                 370                 375
Phe Leu Pro Glu Ser Phe Asp Gly Asp Pro Ala Ser Asn Thr Ala
                380                 385                 390
Pro Leu Gln Pro Glu Gln Leu Gln Val Phe Glu Thr Leu Glu Glu
                395                 400                 405
Ile Thr Gly Tyr Leu Tyr Ile Ser Ala Trp Pro Asp Ser Leu Pro
                410                 415                 420
Asp Leu Ser Val Phe Gln Asn Leu Gln Val Ile Arg Gly Arg Ile
                425                 430                 435
Leu His Asn Gly Ala Tyr Ser Leu Thr Leu Gln Gly Leu Gly Ile
                440                 445                 450
Ser Trp Leu Gly Leu Arg Ser Leu Arg Glu Leu Gly Ser Gly Leu
                455                 460                 465
Ala Leu Ile His His Asn Thr His Leu Cys Phe Val His Thr Val
                470                 475                 480
Pro Trp Asp Gln Leu Phe Arg Asn Pro His Gln Ala Leu Leu His
                485                 490                 495
Thr Ala Asn Arg Pro Glu Asp Glu Cys Val Gly Glu Gly Leu Ala
                500                 505                 510
Cys His Gln Leu Cys Ala Arg Gly His Cys Trp Gly Pro Gly Pro
                515                 520                 525
Thr Gln Cys Val Asn Cys Ser Gln Phe Leu Arg Gly Gln Glu Cys
                530                 535                 540
Val Glu Glu Cys Arg Val Leu Gln Gly Leu Pro Arg Glu Tyr Val
                545                 550                 555
```

-continued

Asn Ala Arg His Cys Leu Pro Cys His Pro Glu Cys Gln Pro Gln
                560                 565                 570

Asn Gly Ser Val Thr Cys Phe Gly Pro Glu Ala Asp Gln Cys Val
            575                 580                 585

Ala Cys Ala His Tyr Lys Asp Pro Pro Phe Cys Val Ala Arg Cys
            590                 595                 600

Pro Ser Gly Val Lys Pro Asp Leu Ser Tyr Met Pro Ile Trp Lys
            605                 610                 615

Phe Pro Asp Glu Glu Gly Ala Cys Gln Pro Cys Pro Ile Asn Cys
            620                 625                 630

Thr His Ser Cys Val Asp Leu Asp Asp Lys Gly Cys Pro Ala Glu
            635                 640                 645

Gln Arg Ala Ser Pro Leu Thr Ser Ile Ile Ser Ala Val Val Gly
            650                 655                 660

Ile Leu Leu Val Val Val Leu Gly Val Val Phe Gly Ile Leu Ile
            665                 670                 675

Lys Arg Arg Gln Gln Lys Ile Arg Lys Tyr Thr Met Arg Arg Leu
            680                 685                 690

Leu Gln Glu Thr Glu Leu Val Glu Pro Leu Thr Pro Ser Gly Ala
            695                 700                 705

Met Pro Asn Gln Ala Gln Met Arg Ile Leu Lys Glu Thr Glu Leu
            710                 715                 720

Arg Lys Val Lys Val Leu Gly Ser Gly Ala Phe Gly Thr Val Tyr
            725                 730                 735

Lys Gly Ile Trp Ile Pro Asp Gly Glu Asn Val Lys Ile Pro Val
            740                 745                 750

Ala Ile Lys Val Leu Arg Glu Asn Thr Ser Pro Lys Ala Asn Lys
            755                 760                 765

Glu Ile Leu Asp Glu Ala Tyr Val Met Ala Gly Val Gly Ser Pro
            770                 775                 780

Tyr Val Ser Arg Leu Leu Gly Ile Cys Leu Thr Ser Thr Val Gln
            785                 790                 795

Leu Val Thr Gln Leu Met Pro Tyr Gly Cys Leu Leu Asp His Val
            800                 805                 810

Arg Glu Asn Arg Gly Arg Leu Gly Ser Gln Asp Leu Leu Asn Trp
            815                 820                 825

Cys Met Gln Ile Ala Lys Gly Met Ser Tyr Leu Glu Asp Val Arg
            830                 835                 840

Leu Val His Arg Asp Leu Ala Ala Arg Asn Val Leu Val Lys Ser
            845                 850                 855

Pro Asn His Val Lys Ile Thr Asp Phe Gly Leu Ala Arg Leu Leu
            860                 865                 870

Asp Ile Asp Glu Thr Glu Tyr His Ala Asp Gly Gly Lys Val Pro
            875                 880                 885

Ile Lys Trp Met Ala Leu Glu Ser Ile Leu Arg Arg Arg Phe Thr
            890                 895                 900

His Gln Ser Asp Val Trp Ser Tyr Gly Val Thr Val Trp Glu Leu
            905                 910                 915

Met Thr Phe Gly Ala Lys Pro Tyr Asp Gly Ile Pro Ala Arg Glu
            920                 925                 930

Ile Pro Asp Leu Leu Glu Lys Gly Glu Arg Leu Pro Gln Pro Pro
            935                 940                 945

Ile Cys Thr Ile Asp Val Tyr Met Ile Met Val Lys Cys Trp Met
            950                 955                 960

```
Ile Asp Ser Glu Cys Arg Pro Arg Phe Arg Glu Leu Val Ser Glu
            965                 970                 975

Phe Ser Arg Met Ala Arg Asp Pro Gln Arg Phe Val Val Ile Gln
            980                 985                 990

Asn Glu Asp Leu Gly Pro Ala Ser Pro Leu Asp Ser Thr Phe Tyr
            995                 1000                1005

Arg Ser Leu Leu Glu Asp Asp Met Gly Asp Leu Val Asp Ala
            1010                1015                1020

Glu Glu Tyr Leu Val Pro Gln Gln Gly Phe Phe Cys Pro Asp Pro
            1025                1030                1035

Ala Pro Gly Ala Gly Gly Met Val His His Arg His Arg Ser Ser
            1040                1045                1050

Ser Thr Arg Ser Gly Gly Gly Asp Leu Thr Leu Gly Leu Glu Pro
            1055                1060                1065

Ser Glu Glu Glu Ala Pro Arg Ser Pro Leu Ala Pro Ser Glu Gly
            1070                1075                1080

Ala Gly Ser Asp Val Phe Asp Gly Asp Leu Gly Met Gly Ala Ala
            1085                1090                1095

Lys Gly Leu Gln Ser Leu Pro Thr His Asp Pro Ser Pro Leu Gln
            1100                1105                1110

Arg Tyr Ser Glu Asp Pro Thr Val Pro Leu Pro Ser Glu Thr Asp
            1115                1120                1125

Gly Tyr Val Ala Pro Leu Thr Cys Ser Pro Gln Pro Glu Tyr Val
            1130                1135                1140

Asn Gln Pro Asp Val Arg Pro Gln Pro Pro Ser Pro Arg Glu Gly
            1145                1150                1155

Pro Leu Pro Ala Ala Arg Pro Ala Gly Ala Thr Leu Glu Arg Pro
            1160                1165                1170

Lys Thr Leu Ser Pro Gly Lys Asn Gly Val Val Lys Asp Val Phe
            1175                1180                1185

Ala Phe Gly Gly Ala Val Glu Asn Pro Glu Tyr Leu Thr Pro Gln
            1190                1195                1200

Gly Gly Ala Ala Pro Gln Pro His Pro Pro Pro Ala Phe Ser Pro
            1205                1210                1215

Ala Phe Asp Asn Leu Tyr Tyr Trp Asp Gln Asp Pro Pro Glu Arg
            1220                1225                1230

Gly Ala Pro Pro Ser Thr Phe Lys Gly Thr Pro Thr Ala Glu Asn
            1235                1240                1245

Pro Glu Tyr Leu Gly Leu Asp Val Pro Val
            1250                1255

<210> SEQ ID NO 18
<211> LENGTH: 344
<212> TYPE: PRT
<213> ORGANISM: Homo sapiens

<400> SEQUENCE: 18

Met Gly Pro Pro Ser Ala Pro Pro Cys Arg Leu His Val Pro Trp
  1               5                  10                  15

Lys Glu Val Leu Leu Thr Ala Ser Leu Leu Thr Phe Trp Asn Pro
                 20                  25                  30

Pro Thr Thr Ala Lys Leu Thr Ile Glu Ser Thr Pro Phe Asn Val
                 35                  40                  45

Ala Glu Gly Lys Glu Val Leu Leu Leu Ala His Asn Leu Pro Gln
                 50                  55                  60
```

```
Asn Arg Ile Gly Tyr Ser Trp Tyr Lys Gly Glu Arg Val Asp Gly
             65                  70                  75

Asn Ser Leu Ile Val Gly Tyr Val Ile Gly Thr Gln Gln Ala Thr
             80                  85                  90

Pro Gly Pro Ala Tyr Ser Gly Arg Glu Thr Ile Tyr Pro Asn Ala
             95                 100                 105

Ser Leu Leu Ile Gln Asn Val Thr Gln Asn Asp Thr Gly Phe Tyr
            110                 115                 120

Thr Leu Gln Val Ile Lys Ser Asp Leu Val Asn Glu Glu Ala Thr
            125                 130                 135

Gly Gln Phe His Val Tyr Pro Glu Leu Pro Lys Pro Ser Ile Ser
            140                 145                 150

Ser Asn Asn Ser Asn Pro Val Glu Asp Lys Asp Ala Val Ala Phe
            155                 160                 165

Thr Cys Glu Pro Glu Val Gln Asn Thr Thr Tyr Leu Trp Trp Val
            170                 175                 180

Asn Gly Gln Ser Leu Pro Val Ser Pro Arg Leu Gln Leu Ser Asn
            185                 190                 195

Gly Asn Met Thr Leu Thr Leu Leu Ser Val Lys Arg Asn Asp Ala
            200                 205                 210

Gly Ser Tyr Glu Cys Glu Ile Gln Asn Pro Ala Ser Ala Asn Arg
            215                 220                 225

Ser Asp Pro Val Thr Leu Asn Val Leu Tyr Gly Pro Asp Val Pro
            230                 235                 240

Thr Ile Ser Pro Ser Lys Ala Asn Tyr Arg Pro Gly Glu Asn Leu
            245                 250                 255

Asn Leu Ser Cys His Ala Ala Ser Asn Pro Pro Ala Gln Tyr Ser
            260                 265                 270

Trp Phe Ile Asn Gly Thr Phe Gln Gln Ser Thr Gln Glu Leu Phe
            275                 280                 285

Ile Pro Asn Ile Thr Val Asn Asn Ser Gly Ser Tyr Met Cys Gln
            290                 295                 300

Ala His Asn Ser Ala Thr Gly Leu Asn Arg Thr Thr Val Thr Met
            305                 310                 315

Ile Thr Val Ser Gly Ser Ala Pro Val Leu Ser Ala Val Ala Thr
            320                 325                 330

Val Gly Ile Thr Ile Gly Val Leu Ala Arg Val Ala Leu Ile
            335                 340

<210> SEQ ID NO 19
<211> LENGTH: 411
<212> TYPE: PRT
<213> ORGANISM: Homo sapiens

<400> SEQUENCE: 19

Met Trp Ser Gly Trp Trp Leu Trp Pro Leu Val Ala Val Cys Thr
  1               5                  10                  15

Ala Asp Phe Phe Arg Asp Glu Ala Glu Arg Ile Met Arg Asp Ser
             20                  25                  30

Pro Val Ile Asp Gly His Asn Asp Leu Pro Trp Gln Leu Leu Asp
             35                  40                  45

Met Phe Asn Asn Arg Leu Gln Asp Glu Arg Ala Asn Leu Thr Thr
             50                  55                  60

Leu Ala Gly Thr His Thr Asn Ile Pro Lys Leu Arg Ala Gly Phe
             65                  70                  75
```

```
Val Gly Gly Gln Phe Trp Ser Val Tyr Thr Pro Cys Asp Thr Gln
            80                  85                  90

Asn Lys Asp Ala Val Arg Arg Thr Leu Glu Gln Met Asp Val Val
            95                 100                 105

His Arg Met Cys Arg Met Tyr Pro Glu Thr Phe Leu Tyr Val Thr
           110                 115                 120

Ser Ser Ala Gly Ile Arg Gln Ala Phe Arg Glu Gly Lys Val Ala
           125                 130                 135

Ser Leu Ile Gly Val Glu Gly Gly His Ser Ile Asp Ser Ser Leu
           140                 145                 150

Gly Val Leu Arg Ala Leu Tyr Gln Leu Gly Met Arg Tyr Leu Thr
           155                 160                 165

Leu Thr His Ser Cys Asn Thr Pro Trp Ala Asp Asn Trp Leu Val
           170                 175                 180

Asp Thr Gly Asp Ser Glu Pro Gln Ser Gln Gly Leu Ser Pro Phe
           185                 190                 195

Gly Gln Arg Val Val Lys Glu Leu Asn Arg Leu Gly Val Leu Ile
           200                 205                 210

Asp Leu Ala His Val Ser Val Ala Thr Met Lys Ala Thr Leu Gln
           215                 220                 225

Leu Ser Arg Ala Pro Val Ile Phe Ser His Ser Ser Ala Tyr Ser
           230                 235                 240

Val Cys Ala Ser Arg Arg Asn Val Pro Asp Asp Val Leu Arg Leu
           245                 250                 255

Val Lys Gln Thr Asp Ser Leu Val Met Val Asn Phe Tyr Asn Asn
           260                 265                 270

Tyr Ile Ser Cys Thr Asn Lys Ala Asn Leu Ser Gln Val Ala Asp
           275                 280                 285

His Leu Asp His Ile Lys Glu Val Ala Gly Ala Arg Ala Val Gly
           290                 295                 300

Phe Gly Gly Asp Phe Asp Gly Val Pro Arg Val Pro Glu Gly Leu
           305                 310                 315

Glu Asp Val Ser Lys Tyr Pro Asp Leu Ile Ala Glu Leu Leu Arg
           320                 325                 330

Arg Asn Trp Thr Glu Ala Glu Val Lys Gly Ala Leu Ala Asp Asn
           335                 340                 345

Leu Leu Arg Val Phe Glu Ala Val Glu Gln Ala Ser Asn Leu Thr
           350                 355                 360

Gln Ala Pro Glu Glu Glu Pro Ile Pro Leu Asp Gln Leu Gly Gly
           365                 370                 375

Ser Cys Arg Thr His Tyr Gly Tyr Ser Ser Gly Ala Ser Ser Leu
           380                 385                 390

His Arg His Trp Gly Leu Leu Leu Ala Ser Leu Ala Pro Leu Val
           395                 400                 405

Leu Cys Leu Ser Leu Leu
           410

<210> SEQ ID NO 20
<211> LENGTH: 553
<212> TYPE: PRT
<213> ORGANISM: Homo sapiens

<400> SEQUENCE: 20

Met Arg Ala Pro Gly Arg Pro Ala Leu Arg Pro Leu Pro Leu Pro
  1               5                  10                  15
```

```
Pro Leu Leu Leu Leu Leu Ala Ala Pro Trp Gly Arg Ala Val
            20                  25                  30

Pro Cys Val Ser Gly Leu Pro Lys Pro Ala Asn Ile Thr Phe
            35                  40                  45

Leu Ser Ile Asn Met Lys Asn Val Leu Gln Trp Thr Pro Glu
            50                  55                  60

Gly Leu Gln Gly Val Lys Val Thr Tyr Thr Val Gln Tyr Phe Ile
            65                  70                  75

Tyr Gly Gln Lys Lys Trp Leu Asn Lys Ser Glu Cys Arg Asn Ile
            80                  85                  90

Asn Arg Thr Tyr Cys Asp Leu Ser Ala Glu Thr Ser Asp Tyr Glu
            95                  100                 105

His Gln Tyr Tyr Ala Lys Val Lys Ala Ile Trp Gly Thr Lys Cys
            110                 115                 120

Ser Lys Trp Ala Glu Ser Gly Arg Phe Tyr Pro Phe Leu Glu Thr
            125                 130                 135

Gln Ile Gly Pro Pro Glu Val Ala Leu Thr Thr Asp Glu Lys Ser
            140                 145                 150

Ile Ser Val Val Leu Thr Ala Pro Glu Lys Trp Lys Arg Asn Pro
            155                 160                 165

Glu Asp Leu Pro Val Ser Met Gln Gln Ile Tyr Ser Asn Leu Lys
            170                 175                 180

Tyr Asn Val Ser Val Leu Asn Thr Lys Ser Asn Arg Thr Trp Ser
            185                 190                 195

Gln Cys Val Thr Asn His Thr Leu Val Leu Thr Trp Leu Glu Pro
            200                 205                 210

Asn Thr Leu Tyr Cys Val His Val Glu Ser Phe Val Pro Gly Pro
            215                 220                 225

Pro Arg Arg Ala Gln Pro Ser Glu Lys Gln Cys Ala Arg Thr Leu
            230                 235                 240

Lys Asp Gln Ser Ser Glu Phe Lys Ala Lys Ile Ile Phe Trp Tyr
            245                 250                 255

Val Leu Pro Ile Ser Ile Thr Val Phe Leu Phe Ser Val Met Gly
            260                 265                 270

Tyr Ser Ile Tyr Arg Tyr Ile His Val Gly Lys Glu Lys His Pro
            275                 280                 285

Ala Asn Leu Ile Leu Ile Tyr Gly Asn Glu Phe Asp Lys Arg Phe
            290                 295                 300

Phe Val Pro Ala Glu Lys Ile Val Ile Asn Phe Ile Thr Leu Asn
            305                 310                 315

Ile Ser Asp Asp Ser Lys Ile Ser His Gln Asp Met Ser Leu Leu
            320                 325                 330

Gly Lys Ser Ser Asp Val Ser Ser Leu Asn Asp Pro Gln Pro Ser
            335                 340                 345

Gly Asn Leu Arg Pro Pro Gln Glu Glu Glu Val Lys His Leu
            350                 355                 360

Gly Tyr Ala Ser His Leu Met Glu Ile Phe Cys Asp Ser Glu Glu
            365                 370                 375

Asn Thr Glu Gly Thr Ser Phe Thr Gln Gln Glu Ser Leu Ser Arg
            380                 385                 390

Thr Ile Pro Pro Asp Lys Thr Val Ile Glu Tyr Glu Tyr Asp Val
            395                 400                 405

Arg Thr Thr Asp Ile Cys Ala Gly Pro Glu Glu Gln Glu Leu Ser
```

```
                             410                 415                 420
Leu Gln Glu Glu Val Ser Thr Gln Gly Thr Leu Leu Glu Ser Gln
                 425                 430                 435
Ala Ala Leu Ala Val Leu Gly Pro Gln Thr Leu Gln Tyr Ser Tyr
                 440                 445                 450
Thr Pro Gln Leu Gln Asp Leu Asp Pro Leu Ala Gln Glu His Thr
                 455                 460                 465
Asp Ser Glu Glu Gly Pro Glu Glu Pro Ser Thr Thr Leu Val
                 470                 475                 480
Asp Trp Asp Pro Gln Thr Gly Arg Leu Cys Ile Pro Ser Leu Ser
                 485                 490                 495
Ser Phe Asp Gln Asp Ser Glu Gly Cys Glu Pro Ser Glu Gly Asp
                 500                 505                 510
Gly Leu Gly Glu Glu Gly Leu Leu Ser Arg Leu Tyr Glu Glu Pro
                 515                 520                 525
Ala Pro Asp Arg Pro Pro Gly Glu Asn Glu Thr Tyr Leu Met Gln
                 530                 535                 540
Phe Met Glu Glu Trp Gly Leu Tyr Val Gln Met Glu Asn
                 545                 550

<210> SEQ ID NO 21
<211> LENGTH: 911
<212> TYPE: PRT
<213> ORGANISM: Homo sapiens

<400> SEQUENCE: 21

Met Ala Gln Leu Phe Leu Pro Leu Leu Ala Ala Leu Val Leu Ala
  1               5                  10                  15
Gln Ala Pro Ala Ala Leu Ala Asp Val Leu Glu Gly Asp Ser Ser
                 20                  25                  30
Glu Asp Arg Ala Phe Arg Val Arg Ile Ala Gly Asp Ala Pro Leu
                 35                  40                  45
Gln Gly Val Leu Gly Gly Ala Leu Thr Ile Pro Cys His Val His
                 50                  55                  60
Tyr Leu Arg Pro Pro Pro Ser Arg Arg Ala Val Leu Gly Ser Pro
                 65                  70                  75
Arg Val Lys Trp Thr Phe Leu Ser Arg Gly Arg Glu Ala Glu Val
                 80                  85                  90
Leu Val Ala Arg Gly Val Arg Val Lys Val Asn Glu Ala Tyr Arg
                 95                 100                 105
Phe Arg Val Ala Leu Pro Ala Tyr Pro Ala Ser Leu Thr Asp Val
                110                 115                 120
Ser Leu Ala Leu Ser Glu Leu Arg Pro Asn Asp Ser Gly Ile Tyr
                125                 130                 135
Arg Cys Glu Val Gln His Gly Ile Asp Asp Ser Ser Asp Ala Val
                140                 145                 150
Glu Val Lys Val Lys Gly Val Val Phe Leu Tyr Arg Glu Gly Ser
                155                 160                 165
Ala Arg Tyr Ala Phe Ser Phe Ser Gly Ala Gln Glu Ala Cys Ala
                170                 175                 180
Arg Ile Gly Ala His Ile Ala Thr Pro Glu Gln Leu Tyr Ala Ala
                185                 190                 195
Tyr Leu Gly Gly Tyr Glu Gln Cys Asp Ala Gly Trp Leu Ser Asp
                200                 205                 210
Gln Thr Val Arg Tyr Pro Ile Gln Thr Pro Arg Glu Ala Cys Tyr
```

```
                215                 220                 225
Gly Asp Met Asp Gly Phe Pro Gly Val Arg Asn Tyr Gly Val Val
                230                 235                 240
Asp Pro Asp Leu Tyr Asp Val Tyr Cys Tyr Ala Glu Asp Leu
                245                 250                 255
Asn Gly Glu Leu Phe Leu Gly Asp Pro Glu Lys Leu Thr Leu
                260                 265                 270
Glu Glu Ala Arg Ala Tyr Cys Gln Glu Arg Gly Ala Glu Ile Ala
                275                 280                 285
Thr Thr Gly Gln Leu Tyr Ala Ala Trp Asp Gly Gly Leu Asp His
                290                 295                 300
Cys Ser Pro Gly Trp Leu Ala Asp Gly Ser Val Arg Tyr Pro Ile
                305                 310                 315
Val Thr Pro Ser Gln Arg Cys Gly Gly Gly Leu Pro Gly Val Lys
                320                 325                 330
Thr Leu Phe Leu Phe Pro Asn Gln Thr Gly Phe Pro Asn Lys His
                335                 340                 345
Ser Arg Phe Asn Val Tyr Cys Phe Arg Asp Ser Ala Gln Pro Ser
                350                 355                 360
Ala Ile Pro Glu Ala Ser Asn Pro Ala Ser Asn Pro Ala Ser Asp
                365                 370                 375
Gly Leu Glu Ala Ile Val Thr Val Thr Glu Thr Leu Glu Glu Leu
                380                 385                 390
Gln Leu Pro Gln Glu Ala Thr Glu Ser Glu Ser Arg Gly Ala Ile
                395                 400                 405
Tyr Ser Ile Pro Ile Met Glu Asp Gly Gly Gly Ser Ser Thr
                410                 415                 420
Pro Glu Asp Pro Ala Glu Ala Pro Arg Thr Leu Leu Glu Phe Glu
                425                 430                 435
Thr Gln Ser Met Val Pro Pro Thr Gly Phe Ser Glu Glu Glu Gly
                440                 445                 450
Lys Ala Leu Glu Glu Glu Lys Tyr Glu Asp Glu Glu Lys
                455                 460                 465
Glu Glu Glu Glu Glu Glu Glu Val Glu Asp Glu Ala Leu Trp
                470                 475                 480
Ala Trp Pro Ser Glu Leu Ser Ser Pro Gly Pro Glu Ala Ser Leu
                485                 490                 495
Pro Thr Glu Pro Ala Ala Gln Glu Lys Ser Leu Ser Gln Ala Pro
                500                 505                 510
Ala Arg Ala Val Leu Gln Pro Gly Ala Ser Pro Leu Pro Asp Gly
                515                 520                 525
Glu Ser Glu Ala Ser Arg Pro Pro Arg Val His Gly Pro Pro Thr
                530                 535                 540
Glu Thr Leu Pro Thr Pro Arg Glu Arg Asn Leu Ala Ser Pro Ser
                545                 550                 555
Pro Ser Thr Leu Val Glu Ala Arg Glu Val Gly Glu Ala Thr Gly
                560                 565                 570
Gly Pro Glu Leu Ser Gly Val Pro Arg Gly Glu Ser Glu Glu Thr
                575                 580                 585
Gly Ser Ser Glu Gly Ala Pro Ser Leu Leu Pro Ala Thr Arg Ala
                590                 595                 600
Pro Glu Gly Thr Arg Glu Leu Glu Ala Pro Ser Glu Asp Asn Ser
                605                 610                 615
```

-continued

Gly Arg Thr Ala Pro Ala Gly Thr Ser Val Gln Ala Gln Pro Val
             620                 625                 630

Leu Pro Thr Asp Ser Ala Ser Arg Gly Gly Val Ala Val Val Pro
             635                 640                 645

Ala Ser Gly Asp Cys Val Pro Ser Pro Cys His Asn Gly Gly Thr
             650                 655                 660

Cys Leu Glu Glu Glu Glu Gly Val Arg Cys Leu Cys Leu Pro Gly
             665                 670                 675

Tyr Gly Gly Asp Leu Cys Asp Val Gly Leu Arg Phe Cys Asn Pro
             680                 685                 690

Gly Trp Asp Ala Phe Gln Gly Ala Cys Tyr Lys His Phe Ser Thr
             695                 700                 705

Arg Arg Ser Trp Glu Glu Ala Glu Thr Gln Cys Arg Met Tyr Gly
             710                 715                 720

Ala His Leu Ala Ser Ile Ser Thr Pro Glu Glu Gln Asp Phe Ile
             725                 730                 735

Asn Asn Arg Tyr Arg Glu Tyr Gln Trp Ile Gly Leu Asn Asp Arg
             740                 745                 750

Thr Ile Glu Gly Asp Phe Leu Trp Ser Asp Gly Val Pro Leu Leu
             755                 760                 765

Tyr Glu Asn Trp Asn Pro Gly Gln Pro Asp Ser Tyr Phe Leu Ser
             770                 775                 780

Gly Glu Asn Cys Val Val Met Val Trp His Asp Gly Gln Trp
             785                 790                 795

Ser Asp Val Pro Cys Asn Tyr His Leu Ser Tyr Thr Cys Lys Met
             800                 805                 810

Gly Leu Val Ser Cys Gly Pro Pro Pro Glu Leu Pro Leu Ala Gln
             815                 820                 825

Val Phe Gly Arg Pro Arg Leu Arg Tyr Glu Val Asp Thr Val Leu
             830                 835                 840

Arg Tyr Arg Cys Arg Glu Gly Leu Ala Gln Arg Asn Leu Pro Leu
             845                 850                 855

Ile Arg Cys Gln Glu Asn Gly Arg Trp Glu Ala Pro Gln Ile Ser
             860                 865                 870

Cys Val Pro Arg Arg Pro Ala Arg Ala Leu His Pro Glu Glu Asp
             875                 880                 885

Pro Glu Gly Arg Gln Gly Arg Leu Leu Gly Arg Trp Lys Ala Leu
             890                 895                 900

Leu Ile Pro Pro Ser Ser Pro Met Pro Gly Pro
             905                 910

<210> SEQ ID NO 22
<211> LENGTH: 987
<212> TYPE: PRT
<213> ORGANISM: Homo sapiens

<400> SEQUENCE: 22

Met Ala Leu Arg Arg Leu Gly Ala Ala Leu Leu Leu Leu Pro Leu
  1               5                  10                  15

Leu Ala Ala Val Glu Glu Thr Leu Met Asp Ser Thr Thr Ala Thr
             20                  25                  30

Ala Glu Leu Gly Trp Met Val His Pro Pro Ser Gly Trp Glu Glu
             35                  40                  45

Val Ser Gly Tyr Asp Glu Asn Met Asn Thr Ile Arg Thr Tyr Gln
             50                  55                  60

-continued

```
Val Cys Asn Val Phe Glu Ser Ser Gln Asn Asn Trp Leu Arg Thr
             65                  70                  75
Lys Phe Ile Arg Arg Arg Gly Ala His Arg Ile His Val Glu Met
             80                  85                  90
Lys Phe Ser Val Arg Asp Cys Ser Ser Ile Pro Ser Val Pro Gly
             95                 100                 105
Ser Cys Lys Glu Thr Phe Asn Leu Tyr Tyr Tyr Glu Ala Asp Phe
            110                 115                 120
Asp Ser Ala Thr Lys Thr Phe Pro Asn Trp Met Glu Asn Pro Trp
            125                 130                 135
Val Lys Val Asp Thr Ile Ala Ala Asp Glu Ser Phe Ser Gln Val
            140                 145                 150
Asp Leu Gly Gly Arg Val Met Lys Ile Asn Thr Glu Val Arg Ser
            155                 160                 165
Phe Gly Pro Val Ser Arg Ser Gly Phe Tyr Leu Ala Phe Gln Asp
            170                 175                 180
Tyr Gly Gly Cys Met Ser Leu Ile Ala Val Arg Val Phe Tyr Arg
            185                 190                 195
Lys Cys Pro Arg Ile Ile Gln Asn Gly Ala Ile Phe Gln Glu Thr
            200                 205                 210
Leu Ser Gly Ala Glu Ser Thr Ser Leu Val Ala Ala Arg Gly Ser
            215                 220                 225
Cys Ile Ala Asn Ala Glu Glu Val Asp Val Pro Ile Lys Leu Tyr
            230                 235                 240
Cys Asn Gly Asp Gly Glu Trp Leu Val Pro Ile Gly Arg Cys Met
            245                 250                 255
Cys Lys Ala Gly Phe Glu Ala Val Glu Asn Gly Thr Val Cys Arg
            260                 265                 270
Gly Cys Pro Ser Gly Thr Phe Lys Ala Asn Gln Gly Asp Glu Ala
            275                 280                 285
Cys Thr His Cys Pro Ile Asn Ser Arg Thr Thr Ser Glu Gly Ala
            290                 295                 300
Thr Asn Cys Val Cys Arg Asn Gly Tyr Tyr Arg Ala Asp Leu Asp
            305                 310                 315
Pro Leu Asp Met Pro Cys Thr Thr Ile Pro Ser Ala Pro Gln Ala
            320                 325                 330
Val Ile Ser Ser Val Asn Glu Thr Ser Leu Met Leu Glu Trp Thr
            335                 340                 345
Pro Pro Arg Asp Ser Gly Gly Arg Glu Asp Leu Val Tyr Asn Ile
            350                 355                 360
Ile Cys Lys Ser Cys Gly Ser Gly Arg Gly Ala Cys Thr Arg Cys
            365                 370                 375
Gly Asp Asn Val Gln Tyr Ala Pro Arg Gln Leu Gly Leu Thr Glu
            380                 385                 390
Pro Arg Ile Tyr Ile Ser Asp Leu Leu Ala His Thr Gln Tyr Thr
            395                 400                 405
Phe Glu Ile Gln Ala Val Asn Gly Val Thr Asp Gln Ser Pro Phe
            410                 415                 420
Ser Pro Gln Phe Ala Ser Val Asn Ile Thr Thr Asn Gln Ala Ala
            425                 430                 435
Pro Ser Ala Val Ser Ile Met His Gln Val Ser Arg Thr Val Asp
            440                 445                 450
Ser Ile Thr Leu Ser Trp Ser Gln Pro Asp Gln Pro Asn Gly Val
            455                 460                 465
```

```
Ile Leu Asp Tyr Glu Leu Gln Tyr Tyr Glu Lys Glu Leu Ser Glu
            470                 475                 480

Tyr Asn Ala Thr Ala Ile Lys Ser Pro Thr Asn Thr Val Thr Val
            485                 490                 495

Gln Gly Leu Lys Ala Gly Ala Ile Tyr Val Phe Gln Val Arg Ala
            500                 505                 510

Arg Thr Val Ala Gly Tyr Gly Arg Tyr Ser Gly Lys Met Tyr Phe
            515                 520                 525

Gln Thr Met Thr Glu Ala Glu Tyr Gln Thr Ser Ile Gln Glu Lys
            530                 535                 540

Leu Pro Leu Ile Ile Gly Ser Ser Ala Ala Gly Leu Val Phe Leu
            545                 550                 555

Ile Ala Val Val Val Ile Ala Ile Val Cys Asn Arg Arg Arg Gly
            560                 565                 570

Phe Glu Arg Ala Asp Ser Glu Tyr Thr Asp Lys Leu Gln His Tyr
            575                 580                 585

Thr Ser Gly His Met Thr Pro Gly Met Lys Ile Tyr Ile Asp Pro
            590                 595                 600

Phe Thr Tyr Glu Asp Pro Asn Glu Ala Val Arg Glu Phe Ala Lys
            605                 610                 615

Glu Ile Asp Ile Ser Cys Val Lys Ile Glu Gln Val Ile Gly Ala
            620                 625                 630

Gly Glu Phe Gly Glu Val Cys Ser Gly His Leu Lys Leu Pro Gly
            635                 640                 645

Lys Arg Glu Ile Phe Val Ala Ile Lys Thr Leu Lys Ser Gly Tyr
            650                 655                 660

Thr Glu Lys Gln Arg Arg Asp Phe Leu Ser Glu Ala Ser Ile Met
            665                 670                 675

Gly Gln Phe Asp His Pro Asn Val Ile His Leu Glu Gly Val Val
            680                 685                 690

Thr Lys Ser Thr Pro Val Met Ile Ile Thr Glu Phe Met Glu Asn
            695                 700                 705

Gly Ser Leu Asp Ser Phe Leu Arg Gln Asn Asp Gly Gln Phe Thr
            710                 715                 720

Val Ile Gln Leu Val Gly Met Leu Arg Gly Ile Ala Ala Gly Met
            725                 730                 735

Lys Tyr Leu Ala Asp Met Asn Tyr Val His Arg Asp Leu Ala Ala
            740                 745                 750

Arg Asn Ile Leu Val Asn Ser Asn Leu Val Cys Lys Val Ser Asp
            755                 760                 765

Phe Gly Leu Ser Arg Phe Leu Glu Asp Asp Thr Ser Asp Pro Thr
            770                 775                 780

Tyr Thr Ser Ala Leu Gly Gly Lys Ile Pro Ile Arg Trp Thr Ala
            785                 790                 795

Pro Glu Ala Ile Gln Tyr Arg Lys Phe Thr Ser Ala Ser Asp Val
            800                 805                 810

Trp Ser Tyr Gly Ile Val Met Trp Glu Val Met Ser Tyr Gly Glu
            815                 820                 825

Arg Pro Tyr Trp Asp Met Thr Asn Gln Asp Val Ile Asn Ala Ile
            830                 835                 840

Glu Gln Asp Tyr Arg Leu Pro Pro Pro Met Asp Cys Pro Ser Ala
            845                 850                 855

Leu His Gln Leu Met Leu Asp Cys Trp Gln Lys Asp Arg Asn His
```

```
                              860                 865                 870
Arg Pro Lys Phe Gly Gln Ile Val Asn Thr Leu Asp Lys Met Ile
        875                 880                 885
Arg Asn Pro Asn Ser Leu Lys Ala Met Ala Pro Leu Ser Ser Gly
        890                 895                 900
Ile Asn Leu Pro Leu Leu Asp Arg Thr Ile Pro Asp Tyr Thr Ser
        905                 910                 915
Phe Asn Thr Val Asp Glu Trp Leu Glu Ala Ile Lys Met Gly Gln
        920                 925                 930
Tyr Lys Glu Ser Phe Ala Asn Ala Gly Phe Thr Ser Phe Asp Val
        935                 940                 945
Val Ser Gln Met Met Met Glu Asp Ile Leu Arg Val Gly Val Thr
        950                 955                 960
Leu Ala Gly His Gln Lys Lys Ile Leu Asn Ser Ile Gln Val Met
        965                 970                 975
Arg Ala Gln Met Asn Gln Ile Gln Ser Val Glu Val
        980                 985

<210> SEQ ID NO 23
<211> LENGTH: 282
<212> TYPE: PRT
<213> ORGANISM: Homo sapiens

<400> SEQUENCE: 23

Met Ala Ser Leu Gly Gln Ile Leu Phe Trp Ser Ile Ile Ser Ile
  1               5                  10                  15
Ile Ile Ile Leu Ala Gly Ala Ile Ala Leu Ile Ile Gly Phe Gly
                 20                  25                  30
Ile Ser Gly Arg His Ser Ile Thr Val Thr Thr Val Ala Ser Ala
                 35                  40                  45
Gly Asn Ile Gly Glu Asp Gly Ile Leu Ser Cys Thr Phe Glu Pro
                 50                  55                  60
Asp Ile Lys Leu Ser Asp Ile Val Ile Gln Trp Leu Lys Glu Gly
                 65                  70                  75
Val Leu Gly Leu Val His Glu Phe Lys Glu Gly Lys Asp Glu Leu
                 80                  85                  90
Ser Glu Gln Asp Glu Met Phe Arg Gly Arg Thr Ala Val Phe Ala
                 95                 100                 105
Asp Gln Val Ile Val Gly Asn Ala Ser Leu Arg Leu Lys Asn Val
                110                 115                 120
Gln Leu Thr Asp Ala Gly Thr Tyr Lys Cys Tyr Ile Ile Thr Ser
                125                 130                 135
Lys Gly Lys Lys Asn Ala Asn Leu Glu Tyr Lys Thr Gly Ala Phe
                140                 145                 150
Ser Met Pro Glu Val Asn Val Asp Tyr Asn Ala Ser Ser Glu Thr
                155                 160                 165
Leu Arg Cys Glu Ala Pro Arg Trp Phe Pro Gln Pro Thr Val Val
                170                 175                 180
Trp Ala Ser Gln Val Asp Gln Gly Ala Asn Phe Ser Glu Val Ser
                185                 190                 195
Asn Thr Ser Phe Glu Leu Asn Ser Glu Asn Val Thr Met Lys Val
                200                 205                 210
Val Ser Val Leu Tyr Asn Val Thr Ile Asn Asn Thr Tyr Ser Cys
                215                 220                 225
Met Ile Glu Asn Asp Ile Ala Lys Ala Thr Gly Asp Ile Lys Val
```

```
                         230                 235                 240
Thr Glu Ser Glu Ile Lys Arg Arg Ser His Leu Gln Leu Leu Asn
                 245                 250                 255

Ser Lys Ala Ser Leu Cys Val Ser Ser Phe Ala Ile Ser Trp
                 260                 265                 270

Ala Leu Leu Pro Leu Ser Pro Tyr Leu Met Leu Lys
                 275                 280

<210> SEQ ID NO 24
<211> LENGTH: 123
<212> TYPE: PRT
<213> ORGANISM: Homo sapiens

<400> SEQUENCE: 24

Met Lys Ala Val Leu Ala Leu Leu Met Ala Gly Leu Ala Leu
 1               5                  10                  15

Gln Pro Gly Thr Ala Leu Leu Cys Tyr Ser Cys Lys Ala Gln Val
                 20                  25                  30

Ser Asn Glu Asp Cys Leu Gln Val Glu Asn Cys Thr Gln Leu Gly
                 35                  40                  45

Glu Gln Cys Trp Thr Ala Arg Ile Arg Ala Val Gly Leu Leu Thr
                 50                  55                  60

Val Ile Ser Lys Gly Cys Ser Leu Asn Cys Val Asp Asp Ser Gln
                 65                  70                  75

Asp Tyr Tyr Val Gly Lys Lys Asn Ile Thr Cys Cys Asp Thr Asp
                 80                  85                  90

Leu Cys Asn Ala Ser Gly Ala His Ala Leu Gln Pro Ala Ala
                 95                  100                 105

Ile Leu Ala Leu Leu Pro Ala Leu Gly Leu Leu Leu Trp Gly Pro
                 110                 115                 120

Gly Gln Leu

<210> SEQ ID NO 25
<211> LENGTH: 236
<212> TYPE: PRT
<213> ORGANISM: Homo sapiens

<400> SEQUENCE: 25

Met Pro Gly Ala Ala Ala Ala Ala Ala Ala Ala Ala Ala Met
 1               5                  10                  15

Leu Pro Ala Gln Glu Ala Ala Lys Leu Tyr His Thr Asn Tyr Val
                 20                  25                  30

Arg Asn Ser Arg Ala Ile Gly Val Leu Trp Ala Ile Phe Thr Ile
                 35                  40                  45

Cys Phe Ala Ile Val Asn Val Val Cys Phe Ile Gln Pro Tyr Trp
                 50                  55                  60

Ile Gly Asp Gly Val Asp Thr Pro Gln Ala Gly Tyr Phe Gly Leu
                 65                  70                  75

Phe His Tyr Cys Ile Gly Asn Gly Phe Ser Arg Glu Leu Thr Cys
                 80                  85                  90

Arg Gly Ser Phe Thr Asp Phe Ser Thr Leu Pro Ser Gly Ala Phe
                 95                  100                 105

Lys Ala Ala Ser Phe Phe Ile Gly Leu Ser Met Met Leu Ile Ile
                 110                 115                 120

Ala Cys Ile Ile Cys Phe Thr Leu Phe Phe Phe Cys Asn Thr Ala
                 125                 130                 135
```

```
Thr Val Tyr Lys Ile Cys Ala Trp Met Gln Leu Thr Ser Ala Ala
            140                 145                 150

Cys Leu Val Leu Gly Cys Met Ile Phe Pro Asp Gly Trp Asp Ser
            155                 160                 165

Asp Glu Val Lys Arg Met Cys Gly Glu Lys Thr Asp Lys Tyr Thr
            170                 175                 180

Leu Gly Ala Cys Ser Val Arg Trp Ala Tyr Ile Leu Ala Ile Ile
            185                 190                 195

Gly Ile Leu Asp Ala Leu Ile Leu Ser Phe Leu Ala Phe Val Leu
            200                 205                 210

Gly Asn Arg Gln Asp Ser Leu Met Ala Glu Glu Leu Lys Ala Glu
            215                 220                 225

Asn Lys Val Leu Leu Ser Gln Tyr Ser Leu Glu
            230                 235

<210> SEQ ID NO 26
<211> LENGTH: 184
<212> TYPE: PRT
<213> ORGANISM: Homo sapiens

<400> SEQUENCE: 26

Met Arg Arg Gly Pro Arg Ser Leu Arg Gly Arg Asp Ala Pro Ala
  1               5                  10                  15

Pro Thr Pro Cys Val Pro Ala Glu Cys Phe Asp Leu Leu Val Arg
             20                  25                  30

His Cys Val Ala Cys Gly Leu Leu Arg Thr Pro Arg Pro Lys Pro
             35                  40                  45

Ala Gly Ala Ser Ser Pro Ala Pro Arg Thr Ala Leu Gln Pro Gln
             50                  55                  60

Glu Ser Val Gly Ala Gly Ala Gly Glu Ala Ala Leu Pro Leu Pro
             65                  70                  75

Gly Leu Leu Phe Gly Ala Pro Ala Leu Leu Gly Leu Ala Leu Val
             80                  85                  90

Leu Ala Leu Val Leu Val Gly Leu Val Ser Trp Arg Arg Arg Gln
             95                 100                 105

Arg Arg Leu Arg Gly Ala Ser Ser Ala Glu Ala Pro Asp Gly Asp
            110                 115                 120

Lys Asp Ala Pro Glu Pro Leu Asp Lys Val Ile Ile Leu Ser Pro
            125                 130                 135

Gly Ile Ser Asp Ala Thr Ala Pro Ala Trp Pro Pro Pro Gly Glu
            140                 145                 150

Asp Pro Gly Thr Thr Pro Pro Gly His Ser Val Pro Val Pro Ala
            155                 160                 165

Thr Glu Leu Gly Ser Thr Glu Leu Val Thr Thr Lys Thr Ala Gly
            170                 175                 180

Pro Glu Gln Gln

<210> SEQ ID NO 27
<211> LENGTH: 847
<212> TYPE: PRT
<213> ORGANISM: Homo sapiens

<400> SEQUENCE: 27

Met His Leu Leu Gly Pro Trp Leu Leu Leu Val Leu Glu Tyr
  1               5                  10                  15

Leu Ala Phe Ser Asp Ser Ser Lys Trp Val Phe Glu His Pro Glu
             20                  25                  30
```

Thr Leu Tyr Ala Trp Glu Gly Ala Cys Val Trp Ile Pro Cys Thr
                35                  40                  45

Tyr Arg Ala Leu Asp Gly Asp Leu Glu Ser Phe Ile Leu Phe His
                50                  55                  60

Asn Pro Glu Tyr Asn Lys Asn Thr Ser Lys Phe Asp Gly Thr Arg
                65                  70                  75

Leu Tyr Glu Ser Thr Lys Asp Gly Lys Val Pro Ser Glu Gln Lys
                80                  85                  90

Arg Val Gln Phe Leu Gly Asp Lys Asn Lys Asn Cys Thr Leu Ser
                95                  100                 105

Ile His Pro Val His Leu Asn Asp Ser Gly Gln Leu Gly Leu Arg
                110                 115                 120

Met Glu Ser Lys Thr Glu Lys Trp Met Glu Arg Ile His Leu Asn
                125                 130                 135

Val Ser Glu Arg Pro Phe Pro Pro His Ile Gln Leu Pro Pro Glu
                140                 145                 150

Ile Gln Glu Ser Gln Glu Val Thr Leu Thr Cys Leu Leu Asn Phe
                155                 160                 165

Ser Cys Tyr Gly Tyr Pro Ile Gln Leu Gln Trp Leu Leu Glu Gly
                170                 175                 180

Val Pro Met Arg Gln Ala Ala Val Thr Ser Thr Ser Leu Thr Ile
                185                 190                 195

Lys Ser Val Phe Thr Arg Ser Glu Leu Lys Phe Ser Pro Gln Trp
                200                 205                 210

Ser His His Gly Lys Ile Val Thr Cys Gln Leu Gln Asp Ala Asp
                215                 220                 225

Gly Lys Phe Leu Ser Asn Asp Thr Val Gln Leu Asn Val Lys His
                230                 235                 240

Thr Pro Lys Leu Glu Ile Lys Val Thr Pro Ser Asp Ala Ile Val
                245                 250                 255

Arg Glu Gly Asp Ser Val Thr Met Thr Cys Glu Val Ser Ser Ser
                260                 265                 270

Asn Pro Glu Tyr Thr Thr Val Ser Trp Leu Lys Asp Gly Thr Ser
                275                 280                 285

Leu Lys Lys Gln Asn Thr Phe Thr Leu Asn Leu Arg Glu Val Thr
                290                 295                 300

Lys Asp Gln Ser Gly Lys Tyr Cys Cys Gln Val Ser Asn Asp Val
                305                 310                 315

Gly Pro Gly Arg Ser Glu Glu Val Phe Leu Gln Val Gln Tyr Ala
                320                 325                 330

Pro Glu Pro Ser Thr Val Gln Ile Leu His Ser Pro Ala Val Glu
                335                 340                 345

Gly Ser Gln Val Glu Phe Leu Cys Met Ser Leu Ala Asn Pro Leu
                350                 355                 360

Pro Thr Asn Tyr Thr Trp Tyr His Asn Gly Lys Glu Met Gln Gly
                365                 370                 375

Arg Thr Glu Glu Lys Val His Ile Pro Lys Ile Leu Pro Trp His
                380                 385                 390

Ala Gly Thr Tyr Ser Cys Val Ala Glu Asn Ile Leu Gly Thr Gly
                395                 400                 405

Gln Arg Gly Pro Gly Ala Glu Leu Asp Val Gln Tyr Pro Pro Lys
                410                 415                 420

Lys Val Thr Thr Val Ile Gln Asn Pro Met Pro Ile Arg Glu Gly

-continued

```
                425                 430                 435
Asp Thr Val Thr Leu Ser Cys Asn Tyr Asn Ser Ser Asn Pro Ser
                440                 445                 450
Val Thr Arg Tyr Glu Trp Lys Pro His Gly Ala Trp Glu Glu Pro
                455                 460                 465
Ser Leu Gly Val Leu Lys Ile Gln Asn Val Gly Trp Asp Asn Thr
                470                 475                 480
Thr Ile Ala Cys Ala Arg Cys Asn Ser Trp Cys Ser Trp Ala Ser
                485                 490                 495
Pro Val Ala Leu Asn Val Gln Tyr Ala Pro Arg Asp Val Arg Val
                500                 505                 510
Arg Lys Ile Lys Pro Leu Ser Glu Ile His Ser Gly Asn Ser Val
                515                 520                 525
Ser Leu Gln Cys Asp Phe Ser Ser Ser His Pro Lys Glu Val Gln
                530                 535                 540
Phe Phe Trp Glu Lys Asn Gly Arg Leu Leu Gly Lys Glu Ser Gln
                545                 550                 555
Leu Asn Phe Asp Ser Ile Ser Pro Glu Asp Ala Gly Ser Tyr Ser
                560                 565                 570
Cys Trp Val Asn Asn Ser Ile Gly Gln Thr Ala Ser Lys Ala Trp
                575                 580                 585
Thr Leu Glu Val Leu Tyr Ala Pro Arg Arg Leu Arg Val Ser Met
                590                 595                 600
Ser Pro Gly Asp Gln Val Met Glu Gly Lys Ser Ala Thr Leu Thr
                605                 610                 615
Cys Glu Ser Asp Ala Asn Pro Pro Val Ser His Tyr Thr Trp Phe
                620                 625                 630
Asp Trp Asn Asn Gln Ser Leu Pro His His Ser Gln Lys Leu Arg
                635                 640                 645
Leu Glu Pro Val Lys Val Gln His Ser Gly Ala Tyr Trp Cys Gln
                650                 655                 660
Gly Thr Asn Ser Val Gly Lys Gly Arg Ser Pro Leu Ser Thr Leu
                665                 670                 675
Thr Val Tyr Tyr Ser Pro Glu Thr Ile Gly Arg Arg Val Ala Val
                680                 685                 690
Gly Leu Gly Ser Cys Leu Ala Ile Leu Ile Leu Ala Ile Cys Gly
                695                 700                 705
Leu Lys Leu Gln Arg Arg Trp Lys Arg Thr Gln Ser Gln Gln Gly
                710                 715                 720
Leu Gln Glu Asn Ser Ser Gly Gln Ser Phe Phe Val Arg Asn Lys
                725                 730                 735
Lys Val Arg Arg Ala Pro Leu Ser Glu Gly Pro His Ser Leu Gly
                740                 745                 750
Cys Tyr Asn Pro Met Met Glu Asp Gly Ile Ser Tyr Thr Thr Leu
                755                 760                 765
Arg Phe Pro Glu Met Asn Ile Pro Arg Thr Gly Asp Ala Glu Ser
                770                 775                 780
Ser Glu Met Gln Arg Pro Pro Arg Thr Cys Asp Asp Thr Val Thr
                785                 790                 795
Tyr Ser Ala Leu His Lys Arg Gln Val Gly Asp Tyr Glu Asn Val
                800                 805                 810
Ile Pro Asp Phe Pro Glu Asp Glu Gly Ile His Tyr Ser Glu Leu
                815                 820                 825
```

```
Ile Gln Phe Gly Val Gly Glu Arg Pro Gln Ala Gln Glu Asn Val
            830                 835                 840

Asp Tyr Val Ile Leu Lys His
            845
```

<210> SEQ ID NO 28
<211> LENGTH: 226
<212> TYPE: PRT
<213> ORGANISM: Homo sapiens

<400> SEQUENCE: 28

```
Met Pro Gly Gly Pro Gly Val Leu Gln Ala Leu Pro Ala Thr Ile
  1               5                  10                  15

Phe Leu Leu Phe Leu Leu Ser Ala Val Tyr Leu Gly Pro Gly Cys
                 20                  25                  30

Gln Ala Leu Trp Met His Lys Val Pro Ala Ser Leu Met Val Ser
                 35                  40                  45

Leu Gly Glu Asp Ala His Phe Gln Cys Pro His Asn Ser Ser Asn
                 50                  55                  60

Asn Ala Asn Val Thr Trp Trp Arg Val Leu His Gly Asn Tyr Thr
                 65                  70                  75

Trp Pro Pro Glu Phe Leu Gly Pro Gly Glu Asp Pro Asn Gly Thr
                 80                  85                  90

Leu Ile Ile Gln Asn Val Asn Lys Ser His Gly Gly Ile Tyr Val
                 95                 100                 105

Cys Arg Val Gln Glu Gly Asn Glu Ser Tyr Gln Gln Ser Cys Gly
                110                 115                 120

Thr Tyr Leu Arg Val Arg Gln Pro Pro Arg Pro Phe Leu Asp
                125                 130                 135

Met Gly Glu Gly Thr Lys Asn Arg Ile Ile Thr Ala Glu Gly Ile
                140                 145                 150

Ile Leu Leu Phe Cys Ala Val Val Pro Gly Thr Leu Leu Leu Phe
                155                 160                 165

Arg Lys Arg Trp Gln Asn Glu Lys Leu Gly Leu Asp Ala Gly Asp
                170                 175                 180

Glu Tyr Glu Asp Glu Asn Leu Tyr Glu Gly Leu Asn Leu Asp Asp
                185                 190                 195

Cys Ser Met Tyr Glu Asp Ile Ser Arg Gly Leu Gln Gly Thr Tyr
                200                 205                 210

Gln Asp Val Gly Ser Leu Asn Ile Gly Asp Val Gln Leu Glu Lys
                215                 220                 225

Pro
```

<210> SEQ ID NO 29
<211> LENGTH: 372
<212> TYPE: PRT
<213> ORGANISM: Homo sapiens

<400> SEQUENCE: 29

```
Met Asn Tyr Pro Leu Thr Leu Glu Met Asp Leu Glu Asn Leu Glu
  1               5                  10                  15

Asp Leu Phe Trp Glu Leu Asp Arg Leu Asp Asn Tyr Asn Asp Thr
                 20                  25                  30

Ser Leu Val Glu Asn His Leu Cys Pro Ala Thr Glu Gly Pro Leu
                 35                  40                  45

Met Ala Ser Phe Lys Ala Val Phe Val Pro Val Ala Tyr Ser Leu
                 50                  55                  60
```

```
Ile Phe Leu Leu Gly Val Ile Gly Asn Val Leu Val Leu Val Ile
                65                  70                  75

Leu Glu Arg His Arg Gln Thr Arg Ser Ser Thr Glu Thr Phe Leu
         80                  85                  90

Phe His Leu Ala Val Ala Asp Leu Leu Leu Val Phe Ile Leu Pro
         95                 100                 105

Phe Ala Val Ala Glu Gly Ser Val Gly Trp Val Leu Gly Thr Phe
            110                 115                 120

Leu Cys Lys Thr Val Ile Ala Leu His Lys Val Asn Phe Tyr Cys
            125                 130                 135

Ser Ser Leu Leu Leu Ala Cys Ile Ala Val Asp Arg Tyr Leu Ala
            140                 145                 150

Ile Val His Ala Val His Ala Tyr Arg His Arg Leu Leu Ser
            155                 160                 165

Ile His Ile Thr Cys Gly Thr Ile Trp Leu Val Gly Phe Leu Leu
            170                 175                 180

Ala Leu Pro Glu Ile Leu Phe Ala Lys Val Ser Gln Gly His His
            185                 190                 195

Asn Asn Ser Leu Pro Arg Cys Thr Phe Ser Gln Glu Asn Gln Ala
            200                 205                 210

Glu Thr His Ala Trp Phe Thr Ser Arg Phe Leu Tyr His Val Ala
            215                 220                 225

Gly Phe Leu Leu Pro Met Leu Val Met Gly Trp Cys Tyr Val Gly
            230                 235                 240

Val Val His Arg Leu Arg Gln Ala Gln Arg Arg Pro Gln Arg Gln
            245                 250                 255

Lys Ala Val Arg Val Ala Ile Leu Val Thr Ser Ile Phe Phe Leu
            260                 265                 270

Cys Trp Ser Pro Tyr His Ile Val Ile Phe Leu Asp Thr Leu Ala
            275                 280                 285

Arg Leu Lys Ala Val Asp Asn Thr Cys Lys Leu Asn Gly Ser Leu
            290                 295                 300

Pro Val Ala Ile Thr Met Cys Glu Phe Leu Gly Leu Ala His Cys
            305                 310                 315

Cys Leu Asn Pro Met Leu Tyr Thr Phe Ala Gly Val Lys Phe Arg
            320                 325                 330

Ser Asp Leu Ser Arg Leu Leu Thr Lys Leu Gly Cys Thr Gly Pro
            335                 340                 345

Ala Ser Leu Cys Gln Leu Phe Pro Ser Trp Arg Arg Ser Ser Leu
            350                 355                 360

Ser Glu Ser Glu Asn Ala Thr Ser Leu Thr Thr Phe
            365                 370

<210> SEQ ID NO 30
<211> LENGTH: 273
<212> TYPE: PRT
<213> ORGANISM: Homo sapiens

<400> SEQUENCE: 30

Met Gly Ser Gly Trp Val Pro Trp Val Ala Leu Leu Val Asn
  1               5                  10                  15

Leu Thr Arg Leu Asp Ser Ser Met Thr Gln Gly Thr Asp Ser Pro
                 20                  25                  30

Glu Asp Phe Val Ile Gln Ala Lys Ala Asp Cys Tyr Phe Thr Asn
                 35                  40                  45
```

-continued

Gly Thr Glu Lys Val Gln Phe Val Val Arg Phe Ile Phe Asn Leu
             50                  55                  60

Glu Glu Tyr Val Arg Phe Asp Ser Asp Val Gly Met Phe Val Ala
             65                  70                  75

Leu Thr Lys Leu Gly Gln Pro Asp Ala Glu Gln Trp Asn Ser Arg
             80                  85                  90

Leu Asp Leu Leu Glu Arg Ser Arg Gln Ala Val Asp Gly Val Cys
             95                 100                 105

Arg His Asn Tyr Arg Leu Gly Ala Pro Phe Thr Val Gly Arg Lys
            110                 115                 120

Val Gln Pro Glu Val Thr Val Tyr Pro Glu Arg Thr Pro Leu Leu
            125                 130                 135

His Gln His Asn Leu Leu His Cys Ser Val Thr Gly Phe Tyr Pro
            140                 145                 150

Gly Asp Ile Lys Ile Lys Trp Phe Leu Asn Gly Gln Glu Glu Arg
            155                 160                 165

Ala Gly Val Met Ser Thr Gly Pro Ile Arg Asn Gly Asp Trp Thr
            170                 175                 180

Phe Gln Thr Val Val Met Leu Glu Met Thr Pro Glu Leu Gly His
            185                 190                 195

Val Tyr Thr Cys Leu Val Asp His Ser Ser Leu Leu Ser Pro Val
            200                 205                 210

Ser Val Glu Trp Arg Ala Gln Ser Glu Tyr Ser Trp Arg Lys Met
            215                 220                 225

Leu Ser Gly Ile Ala Ala Phe Leu Leu Gly Leu Ile Phe Leu Leu
            230                 235                 240

Val Gly Ile Val Ile Gln Leu Arg Ala Gln Lys Gly Tyr Val Arg
            245                 250                 255

Thr Gln Met Ser Gly Asn Glu Val Ser Arg Ala Val Leu Leu Pro
            260                 265                 270

Gln Ser Cys

<210> SEQ ID NO 31
<211> LENGTH: 422
<212> TYPE: PRT
<213> ORGANISM: Homo sapiens

<400> SEQUENCE: 31

Met Gly Gln Ala Gly Cys Lys Gly Leu Cys Leu Ser Leu Phe Asp
 1                5                  10                  15

Tyr Lys Thr Glu Lys Tyr Val Ile Ala Lys Asn Lys Lys Val Gly
             20                  25                  30

Leu Leu Tyr Arg Leu Leu Gln Ala Ser Ile Leu Ala Tyr Leu Val
             35                  40                  45

Val Trp Val Phe Leu Ile Lys Lys Gly Tyr Gln Asp Val Asp Thr
             50                  55                  60

Ser Leu Gln Ser Ala Val Ile Thr Lys Val Lys Gly Val Ala Phe
             65                  70                  75

Thr Asn Thr Ser Asp Leu Gly Gln Arg Ile Trp Asp Val Ala Asp
             80                  85                  90

Tyr Val Ile Pro Ala Gln Gly Glu Asn Val Phe Phe Val Val Thr
             95                 100                 105

Asn Leu Ile Val Thr Pro Asn Gln Arg Gln Asn Val Cys Ala Glu
            110                 115                 120

```
Asn Glu Gly Ile Pro Asp Gly Ala Cys Ser Lys Asp Ser Asp Cys
            125                 130                 135

His Ala Gly Glu Ala Val Thr Ala Gly Asn Gly Val Lys Thr Gly
            140                 145                 150

Arg Cys Leu Arg Arg Glu Asn Leu Ala Arg Gly Thr Cys Glu Ile
            155                 160                 165

Phe Ala Trp Cys Pro Leu Glu Thr Ser Ser Arg Pro Glu Glu Pro
            170                 175                 180

Phe Leu Lys Glu Ala Glu Asp Phe Thr Ile Phe Ile Lys Asn His
            185                 190                 195

Ile Arg Phe Pro Lys Phe Asn Phe Ser Lys Ser Asn Val Met Asp
            200                 205                 210

Val Lys Asp Arg Ser Phe Leu Lys Ser Cys His Phe Gly Pro Lys
            215                 220                 225

Asn His Tyr Cys Pro Ile Phe Arg Leu Gly Ser Val Ile Arg Trp
            230                 235                 240

Ala Gly Ser Asp Phe Gln Asp Ile Ala Leu Glu Gly Gly Val Ile
            245                 250                 255

Gly Ile Asn Ile Glu Trp Asn Cys Asp Leu Asp Lys Ala Ala Ser
            260                 265                 270

Glu Cys His Pro His Tyr Ser Phe Ser Arg Leu Asp Asn Lys Leu
            275                 280                 285

Ser Lys Ser Val Ser Ser Gly Tyr Asn Phe Arg Phe Ala Arg Tyr
            290                 295                 300

Tyr Arg Asp Ala Ala Gly Val Glu Phe Arg Thr Leu Met Lys Ala
            305                 310                 315

Tyr Gly Ile Arg Phe Asp Val Met Val Asn Gly Lys Gly Ala Phe
            320                 325                 330

Phe Cys Asp Leu Val Leu Ile Tyr Leu Ile Lys Lys Arg Glu Phe
            335                 340                 345

Tyr Arg Asp Lys Lys Tyr Glu Glu Val Arg Gly Leu Glu Asp Ser
            350                 355                 360

Ser Gln Glu Ala Glu Asp Glu Ala Ser Gly Leu Gly Leu Ser Glu
            365                 370                 375

Gln Leu Thr Ser Gly Pro Gly Leu Leu Gly Met Pro Glu Gln Gln
            380                 385                 390

Glu Leu Gln Glu Pro Pro Glu Ala Lys Arg Gly Ser Ser Ser Gln
            395                 400                 405

Lys Gly Asn Gly Ser Val Cys Pro Gln Leu Leu Glu Pro His Arg
            410                 415                 420

Ser Thr

<210> SEQ ID NO 32
<211> LENGTH: 359
<212> TYPE: PRT
<213> ORGANISM: Homo sapiens

<400> SEQUENCE: 32

Met Ala Glu Ala Ile Thr Tyr Ala Asp Leu Arg Phe Val Lys Ala
  1               5                  10                  15

Pro Leu Lys Lys Ser Ile Ser Ser Arg Leu Gly Gln Asp Pro Gly
                 20                  25                  30

Ala Asp Asp Asp Gly Glu Ile Thr Tyr Glu Asn Val Gln Val Pro
                 35                  40                  45

Ala Val Leu Gly Val Pro Ser Ser Leu Ala Ser Ser Val Leu Gly
```

```
                    50                  55                  60
Asp Lys Ala Ala Val Lys Ser Glu Gln Pro Thr Ala Ser Trp Arg
            65                  70                  75

Ala Val Thr Ser Pro Ala Val Gly Arg Ile Leu Pro Cys Arg Thr
            80                  85                  90

Thr Cys Leu Arg Tyr Leu Leu Leu Gly Leu Leu Leu Thr Cys Leu
            95                 100                 105

Leu Leu Gly Val Thr Ala Ile Cys Leu Gly Val Arg Tyr Leu Gln
           110                 115                 120

Val Ser Gln Gln Leu Gln Gln Thr Asn Arg Val Leu Glu Val Thr
           125                 130                 135

Asn Ser Ser Leu Arg Gln Gln Leu Arg Leu Lys Ile Thr Gln Leu
           140                 145                 150

Gly Gln Ser Ala Glu Asp Leu Gln Gly Ser Arg Arg Glu Leu Ala
           155                 160                 165

Gln Ser Gln Glu Ala Leu Gln Val Glu Gln Arg Ala His Gln Ala
           170                 175                 180

Ala Glu Gly Gln Leu Gln Ala Cys Gln Ala Asp Arg Gln Lys Thr
           185                 190                 195

Lys Glu Thr Leu Gln Ser Glu Gln Gln Arg Arg Ala Leu Glu
           200                 205                 210

Gln Lys Leu Ser Asn Met Glu Asn Arg Leu Lys Pro Phe Phe Thr
           215                 220                 225

Cys Gly Ser Ala Asp Thr Cys Cys Pro Ser Gly Trp Ile Met His
           230                 235                 240

Gln Lys Ser Cys Phe Tyr Ile Ser Leu Thr Ser Lys Asn Trp Gln
           245                 250                 255

Glu Ser Gln Lys Gln Cys Glu Thr Leu Ser Ser Lys Leu Ala Thr
           260                 265                 270

Phe Ser Glu Ile Tyr Pro Gln Ser His Ser Tyr Tyr Phe Leu Asn
           275                 280                 285

Ser Leu Leu Pro Asn Gly Gly Ser Gly Asn Ser Tyr Trp Thr Gly
           290                 295                 300

Leu Ser Ser Asn Lys Asp Trp Lys Leu Thr Asp Asp Thr Gln Arg
           305                 310                 315

Thr Arg Thr Tyr Ala Gln Ser Ser Lys Cys Asn Lys Val His Lys
           320                 325                 330

Thr Trp Ser Trp Trp Thr Leu Glu Ser Glu Ser Cys Arg Ser Ser
           335                 340                 345

Leu Pro Tyr Ile Cys Glu Met Thr Ala Phe Arg Phe Pro Asp
           350                 355

<210> SEQ ID NO 33
<211> LENGTH: 661
<212> TYPE: PRT
<213> ORGANISM: Homo sapiens

<400> SEQUENCE: 33

Met Ala Phe Asp Val Ser Cys Phe Phe Trp Val Val Leu Phe Ser
  1               5                  10                  15

Ala Gly Cys Lys Val Ile Thr Ser Trp Asp Gln Met Cys Ile Glu
                 20                  25                  30

Lys Glu Ala Asn Lys Thr Tyr Asn Cys Glu Asn Leu Gly Leu Ser
                 35                  40                  45

Glu Ile Pro Asp Thr Leu Pro Asn Thr Thr Glu Phe Leu Glu Phe
```

-continued

```
                50                  55                  60
Ser Phe Asn Phe Leu Pro Thr Ile His Asn Arg Thr Phe Ser Arg
                65                  70                  75
Leu Met Asn Leu Thr Phe Leu Asp Leu Thr Arg Cys Gln Ile Asn
                80                  85                  90
Trp Ile His Glu Asp Thr Phe Gln Ser His His Gln Leu Ser Thr
                95                  100                 105
Leu Val Leu Thr Gly Asn Pro Leu Ile Phe Met Ala Glu Thr Ser
                110                 115                 120
Leu Asn Gly Pro Lys Ser Leu Lys His Leu Phe Leu Ile Gln Thr
                125                 130                 135
Gly Ile Ser Asn Leu Glu Phe Ile Pro Val His Asn Leu Glu Asn
                140                 145                 150
Leu Glu Ser Leu Tyr Leu Gly Ser Asn His Ile Ser Ser Ile Lys
                155                 160                 165
Phe Pro Lys Asp Phe Pro Ala Arg Asn Leu Lys Val Leu Asp Phe
                170                 175                 180
Gln Asn Asn Ala Ile His Tyr Ile Ser Arg Glu Asp Met Arg Ser
                185                 190                 195
Leu Glu Gln Ala Ile Asn Leu Ser Leu Asn Phe Asn Gly Asn Asn
                200                 205                 210
Val Lys Gly Ile Glu Leu Gly Ala Phe Asp Ser Thr Val Phe Gln
                215                 220                 225
Ser Leu Asn Phe Gly Gly Thr Pro Asn Leu Ser Val Ile Phe Asn
                230                 235                 240
Gly Leu Gln Asn Ser Thr Thr Gln Ser Leu Trp Leu Gly Thr Phe
                245                 250                 255
Glu Asp Ile Asp Asp Glu Asp Ile Ser Ser Ala Met Leu Lys Gly
                260                 265                 270
Leu Cys Glu Met Ser Val Glu Ser Leu Asn Leu Gln Glu His Arg
                275                 280                 285
Phe Ser Asp Ile Ser Ser Thr Thr Phe Gln Cys Phe Thr Gln Leu
                290                 295                 300
Gln Glu Leu Asp Leu Thr Ala Thr His Leu Lys Gly Leu Pro Ser
                305                 310                 315
Gly Met Lys Gly Leu Asn Leu Lys Lys Leu Val Leu Ser Val
                320                 325                 330
Asn His Phe Asp Gln Leu Cys Gln Ile Ser Ala Ala Asn Phe Pro
                335                 340                 345
Ser Leu Thr His Leu Tyr Ile Arg Gly Asn Val Lys Lys Leu His
                350                 355                 360
Leu Gly Val Gly Cys Leu Glu Lys Leu Gly Asn Leu Gln Thr Leu
                365                 370                 375
Asp Leu Ser His Asn Asp Ile Glu Ala Ser Asp Cys Cys Ser Leu
                380                 385                 390
Gln Leu Lys Asn Leu Ser His Leu Gln Thr Leu Asn Leu Ser His
                395                 400                 405
Asn Glu Pro Leu Gly Leu Gln Ser Gln Ala Phe Lys Glu Cys Pro
                410                 415                 420
Gln Leu Glu Leu Leu Asp Leu Ala Phe Thr Arg Leu His Ile Asn
                425                 430                 435
Ala Pro Gln Ser Pro Phe Gln Asn Leu His Phe Leu Gln Val Leu
                440                 445                 450
```

```
Asn Leu Thr Tyr Cys Phe Leu Asp Thr Ser Asn Gln His Leu Leu
                455                 460                 465

Ala Gly Leu Pro Val Leu Arg His Leu Asn Leu Lys Gly Asn His
                470                 475                 480

Phe Gln Asp Gly Thr Ile Thr Lys Thr Asn Leu Leu Gln Thr Val
                485                 490                 495

Gly Ser Leu Glu Val Leu Ile Leu Ser Ser Cys Gly Leu Leu Ser
                500                 505                 510

Ile Asp Gln Gln Ala Phe His Ser Leu Gly Lys Met Ser His Val
                515                 520                 525

Asp Leu Ser His Asn Ser Leu Thr Cys Asp Ser Ile Asp Ser Leu
                530                 535                 540

Ser His Leu Lys Gly Ile Tyr Leu Asn Leu Ala Ala Asn Ser Ile
                545                 550                 555

Asn Ile Ile Ser Pro Arg Leu Leu Pro Ile Leu Ser Gln Gln Ser
                560                 565                 570

Thr Ile Asn Leu Ser His Asn Pro Leu Asp Cys Thr Cys Ser Asn
                575                 580                 585

Ile His Phe Leu Thr Trp Tyr Lys Glu Asn Leu His Lys Leu Glu
                590                 595                 600

Gly Ser Glu Glu Thr Thr Cys Ala Asn Pro Pro Ser Leu Arg Gly
                605                 610                 615

Val Lys Leu Ser Asp Val Lys Leu Ser Cys Gly Ile Thr Ala Ile
                620                 625                 630

Gly Ile Phe Phe Leu Ile Val Phe Leu Leu Leu Ala Ile Leu
                635                 640                 645

Leu Phe Phe Ala Val Lys Tyr Leu Leu Arg Trp Lys Tyr Gln His
                650                 655                 660

Ile

<210> SEQ ID NO 34
<211> LENGTH: 429
<212> TYPE: PRT
<213> ORGANISM: Homo sapiens

<400> SEQUENCE: 34

Met Leu Pro Arg Leu Leu Leu Ile Cys Ala Pro Leu Cys Glu
  1             5                  10                  15

Pro Ala Glu Leu Phe Leu Ile Ala Ser Pro Ser His Pro Thr Glu
                20                  25                  30

Gly Ser Pro Val Thr Leu Thr Cys Lys Met Pro Phe Leu Gln Ser
                35                  40                  45

Ser Asp Ala Gln Phe Gln Phe Cys Phe Phe Arg Asp Thr Arg Ala
                50                  55                  60

Leu Gly Pro Gly Trp Ser Ser Ser Pro Lys Leu Gln Ile Ala Ala
                65                  70                  75

Met Trp Lys Glu Asp Thr Gly Ser Tyr Trp Cys Glu Ala Gln Thr
                80                  85                  90

Met Ala Ser Lys Val Leu Arg Ser Arg Arg Ser Gln Ile Asn Val
                95                 100                 105

His Arg Val Pro Val Ala Asp Val Ser Leu Glu Thr Gln Pro Pro
                110                 115                 120

Gly Gly Gln Val Met Glu Gly Asp Arg Leu Val Leu Ile Cys Ser
                125                 130                 135

Val Ala Met Gly Thr Gly Asp Ile Thr Phe Leu Trp Tyr Lys Gly
```

-continued

```
                140                 145                 150
Ala Val Gly Leu Asn Leu Gln Ser Lys Thr Gln Arg Ser Leu Thr
                155                 160                 165
Ala Glu Tyr Glu Ile Pro Ser Val Arg Glu Ser Asp Ala Glu Gln
                170                 175                 180
Tyr Tyr Cys Val Ala Glu Asn Gly Tyr Gly Pro Ser Pro Ser Gly
                185                 190                 195
Leu Val Ser Ile Thr Val Arg Ile Pro Val Ser Arg Pro Ile Leu
                200                 205                 210
Met Leu Arg Ala Pro Arg Ala Gln Ala Ala Val Glu Asp Val Leu
                215                 220                 225
Glu Leu His Cys Glu Ala Leu Arg Gly Ser Pro Pro Ile Leu Tyr
                230                 235                 240
Trp Phe Tyr His Glu Asp Ile Thr Leu Gly Ser Arg Ser Ala Pro
                245                 250                 255
Ser Gly Gly Gly Ala Ser Phe Asn Leu Ser Leu Thr Glu Glu His
                260                 265                 270
Ser Gly Asn Tyr Ser Cys Glu Ala Asn Asn Gly Leu Gly Ala Gln
                275                 280                 285
Arg Ser Glu Ala Val Thr Leu Asn Phe Thr Val Pro Thr Gly Ala
                290                 295                 300
Arg Ser Asn His Leu Thr Ser Gly Val Ile Glu Gly Leu Leu Ser
                305                 310                 315
Thr Leu Gly Pro Ala Thr Val Ala Leu Leu Phe Cys Tyr Gly Leu
                320                 325                 330
Lys Arg Lys Ile Gly Arg Arg Ser Ala Arg Asp Pro Leu Arg Ser
                335                 340                 345
Leu Pro Ser Pro Leu Pro Gln Glu Phe Thr Tyr Leu Asn Ser Pro
                350                 355                 360
Thr Pro Gly Gln Leu Gln Pro Ile Tyr Glu Asn Val Asn Val Val
                365                 370                 375
Ser Gly Asp Glu Val Tyr Ser Leu Ala Tyr Tyr Asn Gln Pro Glu
                380                 385                 390
Gln Glu Ser Val Ala Ala Glu Thr Leu Gly Thr His Met Glu Asp
                395                 400                 405
Lys Val Ser Leu Asp Ile Tyr Ser Arg Leu Arg Lys Ala Asn Ile
                410                 415                 420
Thr Asp Val Asp Tyr Glu Asp Ala Met
                425

<210> SEQ ID NO 35
<211> LENGTH: 977
<212> TYPE: PRT
<213> ORGANISM: Homo sapiens

<400> SEQUENCE: 35

Met Leu Leu Trp Val Ile Leu Leu Val Leu Ala Pro Val Ser Gly
  1               5                  10                  15

Gln Phe Ala Arg Thr Pro Arg Pro Ile Ile Phe Leu Gln Pro Pro
                 20                  25                  30

Trp Thr Thr Val Phe Gln Gly Glu Arg Val Thr Leu Thr Cys Lys
                 35                  40                  45

Gly Phe Arg Phe Tyr Ser Pro Gln Lys Thr Lys Trp Tyr His Arg
                 50                  55                  60

Tyr Leu Gly Lys Glu Ile Leu Arg Glu Thr Pro Asp Asn Ile Leu
```

```
                         65                  70                  75
Glu Val Gln Glu Ser Gly Glu Tyr Arg Cys Gln Ala Gln Gly Ser
                 80                  85                  90

Pro Leu Ser Ser Pro Val His Leu Asp Phe Ser Ser Ala Ser Leu
                 95                 100                 105

Ile Leu Gln Ala Pro Leu Ser Val Phe Glu Gly Asp Ser Val Val
                110                 115                 120

Leu Arg Cys Arg Ala Lys Ala Glu Val Thr Leu Asn Asn Thr Ile
                125                 130                 135

Tyr Lys Asn Asp Asn Val Leu Ala Phe Leu Asn Lys Arg Thr Asp
                140                 145                 150

Phe His Ile Pro His Ala Cys Leu Lys Asp Asn Gly Ala Tyr Arg
                155                 160                 165

Cys Thr Gly Tyr Lys Glu Ser Cys Cys Pro Val Ser Ser Asn Thr
                170                 175                 180

Val Lys Ile Gln Val Gln Glu Pro Phe Thr Arg Pro Val Leu Arg
                185                 190                 195

Ala Ser Ser Phe Gln Pro Ile Ser Gly Asn Pro Val Thr Leu Thr
                200                 205                 210

Cys Glu Thr Gln Leu Ser Leu Glu Arg Ser Asp Val Pro Leu Arg
                215                 220                 225

Phe Arg Phe Phe Arg Asp Asp Gln Thr Leu Gly Leu Gly Trp Ser
                230                 235                 240

Leu Ser Pro Asn Phe Gln Ile Thr Ala Met Trp Ser Lys Asp Ser
                245                 250                 255

Gly Phe Tyr Trp Cys Lys Ala Ala Thr Met Pro His Ser Val Ile
                260                 265                 270

Ser Asp Ser Pro Arg Ser Trp Ile Gln Val Gln Ile Pro Ala Ser
                275                 280                 285

His Pro Val Leu Thr Leu Ser Pro Glu Lys Ala Leu Asn Phe Glu
                290                 295                 300

Gly Thr Lys Val Thr Leu His Cys Glu Thr Gln Glu Asp Ser Leu
                305                 310                 315

Arg Thr Leu Tyr Arg Phe Tyr His Glu Gly Val Pro Leu Arg His
                320                 325                 330

Lys Ser Val Arg Cys Glu Arg Gly Ala Ser Ile Ser Phe Ser Leu
                335                 340                 345

Thr Thr Glu Asn Ser Gly Asn Tyr Tyr Cys Thr Ala Asp Asn Gly
                350                 355                 360

Leu Gly Ala Lys Pro Ser Lys Ala Val Ser Leu Ser Val Thr Val
                365                 370                 375

Pro Val Ser His Pro Val Leu Asn Leu Ser Ser Pro Glu Asp Leu
                380                 385                 390

Ile Phe Glu Gly Ala Lys Val Thr Leu His Cys Glu Ala Gln Arg
                395                 400                 405

Gly Ser Leu Pro Ile Leu Tyr Gln Phe His His Glu Asp Ala Ala
                410                 415                 420

Leu Glu Arg Arg Ser Ala Asn Ser Ala Gly Gly Val Ala Ile Ser
                425                 430                 435

Phe Ser Leu Thr Ala Glu His Ser Gly Asn Tyr Tyr Cys Thr Ala
                440                 445                 450

Asp Asn Gly Phe Gly Pro Gln Arg Ser Lys Ala Val Ser Leu Ser
                455                 460                 465
```

-continued

```
Ile Thr Val Pro Val Ser His Pro Val Leu Thr Leu Ser Ser Ala
            470                 475                 480

Glu Ala Leu Thr Phe Glu Gly Ala Thr Val Thr Leu His Cys Glu
            485                 490                 495

Val Gln Arg Gly Ser Pro Gln Ile Leu Tyr Gln Phe Tyr His Glu
            500                 505                 510

Asp Met Pro Leu Trp Ser Ser Ser Thr Pro Ser Val Gly Arg Val
            515                 520                 525

Ser Phe Ser Phe Ser Leu Thr Glu Gly His Ser Gly Asn Tyr Tyr
            530                 535                 540

Cys Thr Ala Asp Asn Gly Phe Gly Pro Gln Arg Ser Glu Val Val
            545                 550                 555

Ser Leu Phe Val Thr Val Pro Val Ser Arg Pro Ile Leu Thr Leu
            560                 565                 570

Arg Val Pro Arg Ala Gln Ala Val Val Gly Asp Leu Leu Glu Leu
            575                 580                 585

His Cys Glu Ala Pro Arg Gly Ser Pro Pro Ile Leu Tyr Trp Phe
            590                 595                 600

Tyr His Glu Asp Val Thr Leu Gly Ser Ser Ala Pro Ser Gly
            605                 610                 615

Gly Glu Ala Ser Phe Asn Leu Ser Leu Thr Ala Glu His Ser Gly
            620                 625                 630

Asn Tyr Ser Cys Glu Ala Asn Asn Gly Leu Val Ala Gln His Ser
            635                 640                 645

Asp Thr Ile Ser Leu Ser Val Ile Val Pro Val Ser Arg Pro Ile
            650                 655                 660

Leu Thr Phe Arg Ala Pro Arg Ala Gln Ala Val Val Gly Asp Leu
            665                 670                 675

Leu Glu Leu His Cys Glu Ala Leu Arg Gly Ser Ser Pro Ile Leu
            680                 685                 690

Tyr Trp Phe Tyr His Glu Asp Val Thr Leu Gly Lys Ile Ser Ala
            695                 700                 705

Pro Ser Gly Gly Gly Ala Ser Phe Asn Leu Ser Leu Thr Thr Glu
            710                 715                 720

His Ser Gly Ile Tyr Ser Cys Glu Ala Asp Asn Gly Pro Glu Ala
            725                 730                 735

Gln Arg Ser Glu Met Val Thr Leu Lys Val Ala Val Pro Val Ser
            740                 745                 750

Arg Pro Val Leu Thr Leu Arg Ala Pro Gly Thr His Ala Ala Val
            755                 760                 765

Gly Asp Leu Leu Glu Leu His Cys Glu Ala Leu Arg Gly Ser Pro
            770                 775                 780

Leu Ile Leu Tyr Arg Phe Phe His Glu Asp Val Thr Leu Gly Asn
            785                 790                 795

Arg Ser Ser Pro Ser Gly Gly Ala Ser Leu Asn Leu Ser Leu Thr
            800                 805                 810

Ala Glu His Ser Gly Asn Tyr Ser Cys Glu Ala Asp Asn Gly Leu
            815                 820                 825

Gly Ala Gln Arg Ser Glu Thr Val Thr Leu Tyr Ile Thr Gly Leu
            830                 835                 840

Thr Ala Asn Arg Ser Gly Pro Phe Ala Thr Gly Val Ala Gly Gly
            845                 850                 855

Leu Leu Ser Ile Ala Gly Leu Ala Ala Gly Ala Leu Leu Leu Tyr
            860                 865                 870
```

-continued

```
Cys Trp Leu Ser Arg Lys Ala Gly Arg Lys Pro Ala Ser Asp Pro
            875                 880                 885

Ala Arg Ser Pro Pro Asp Ser Asp Ser Gln Glu Pro Thr Tyr His
            890                 895                 900

Asn Val Pro Ala Trp Glu Glu Leu Gln Pro Val Tyr Thr Asn Ala
            905                 910                 915

Asn Pro Arg Gly Glu Asn Val Val Tyr Ser Glu Val Arg Ile Ile
            920                 925                 930

Gln Glu Lys Lys Lys His Ala Val Ala Ser Asp Pro Arg His Leu
            935                 940                 945

Arg Asn Lys Gly Ser Pro Ile Ile Tyr Ser Glu Val Lys Val Ala
            950                 955                 960

Ser Thr Pro Val Ser Gly Ser Leu Phe Leu Ala Ser Ser Ala Pro
            965                 970                 975

His Arg

<210> SEQ ID NO 36
<211> LENGTH: 374
<212> TYPE: PRT
<213> ORGANISM: Homo sapiens

<400> SEQUENCE: 36

Met Val Leu Trp Glu Ser Pro Arg Gln Cys Ser Ser Trp Thr Leu
 1               5                  10                  15

Cys Glu Gly Phe Cys Trp Leu Leu Leu Pro Val Met Leu Leu
                20                  25                  30

Ile Val Ala Arg Pro Val Lys Leu Ala Ala Phe Pro Thr Ser Leu
                35                  40                  45

Ser Asp Cys Gln Thr Pro Thr Gly Trp Asn Cys Ser Gly Tyr Asp
                50                  55                  60

Asp Arg Glu Asn Asp Leu Phe Leu Cys Asp Thr Asn Thr Cys Lys
                65                  70                  75

Phe Asp Gly Glu Cys Leu Arg Ile Gly Asp Thr Val Thr Cys Val
                80                  85                  90

Cys Gln Phe Lys Cys Asn Asn Asp Tyr Val Pro Val Cys Gly Ser
                95                  100                 105

Asn Gly Glu Ser Tyr Gln Asn Glu Cys Tyr Leu Arg Gln Ala Ala
                110                 115                 120

Cys Lys Gln Gln Ser Glu Ile Leu Val Val Ser Glu Gly Ser Cys
                125                 130                 135

Ala Thr Asp Ala Gly Ser Gly Ser Gly Asp Gly Val His Glu Gly
                140                 145                 150

Ser Gly Glu Thr Ser Gln Lys Glu Thr Ser Thr Cys Asp Ile Cys
                155                 160                 165

Gln Phe Gly Ala Glu Cys Asp Glu Asp Ala Glu Asp Val Trp Cys
                170                 175                 180

Val Cys Asn Ile Asp Cys Ser Gln Thr Asn Phe Asn Pro Leu Cys
                185                 190                 195

Ala Ser Asp Gly Lys Ser Tyr Asp Asn Ala Cys Gln Ile Lys Glu
                200                 205                 210

Ala Ser Cys Gln Lys Gln Glu Lys Ile Glu Val Met Ser Leu Gly
                215                 220                 225

Arg Cys Gln Asp Asn Thr Thr Thr Thr Lys Ser Glu Asp Gly
                230                 235                 240
```

```
His Tyr Ala Arg Thr Asp Tyr Ala Glu Asn Ala Asn Lys Leu Glu
                245                 250                 255

Glu Ser Ala Arg Glu His His Ile Pro Cys Pro Glu His Tyr Asn
                260                 265                 270

Gly Phe Cys Met His Gly Lys Cys Glu His Ser Ile Asn Met Gln
                275                 280                 285

Glu Pro Ser Cys Arg Cys Asp Ala Gly Tyr Thr Gly Gln His Cys
                290                 295                 300

Glu Lys Lys Asp Tyr Ser Val Leu Tyr Val Val Pro Gly Pro Val
                305                 310                 315

Arg Phe Gln Tyr Val Leu Ile Ala Ala Val Ile Gly Thr Ile Gln
                320                 325                 330

Ile Ala Val Ile Cys Val Val Val Leu Cys Ile Thr Arg Lys Cys
                335                 340                 345

Pro Arg Ser Asn Arg Ile His Arg Gln Lys Gln Asn Thr Gly His
                350                 355                 360

Tyr Ser Ser Asp Asn Thr Thr Arg Ala Ser Thr Arg Leu Ile
                365                 370
```